(12) United States Patent
Ricciardi et al.

(10) Patent No.: US 8,382,008 B1
(45) Date of Patent: Feb. 26, 2013

(54) OPTIMIZED AND MINIATURIZED AEROSOL GENERATOR

(76) Inventors: Jonathan J. Ricciardi, Kennewick, WA (US); Carl L. Ricciardi, Tomahawk, WI (US); John D. Wolf, II, Edwardsburg, MI (US)

( * ) Notice: Subject to any disclaimer, the term of this patent is extended or adjusted under 35 U.S.C. 154(b) by 0 days.

(21) Appl. No.: 13/425,478

(22) Filed: Mar. 21, 2012

Related U.S. Application Data

(63) Continuation-in-part of application No. 12/816,986, filed on Jun. 16, 2010, now Pat. No. 8,177,142, and a continuation-in-part of application No. 12/114,454, filed on May 2, 2008, now Pat. No. 7,871,016, and a continuation-in-part of application No. 11/509,332, filed on Aug. 24, 2006, now Pat. No. 7,641,130.

(60) Provisional application No. 61/295,869, filed on Jan. 18, 2010, provisional application No. 60/915,524, filed on May 2, 2007, provisional application No. 60/711,858, filed on Aug. 26, 2005.

(51) Int. Cl.
*B05B 17/06* (2006.01)
*B05B 1/08* (2006.01)

(52) U.S. Cl. .. 239/102.2; 239/71; 239/338; 128/200.16; 261/DIG. 48

(58) Field of Classification Search ................ 239/4, 71, 239/73, 74, 102.1, 102.2, 338; 261/28–30, 261/34.1, 81, 119.1, DIG. 48; 422/20, 28, 422/128, 292; 128/200.16
See application file for complete search history.

(56) References Cited

U.S. PATENT DOCUMENTS

| 3,433,461 | A | | 3/1969 | Scarpa |
| 3,729,138 | A | | 4/1973 | Tysk |
| 3,989,042 | A | * | 11/1976 | Mitsui et al. ............. 128/200.16 |
| 4,109,863 | A | | 8/1978 | Olson et al. |
| 4,366,125 | A | | 12/1982 | Kodera et al. |

(Continued)

FOREIGN PATENT DOCUMENTS

| FR | 2860721 | 4/2005 |
| GB | 1128245 | 9/1968 |

OTHER PUBLICATIONS

William C. Hinds, Aerosol Technology, 1999 by John Wiley & Sons, Inc.

*Primary Examiner* — Darren W Gorman
(74) *Attorney, Agent, or Firm* — Donald J. Ersler

(57) ABSTRACT

An optimized and miniaturized aerosol generator preferably includes a transducer plate, at least one transducer, a level float, a fluid container, at least one aerosol output member and an air input member. At least one transducer counterbore is formed in the transducer plate to retain the at least one transducer. The fluid container includes a float chamber and an aerosol chamber. The at least one aerosol output and the air input member are retained in a top of the aerosol chamber. A sealing gasket is preferably placed between a top of the transducer plate and a bottom of the fluid. The level float is contained in the float chamber. Air is pumped into the aerosol chamber through the air input member. A transducer driver powers the at least one transducer. The at least one transducer vibrates and produces an aerosol, which exits the at least one aerosol output member.

14 Claims, 111 Drawing Sheets

U.S. PATENT DOCUMENTS

| | | |
|---|---|---|
| 4,512,951 A | 4/1985 | Koubek |
| 4,776,990 A * | 10/1988 | Verity .......................... 261/128 |
| 4,952,370 A | 8/1990 | Cummings et al. |
| 4,976,259 A | 12/1990 | Higson et al. |
| 4,986,937 A * | 1/1991 | Sorio ............................. 261/81 |
| 5,300,260 A * | 4/1994 | Keshet et al. ................... 261/81 |
| 5,407,604 A * | 4/1995 | Luffman ........................... 261/4 |
| 5,766,958 A * | 6/1998 | Sullivan et al. ............... 436/174 |
| 5,878,355 A | 3/1999 | Berg et al. |
| 5,925,966 A | 7/1999 | Riftin et al. |
| 6,102,992 A | 8/2000 | Berg et al. |
| 7,524,454 B1 | 4/2009 | Sparks |
| 2002/0121274 A1 | 9/2002 | Borland |
| 2005/0042130 A1 | 2/2005 | Lin et al. |
| 2006/0213508 A1* | 9/2006 | Murray et al. ........... 128/200.16 |
| 2006/0237860 A1* | 10/2006 | Huang et al. .................... 261/81 |
| 2007/0053789 A1 | 3/2007 | Ricciardi |
| 2007/0224079 A1 | 9/2007 | Sparks et al. |
| 2007/0224080 A1 | 9/2007 | Sparks et al. |
| 2008/0223953 A1* | 9/2008 | Tomono et al. ............ 239/102.2 |

\* cited by examiner

OPTIMIZED AND MINIATURIZED AEROSOL GENERATOR

CROSS-REFERENCE TO RELATED APPLICATIONS

This continuation-in-part application claims priority from U.S. Non-provisional application Ser. No. 12/816,986, filed on Jun. 16, 2010 now U.S. Pat. No. 8,177,142, which claims priority from U.S. Provisional Application Ser. No. 61/295,869, filed Jan. 18, 2010, and as a continuation-in-part of U.S. Non-Provisional patent application Ser. No. 12/114,454, filed on May 2, 2008, now U.S. Pat. No. 7,871,016, which claims priority both from U.S. Provisional Patent Application Ser. No. 60/915,524, filed on May 2, 2007, and as a continuation-in-part from U.S. patent application Ser. No. 11/509,332, filed on Aug. 24, 2006, now U.S. Pat. No. 7,641,130, which claims priority from U.S. Provisional Patent Application Ser. No. 60/711,858, filed on Aug. 26, 2005 and all of the above patent documents are expressly incorporated herein by reference in their entirety.

TECHNICAL FIELD OF THE INVENTION

The present invention relates to improved apparatuses and methods for the generation and application of an ultrasonically generated aerosol for uses including but not limited to the sanitization, detoxification, disinfection, high-level disinfection, or sterilization of one or more areas and the surfaces in those areas, as well as the delivery of other types of liquid agents, for various purposes to one or more areas, and without limitation, the surfaces in those area(s).

BACKGROUND OF THE INVENTION

The apparatus described in U.S. Pat. No. 4,366,125, which is incorporated herein by reference in its entirety, including any references cited therein, generates a hydrogen peroxide mist by an ultrasonic wave vibrator. The mist adheres to the surface of materials being sterilized and is then irradiated with ultraviolet-ray lamps. U.S. Pat. Nos. 5,878,355 and 6,102,992, each of which is incorporated herein by reference in its entirety, including any references cited therein, disclose a method and device for decontamination of a contaminated process area whereby a fine aerosol of an encapsulant is generated to encapsulate contaminants within a contaminated environment. The aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are made from lead-zirconate-titanate-four (PZT-4) or other piezoelectric materials. This material is coated with a conductive coating (electrode material) that enables an electrical signal to energize the transducer and causes it to emit high frequency pressure (energy).

While operating these prior art apparatuses and similar apparatuses, it has been found that certain liquids, especially acidic solutions, chemically react with the electrode materials of the transducers that generate the aerosol. The result is a noticeable deterioration of both the transducers and their performance. For example, acidic solutions of hydrogen peroxide and peroxyacetic acid have caused noticeable deterioration of the transducers within minutes of operation.

An attempt was made to prevent transducer degradation by coating the face of the transducers with a thin coating of different materials. None of these efforts have been successful. For example, U.S. Pat. No. 4,109,863, which is incorporated herein by reference in its entirety, including any references cited therein, discloses similar findings. The protective coating on the transducer deteriorated to a point where the transducer failed to be energized. It was initially believed that this deterioration was caused by transducer induced cavitation within the tank; however, the aforementioned coatings were also shown to fail in simple immersion tests, conducted over time in an acidic solution, with unpowered transducers. For example, laboratory work indicated that PZT material coated with an electroless nickel plating, or a glaze, were both found to be incompatible with a 4% solution of hydrogen peroxide and peroxyacetic acid, after being exposed to the solution for two weeks at 160° F.

In addition, it was found that various materials used to construct the transducer housing and assembly experienced deterioration after being subjected to a simulated long-term exposure to an acid solution of hydrogen peroxide and peroxyacetic acid. This was observed with an accelerated aging test. This test consisted of placing components constructed of various material types in vessels containing the hydrogen peroxide and peroxyacetic acid solution and subjecting them to increased temperature over a course of time. Without being limited to the theory, this test is based on the theory recognized in the art that at higher temperatures chemical or physical reactions will proceed faster due to the increased probability that two molecules will collide and chemically react.

Without being limited to a particular mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) either killing the bacteria, fungus, or spores, neutralizing or destroying toxins, or rendering a protein structure incapable of replication or otherwise interfering with the target's cellular physiology. These chemically reactive liquids may be provided as an aerosol. For example, U.S. Pat. No. 4,512,951, which is incorporated herein by reference in its entirety, including any references cited therein, teaches using hydrogen peroxide to sterilize medical devices by condensing hydrogen peroxide-water vapors to deposit a film of liquid on the devices. The liquid film is then evaporated.

While the prior art attempted to coat the transducer with a protective substance, there were problems with these coatings. U.S. Pat. Nos. 3,729,138; 4,109,863; and 4,976,259, each of which is incorporated herein by reference in its entirety, including any references cited therein, teach that the optimum thickness of a glass barrier, which may be used as a protective plate and/or cover, on a transducer should be any multiple of one-half (½) the wavelength of the transmitted pressure (energy). The thicknesses of protective barriers have been calculated using wave transmission theories and their respective mathematical formulas known to those skilled in the art. It is estimated that twenty percent (20%) of the energy emitted from the transducers is being transmitted into the liquid beyond the protective barrier. The prior art does not include techniques for further increasing the energy emitted from the transducer with a protective plate and/or cover.

U.S. Pat. Nos. 3,433,461; 3,729,138; 4,109,863; and 4,976,259, each of which is incorporated herein by reference in its entirety, including any references cited therein, teach that an effective thickness of a protective barrier material "interfaced with" a transducer can be approximately any multiple of one-half (½) the wavelength of the transmitted pressure (energy) from the transducer. Prior art has taught that barriers having a thickness equal to or about one-half (½) wavelength constructed from non-conductive and/or insulating type materials like glass, could be effectively coupled with an ultrasonic transducer for generating aerosol, as long as they included a special design consideration for cooling the transducer, or the transducer was separated from the glass barrier with a layer of liquid. U.S. Pat. No. 3,433,461 teaches utilizing a 1.5 inch diameter transducer bonded to a metal barrier that is a one-half wavelength thick. A problem associated with using metal barriers is corrosion, which was acknowledged in U.S. Pat. No. 3,729,138. In addition, U.S. Pat. No. 3,433,461 discloses that heat has a detrimental effect associated with the operation of a transducer and that a metal barrier interfaced with a transducer permitted the use of much higher driving powers than in prior art devices, since it provided more heat dissipation. Further, the driving power supplied to the transducers is limited by the heat dissipation in the device, which is a function, in each case, of the total area of the generator.

According to U.S. Pat. No. 4,976,259, an attempt was made to bond a glass barrier to a piezoelectric crystal with an adhesive, but such an attempt did not improve on the prior art and resulted in a major loss of acoustic coupling of the ultrasonic energy into the glass cover as the adhesive bond deteriorated. The deterioration was due to high localized temperatures caused by reflected energy resulting from mismatched acoustical impedances.

The prior art does not currently include commercially effective techniques for constructing and operating a high frequency and high power aerosol producing transducer assembly consisting of one or more transducers bonded or adhered to a protective barrier constructed from non-metallic and/or insulative type materials, such as glass, with a thickness that is not one-half (½) of a wavelength. Furthermore, the prior art does not currently include high frequency and high power aerosol producing glass barrier and transducer assemblies that are capable of operating without additional liquid layers or liquid cooling means incorporated into the transducer assembly design.

Therefore, the need for a protective barrier for the aerosol producing transducer that is highly resistant to degradation caused by chemically reactive solutions exists. The protective barrier should withstand the heat generated by a transducer and should function effectively with the transducer to produce a fine aerosol at high output levels (which requires high energy emitted by the transducer). This heat is due to the high frequency and energy that is needed to achieve a high output of aerosolized liquid per hour with the aerosol droplets being less than about 10 microns in size. In general, within the effective frequency band, the higher the power at the effective aerosol producing frequencies, the larger the quantity of aerosol produced; and the higher the effective frequency the smaller the droplet size in the aerosol.

The complete and assured sanitization, disinfection, high-level disinfection, or sterilization of devices, tools, machinery, or other objects or surfaces, within enclosed or unenclosed targeted areas or surfaces, related to industries including, but not limited to, health care, food production, medical device or products, clean rooms, and pharmaceutical, has always been a challenge in terms of overall effectiveness, processing time, cost, and engineering tradeoffs. In addition, the applied agents must have limited toxicity, be reasonably safe, as well as non-harmful to the materials or substances to which they are applied.

The prior art has extensively taught that relatively quick disinfection and sterilization of surfaces can be achieved by exposing them to an aerosol of a disinfectant/sterilizing agent created by ultrasonic nebulization. The apparatus described in U.S. Pat. No. 4,366,125 (Kodera et al., 1980), which is incorporated herein by reference in its entirety, including any references cited therein, generates a hydrogen peroxide mist by an ultrasonic waves vibrator. The aqueous hydrogen peroxide is heated as it travels from a tank into a basin (col. 4, line 6-8) where it is turned into a fog or mist as the surface of the germicidal liquid in the basin is acted upon by ultrasonic waves. The fog or mist will adhere to the surface of materials being sterilized or disinfected. The surface is then irradiated with ultraviolet-ray lamps.

G.B. Patent No. 1,128,245, (Rosdahl et al., 1968) which is incorporated herein by reference in its entirety, including any references cited therein, describes a device for disinfecting apparatuses and instruments, including medical instruments. This apparatus also generates a mist of disinfectant, including hydrogen peroxide, by means of an ultrasonic aerosol generator. According to Rosdahl et al., this patent was "primarily adapted for the disinfection of small medical instruments such as scalpels, tongs, syringes, or the like, positioned on a grid in a container" (pg. 3 col. 23-30). However, another separate intended use for a second described apparatus was to disinfect the interior surfaces of objects such as hollow tubing used for "breathing apparatuses" and "heart lung machines" (pg. 1 line 30-36 and pg 2 line 95-101). Rosdahl et al. also taught the use of the germicidal fogging technology to disinfect rooms, apartments and the like (pg. 2 col. 28-30). The pressurized air in Rosdahl et al. is supplied by way of a fan etc. or carrier gas, (pg. 2 line 48-49) and is used to move the generated aerosol as well as to dry objects placed within the enclosed area of the described apparatus. Rosdahl et al. also incorporated "a heating element in the flow path of the carrier gas, to increase drying efficiency" (pg. 3 line 123-127).

Ultrasonic nebulizers have a unique advantage in that they can create aerosol droplets less than 10 microns in size depending on the power and frequency used in their operation. The small size of the droplets enables them to penetrate small cracks and crevices and to behave like a gas due to Brownian movement and diffusion. In addition, the dense cloud of small droplets is able to form a very thin coating or film over surfaces. The thin coating or film of disinfectant or sterilization agent is able to dry much faster than coatings created by aerosols consisting of larger diameter droplets. It is also theorized that even partial contact of the aerosol droplets with the targeted contaminate(s), can contribute to the overall efficacy of the process. U.S. Pat. No. 4,366,125, (Kodera et al., 1980) taught that heated H2O2 was more efficacious than H2O2 used at room temperature (col. 1, line 19-25). In other words, (Kodera et al., 1980) taught that the efficacious nature of a liquid agent can be increased as it is heated to temperatures higher than ambient temperature. This is desired, without limitation, in the present invention. The text entitled, "Aerosol Technology" by William C. Hinds (1982), which is incorporated herein by reference in its entirety, including any references cited therein, also taught that the size of the aerosol particles produced by ultrasonic means is not only affected by the frequency of the transducer operation, but also by the surface tension and density of the liquid as shown by the following mathematical expression (page 382):

$$CMD=((y)/(pL)(f^{\wedge}2))^{\wedge}1/3 \quad \text{Equation 1:}$$

where: CMD=particle size produced; y=surface tension; pL=liquid density; and f=frequency It is commonly known that heating a liquid to point less than its boiling point will reduce its surface tension. Therefore, according to Equation 1 above, a direct relationship was established by William C. Hinds (1982) where one skilled in the art can ascertain that the higher the temperature of the liquid, the lower the liquid's surface tension, which will result in smaller sized aerosol particles. This principal is incorporated without limitation, in the present invention. William C. Hinds (1982) also taught in the same text that smaller diameter particles demonstrate characteristics such as but not limited to, a lower settling velocity, a higher diffusion coefficient, and a higher Brownian displacement (movement), which is desired, without limitation, in the present invention. William C. Hinds (1982) further taught that ultrasonic aerosol generating transducers can heat the surrounding liquid (page 382). This is also desired in the present invention.

Despite the plethora of advancements shown in the current art, limitations exist in many areas that reduce the effectiveness or viability of the ultrasonic aerosol generator technology in actual commercial applications. The methods and apparatuses of the present invention address the need for an ultrasonic aerosol generator that is, without limitation: (a) designed so that the apparatus can be quickly and easily set up and operated in a reproducible manner on uneven or angled surfaces(s), (b) designed so that the transducers can quickly heat the liquid and liquid surface above and/or around them, (c) designed to prevent or limit dust and debris contamination inside the pressurized air channels or pipes of the apparatus or in the tank in which one or more transducer(s) are located, (d) designed so that if a valve of a liquid storage, holding tank, or reservoir, breaks the tank(s) or reservoir(s) in which the transducer(s) is located is not flooded, (e) designed so that excess, leaked, or spilled liquid can be transferred to a separate containment tank or basin from sources such as but not limited to the fill pipe(s), blower housing(s), internal catch pan(s), transducer tank(s) or basin(s), (f) designed so that the liquid in the tank in which the transducers are located does not drop below the minimum or exceed the maximum operating temperature for that liquid or particular process, coupled with one or more sensor(s) that can determine when an effective or sufficient amount of aerosol has been applied or administered to the targeted area and/or surfaces, (g) designed so that a partially empty apparatus can be easily and effectively refilled, (h) designed to prevent expired liquid that has been added or is otherwise available to the apparatus from being administered by or deployed from the apparatus, (i) designed so that the stream of aerosol deployed from the apparatus can be simultaneously delivered to one or more separate areas.

It is obvious to those skilled in the art that an apparatus can automatically shut down if an insufficient amount of inventory or product is available with which to complete its defined operational cycle. This activity is also mentioned in French Patent No. FR2860721 (Schwal et al.), which is incorporated herein by reference in its entirety, including any references cited therein. This patent claims the use, by any aerosol generator, of single-use liquid refill/fill cartridges that are associated with specific identifiers, and a reader integrated into the aerosol generator apparatus that can read the said identifiers, all of which is dependently combined with a system of defined steps to establish a set process whereby the apparatus will not generate aerosol if there are any non-conformances related to the entire process, and each cycle of use is terminated with a recording of various information pertaining to the process as a whole. However, according to patent No. FR2860721, the apparatus only notifies the operator if an insufficient liquid quantity is available (pg. 6 line 15-25 and pg. 10 line 10-25) and when it is necessary to replace a filler cartridge (pg. 10 line 15-25).

Patent No. FR2860721, does not teach or describe an aerosol generator apparatus that can communicate, by any means, to the apparatus operator the quantity of liquid or at least the exact minimum quantity of liquid, expressed in units of measurement, that is necessary to add or make available to the apparatus so that it may successfully complete its desired or chosen operational time or run cycle. The methods and apparatuses of the present invention address the need to provide this information.

French Patent No. FR2860721 also fails to address the issue of preventing the apparatus from using expired or outdated liquid that is available to the apparatus from, without limitation, one or more tanks or reservoirs inside or attached to the apparatus that have been fed, supplied, or filled by a refill/fill cartridge or other means. This is critical since some liquid agents have a defined period of time of efficacious use once they have undergone, without limitation, dilution from a concentrate or exposure to air. The methods and apparatuses of the present invention address the need to prevent the use or deployment of a liquid agent that is available to the apparatus, but has expired, is unusable, or undesired.

The need for an ultrasonic aerosol generator that can be positioned and operated from within the area in which the aerosol is being dispersed so as to, without limitation, eliminate or reduce the effects of increased air pressure within the targeted area and operate without damage to its internal and external structures and components is also addressed in the present invention and includes, without limitation, methods and apparatuses such as: (a) means for cooling the various motors, electronics, and other components; (b) properly housing various motors, electronics, and other components to prevent their exposure to the environment surrounding the apparatus; (c) the remote control of and remote communication with the apparatus; (d) preventing any parts of the apparatus that are exposed to the aerosol from becoming higher in temperature than the temperature of the atmosphere surrounding the apparatus.

There is also a continued need in the market place to increase efficacy and effectiveness from the aerosol and the process of its administration, as well as a system that offers shortened cycle times. The present invention addresses these issues. One such means in the present invention is the utilization of thermal forces and their resultant effects, by cooling or decreasing the temperature of the objects, the atmosphere in which they reside, or the targeted area for the administration of an aerosol as well any surfaces in that area, before the administration of the aerosol to the targeted area or surfaces. Prior art has taught the step of cooling an enclosed area and its surfaces before the administration of a hydrogen peroxide disinfectant, however the hydrogen peroxide was first vaporized into a gaseous state before its administration, and the cooling step was intended to condense the vaporized hydrogen peroxide gas out of the atmosphere in which it was administered and onto the intended surfaces, as taught in U.S. Pat. No. 4,512,951 (Koubek et al., 1983), which is incorporated herein by reference in its entirety, including any references cited therein. More specifically, Koubek et al., teaches a method of sterilization where a liquid of aqueous hydrogen peroxide is vaporized, and the uniformly vaporized mixed hydrogen peroxide-water vapors are delivered into an evacuated sterilizer chamber. The articles to be sterilized are cooled if necessary prior to the introduction of the vapor (or are cooled by the evacuation of air from the sterilizing zone) to a temperature below the dew point of the entering vapors and the condensing vapor deposits a film of liquid on all such cool surfaces (col 2, line 40-51). Koubek et al., also mentions in claim 2 that the result of vaporization was a mixed "gaseous vapor" consisting of hydrogen peroxide and water vapor free of solid contaminants.

U.S. Pat. No. 4,952,370 (Cummings et al., 1988), which is incorporated herein by reference in its entirety, including any references cited therein, teaches a similar method of sterilization where a liquid of aqueous hydrogen peroxide is also vaporized into a gaseous state before its administration into an evacuated sterilizer chamber. However, Cummings et al., teaches improvements to the art where the hydrogen peroxide-water vapor is applied under vacuum to surfaces that are below 10 degree centigrade, or surfaces in an environment that are both below 10 degree centigrade and above 10 degree centigrade. The cold surfaces mentioned in Cummings et al., were not cooled to accentuate or enhance the process, but were surfaces of components that were inherently cold for their own operational purposes. This is mentioned in sections such as (col 2, line 4-9), (col 2, line 29-33), and (col 4, line 67 to col 5, line 2).

U.S. Patent Application No. 2005/0042130 A1 (Lin et al., 2003), which is incorporated herein by reference in its entirety, including any references cited therein, claims the use of an applied vacuum to move an ultrasonically derived aerosol, consisting of a sterilant, throughout the area of an enclosed chamber. The use of various vacuum pressures below atmospheric pressure was also mentioned as well as the possibility that vacuum pressures lower than 5 torr lower than atmospheric pressure would likely "enhance the results", and that using a vacuum pressure low enough to vaporize the sterilant generally enhances sterilization (pg. 2, paragraph 28). However, Lin et al, was silent with respect to how the lower vacuum pressures would "enhance the results" other than any enhancement that vaporization of the aerosol might bring. Lin et al, was also silent with respect to the amount of time that is needed to elapse between lowering the pressure within the enclosed chamber and the application of an aerosol, in order to obtain the needed or desired level of efficacy. (Lin et al., 2003) was silent with respect to cooling any surfaces within the sterilization chamber or applying the aerosol to any cooled surfaces.

It is important to note that Lin et al, did not mention any process or method to heat the liquid of the aerosol or cool the surfaces in the sterilization chamber before or during the delivery of the aerosol, or any means to incur condensation if the liquid was vaporized. In fact, the 5 torr negative pressure that was used by Lin et al. to generate their findings was reported to be sufficient enough to disperse the mist within the sterilization chamber (pg. 2, paragraph 28), but was never mentioned to have cooled the surfaces within the sterilization chamber or to have that intended effect.

In addition, it is important to note that the cooling of a targeted environment(s) and/or the surfaces contained therein addressed by the present invention is intended, without limitation, for a completely different application and purpose. The present invention utilizes the principals of aerosol behavior to increase the performance of the process of the present invention, and not the condensation of a gas as taught in the prior art. This is further addressed in the present invention.

By comparison, the current invention utilizes, without limitation, the cooling of the targeted environment(s) and its surfaces to enhance the performance and efficacy of the aerosol administration process and not to condense a gas as taught by the prior art. The methods and apparatuses of the present invention also address the need to apply an aerosol to surfaces that are without limitation, difficult, impossible, time consuming, or not cost effective to enclose.

SUMMARY OF THE INVENTION

In view of the need for improvements in the current art, the present invention includes improved apparatuses and methods for the generation and application of an ultrasonically generated aerosol for uses including, but not limited to, the sanitization, disinfection, high-level disinfection, or sterilization of one or more areas and the surfaces in those areas, as well as the delivery of other types of liquid agents, for various purposes, to one or more areas, and the surfaces found therein.

It is preferred, without limitation, that the aerosol is generated within the apparatus and administered into a targeted area and/or onto targeted surfaces by pressurized air or the movement of air or gas. The generated aerosol can be of various sizes, mass concentration or density, and number concentration. It is preferred without limitation that the aerosol is a submicron droplet fog or aerosol of an anti-pathogen, toxin, fungal, sterilization, disinfection, or sporicidal agent(s) or mixtures thereof (herein collectively "agent(s)"). However, any liquid agent(s) may be used in the present invention for various purposes. The fog or aerosol can, without limitation, consist substantially of ten micron to submicron size aerosolized droplets. It is preferred, without limitation, that the aerosol has a higher rather than lower mass concentration or density of droplets. It is also preferred, without limitation, that the aerosol has a higher rather than lower number concentration of droplets.

The apparatus and methods described in the present invention can pertain to any ultrasonic aerosol producing apparatus. They can also pertain to an aerosol producing apparatus as described in the present invention. This apparatus, briefly described, has one or more piezoelectric transducers that are operated in parallel or series. The transducers are submerged in one or more tanks or reservoirs, and cause a surface disturbance, which results in the formation of an aerosol of the liquid in the tanks or reservoir(s). The one or more tanks or reservoirs in which the transducers are located can be connected to one or more additional tanks or reservoirs that hold the liquid agent. The liquid level in the tank(s) or reservoir(s) in which the transducers are located is controlled by one or more valves which are actuated when the liquid level drops to a certain level causing the valves to open and allows additional liquid to flow in. The tanks or reservoirs also have a means to sense if they are under or overfilled, and can cause the apparatus to shut down if this occurs. The tank(s) or reservoir(s) in which the transducers are located, can be positioned in a chamber that can have a flow of pressurized air/gas, or can be constructed in such a way so that pressurized air/gas can flow through or over them. The pressurized air/gas is intended to move the generated aerosol from the apparatus to the targeted areas or surfaces. The pressurized air/gas can be supplied from sources such as, but not limited to, one or more, fan(s), blower(s), or supply of pressurized air or gas. The apparatus in the present invention can be operated either from inside or outside of the targeted area.

An apparatus and method of an embodiment of the present invention, briefly summarized, comprises constructing the apparatus so that the aerosol producing transducer(s) and/or their liquid facing surfaces, are able to, without limitation, automatically align themselves with, match the angle of, or remain level with, the surface of the liquid above them. This allows the apparatus to be quickly and easily set up and operated, in a reproducible manner, on uneven or angled surfaces. It also eliminates, without limitation, the need to operate the apparatus on level surfaces. This embodiment includes placing, positioning, or mounting the transducers to or with a gimbal or other similar means known in the art, where the transducers are located at an effective range or depth below the surface of the liquid during their operation. However, it is preferred without limitation that the transducer(s) and their associated parts and housing(s) are designed so that they can be suspended, positioned, held, or maintained, in numerous ways at an effective range or depth below the surface of the liquid during their operation. Without being limited, the transducer(s) and their housing(s) can be suspended, positioned, held, or maintained, at an effective range or depth below the surface of the liquid from an object or component that is floating on the surface of the liquid, partially submerged in the liquid, or completely submerged in the liquid.

An apparatus and method of an embodiment of the present invention, briefly summarized, comprises interfacing the transducer(s) with a protective barrier that is ground and polished on one or more sides. Polishing the side of the barrier that interfaces with the liquid in the reservoir(s) offers advantages including, but not limited to, ease of cleaning, increased resistance to mineral or foreign object debris deposition or buildup, efficient and effective movement of liquid off of the barrier. In addition, polishing the side of the barrier that interfaces with the adhesive and transducer(s), offers advantages including, but not limited to, reduced variability in adhesive thickness due to diminished variability in the protective barrier's surface features, which can without limitation, reduce variability in transmission related issues.

An apparatus and method of an embodiment of the present invention, briefly summarized, comprises constructing the enclosing glass plate to have approximately a thickness of about ¼ the wavelength in glass or other material forming the barrier of the transmitted pressure wave generated by the transducer at the natural resonant frequency of the transducer. When the barrier thickness has been calculated, the transducer can be operated at an operational frequency up to 60% percent greater than the natural resonant frequency to achieve a much more efficient operation for the transducer in forming the aerosol. Alternatively, the thickness of the barrier can be varied from the optimal thickness in the range of −0.010 inches to +0.024 inches to increase the efficiency of operation of the transducer. Further, it has been found that the glass or other material barrier thickness may be increased to around various odd multiples of ¼ wavelength and still operate effectively to provide a high volume small aerosol particle output.

An apparatus and method of an embodiment of the present invention, briefly summarized, comprises enclosing or encircling aerosol producing transducers with one or more wall(s) or barrier(s), that can be, without limitation, continuous or discontinuous, sealed, partially sealed, or unsealed, of various heights including, but not limited to, above the surface of the liquid above the transducers. The purpose of the wall(s) or barrier(s) is to contain the liquid above and around the transducers and use the heat from the transducers to heat that liquid above and around the transducers, and without limitation, the liquid surface above the transducers. The wall(s) or barrier(s) can be perforated or have holes or notches in various orientations or locations in order to allow liquid of various temperatures to flow in and out of the enclosed or encircled areas.

An apparatus and method of an embodiment of the present invention, briefly summarized, comprises filtering the pressurized air before it enters the apparatus, or at least before entering the aerosol generation chamber. Without limitation, it is preferred that one or more filter(s) is located where the air is drawn or pulled into the apparatus by a blower or fan. The filter(s) can be located either on the inside or outside of the apparatus. The addition of one or more filter(s) prevents or limits dust and debris contamination inside the pressurized air channels or pipes of the apparatus or in the tank or area in which the transducer(s) are located. Various types of filters can be used in the present invention and is dependent on the application. The filter(s), are not used in any configuration(s) or application(s) where aerosol is pulled or pushed from the area in which it was administered, back through the aerosol generator and filtered before it is exhausted out from the targeted or treated area.

An apparatus and method of an embodiment of the present invention, briefly summarized, comprises connecting one or more tanks between the main tank(s) in which the liquid is stored in the apparatus, and the tank(s) in which the transducer(s) are located, and without limitation, each of the aforementioned tanks have one or more inline valve(s) or float valve(s) that controls the flow of liquid. Without limitation, these connecting tank(s) and valve(s) system(s) act as a check or failsafe mechanism to ensure that the tank(s) or basin(s) in which the transducer(s) are located is not over filled or flooded.

An apparatus and method of an embodiment of the present invention, briefly summarized, comprises connecting, without limitation, the fill pipe(s) or their spill over tray(s) or basin(s), blower or fan housing(s), internal catch pan(s) or basin(s), transducer tank(s) or basin(s), to one or more liquid containment tank(s). Without limitation, the liquid containment tank(s) are designed to collect excess, spilled, leaked, gathered, or coalesced liquid. This collection system can be connected to the pipe(s) and valve(s) used to drain the apparatus, or it can also have its own drain pipe(s) and valve(s).

An apparatus and method of an embodiment of the present invention, briefly summarized, comprises the incorporation of a means to control or prevent the temperature of the liquid in the tank or basin in which the transducer(s) are located from exceeding the maximum desired, established, or required operating temperature for that liquid or particular process. The prior art has taught that the transducers impart heat into the liquid during their operation. The air that is used to transfer the aerosol from the basin or tank in which the transducer(s) are located to the targeted area(s), can function as a heat removal system. However this pressurized air flow can only remove a certain or calculated number of BTUs or watts of heat due to factors including, but not limited to, the surface area of the liquid in the basin or tank, and the volume and velocity of air that moves over that surface area. If more heat is imparted into the liquid than is removed or dissipated over time, the temperature of the liquid will continue to rise. The means to control or prevent the temperature of the liquid in the tank(s) or basin(s) in which the transducers are located from exceeding the aforementioned maximum desired, established, or required operating temperature, includes without limitation, pumping or otherwise moving the liquid that is in the basin(s) or tank(s) in which the transducer(s) are located, or any other liquid that could possibly have contact with that liquid, through one or more heat exchanger, cooling fins, cooling plate, cooling block, chiller, chilling or cooling apparatus, or other means to remove heat from the liquid. Without limitation, the liquid from the basin(s) or tank(s) in which the transducer(s) are located, can be pumped or moved through one or more cooling fins, chill block, or heat exchanger that is located in the path of the pressurized air that is used to move the generated aerosol out from the apparatus.

An apparatus and method of an embodiment of the present invention, briefly summarized, comprises the remote control of and communication with the apparatus in the present invention. This improvement in the present invention offers many advantages such as, but not limited to, reducing or eliminating the chance of the operator having an accidental exposure to the aerosol from an apparatus that is operated from within the same environment in which the aerosol is applied. The remote control of and communication with the apparatus can be accomplished by means such as, but not limited to, any radio frequency, any light frequency, or directly or indirectly connected wires, or any combination of the said means. Various information, data, and commands can be communicated between the apparatus and a separate means to send and receive information, data, or commands.

An apparatus and method of an embodiment of the present invention, briefly summarized, comprises the apparatus having one or more sensors or the communication with one or more sensors to determine when an effective or sufficient amount of aerosol has been applied to the targeted area and/or surfaces. The sensor(s) consists of a means of varying intensity to project one or more beams of light or a light source, and one or more means to sense the beam(s) of light or light source(s) and indicate its absence or presence. Without limitation, the means to sense the light can vary widely in its sensitivity, and can indicate the presence or absence of the beam or light with a signal such as but not limited to any electrical, fiber optic, or radio frequency signal. It is preferred, without limitation, the sensor consists of a laser and a photoelectric sensor. The means to sense the beam of light communicates with a programmable logic circuit, computer, control mechanism or device, or other electronics that control or operate the apparatus (herein called "PLC"), and the presence or absence of a signal or communication causes or results in the apparatus to take actions or undergo activities, such as but not limited to, ceasing the production of aerosol, ceasing the operation of the blower or fan, or even shutting down. It is the intent of the present invention to generate and deliver aerosol into an area until a sufficient amount or density of aerosol is present which will, disrupt, diminish, or completely prevent, the light, beams of light, or light source, from reaching the means to sense the light. The amount of this applied aerosol can vary depending on the application.

An apparatus and method of an embodiment of the present invention, briefly summarized, comprises the apparatus alerting or communicating with the operator if he/she programs the apparatus or otherwise undertakes an activity that would cause the apparatus to operate and generate aerosol for a specific period of time or to fill a specific volume of space with aerosol, and there is an insufficient amount of liquid available in or available to the apparatus for the chosen operating time or volume of space to fill with aerosol, and communicating to the operator the quantity of liquid or at least the exact minimum quantity of liquid, expressed in units of measurement, that is necessary to add or make available to the apparatus so that it may successfully complete its desired or chosen operational time or run cycle. The actual number of needed fill/refill cartridges can also be communicated to the operator. This embodiment includes without limitation, the apparatus having the ability to sense or detect the liquid level or amount of liquid available to the apparatus, or calculating the total amount of liquid available in one or more reservoir(s) that are, without limitation, inside, attached, or otherwise connected to the apparatus. In addition, the means to alert and communicate information to the operator can include but is not limited to any alphanumeric image shown on a screen, monitor, or human-machine-interface (herein called "HMI"), any graphic-user-interface (GUI) shown on a screen, monitor, or human-machine-interface (HMI), lights, lights with associated text, voice commands or directions, or any audible signal.

An apparatus and method of an embodiment of the present invention, briefly summarized, comprises the apparatus having the ability to prevent the liquid agent from being dispersed, that is available to the apparatus from, without limitation, one or more tanks or reservoirs inside, attached, or connected, to the apparatus, which has exceeded its time or date of expiration, exceeded the time or date in which it can be efficaciously used, or has reached a point of time or date where it has degraded or aged to a point where its use is unacceptable. This embodiment does not encompass refill/fill cartridges. The apparatus in this embodiment possesses a means known in the art for measuring, comparing, calculating, or otherwise keeping track of the time between when the apparatus is initially charged or filled with the liquid agent, or the last purge of the apparatus of undesired or unusable liquid, and when the time has been reached when that liquid agent cannot be used and must be disposed of Once the usable time for the liquid agent has expired, the apparatus can prevent the liquid agent from being dispersed with means including, but is not limited to, using a programmable logic circuit (PLC), control mechanism or device, or other electronics that control or operate the apparatus, to take action(s) that result in stopping the apparatus from generating aerosol. In addition, the apparatus can alert or communicate to the operator that the liquid agent has expired. The means to alert and communicate information to the operator can include but is not limited to any alphanumeric image shown on a screen, monitor, or human-machine-interface (HMI), any graphic-user-interface (GUI) shown on a screen, monitor, or human-machine-interface (HMI), lights, lights with associated text, voice commands or directions, any audible signal.

An apparatus and method of an embodiment of the present invention, briefly summarized, addresses the cooling of components that can heat up inside of the apparatus when it is being operated in areas such as, but not limited to, the area in which the aerosol is being applied. This situation presents engineering challenges because as the apparatus is operated, its components such as, but not limited to, motors or electronics heat up over time. They cannot be cooled by blowing air from outside of the apparatus past or onto them to remove heat if they are in an aerosol filled environment. This air would contain the administered aerosol and be wet. This condition could pose a risk for unwanted chemical reactions with the components depending on the chemical agent that is present in the aerosol. In one part of this embodiment, the electronics that are used to operate or power the transducer(s) are located in a sealed enclosure and cooled with a means that transfers the heat generated from the electronics into a pressurized air stream. It is preferred, without limitation, that this pressurized air stream is the same air stream that is used to move the generated aerosol out of the apparatus. This helps, without limitation, to minimize the total amperage that is utilized or needed for proper or effective function of the apparatus, which is a critical issue with regard to aerosol generators of this complexity. The one or more heat transfer point(s) can be located before or after the fan(s) or blower(s) that create the pressurized air stream. It is also preferred, without limitation, that the heat generated from the electronics is transferred in various ways known in the art to a heat sink that has fins or other cooling enhancements also known in the art, and the heat sink is positioned in the pressurized air stream. In another part of this embodiment, the components other than the electronics that are used to operate or power the transducer(s), including but not limited to motors or electronics, or the atmosphere in their enclosure(s), are also cooled with a means that transfers the heat generated from the components into a pressurized air stream.

An apparatus and method of an embodiment of the present invention, briefly summarized, comprises constructing the apparatus in a way that prevents any exterior parts of the apparatus that are exposed to the aerosol from becoming higher in temperature than the temperature of the atmosphere surrounding the apparatus. Generally speaking, this is important because aerosol particles experience a force in the direction of decreasing temperature. This embodiment is applicable and especially beneficial for applications where the apparatus is operated from within the same environment in which the aerosol is applied, and it is desired or required that all of the exterior surfaces of the apparatus have interaction or contact with the administered aerosol. Without this improvement to the current art, the exterior surfaces of the apparatus could become warmer in temperature than the surrounding atmosphere and repel the aerosol, which would prevent the exterior surfaces from having interaction or contact with the administered aerosol if it is desired or required. The apparatus can be constructed in ways that include, but are not limited to, enclosing the components or parts that can heat up in a sealed enclosure and then placing that enclosure inside of another closure that is sealed or unsealed, or insulating the outer skin of the apparatus.

An apparatus and method of an embodiment of the present invention, briefly summarized, comprises cooling or decreasing the temperature of the objects, the atmosphere in which they reside, or the targeted area for the administration of an aerosol as well any surfaces in that area with refrigerated or chilled air, before the administration of the aerosol to the targeted area or surfaces. This cooling activity or process enables the present invention to utilize the principals of aerosol behavior to increase the efficacy or performance of the process of the present invention. Aerosol particles experience a force in the direction of decreasing temperature. By decreasing the surface temperature of the targeted surfaces, the administered aerosol, and especially an aerosol where the liquid was heated, is drawn towards the cooled surfaces in the targeted area or environment where they interact, interface, or coat the said surfaces with the liquid agent.

An apparatus and method of an embodiment of the present invention, briefly summarized, comprises utilizing a means to administer the mixture of aerosol and gas or air that is ejected or moved out of the apparatus to one or more separate enclosed rooms or areas. This embodiment does not encompass applications where the areas are within the same room, since this is already known in the art. The said means can include but is not limited to connecting one or more tubes to the apparatus, or splitting the flow from these tube(s) so that they can connect, interface, or otherwise empty into the one or more separate enclosed areas. The said means can also have a means to close off the flow of the air/gas and aerosol to one or more of the said tube(s).

An apparatus and method of an embodiment of the present invention, briefly summarized, comprises designing the apparatus so that the electronics that operate or energize the transducer(s) may be able to adjust the frequency or frequency range of the signal that is sent to the transducer(s) multiple times during the lifespan of the transducer(s) so that the transducer(s) are able to be consistently operated at a frequency or within frequency range in which the they are able to have an effective or functional output and/or operate at their maximum performance or aerosol output.

An apparatus and method of an embodiment of the present invention, briefly summarized, comprises connecting, interfacing, or attaching, the aerosol generating apparatus in the present invention to one or more sealed, semi-sealed, or semi-open enclosures or areas. The enclosure(s) has at least five distinguishing features: a) the enclosure(s) is designed to fit over or under various things such as, but not limited to, equipment, objects, or architectural features, etc., b) any walls can have various openings through which any objects may be moved or accessed, c) the enclosure can hang from hooks or other means of attachment that connect to the ceiling or other locations of the area in which the enclosure(s) is located, d) the floors of the enclosure(s) can be constructed with or utilize a surface design or accessory(s) so as to reduce any potential for slip hazards inside the enclosure(s), e) the enclosure can be interfaced with one or means for fire suppression inside or outside of the enclosure.

An apparatus and method of an embodiment of the present invention, briefly summarized, comprises administering an aerosol into an enclosed area where the floor of that enclosed area is removed, and the surface(s) which the walls of the enclosed area interfaces forms the floor of the enclosed area. This interface can be fully sealed, semi sealed, or unsealed. In addition, one or more holes for access to the enclosed area can also be present in the walls of the enclosed area and the holes can be covered in a matter so that they are sealed or semi-sealed closed, or they can be open and unsealed.

An apparatus and method of an embodiment of the present invention, briefly summarized, comprises the incorporation of a means to add or remove one or more sources of weight or mass from various locations on any of the floated parts of the apparatus including, but not limited to, transducer housing(s), the buoyant objects or components, and/or any of the parts that are directly or indirectly connected to the buoyant objects or components, in order to position or maintain the position of each of the transducer(s) and/or their housing(s) at an effective range or depth below the surface of the liquid.

An apparatus and method of an embodiment of the present invention, briefly summarized, comprises without limitation, allowing the buoyant objects or components, and/or any of the parts that are directly or indirectly connected to the buoyant objects or components, as well as the transducers and their housing(s), to freely float in any tank(s) or reservoir(s), where the only anchor point(s) for these parts is the location where the transducer electrical cable(s) and any tubing through which they travel connect either directly or indirectly to the walls of the tank(s) or reservoir(s).

An apparatus and method of an embodiment of the present invention, briefly summarized, comprises locating the inlet for the inbound air opposite from the air outlet of the fog tank or reservoir in which the transducers are located, and directing or moving the inbound air downward into the one or more reservoir(s) in which the transducer(s) are located. This is coupled with locating one or more openings of various sizes and shapes in the roof of the reservoir opposite from the air outlet. This means can reduce the number of larger droplets in the exiting air stream.

An apparatus and method of an embodiment of the present invention, briefly summarized, comprises using one or more means to distribute the inbound air to more than one location in the fog tank(s) or reservoir(s) for purposes including, but not limited to eliminating or diminishing any, uneven airflow, uneven air distribution, turbulent air, or vortices, within the interior air space of the fog tank or reservoir. This means to move the air can also be perforated in various orientations with one or more orifices of various sizes and shapes.

An apparatus and method of an embodiment of the present invention, briefly summarized, comprises reducing the feet per second output of the air exiting from the fog tank(s) or reservoir(s) in which the transducers are located, or otherwise the aerosol generating apparatus, any time near the end of the aerosol generation and delivery cycle. This procedure will promote faster accumulation of the aerosol cloud in the immediate vicinity of the aerosol generating apparatus.

An apparatus and method of an embodiment of the present invention, briefly summarized, comprises equipping the aerosol generating apparatus with one or more sensors to determine when an effective or sufficient amount of aerosol has been applied to the targeted area and/or its targeted surfaces. The sensor(s) may be directly or indirectly attached to the apparatus, or they may be remotely located in any location where the aerosol is applied or administered. The sensor(s) can be positioned in any orientation and communicate with the aerosol generating apparatus in various ways such as, but not limited to, radio, sound, fiber optics, or wires, all in a manner known to those skilled in the art.

An apparatus and method of an embodiment of the present invention, briefly summarized, comprises the operation of a means to dehumidify the area in which the aerosol was administered, any time after the aerosol deployment cycle has finished, or the aerosol generating apparatus was shut down for any reason(s). In one embodiment, a dehumidifier is used as an independent apparatus "not" connected to the aerosol generating apparatus. It may be remotely controlled or programmed by the operator all in a manner all known to those skilled in the art. In another embodiment, an independent dehumidifier is used, but in this particular embodiment it is controlled by, and electrically connected to, the aerosol generating apparatus. The operation of the dehumidifying apparatus is controlled by the software or computer program that operates or controls the aerosol generating apparatus. In an additional embodiment, the means to dehumidify the area in which the aerosol was administered, is enhanced so that it contains one or more filter media to filter the aerosol before, during, or after it passes over the chill coils.

Filtering the deployed aerosol was initially demonstrated by the inventors of the present invention in a public area at the Richland, Wash. Municipal Airport on Oct. 9, 2003. Staff from Washington State University, observed aerosol created by the aerosol generating apparatus described in the present invention, pass through a long tortuous path created with 150 feet of six inch diameter flex ducting, that terminated with various filter media including a HEPA filter and a furnace filter. This same system was used to dehumidify and dry the system of ductwork, after the aerosol was deployed.

In an embodiment, the dehumidifier can also incorporate a means to receive any type of signal from various sources including, but not limited to, the aerosol generating apparatus, or any means for remote control, to not only signal the dehumidifier to dehumidify a targeted area or environment, but also to complete or terminate the dehumidification process by moving, switching, or directing the air flow through a separate filter, such as, but not limited to, an activated carbon filter, or any filter that can remove various gases or vapor(s) from the treated area(s).

An apparatus and method of an embodiment of the present invention, briefly summarized, comprises the construction and use of a means to effectively cover and/or seal the various types of vents that can be found in treated areas including, but not limited to, inbound and outbound air vents for a building HVAC system. These air vents are commonly found in facilities such as, hospitals, schools, clinics, factories, laboratories, and clean rooms. Many times these vents have one or more protruding metal geometries, which makes sealing the vents difficult or impossible with current means. In addition, sealing these vents can be time consuming as well as dangerous because ladders are often necessitated to reach the ceiling mounted vents. The improved means to effectively cover or seal the various types of vents, consists of parts such as but not limited to, a vent cover with sealing material to seal it to the vent or any surrounding or connected areas or materials, any pole which can, without limitation, be adjusted or modified for length, and a means to directly or indirectly connect the pole to the vent cover. In another embodiment, the pole with adjustable length can be constructed so that its one or more ends that are opposite from the vent cover has a means to swivel or articulate so that the base(s) of the pole can articulate at any angle with the floor or any other surface that it contacts. In an additional embodiment, any surfaces of the end(s) of the pole that is compressed or pushed down onto any surface that results in the compression of the vent cover or its seal material can be, without limitation, formed from, coated with, adhered with, or consist of any absorbent material. This material can be, without limitation, treated or saturated with any liquid, at any time, consisting of any anti-pathogen, toxin, fungal, sterilization, disinfection, or sporicidal agent(s) or mixtures thereof (herein collectively "agent(s)"). However, any liquid agent(s) may be used in the present invention for various purposes.

An apparatus and method of an embodiment of the present invention, briefly summarized, comprises modifying a magnetic vent cover so that it has one or more attachment points where a means, such as, but not limited to, rope, cord, thread, wire, cable, twine, tube, or hose, can be attached to the vent cover so that it may be easily removed from a ceiling or ceiling vent eliminating the need to use a ladder. The magnetic vent cover is known to those skilled in the art, and is commonly found in the form of a flexible sheet that is embedded with one or magnets, or coated or laminated with one or more magnetic materials.

An apparatus and method of an embodiment of the present invention, briefly summarized, comprises the utilization of one or more means or holder to prop or hold any items such as, but not limited to, any hose(s), wire(s), cord(s) that are present in the area in which the aerosol is administered or lead to or from the aerosol generator(s), so that they are prevented from touching or contacting any floor or surface on which the holder is placed. The use of the holder(s) helps to reduce or eliminate an incomplete treatment or administration of the aerosol to all of the desired or needed surfaces in a targeted area. The holder(s) can, without limitation, have absorbent material placed between the holder and any surface(s) on which the holder is placed or interfaces. Absorbent material can also, without limitation, be placed between the holder(s) and any object(s) that it holds or supports. The absorbent material may, without limitation, be soaked, saturated, or contacted with any liquid or substance for various purposes before, during, or after the holder is interfaced with an object(s) or placed on a surface(s) or floor.

An apparatus and method of an embodiment of the present invention, briefly summarized, comprises without limitation, the construction and use of a means to isolate or maintain one or more wheels, tracks, or other means for providing movement (herein collectively "wheel(s)"), that are directly or indirectly connected to the aerosol generating apparatus or any aerosol or vapor generating apparatus, so that they are in direct or indirect contact with one or more materials (herein collectively "absorbent material(s)") that can hold, contain, or absorb, without limitation, any liquid, (a) mixture or solids suspended in any liquid, (b) solution, (c) medication, (d) organisms suspended in any liquid, (e) anti-pathogen/toxin/fungal/sporicidal agent(s) or substance(s), (herein collectively "agent(s)"), and prohibit the wheel(s) from directly touching any floor or other surface that it would otherwise come in contact with when it is moved, stopped, or held in a static or semi-static position. Furthermore, the absorbent material in this embodiment is treated with any liquid agent, in various ways known to those skilled in the art, and enables, without limitation, wheel surfaces and surfaces under the wheel to be treated or come in contact with the intended or applied agent(s). The implementation of this means improves the art, and can ensure, without limitation, that any surfaces under or associated with any wheels, tracks, or other supporting structures, are sterilized, sanitized, disinfected, high level disinfected, decontaminated, or otherwise treated with any agent(s) for any intended effect.

An apparatus and method of an embodiment of the present invention, briefly summarized, comprises without limitation, filtering any liquid utilized, processed, or located in the apparatus, in one of more locations, as well as anywhere along the path of any circulating or moving liquid in the apparatus. Furthermore, the aerosol generating device may be designed so that all pipes, filters, pumps, and valves may all be positioned and plumbed so that when the apparatus is drained, all of these components and plumbing may be fully emptied of any liquid.

An apparatus and method of an embodiment of the present invention, briefly summarized, comprises without limitation, the design and/or plumbing of any housing, conduit, or cover, for any blower, fan, or other source of pressurized air, so that it can be drained of any accumulated liquid that may reside inside. The liquid can be drained to any location or ports in the apparatus in a manner known to those skilled in the art.

An apparatus and method of an embodiment of the present invention, briefly summarized, comprises without limitation, the design of a sealed or semi-sealed tank or reservoir in which any aerosol is generated, where one or more pipe(s), tube(s), hose(s), or other enclosed means for transporting the generated aerosol (herein collectively "fog tube(s)") out of the fog tank, protrudes into the fog tank or reservoir from the exterior of the machine, fog tank, or reservoir, and the orifice or open end of each fog tube is located approximately above and/or to the side, of each transducer, or other type of aerosol emanating device. The effectiveness of the fog tubes(s) diminishes at a distance greater than three (3) inches from the surface of the liquid under which the transducer(s) is located, or the source of the generated aerosol. Performance and effectiveness is also impacted by the length of the fog tube(s). A visually noticeable and desired behavior and consistency of the deployed aerosol is observed when these fog tube(s) are utilized. The deployed aerosol appears visually lighter, and it appears to float longer in the air, supporting the theory that this design enhancement enables the apparatus to deploy aerosol droplets with a smaller average size.

An apparatus and method of an embodiment of the present invention, briefly summarized, comprises without limitation, the design of the air outlet of the fog tank or reservoir, so that it has a door or cover that can, without limitation, be effectively sealed closed or opened. This door can be mounted, removed, or attached, all in a manner known to those skilled in the art. This improvement can, without limitation, reduce or eliminate any vapor emanating from the apparatus when it is moved or sitting idle.

An apparatus and method of an embodiment of the present invention, briefly summarized, comprises without limitation, the design of the apparatus and its software so that the programmable logic circuit (PLC) and/or HMI shall keep a record of the time between purges of the liquid agent(s) in the apparatus to ensure that expired agents are not utilized by preventing the operation of the apparatus. The apparatus can, without limitation, be prevented from or cease to function until the apparatus is drained and replenished with fresh liquid after it has expired or reached a point where it loses efficaciousness, or at a minimum prompting the operator though the use of an HMI that the liquid or agent in the apparatus has expired. This can help maintain quality control and quality assurance for the apparatus and its processes in a manner known to those skilled in the art.

An apparatus and method of an embodiment of the present invention, briefly summarized, comprises without limitation, the positioning of one or more sensors to determine when an effective or sufficient amount of aerosol has been applied to the targeted area and/or surfaces, near the ceiling of the area in which the aerosol or agent is deployed. The sensor(s) can be, without limitation, mounted on any pole, tripod, or connected anywhere to any structure or apparatus. Furthermore, the sensor(s) mounted near the ceiling can work in tandem with similar sensor(s) located near approximately ground level. This is important since aerosol behavior can be impacted by various attributes such as, but not limited to, the temperature of the deployed aerosol, and the temperature of the atmosphere in the area in which the aerosol is deployed. This embodiment further improves the art to account for these different operating scenarios.

An apparatus and method of an embodiment of the present invention, briefly summarized, comprises without limitation, the incorporation and use of a device that includes one or more of any housing or area (herein collectively "blade housing(s)") that holds, without limitation, a plurality of any paddle(s), blade(s), or other moving surface(s) (herein collectively "paddle(s)"), that are otherwise moved, rotated, or spun. This device is intended to cause aerosol particles to impact against, without limitation, any of the paddle(s) and/or any of the interior surfaces of the blade housing(s), resulting in the removal of aerosol from the air. It is preferred, without limitation, that one or more paddles attached to a movable shaft are positioned in front of each inlet and outlet for each blade housing(s). It is even more preferred, without limitation, that these paddles are mounted to a common shaft in different angles or orientations to create a more tortuous path for the air/gas and aerosol as it moves through the blade housing(s).

This device can improve the effectiveness and efficiency that is needed to remove various amounts of aerosol from any air or gas when it is necessary or desired to do so. This device can, without limitation, function independently, or be installed within any airflow of any apparatus, such as, but not limited to any aerosol generating apparatus, or any dehumidification apparatus.

An apparatus and method of an embodiment of the present invention, briefly summarized, comprises improvements to the art as taught by U.S. Patent and U.S. application Ser. Nos. 09/855,546 Morneault et al., 10/671,837 Morneault et al., and U.S. Pat. No. 7,045,096 B2 to D'Ottone, which are incorporated herein by reference in its entirety, including any references cited therein. The prior art and the improvements that they teach, as well as these new improvements can, without limitation, be incorporated into the present invention in order to help reduce or eliminate any odors at the end of a treatment cycle from any aerosol or vapor generating apparatus.

In the first part of this embodiment, one or more of any ultraviolet (UV) light sources of any wavelength can be, without limitation, contained in one or more of any enclosure connected to any air or gas stream, and the enclosure(s) can be of any size, shape, or made from any materials. Furthermore, at least one, but preferably all of the walls, ceilings, and floor, of the enclosure are, without limitation, lined with mirrors. The mirrors can help to increase the effectiveness and efficiency of the process of treating the air or gas that is moved through the enclosure, as greater amounts of the emitted light is bounced back or redirected from the mirrored surfaces and into the enclosure space.

In the second part of this embodiment, the processed air or gas can be, without limitation, channeled or moved through one or more tortuous path(s) or complex maze(s) of mirrored channels populated with one or more of any ultraviolet light sources positioned in various areas of the channels. This torturous path or complex maze serves various purposes including, but not limited to, increasing the amount of UV light exposure to the processed air or gas.

In the third part of this embodiment, the flow air or gas can be, without limitation, disrupted with various means, such as but not limited to baffles to cause a turbulent flow of air or gas at various locations within the enclosure in which the UV light sources are located, including, but not limited to, near the source(s) of UV light, or between the sources of UV light.

In the fourth part of this embodiment, the UV light lamps or bulbs, can not only be installed so that they are vertical and offset to the direction of the air or gas flow as taught by Morneault et al, in U.S. application Ser. No. 10/671,837, (paragraphs 19-20) but they may also, without limitation, be located in any angled orientations relative to the direction of the air or gas flow, and they can also be offset to one another as well. This can also help to increase the efficiency of the process as, without limitation, the UV light contacts the air or gas, first as the emitted UV light is redirected by the mirrors, and then again as the air or gas flows closer and then past the UV light source(s). The UV light source(s) can also be installed horizontally and offset, to the direction of the air or gas flow. This can, without limitation, be combined with the mirrored surfaces of the UV light source enclosure previously mentioned above.

In the fifth part of this embodiment, one or more of any UV light source(s) can be, without limitation, positioned anywhere in the air or gas stream of a dehumidifying apparatus. In addition any air or gas, from any area treated by any aerosol or vapor generating apparatus, can be processed or treated with any UV light source and/or any dehumidifier, at any time or during any stage of any treatment cycle, for any period of time, to reduce or eliminate any unwanted or undesired odors. The treated air or gas can, without limitation, contain any concentration of any aerosol or gas that contains any applied agent(s) in any concentration. The dehumidifier and UV light source(s) can, without limitation, be operated at the same time, or at different times.

In the sixth part of this embodiment, any aerosol generator can, without limitation, incorporate the use of one or more of any UV light source(s), and/or any dehumidification technology, anywhere in its design. The dehumidifier and UV light source(s) can, without limitation, be operated at the same time, or at different times. Any air or gas, from any area treated by any aerosol or vapor generating apparatus, with any liquid agent(s) can also be processed or treated with any UV light source and/or any dehumidifier, at any time and for any duration, or during any stage of any treatment cycle to reduce or eliminate any unwanted or undesired odors in the treated area.

In the seventh part of this embodiment, the UV light source(s) can, without limitation, be combined with any aerosol or vapor generating apparatus that emits an aerosol or vapor containing one or more of, in any concentration, hydrogen peroxide, peroxyacetic acid (PAA), or any other aqueous solutions or agent(s) that are acidic, or any combinations thereof. This embodiment can also, without limitation, be combined with the use of a dehumidification technology. According to U.S. Pat. No. 7,045,096 B2 to D'Ottone, a high relative humidity (RH) increases the effectiveness of the invention as water droplets can deliver concentrated solutions of hydroxyl free radicals throughout the area in which it is employed ('096 patent, line 56). This effect can be, without limitation, enhanced in the present invention, as the dense cloud of very small aerosol droplets and vapor that is suspended in the air or gas in the treated area(s), is pulled into the enclosure or area that houses the UV light source(s) and is treated by the UV light and then deployed back into the treated area(s). This may, without limitation, be more enhanced when the aerosol or vapor droplets are less than ten (10) micron in size. This may, without limitation, be even more enhanced when the droplets are generated with ultrasonic processes, which are known to emit large amounts of aerosol droplets less than five (5) microns in diameter.

The use of any dehumidifier that is, without limitation, directly or indirectly connected to one or more UV light source(s) can also add an additional synergistic effect by reducing the relative humidity of the air or gas stream that is presented to the UV light source(s) after one or more passes of the same air or gas from the treated area(s). This may be beneficial as it may, without limitation, be possible to initially inundate the UV light source(s) with limiting conditions such as, but not limited to, too much humidity, or too much aerosol, which could wet the UV light source(s) under certain conditions known to those skilled in the art, and their performance or efficiency of the UV light source(s), such as in eliminating bacteria in the air or gas stream, could be decreased. In addition, according to U.S. Pat. No. 7,045,096 B2 to D'Ottone, to reduce the rate at which the ozone spontaneously decomposes into oxygen it is preferable, if possible, to lower the temperature of the inside of the enclosure ('096 patent, lines 48-51), where the UV light source(s) are located. The UV light source(s) can, without limitation, be located in close proximity to, in the same enclosure as, or effectively near, any chill coil(s), cooling tube(s), or cooling surface(s), associated with any dehumidifier designs known to those skilled in the art, to help reduce the temperature of the air or gas near the UV light source(s) to an effective temperature between 0-70 degree Centigrade, and more preferably near 0-15 degree Centigrade.

According to U.S. application Ser. No. 10/671,837 by Morneault et al, (paragraph 8), "A variation of photocatalytic oxidation, dubbed Advanced Photocatalytic Oxidation (APO) is defined by the complementary utilization of any ozone, hydrogen peroxide, or reactive material surfaces such as titanium dioxide in tandem with UV energy, and is deemed to yield higher oxidation performance, but it comes with the higher costs to operate and bulkiness to the apparatus." This effect can also, without limitation, be enhanced in the present invention, as the aqueous aerosol or vapor, containing any amount of hydrogen peroxide or peroxyacetic acid (PAA), is pulled into the enclosure or area that houses the UV light source(s), from the treated area(s), and is treated by the UV light. The aqueous aerosol or vapor in the present invention is unique because it provides the benefit of inherently providing the needed substance(s) to yield higher oxidation performance without any additional cost, bulkiness, or complexity to the apparatus. This synergism may also, without limitation, be accomplished with any other aerosols consisting of any other agent(s) that can have the same or similar effect.

The combination of one or more of these various technologies such as, but not limited to, any enclosed UV light source(s), dehumidification, and any aqueous aerosol generator or vapor generator, technologies, especially when combined with the use of any aerosol containing any hydrogen peroxide and/or peroxyacetic acid (PAA), can without limitation, create an enhanced synergy that can be used for a quicker process to not only decontaminate, sanitize, disinfect, or sterilize, a targeted area and various surfaces within the targeted area, but to also quickly reduce or eliminate odors or smells in the targeted area that results from these activities. This can, without limitation, be especially important when using agent(s) that contain ingredients such as, but not limited to, peroxyacetic acid (PAA). This synergy, can also, without limitation, be even more enhanced when acidic agent(s) are deployed into a targeted area and treated by the UV light source(s). This can translate to quicker overall cycle or turn over times for a treated space.

An apparatus and method of an embodiment of the present invention, briefly summarized, comprises using any combination of sensors, programmable logic circuit (PLC), computer software, algorithms, or other automated means known to those skilled in the art, to automatically adjust and modify the timing sequences and time periods of various steps of the operational cycle performed by any aerosol generating apparatus or any ancillary equipment, at any time, to account for various attributes such as, but not limited to, the total volume of the treated space, temperature of the air or gas in the treated space, the relative humidity level in the treated space, the dew point in the treated space, and the atmospheric pressure in the treated space. In addition, the operator of the apparatus can, without limitation, manually enter into the apparatus one or more values such as, but not limited to, the volume of the room or treated space, or the desired operational time for any of the various steps of any operation cycle.

An apparatus and method of an embodiment of the present invention, briefly summarized, comprises the aerosol generator conducting or carrying out, without limitation, the following operational steps or sequences. One or more of the following steps can also, without limitation, be bypassed either temporarily or permanently per the desires or needs of the operator. Each step can vary for any length of time for any reason known to those skilled in the art. In addition the time between each step can also vary for any length of time for any reason. The first step is aerosol generation and deployment into the one or more targeted area(s). This step includes, without limitation, the additional step of heating the liquid that will be aerosolized to any preset temperature. The second step provides a dwell time to allow the aerosol and any vapor component to have efficacious contact with any targeted surfaces and/or area(s). The third step is dehumidification. Dehumidification can be achieved in various ways known to those skilled in the art. Dehumidification can also, without limitation, include operating any spinning paddles or blades as mentioned in the present invention, and this can be operated with our without any other dehumidification device(s) or methodologies. The fourth step is deodorization. This is achieved by using one or more UV light source(s) as described in the present invention. The fifth step is filtering the air with one or more of any filter(s) to remove any amount of any unwanted gases or vapor. Furthermore, the aerosol generating apparatus may stop all other steps and enter into or start the dehumidification step at any time for any reason. The dehumidification step may be started for reasons including, but not limited to, the apparatus or operator has detected a fault with any part or operation of the apparatus or any other ancillary equipment, an emergency stop has been actuated, or the operator has chosen to abort or stop the function of the apparatus. Finally, the operator of the apparatus can, without limitation, manually operate the dehumidification step or deodorization step either any time before the aerosol generating apparatus has started to generate and deploy any aerosol, or any time after the entire operational cycle is complete.

An apparatus and method of an embodiment of the present invention, briefly summarized, comprises the construction and use of one or more means to effectively cover, plug, and/or seal any space(s) or gap(s) that can be present near or at the bottom of any door or set of doors when they are closed. These space(s) or gap(s) can also occur even when seals are attached to the bottom of a door(s). These spaces(s) or gap(s) can, without limitation, leak any applied aerosol depending on various variables known in the art, when a room or space is treated.

Various door seals are used in the present art to prevent drafts from emanating from under doors. However, the present invention improves the current art, by designing and constructing an enhanced door seal that it not only effectively seals the door, but it also insures that various surfaces such as, but not limited to, the surfaces of the door and door seal that are in contact with each other, as well as any floor, door frame, or flooring material, have sufficient exposure to any applied agent(s) so they may be sterilized, sanitized, disinfected, high level disinfected, or decontaminated.

An apparatus and method of an embodiment of the present invention, briefly summarized, comprises without limitation, moving or pumping any quantity of air or gas from any area treated with any agent(s), in the form of an aerosol, through a liquid contained in one or more tank(s) or reservoir(s). The liquid is any substance that can, without limitation, neutralize, degrade, or remove, any odors or vapor from the processed air or gas. The liquid can also, without limitation, neutralize or degrade any liquid agent(s) that the aerosol may contain. The air or gas can be, without limitation, recirculated one or more times before it returned to the treated area or any other designated space.

An optimized and miniaturized aerosol generator preferably includes a transducer plate, at least one transducer, a level float, a fluid container, at least one aerosol output member and an air input member. At least one transducer counterbore is formed in the transducer plate to retain the at least one transducer. The fluid container includes a float chamber and an aerosol chamber. An air input hole is formed through a top of the fluid container to receive the air input member. At least one output hole is formed through a top of the fluid container to receive the at least one aerosol output member. A sealing gasket is placed between a top of the transducer plate and a bottom of the fluid container to prevent leakage of aerosol solution in the fluid container. At least one solution passage is preferably cut through a middle rib of the sealing gasket. The level float is contained in the float chamber. The aerosol solution is pumped into the float chamber through a solution input port. The aerosol flows through the solution passage into the aerosol chamber. Air is pumped into the aerosol chamber through the air input member. A transducer driver powers the at least one transducer. The at least one transducer vibrates and produces an aerosol, which exits the at least one aerosol output member.

Numerous other features, aspects and advantages of the present invention will be made apparent from the following detailed description taken together with the drawing figures.

BRIEF DESCRIPTION OF THE DRAWINGS

The methods and devices for the present invention, is best understood with reference to the following detailed description of the invention and the drawings in which:

FIG. 106-B is an optimized and miniaturized aerosol generator, showing more fully showing an air outlet pipes located within an air inlet pipe according to the present invention;

FIG. 117-B is a schematic view of an optimized and miniaturized aerosol generator connected to a shared fan and blower according to the present invention.

FIG. 118 is an exploded perspective view of an aerosol compartment and a liquid level sensor compartment created by a removable barrier of an optimized and miniaturized aerosol generator according to the present invention.

FIG. 119 is a schematic side view of an aerosol deposit sensor positioned in an area targeted for aerosol deposition and/or deployment, showing the deposited aerosol droplets located on an insulator material as well as between, and effectively connecting, various conductors of an aerosol deposit sensor, according to the present invention.

FIG. 120 is a schematic side view of an aerosol deposit sensor positioned in an area targeted for aerosol deposition and/or deployment, showing a liquid film that is formed by the deposited of aerosol droplets on an insulator material as well as between, and effectively connecting, various conductors of an aerosol deposit sensor, according to the present invention.

FIG. 121 is a schematic side view of an aerosol deposit sensor positioned in an area targeted for aerosol deposition and/or deployment, showing various contact surface(s) and insulator material(s), that are located between the various conductors of an aerosol deposit sensor, according to the present invention.

FIG. 122 is a schematic view of an aerosol deposit sensor, showing an insulator material, conductors, wires, and various channels, where the various channels connect with one another of an aerosol deposit sensor, according to the present invention.

FIG. 123 is a schematic view of an aerosol deposit sensor, showing insulator material(s), conductors, wires, and various channels, where the various channels connect with one another, and one or more circuit paths may be established with the various conductors and wires utilized of an aerosol deposit sensor, according to the present invention.

FIG. 124 is a schematic view of an aerosol deposit sensor, showing insulator material(s), conductors, and wires, and one or more circuit paths established with the various conductors and the wires utilized of an aerosol deposit sensor, according to the present invention.

FIG. 125 is a schematic view of an aerosol deposit sensor, showing insulator material(s), conductors, wires, and a conductivity sensor of an aerosol deposit sensor, according to the present invention.

FIG. 126 is a schematic view of an aerosol deposit sensor, showing insulator material(s), conductors, and wires, where at least one circuit path may be established with the various conductors and wires utilized, and the various wires suitably connect with a remote PLC of an aerosol deposit sensor, according to the present invention.

FIG. 127 is a schematic view of an aerosol deposit sensor, showing insulator material(s), conductive path(s), conductors, wires, an amplifier, and conductivity sensor(s) of an aerosol deposit sensor, according to the present invention.

FIG. 128 is a schematic view of an aerosol deposit sensor, showing insulator material(s), conductive paths, conductors, and wires and the various wires are connected to a remote PLC of an aerosol deposit sensor, according to the present invention.

FIG. 129 is a schematic top view of an aerosol deposit sensor, showing insulator material(s), and at least two conductors opposed to one another of an aerosol deposit sensor, according to the present invention.

Figure 130:
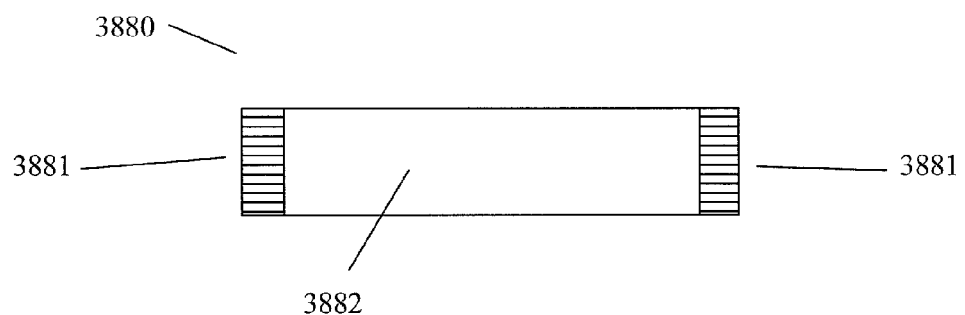

FIG. 130 is a schematic top view of an aerosol deposit sensor, showing the insulator material(s), and at least two conductors that are opposed to one another in a parallel configuration of an aerosol deposit sensor, according to the present invention.

Figure 131:
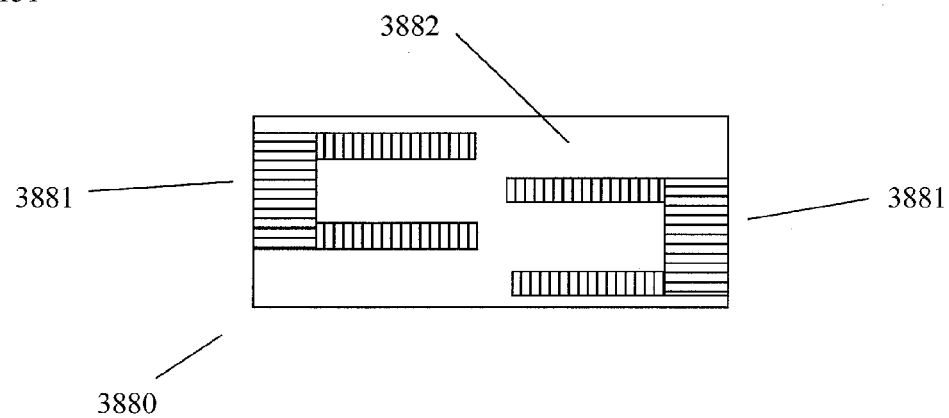

FIG. 131 is a schematic top view of an aerosol deposit sensor, showing insulator material(s), and at least two conductors that are opposed to one another, each including complex geometries and offset positioning of an aerosol deposit sensor, according to the present invention.

Figure 132:
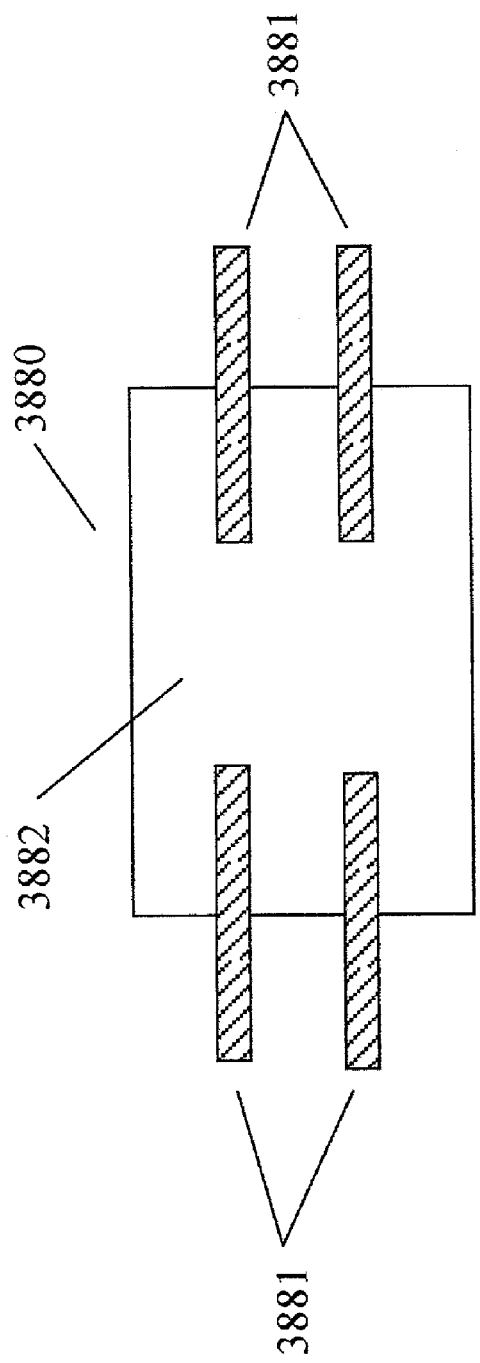

FIG. 132 is a schematic top view of an aerosol deposit sensor, showing insulator material(s), and at least four conductors that are opposed to one another of an aerosol deposit sensor, according to the present invention.

Figure 133:
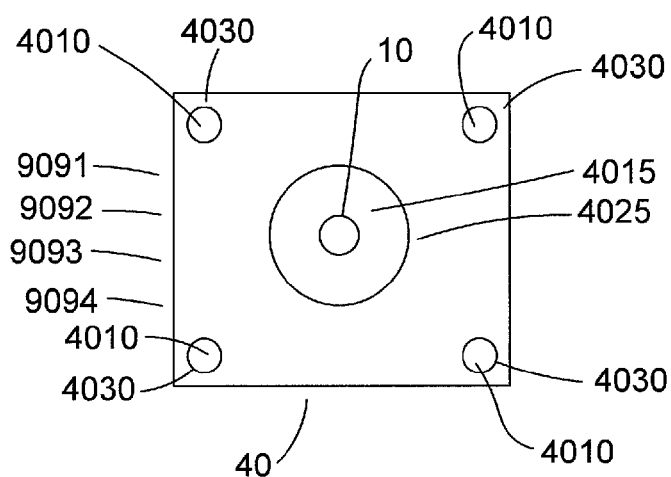

FIG. 133 is a schematic top view of a reservoir including a transducer, where an air outlet pipe is centered above thereof and one or more airflow inlets is located around the transducer, according to the present invention.

Figure 134:
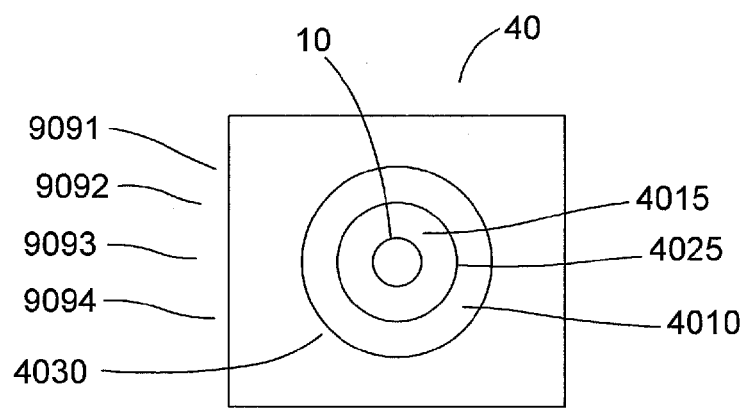

FIG. 134 is a schematic top view of a reservoir including a transducer, where an air outlet pipe and airflow inlet are centered around the transducer, according to the present invention.

Figure 135:
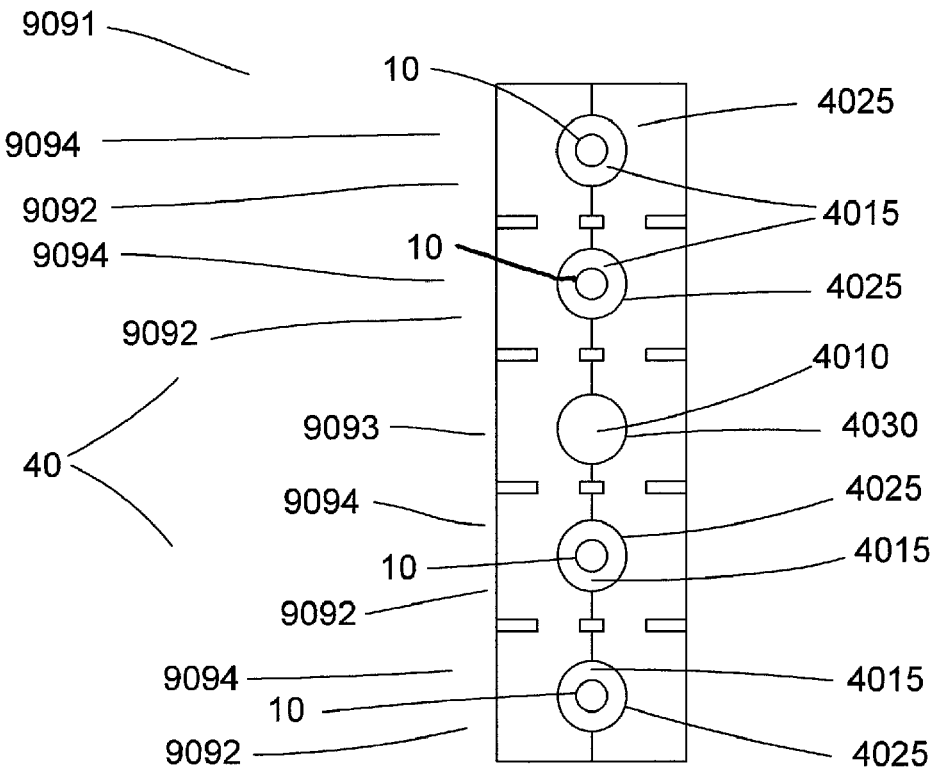

FIG. 135 is a schematic top view of a reservoir including five reservoir building segments, where all of the reservoir building segments include a transducer and at least one airflow outlet, except the center most reservoir building segment, and the center most reservoir building segment includes at least one airflow inlet, according to the present invention.

Figure 136:
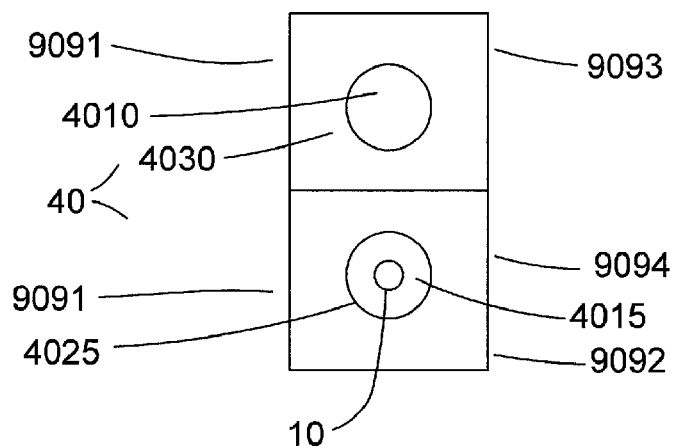

FIG. 136 is a schematic top view of a reservoir including two reservoir building segments, where the first reservoir building segment includes a transducer and at least one airflow outlet and a second reservoir building segment includes at least one airflow inlet, according to the present invention.

Figure 137:
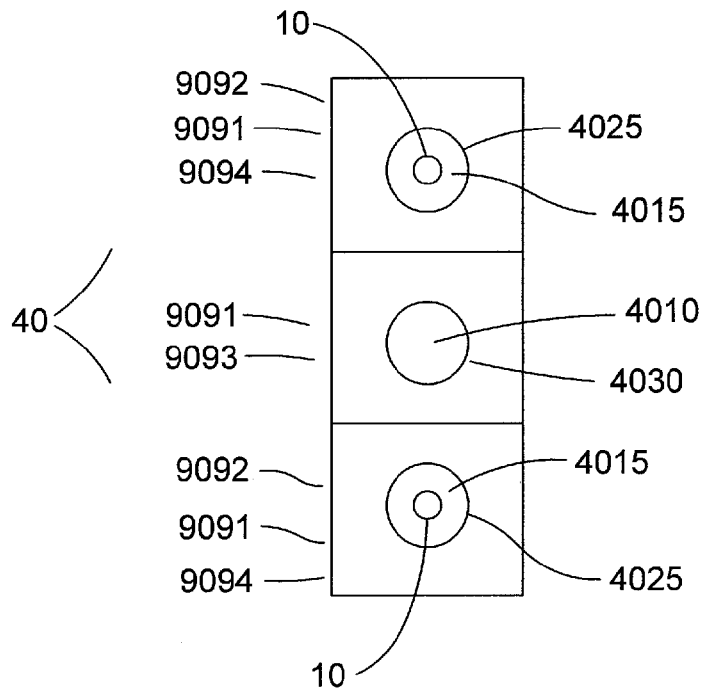

FIG. 137 is a schematic top view of a reservoir including three reservoir building segments, where all of the reservoir building segments include a transducer and at least one airflow outlet, except the center reservoir building segment, and the center reservoir building segment includes at least one airflow inlet, according to the present invention.

Figure 138:
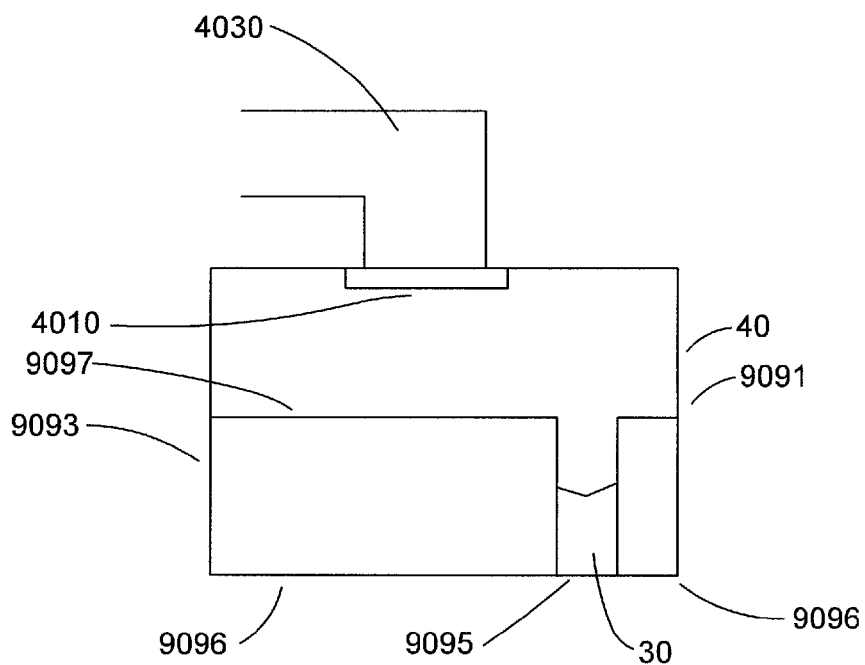

FIG. 138 is a schematic side view of a reservoir including the side view of a reservoir building segment, where the reservoir building segment includes at least one reservoir shelf centered under the airflow inlet, according to the present invention.

DETAILED DESCRIPTION OF THE PREFERRED EMBODIMENTS

Detailed references to the embodiments of the invention, are illustrated in the accompanying drawings that serve as examples. While the invention will be described in conjunction with the embodiments, it is understood that they are not intended to limit the invention to those embodiments. On the contrary, the invention is intended to cover alternatives, modifications, and equivalents, which may be included within the spirit and scope of the invention as defined by the appended claims.

As illustrated in FIGS. 1-5B, an embodiment of the invention includes a method and apparatus for protecting and enhancing the performance of one or more aerosol generating ultrasonic transducer(s) (10) by adhering one or more protective barrier(s) (60) to a transducer(s) (10). Unless otherwise stated, adhering in this specification includes, but is not limited to adhering, coupling, gluing, attaching, cementing, cohering, fastening, pasting, depositing, applying, melting onto or melting together, and chemically, thermally, or physically bonding. According to an embodiment the transducer(s) (10) may be made of a piezoelectric material, preferably a lead-zirconate-titanate (PZT) material, and more preferably lead-zirconate-titanate-four (PZT-4). According to an embodiment, the protective barrier (60) may be any material that has an effective or high chemical resistance to a liquid (30); however any material that has an effective coefficient of conductivity for pressure (energy) could also be used. Further, the protective barrier (60) may be a pane, sheet, or plate, and may be made of materials such as glass, ceramic, or a polymer. According to an embodiment, the thickness of the protective barrier(s) (60) can range from about 0.001 inches to about 0.125 inches, wherein the thickness is not equal to or about n/2 of a wavelength of sound or pressure (energy), preferably in the form of a wave, generated by the transducer(s) (10) at a frequency, wherein n is any integer. In an embodiment, the liquid (30) may be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like. According to an embodiment, the liquid (30) may also be heated to achieve a desired aerosol (200) output.

According to an embodiment, a protective barrier (60) is adhered to the side of the transducer(s) 10 that faces the liquid (30), preferably hydrogen peroxide and peroxyacetic acid in solution, to separate the transducer(s) (10) from the liquid (30). In an embodiment, the protective barrier (60) is quartz glass and is adhered to the transducer(s) (10) by an adhesive (70) whose performance is unaffected and/or not adversely affected by heat. No liquid or other medium, other than the adhesive (70) (and optionally, a conductive coating (50)), is necessary between the transducer(s) (10) and the protective barrier (60) for the transducer(s) (10) to function properly. According to an embodiment, the thickness of the protective barrier (60) ranges from about 0.001 inches to about 0.125 inches, wherein the thickness is not equal to or about n/2 of a wavelength of pressure generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Referring to FIGS. 1 and 2, an embodiment of the invention includes one or more aerosol generating ultrasonic transducer(s) (10) (and their housings (20), if utilized) located below the surface of a solution, fluid, or liquid (herein collectively "liquid") (30) in a reservoir (40). According to an embodiment, the liquid (30) can be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like.

According to a preferred embodiment, a preferred liquid (30) is hydrogen peroxide and peroxyacetic acid in an aqueous solution, which may be effective in sanitization, disinfection, high-level disinfection, and sterilization, and other applications, preferably approximately 2.2% hydrogen peroxide and approximately 0.45% peroxyacetic acid in solution, more preferably approximately 1% hydrogen peroxide and approximately 0.25% peroxyacetic acid in an aqueous solution. Other liquids (30) that may be used include, but are not limited to chlorine dioxide in solution and ozone in solution.

The tank or reservoir (40) may be made of any suitable material that is not affected by the chemical action of the liquid (30). Suitable materials of the reservoir (40) may include PVC, polypropylene, and stainless steel, but other suitable materials may be used. The aerosol (200) generated by operation of the transducer(s) (10) forms above the surface of the liquid (30) in the reservoir (40) and may be transferred from the reservoir (40) to the space to be treated by a blower (180) or other source of pressurized air, as will be described in greater detail below.

The output of the protected transducer(s) (10) may be focused or directed to a point and/or an area near the surface of the liquid (30) to cause a surface disturbance, which results in the formation of an aerosol (200) of the liquid (30) in the reservoir (40). The aerosol (200) is then blown or otherwise moved with pressurized air, into one or more targeted areas or chambers.

According to an embodiment, the transducer(s) (10) may be made of a piezoelectric material, preferably a lead-zirconate-titanate (PZT) material, and more preferably lead-zirconate-titanate-four (PZT-4). With reference to FIG. 2, the transducer(s) (10) is coated with a conductive coating (50) that enables an electrical signal to energize or drive the transducer(s) (10) causing it to emit pressure (energy) of a desired character. When a protective barrier (60) is adhered or otherwise coupled to a transducer(s) (10) it is understood to mean herein that a conductive coating (50) may exist between the protective barrier (60) and the transducer(s) (10). According to an embodiment, some or all of the conductive coating (50) may be removed from the back of the transducer(s) (10) to allow it to receive the radio frequency (RF) output from the amplifier. Moreover, according to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

According to an embodiment, the transducer(s) (10) may be manufactured into various shapes and sizes according to a desired application, preferably circular in shape. Also, according to an embodiment, the transducer(s) (10) may have a diameter of various lengths, preferably about one (1) inch. By using a protective barrier (60) of the present invention, the transducer(s) (10) may have a smaller diameter and smaller surface area than that taught in the prior art without the problems of overheating and/or failing during operation, the need for a cooling mechanism to prevent the transducer(s) (10) from overheating and/or failing, and/or putting space between the protective barrier (60) and the transducer(s) (10) and/or filling that space with various cooling fluids.

Examples of electronic equipment and methods for operating or driving the transducer(s) (10) are discussed in U.S. Pat. Nos. 5,878,355 and 6,102,992 (both of which are incorporated herein by reference in its entirety, including any references cited therein). U.S. Pat. No. 5,925,966, which is incorporated herein by reference in its entirety, including any references cited therein, also provides details of the hardware necessary to operate the transducer(s) (10). Additional electronic equipment, tolerances, and methods for operating or driving the transducer(s) (10) known in the art may also be used. A variable frequency oscillator or signal generator is used to generate a high frequency wave, preferably a sine or square wave.

Figure 1:
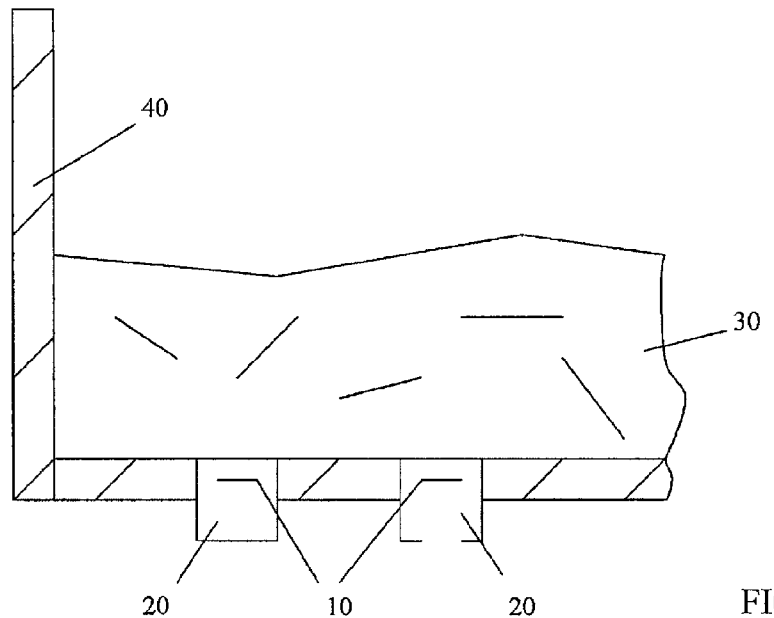
FIG. 1 is a schematic view of an embodiment of a reservoir where one or more aerosol generating ultrasonic transducers are located below the surface of a liquid held within the reservoir.
Figure 2:
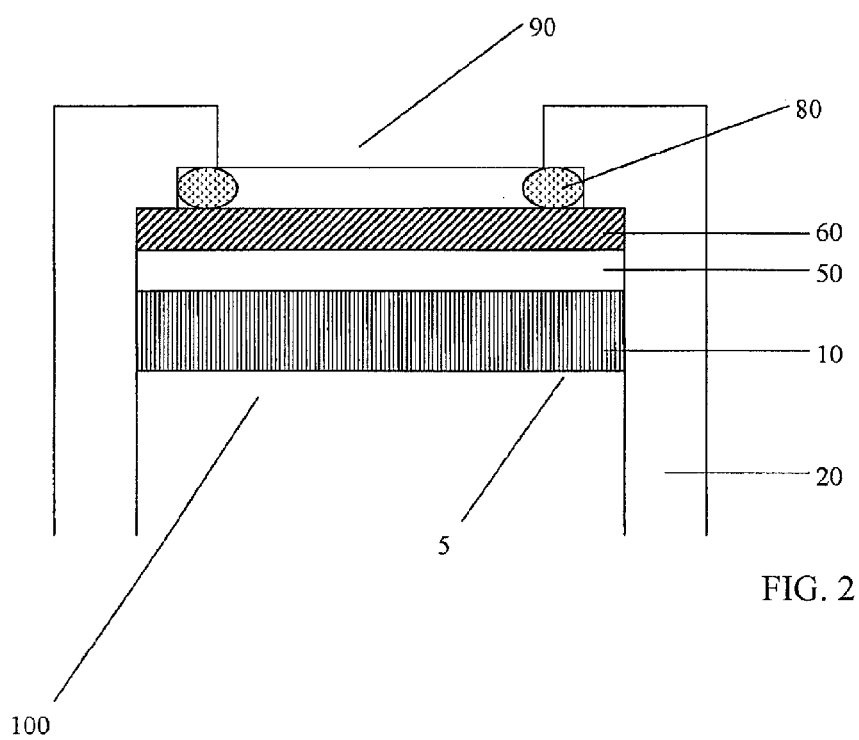
FIG. 2 is a schematic view of an embodiment of a transducer assembly comprising a housing, a transducer, and a protective O-ring interface, wherein a protective barrier is applied to the side of a transducer that faces a liquid.
Figure 3:
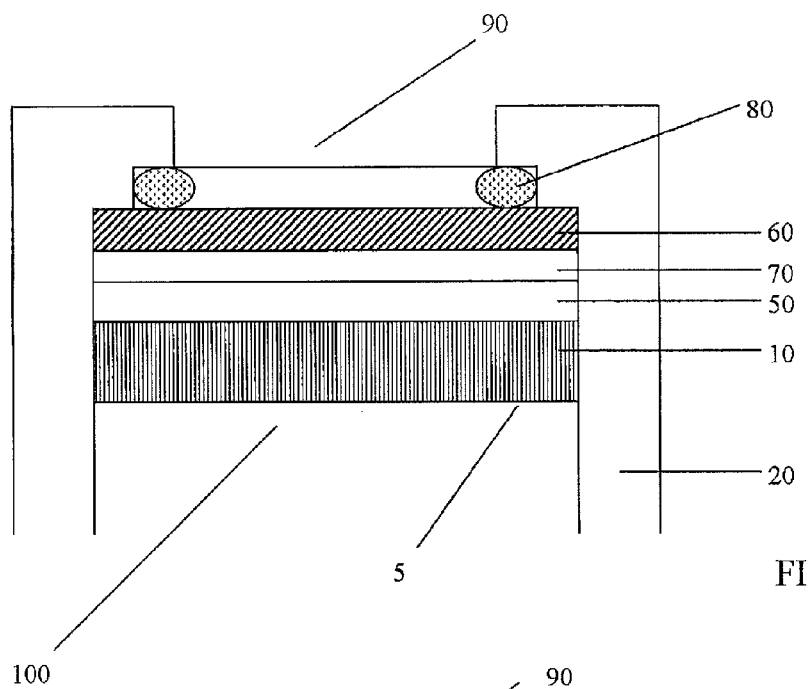
FIG. 3 is a schematic view of an embodiment of a transducer assembly comprising a housing, a transducer coupled with a protective barrier such as a pane, plate, or sheet of glass or other material, and a protective interface above the protective barrier.
Figure 4:
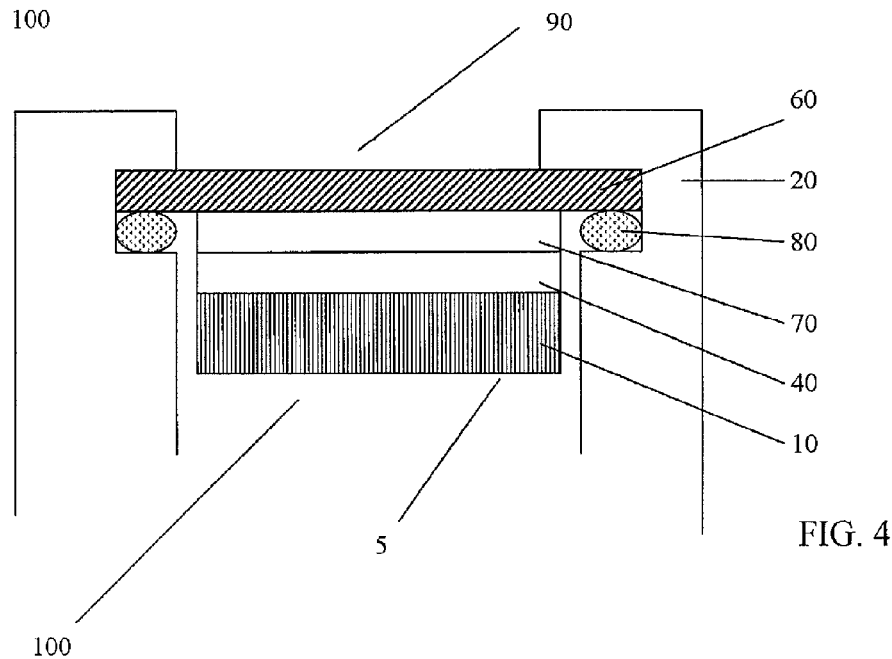
FIG. 4 is a schematic view of an embodiment of a transducer assembly comprising a housing, a transducer coupled with a protective barrier, and a protective seal below the protective barrier.
Figure 5A:
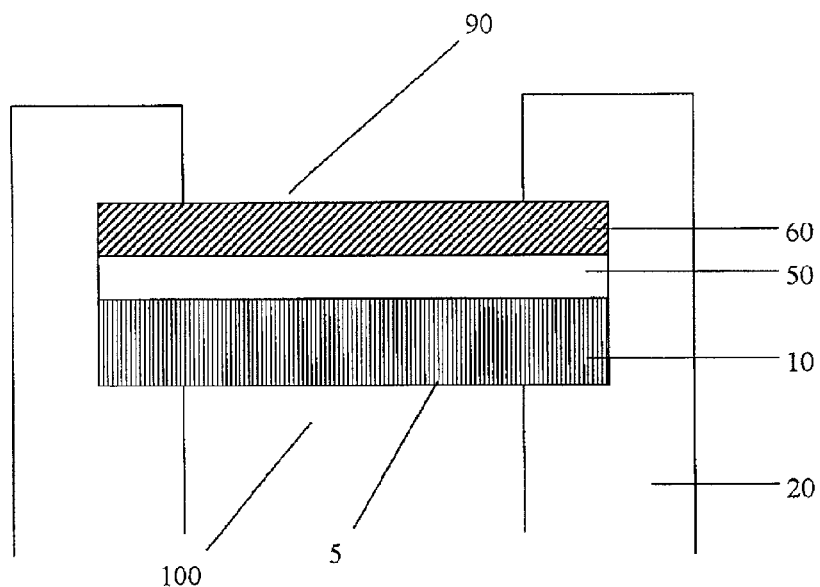
FIG. 5a and b are a schematic views of embodiments of a transducer assembly according to the present invention.
Figure 5B:
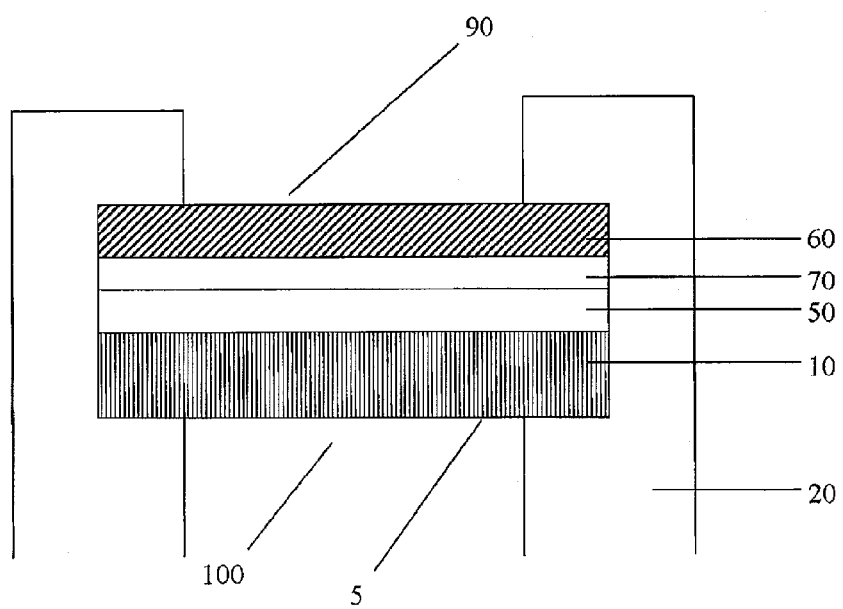
Figure 6:
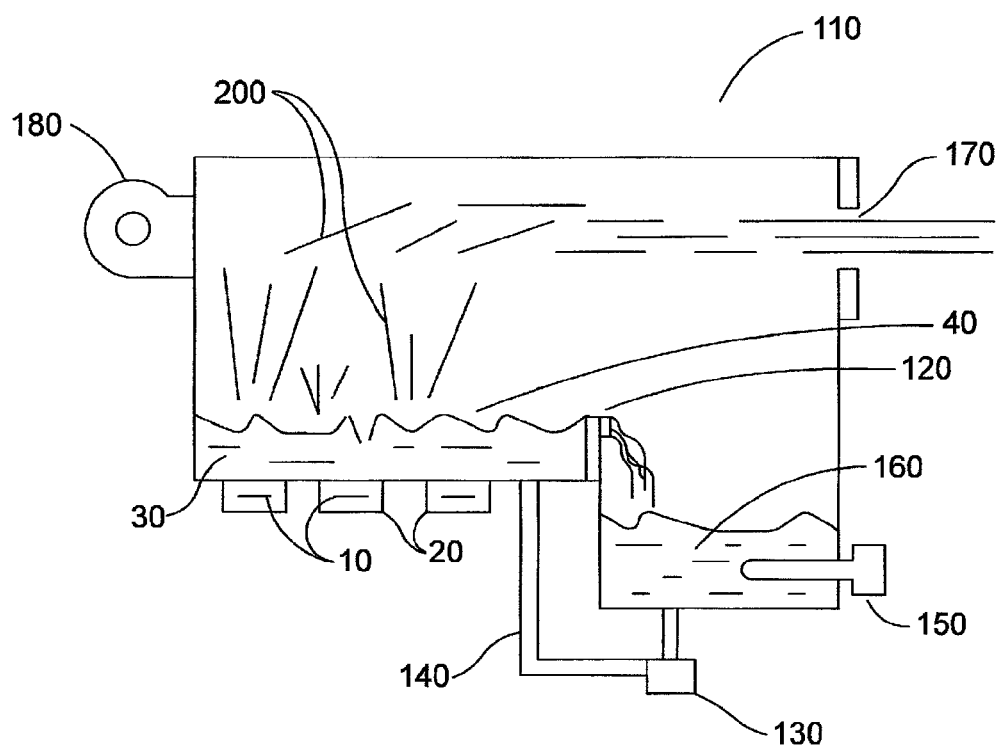
FIG. 6 is a schematic view of an embodiment of an aerosol generator according to the present invention.

According to an embodiment, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s) (10). A direct current (D.C.) offset between −10 v to +10 v can be added to any of the output waveforms.

In one embodiment, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers and the peak to peak voltages could also be increased, preferably about 100 watts of linear power per transducer(s) (10) with about 190 to about 230 Vp-p.

The amplified signal from the amplifier is used to operate or drive one or a plurality of transducer(s) (10), where in an embodiment each transducer(s) (10) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) (10) has a resonant frequency between about 0.025 and about 10.0 MHz or higher. The operating frequency is the frequency at which the transducer(s) (10) is being driven or operated. The resonant frequency is the frequency of the transducer(s) (10), unloaded in air, without being adhered to the protective barrier (60) or other parts of the transducer assembly (100).

Optionally, in one embodiment, the conductive coating (50) may be applied to the entirety of the surface of each transducer(s) (10) so that it can be energized. According to an embodiment, some or all of the conductive coating (50) may be removed from the side (5) that faces away from the liquid (30) in the reservoir (40). The side (5) of the transducer(s) (10) is also the side that receives the radio frequency (RF) output from the amplifier. According to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

The transducer(s) (10) is protected from chemical interaction with a liquid (30), as well as any erosion that could be caused by cavitation, by utilizing a protective barrier (60). In an embodiment, referring to FIG. 2, applying a protective barrier (60) onto the side of the transducer(s) (10) that faces the liquid (30); where the protective barrier (60) is first heated to a pliable or molten state and then applied to the transducer(s) (10). In another embodiment, referring to FIG. 3, adhering, or bonding the surface of one or more transducer(s) (10) that faces the liquid (30) with a protective barrier (60). According to an embodiment, the protective barrier (60) may be a pane or plate, and/or be made of materials such as glass, ceramic, or a polymer. Preferably the protective barrier (60) is a sheet of quartz glass. The material of a protective barrier (60) should have an effective or high chemical resistance to the liquid (30) used. The thickness of a protective barrier (60) is held to specific tolerances. In one embodiment, an adhesive, cement, epoxy, or bonding agent/compound, etc. (herein, collectively "adhesive" (70)), whose performance is unaffected and/or not adversely affected by heat, is utilized for adhering, or otherwise connecting a protective barrier (60) with a transducer(s) (10). An interface and/or connection between a protective barrier (60) and a transducer(s) (10) may also be established by other means known to those skilled in the art. Further, no liquid or other medium, other than the adhesive (70) (and optionally, a conductive coating (50)), is necessary between a transducer(s) (10) and a protective barrier (60) for the transducer(s) (10) to function properly. According to an embodiment, glass was chosen due to attributes including, but not limited to its physical and/or mechanical properties, and ability to withstand the heat generated by a transducer(s) (10) and its general ability to withstand chemical attack. The technique of adhering a transducer to a glass barrier material is taught in U.S. Pat. Nos. 4,109,863; 3,433,461; 3,729,138; and 4,976,259, each of which is incorporated herein by reference in its entirety, including the references cited therein.

According to a preferred embodiment, a transducer(s) (10) and/or a transducer assembly (100) are placed in a chemically resistant housing (20) or other chemically resistant means to hold, holdfast, secure, and/or protect the transducer(s) (10). Certain metals and plastics have demonstrated high chemical resistance to various liquids. A chemical resistant seal or O-ring (herein "O-ring") (80) serves as a seal between the transducer assembly (100), and the liquid (30) in the reservoir (40). According to an embodiment, the O-ring (80) may be made of any chemically resistant material depending upon the composition of the liquid (30) utilized, preferably Viton®. The preferred material has the highest chemical resistance to the liquid used.

In each of the embodiments shown in FIGS. 2-5, the transducer assembly (100), including the transducer(s) (10) and the protective barrier (60), is enclosed or packaged in, assembled with, or coupled with, a housing (20). According to an embodiment, the housing (20) may be a hermitically or non-hermitically sealed or unsealed housing, or other hermitically or non-hermitically sealed or unsealed means to hold, holdfast, secure, and/or protect transducer(s) 10, that is either interfaced with the reservoir (40), or mounted to or in the reservoir (40), or positioned within the reservoir (40), or preferably coupled or attached to the bottom wall of the reservoir (40). According to an embodiment, a sealed interface exists between the protective barrier (60) and/or the housing (20) or means to hold, holdfast, secure, and/or protect the transducer(s) (10).

In one embodiment, see FIGS. 2 and 3, the O-ring seal (80) seals the interface between the protective barrier (60) and the open upper end (90) of the housing (20). In FIG. 4, the O-ring seal (80) is positioned below the protective barrier (60).

In FIGS. 5*a* and 5*b*, the transducer(s) 10 and the protective barrier (60), where the protective barrier (60) is formed and/or assembled by method (1) or (2), is molded, thermoformed, cemented, adhered, or otherwise interfaced with/to the reservoir (40), or the housing (20) or other means to hold, holdfast, secure, and/or protect the transducer(s) (10), which establishes an effective seal between the interfacing materials. Other methods known in the art can also be used to establish this interface. In an another embodiment, the surfaces within the reservoir (40), or other surfaces to which the transducer assembly (100) is coupled, interfaced, connected, or mounted, may also act or function as the housing (20) and FIGS. 2-4 are also applicable in this capacity. Finally, a sealed interface may also exist between the housing (20) or the means to hold, holdfast, secure, and/or protect the transducer(s) (10), and a wall of the reservoir (40), or other surface(s) with which it interfaces.

According to an embodiment, it is preferred that with both protective barrier (60) methods (1) and (2), when glass is used, the glass type used may be of any acid and/or alkaline resistant glass such as, for example, quartz, or Type I (borosilicate glass or Pyrex) or Type II glass as defined by the United States Pharmacopoeia. The protective barrier (60) may be any chemically resistant material. Preferably, the protective barrier (60) has a high chemical resistance to the liquid (30) used.

The selection of a material for either of the two protective barrier (60) assemblies and methods is further determined by the material's impedance properties according to known wave transmission theories. In other words, some materials are better at transmitting pressure (energy) than others. This correlates directly with the efficiency and effectiveness of the transducer(s) (10) and is represented by the maximum amount of aerosol (200) generated by the aerosol generating system (110) per unit of time. In order to maximize the energy transfer into the liquid (30), transmission coefficients for various protective barrier (60) materials are calculated by means of known mathematical formulas pertaining to the various theories of wave transmission known to those of skill in the art. The transmission coefficients are calculated and then compared and the highest transmission coefficient is chosen. Generally, the higher the energy transmitted through the protective barrier (60), the higher the aerosol (200) output. In addition, the higher the frequency, the smaller the particles. According to an embodiment, good wave transmission is achieved through the use of a quartz glass or a borosilicate glass protective barrier (60).

The thickness of the material of the protective barrier (60) is another factor that influences the efficiency and effectiveness of the transducer(s) (10) or the total amount of or size of aerosol (200) the transducer(s) (10) is able to generate. This relates to the fact that operational frequencies will dictate selected glass thicknesses, thinner glass being selected with higher frequencies. These higher operational frequencies produce smaller droplet sizes. In the first protective barrier method, the protective barrier (60) is either formed or applied to the proper thickness. If the thickness of the protective barrier (60) is not within specifications, the protective barrier (60) may be further processed or machined to achieve the proper thickness. The second protective barrier method involves adhering, or otherwise connecting the protective barrier (60), which may be processed or machined to the proper thickness, with the transducer(s) (10). In both methods, the thickness of the protective barrier (60) is controlled to tight tolerances in order to control its transmission coefficient.

It was thought in the prior art that the optimum protective barrier thickness was equal to or about one-half (½) or any multiple of one-half (½) of the wavelength of the transmitted pressure (energy) wave. According to the prior art, at this thickness, the protective barrier material looks acoustically invisible and roughly twenty percent (20%) of the energy emitted from the transducers is being transmitted into the liquid beyond the protective barrier.

However, according to an embodiment of the present invention, it has been found that the transmission of energy through a material can be further optimized or enhanced if the thickness of that material, is between about 0.001 inches and about 0.125 inches, wherein the thickness is not n/2 or about n/2 of the wavelength of a transmitted pressure (energy) that is generated by the transducer(s) (10), wherein n is any integer. Without being limited to the mechanism, it is believed that roughly seventy percent (70%) of the energy emitted from the transducer(s) (10) may be transmitted into the liquid (30) beyond the protective barrier (60) with the thicknesses of the present invention, which is significantly higher than the 20% emitted from the protective barrier (60) with a prior art thickness of one-half (½) or any multiple of ½ the wavelength. Without being limited to the mechanism of action, the material of the protective barrier (60) may actually maximize the transmission coefficient of the pressure (energy) and thus increase the efficiency and effectiveness of the aerosol (200) output of the transducer(s) (10), in addition to protecting the electrode material. A preferred material of the protective barrier (60) may be glass, more preferably quartz glass.

Based upon an embodiment, the invention gave rise to unexpected results, including, but not limited to a significant increase in aerosol (200) output, smaller aerosol (200) particle size, and more energy being transferred to the liquid (30). Additionally, in an embodiment of the apparatus and methods of protecting a transducer(s) (10), a cooling system to prevent the transducer(s) (10) from burning or otherwise failing at various operating frequencies is not necessary. For example, U.S. Pat. No. 4,109,863, which is incorporated herein by reference in its entirety, including the references cited therein, requires a means for circulating a fluid over the transducer and glass for cooling and stabilizing a transducer. However, according to U.S. Pat. No. 4,976,259, this method has the undesirable effect of acoustically dampening the back side of the transducer which reduces the efficiency of the nebulizer system.

When calculating the optimum thickness of the protective barrier (60) in an embodiment of the present invention, the following are considered: (1) operating frequency; (2) the specific natural frequency of the transducer(s) (10); (3) the type of protective barrier (60) material; (4) the thickness of the protective barrier (60); (5) optionally, a suitable adhesive/bonding agent (70); and (6) an acceptable and optimum level of aerosol (200) by sweeping the transducer assembly (100) with a range of frequencies and power to find the desired aerosol (200) output.

According to an embodiment, once the transducer assembly (100) is assembled it can be operated at a range of frequencies. The thickness of the protective barrier (60) may range depending upon the operating frequency of the transducer(s) (10). According to an embodiment, the thickness of the protective barrier (60) ranges from about 0.001 inches to about 0.125 inches, wherein the thickness is not equal to or about n/2 of the wavelength of pressure (energy) generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Empirical testing for hydrogen peroxide and peroxyacetic acid in solution; and water determined that the transducer(s) (10) generated the greatest amount of aerosol (200) when the liquid (30) above them was maintained at a temperature above about 80° F., preferably about 105° F. This is most likely due to the reduction of the surface tension of the liquid (30) as its temperature increases.

According to an embodiment, the liquid (30) may not have to be at least 80° F. for effective performance in certain circumstances where high aerosol output is not necessary, or the liquid already has a low enough surface tension to achieve a desired result. Further, according to an embodiment, any variations in the temperature may be made to optimize the aerosol (200) output based upon the type of liquid (30) used and the results desired by the user.

According to an embodiment, a protective barrier (60) for an aerosol (200) producing transducer(s) (10) has a thickness between about 0.001 inches and 0.125 inches, wherein the thickness is other than equal to or about n/2 of the wavelength of the transmitted pressure (energy) waves that are generated by the transducer(s) (10), wherein n is any integer. Thus, the thickness of the protective barrier (60) as described above permits the transducer(s) (10) to operate effectively to provide a high volume small aerosol (200) particle output, which is preferred, or any other desired output without the need for space between the transducer(s) (10) and the protective barrier (60) or a cooling mechanism.

Most preferably, in accordance with one aspect of the present invention, it has been found that the transmission of energy through a material can also be optimized if the thickness of that material, in this case glass, is about one quarter (¼) or any multiple of one quarter (¼) of the wavelength of the transmitted pressure waves generated at the natural resonant frequency of the transducer. The barrier material in this case will not only look acoustically invisible but will also maximize the transmission coefficient of the pressure waves and thus increase the efficiency and effectiveness of the transducer's aerosol output. The gain in power transmission for a particular transducer can, without limitation, increase from approximately 20%, for a barrier sized at one half (½) of the wavelength of the transmitted pressure waves generated by the transducer at the natural resonant frequency of the transducer, to approximately 71% for a barrier sized at one quarter (¼) of the wavelength of the transmitted pressure waves generated by the same transducer at the natural resonant frequency of that transducer.

Testing was conducted in the laboratory to determine what glass thickness when adhered to the transducer would generate the maximum amount of aerosol. Transducers with an adhered quartz glass thickness of 0.096 inch and 0.125 inch were tested first, and both suffered damage when the heat from operating the transducer burned the epoxy, which is used to adhere the glass to the transducer. This was evidence that a thinner glass material was needed in order to, without limitation, more effectively transmit the energy and heat produced by the transducer into the liquid above the glass. A quartz glass barrier of about ¼ wave length of the propagated pressure wave for a 1.5 Mhz transducer, or 0.036 inch, was manufactured, and its output greatly exceeded the target of 800 milliliters of aerosolized liquid per hour with an average output of 1500 milliliters per hour, as shown in the data in Table 1, along with data illustrating the effectiveness of barriers having other thicknesses with the 1.5 Mhz transducer.

TABLE 1

Experimental Data

| Frequency (Mhz) | Wavelength | Protective Barrier Thickness (inches) | Aerosol Results: Output Observations/Volumes (ml/hr) |
|---|---|---|---|
| 1.87 | 0.311 | 0.036 | 2138 ml per hr |
| 1.85 | 0.308 | 0.036 | 1769 ml per hr |
| 1.86 | 0.309 | 0.036 | 2064 ml per hr |
| 1.89 | 0.314 | 0.036 | 1622 ml per hr |
| 1.89 | 0.314 | 0.036 | 1843 ml per hr |
| 1.88 | 0.313 | 0.036 | 0 ml per hr; transducer burned |
| 1.90 | 0.316 | 0.036 | 1460 ml per hr |
| 1.84 | 0.306 | 0.036 | 1695 ml per hr |
| 1.85 | 0.308 | 0.036 | 1500 ml per hr |
| 1.86 | 0.309 | 0.036 | 1825 ml per hr |
| 1.89 | 0.314 | 0.036 | 1870 ml per hr |

TABLE 1-continued

Experimental Data

| Frequency (Mhz) | Wavelength | Protective Barrier Thickness (inches) | Aerosol Results: Output Observations/Volumes (ml/hr) |
|---|---|---|---|
| 1.90 | 0.316 | 0.036 | 1550 ml per hr |
| 1.90 | 0.316 | 0.036 | 1550 ml per hr |
| 2.11 | 0.283 | 0.029 | Est. <500 ml per hr |
| 1.83 | 0.338 | 0.040 | 1971 ml per hr |
| 1.81 | 0.334 | 0.040 | 2138 ml per hr |
| 1.83 | 0.338 | 0.040 | 2005 ml per hr |
| 1.68 | 0.388 | 0.050 | 1769 ml per hr |
| 1.91 | 0.847 | 0.096 | 0 ml per hr; transducer burned |
| 1.58 | 0.912 | 0.125 | 0 ml per hr |
| 1.59 | 0.918 | 0.125 | 0 ml per hr |
| 1.88 | 0.313 | 0.036 | 0 ml per hr; transducer burned |
| 1.90 | 0.316 | 0.036 | 1900 ml per hr; amplifier issue - ran hot |
| 1.80 | 0.299 | 0.036 | 0 ml per hr; transducer burned |
| 1.82 | 0.303 | 0.036 | 0 ml per hr; lens may have been cracked |
| 1.71 | 0.355 | 0.045 | 0 ml per hr |
| 1.74 | 0.362 | 0.045 | 0 ml per hr |

As a result of this testing, it has recently been determined that the transducer incorporating the barrier provides the best results when the thickness is calculated as a multiple of about n/4 of the wavelength of the natural resonant frequency (unloaded in air) of the transducer. The transducer including the barrier having this calculated thickness must also be operated at an operational frequency that is greater than the natural resonant frequency of the transducer by between about 4% and about 60% of the natural resonant frequency of the transducer. This calculation of the barrier thickness and the resulting operational frequency to optimize the aerosol generation by the transducer can be utilized for transducers having natural resonant frequencies in the range of 0.5 Mhz to 8.0 Mhz.

Further empirical testing in the laboratory for a particular transducer also determined that the actual effective range of glass thickness for aerosol output of a transducer having a natural resonant frequency of 1.5 Mhz was minus 0.010 inches and plus 0.024 inches, from 0.036 inches, or the calculated barrier thickness of one quarter (¼) of the wavelength of the transmitted pressure waves from the 1.5 Mhz transducer. It was also found that this asymmetrical range is, without limitation, strongly correlated with the admittance vs. frequency sweeps for transducers with glass barriers of this type. These sweeps include, but are not limited to, showing two distinct and separate peaks or amplitudes that both exhibit a curve that has a pronounced or sharp drop to the right of each amplitude. Thus, the operation and effectiveness of the aerosol generator including the transducer (10) including the barrier (60) can also be increased by utilizing a barrier having a thickness in this range above and below the calculated barrier thickness at approximately n/4 for the wavelength of the transducer at its natural resonant frequency.

Also, empirical testing determined that the transducers generated the greatest amount of aerosol when the liquid above them was maintained at a temperature above 80 degree Fahrenheit. This is most likely due to the reduction of the liquid's surface tension as its temperature increases.

Therefore, in the present invention the optimum glass barrier thickness for the aerosol producing transducer, is approximately one quarter (¼) or approximately any multiple of one quarter (e.g., 0.5/4, 1/4, 1.5/4, 2.5/4, 3/4, 3.5/4, 5/4 . . . or n/4 where n=about any odd number, or the result of any mathematical operation) but not equal or about equal to any multiple of n/2 of the wavelength of the transmitted pressure waves from the transducer as calculated by the formula:

$$\lambda(\text{wavelength}) = \frac{c(\text{speed of sound in the selected material})}{f(\text{natural resonance frequency})}$$

when the transducer is operated at an operation frequency of up to 60% above, preferably between 4% and 60% above, more preferably between 9% and 50% above or about 10% to about 45% above, and most preferably between about 18% and 27% above the natural resonant frequency of the transducer.

Additionally, the transducer can be constructed with a barrier within a range of minus 0.010 inches (−0.010 inches) and plus 0.024 inches (+0.024 inches) from the calculated optimum barrier thickness, where the n/4 multiple of the wavelength is not equal to or approximately equal to any multiple of one half (½) of a wavelength. These methods in their entirety can be used with any transducer with a natural resonant frequency, unloaded in air, between 0.5 MHz to 8.0 MHz.

Specifically, maximum aerosol output is achieved with a glass thickness within the range of minus (−) 0.010 inches and plus (+) 0.024 inches, from the optimum thickness calculated as the multiple of n/4 of the wavelength of the transmitted pressure waves, with this multiple more preferably being a multiple where n=an odd number (i.e., 1, 3, 5, 7, 9, etc.) and where n/4 is not equal to any multiple of n/2. More preferably, n is from 1 to 9. In a particularly preferred embodiment, the calculated glass barrier thickness is 0.036 inches (0.036−0.010 to 0.036+0.024 inches).

In a preferred embodiment, the transducers utilized with the barriers having these thicknesses have a natural resonant frequency, unloaded in air, between 1.25 to 1.65 MHz and their operating frequency range in liquid is between 1.71 to 2.00 MHz.

In one embodiment, the liquid depth above the transducers can range from 0.5 to 5.0 inches. In addition the liquid in the tank above the transducers should be maintained at a temperature of 80 degree Fahrenheit or greater in order to maximize the amount of aerosol that is generated.

When utilizing a barrier (60) having a thickness in this calculated range, the transmission of energy from the transducer (10) through the barrier (60) to the liquid (30) is increased from around 20% to around 70%. This increased transmission percentage greatly reduces the degradation of the bond formed by the adhesive (70) binding the barrier (60) to the transducer (10), allowing the adhesive (70) to hold the barrier (60) in place during operation of the transducer (10).

According to an embodiment, many depths of the liquid (30) above the transducer(s) (10) may be used; preferably the depth of the liquid (30) above the transducer(s) (10) is from about 0.25 inches to about 8.0 inches, and more preferably a depth of about 1.25 inches. However, it may be possible to operate the invention at levels below 0.25 inches if lower power and/or frequencies are used. Moreover, according to an embodiment, the liquid (30) may be maintained at any temperature necessary to achieve the desired results based upon the preferences of the user or the type of liquid used. Preferably any liquid (30), such as peroxyacetic acid and hydrogen peroxide, in the reservoir (40) may be maintained at a temperature of about 80° F. or greater in order to maximize the amount of aerosol (200) that is generated. However, the temperature of the liquid (30) may vary depending upon such parameters as the desired aerosol (200) output, the type of liquid (30) used, and the surface tension of the liquid (30).

Referring to FIGS. 6-15, there are shown embodiments of an aerosol generator (110) according to the present invention. The reservoir (40) contains a volume of liquid (30), the level of which is controlled by a dam (or weir gate) (120) operatively associated with a supply pump (130) and a supply line (140) to maintain the level of the liquid (30) at a preferred level above the transducer(s) (10) mounted on the bottom wall of the reservoir (40). The transducer(s) (10) may be individually mounted in separate housings (20), as shown in one of the embodiments of FIGS. 2-4, or they may all be coupled to a common protective barrier (60) wall and appropriately sealed from contact with the liquid (30). It has been found that efficiency of aerosol (200) generation is enhanced by heating the liquid (30) to at least 20° F. above ambient, preferably to at least about 80° F.; however the temperature may vary depending upon the type of liquid (30) used. A heater element (150) is coupled with a liquid supply sump (160) to control the temperature of the liquid (30). The aerosolized liquid (200) is delivered to the space to be treated via an exit orifice (170) of the aerosol generator (110) to which suitable piping (not shown) may be attached for delivery. A blower (180), fan, or other source of pressurized air generates the air flow necessary to deliver the aerosol (200), all in a manner well-known in the art.

According to an embodiment, the transducer(s) (10) and the protective barrier (60) may be sized to provide an optimized resonant frequency that is operative when driven or operated at an operating frequency in the range of about 0.5 MHz to about 2.5 MHz. This large range is due to the appearance of two separate operating ranges that are apparently unique to the transducer assembly (100). For example, using a transducer(s) (10) having a resonant frequency of about 1.40 MHz to about 1.48 MHz with a protective barrier (60) thickness of about 0.036 inches, driven at an operating frequency ranging from about 1.78 MHz to about 1.98 MHz will most commonly show a maximized aerosol (200) output of at least about 1,000 ml per hour of the liquid (30). A second effective operating frequency with lower output is noted at about 1.2 MHz. According to an embodiment, for certain applications where the volume of the space to be treated is small, an output of at least 1,000 ml/hr may not be necessary. In such a situation, the transducer(s) (10) may be operated or driven with various combinations of power or volts peak to peak, and frequencies that result in the generation of lower aerosolized (200) liquid output. For example, in the treatment of a space the size of about a small glove box or the like, an output of 10 ml/hr or less may be adequate.

The apparatus and methods of the present invention may yield aerosol (200) droplets of various sizes. According to an embodiment, they may yield aerosol (200) droplets with a defined size distribution of mostly less than about one (1) microns in diameter, without being limited to a mechanism it is believed this allows the droplets to behave more like a gas with respect to Brownian movement and diffusion. The size of the aerosol (200) droplets may be adjusted upward or downward according to the desired results. The small aerosol (200) droplet size enables the drops to penetrate small cracks and crevices, and apply very thin films on surfaces. In addition, the aerosol (200) may effectively reach and disinfect areas of contamination and areas of otherwise limited accessibility. Any means to create an aerosol (200) with droplets less than about 10 microns in size could be used in the present invention. Larger particles will by their nature cause less penetration and decrease the effectiveness for many but not all possible application. Thus, the present invention may generate predominantly submicron size droplets or sizes may be controlled for a desired result. According to an embodiment, the average particle size may range from less than one micron to about 10 microns, preferably less than about 5 microns, more preferably less than one micron, and even more preferably about 0.68 microns.

According to an embodiment, multiple transducer(s) (10) are typically used to provide an output volume of aerosolized liquid (200) sufficient to rapidly treat a large enclosed space. In such a case, the transducer(s) (10) may be mounted individually, or a plurality of transducer(s) (10) may be coupled to a single protective barrier (60), with one or more of the protective barrier (60) being coupled, mounted on or in a reservoir (40), or positioned within a reservoir (40) with an appropriate coupling device. Multiple transducer(s) (10) may be coupled to a single protective barrier (60) at varying distances apart, preferably between at least about 0.25 inches apart, more preferably about 0.75 inches apart.

Figure 7:
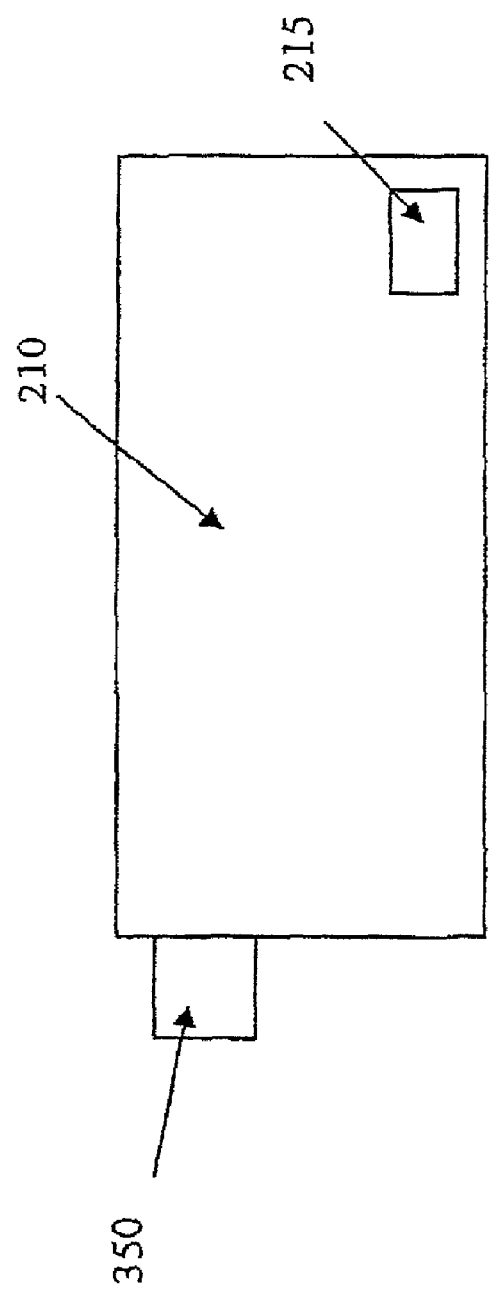
FIG. 7 is a schematic view of an embodiment of a targeted area(s) for administering the aerosol from the aerosol generating apparatus.
Figure 8:
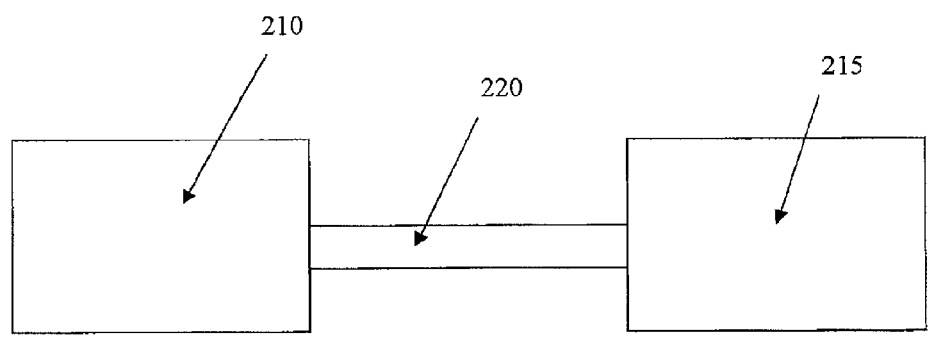
FIG. 8 is a schematic view of an embodiment of an aerosol generating apparatus connected to a targeted area(s) with a pipe through which aerosol can be administered.
Figure 9:
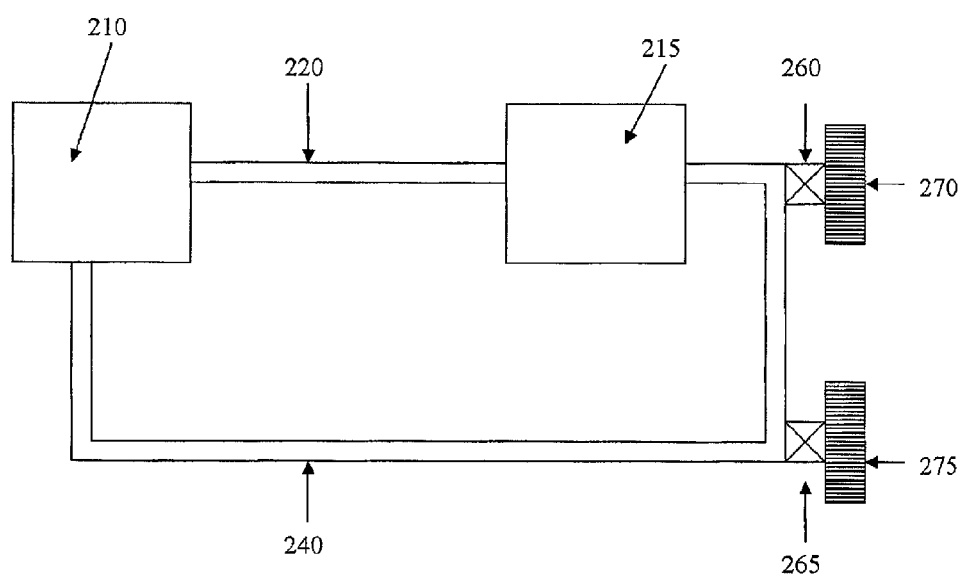
FIG. 9 is a schematic view of an embodiment of an aerosol generating apparatus connected to the targeted area(s) in a closed loop system.

The present invention includes apparatuses and methods related to the generation and delivery or application of an aerosol (200) of liquid (30) that is created with ultrasound or piezoelectric transducers (10), for a wide range of uses including but not limited to: (a) the sanitization, disinfection, high-level disinfection, or sterilization of one or more areas and the surfaces in those areas, (b) the delivery of other types of liquid (30) in the form of an aerosol (200) for various purposes, such as, but not limited to, the application of pesticides, moisture, medication, particles, or nano sized or smaller machines, to one or more areas and surfaces within those area(s). The attributes of the area to which the aerosol (200) is delivered or applied can vary and can include, but is not limited to: spaces that are open, enclosed, semi-enclosed, unsealed, sealed, or partially sealed. It is preferred, without limitation, that the area in which the aerosol is administered in the present invention is enclosed and effectively sealed to prevent the leakage of the aerosol from the enclosed area. Referring initially to FIGS. 7-9, the apparatus (215) can be operated either outside, partially inside and partially outside, or within the area in which the aerosol is deployed or administered.

Preferably and without limitation, an aerosol (200) of a liquid is first generated and/or administered in or into the intended or targeted area (210). This area can also, without limitation, contain one or more objects and surfaces. The aerosol (200) may have various mass concentrations, which is the mass of particulate matter in a unit volume of aerosol. The number concentration of the aerosol (200) may also vary. The number concentration is the number of particles per unit volume of aerosol. It is preferred without limitation, that the aerosol (200) has a higher rather than lower mass concentration of droplets. It is preferred without limitation, that the aerosol (200) has a higher rather than lower number concentration of droplets. The aerosol (200) droplets may be of various sizes. The aerosol may be created from any liquid containing one or more chemical(s) of any kind, or a combination of liquids each containing one or more of any kind of chemical(s).

According to an embodiment, it is preferred, without limitation, that the aerosol (200) is a ten micron to submicron size droplet. The fog or aerosol can, without limitation, consist substantially of submicron aerosolized droplets. The fog or aerosol can, without limitation, have characteristics that include but are not limited to (1) a faster anti-pathogen, toxin, fungal, sterilization, disinfection, or sporicidal effect than the non-aerosolized liquid; (2) the ability to penetrate and disinfect, high-level disinfect or sterilize, areas and surfaces where aerosols comprised of droplets greater than two microns may not work; (3) resists coalescence and condensation typical of larger size droplets; and/or (4) dense packing of small particles provides an unprecedented droplet surface area per volume of gas.

The apparatus and methods described in the present invention can pertain to any aerosol generator or aerosol generator that uses ultrasound or piezoelectric transducers (10). They may also pertain to an aerosol producing apparatus as described in the present invention, including the specifics of the present invention hereto mentioned. This apparatus is further described with the attributes discussed below. Referring to FIGS. 11-13, 16-32 and 35-36, which shows the preferred apparatus (215) in the present invention, the apparatus (215) generates aerosol (200) by operating one or more piezoelectric transducers (10), in parallel or series. One or more amplifiers (230) may be used. It is preferred, without limitation, that the transducer(s) (10) receive signal or power from at least one amplifier(s) (230), and that multiple transducers are operated in parallel. One or more transducers (10) are located under the surface of the liquid (30) in one or more reservoirs, chambers, basins, or tanks (40) (herein referred to as reservoir(s)) at an effective depth and orientation. The reservoir(s) (40) may be made from any material that is compatible, and suitable for use with the liquid (30). The aerosol (200) generated by operation of the transducer(s) (10) forms above the surface of the liquid (30) in the reservoir(s) (40) and may be transferred from the reservoir(s) (40) to one or more targeted area(s) or chamber(s) by one or more fan(s) or blower(s) or other source of pressurized air or gas (herein referred to as blower(s)) (180).

The air and aerosol (200) can, without limitation, flow from the aerosol generator (110) to the one or more targeted area(s) (210) through one or more pipe(s) (220). It is preferred, without limitation, that only one reservoir (40) in which the transducer(s) are located is utilized in the apparatus (215) of the present invention. The reservoir(s) (40) can be, without limitation, unenclosed, semi-enclosed, or enclosed. It is preferred, without limitation that an enclosed reservoir(s) is utilized, and is built in a manner known in the art so that air from a fan or blower can flow through it and carry the generated aerosol out of the reservoir and away from the apparatus (215).

The air and aerosol can flow through a zig-zag path or be directed around one or more baffle plates (250), positioned anywhere in the path of the air/aerosol as it moves from the reservoirs in which the transducers are located to the exterior of the apparatus (215). The use of the aforementioned baffle plate(s) is taught at (col. 4, line 18-22) of U.S. Pat. No. 4,366,125 (Kodera et al., 1980), which is incorporated herein by reference in its entirety, including any references cited therein.

If needed or desired, the apparatus (215) in the present invention can be connected in a closed loop or system as shown in FIG. 9, to the targeted area(s) or chamber(s) (210), as taught at (pg. 3 col. 23-34) of G.B. Patent No. 1,128,245, (Rosdahl et al., 1968), which is incorporated herein by reference in its entirety, including any references cited therein. The air and aerosol (200) discharged from the apparatus (215) in the present invention, can be delivered with one or more pipe(s) or conduit(s) (220). The air and aerosol (200) may also be recirculated through one or more return pipe(s) or conduit(s) (240) from the targeted area(s) or chamber(s) (210), back to the air/gas intake(s) (255) for the fan(s) or blower(s) (180). Throughout the present invention, the terms "pipe", "pipes", or "piping" includes pipes, ducts, conduits, tunnels, and the like. In addition, the aforementioned closed loop or system can have, without limitation, one or more air/gas valve(s) (260) that can allow non-filtered or filtered inbound air/gas into the said closed loop or system, as well as one or more air/gas valve(s) (265) that can allow non-filtered or filtered inbound air/gas out of the said closed loop or system. The air/gas that is supplied via the inbound air/gas valve(s) (260) can be supplied, without limitation, from the atmosphere surrounding the apparatus (215) and the air/gas that passes through the outbound air/gas valve can be, without limitation, vented into the atmosphere surrounding the apparatus (215). The filter(s) (265) can be or consist of any filter design, material, or other effective means for the intended application. The filter or its application can include, without limitation, what is taught in U.S. Pat. No. 4,512,951 (Koubek et al., 1983), and incorporated herein by reference in its entirety, including any references cited therein. The said air/gas valves (260) or (265) can, without limitation, be electronically or electrically opened and closed in a manner known to those skilled in the art, and can be positioned or interfaced in numerous places in the closed loop or system. The outbound air or aerosol can, without limitation, be filtered with one or more filters (270) to prevent any employees or operators from being exposed to any vented aerosol, and to comply with any worker safety or environmental safety guidelines or regulations.

The liquid capacity of the reservoir(s) (40) in which the transducer(s) (10) are located can vary, but the liquid level is at least at a suitable depth or level so that the transducer(s) (10) can effectively and safely operate. The reservoir(s) (40) in which the transducer(s) (10) are located is connected to one or more tanks(s) (280) that are connected and feed liquid to the reservoir(s) (40). The tank(s) (280) that feeds or supplies the liquid (30) can be of any size, geometry, shape, and capacity, and may be made from any material that is compatible, and suitable for use with the liquid (30). The tank(s) (280) may be non-ventilated, or ventilated in one or more places in a way know to those skilled in the art, and the means to ventilate the tank(s) (280) can incorporate a suitable filter. The filter(s) are any suitable filter for the intended application, and are known to those skilled in the art. It is preferred, without limitation, that the apparatus (215) in the present invention has only one tank (280) that feeds or supplies liquid to the reservoir (40) in which the transducer(s) (10) are located. However, a means known to those skilled in the art can be provided so that additional tanks (280) can be attached to or interfaced with the apparatus (215) and feed liquid to either the main feed or supply tank (280) or the reservoir(s) (40) in which the transducers (10) are located.

The one or more tank(s) (280), that feeds or supplies the liquid (30) to the reservoir(s) (40) in which the transducer(s) (10) are located, can be filled in various ways, including, but not limited to, directly pouring a liquid that is either mixed or unmixed into one or more feed interface(s) (285) or pipe(s) (295) that are connected to the said tank(s) (280). Without limitation, the feed interface(s) (285) or pipe(s) (295) orifices can have: (a) a funnel or be shaped like a funnel to make pouring the liquid (30) into the feed interface(s) (285) or pipe(s) orifices (295) easier, (b) a tray or bowl located under or around the outer edges of the feed interface(s) (285) or pipe(s) orifices (295) to catch any spilled liquid (30) in a manner known in the art. Without limitation, the apparatus (215) in the present invention can also be designed and constructed, in a manner that is known to those skilled in the art, so that it can interface with one or more disposable or reusable containers or cartridges (herein referred to as "cartridge", "cartridges", or "cartridge(s)") (290) used to supply, fill, or refill the apparatus (215) with liquid (30). Without being limited, the cartridges (290) and apparatus (215) can be designed in a manner known in the art, so that only unique, special, or proprietary cartridges (290) may be used. The means to interface the cartridge(s)s with the apparatus (215) so that the liquid is effectively and safely transferred from the cartridges (290) into the said reservoir(s) (40), is known to those skilled in the art.

The reservoir(s) (40) in which the transducer(s) (10) are located can also have one or more valves (300) that can, without limitation, control the flow of liquid (30) from the tank(s) (280) that feed or supply the said reservoir(s) (40). Without limitation, the valve(s) (300) can be connected to one or more sensor(s) (305) or PLC(s) (315) which are known to those skilled in the art, that can cause the valve(s) (300) to close or open and allow liquid (30) to flow into the reservoir(s) (40) in which the transducer(s) (10) are located when the liquid (30) level or depth in the reservoir(s) (40) reaches a specified level. The depth or level of the liquid (30) causing the valve (300) to open can vary. The sensor (305) can include, but is not limited to a float switch. The valve (300) can include, but is not limited to, a solenoid valve. However, it is preferred in the present invention that at least one float-valve is used, which consists of a valve (300) that is mechanically or electrically opened or closed by the movement of a float which acts as the sensor (305).

The reservoir(s) (40) in which the transducer(s) (10) are located, can have one or more float switch(s) or other sensor(s) (305) that can cause the apparatus (215), the PLC, (315), HMI (320), or any other parts or components, to enter a fault/error mode or completely shut down if the depth of the liquid (30) exceeds a certain specified depth or level. The float switch or other sensor(s) (305) is actuated and communicates or is connected to suitable circuitry, all in a way known to those skilled in the art, to cause the apparatus (215), the PLC, (315), HMI (320), or any other parts or components to shut down or enter a fault or error mode when the depth or level of liquid (30) exceeds a specified depth. The positioning of the float switch(s) or other sensor(s) (305) can vary inside the reservoir(s) (40). It is preferred in the present invention that at least one float switch (305) is utilized for this purpose.

A float switch or other liquid level sensor(s) (305) can also be used to detect and communicate or is connected to suitable circuitry, all in a way known to those skilled in the art, to cause the apparatus (215), the PLC, (315), HMI (320), or any other parts or components to shut down or enter a fault or error mode when the depth or level of liquid (30) drops below a certain point or depth in the reservoir(s) (40) in which the transducer(s) (10) are located. This can, without limitation, prevent the liquid (30) in the reservoir(s) (40) from dropping to an ineffective or unsafe depth or level. This condition may occur from situations including, but not limited to, a valve (300) that is stuck closed from a tank (280) that supplies the liquid, or a leaking tank. The positioning of the float switch(s) or other sensor(s) (305) can vary inside the reservoir(s) (40). It is preferred in the present invention that at least one float switch or liquid level sensor (305) is utilized for this purpose.

The fan or blower (180), or other source of pressurized air or gas, may also be constructed from any suitable material that is not affected by the chemical action of the liquid (30). Suitable materials may include PVC, polypropylene, and stainless steel, but other suitable materials may also be used. The blower(s) can either push or pull the air or gas, as well as aerosol, through, or across, the chamber, reservoir, or other area in which the aerosol is generated to remove it from the apparatus (215). The blower(s) (180) or other source of pressurized air or gas can move any quantity of air at any speed sufficient for the intended application. The blower(s) (180) can also be chosen, without limitation, to meet the following variables that include, but are not limited to: (a) the quantity of aerosol that is being generated, (b) the amount of surface disruption that it might create and its effect on aerosol production, (c) the desired quantity of aerosol that is evacuated from the apparatus (215), (d) the geometry and volume of the targeted area, (e) the geometry and volume of any conduit or piping that may be used to deliver the aerosol, (f) the manner and effectiveness in which the targeted area is sealed, (g) and uniformity of the aerosol (200) deployment or administration in or into the targeted area. Without limitation, the blower(s) (180) can be controlled by the PLC (315) in a manner known in the art.

Certain applications will require lower airflows, while other applications will require higher airflows. It is preferred, without limitation, that the blower (180) used in the present invention is a centrifugal fan or blower and that it is constructed using polypropylene for a housing and impeller, and 316L stainless steel for its drive shaft. It is further preferred, without limitation, that the fan or blower (180) pushes air/gas and aerosol out of the chamber, reservoir, or other area in which the aerosol is generated. The housing or enclosure for the blower(s) (180) can be plumbed to remove any excess liquid that may collect as the blower is operated. It is preferred, without limitation, that the housing or enclosure for the blower(s) (180) is plumbed in the present invention.

According to the prior art established by U.S. Pat. No. 4,366,125 (Kodera et al., 1980), and the book titled, "Aerosol Technology" by William C. Hinds (1982), the liquid (30) utilized in the present invention can be heated by using three different means, or a combination of one or more of the three different means. First, the liquid (30) can be heated inside the reservoir(s) (40) in which the transducers (10) are located, by utilizing one or more means to provide heat (150) that is either in direct contact with the liquid or interface with the walls of the reservoir(s) (40), or both. Second, the liquid (30) in the reservoir(s) in which the transducer(s) (10) are located can also be heated by circulating it through one or more means to heat (310) the liquid, and back into the reservoir(s) (40). Third, the liquid can be heated as it flows from one or more tank(s) (280), that feeds or supplies the liquid (30) to the reservoir(s) (40) in which the transducers (10) are located.

In addition, and without limitation, the one or more valves (300) that control the flow of the liquid (30) can be electrically or electronically signaled to open, close, or semi-open, in a manner known in the art. A pump or other means (130) can move the liquid (30) intermittently or can continuously circulate the liquid (30) from the reservoir(s) (40) in which the transducers (10) are located, back to the aforementioned tank(s) that feeds or supplies the liquid (30) to the reservoir(s) (40). Without being limited, the valves (300) in this situation can be maintained in a semi-open or open position unless signaled or caused by some other means including, but not limited to, an electrical signal from an electronic controller or programmable logic circuit (315), to close, for various reasons including, but not limited to, a pump (130) failure that would cause the reservoir(s) (40) in which the transducers (10) are located to overflow.

It is preferred, without limitation, that one or more means (150) for heating the liquid (30) is located inside or partially inside the reservoir(s) (40) in which the transducers (10) are located, and is installed into or interfaced with the said reservoir(s) (40) in a way that is known to those skilled in the art. It is further preferred, without limitation, that the said means for heating (150) the liquid (30) is a cartridge heater.

The three aforementioned means to heat the liquid (30) are known to those skilled in the art, and are sufficiently designed and built for their intended purpose, and may be constructed from any material that is compatible, and suitable for use with the liquid (30). Properly heating the liquid (30) to the desired, or efficacious temperature can involve issues such as, but not limited to, the type of heater(s) that would be effective, the number of heater(s) used, the heat output of each heater, the duration and timing of operation for each heater, the intensity of the heat generated, the materials of construction, and are known to those skilled in the art. In addition, the pump or other means (130) used to circulate the liquid (30) provides the necessary flow rate or pumping capacity, which can vary, for the intended application and may be constructed from any material that is compatible, and suitable for use with the liquid (30).

Figure 10:
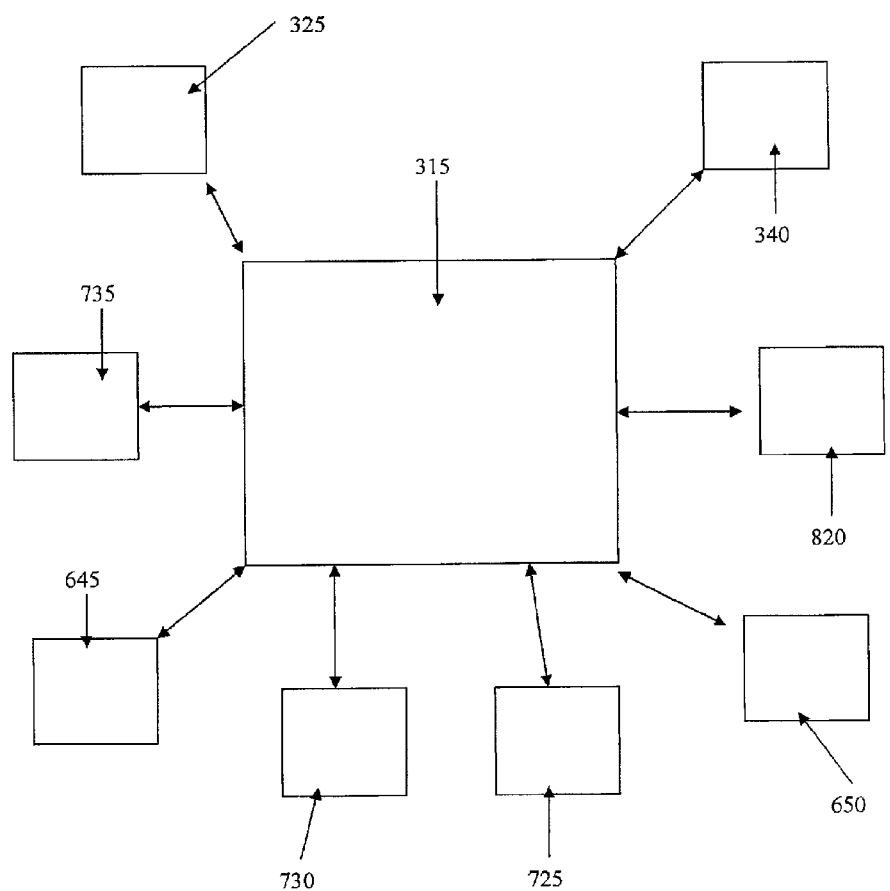
FIG. 10 is a schematic view of an embodiment of a PLC connected to various components of the aerosol generating apparatus.
Figure 11:
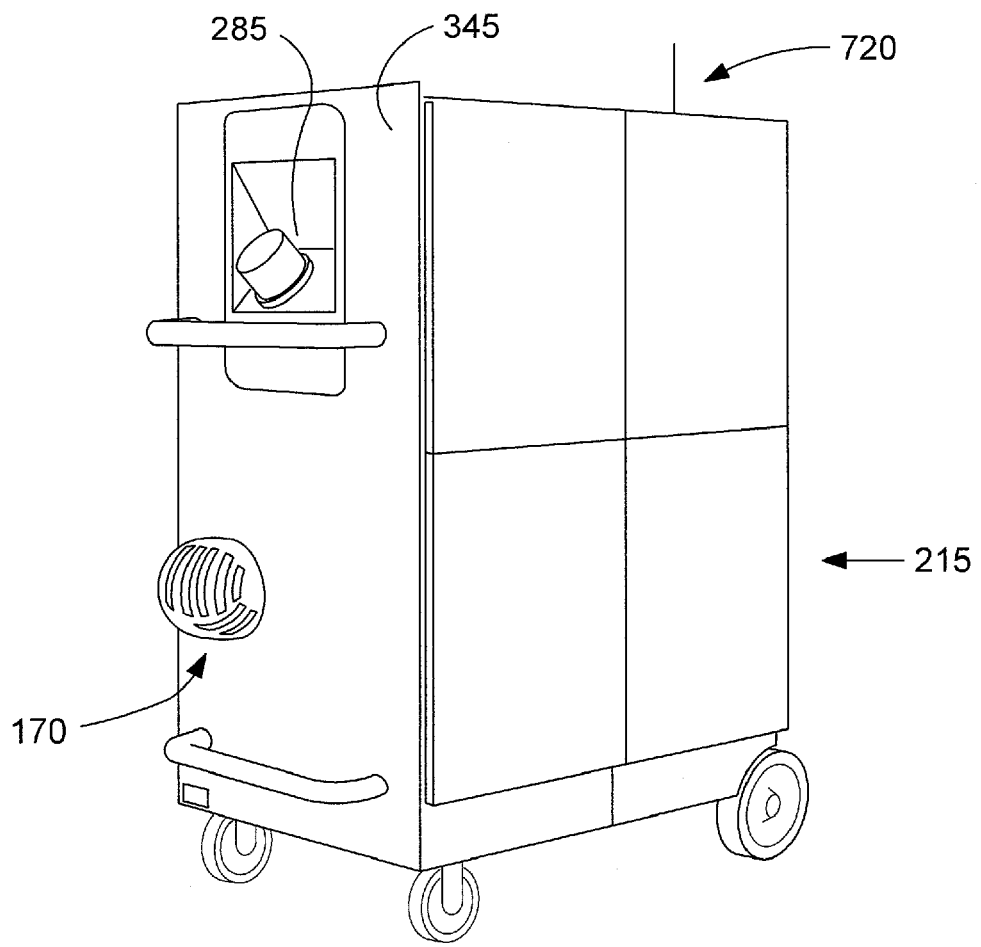
FIG. 11 is an isometric view of an embodiment of an aerosol generating apparatus according to the present invention.
Figure 12:
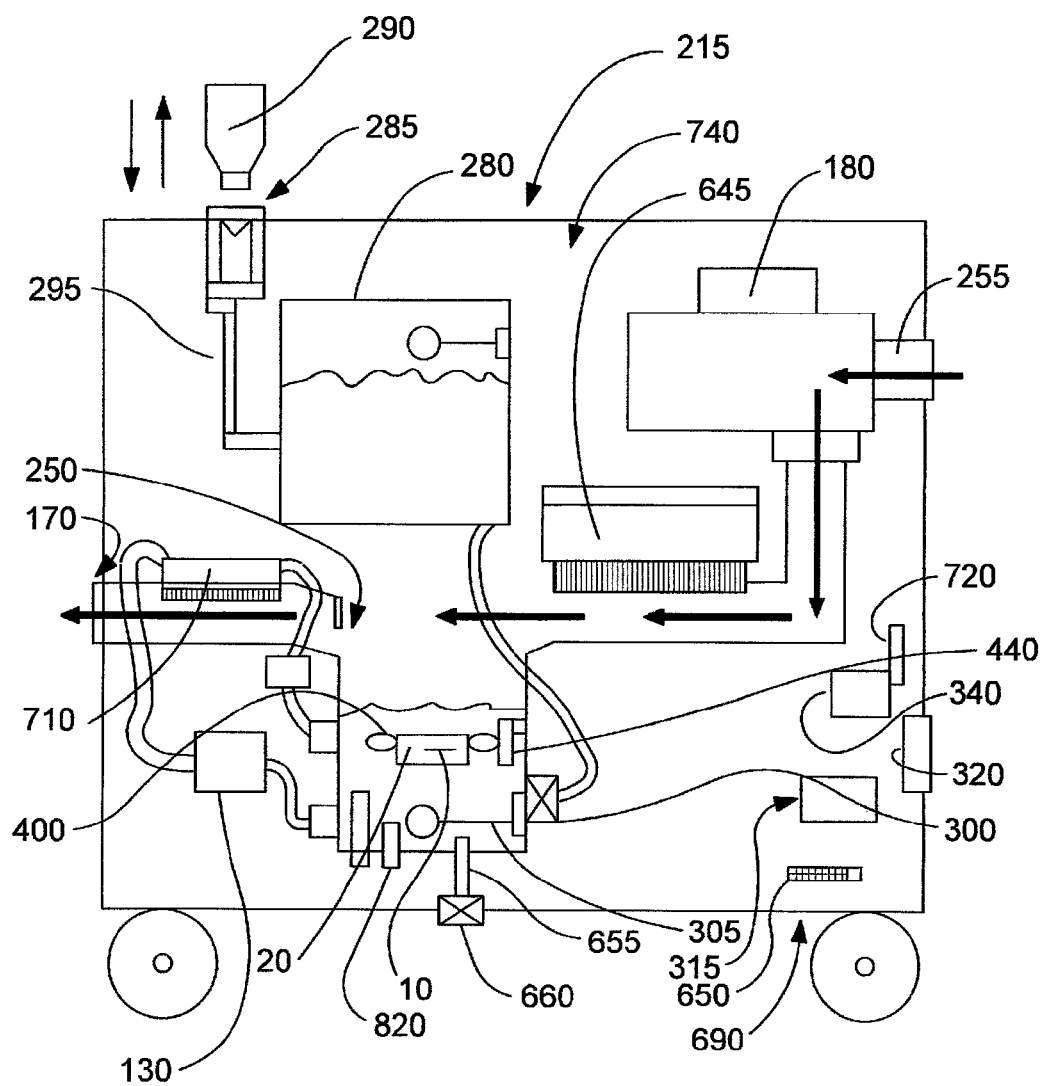
FIG. 12 is a schematic view of an embodiment of an aerosol generating apparatus according to the present invention.
Figure 13:
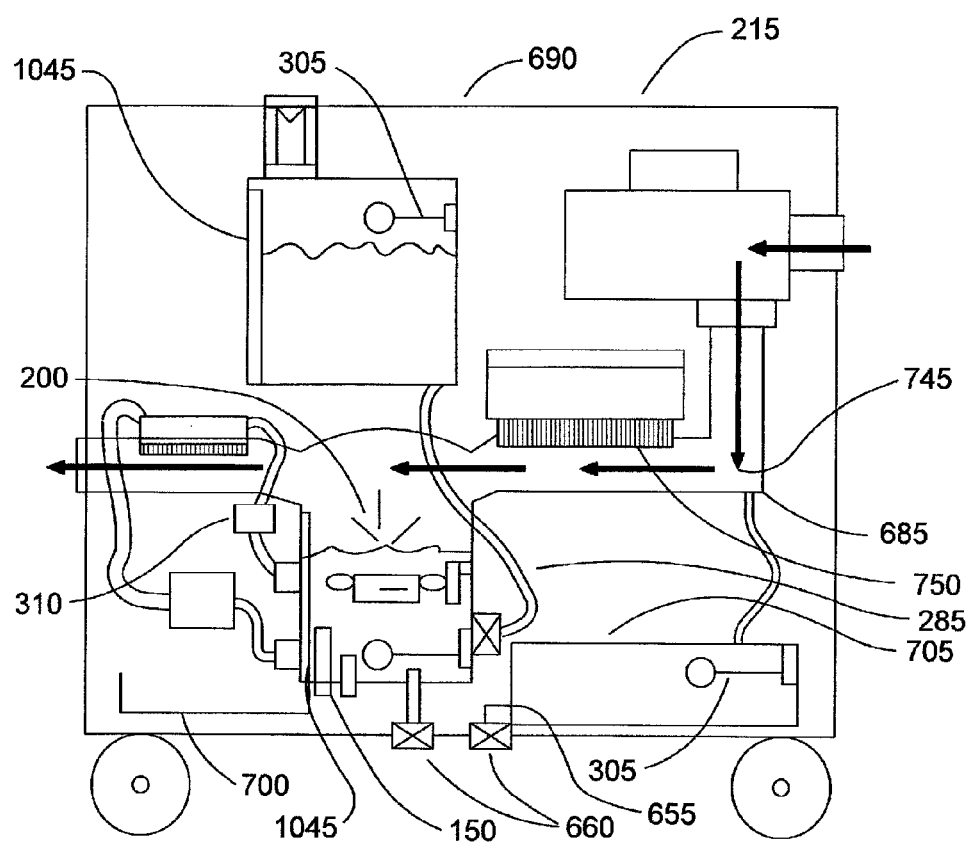
FIG. 13 is a schematic view of an embodiment of an aerosol generating apparatus according to the present invention.
Figure 14:
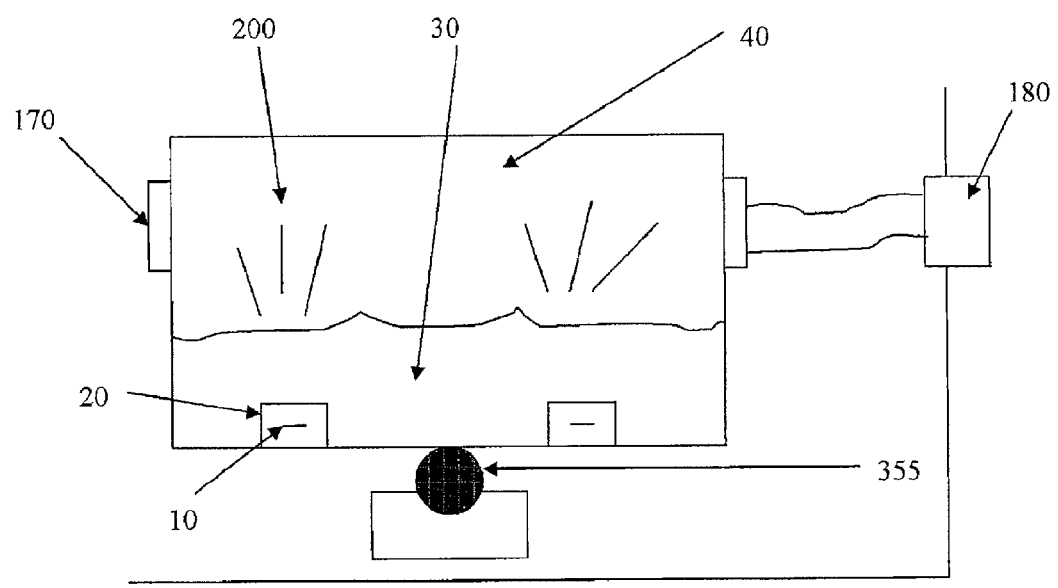
FIG. 14 is a schematic view of an embodiment of aerosol generating transducers attached to a reservoir that is connected to a means that can enable the transducers and/or their liquid facing surfaces to match the angle of or remain aligned with, the surface of the liquid above them.
Figure 15:
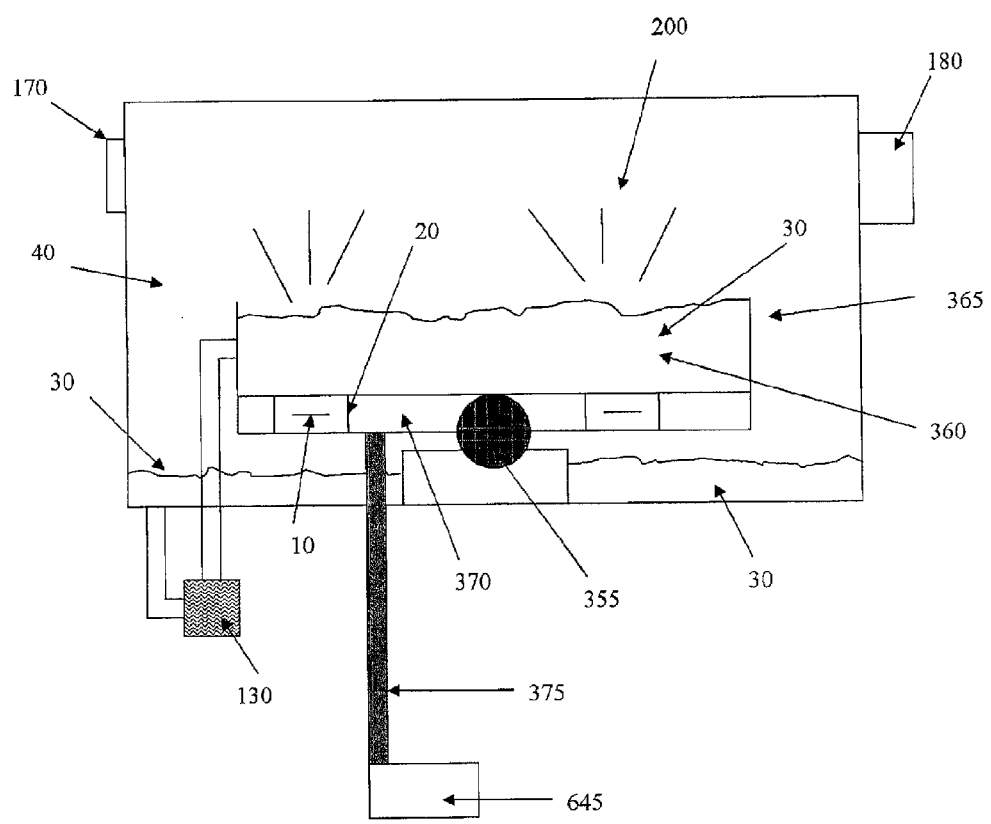
FIG. 15 is a schematic view of an embodiment of aerosol generating transducers attached to a secondary reservoir inside of a main reservoir and that is connected to a means that can enable the transducers and/or their liquid facing surfaces to match the angle of or remain aligned with, the surface of the liquid above them.
Figure 16:
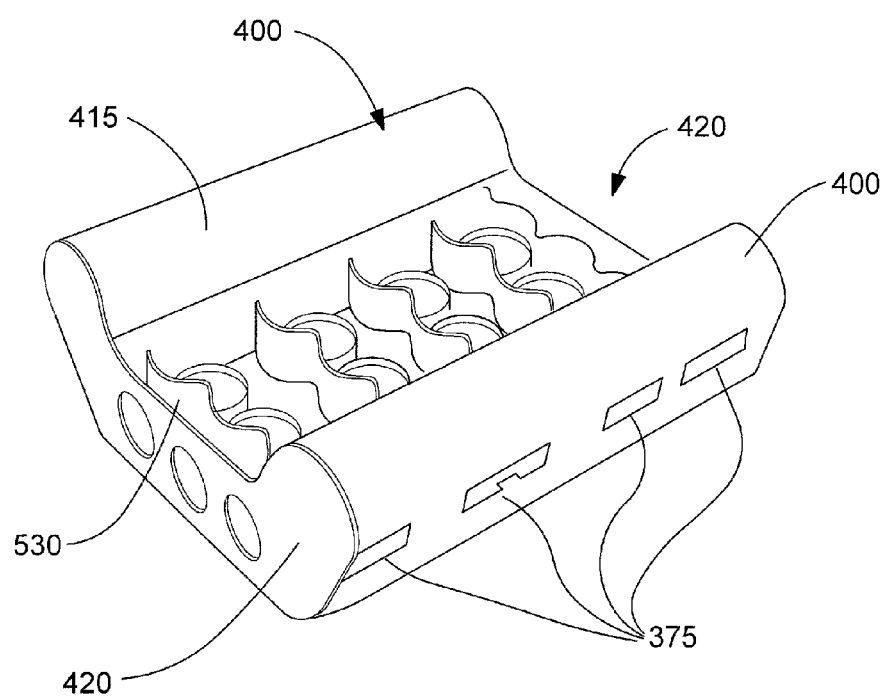
FIG. 16 is an isometric view of an embodiment of multiple transducers interfaced with multiple housings, and the housings are attached to multiple buoyant objects.
Figure 17:
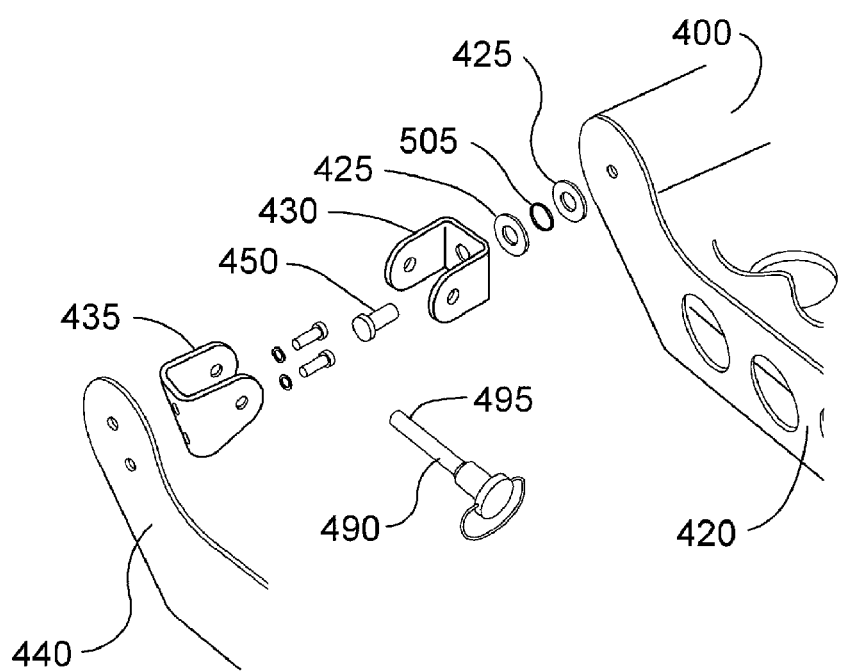
FIG. 17 is a partially broken away, exploded isometric view of an embodiment of more than one clevis assembly that allows various ranges of motion for various parts and components such as, the transducers, housings, and buoyant objects according to the present invention.
Figure 18:
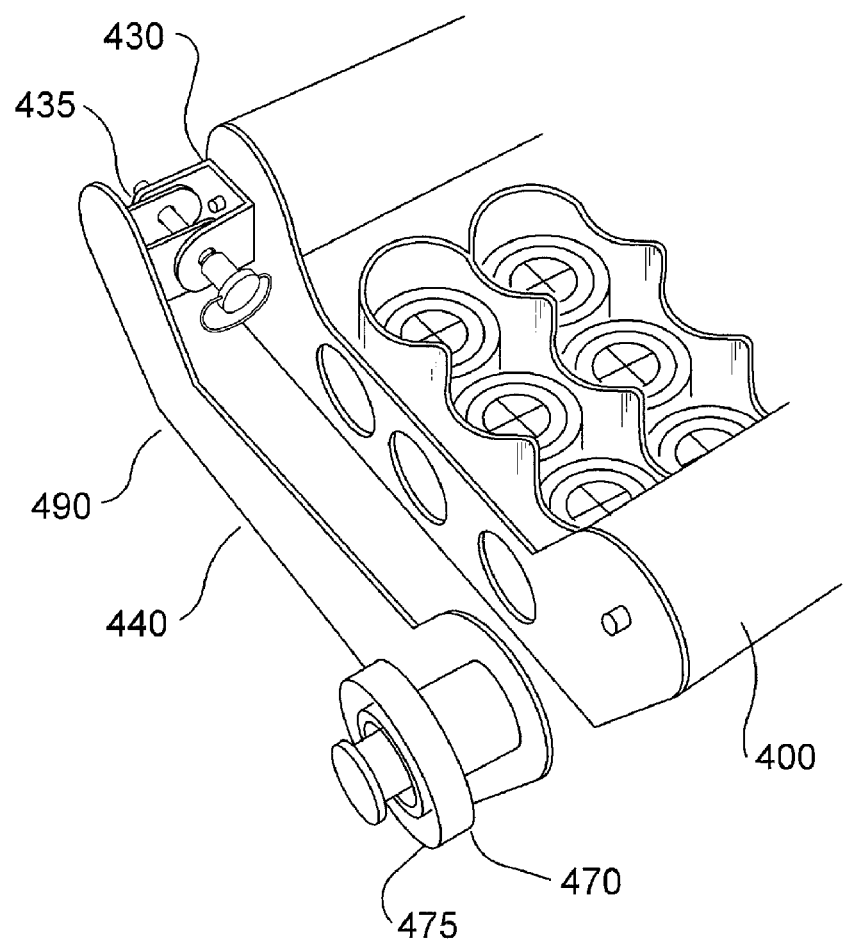
FIG. 18 is a partially broken away isometric view of an embodiment of the pivot arm assembly that allows various ranges of motion for various parts and components such as, the transducers, housings, and buoyant objects, according to the present invention.
Figure 19:
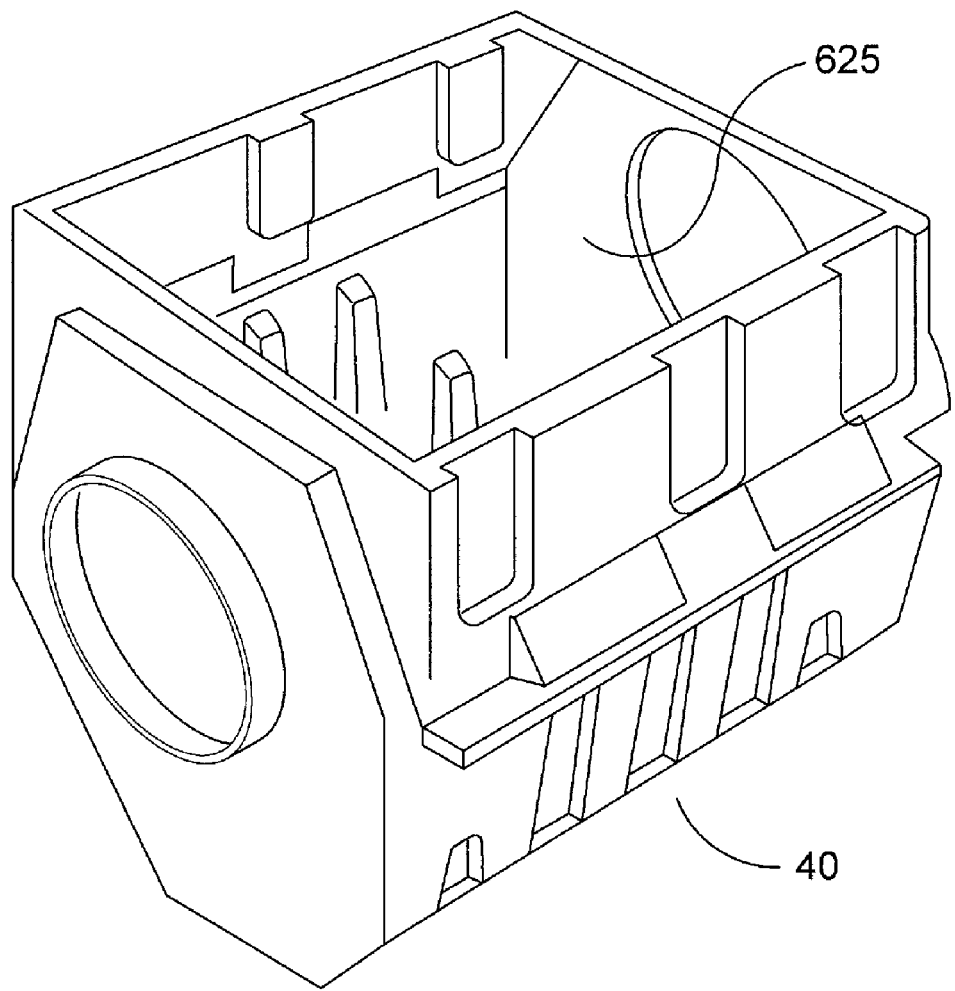
FIG. 19 is a schematic view of an embodiment of the reservoir in which the transducers are located according to the present invention.
Figure 20:
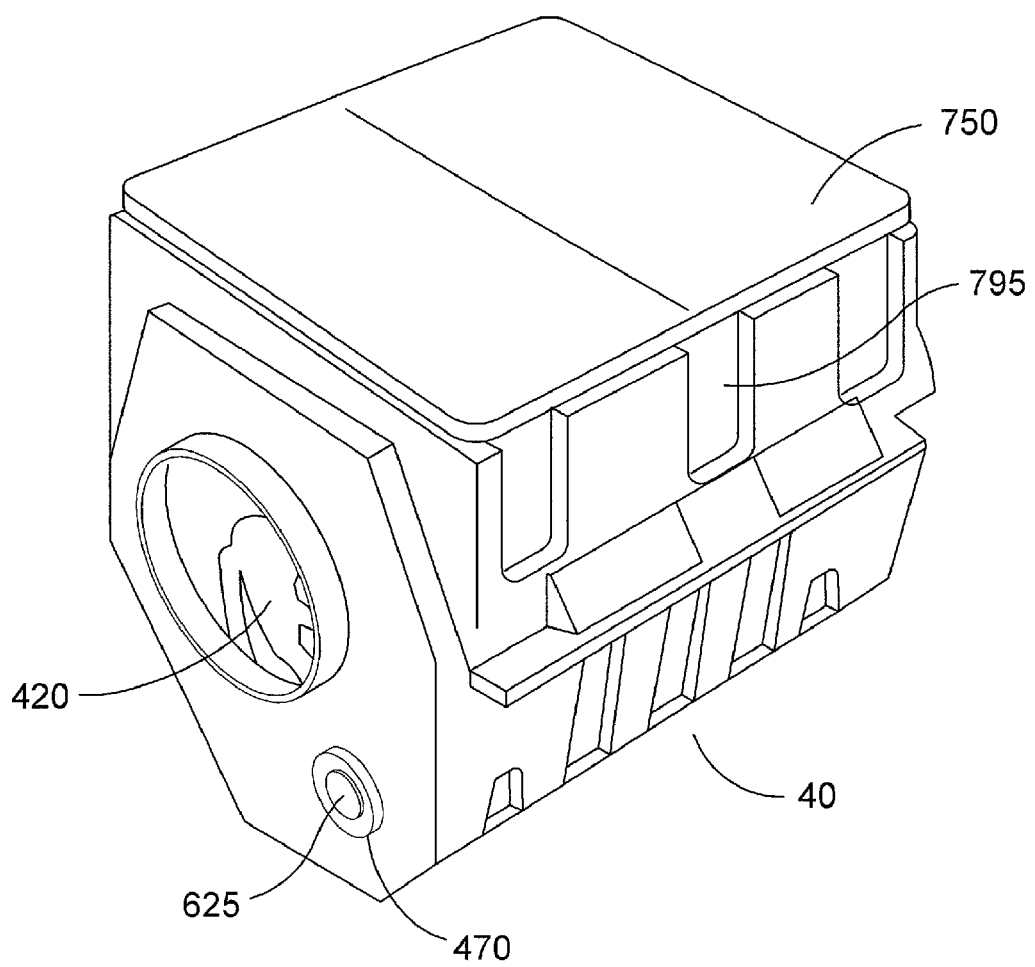
FIG. 20 is an isometric view of an embodiment of a heat sink interfacing with the reservoir in which the transducers are located with the cooling fins of the heat sink effectively positioned within the air stream that passes through the reservoir, in addition a hole which interfaces with the pivot arm is positioned within the wall of the reservoir.
Figure 21:
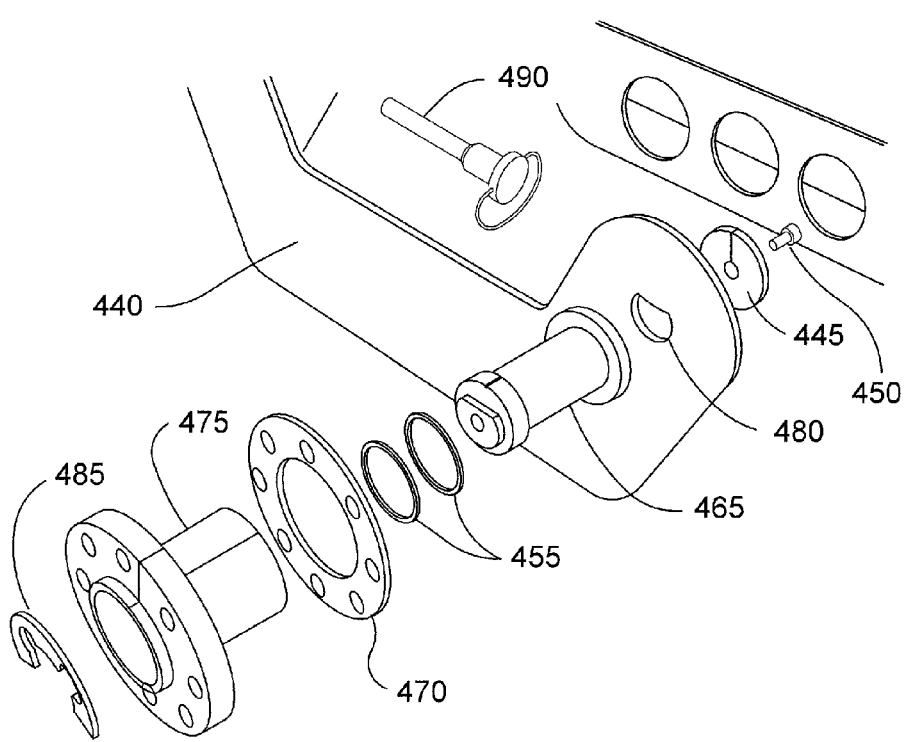
FIG. 21 is a partially broken away, exploded isometric view of an embodiment of the pivot arm assembly that consists of various parts and components according to the present invention.
Figure 22:
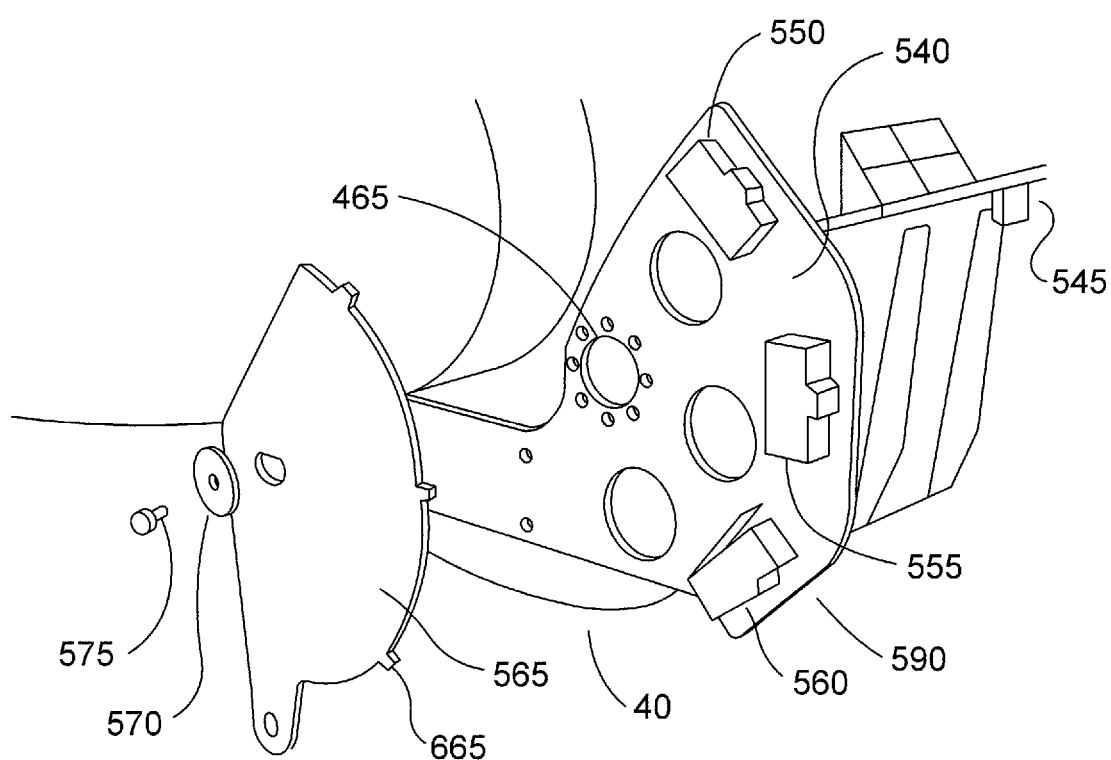
FIG. 22 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, and base plate.
Figure 23:
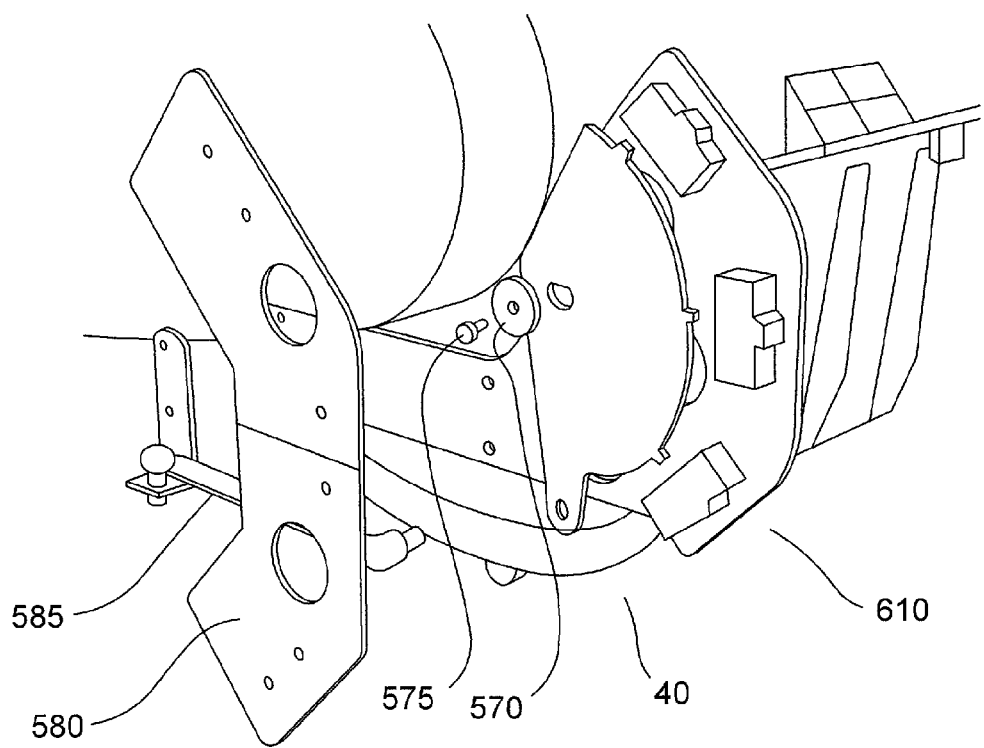
FIG. 23 is a partially broken away, exploded isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 24:
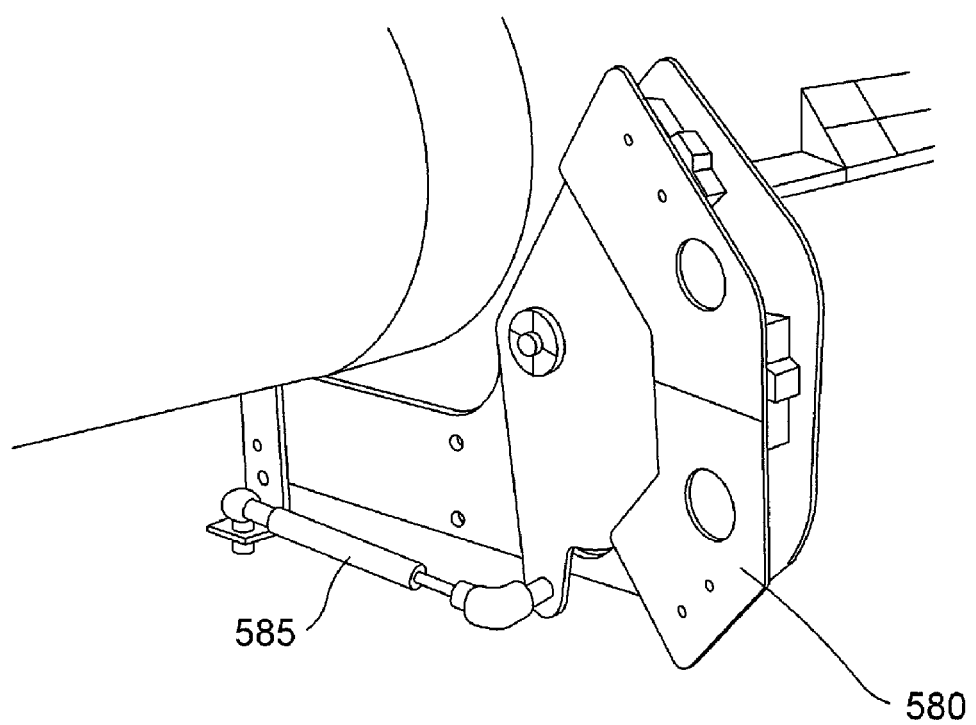
FIG. 24 is a partially broken away isometric view of an embodiment of the means used to actuate the various switches to communicate any information or status related to the reservoir or within the reservoir to the PLC, and consists of components such as, switches, switch actuator plate, protrusions, torque tube, base plate, cover plate, and hydraulic dampener.
Figure 25:
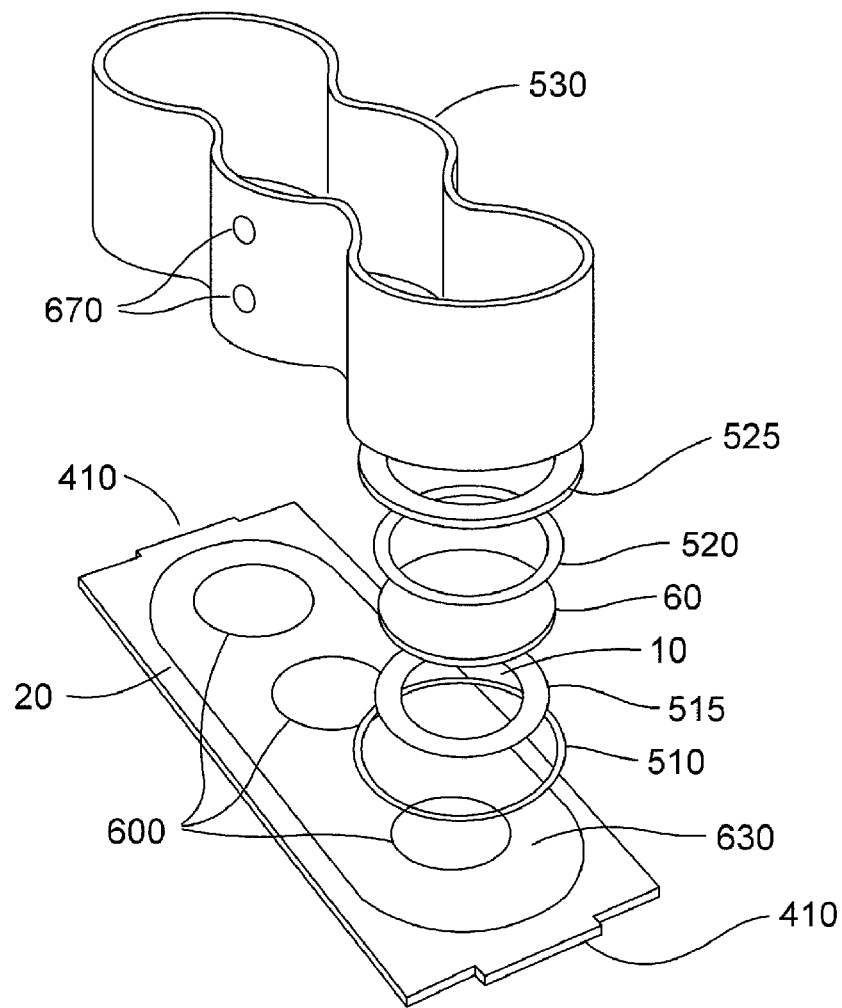
FIG. 25 is an exploded isometric view of an embodiment of an enhanced design for interfacing one or more transducers or transducer assemblies with their housing, consisting of various features, parts, and components according to the present invention.
Figure 26:
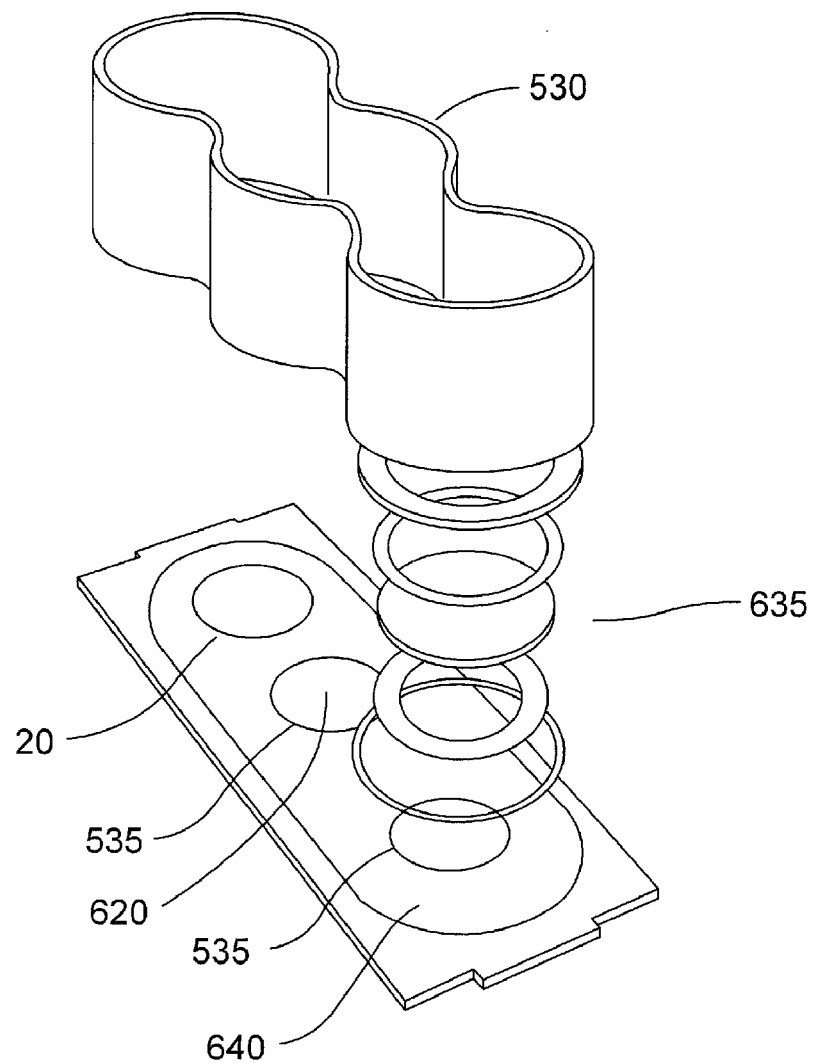
FIG. 26 is an exploded isometric view of an embodiment of an enhanced design for interfacing one or more transducers or transducer assemblies with their housing, consisting of various features, parts, and components according to the present invention.
Figure 27:
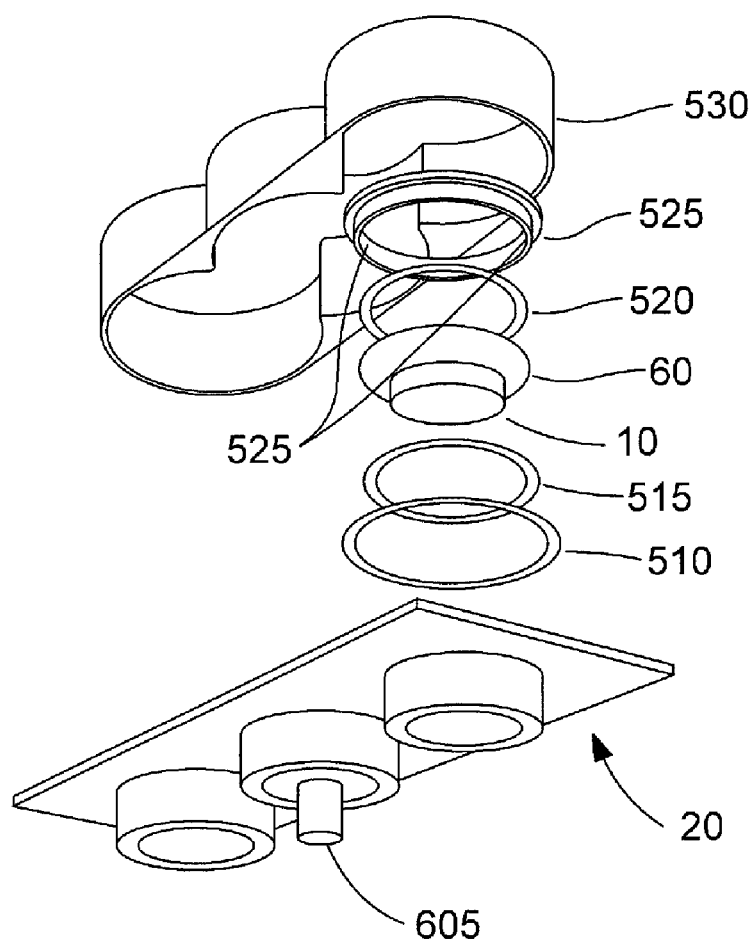
FIG. 27 is an isometric view of an embodiment of an enhanced design for interfacing one or more transducers with their housing, consisting of various features, parts, and components according to the present invention.
Figure 28:
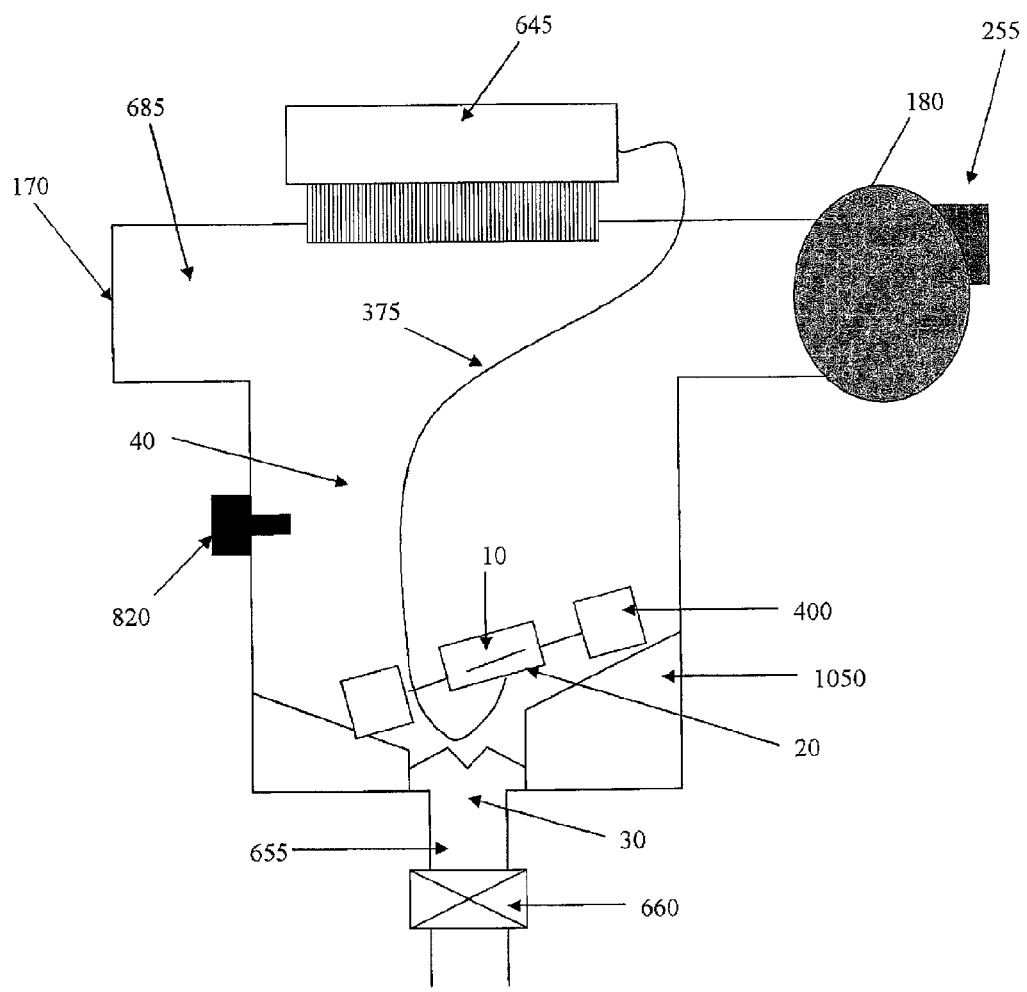
FIG. 28 is a schematic view of an embodiment of a means for the transducer housing, buoyant objects, or other parts and components to interact with any means so that the transducers or transducer assemblies are angled when the liquid in the reservoir is at a specified level or is drained.
Figure 29:
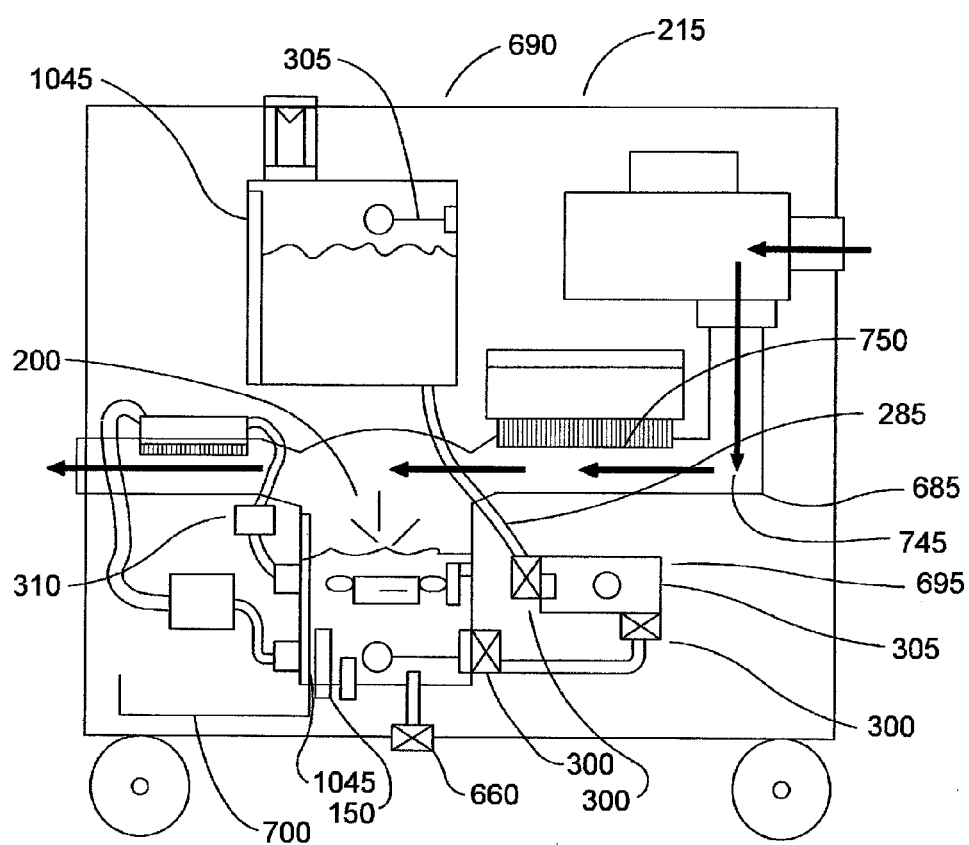
FIG. 29 is a schematic view of an embodiment of an aerosol generating apparatus according to the present invention.
Figure 30:
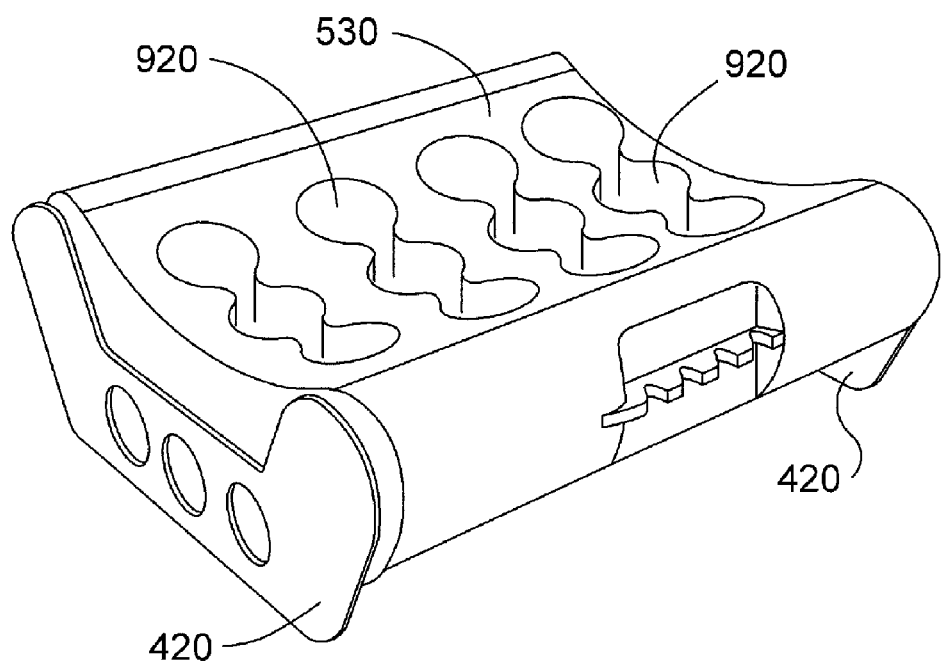
FIG. 30 is an isometric view of an embodiment of a buoyant object interfaced with multiple transducer assemblies and end plates, according to the present invention.
Figure 31:
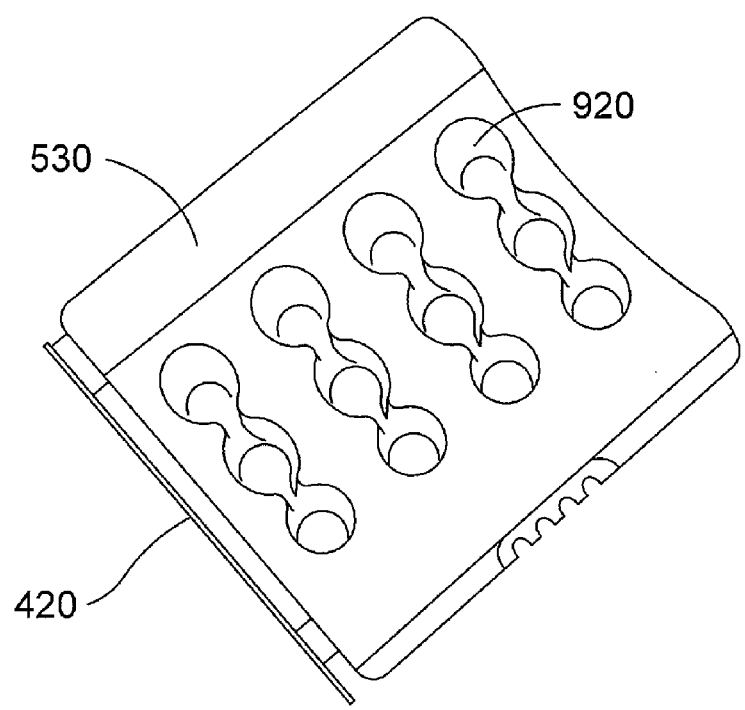
FIG. 31 is a top plan view of an embodiment of a buoyant object interfaced with multiple transducer assemblies and end plates, according to the present invention.
Figure 32:
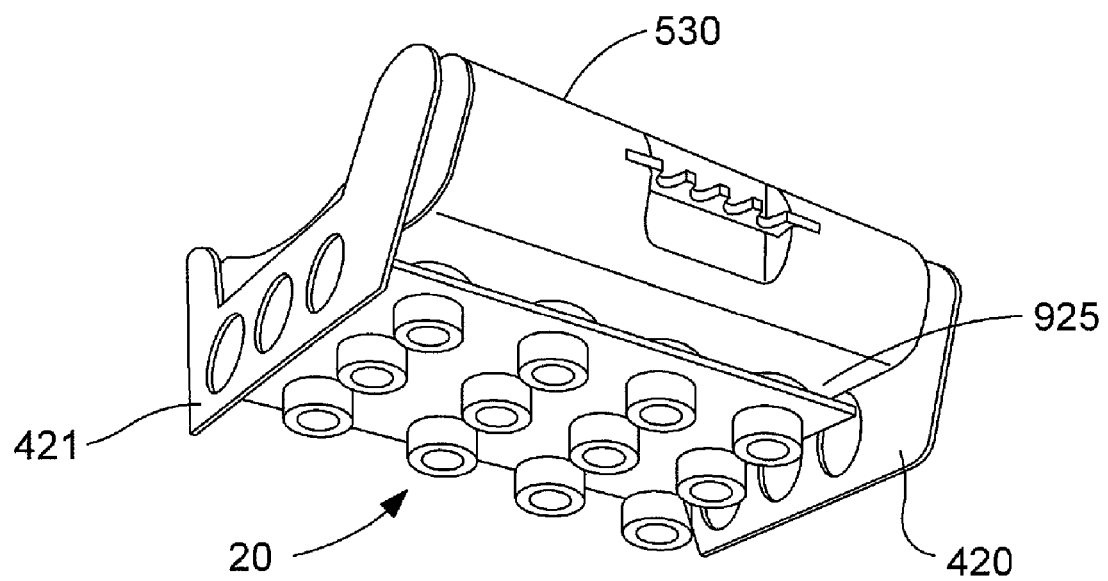
FIG. 32 is an isometric view of an embodiment of a buoyant object interfaced with multiple transducer assemblies and end plates, and spaces or gaps exist, especially above the transducers, between the housing and the buoyant object that is positioned above the transducers, according to the present invention.
Figure 33:
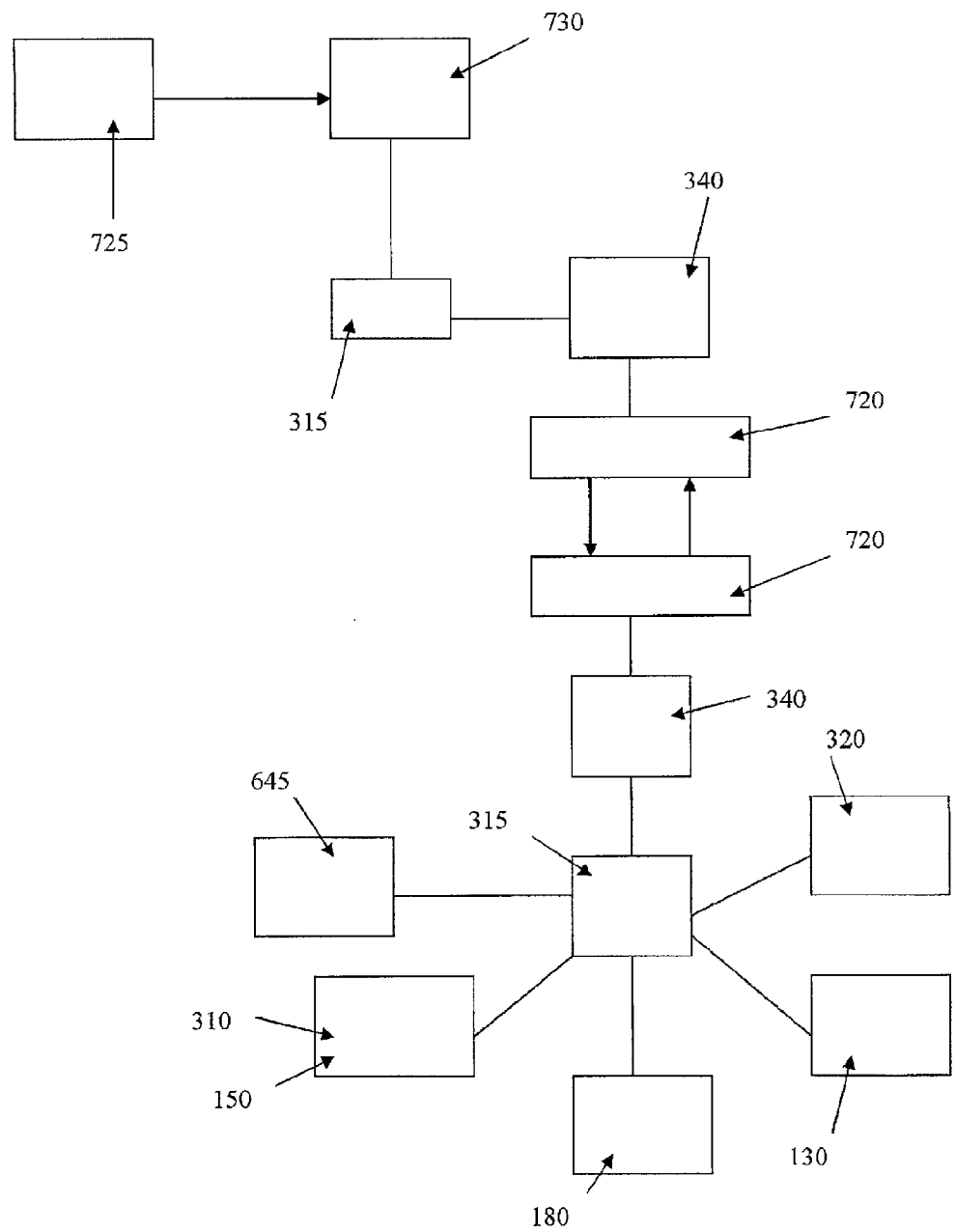
FIG. 33 is a schematic view of an embodiment of a light source and light sensor that communicates with a PLC that communicates with various parts and components of an aerosol generating apparatus, according to the present invention.
Figure 34:
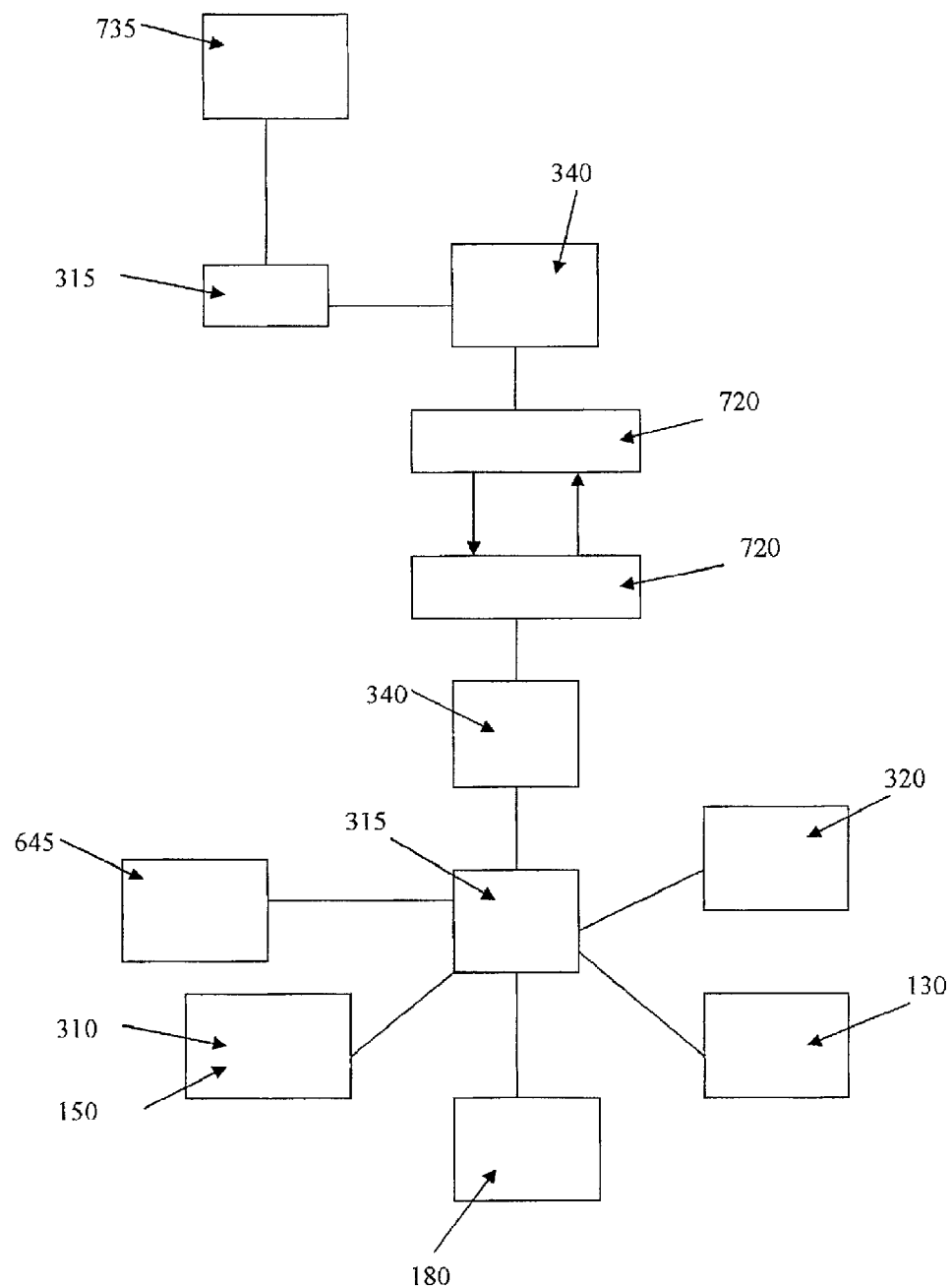
FIG. 34 is a schematic view of an embodiment of a relative humidity sensor that communicates with a PLC that communicates with a transceiver that communicates with various parts and components of an aerosol generating apparatus, according to the present invention.
Figure 35:
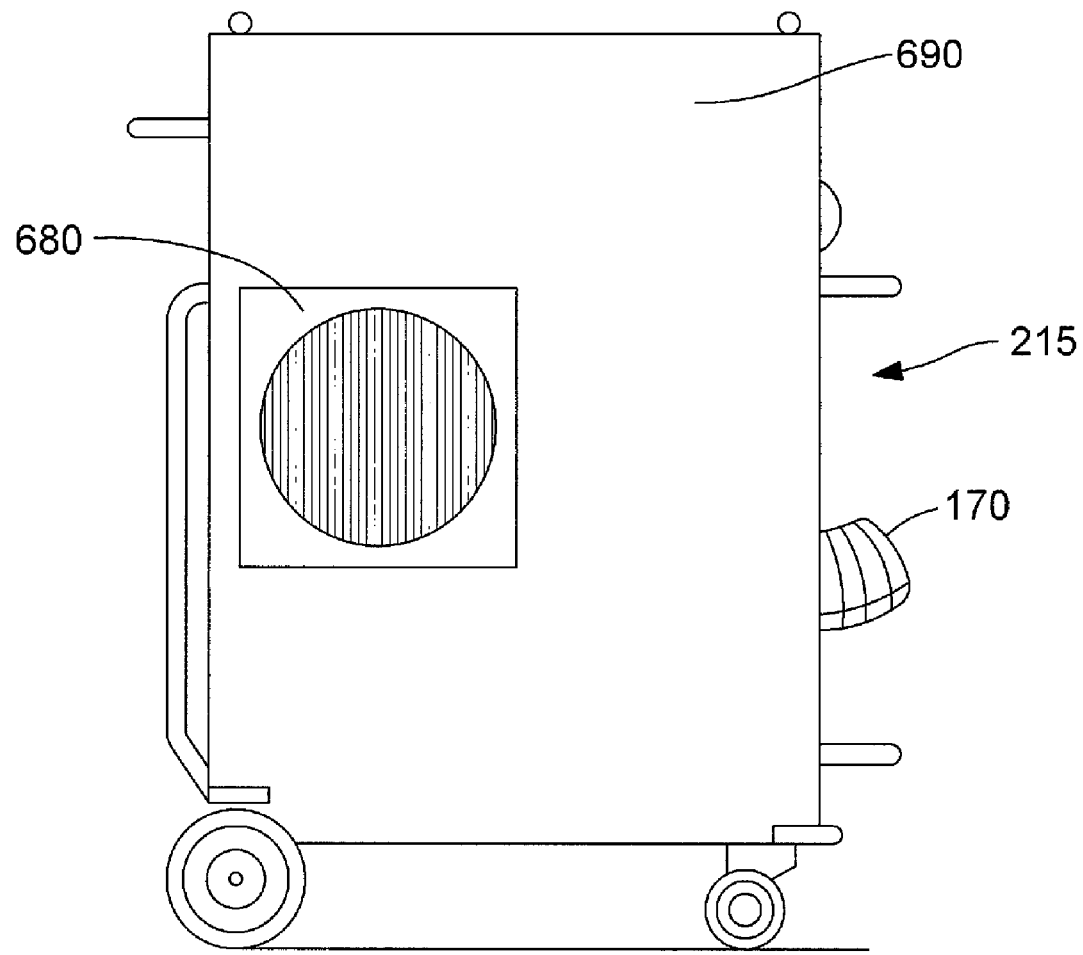
FIG. 35 is a side plan view of an embodiment of an aerosol generating apparatus according to the present invention.
Figure 36:
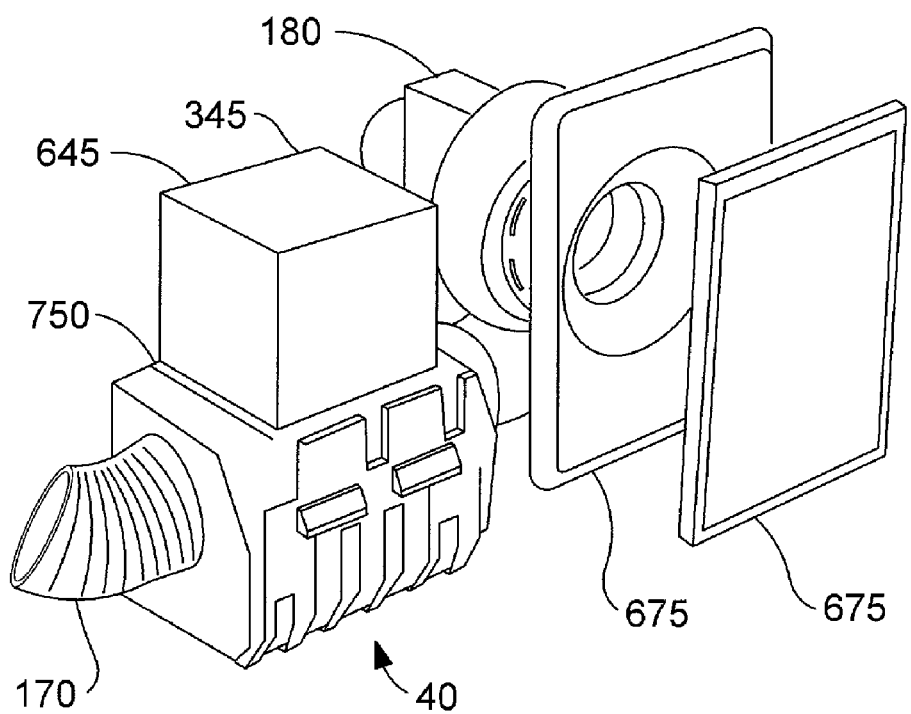
FIG. 36 is a partially broken away, exploded isometric view of an embodiment of various parts and components of the aerosol generating apparatus such as, filters, blower, pipes, reservoir, drive electronics and exit orifice, according to the present invention.
Figure 37:
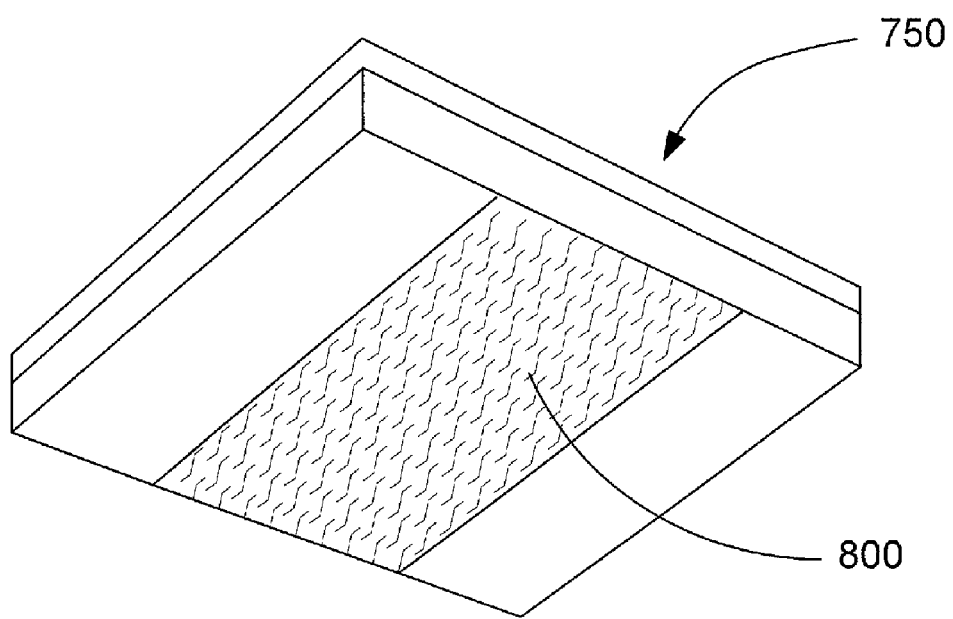
FIG. 37 is an isometric view of an embodiment of a heat sink that interfaces with parts and components such as, the drive electronics and a reservoir, according to the present invention.
Figure 38:
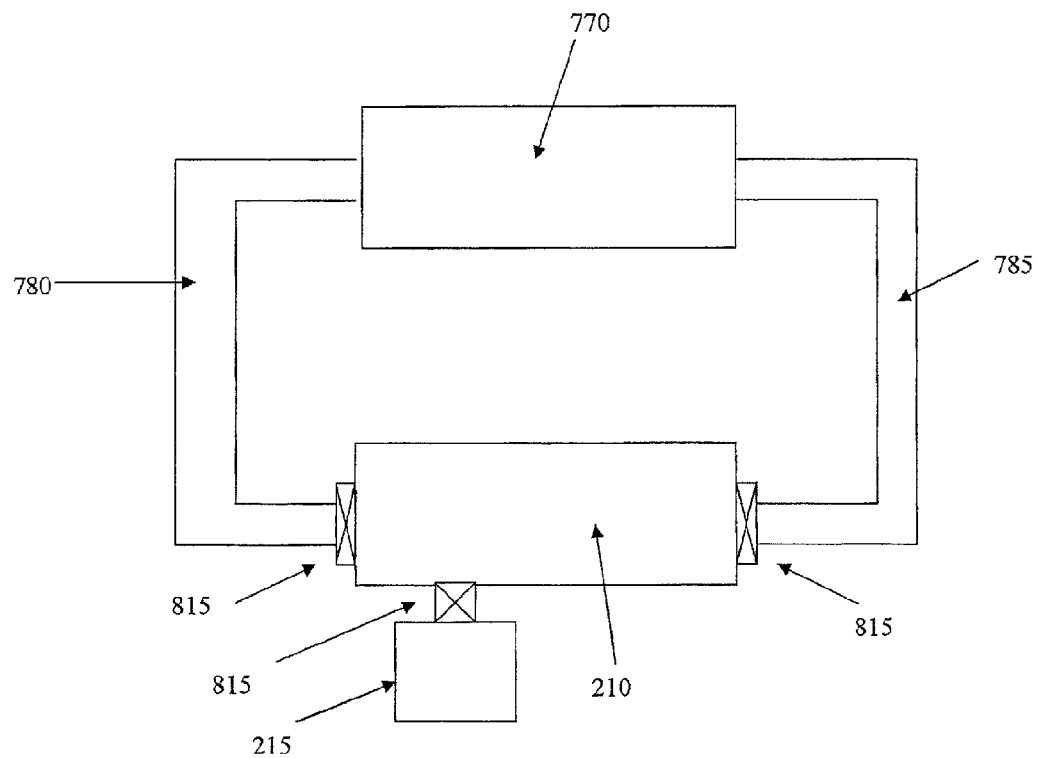
FIG. 38 is a schematic view of an embodiment of a means to decrease the temperature of the atmosphere and surfaces in the targeted area(s) consisting of generating, moving, and recirculating cooled or chilled air into the targeted area(s), as well as the interface of valves with the targeted area(s), according to the present invention.
Figure 39:
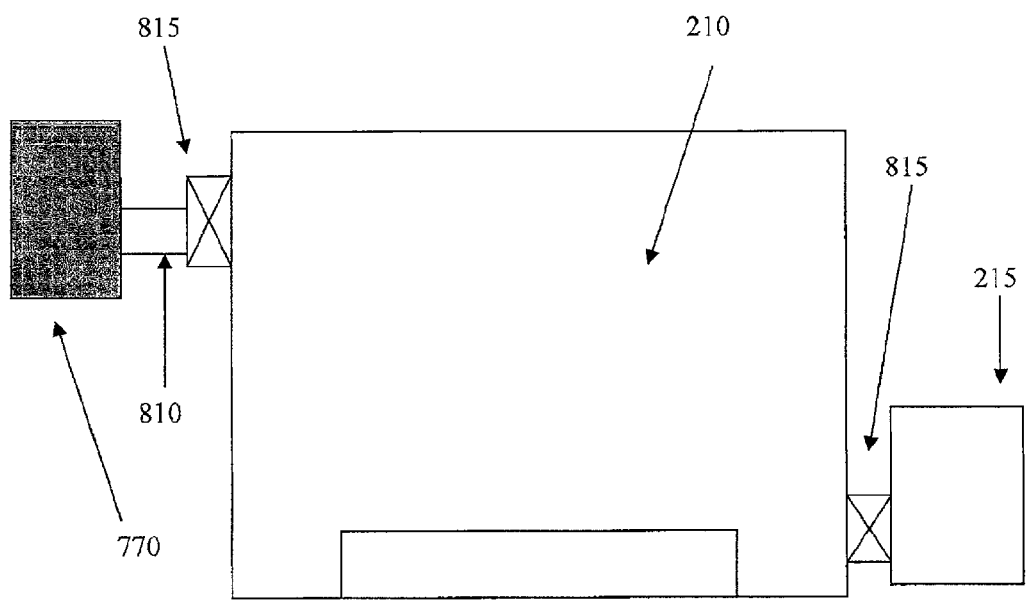
FIG. 39 is a schematic view of an embodiment of a means to decrease the temperature of the atmosphere and surfaces in the targeted area(s) consisting of generating, and moving, cooled or chilled air into the targeted area(s), as well as the interface of a valve before or at the entrance to the targeted area(s), according to the present invention.
Figure 40:
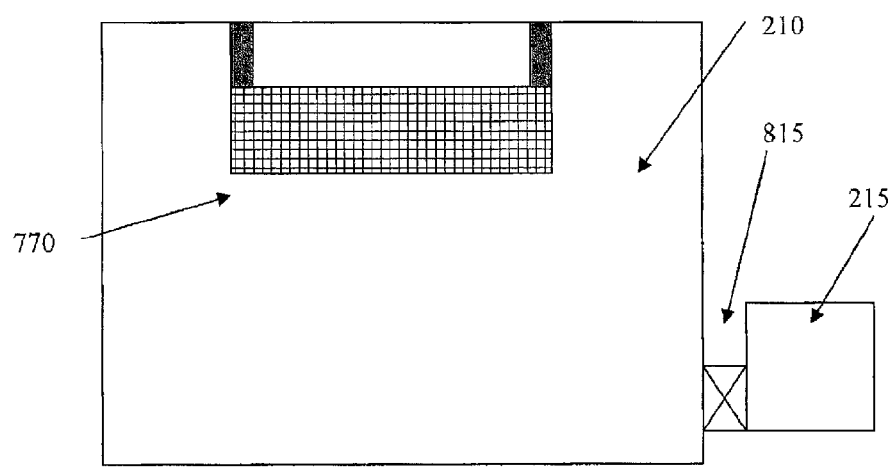
FIG. 40 is a schematic view of an embodiment of a means to decrease the temperature of the atmosphere and surfaces in the targeted area(s) consisting of generating, cooled or chilled air inside the targeted area(s), according to the present invention.
Figure 41:
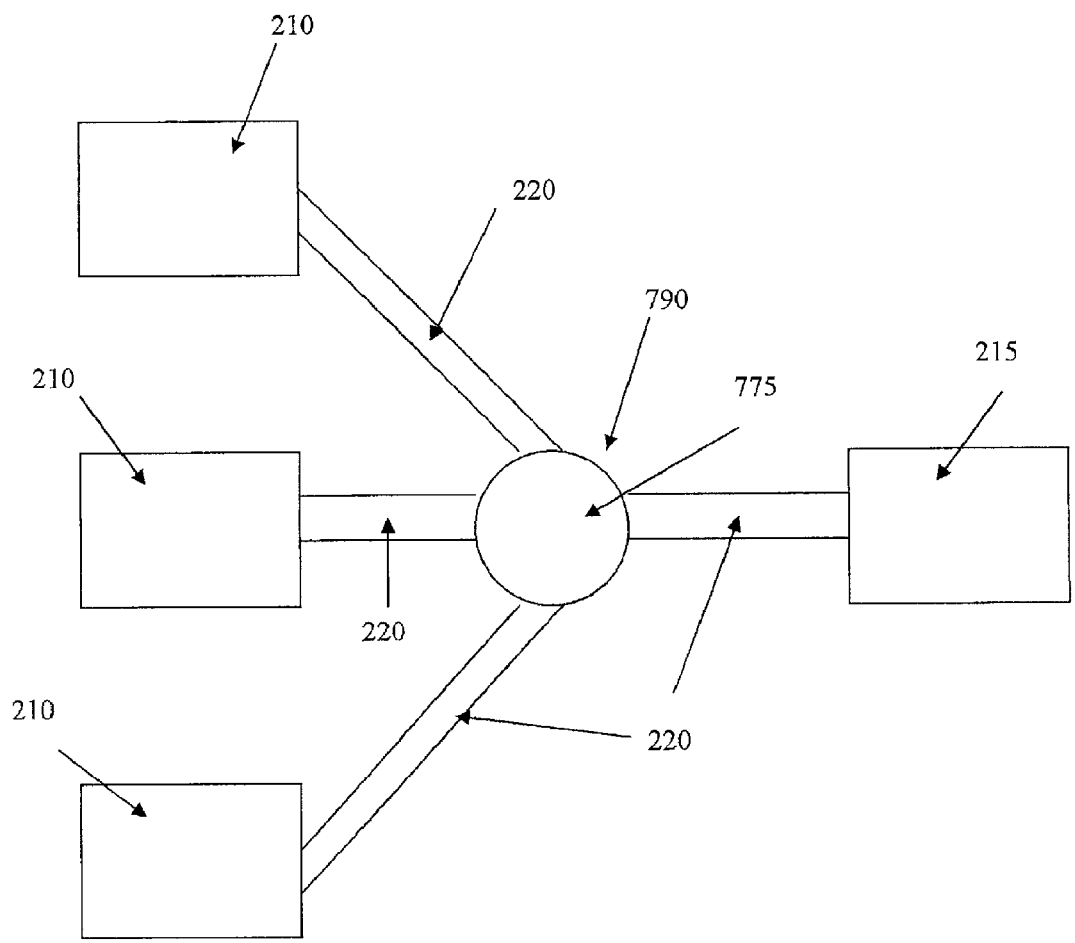
FIG. 41 is a schematic view of an embodiment of a means to divert air/gas and aerosol emanating from the aerosol generating apparatus, to multiple separate enclosed targeted areas, and consists of parts and components such as a pipe junction and valve, according to the present invention.
Figure 42:
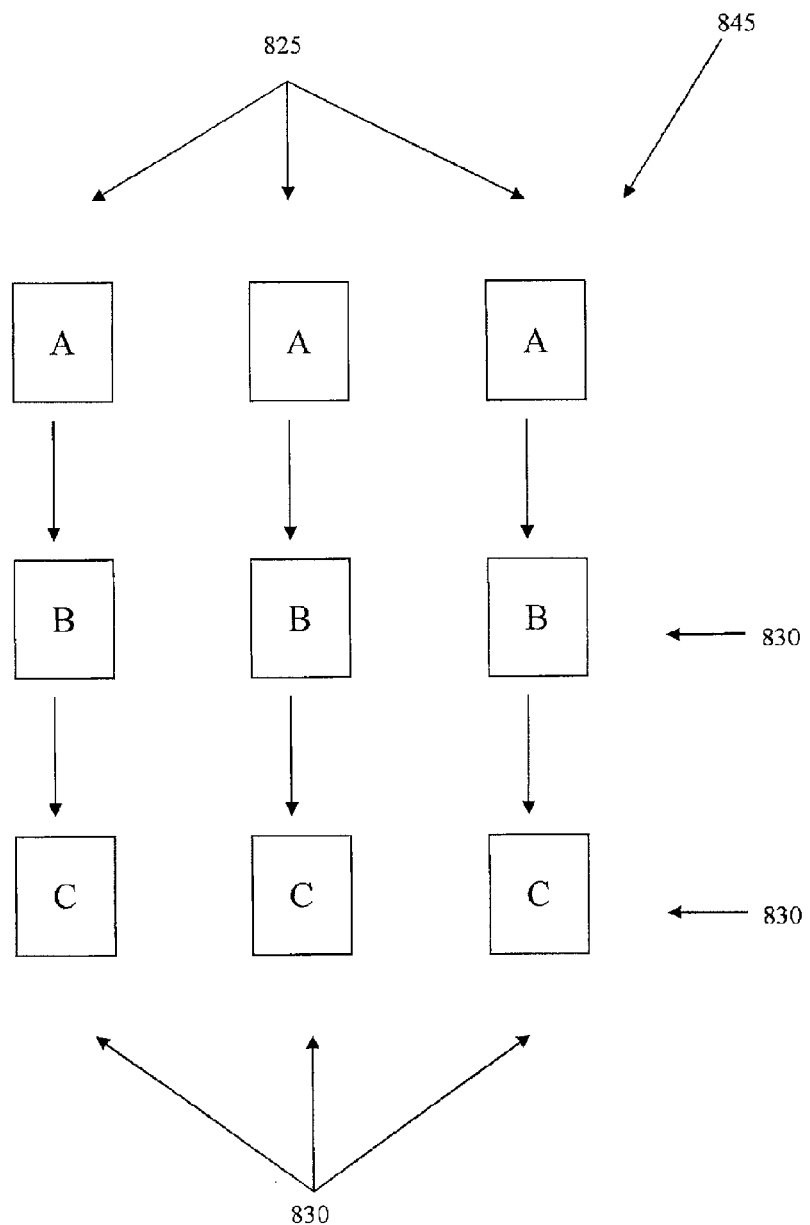
FIG. 42 is a schematic view of an embodiment of a means to compensate for any shifting of transducer frequencies, where a crystal is initially used to generate one specific frequency or specific frequency range for a transducer(s), and is then switched to a different crystal that is used to generate another specific frequency or specific frequency range for the transducer(s), and this can be performed multiple times for a plurality of transducers, according to the present invention.
Figure 43:
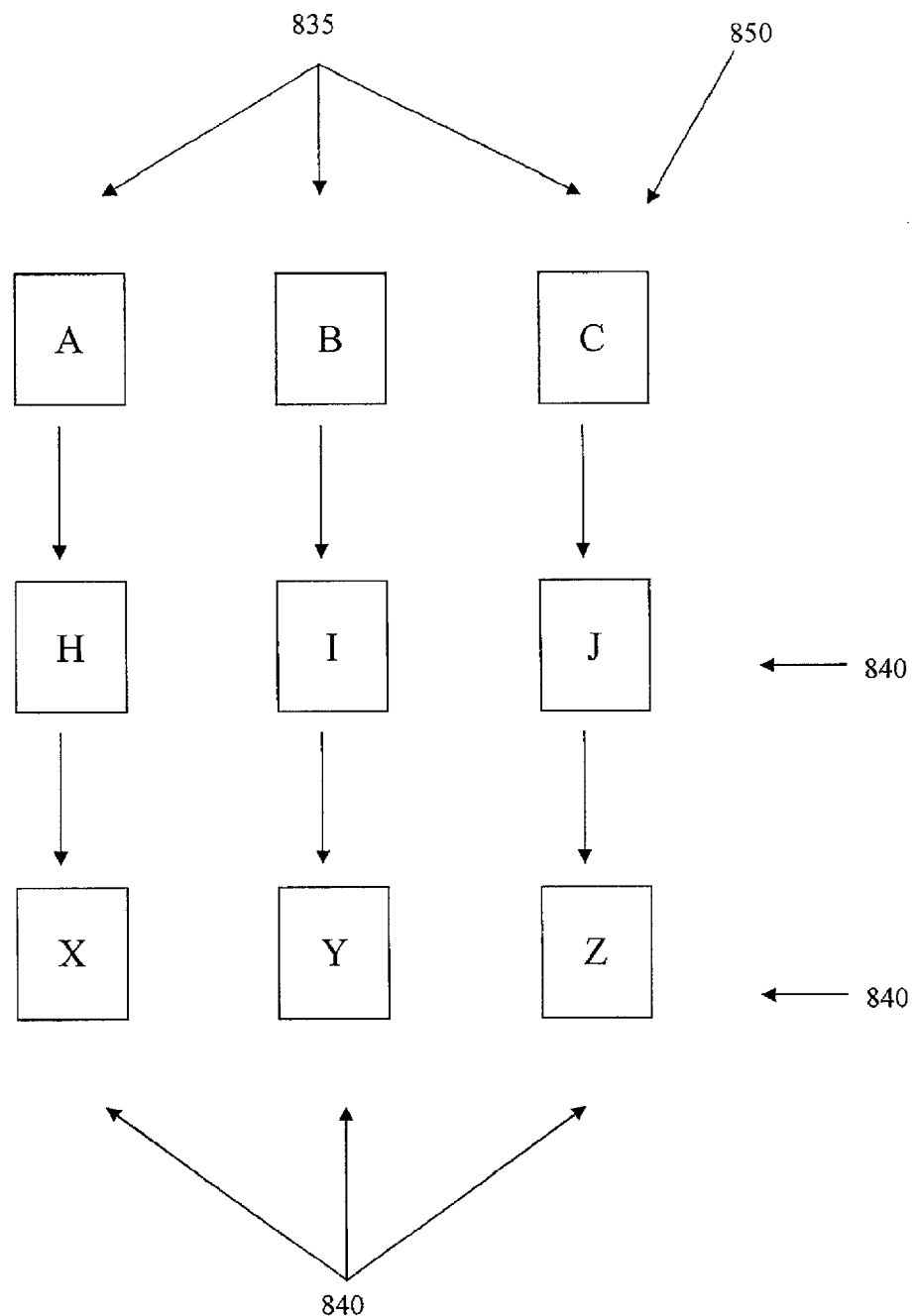
FIG. 43 is a schematic view of an embodiment of a means to compensate for any shifting of transducer frequencies, where a signal generator is initially used to generate one specific frequency or specific frequency range for a transducer(s), and is then switched to a different signal generator that is used to generate another specific frequency or specific frequency range for the transducer(s), and this can be performed multiple times for a plurality of transducers, according to the present invention.
Figure 44:
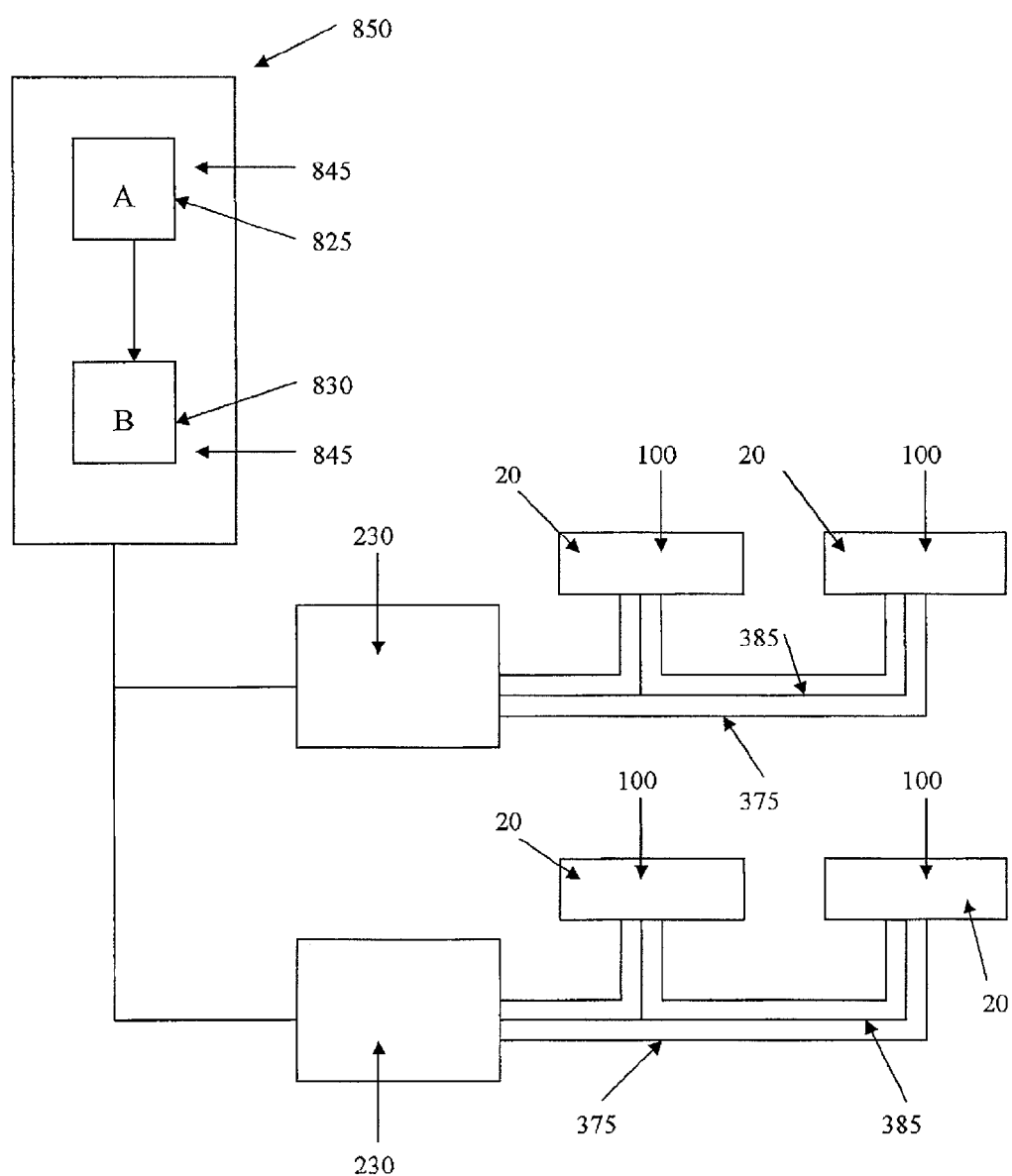
FIG. 44 is a schematic view of an embodiment of a means to compensate for any shifting of transducer frequencies, where a crystal that is a part or component of a signal generator is initially used to generate one specific frequency or specific frequency range for a transducer(s), is then switched to a different crystal that is a part or component of the same signal generator, and is used to generate another specific frequency or specific frequency range for the transducer(s), and the signal generated from the activated crystal is sent via the signal generator to an amplifier(s) that is connected to one or more transducers, according to the present invention.
Figure 45:
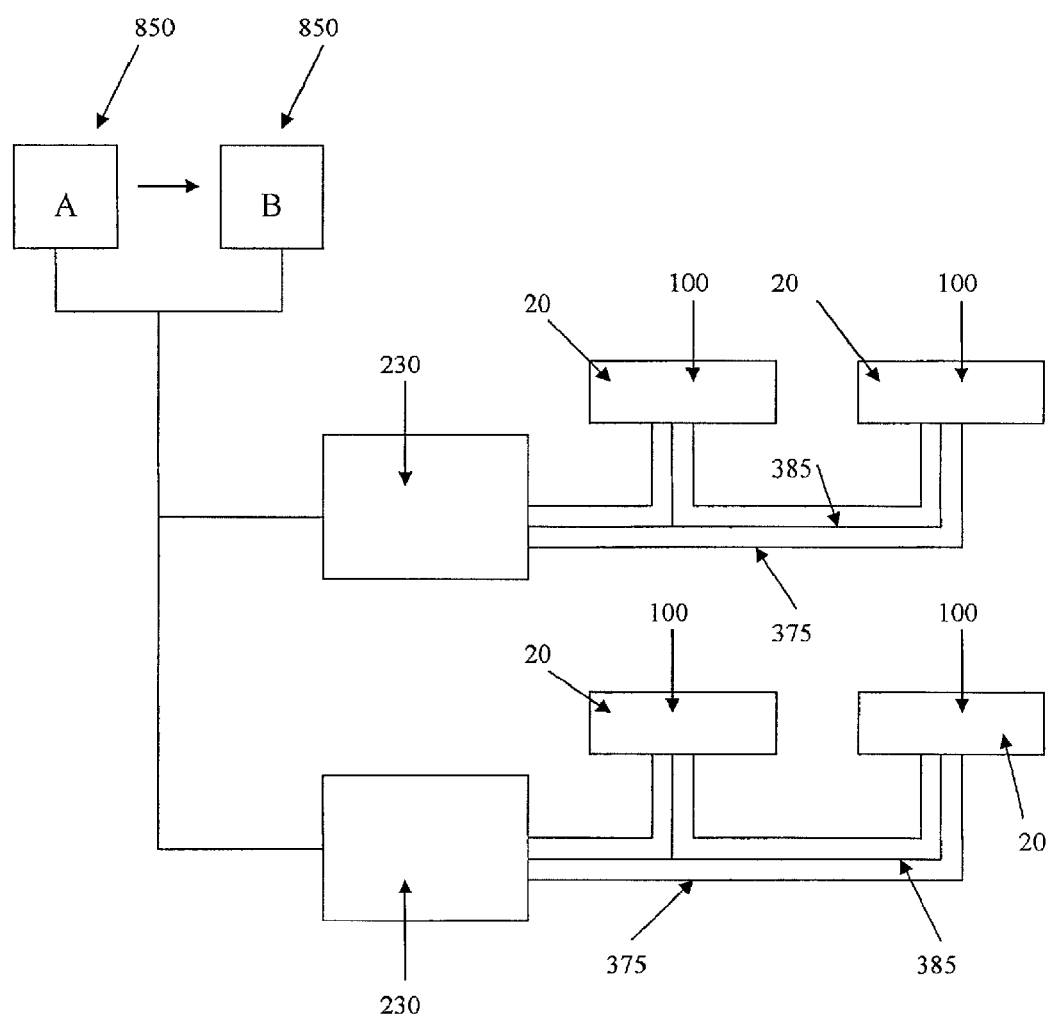
FIG. 45 is a schematic view of an embodiment of a means to compensate for any shifting of transducer frequencies, where a signal generator is initially used to generate one specific frequency or specific frequency range for a transducer(s), is then switched to a different signal generator, that is used to generate another specific frequency or specific frequency range for the transducer(s), and the signal generated from the activated signal generator is sent to an amplifier(s) that is connected to one or more transducers, according to the present invention.

As best shown in FIG. 10, the apparatus (215) in the present invention can be controlled, without limitation, by one or more programmable logic circuit(s) (PLC) or other suitable circuitry, computer, electrical system, or electronics (herein called "PLC or PLC(s)") (315), and related software and program(s), known to those skilled in the art. Without limitation, one or more human machine interface(s) (HMI), screen, or other means to interact with the operator (herein called "HMI or HMI(s)") (320), and related software and program(s), known to those skilled in the art, can be used, without limitation, to convey information as well as allow the operator to set parameters or enter commands. The PLC (315) and HMI (320) can be configured or programmed to enable the operator to, without limitation, enter information into the HMI (320) or PLC (315), program the HMI (320) or PLC (315), or execute command(s). The HMI (320) or PLC (315) can also provide a means, without limitation, for the operator to choose a specific volume or area for the apparatus (215) to administer or deploy the generated aerosol, or choose a specific aerosol deployment time. The HMI (320) or PLC (315) can be programmed to associate one or more values for volumes or areas chosen by the operator with specific aerosol deployment time(s). The menus, software, and programming for the HMI (320) or PLC (315) can be customized for each customer's needs and may include, without limitation, providing the operator with one or more menus that presents a plurality of room numbers or other attributes that the operator can choose, and each room number or attribute is associated with operational parameters and variables such as, but not limited to, liquid temperature(s), volume of the room or targeted area, and the total cycle time that the apparatus (215) would need to operate in order to efficaciously and effectively deploy the aerosol into the chosen room or targeted area. In addition, and without limitation, the HMI (320) or PLC (315) can have a provision in its program(s) or software to change the operational parameters that effect the performance of the apparatus (215) or process due to temperature and humidity values that are either reported to the HMI (320) or PLC (315) by the operator or by automated means known to those skilled in the art. The PLC (315) can, without limitation, include any PID, PID tuning, or PID auto tuning, functions, attributes, or activities. The PLC (315) can, without limitation, control and maintain the temperature of any liquid (30) to any desired or necessary temperature in any reservoir(s), including, but not limited to, the reservoir(s) (40) in which the transducers (10) are located. Without limitation, the PLC (315) can control liquid (30) temperature, by controlling one or more part(s) and component(s) of the apparatus (215) such as, but not limited to any: (a) blower(s), (b) valve(s), (c) heater(s), (d) pump(s), (e) amplifier(s) or other means to power or control the transducer(s) (10), or (f) any means used to cool the liquid (30). Without limitation, the PLC (315) can control liquid (30) temperature, by controlling or communicating with one or more part(s) and component(s) of the apparatus (215) such as, but not limited to any: (a) any thermostat or temperature controlling device (b) blower(s), (c) valve(s), (d) heater(s), (e) pump(s), (f) amplifier(s) or other means to power or control the transducer(s) (10), or (g) any means used to cool the liquid (30).

The PLC (315) can also, without limitation, send or receive or detect any signal, current, or other modes of communication, or their absence, from various components or parts of the apparatus (215) or components or parts related to effective operation of the apparatus (215). These signals, current, or other modes of communication, or their absence, can without limitation, be used by the PLC (315) to, control the apparatus (215) or its components and functions, or monitor the function or status of components or parts of the apparatus (215). Without limitation, the signals, current, or other modes of communication, or their absence, sent by the PLC or to the PLC, can result from the direct or indirect connection and communication of the PLC (315) with components such as, but not limited to, any: (a) current sensor(s) (325), (b) liquid level sensor(s) (305), (c) electronics that power, operate, or control, the transducer(s) (10) (herein referred to as "drive electronics") (645), (d) air/gas temperature sensing thermocouple(s) (650) or other means to sense air/gas temperature, (e) liquid temperature sensing thermocouple(s) (820) or other means to sense liquid temperature, (f) humidity sensor(s) (335), (g) valve(s) (300) (660) that control the flow of liquid, (h) valve(s) (260) (265) (210) (815) (775) that control the flow of any air/gas or aerosol that can flow into or out of a targeted area, (i) wireless transceiver(s) (340) or other signal transmitter(s)/receiver(s).

One or more air/gas temperature sensor(s) (650) can be placed in various locations inside or outside of the apparatus(s) (215). It is preferred, without limitation, that at least one air/gas temperature sensor is positioned in any enclosure or NEMA or IP rated sealed enclosure (345) that has the potential for its internal atmosphere (740) to increase in temperature due to the operation of the apparatus(s) (215). The PLC(s) (315) can, without limitation, use the input from any sensors including, but not limited to, liquid temperature, air/gas temperature, or any other temperature sensor(s), to control activities such as, but not limited to, heating of any liquid and any related activities (30), cooling of any liquid and any related activities (30), or cooling of any part(s), component(s), or atmosphere(s) (740) in any enclosed space(s) found in the apparatus(s) (215) and any related activities. Any valve(s) utilized in the present invention can also, without limitation, be manually controlled and operated, or electronically controlled and operated by one or more PLC(s) (315) in a manner known to those skilled in the art. It is preferred, without limitation, that any electrically or electronically controlled valve(s) that can be utilized for various purposes and at various locations, are solenoid valve(s).

The drive electronics (645) can include, but is not limited to, the following parts or components: (a) one or more power supply(s), (b) one or more signal or waveform generator(s) (herein referred to as "signal generator(s)") (c) one or more amplifier(s), or (d) other electronic equipment, components, parts, and methods for operating or driving the transducer(s) (10) known in the art may also be used. In addition, one or more sensors or means (1045) for determining the liquid level or the amount of liquid in the reservoir(s) (40) in which the transducers (10) are located or in the tank(s) (280) that feeds or supplies liquid (30) to the said reservoir(s) (40), can also be connected or communicate with the PLC (315), in a manner known in the art, and can enable the PLC (315) to determine if a sufficient quantity of liquid is available for any application time or volume of space chosen by the operator.

More specifically, the various signals, current, or other modes of communication, or their absence, received or detected by the PLC (315) can be used, without limitation to determine if the apparatus is functioning or operating within acceptable operational parameters. If the apparatus (215) is not operating within acceptable operational parameters, the PLC (315) can shut down, without limitation, the aerosol generation activity, any blower(s) (180), any means to heat the liquid (30), any means to cool the liquid (30), or any fluid pumps (130). The PLC (315) can also cause the apparatus (215) to shut down and enter a fault or error mode if the apparatus (215) is not functioning or operating within acceptable parameters. These can include, without limitation, the apparatus (215) shutting down all components and displaying a fault or error message on the HMI (320) communicating the source of the fault or error. Faults or errors can result from sources or situations including, but not limited to, insufficient liquid (30) availability to start or complete a cycle, failure to heat the liquid (30) to effective temperatures, overheating of the liquid (30) or components, failure of one or more components evidenced by the lack of current detected by a current sensor, under filling or over filling of the tank(s) (280) or reservoir(s) (40), failure of any drive electronics (645), failure of a transceiver(s) (340). If the apparatus (215) is not functioning or operating within acceptable operational parameters, the PLC (315) can also cause the apparatus (215) to emit an audible as well as visual warning. Without limitation, an audible as well as visual signal can also be communicated to the operator after the apparatus (215) has successfully completed administering the aerosol. The HMI (320) can be located inside, outside, or partially inside and outside of the apparatus (215).

At the end of the operational cycle, or upon a premature shut down of the apparatus (215) due to a failure of the apparatus (215) to function or operate within acceptable operational parameters, the apparatus (215) can create a record or report that can include, but is not limited to, whether or not there were any faults or errors during operation, the source of any faults or errors if they transpired, the lowest and highest recorded liquid (30) temperature that is in the reservoir(s) (40), the total time the aerosol was administered, the date and time the cycle was started, the date and time the cycle was completed, the room number or name if applicable, operator descriptor. The record or report may be stored, without limitation, in the memory of the PLC (315) or HMI (320), or on removable memory media, or other means known to those skilled in the art. The record or data may also be made available for printing or download via a USB port or other means known to those skilled in the art.

The PLC (315) can, without limitation, operate, energize, shut down, suspend, idle, or deactivate, one or more parts or components including, but not limited to any, (a) heater(s), (b) pump(s), (c) transceiver(s), (d) blower(s), (e) valve(s), (f) HMI(s), or (g) drive electronics, numerous times of various duration during the operation of the apparatus (215). This is particularly useful in situations that include, but are not limited to: (a) an insufficient amount of power is available to the apparatus(s) (215) to operate one or more of its parts or components simultaneously, necessitating that one or more parts and components such as, but not limited to, the blower(s) (180) and/or drive electronics (645) are temporarily idled, shut down, turned off, or suspended, to provide or make sufficient power available to the heater(s) (150) or (310), or other parts and components, (b) an insufficient amount of power is available to the apparatus(s) (215) to operate one or more of its parts or components simultaneously, necessitating that one or more parts and components such as, but not limited to, the heater(s) (150) or (310) is temporarily idled, shut down, turned off, or suspended, to provide or make sufficient power available to the drive electronics (645), or other parts or components.

The apparatus (215) can be designed, without limitation, so that all of the components or parts are mounted inside the skin or covering of the machine. For applications where the apparatus (215) is operated from within the area in which the aerosol is deployed or administered, the components or parts can be housed inside a suitable and effective NEMA or IP rated enclosure (345) that can keep any liquid, aerosol, or humidity from reaching or contacting any parts or components, and is accomplished in a manner known to those skilled in the art. The components can be independently or collectively housed in the aforementioned enclosure(s). The exterior or outside walls (755) (the term "wall(s)" can also refer to ceilings and floors in the present invention) of the apparatus (215) can, without limitation, form the NEMA or IP rated enclosure.

The apparatus (215) can, without limitation, be designed so that it can be mobile and easy to move. Without being limited, the apparatus (215) can have features including, but not limited to, a robust frame, robust wheels, bumpers, multiple grab and hoist points, and other design features known to those skilled in the art for designing a mobile apparatus (215) that can be of variable weight and size. The apparatus (215) may be constructed from any material that is compatible, and suitable for use with the liquid (30).

Without limitation, the administered or applied aerosol (200) can be removed from the area(s) in which it is applied during or after the application of the aerosol and can be accomplished with various means know to those skilled in the art. It is preferred, without limitation, that one or more ventilation or exhaust blower(s) (350) be used to pull or push air or gas and aerosol (200) out of the area(s) (210) in which the aerosol is administered or deployed. The said ventilation or exhaust blower(s) (350) can be controlled with one or more PLC(s) either not connected or connected directly or indirectly to the PLC(s) (315) of the apparatus of the present invention. The ventilation or exhaust blower(s) (350) can move any quantity of air/gas at any speed, but should have effective attributes and design for the intended application, all which is known by those skilled in the art. Anything that is removed from the area(s) (210) with the ventilation or exhaust blower(s) (350) can be done so in a manner known to those skilled in the art.

The ventilation or exhaust blower(s) (350) can also be used to bring fresh air into the area(s) in which the aerosol is applied either during or after the administration or deployment of the aerosol. The air or gas that is either removed or brought into the process area(s) can be accomplished in a manner known to those skilled in the art. The blower(s) (350) and related parts may be constructed from any material that is compatible, and suitable for use with the liquid (30).

The liquid (30) in any tank(s) or reservoir(s) (40) can be removed from the apparatus via one or more drain (655) in a manner known in the art. The movement of any liquid (30) out of the apparatus (215) can be controlled with one or more valve(s) (660). It is preferred, without limitation, that the valve(s) (660) is a solenoid valve and can communicate or send signal to one or more PLC(s) (315).

According to an embodiment, the apparatus is designed and constructed so that the aerosol producing transducer(s) (10) and/or their liquid facing surfaces or the surfaces from which there is aerosol-producing output, are able to match the angle of or remain level or parallel with, the surface of the liquid (30) above them. This is made possible by means including, but not limited to, a float assembly that holds, houses, or otherwise positions the transducers, and a gimbaled or articulating arm or holding assembly, as best shown in FIGS. 16-32. This embodiment is important for reasons including, but not limited to, the need to cover the transducers (10) with an effective amount or depth of liquid (30) to prevent the transducers (10) from being damaged due to being covered with an insufficient amount or depth of liquid (30), or to prevent the transducers (10) from being damaged by being operated without liquid above them. (30). This embodiment permits the present invention to be operated on or interfaced with surfaces that are without limitation, flat, semi-angled, angled, sloped, not sloped, or have various orientations. This embodiment does not claim, or attempt to claim, leveling the apparatus (215) by utilizing height adjustable legs or wheels that extend from the apparatus (215) and interface with a floor(s), a table top(s), or other surface(s) on which the apparatus (215) is placed or otherwise resting on, since this feature is taught in (col. 8, line 42-51) by U.S. Pat. No. 5,878,355 (Berg et al. 1996), and in (col. 8, line 50-58) by U.S. Patent No. 6,102,992 (Berg et al. 1998). This embodiment includes interfacing, connecting, positioning, placing, or mounting, the transducers (10) to a means, or a material or object that is connected to a means, that can enable the transducer(s) (10) and/or their liquid facing surfaces or the surfaces from which there is aerosol-producing output, to match the angle of or remain aligned, level, or parallel with, the surface of the liquid (30) above them.

Figure 51:
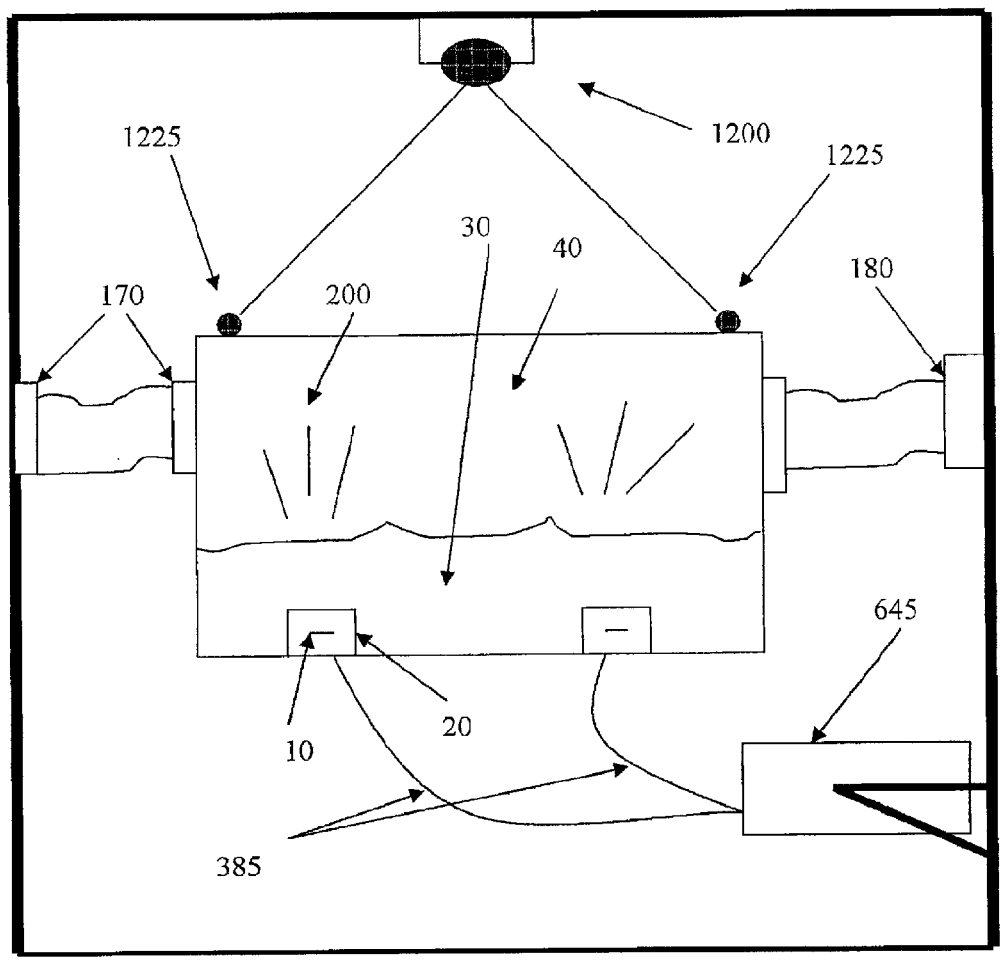
FIG. 51 is a schematic view of an embodiment of the aerosol generator that suspends the tank or reservoir including the transducers from a vertically-elevated support surface.

The first aspect of this embodiment includes, without limitation, mounting, interfacing, or connecting the aerosol generating transducers (10) to a reservoir (40) or into a reservoir (40), or to a means such as, but not limited to, one or more float(s) or float assembly(s) positioned or located in a reservoir (40), and the transducers (10) or reservoir(s) (40) is interfaced, connected, positioned, placed, or mounted, to a means (355), or a material or object that is connected to a means, that can enable the transducer(s) (10) and/or their liquid (30) facing surfaces or the surfaces from which there is aerosol (200) producing output, to match the angle of or remain aligned, level, or parallel with, the surface of the liquid (30) above them. The said means can include, but is not limited to, a ball joint, gimbal, or other means known to those skilled in the art. The components are designed and assembled in a manner known to those skilled in the art, but at least, without limitation, addresses design and assembly issues such that design considerations or variables like center of gravity and balance of the total system are sufficiently addressed and results in an effective apparatus (215). The transducers (10) in this first aspect can be, without limitation, mounted or interfaced with the reservoir(s) (40) through openings in the reservoir(s) in a way that is known to those skilled in the art, or they can be mounted, interfaced, or connected to the reservoir(s) either inside or outside of the reservoir. Without limitation, the reservoir(s) (40) can be fixed in position, free floated, or allowed to freely move. Without limitation, the reservoir(s) (40) can be enclosed, not enclosed, or semi-enclosed, so that air/gas can flow through it and carry the generated aerosol (200) away from the apparatus (215). The said means can also include, but is not limited to, hanging or suspending the entire nebulizing apparatus(s), or at least one or more of the reservoirs (40) in which the aerosol (200) is generated, from any means that would allow them to be freely hung or suspended in air or in a liquid, and have an effective free range of motion so that the transducer(s) (10) are covered with a sufficient or effective amount of liquid (30). It is preferred, without limitation, that if more than one transducer (10) is utilized, they are not only effectively covered with liquid, but that they are covered with an equal depth or amount of liquid (30). This may, without limitation, include suspending or hanging the entire nebulizing apparatus(s) or one or more of the reservoir(s) (40) in which the aerosol (200) is generated, from one or more of any pivot point, swivel, ball joint, gimbal, or other means known to those skilled in the art (1200), as shown in FIG. 51. The one or more attachment points that enable the entire nebulizing apparatus(s), reservoir(s), or chambers to be suspended or hung, are effectively positioned. The means to hang (1200) the reservoir(s) (40) or chambers may also, without limitation, attach to one or more of any pivot point, swivel, ball joint, gimbal, or other similar means known to those skilled in the art (1225), that may also be effectively connected or otherwise directly or indirectly attached to the entire nebulizing apparatus(s), or reservoir(s) (40). The nebulizing apparatus(s), reservoir(s) (40), or any related parts or components in the present invention may be attached to any material or components including, but not limited to, wiring, tubing, piping, or conduits, and they may be, without limitation, flexible. They may also, without limitation, have sufficient flexibility to enable the entire nebulizing apparatus(s) or reservoir(s) (40) to freely hang, suspend, or have an effective free range of motion.

The second aspect of this embodiment includes, without limitation, placing one or more reservoir(s) (herein referred to as "secondary reservoir(s)") (360) inside of another reservoir(s) (herein referred to as "primary reservoir(s)") (40). Transducer(s) (10) are mounted or interfaced to or with the secondary reservoir(s) (360) in a way that is effective and is known in the art, or they can be mounted, interfaced, or connected to the secondary reservoir(s) (360) either inside or outside of that reservoir(s) (360), in a way that is effective and known to those skilled in the art. The secondary reservoir(s) (360) may also be interfaced, connected, positioned, placed, or mounted, to a means (355), or a material or object that is connected to a means, that can enable the transducer(s) (10) and/or their liquid facing surfaces or the surfaces from which there is aerosol (200) producing output, to match the angle of or remain aligned, level, or parallel with, the surface of the liquid (30) above them. The said means can include, but is not limited to a spherical ball joint or gimbal. Without limitation, the secondary reservoir(s) (40) can be free floated or allowed to freely move. Again, the components are designed and assembled in a manner known to those skilled in the art, but at least, without limitation, addresses design and assembly issues such that the center of gravity and balance of the total system are effectively or sufficiently accommodated.

Liquid (30) from the primary reservoir(s) (40) may be pumped into the secondary reservoir(s) (360) in various ways and fill the secondary reservoir(s) (360) so that it an effective depth or amount of liquid (30) is maintained. The walls (365) of the secondary reservoir(s) (360) can be of various heights, including, but not limited to, a height that allows the liquid (30) in the secondary reservoir(s) (360) to attain at least an effective depth. More specifically, the effective liquid (30) depth in the secondary reservoir(s) (360) may be attained by means including, but not limited to, positioning one or more openings or notches in the walls (365) of the secondary reservoir(s) (360) so that a sufficient amount of liquid (30) is able to drain out into the primary reservoir(s) (40) to maintain an effective depth of liquid in the secondary reservoir(s) (360). However, it is preferred, without limitation, that the walls (365) of the secondary reservoir(s) (360) are of a height so that the liquid (30) crests and spills over the walls (365) and back into the primary reservoir(s) (40), to ensure that an effective depth of liquid (30) is maintained. The height of the walls (365) of the secondary reservoir(s) (360) can also be adjusted to compensate for any drain holes that may be present to ensure that the secondary reservoir(s) (360) may effectively drain into the primary reservoir(s) (40) once the apparatus (215) has shut down.

Without limitation, the secondary reservoir(s) (360) can be designed so that a hermitically sealed area or compartment(s) (370) with a sufficient airspace known to those skilled in the art, can connect to or is extended from at least the floor or bottom of the secondary reservoir(s) (360), or even its walls (365), to facilitate the mounting or interface of the transducers (10) and provide an environment where the transducers (10) can safely and effectively operate. Without limitation, the hermitically sealed compartment(s) (370) can extend with flexible wall material and interface with the floor, bottom, or wall(s), of the primary reservoir(s) (40), or even extend through the floor, bottom, or wall(s), of the primary reservoir(s) (40). The flexible wall material is sufficiently flexible to allow the secondary reservoir(s) (360) to effectively move. However, it is preferred without limitation that flexible tubing (375) connect the aforementioned hermitically sealed compartment(s) (370) with any airspace in which the drive electronics (645) or amplifier(s) (230) is located. Wiring from the drive electronics (645) or amplifier(s) (230) can travel through this tubing to the transducer(s) (10). The secondary reservoir(s) (360) and related components, hermitically sealed area(s) or compartment(s) (370), flexible wall material, and tubing, are constructed from any material that is compatible, and suitable for use with the liquid (30). The secondary reservoir(s) (360) can also have sensor(s) to determine if the liquid (30) is either above or below what is desired or needed. In addition, any reference made in the present invention, to any reservoir(s) (40) in which the transducer(s) (10) are located, can also apply to the reservoir(s) (360) and (40) referenced in this second aspect of the embodiment.

The third aspect of this embodiment is preferred, and it includes, without limitation, locating or suspending one or more transducer(s) (10), their wiring, and housing(s) (20), where the housing (20) can be shared or used independently with the one or more transducer(s) (10), with the transducer(s) (10) being independently, interchangeably or collectively mounted to the housing (20), and other associated circuitry, parts and components, (herein referred to as "transducer assembly(s)") (100), at an effective orientation, depth, or distance below the surface of the liquid (30) in the reservoir(s) (40) during their operation. The transducer(s) (10) are a part of the transducer assembly(s) (100) and the transducer assembly(s) (100) may consist of one or more transducers (10). The transducer assembly(s) (100) consists of one or more transducer(s) (10) and their related parts, which are hermitically sealed in a housing (100). One or more transducers (10) and its associated parts may be located in or with a housing (20). There are numerous ways to effectively locate, position, or suspend the transducer assembly(s) (100) in the liquid (30) and includes, but is not limited to locating or suspending the transducer assembly(s) (100) at an effective distance, range, or depth, below the surface of the liquid (30), from one or more, wire(s), cable(s), tube(s), conduit(s), beam(s), or other means, that interfaces with or is attached to various locations, including, but not limited to, the walls or roof of the reservoir(s) (40), or secondary reservoir(s) (360) if it is used, or the walls or roof of the targeted area or sterilization chamber (210). The wire(s) (385) that connects from the transducer(s) (10) or transducer assembly(s) (100) to any drive electronics (645) or amplifier(s) (230) that sends signal to or operates the transducer(s) (10), can be, without limitation, protected from the liquid (30) or aerosol (200) in various ways including, but not limited to, placing, positioning, or running the wire(s) (385) inside or through tubing, pipes, conduit, beams, or other means to contain or embed the wire(s) (375) (herein referred to as "tubing"), and keep the wire(s) (385) separated from any aerosol (200) or any liquid (30). The tubing (375) may be constructed from any material that is compatible and suitable for use with the liquid (30). The wire(s) (385) may also be constructed from any material that is compatible, and suitable for use with the liquid (30). It is even more preferred that flexible tubing (375) connect the hermitically sealed transducer assembly(s) (100) with any airspace, that is hermitically or not hermitically sealed, in which the drive electronics (645) or amplifier(s) (230) is located. The flexible tubing (375) can also, without limitation, connect the environments of the transducer assembly(s) (100) and the drive electronics (645) or amplifier(s) (230) in a manner that is effective and safe, and known to those skilled in the art.

It is also preferred, without limitation, that the said tubing (375) or wire(s) (385) can connect with a suitable, effective, and usable, interface at various locations underneath the transducer assembly(s) (100). The wire(s) (385) and tubing (375) can also connect at other locations of the transducer assembly(s) (100) and in various ways known to those skilled in the art. It is further preferred that the wire(s) (385) or tubing (375) connects or interfaces with the underside of the transducer assembly(s) (100) with a watertight seal in a manner known to those skilled in the art. The wire(s) (385) or tubing (375) and wire(s) (385) can then travel through the wall(s) of the transducers assembly(s) (100) into its interior and connect to the transducer(s) (10). Without limitation, any clamp (390) made of a material that is compatible with the liquid (30), can help to create an effective seal between the tubing (375), and the housing (20) or transducer assembly(s) (100). It is even further preferred, without limitation, that the interface of the wire(s) (385) or tubing (375) with the transducer assembly(s) (100) is effectively or hermitically sealed from at least the inside of the transducer assembly(s) (100) with a means that includes, but is not limited to any, caulk, glue, sealant, or other means known to those skilled in the art, that is compatible and suitable for use with the liquid (30).

It is also preferred, without limitation, that the transducer(s) (10) or transducer assembly(s) (100), is located or suspended at an effective distance, range, or depth, below the surface of the liquid (30) by being directly or indirectly attached to or suspended from, without limitation, one or more buoyant object(s) (400), an interconnection or system of buoyant object(s) (400), or one or more components or parts that are connected or interconnected to one or more buoyant object(s) (400), where the said buoyant object(s) (400): (a) has buoyancy or neutral buoyancy but is completely submerged in the liquid (30), (b) has the ability to float partially submerged in the liquid (30), or (c) have the ability to float on the surface of the liquid (30). Without limitation, the transducer assembly(s) (100) can also be designed so that it can independently, have buoyancy or neutral buoyancy but is completely submerged in the liquid (30), have the ability to float partially submerged in the liquid (30), or have the ability to float on the surface of the liquid (30).

The transducer assembly(s) (100) and the said buoyant object(s) (400) can be designed to rise and fall in the reservoir(s) (40) to match any fluctuations in the depth of the liquid (30) in the reservoir(s) (40) so that an effective orientation and effective depth or distance below the surface of the liquid (30) in the reservoir(s) (40) is constantly maintained during the operation of the transducer(s) (10). It is also preferred, without limitation, that the transducer assembly(s) (100), as well as buoyant object(s) (400) if they are used, in the preferred aspect, be maintained in the proper, designated, or desired position(s), in an X-Y-Z coordinate plane or desired area(s) in the reservoir(s) (40), especially if the liquid (30) level fluctuates. This can be accomplished, without limitation, by connecting the transducer assembly(s) (100) or buoyant object(s) (400) with one or more control arm(s) (440) or other means, which is directly or indirectly connected to or interfaced with the walls, floors, roof, or any surfaces, of the reservoir(s) (40). The control arm(s) (440) or other means can, without limitation, be connected to any buoyant object (400). It is further preferred, without limitation that the control arm(s) (440) be designed in a manner known to those skilled in the art, so it can pivot or move in various directions or orientations. The control arm(s) (440) can also, without limitation, have one or more additional means to allow the transducer assembly(s) to freely pivot or move in various directions or orientations, and without limitation, directly or indirectly interface with the transducer assembly(s) (100). The control arm(s) (440) can be designed to keep the transducer assembly(s) (100) from inadvertently contacting any walls or surfaces of the reservoir(s) (40). The various components and parts that interface with the transducer housing(s) (20), or assist in holding or positioning the transducer housing(s) (20), are constructed from any material that is compatible and suitable for use with the liquid (30).

The control arm(s) (405) or other similar means, can also, without limitation, incorporate sensors into their design or the design of direct or indirectly connected parts and components, or in the design of the walls or ceiling of the reservoir(s) (40) so that the apparatus (215) will shut down or enter a fault or error mode if the control arm(s) (405) or related parts or components rises beyond a predetermined point due to a rise in the depth of the liquid (30) in the reservoir(s) (40), or drops below a predetermined point due to a drop in the depth of the liquid (30) in the reservoir. The type of sensors and their incorporation into the design of the apparatus (215), as well as their communication with the PLC (315) can vary. The various components utilized in this embodiment can be, without limitation, designed and assembled to address issues such as center of gravity and balance of the total system.

It is more preferred, without limitation, that one or more transducer assembly(s) (100) are effectively positioned within the reservoir(s) (40) using a combination of one or more, but not limited to, the following features or attributes: First, the transducer housing(s) (20) is located between or connected to one or more buoyant object(s) (400) of various size, shape, material, and buoyancy. Second, one or more spring clip(s) (415) are attached or connected to each buoyant object(s) (400) and interface, hold, or support the transducer housing(s) (20). Other means may also be used to connect or interface the transducer housing(s) (20) with the buoyant object(s) (400). The spring clip(s) (415) can interface with the transducer housing(s) (20) in various ways. It is preferred, without limitation, that one or more protrusions (410) from the transducer housing(s) (20) engage one or more trough(s), hole(s), or grove(s) of any shape and size present in the spring clip(s) (415). This supports or holds the transducer assembly(s) (100). Third, one or more end plates (420) connect with the buoyant object(s) (400). Fourth, one or more buoyant object(s) (400) or end plate(s) (420) connects with a spacer washer (425), which is connected to a wave washer (505) that also connects with another spacer washer (425). Fifth, a rotating clevis (430) connects to the spacer washer (425) furthest from the buoyant object(s) (400) or end plate(s) (420). Sixth, a shoulder bolt (500) connects with the rotating clevis (430), spacer washer (425), wave washer (505), another spacer washer (425), and end plate(s) (420) or buoyant object(s) (400). Seventh, the interface or connection of the shoulder bolt (500), spacer washers (425), and the wave washer (505), enables the transducer housing(s) (20) and buoyant object(s) (400) to have a free range of motion about the longitudinal axis of the shoulder bolt (500).

Eighth, a second clevis (435) is attached or connected to a pivot arm (herein referred to as "control arm") (440). The second clevis (435) can either move or be fixed in position. Ninth, the second clevis (435) can move by being connected or attached to the control arm (440) in the same manner that the rotating clevis (430) connects to the buoyant object(s) (400) or end plate(s) (420). Tenth, it is preferred, without limitation, that the fixed clevis (435) is held in place to the control arm (440) with bolts or screws. Eleventh, the fixed clevis (435) and rotating clevis (430) are connected and held together with a bolt, pin, or quick release pin (herein referred to as "pin") (490). The pin (490) can have a locking mechanism (495). Twelfth, the interface of the fixed clevis (435), rotating clevis (430), and pin (490), enable the transducer housing(s) (20) to have a free range of motion about the longitudinal axis of the pin (490).

Thirteenth, the control arm (440) has a hole (480) into or through which a torque tube (465) is positioned or connected. Fourteenth, the torque tube (465) interfaces with a washer (445) and bolt (450) from the interior side of the reservoir (40). Fifteenth, the torque tube (465) can have one or more notches or grooves located at any effective location where at least one, but preferably two or more o-rings (455) are seated. Sixteenth, the flange plate (470) fits over and interfaces with the bearing (475). Both the o-rings (455) and flange plate (470) are made of any suitable, effective, and chemically compatible material, and their hardness can vary. Seventeenth, the bearing (475) fits over and interfaces with the torque tube (465). Eighteenth, it is preferred, without limitation, that the torque tube (465) and bearing (475) are interfaced by inserting the torque tube (465) through a pivot hole (625) in the wall of the reservoir(s) (40), from the interior side of the reservoir(s) (40), and inserting the bearing (475) into the same hole (625) from outside of the reservoir(s) (40). Nineteenth, it is further preferred, without limitation, that the flange plate (470) interfaces with the bearing (475) outside of the reservoir(s) (40). Twentieth, the retaining spring plate (485) interfaces with the bearing (475). Twenty-first, the bearing (475) can also, without limitation, be connected or attached to the control arm (440), and the torque tube (465) and bearing (475) can be interfaced by inserting the bearing (475) and related components, through a hole (625) in the wall of the reservoir(s) (40), from the interior side of the reservoir(s) (40), and inserting the torque tube (465) and related components, into the same hole (480) from outside of the reservoir(s) (40). In this situation, the flange plate (470) would interface with the bearing (475) inside of the reservoir(s) (40).

Twenty-second, one or more control arm(s) (440) and any direct or indirectly connected parts or components can be used. The control arm(s) may have any range, angle, or degree of motion or movement. It is preferred, without limitation, that the control arm(s) (440) can have up to thirteen degrees in vertical, arc, or semi-vertical motion. Twenty-third, in essence, the control arm(s) (440) is connected to a torsional tube (445) that transfers motion from the inside of the reservoir(s) (40) through the reservoir(s) (40) walls, to the switch actuator plate (565).

Twenty-fourth, one or more switch actuator plates (565) is interfaced with the torsional tube (445) or bearing (475) and is located at the exterior of the reservoir(s) (40). It is preferred, without limitation, that the switch actuator plate(s) (565) is interfaced with the torsional tube (445). Twenty-fifth, the movement of the control arm(s) (440) directly or indirectly causes the switch actuator plate(s) (565) to move. Twenty-sixth, the switch actuator plate(s) (565) is designed so that its movement causes the actuation of one or more various switch(s) (590). The switch actuator plate(s) (565) can be of many different shapes, sizes, and geometries. Twenty-seventh, any type and number of switch(s) (590) may be used to indicate or communicate any condition(s) or situation (s) in the reservoir(s) (40). Twenty-eighth, the switch(s) (590) may be located anywhere around, in front of, or at any effective proximity to the switch actuator plate(s) (565). It is preferred, without limitation, that the switch actuator plate(s) (565) has one or more protrusion(s), groove(s), or indentation(s) (665), which can interface with and contact or actuate one or more switch(s) (590). Twenty-ninth, one or more switch(s) (590) are interfaced with or connected to one or more base plate(s) (540) which is interfaced with the exterior wall(s) of the reservoir(s) (40) or other surfaces. Thirtieth, the position and meaning of each switch (590) connected to a base plate(s) (540) can vary and be interchanged. It is preferred, without limitation, that three switches (590) are used to indicate or communicate to the PLC(s) (315) the various liquid levels in the reservoir(s) (40). The first switch is the tank full switch (550). Without limitation, the interaction or lack of interaction of the switch actuator plate(s) (565) with this switch (550) can indicate or communicate to the PLC(s) (315) that the liquid (30) level in the reservoir(s) (40) is at or above a designated or specified level. This can, without limitation, cause one or more valves (300) that control the flow of liquid (30) into the reservoir(s) (40) to close. The second switch is the tank refill switch (555). Without limitation, the interaction or lack of interaction of the switch actuator plate(s) (565) with this switch (555) can indicate or communicate to the PLC(s) (315) that the liquid (30) level in the reservoir(s) (40) is at or below a designated or specified level and the reservoir(s) (40) needs refilling. This can, without limitation, cause one or more valves (300) that control the flow of liquid (30) into the reservoir(s) (40) to open or semi-open. The third switch is the tank low level switch (560). Without limitation, the interaction or lack of interaction of the switch actuator plate(s) (565) with this switch (560) can indicate or communicate to the PLC(s) (315) that the liquid (30) level in the reservoir(s) (40) is at or below a designated or specified level. This can, without limitation, cause various components of the apparatus (215) to shut down such as, but not limited to any, pump(s) (130), blower(s) (180), heater(s) (150) or (310), or any drive electronics (645) or amplifier(s) (230).

Thirty-first, one or more cover plate(s) (580) fit over the switch(s) (590). The cover plate(s) can, without limitation, provide rigidity to the various connected components (610) and prevent damage to the switches (590) resulting from possible contact with any objects. The cover plate(s) (580) can also prevent certain shock hazards as well as act as a passive terminal protection for the various switch(s) (590).

Thirty-second, one or more hydraulic dampener(s) are connected to the switch actuator plate(s) (565) or any other components that directly or indirectly connect to the transducer assembly(s) (100), buoyant objects (400), or control/ control arm (440). The hydraulic dampener(s) (585) is a push or pull hydraulic mechanism whose design and function is known in the art. The hydraulic dampener(s) (585) can, without limitation, dampen any rotation or movement of the control arm (440), transducer housing(s) (20), switch actuator plate (565), or other related components, resulting from any shock and vibration that the apparatus (215) may encounter.

It is further preferred, without limitation, that an enhanced design for interfacing one or more transducer(s) (10) with one or more housing(s) (20) in various and modifiable configurations is utilized in the present invention. This design includes, without limitation, the following features. First, each housing (20) that is utilized is constructed so that it has one or more space(s) or recess(s) (600) that interface with one or more transducer(s) (10) as desired. The housing(s) may be made of any suitable material that is not affected by the chemical action of the liquid (30). Suitable materials for the housing(s) (20) may include PVC, polypropylene, and stainless steel, but other suitable materials may be used. It is preferred without limitation that the housing(s) (20) is made from stainless steel. It is preferred, without limitation, that three spaces or recesses (600) are utilized per transducer housing (20), and the center space or recess (620) connects with the other spaces or recesses (600) through one or more hole(s), opening(s), pipe(s), channel(s), or conduit(s) (herein referred to as "holes") (535). The wire(s) (385) that connect the amplifier(s) (230) to the transducer(s) (10), enter the housing(s) (20) through one or more hole(s), opening(s), pipe(s), channel(s), or conduit(s) (605) located anywhere on the side of the housing (20) that faces opposite from the surface of the liquid (30) in the reservoir(s) (40). The wire(s) (385) can, without limitation, enter the center space(s) or recess(s) (620) and travel through the hole(s) (535) to connect with their respective transducer(s) (10). The wire(s) (385) connect with the transducer(s) in a manner known to those skilled in the art.

Each space(s) or recess(s) (600) or their surrounding surfaces (640) can interface with one or more o-rings (635). It is preferred, without limitation, that each space(s) or recess(s) (600) interfaces directly or indirectly with at least three different o-rings and various other parts or components. The first o-ring is the secondary o-ring (515), and it interfaces with a concentric shelf (630) that is built into each space or recess (600). The second o-ring is the outside o-ring (510), and it interfaces with the outside circumference of the compression ring (525). Without limitation, any surface of each housing (20) can have groves or indentations of various construction in which the o-rings can be seated, and the groves are designed and constructed in a manner known to those skilled in the art. The transducer (10) is interfaced or adhered to the barrier (60). It is preferred, without limitation, that the barrier (60) is constructed from glass. The barrier (60) is interfaced with, seated into, or nested on top of the secondary o-ring (515). The third o-ring is the primary o-ring (520), and it interfaces with the liquid (30) facing side of the barrier (60) and any of the inside surfaces (525) of the compression ring (525). The compression ring (525) can be constructed from any suitable material that is not affected by the chemical action of the liquid (30). Suitable materials of the compression ring (525) may include PVC, polypropylene, and stainless steel, but other suitable materials may be used. It is preferred, without limitation that the compression ring (525) is made from stainless steel. Any o-rings, including the secondary o-ring (515), outside o-ring (510), and primary o-ring (520), can have any cross section shape, or hardness, and are constructed from any suitable material that is not affected by the chemical action of the liquid (30). It is preferred, without limitation, that the primary o-ring (520) and secondary o-ring (515) have a double seal cross-section shape, and the outside o-ring (510) has a round cross-section shape, and these various o-rings are constructed from Viton material. The various components, except for the transducer (10) and barrier (60) are assembled and compressed together to form a watertight seal in various ways known to those skilled in the art. Without limitation, tub walls (530) may also interface with any housing(s) (20).

The control arm(s) (405), transducer assembly(s) (100), reservoir(s) (40), and other related component(s), can be designed, so that when the reservoir(s) (40) is drained, the buoyant object(s) (400), transducer assembly(s) (100), control arm(s) (405), or other connected parts or components will move down into or onto, one or more of any means to sufficiently and effectively prop, position, stabilize, or hold, the buoyant object(s) (400), transducer assembly(s) (100), control arm(s) (405), or other connected parts or components, at any angle or orientation, within the reservoir(s) (40). This may include, without limitation, any mechanism(s), apparatus(s), structure(s), inset mold(s), nest(s), groove(s), indentation(s), or protrusion(s) (herein referred to as "structure") (1050) that can, interface with the buoyant object(s) (400), transducer assembly(s) (100), control arm(s) (405), or other connected parts or components, or without limitation, partially, generally, roughly, or exactly, mirror or generally mirror, at least a sufficient amount of the contours or geometry of the buoyant object(s) (400), transducer assembly(s) (100), control arm(s) (405), or other connected parts or components, to be effective. The said mold(s), inset(s), nest(s), groove(s), indentation(s), or other structures can be designed to drain if necessary or when desired, in a manner known to those skilled in the art. When the reservoir(s) (40) is drained the buoyant object(s) (400), transducer assembly(s) (100), control arm(s) (405), or other connected parts or components, can rest, without limitation, at any angle or orientation to provide an angle that is steep enough for any deposited liquid to move off or drain from any surfaces of the transducer assembly(s) (100), including any surfaces above or interfaced with the transducers(s) (10), into the reservoir(s)'s (40) drain(s) (655).

According to an embodiment, the protective barrier (60) that interfaces with the transducer(s) (10) can be polished on one or more sides. When a protective barrier (60) is ground to a specific thickness, its ground sides may have an appearance or characteristics that can include, but is not limited to, unpolished, rough, hazy, or frosted due to the grinding process. This is, without limitation, especially true with protective barriers (60) that are constructed from any type of glass that is ground. The prior art has taught the use of protective barriers (60), including glass, in U.S. Pat. No. 3,433,461 (Scarpa et al.), U.S. Pat. No. 3,729,138 (Tysk), U.S. Pat. No. 4,109,863 (Olson et al.), and U.S. Pat. No. 4,976,259 (Higson et al.), which are incorporated herein by reference in their entirety, including any references cited therein. However, the prior art is silent with respect to the use of a polished barrier(s). It can be assumed that the protective barriers (60) mentioned in the prior art were ground to their specific thicknesses but not polished after being ground. Polishing the liquid side of the protective barrier (60) can, without limitation: (a) reduce or eliminate the texture or surface features that can catch or hold undesirable foreign objects or debris, (b) provide a surface that easier to clean and/or be more effectively cleaned, (c) reduce the amount of texture or surface features that may promote the build up of mineral deposits, (d) promote easier movement of liquid (30), foreign objects, or debris, off of the protective barrier (60) surface(s) when the reservoir(s) (40) is emptied. Polishing the side of the protective barrier (60) that is not in contact with the liquid can, without limitation: (a) reduce surface variability on the side of the protective barrier (60) that interfaces with any adhesive (70), which can reduce the variability in the thickness of the adhesive (70) between the protective barrier (60) and transducer(s) (10) which may in turn, without being limited, reduce variability in certain energy transmission characteristics or other transmission related issues. An unpolished protective barrier (60) surface that interfaces with an adhesive (70) can enhance the bonding between the protective barrier (60) and the transducer(s) (10) for reasons known to those skilled in the art. The protective barrier (60) in the present invention can, without limitation, be polished or unpolished on both the liquid (30) and transducer (10) facing sides. However, it is preferred, without limitation, that the protective barrier (60) is polished on the side that faces the liquid (30) and remain unpolished on the side that faces the transducer(s) (10). Polishing in this embodiment can vary in ways including, but not limited to its, depth, completeness, precision, quality, and accuracy.

According to an embodiment, the apparatus can be designed and constructed so that more than one aerosol producing transducer (10) is surrounded, enclosed, or encircled by one or more walls or barriers (herein referred to as "tub walls") (530). However, if only one transducer (10) is used in the present invention, it may also be surrounded, enclosed, or encircled by one or more tub walls (530). This embodiment should not be confused with what is taught in U.S. Pat. No. 5,300,260 (Keshet et al., 1993) in (col. 3, line 15-21) and (col. 3, line 50-51), which is incorporated herein by reference in its entirety, including any references cited therein. Keshet et al., taught the positioning of baffles between each aerosol producing transducer as a means to suppress waves. The tub walls (530) in this embodiment are not positioned between individual transducers (10) so as to not conflict with U.S. Pat. No. 5,300,260. The performance of the transducers (10) in the present invention was found in the laboratory not to be adversely effected by waves created by neighboring, or even closely positioned transducers (10). The art taught by Keshet et al. is inapplicable to the present invention. The walls (10) in the present invention are intended to contain the liquid (30) above and around the transducers (10) and use the heat generated by the transducer(s) (10) to heat the liquid (30) above and around the transducer(s) (10), as well as the liquid (30) at the liquid (30) surface above the transducers (10). This embodiment may, without limitation, eliminate the need for any additional means to heat the liquid in certain circumstances known to those skilled in the art. This embodiment utilizes teachings from the book titled, "Aerosol Technology" by William C. Hinds (1982), which is incorporated herein by reference in its entirety, including any references cited therein, where it is taught that ultrasonic aerosol generating transducers can heat the surrounding liquid (page 382). This embodiment can without limitation, offer the added benefit of enabling the transducers (10) to quickly heat the surrounding liquid (30) and liquid (30) surface above them. The tub walls (530) can also, without limitation, be designed or modified in a manner known to those skilled in the art so that the liquid (30) contained within the tub walls (530) is able to reach or experience an effective exchange with the surrounding liquid (30) outside of the tub walls (530), so that the liquid (30) within the tub walls (530) is not able to either exceed a given temperature or drop below a given temperature. Without limitation, the tub walls (530) can be continuous or non-continuous, and they can have one or more openings (670) of various size, shape, and in various locations. The tub walls (530) can, without limitation, be sealed or partially sealed, interfaced or not interfaced, interlocked either tightly or loosely, or be unsealed. The tub walls (530) can without limitation, interface completely or intermittently, or not interface, with the surfaces of the transducer assembly(s) (100) or the housing (20), and the height of the tub walls (530) can also vary. Any gap or distance (925) may exist between the tub walls (530) and any surfaces of the transducer assembly(s) (100) or the housing (20). It is preferred without limitation, that the tub walls (530) extend to an effective height above the surface of the liquid (30). Without being limited, one or more notches can also be cut into the top of the walls and can be of various size, shape, and in various locations. The tub walls (530) and associated parts may be constructed from any material that is compatible, and suitable for use with the liquid (30). The tub wall(s) (530) can also be designed and constructed to perform the same function(s) as the buoyant object(s) (400), or share any of the same features of the buoyant object(s) (400). The tub wall(s) (530) can, without limitation, have any density, buoyancy, air space, thickness, size, shape, and can be injection or blow molded. Without limitation, the tub wall(s) can be directly or indirectly positioned or interfaced anywhere with and in any orientation to the transducer assembly(s) (100) or housing(s) (20). The tub wall(s) (530) can have any number of vertical or angled voids, holes or openings (herein referred to as "openings") (920) above the transducer(s) (10) or transducer assembly(s) (100). The openings (920) can, without limitation, allow any emitted pressure (energy) resulting from the operation of the transducer(s) (10), to reach the surface of the liquid (30) in the reservoir(s) (40). The openings (920) can be any size, shape, or have any angle or cant.

According to an embodiment shown in FIGS. 53 and 36, the apparatus can be designed and constructed so that air/gas that surrounds the apparatus (215) or outside air/gas that is pulled into the apparatus (215) for purposes including, without limitation, removing the aerosol (200) that is generated by the transducer(s) (10), from the apparatus (215) and into the intended or targeted area (210), is filtered before it enters the apparatus (215), or at least before the air/gas reaches the aerosol generation chamber (40). One or more filters (675) of various kinds and function, may be used, but should be at least sufficient for the intended amount or degree of filtering that is desired or needed, and the correct filter (675) that is used for a specific application is known to those skilled in the art. It is preferred, without limitation that the filter(s) (675) is located at any location where the air/gas is drawn or pulled into the apparatus (215) by a blower or fan or other means (180) to move the air/gas or aerosol (200). It can be located either on the inside or outside of the apparatus (215) and sufficiently interfaced with the apparatus (215) in a manner that is known to those skilled in the art. The filter(s) (675) can, without limitation, prevent or limit dust or debris contamination inside of, on, or in: (a) any liquid (30), (b) any pipe(s) (685) that are used to construct the aerosol generating apparatus (215) through which the air/gas is moved, (c) the fan or blower or other source of pressurized air (180), (d) the chamber (40) in which the transducer(s) (10) are located, or (e) the introduction of various types of contaminates into the intended or targeted area (210) in which the aerosol (200) is deployed. The filter(s) (535) are not used in any configuration(s) or application(s) involving a "closed loop system" where the air/gas or aerosol (200) that is deployed from the apparatus (215) is then recirculated back to the apparatus (215) through one or more return conduit(s) or pipe(s) (240). This avoids any conflict with: (a) (col. 3, line 19-24), (col. 11, line 14-17) and (claim #21) of U.S. Pat. No. 5,878,355 (Berg et al. 1996), and (b) (col. 3 line 26-31), (col. 11, line 20-23) and (claim #8) of U.S. Pat. No. 6,102,992 (Berg et al. 1998), both of which are incorporated herein by reference in its entirety, including any references cited therein. The filter(s) (675) can be, without limitation, disposable. One or more protective covers (680) may also be directly or indirectly connected to the filters (535). The protective covers (680) may be positioned, or installed anywhere in the air/gas stream before the air/gas enters the filter(s). One or more protective cover(s) (680) may also be integrated into any external walls (755) of the apparatus and may be constructed from any material that is compatible, and suitable for use with the liquid (30).

According to an embodiment, the apparatus (215) can be designed and constructed so that one or more tank(s) (herein referred to as "intermediate tank(s)") (695), are connected between the one or more tank(s) (280) in which liquid (30) is stored and the reservoir(s) (40) they feed or supply, in which transducer(s) (10) are located. The intermediate tank(s) (280) can, without limitation, perform the function of a check or failsafe device or design, and prevent the reservoir(s) (40) in which the transducers (10) are located from being overfilled with liquid (30) if one or more valve(s) (300) from the tank(s) (280) that feed or supplies the reservoir(s) (40) fail in an open or semi-open position. The intermediate tanks (695) can have one or more of various types of valves (300) that include, but are not limited to, float valves, or solenoid valves. The valve(s) (300) can control the flow of either inbound or outbound liquid (30). The said valve(s) (300) can, without limitation, be actuated by a PLC (315), or by one or more sensor(s) (305) located in the intermediate tank(s) (695) or reservoir(s) (40) in which the transducer(s) (10) are located, and is accomplished in a manner known in the art. The valve(s) (300) are also installed, and connected to a PLC (315), if applicable, in a manner known to those skilled in the art. The valve(s), immediate tank(s), and associated parts may be constructed from any material that is compatible, and suitable for use with the liquid (30).

According to an embodiment, the apparatus (215) can be designed and constructed so that one or more liquid containment tank(s) (705) is connected to various parts, components, or areas of the apparatus including, but not limited to, the fill pipe(s) (295), blower or fan housing(s) (180), internal catch pan(s) or basin(s) (700), reservoir(s) (40) in which the transducers (10) are located, or pressurized air pipe(s) or conduit(s) (685). Without limitation, the aforementioned liquid containment tank(s) (705) is designed to collect excess, spilled, leaked, coalesced, or other undesired liquid (30). It can be connected to the main drain (655) and valve (660) used to drain the apparatus, or it can have its own drain pipe and valve. The positioning of the liquid containment tank(s) (705) as well as its shape and capacity can vary. A liquid level sensor (305) may be used to detect the presence of any liquid (30) or the depth of the liquid (30) in the containment tank(s) (705). The said liquid level sensor (305) may communicate with a PLC (315) and cause the apparatus to shut down or enter a fault or error mode if the if the liquid level (30) exceeds a defined depth. The liquid containment tank(s) (705) and associated parts may be constructed from any material that is compatible, and suitable for use with the liquid (30). Without limitation, any pipe(s) (685) carrying inbound or outbound air or aerosol, as well as the blower(s) (180) and the pipe(s) (685) that connect it to the reservoir(s) (40) in which the transducers (10) are located, can be canted or angled back toward the reservoir(s) (40) in which the transducer(s) (10) are located to carry out various functions such as, but not limited to, helping collect any liquid (30) from those areas.

According to an embodiment, the apparatus can be designed and constructed so that it has one or more means to control the temperature of the liquid (30) in the various reservoir(s), which includes, but is not limited to, preventing the temperature of the liquid (30) in the reservoir(s) (40) in which the transducers (10) are located, from exceeding the maximum desired, established, or required operating temperature for that liquid (30) or particular process in which the liquid (30) is being used.

As previously discussed, the prior art has taught the heating of the liquid (30) in various ways including, but not limited to, heating the liquid (30) from the heat that is imparted into the liquid (30) during the operation of the transducers (10). It is obvious to one skilled in the art, that the air or gas that is used to remove the generated aerosol (200) from the reservoir(s) (40) in which the transducers (10) are located, can contribute to the removal of heat from the liquid (30). However, this pressurized air/gas flow can only remove a certain quantity of heat and is affected by factors including, but not limited to, the surface area of the liquid (30) in the reservoir(s) (40), and the volume and velocity of air/gas that moves over that surface area. If more heat is imparted into the liquid (30) than is removed over time, the liquid (30) will continue to rise in temperature.

The means to control or prevent the temperature of the liquid (30) in the reservoir(s) (40) in which the transducers (10) are located, from exceeding the aforementioned maximum desired, established, or required operating temperature, includes without limitation, a means to cool the liquid (30) by pumping or otherwise moving the liquid (30) that is in the reservoir(s) (40) in which the transducer(s) (10) are located, or any other liquid (30) that could possibly have contact with the liquid (30) in the reservoir(s) (40) in which the transducer(s) (10) are located, through a heat exchanger, cooling fins, cooling plate, cooling block, chiller, chilling or cooling apparatus, or other means known in the art (710), to remove heat from the liquid (30). It is preferred that this means includes pumping or moving the liquid (30) from the reservoir(s) (40) in which the transducers (10) are located, through cooling fins, chill block, or heat exchanger that is located in the path of the pressurized air/gas that is used to move the generated aerosol (200) away from the apparatus. The means to cool the liquid (30) can also interface or directly interface with the reservoir(s) (40) in which the transducers (10) are located and can include, but is not limited to, the interface or insertion of chill coil(s) or chill block(s) directly into the reservoir(s) (40) in which the transducers (10) are located. The means mentioned in this embodiment to cool the liquid (30) and associated parts may be constructed from any material that is compatible, and suitable for use with the liquid (30). The PLC(s) (315) can monitor the temperature of the liquid (30) in the reservoir(s) (40) with input from one or more liquid temperature sensing device(s) (820). The PLC(s) (315) can activate whatever means necessary to start, maintain, or stop any liquid (30) cooling activities or actions, to maintain any desired or necessary temperature.

An additional aspect of this embodiment includes, without limitation, insulating the reservoir(s) (40) in which the transducer(s) (10) are located, in various ways including, but not limited to, interfacing or applying any type of insulation material (760) to any surfaces of the reservoir(s) (40), or using a double wall construction (765) for the reservoir (40) where the said walls are separated with a layer of air, or other means known to those skilled in the art. Without limitation, insulating the reservoir(s) (40) can be useful in environments where it is important to increase heating efficiency or capacity and diminish heat loss from the system.

According to an embodiment illustrated in FIGS. 33 and 34, the apparatus can be designed and constructed so that it can be remotely communicated with and controlled, by anyone or any means. Without being limited, one or more PLC(s) (315) that control one or more parts of the apparatus can also communicate with or be controlled by any other apparatus and their PLC(s). More specifically, and without limitation, the remote control and communication with the apparatus can be accomplished by means such as, but not limited to, any radio frequency or amplitude, any electrical frequency or amplitude, any light frequency or amplitude, any digital or analog data packet, or by any directly or indirectly connected wire(s), which includes fiber optic wire(s), or any combination of the of the said means. Without limitation, any data, commands, or information can be sent and received by the apparatus and communicated between the apparatus and one or more additional means to send and receive any data, commands, or information. Commands, can include, but are not limited to, a command for the apparatus to start or to end an aerosol generation or deployment cycle. Communicated information or data can include, but is not limited to, the apparatus communicating its current operational status or condition, as well as liquid (30) level and temperature. It is preferred, without limitation, that the apparatus communicates by using one or more radio transceiver(s) (340) that is connected to one or more PLC(s) (315), that is connected to one or more HMI(s) (320), and communicates with one or more remote radio transceiver(s) (315) that is connected to one or more remote PLC(s) (315) which are attached to one or more remote HMI(s) (320) or other parts or components. The one or more antenna(s) (720) connected to the radio transceiver(s) (340), can be located anywhere on or in the apparatus (215), and can be constructed from various materials. The antenna(s) (720) and any related parts may be constructed from any material that is compatible, and suitable for use with the liquid (30). It is preferred, without limitation, that the radio transceiver(s) (340) and antenna(s) (720) be located within any NEMA or IP rated or hermitically sealed container(s) (345) that is constructed from polymer that is compatible, and suitable for use with the liquid (30). Within this embodiment, and without limitation, a plurality of apparatuses, including, but not limited to, apparatuses that are similar in process, or apparatuses that are similar or identical to the apparatus (215) of the present invention, can operate in the same, connected, or shared volume of space, and communicate information including, but not limited to their condition or status of their systems or the apparatus in general, to all of these apparatuses, so that if one apparatus has a problem, or enters into a fault or error condition or state, all of the other apparatuses can also shut down, or at least relay the incident to one or more remote PLC(s) (315), HMI(s) (320) which the operator can monitor. This embodiment also offers many advantages including, but not limited to, reducing or eliminating the chance of accidental exposure to the aerosol (200) from an apparatus (215) that is operating within the same environment (210) in which the aerosol (200) is applied.

According to an embodiment, and without limitation, the apparatus (215) can be designed and constructed so that it has one or more sensors (3530), or the means for indirect or direct communication with one or more sensor(s) (3530), or one or more PLC(s) (315) which are connected to one or more sensor(s) (3530), to determine if an effective or sufficient amount of aerosol (200) has been applied to the targeted area (210) and/or surfaces.

In the first aspect of this embodiment, each sensor (3530) can, without limitation, consist of at least two parts including, but not limited to, a light source (725) and a light sensor (730), known to those skilled in the art. The light source (725) and light sensor (730) can be directly or indirectly connected, or they can be placed or positioned independent from one another. The distance between the light source (725) and light sensor (730) can be any distance, but should be at least an effective distance. The light source (725) and light sensor (730) can be, without limitation, separated by a distance of one (1) foot or less. However, it is preferred, without limitation, that the light source (725) and light sensor (730) are at separated by a distance of one (1) foot or more. It is more preferred, without limitation, that the light source (725) and light sensor (730) are separated by a distance of two (2) feet or more. It is even more preferred, without limitation, that the light source (725) and light sensor (730) are separated by a distance of four (4) feet or more. Without being limited, any effective light source (725) and any effective light sensor (730), known in the art, may be utilized in the present invention. Each sensor(s) can, without limitation, consist of at least one of any effective laser, of any power or class type, for a light source (725), and at least one of any photoelectric sensor, of any type and sensitivity (730), for a light sensor (730). The one or more light source(s) (725) and one or more light sensor(s) (730) that are utilized can be, without limitation, configured or positioned so that the light sensor(s) (730) receives light in various ways such as, but not limited to, directly from one or more light source(s) (725), indirectly from one or more light source(s) (725), or from any reflected light that is generated from one or more light sources(s) (725). Any light that is reflected back to the one or more light sensor(s) after being generated by any light source(s) (7225) may reflect off of one or more of any surface(s) or substance(s) such as, but not limited to any, aerosol (200), reflecting surface(s), or mirrored surface(s). The aerosol (200) may be of any effective density and size. Without being limited, the one or more light source(s) (725) and light sensor(s) (730) may be positioned in any effective direction, angle, orientation, configuration, or position. If light from one or more reflected surface(s) is utilized, the one or more surface(s) from which the light is reflected back to the light sensor(s) (730) can be, without limitation, positioned at any effective distance and any effective orientation or angle from the one or more light sensor(s) (730) and the one or more light source(s) (725). The reflective surface(s) may be, without limitation, any suitable size and shape.

The emitted light or energy, or light source (725) can have, without limitation, any traits or attributes including, but not limited to, any: (a) intensity(s), (b) brightness, (c) period(s), (d) frequency(s), type of light(s), and (e) wavelength(s). The one or more light source(s) (725) and light sensor(s) (730) can, without limitation, be controlled and/or communicate with one or more of any digital, electronic, or analog, controller(s) such as, but not limited to, any PLC. The means to sense the light (730) can, without limitation, vary widely in its sensitivity and ability to sense any kind of light consisting of any traits or attributes including, but not limited to, any: (a) intensity(s), (b) brightness, (c) period(s), (d) frequency(s), type of light(s), and (e) wavelength(s). The means to sense the light (730) can also have various capabilities known in the art, including, without limitation, the ability to have any adjustable sensitivity and trigger level(s), or the ability to communicate with a PLC(s) (315) or other components. The light sensor(s) (730) can, without limitation, indicate to or communicate with any PLC(s) (315) if or when it either receives or ceases to receive any trait or attribute pertaining to light such as, but not limited to, any desired or set level of light stimulus or light intensity. The said communication can be accomplished in various ways known in the art. It is preferred, without limitation, that the PLC(s) (315) is indicated or receives information about the status of any light generated by the light sensor(s) (730), in various ways including, but not limited to any, electrical signal, level or intensity of any electrical signal, or lack of any electrical signal(s) from the light sensor(s) (730). This communication can, without limitation, result in various actions or combination of actions, such as, but not limited to: (a) shutting down any drive electronics (645) or amplifier(s) (230), (b) shutting down any blower (180) or flow of pressurized air, or (c) shutting down any apparatus (215).

Without limitation, an effective or sufficient amount of administered aerosol (200) in this embodiment is indicated by its causing any, disruption, diminishment, decrease, or cessation, of the light that is emitted from the light source(s) (725), before it reaches any light sensor (730). The effective, sufficient amount, or specified quantity, of administered aerosol (200) can vary for any intended or unintended reasons or designs, and the trigger or sensitivity levels for the light sensor(s) (730) can, without limitation, be varied, calibrated, or adjusted, to any amount or level of light disruption, for each situation or any level of aerosol that is equated with an efficacious outcome.

In the second aspect of this embodiment one or more of the sensor(s) (3530) can, without limitation, sense or measure any relative humidity level or humidity level, in a manner known to those skilled in the art. Without being limited, the humidity sensor(s) (4090) can have various capabilities and attributes including, without limitation, varying sensitivity, the ability to have any adjustable trigger level(s), and/or the ability to be controlled and/or communicate with one or more of any digital, electronic, or analog, controller(s) such as, but not limited to, any PLC. The humidity sensor(s) (4090) can, without limitation, indicate or communicate to any PLC(s) (315) any relative humidity data it collects, which can be accomplished in a manner known to those skilled in the art. The relative humidity sensor(s) (4090) can also, without limitation, receive or send any signal of any kind, to or from any other components. It is preferred, without limitation, that the PLC(s) (315) is indicated or receives information about the status of any humidity that is detected in the targeted area (210), in various ways including, but not limited to, receiving any, electrical signal, level or intensity of any electrical signal, or lack of any electrical signal(s) from the humidity sensor(s) (4090). This communication can, without limitation, result in various actions or combination of actions, such as, but not limited to: (a) shutting down any drive electronics (645) or amplifier(s) (230), (b) shutting down any blower (180) or flow of pressurized air, or (c) shutting down any apparatus (215).

Also, without limitation, one or more of any PLC(s) (315) can be programmed to have delays of various length of time after receiving any, data, communication, or signal, to initiate actions such as, but not limited to: (a) shutting down any drive electronics (645) or amplifier(s) (230), (b) shutting down any blower(s) (180) or flow of pressurized air, or (c) shutting down one or more of any apparatus(s) (215), after receiving any signal(s), data, or communication from any sensor(s) such as the light sensor (730) and/or the relative humidity sensor(s) (4090) or any other related components or sensor(s).

According to an embodiment, the apparatus can be designed and constructed so that it can without limitation, measure, determine, or sense, the amount of liquid (30) that is in any tank or reservoir. Without limitation, this information or data may be used, in concert with or without a PLC (315), to: (a) communicate to the operator whether there is either a sufficient or insufficient amount of liquid (30) to execute a chosen operational cycle time, (b) communicate to the operator whether there is either a sufficient or insufficient amount of liquid (30) to execute an operational cycle time associated with a specific volume of space or other attribute(s) chosen by the operator, (c) communicate to the operator the quantity of liquid (30) or at least the minimum quantity of liquid (30), expressed in units of measure, which may be necessary to add or make available to the apparatus so that it may effectively or successfully complete a chosen or desired operational cycle. It is preferred, without limitation, that the units of measure in the present invention include, but are not limited to, any liquid (30) volume quantities expressed in, standard units of measure, imperial units of measure, English units of measure, units of measure according to the metric system, or units of measure according to System International (SI) units. French Patent No. FR2860721 (Schwal et al.), which is incorporated herein by reference in its entirety, including any references cited therein, taught that a fogging apparatus can notify the operator if an insufficient liquid (30) quantity is available (pg. 6 line 15-25 and pg. 10 line 10-25) and when it is necessary to replace a cartridge (290) (pg. 10 line 15-25). However, FR2860721 (Schwal et al.), only mentioned that an indication would be made by the fogging apparatus to the operator to replace an interfaced cartridge (290) (pg. 10 line 15-25), or additional possibly interfaced cartridges (290) (pg. 7 line 3-10), but it was silent with respect to the apparatus itself determining the amount of liquid (30) that is needed to properly or effectively fill the apparatus, and communicating the exact number of a plurality of cartridges (290) that may be needed to fill the apparatus with liquid (30) either partially or to full capacity so that it can successfully and effectively complete a predetermined operational cycle. Therefore, it is more preferred, without limitation, that the units of measure communicated can also include more than one or a plurality of cartridges (290) with a known quantity of liquid (30) that is needed to provide the apparatus with a sufficient quantity of liquid (30) for it to effectively or successfully complete its operational cycle time. It is even more preferred, without limitation, that the units of measure include, any units of measure, including any number of cartridges (290) as long as it is a plurality of cartridges. The apparatus can, without limitation, communicate to the operator the minimum quantity of liquid (30) needed to complete an operational cycle, as well as the quantity of liquid (30) that would be needed to fill the apparatus to capacity. Again, the quantity of liquid (30) may be expressed in any units of measure including, but not limited to, the number of cartridges (290). Information or data can be communicated to or from the apparatus with any means known to those skilled in the art including, but not limited to, human-machine-interface(s) (HMI) (320), terminal(s), remote terminal(s), any button(s) and associated light(s), screen(s), or audible signal(s). The apparatus can, without limitation, require the operator to acknowledge one or more prompts to add a certain amount of liquid (30) or a certain number of cartridges (290) as well as one or more prompts to verify if the action was undertaken. This can be accomplished with an HMI (320) or other means known to those skilled in the art. More specifically, this embodiment includes without limitation, the apparatus having the ability to sense, detect, or determine, with one or more sensor(s) or other effective means, any: (a) liquid (30) level, (b) liquid (30) depth, or (c) amount of liquid (30) in any tank(s), reservoir(s) (40), or other places where liquid (30) is held and available to the apparatus, and communicate that information to a PLC(s) (315). This may be accomplished in a manner known to those skilled in the art. It is preferred, without limitation, that one or more float sensor(s) (305), which can be located in various locations in the apparatus, be utilized for this purpose. They can be constructed from any material that is compatible, and suitable for use with the liquid (30), and their use and configuration are known to those skilled in the art. Any data, information, or signals, can be sent from the said means to sense, detect, or determine the liquid (30) level, liquid (30) depth, or amount of liquid (30) available, and can be sent or communicated, without limitation, to various places or means including, but not limited to, one or more PLC(s) (315) or HMI(s) (320). The PLC(s) (315) or HMI(s) (320) can be programmed in a manner known in the art to use the inbound information, data, or communication to control or interact with the apparatus, as well as communicate information to or from the operator. The PLC(s) (315) can, without limitation, be programmed so that the apparatus (215) will enter into a fault or error condition, or shut down one or more functions, and communicate an audible or visual signal to the operator, as well as communicate with any other PLC(s) (315), if the apparatus receives a command to operate for a certain amount of time or apply aerosol (200) to a certain volume and the PLC(s) (315) determines that an insufficient amount of liquid (30) is available.

According to an embodiment, the apparatus (215) can be designed and constructed so that it will not, without limitation, generate, create, or deploy aerosol (200), when the liquid (30) that is in or available to the reservoir(s) (40) in which the transducer(s) (10) are located cannot be used, administered, or deployed, for reasons including but not limited to: (a) the fluid (30) has exceeded the time or date within which it can be efficaciously used, or (b) the fluid (30) has reached a point in time or date where it has degraded or aged to a point where its use or application would be ineffective, unaccepted, unauthorized, or illegal. The present embodiment does not encompass what is taught in French Patent No. FR2860721 (Schwal et al.), which is incorporated herein by reference in its entirety, including any references cited therein. That patent includes placing or fitting a container(s) or cartridge(s) (290) of single use that is filled with the liquid (30) to be fogged or diffused, on or with an aerosol (200) dispensing device, and reading an identifier on the said container(s) with a reader (pg. 2, line 33-36) to determine its year/date (pg. 9 line 15-20) and suspending the operation of the apparatus if there is non-conformance, or in other words, the identifier(s) is determined to be associated with a container(s) that has expired. However, this embodiment, without limitation, also encompasses the liquid (30) that is in any cartridge(s) (290) (FIG. 12) that interfaces with the apparatus after the cartridge(s) (290) has been read and its use is approved, and the cartridge(s) (290) is opened or its seal is compromised, allowing the liquid (30) to be used or made available to the apparatus. This is important for reasons including, but not limited to, the liquid (30) can have a certain shelf life or period of effectiveness while in a closed container/cartridge (290), but once the container/cartridge (290) is opened, and exposed to its surrounding environment, or diluted, the shelf life or effective period of use is diminished or shortened. This can, without limitation, necessitate the monitoring, measuring, tracking, calculating, comparing, (herein "measuring"), the time that the liquid (30) can be utilized in the present invention until it cannot be used for various reasons known to those skilled in the art. Measuring the time that the liquid (30) can or cannot be used or its useful lifespan, can be accomplished by using a PLC(s) (315), or other mechanism or device known to those skilled in the art. The apparatus (215) in this embodiment can possesses various means to determine the useful lifespan of a liquid (30) or the length of time a liquid (30) can be effectively utilized by the apparatus, and such means may include, but is not limited to, the following or combination of the following: (a) measuring the time between when an empty apparatus (215) is initially filled with liquid (30) and the time when it should be drained of the liquid (30), which is preferred in this embodiment, (b) measuring the time between when the apparatus (215) was last drained of liquid (30) and when it should be drained again, (c) measuring the time between when an empty apparatus (215) is interfaced with the first cartridge(s) (290) to begin filling the apparatus with liquid (30) and the time when it should be drained of the liquid (30). Draining the liquid (30) in these instances pertains to draining all of the liquid (30) from the apparatus (215). This embodiment includes without limitation, the apparatus (215) having the ability to sense, detect, interpret, or determine, with one or more sensor(s) known to those skilled in the art, various activities, status, or conditions such as, but are not limited to, (a) the interface of one or more cartridge(s) (290) or other means to hold liquid (30), with the apparatus (215), (b) the liquid (30) level(s) in any reservoir(s) (40), (c) the opening or closing, or any position or state, of one or more valve(s) (660) to empty the apparatus of any liquid (30) that could be used to generate aerosol (200), (d) the movement or presence of any liquid (30), object, or mechanism, resulting from the emptying of the apparatus (215). The sensor(s) can communicate information with a PLC(s) (315) in a manner known in the art, and the PLC(s) (315) can use that information to help determine the length of time the liquid (30) may be utilized until it must be drained or discarded. The PLC(s) (315) can be programmed to accomplish these tasks in a manner known to those skilled in the art. The PLC(s) (315) can, without limitation, be programmed so that the apparatus will enter into a fault or error condition, or shut down one or more functions, and communicate an audible or visual signal to the operator, as well as communicate with other PLC(s), if a period of time has elapsed where the liquid (30) should have been fully drained but was not. This feature prevents the use of liquid (30) that has, without limitation, exceeded its usefulness for various reasons known to those skilled in the art. All communication between either the PLC(s) or the operator can transpire in a manner known in the art. In addition, any information or data can be communicated to or from the apparatus (215) by means such as, but not limited to, any human-machine-interface (HMI) (320), any terminal and its images, any buttons, any buttons and associated lights, any voice command(s) and directions, or any audible signal. The apparatus (215) can, without limitation, also require the operator to acknowledge any error or fault messages, apparatus status queries, or if any action was taken by the operator. The proper, necessary or effective period of time in which the liquid (30) can be used before it needs to be fully drained, is entered into the PLC'(s)' (315) programming in a manner known to those skilled in the art.

According to an embodiment illustrated in FIGS. 12, 13, 20, 29 and 37, the apparatus (215) can be designed and constructed so that any of its part(s), component(s) or space(s) that will increase in temperature from the operation of the apparatus (215) may be cooled, or any heat that is generated by one or more part(s) or component(s) or any related part(s) can be removed or displaced from the apparatus (215) either collectively or individually. The apparatus (215) in the present invention can be operated from various locations including, but not limited to, within the same area (210) in which the aerosol (200) is administered or applied. The operation of the apparatus (215) in an environment in which the aerosol (200) is applied can introduce various engineering challenges, including, but not limited to, cooling the aforementioned part(s) or component(s) and their related part(s), or surrounding atmosphere(s) (740) in a way that does not: (a) damage the apparatus, (b) damage any part(s) or component(s) of the apparatus (215), or (c) introduce a safety hazard. Cooling the aforementioned part(s) or component(s) and their related part(s), or surrounding atmosphere(s) (740)

while utilizing as little or no amperage as possible is also, without limitation, another engineering challenge addressed in the current invention. Without limitation, many component(s) of the apparatus (215), including but not limited to, any electrical or electronic parts, may not be cooled by aerosol (200) laden air from outside of the apparatus (215). Aerosol (200) laden air/gas may cause electrical problems, electrical hazards, or cause damage to the apparatus (215) or its component(s) or part(s).

Without being limited, the various component(s) or part(s) of the apparatus (215) including, but not limited to any, electrical system(s), drive electronic(s) (645), blower(s) (180), pump(s) (130), or other part(s) or component(s) of the apparatus (215), and their related part(s), can be located in various ways including, but not limited to, locating the components individually or collectively in an enclosure(s) (345) that is impervious to things such as, but not limited to, humidity, dust, liquid, and aerosol. In addition, and without limitation, the atmosphere or various component(s) or part(s) of the apparatus (215) including, but not limited to any, electrical system(s), drive electronic(s) (645), blower(s) (180), pump(s) (130), or other part(s) or component(s) of the apparatus (215), and their related part(s), inside of the enclosure(s) (345), can be directly or indirectly cooled by means known to those skilled in the art. This means for cooling can include, but is not limited to, the use of, circulated coolant liquid, or refrigerated air. Any heat that is generated in the creation of the refrigerated air or that is removed from the enclosure(s) (345), the atmosphere inside of the enclosure(s) (345), or any part(s) or component(s) inside of the enclosure(s) (345), can be transferred to any air stream or direct to the atmosphere surrounding the apparatus (215).

Without limitation, the PLC(s) (315) can monitor the temperature of any surface(s) or atmosphere(s) (740) within the apparatus (215) with input from one or more of any temperature sensing devices or air/gas temperature sensing device(s) (650). The PLC(s) (315) can activate whatever means necessary to start, maintain, or stop any cooling activities or actions for any part(s), component(s), or atmosphere(s) of the apparatus (215), to maintain any desired or necessary temperature.

It is preferred, without limitation that the heat is transferred to an air/gas stream and this air/gas stream is the same air/gas stream (745) that is used to move the generated aerosol (200) out of the apparatus (215). The heat can be transferred to the air/gas stream (745) in one or more locations of the apparatus (215) including, but not limited to, inside any reservoir(s) (40), or inside any pipe(s) (685) before or after the blower(s) (180) that create the air/gas stream (745) that moves the aerosol (200) from the apparatus (215). It is also preferred, without limitation, that the heat generated by the various component(s) or part(s), especially any drive electronics (645) that operate the transducer(s) (10), be transferred to one or more heat sink(s) (750) having one or more fin(s) or other means known in the art to enhance cooling. Without limitation, the heat sink(s) can also interface and transfer heat from any coolant liquid or circulated coolant liquid that is used to cool any part(s), component(s), or atmosphere in a manner known in the art. The heat sink(s) (750) can be positioned anywhere in the air stream (745), before or after the blower(s) (180), so that at least the fin(s) or other cooling enhancement(s) (800) is placed or positioned in the air stream (745). The interface between any heat sinks or other means to transmit heat into the air stream (745) can be sealed in a manner known in the art. It is also preferred without limitation, that the heat sink(s) (750) that interfaces with the drive electronics (645) is interfaced with the top of the reservoir(s) (40) in which the transducers(s) (10) is located, and the heat sink(s) (750) is effectively positioned and sealed in place with one or more clasps (795). Without limitation, the various part(s) and component(s) of the apparatus (215) can interface with any heat sink(s) (750) in any orientation(s), layout(s), and with any methods known to those skilled in the art.

According to an embodiment, the apparatus (215) can be designed and constructed so that any of its exterior skin, walls, or surfaces (755) that can be exposed to the administered or deployed aerosol (200), are prevented from becoming warmer in temperature than the temperature of the atmosphere surrounding the apparatus or other surfaces surrounding the apparatus (215). This is important considering the potential operating environments of the apparatus (215). The book entitled, "Aerosol Technology" by William C. Hinds (1982), which is incorporated herein by reference in its entirety, including any references cited therein, teaches that, "When a temperature gradient is established in a gas, the aerosol particles in that gas experience a force in the direction of decreasing temperature. The motion of the aerosol particle that results from this force is called thermophoresis (page 153)." William C. Hinds (1982), also taught, "The earliest studies of thermophoresis were empirical studies of the dust-free layer observed around a heated object, such as a metal rod immersed in smoke. The smoke particles appear to be repelled by the heated object and form a particle free layer usually less than 1 mm thick, with a well-defined boundary (page 153)." This embodiment is advantageous for reasons including, but not limited to, it can prevent the aerosol (200) from being repelled from the exterior skin, walls, or surfaces (755) of the apparatus (215) in situations where the apparatus (215) is operating within the area (210) in which the aerosol (200) is administered or deployed and where it is needed or required that the exterior skin, walls, or surfaces (755) of the apparatus have contact with the aerosol (200). This embodiment includes, without limitation, constructing the apparatus (215) so that the exterior skin, walls, or surfaces (755) of the apparatus (215) are insulated from heat in various ways, including, but not limited to, applying one or more layers of insulating material (760) to the inside or outside of the exterior skin, walls, or surfaces (755) of the apparatus (215), constructing the exterior skin, walls, or surfaces (755) of the apparatus (215) so that they are double walled with a layer of insulation (765), including air/gas, in the middle of the said walls, or enclosing the components or parts that can increase in temperature, inside a sealed, insulated, or both insulated and sealed, enclosure, and then placing that enclosure inside of another sealed or unsealed enclosure that can also be insulated or not insulated.

According to an embodiment, object(s), the atmosphere(s) in which they reside, or any surfaces in the area targeted (210) for the administration or deployment of an aerosol (200), can be cooled or have their/its temperature decreased, before, or during the time when, the aerosol (200) is administered. This embodiment should not be confused with what was taught by U.S. Pat. No. 4,512,951 (Koubek at al., 1983), which is incorporated herein by reference in its entirety, including any references cited therein. Koubek et al., 1983, taught a method of sterilization where a liquid of aqueous hydrogen peroxide is vaporized, and the uniformly vaporized mixed hydrogen peroxide-water vapors are delivered into an evacuated sterilizer chamber, and the articles to be sterilized are cooled prior to the introduction of the vapor (or are cooled by the evacuation of air from the sterilizing zone) to a temperature below the dew point of the entering vapors. The condensing vapor deposits a film of liquid on all such cool surfaces (col 2, line 40-51). Koubek et al., 1983, also mentions in claim 2 that the result of vaporization was a mixed "gaseous vapor" consisting of hydrogen peroxide and water vapor free of solid contaminants. The present embodiment is intended for a completely different application and purpose since it is related to using principals of aerosol (200) behavior to, without limitation, increase the efficacy or performance of the process of the present invention, and not the condensation of a gas as taught in the prior art.

Basic principles applied in this embodiment are taught in the book entitled, "Aerosol Technology" by William C. Hinds (1982), which is incorporated herein by reference in its entirety, including any references cited therein. Without limitation, the cooling of the said object(s), surfaces, or environment or atmosphere, within the targeted area (210), in the present invention, can accentuate the performance or efficacy of the aerosol (200) generated by the apparatus (215) in the present invention. In addition, and without being limited to a mechanism or method, the aforementioned principles taught by William C. Hinds (1982), show that the efficacy, efficiency, and performance of the process in the present invention can be further increased by introducing an aerosol (200), consisting of a heated liquid (30), into an environment or targeted area(s) (210) with cooled surfaces.

The cooling of object(s), surface(s), space(s), environment(s), or atmosphere(s), within a targeted area(s) (210), can be accomplished with any means except by decreasing the pressure or pulling a vacuum on an enclosed area that is sufficient enough to decrease the temperature of the surfaces or atmosphere within that enclosed area. Creating a vacuum in an enclosed area and applying an aerosol was taught in the prior art by U.S. Patent Application No. 2005/0042130 A1 (Lin et al., 2003). However, Lin et al., was silent with respect to cooling any surfaces within the sterilization chamber or targeted area, and only mentioned the vaporization of the applied aerosol as being any enhancement or advantage that further vacuum past 5 torr would provide (pg. 2 paragraph 28). The vacuum utilized by Lin et al., (pg. 2 paragraph 28) to obtain data, was intended to move the aerosol through the sterilization chamber. In addition, using a vacuum to cool object(s), surfaces, or environment or atmosphere, within a enclosed area, would not be desired in this embodiment due to the complexity and expense involved in designing a chamber for the necessary vacuum and the expense of acquiring the necessary pump, which is all known to those skilled in the art. It is desired that another means for cooling object(s), surfaces, or environment or atmosphere, within a targeted area(s) (210), other than utilizing a vacuum, be utilized.

As shown in FIGS. 38-41, it is preferred, without limitation, that the targeted area(s) (210)) and its atmosphere, environment, objects, or any of the surfaces within the targeted area(s) (210), be cooled with air or gas that is cooled or chilled in a manner known to those skilled in the art. It is further preferred that the air or gas is cooled or chilled with one or more chill coils or refrigerated air systems (770) that are known to those skilled in the art. The means (770) to chill or cool the air or gas can be, without limitation, attached to the apparatus (215) in the present invention, be separate from the apparatus (215) and connect with one or more pipe(s) (810) or outbound cooled air pipe(s) (780) or inbound air pipe(s) (785) that connect with the targeted area(s) (210), or it can be part of or positioned anywhere within the space(s) or targeted area(s) (210) to be treated, and it can be controlled by one or more PLC(s) (315) or remote PLC(s). Without limitation, any pipe(s) that lead to (780) or from (785) the source of the refrigerated or cooled air can be separated from the targeted area (210) with one or more valve(s) (815) that can be controlled by one or more PLC(s) (315) or remote PLC(s). Without limitation, one or more valve(s) (815) may also be positioned at any location between the location where the administered air/gas or aerosol enters any pipe(s) (780) (785) or targeted area(s) (210) and the aerosol generating apparatus (215), and can be controlled by one or more PLC(s) (315) or remote PLC(s). The said valve(s) (815)(775), pipe(s) (220), or other related part(s) or component(s) can all be constructed from any material that is compatible, and suitable for use with the liquid (30). Without limitation, the amount or duration of air or gas that is flowed into or recirculated through the targeted area(s) (210), the locations that the air or gas is flowed into our out of the targeted area(s) (210), the temperature of the air or gas, as well as the temperature of the surfaces within the targeted area(s) (210) can vary depending on variables such as, but not limited to, the application, the level of performance that is desired, desired application time, as well as the volume of the targeted area(s) (210). Without limitation, the temperature of the atmosphere, surfaces, or space(s) in the targeted area(s) (210) can be cooled to at least nine degrees Fahrenheit below the temperature of the applied liquid (30). It is preferred, without limitation, that the temperature of the atmosphere, surfaces, or space(s) in the targeted area(s) (210) be cooled to at least nine to twenty-five degrees Fahrenheit below the temperature of the applied liquid (30). However, it is more preferred, without limitation, that the temperature of the atmosphere, surfaces, or space(s) in the targeted area(s) (210) be cooled to at least forty degrees Fahrenheit or lower. It is further preferred, without limitation, that the temperature of the atmosphere, surfaces, or space(s) in the targeted area(s) (210) be cooled to at least thirty-two degrees Fahrenheit or lower. The temperature of the applied liquid (30) of which the aerosol (200) is created or the temperature to which the aerosol (200) is heated with other means, can also vary. It is also preferred, without limitation, that the aerosol (200) is administered or deployed into an environment or targeted area(s) (210) where all heat emanating lights and/or machinery are turned off before or during the administering or deployment of the aerosol (200).

According to an embodiment, the apparatus (215) can be designed and constructed so that it can administer the generated aerosol (200) to a plurality of separate enclosed targeted areas (210). This can be accomplished, without limitation, through the use of one or more pipes (220) that emanate from or connect to the apparatus (215) and administer the aerosol (200) to the said enclosed areas (210). The flow of air or gas and aerosol (200) that emanates from the apparatus (215) may also, without limitation, be split various times, with one or more, or to one or more pipes (220), and the various pipes (220) can interface, or connect with one or more enclosed areas (210) in which the piped air/gas and aerosol (200) is administered. The one or more pipes (220) that emanate from the apparatus (215) can connect with one or more valve(s) (775) that can open or close one or more pipe(s) (220) that can be connected to one or more pipe(s) (220) or pipe junction(s) (790). The valve(s) (775) can be electronically opened or closed by one or more PLC(s) (315) connected to the apparatus (215), or one or more control PLC(s) external to the apparatus (215), all in a manner known to those skilled in the art. The said valve(s) (775), pipe(s) (220), or other related part(s) or component(s) can all be constructed from any material that is compatible, and suitable for use with the liquid (30). This embodiment does not encompass any configuration(s) or application(s) where the plurality of targeted areas (210) or areas where the aerosol (200) is deployed is within the same room, since this is already known to those skilled in the art. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, the apparatus (215) can, without limitation, be designed and constructed so that the drive electronics (645), or any part of the drive electronics (645) that includes, but is not limited to, one or more signal generator(s), that emit or send electrical signal (herein referred to as "signal" or "signals") to energize the transducer(s) (10), causing it to emit pressure (energy) of a desired character, can have the capability to emit or send various defined signal or signal range(s) for various defined period(s) of time during the lifespan of the transducer(s) (10) in order to, without limitation, continue to operate or energize the transducer(s) (10) at a frequency or within a frequency range in which the transducer(s) (10) are able to have an effective or functional output and/or operate at a frequency or in a frequency range where the transducer(s) (10) are able to operate at or within a range close to or at their maximum performance or aerosol (200) output. It is preferred, without limitation, that this embodiment pertains only to the new aerosol producing transducers (10) taught or claimed in co-owned and co-pending U.S. patent application Ser. No. 11/915,524 titled "Method And Apparatus For Optimizing Aerosol Generation With Ultrasonic Transducers". However, it is more preferred, without limitation, that this embodiment pertain not only to the aerosol (200) producing transducers (10) taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at the resonant frequency of the transducer (10). It is even more preferred, without limitation, that this embodiment pertains not only to the aerosol (200) producing transducers taught in co-owned and co-pending U.S. patent application Ser. No. 11/915,524 titled "Method And Apparatus For Optimizing Aerosol Generation With Ultrasonic Transducers", but also to other transducers (10) intended for aerosol (200) production, except for those that operate at or near the resonant frequency of the transducer (10). The aforementioned exclusions to the preferences are needed since the current art, without limitation, encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by way of the drive electronics (645) in order to compensate for, or match the transducer's (10) resonant frequency change. However, the prior art does not address the adjustment of the signal output from the drive electronics (645) to an aerosol (200) producing transducer (10) that has an effective or optimum operational frequency(s) above or below its resonant frequency that changes over time. One reason for this includes, without limitation, the complexity or difficulty to detect the optimum or effective operating frequency(s) for a transducer (10) at frequencies outside of the resonant frequency of a transducer (10), especially as it changes. This can be appreciated by those skilled in the art.

Aerosol (200) producing transducer(s) (10) in the present invention can have, without limitation, one or more frequency(s), group(s) of frequencies, or frequency range(s) in which they produce an aerosol (200) that can be characterized as effective, functional, or productive. The transducer(s) (10) utilized in the present invention can, without limitation, operate at one or more specific frequency(s), group(s) of frequencies, or frequency range(s), where the transducer(s) (10) are able to generate a greater amount of aerosol when compared to other frequency(s), group(s) of frequencies, or frequency range(s). Furthermore, the transducer(s) (10) utilized in the present invention can, without limitation, have or exhibit one or more specific frequency(s), group(s) of frequencies, or frequency range(s), where the transducer(s) (10) are able to generate not only an effective or functional output of aerosol (200), but generate the maximum amount of aerosol (200) or close to the maximum amount of aerosol (200) for each transducer(s) (10). Without limitation, for any frequency(s), group(s) of frequencies, or frequency range(s), where the transducer(s) (10) produce an effective, functional, or even maximum amount of aerosol (200) that is effective or functional, the aerosol output will decrease as the frequency of the signal sent to the transducer(s) (10) either increases or decreases from these established frequency(s), group(s) of frequencies, or frequency range(s).

Without being limited, any transducer (10) utilized in the present invention, may exhibit or have one or more additional frequency range(s) that encompasses the frequency(s), group(s) of frequencies, or frequency range(s) that will produce an effective, functional, or even maximum amount of aerosol. The magnitude of this frequency range can vary greatly, however, it is preferred without limitation, that this frequency range be within at least plus or minus 0.03 MHz (+/−0.03 MHz) from the frequency where the transducer(s) (10) generates the maximum amount of aerosol (200) or close to the maximum amount of aerosol (200) for a particular group of frequencies or frequency range, and is surrounded by frequency(s), group(s) of frequencies, or frequency range(s), where the transducer(s) (10) do not produce an effective or functional aerosol (200) output. It is more preferred, without limitation, that this frequency range is within at least plus or minus 0.05 MHz (+/−0.05 MHz) from the frequency where the transducer(s) (10) are able to generate the maximum amount of aerosol (200) or close to the maximum amount of aerosol (200) for a particular frequency, group of frequencies or frequency range, and is surrounded by frequency(s), group(s) of frequencies, or frequency range(s), where the transducer(s) (10) do not produce an effective or functional aerosol (200) output. It is even more preferred, without limitation, that this frequency range is within at least plus or minus (+/−0.08 MHz) from the frequency that the transducer(s) (10) are able to generate the maximum amount of aerosol (200) or close to the maximum amount of aerosol (200) for a particular frequency, group of frequencies, or frequency range, and is surrounded by frequency(s), group(s) of frequencies, or frequency range(s), where the transducer(s) (10) do not produce an effective or functional aerosol (200) output.

It has been observed, without limitation, that the transducer(s) (10) in the present invention, can have multiple, separate, or independent, frequency(s), group(s) of frequencies, or frequency range(s), where the transducer(s) (10) are able to generate an effective, functional, or productive aerosol (200) output. In addition, and without limitation, it has been further observed that in between these frequency(s), group(s) of frequencies, or frequency range(s), the transducer(s) (10) do not produce an effective or functional amount of aerosol (200).

It is important to note that the frequency or frequency range(s) in which the transducer(s) (10) produces either the maximum amount of aerosol (200) and/or an effective or functional amount of aerosol (200) can, without limitation, vary, and that it can be at or close to the resonant frequency of the transducer(s) (10) or anywhere above or below the resonant frequency of the transducer(s) (10). Resonant frequency can refer in this embodiment to either the resonant frequency of a free unmounted transducer(s) (10) or a transducer(s) (10) that has been mounted or assembled.

The resonant frequency of a transducer(s) (10) can, without limitation, increase due to age or other variables known to those skilled in the art. The nature of this change in resonant frequency can vary depending on variables known to those skilled in the art. As the resonant frequency of the transducer(s) (10) increases, the frequency range(s) in which the transducer(s) (10) would produce either the maximum amount of aerosol (200) and/or an effective or functional amount of aerosol (200) can, without limitation, also increase.

Referring now to FIGS. 42-45, the drive electronics (645), or any part of the drive electronics (645) that includes, but is not limited to, one or more signal generator(s) or ancillary components, used in the present invention can, without limitation, compensate for this shift or increase in frequency, and continue to operate the transducer(s) (10) at a frequency or frequency range where they produce either the maximum amount of aerosol (200) and/or an effective or functional amount of aerosol (200). This does not pertain to the prior art that encompasses the operation of a transducer (10) at its resonant frequency, as well as the design of the drive electronics (645) or ancillary components to sense any changes in the resonant frequency of the transducer (10), and to automatically adjust the frequency of the signal to the transducer (10) by the drive electronics (645) in order to compensate for, or match the transducer's (10) resonant frequency change. However, due to, without limitation, the complexities or limitations involved with this mode of operation or its successful execution or implementation, the following techniques can also be applied to aerosol (200) producing transducer(s) (10) that operates at or near its resonant frequency. This may be accomplished in ways including, but not limited to: (a) switching from one or more crystal(s) (825) that is initially used to generate one specific frequency or specific frequency range, to one or more different crystal(s) (830) that is used to generate other specific frequency(s) or specific frequency range(s). This can, without limitation, occur numerous times, for various durations of time, over a period of time; or (b) switching from one or more signal generator(s) (835) that is initially used to generate one specific frequency or specific frequency range, to one or more different signal generator(s) (840) that is used to generate other specific frequency(s) or specific frequency range(s). This can, without limitation, occur numerous times, for various durations of time, over a period of time. Without limitation, this switching from one or more crystal(s) or signal generator(s) to another can also be performed multiple times or in multiple series with one or a plurality of crystal(s) or signal generator(s) with any frequency or frequency range output. Also, and without limitation, if a plurality of crystal(s) or signal generator(s) is initially used, they as well as any subsequent set of crystal(s) or signal generator(s) that are utilized may have any, similar, different, identical, approximately identical, frequency or frequency range output. Each of the one or more crystal(s) or signal generator(s) can, without limitation, be utilized to emit or send either a specific frequency, or a range of frequency(s) that is amplified by one or more amplifier(s) (230), drive electronics (645), or other electronics known in the art, and is used to power or operate one or more transducer(s) (10), all in a manner known to those skilled in the art. It is preferred, without limitation, that the crystal(s) (845) is a direct or indirect part(s) or component(s) of the signal generator(s) (850). Each crystal(s) or signal generator(s) is, of a type, design, and construction, known to those skilled in the art. Any type of crystal(s) (845) or signal generator(s) (850) can be used that is effective. However, it is preferred, without limitation, that the crystal(s) (845) is made from quartz and resonates at a frequency that can be used by a signal generator(s) (850) to create a waveform(s) that is then amplified by an amplifier (230), drive electronics (645) or other electronics known in the art, to operate or energize the transducer(s) (10) at a frequency where the one or more transducer(s) (10) can produce either the maximum amount of aerosol (200) and/or an effective or functional amount of aerosol (200); or (c) utilizing, one or more of, without limitation, drive electronics (645), signal generator(s) (850), or other component(s) or circuit board, that has the means, ability, or capacity, to electronically produce the various frequency(s) or frequency range(s) that are needed or desired, and is known to those skilled in the art. It is preferred, without limitation, that these electronics or circuitry has the ability or capacity to be programmed so that various frequencies or frequency ranges may be created or generated, for various durations of time, over a period of time.

The specific resonant frequency(s) for a free unmounted transducer(s) (10) or a transducer(s) (10) that has been mounted or assembled, as well as the specific frequency(s) or frequency range(s) in which the transducer(s) (10) produce either the maximum amount of aerosol (200) and/or an effective or functional amount of aerosol (200), can be determined, planned, calculated, plotted, or projected, over time, in a manner known to those skilled in the art.

This data can be used, without limitation, to program one or more components such as, but not limited to, a signal generator or other related components, or PLC(s) (315) which is, without limitation, either a dedicated part of the signal generator(s) (850), amplifier(s) (230), drive electronics (645), or other components that are used to generate and send signal to energize the transducer(s) (10), or the PLC(s) (315) that is used to control and operate the apparatus in the present invention, to cause the switching from a crystal(s) (845) or signal generator(s) (850) to another in order to operate the transducer(s) (10) at a frequency or frequency range where they produce either the maximum amount of aerosol (200) and/or an effective or functional amount of aerosol (200).

Figure 46:
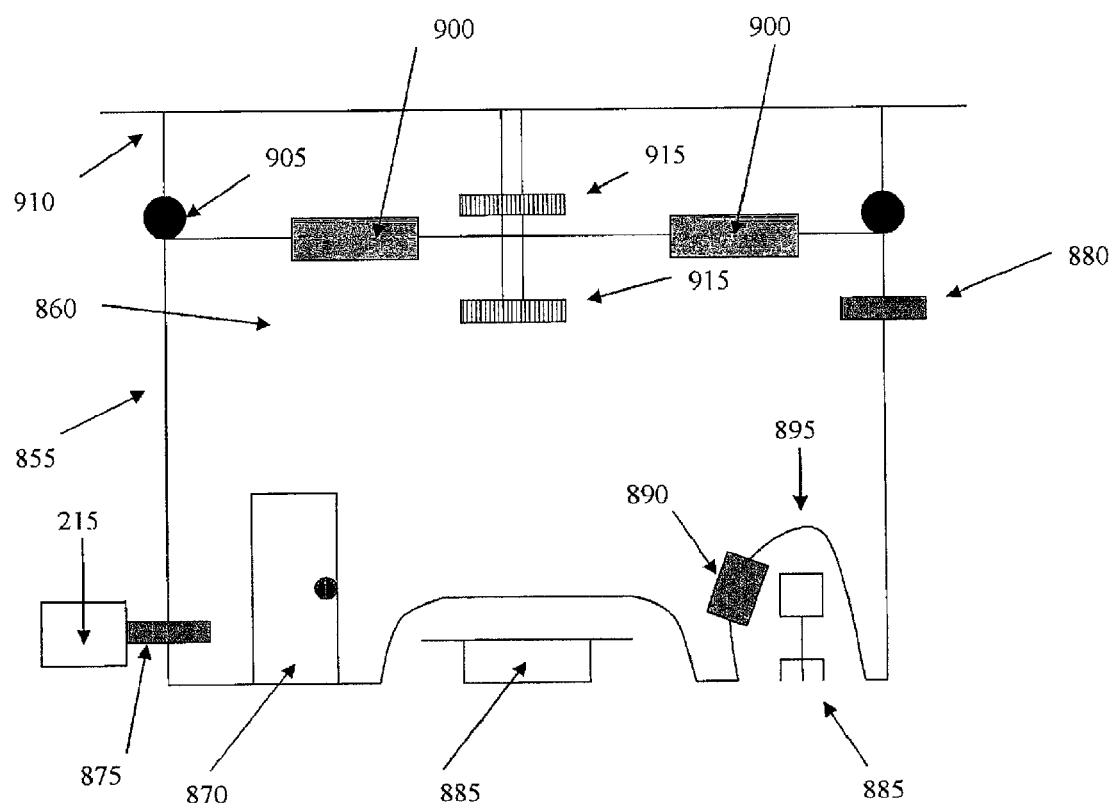
FIG. 46 is a schematic view of an embodiment of an enclosure that is connected to an aerosol generating apparatus, the enclosure having various features, parts, and components, according to the present invention.

As shown in FIG. 46, according to an embodiment, the aerosol (200) generating apparatus (215) in the present invention, can be, without limitation, connected, interfaced, or attached, to one or more sealed, semi-sealed, or semi-open, enclosure(s) or areas (herein referred to as "target enclosure(s)") (855), that is erected, established, constructed, or positioned at any place or within any area that is, without limitation, enclosed, not enclosed, semi-enclosed, sealed, semi-sealed, or unsealed. The said target enclosure(s) (855) can be without limitation, any size, shape, or dimension, and constructed of any material, and can be designed to be disposable or so that it can undergo multiple cycles of having the aerosol (200) applied to the interior of the target enclosure(s) (855) during, after, or both during and after, the use of the interior space of the enclosure(s) (860). The target enclosure(s) (855) can, without limitation, be designed in a manner known in the art so that they can be connected, interconnected, or interfaced, with one or more target enclosures(s) (855). The target enclosure(s) (855) can, without limitation, be supported with a frame that is designed and interfaced with the target enclosure(s) (855) in a manner known to those skilled in the art. Without being limited, the target enclosure(s) (855) can also have one or more doors (870) of various sizes, shapes, and locations, through which objects and people can pass through, and can be designed to be opened, closed, and effectively sealed multiple times in a manner known in the art. Without limitation, the door (870) can be designed and function as an airlock. It is preferred, without limitation, that the enclosure has at least one door (870). The target enclosure(s) (855) can be made from any material. However, it is preferred, without limitation, that the material is at least transparent or translucent. The target enclosure(s) (855) can have one or more inbound air/gas ports (875) or outbound air/gas ports (880) interfaced anywhere with the target enclosure (855), through which air and aerosol (200) may be administered or exhausted. The said ports may connect, in a manner known to those skilled in the art, to one or more aerosol generator(s) (215).

The target enclosure(s) (855) in this embodiment can have at least, but is not limited to, six features that distinguish it from chambers, tents, or bags, which have been used or have been proposed in the prior art. First, any wall(s), floor(s), or ceiling(s), of the target enclosure(s) (855) can be, without limitation, pre-formed, pre-constructed, pre-laminated, pre-seam sealed, or pre-molded, so that the chamber can effectively or functionally follow or fit over or under one or more of any, object(s), fixture(s), architectural feature(s), or equipment or fixture(s) such as, but not limited to, exam tables, x-ray equipment, anesthesia equipment, heart rate monitors, cardiopulmonary equipment, operating room theatre lights, laboratory equipment, or industrial equipment (Herein referred to as "structure(s)" (885). Second, any wall(s), floor(s), or ceiling(s), of the target enclosure(s) (855), including any material (895) that fits over the said objects, fixtures, architectural features, or equipment or fixtures (885), can, without limitation, have various openings (890) of various shapes, sizes, and locations, to allow a person to access, without limitation, any objects, various human machine interfaces, tools, or move any objects in and out of the target enclosure(s) (855). The openings (890) can also have a means so that they can be opened, closed, and effectively sealed multiple times. The openings may be designed or function as an airlock. Third, any wall(s), ceiling(s), or floor(s), of the target enclosure (855) may have one or more holes or openings of any size, shape, or dimension, and be interfaced with one or more of any plastic or glass panels, panes, or pieces (herein referred to as "panels") (900) of any size, shape, or dimension. The panels can be effectively interfaced and sealed with or into the wall(s), ceiling(s), or floor(s), of the target enclosure (855) in a manner known in the art. Any openings (890) may also interface with any plastic or glass panels (900), and the interface can be effectively sealed in a manner known in the art. The plastic or glass panels (900) can, without limitation, offer to: (a) allow light into the target enclosure(s) (855) in situations where the wall(s), floors, or ceiling(s) of the target enclosure (855) are opaque, (b) improve light transmittance or the quality of light that is transmitted into the target enclosure(s) (855), (c) decrease any diffraction of light entering the target enclosure(s) (855). Fourth, the target enclosure(s) (855) can utilize, without limitation, any means known in the art to connect, interface, hang, or suspend the target enclosure(s) (855) within the area in which it is placed, so that the target enclosure(s) (855) is erected or positioned so that its interior space (860) can be effectively or efficiently used. It is preferred without limitation, that the ceiling(s) of the target enclosure(s) (855) is suspended from at least one hook(s) (905) or other means of attachment that is effectively connected or attached to the ceiling (910) or other location(s) in the area in which the target enclosure(s) (855) is located. The various components and designs utilized for this purpose are known those skilled in the art. Fifth, the target enclosure(s) (855) can, without limitation, be constructed with or utilize any means known to those skilled in the art so that the floor(s) of the target enclosure(s) (855) do not present a slip hazard for any people working inside the target enclosure(s) (855). It is preferred, without limitation, that the floor(s) of the target enclosure (855) be textured to reduce any potential slip hazards. Sixth, the target enclosure(s) (855) can, without limitation, be interfaced with one or more means for fire suppression (915) outside or within the target enclosure(s) (855), and can be designed and built for this feature in a manner known in the art. In addition, the components and materials utilized in this embodiment are constructed from any material that is compatible, and suitable for use with the liquid (30), and may also be fireproof or fire resistant. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 47:
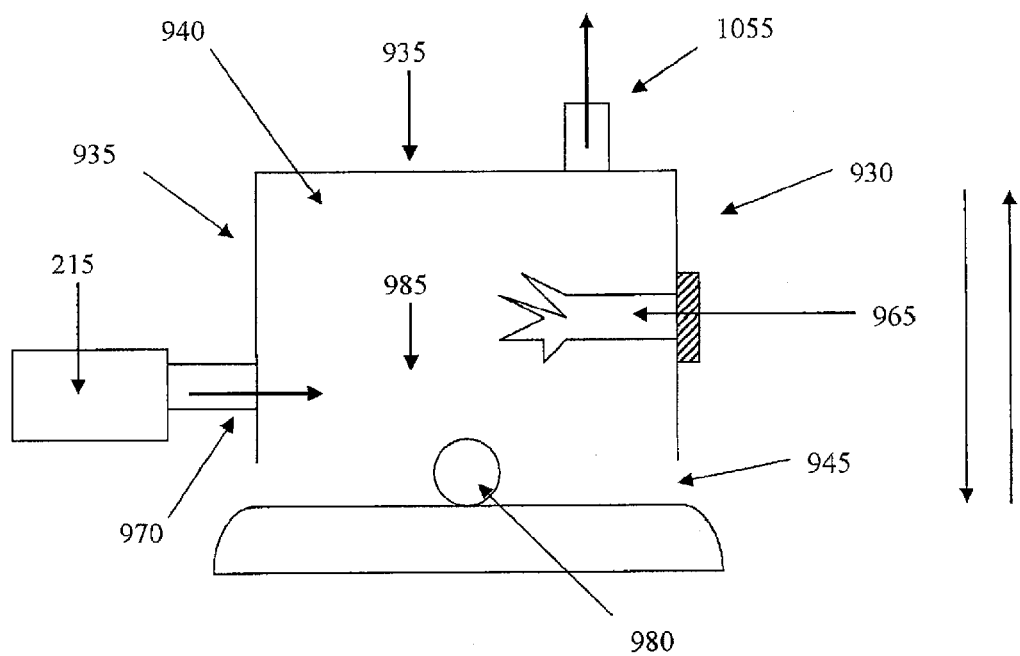
FIG. 47 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, according to the present invention.
Figure 48:
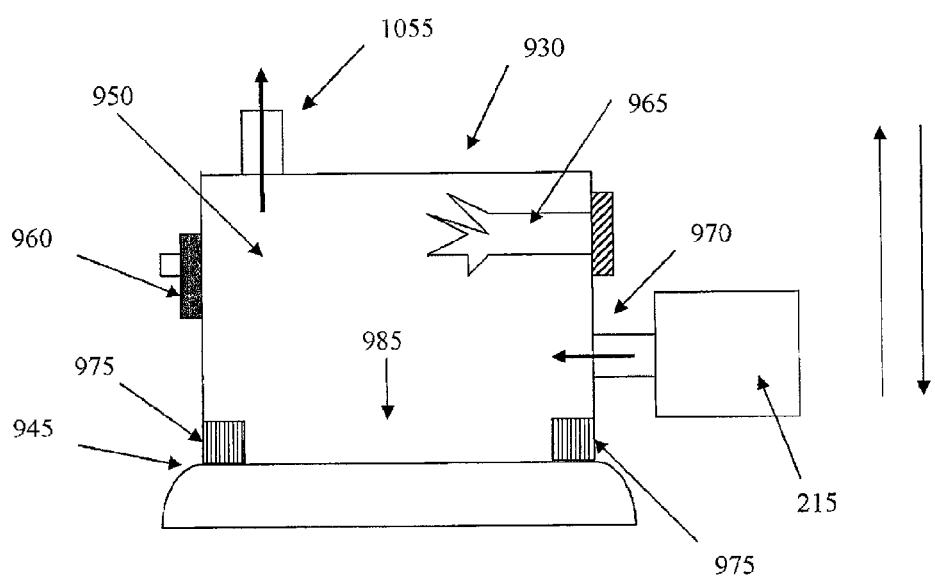
FIG. 48 is a schematic view of an embodiment of an enclosure that is connected to an aerosol generating apparatus, where the surfaces that it interfaces with effectively forms a missing wall, and the enclosure can have various features, parts, and components such as a glove sealed to the wall of the enclosure, seal material that connects with the enclosure and any surfaces with which the enclosure interfaces, according to the present invention.
Figure 49:
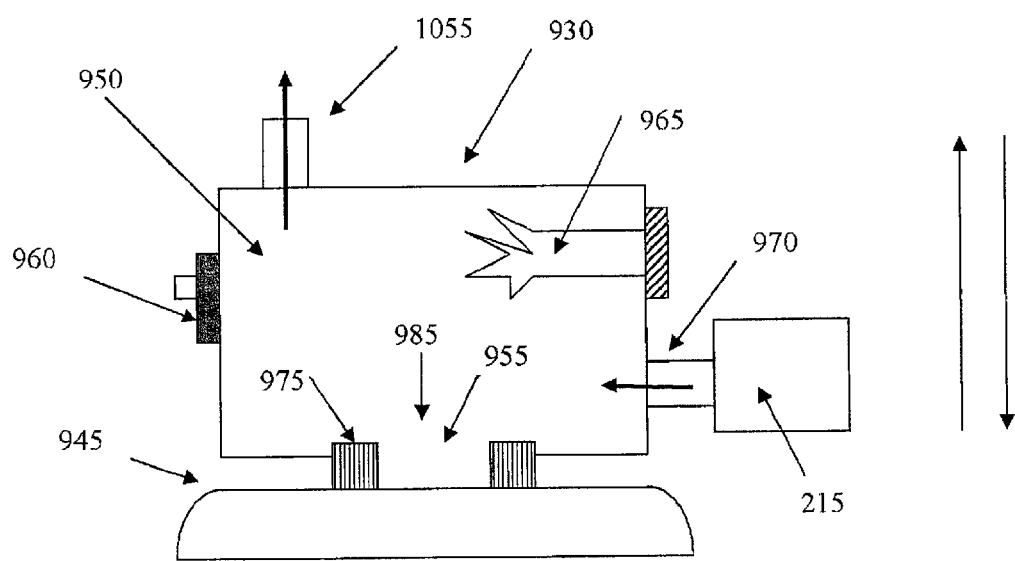
FIG. 49 is a schematic view of an embodiment of an enclosure that is connected to an aerosol generating apparatus, where the surfaces that it interfaces with effectively forms a missing wall, effectively covers or seals a hole, and the enclosure can have various features, parts, and components such as a glove sealed to the wall of the enclosure, seal material that connects with the enclosure and any surfaces with which the enclosure interfaces, and an airlock or access door, according to the present invention.

Looking now at FIGS. 47-49, according to an embodiment, the aerosol (200) generating apparatus (215) in the present invention, can be, without limitation, connected, interfaced, or attached, to one or more specially designed enclosure(s) (herein referred to as "application enclosure(s)") (930) that consists of, one or more wall(s) (935) that form one or more semi-enclosed or unenclosed area(s) (940) and where, without limitation, the interface, connection, or attachment, of any part of these wall(s) (935) with any surface(s) (945), forms one or more enclosed area(s) (950). The one or more wall(s) (935) of the application enclosure(s) (930) may also have one or more openings or holes (herein referred to as hole(s)) (955) of any size, shape, or dimension, and the interface of these hole(s) (955) with any surface(s) (945), forms one or more enclosed area(s) (950). The wall(s) (935) of the application enclosure(s) (930) can be, without limitation, constructed from any, stainless steel, metal, glass, cellulose, cloth, gauze, polyolefin, polymer, natural or manufactured fibers or materials that may be coated or uncoated, combinations of these materials, or other materials known to those skilled in the art. The wall(s) (935) of the application enclosure(s) (930) can be, without limitation, flexible, rigid, semi-rigid, opaque, translucent, or transparent.

The enclosed area(s) formed by the interface or contact of the said wall(s) (935) or hole(s) (955) with any surface(s) (945) can be, without limitation, sealed, fully sealed, semi-sealed, or unsealed, in a manner known to those skilled in the art. Any material that can form or create an effective seal or interface (herein referred to as "seal material") (975) can also be, without limitation, glued, cemented, molded, laminated, adhered, or otherwise attached, to any part of the wall(s) (935) or hole(s) (955) that can come in contact with any surface(s) (945). Without limitation, the seal material (975) can be porous, permeable, semi-permeable, or impermeable, rigid, semi-rigid, or flexible, and can be constructed from materials including, but not limited to any, stainless steel, steel, glass, cellulose, cloth, gauze, polyolefin, polymer, natural or manufactured fibers or materials that may be coated or uncoated, combinations of these materials, or other materials known to those skilled in the art. The seal material (975) or parts of the seal material (975) may also, without limitation, have absorbent characteristics to improve its efficacy. The seal material (975) or wall(s) (935) can have, without limitation, various thicknesses, as well as lengths or heights, or it may even be designed to have the ability to vary its length(s), height(s), or thickness(s), in a manner that is known to those skilled in the art. The walls(s) (935) of the application enclosure(s) (930) can be constructed from the seal material (975).

In addition, the application enclosure(s) (930) can have, without limitation, one or more port(s), opening(s), or airlock(s) (960) of various sizes and shapes, which can be effectively sealed closed, or be in an open, semi-sealed, or unsealed state, in a manner known to those skilled in the art. The enclosure may also, without limitation, have one or more gloves (965) attached to any of the port(s), opening(s), or airlock(s) (960) and be hermitically sealed to the application enclosure(s) (930), all in a manner known to those skilled in the art. This can, without limitation, allow an operator to handle any object(s) in the application enclosure(s) (930) without being exposed to anything in the application enclosure(s) (930) or introducing anything into the application enclosure(s) (930).

The application enclosure(s) (930) can have one or more port(s) (970) at various locations through which inbound air/gas and aerosol, or filtered inbound air/gas from outside of the application enclosure(s) (930), can be administered or moved into the application enclosure(s) (930). The application enclosure(s) (930) can also have one or more port(s) (1055) at various locations through which outbound air/gas or aerosol, can move out of the application enclosure(s) (930). Without limitation, any outbound air/gas or air/gas that is laden with aerosol can be filtered at any port (1055) or at any location after it has been removed from the application enclosure (930), with any means known to those skilled in the art. The application enclosure(s) (930) can have various uses, including, but not limited to, being interfaced, strapped, positioned, or placed, over, with, or onto one or more object(s) or substance(s) (980), or targeted surfaces (985), at any angle or orientation, in order to apply an aerosol (200) onto the various surfaces. This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

According to an embodiment, any objects or items such as, but not limited to, hose(s), wire(s), pipe(s), or cord(s) (herein referred to as "cord(s)") (990), which are present in the targeted area(s) (210) in which the aerosol (200) is administered or deployed, can be, without limitation, held, lifted, or supported, by one or more holder(s) (995), that prevents the cord(s) (990) from touching or contacting the floor or surface(s) (1000) on which the holder(s) (995) are placed, but can also insure that all of the surfaces of the cord(s) (990) which interact with or contact the holder(s) (995) can also have contact, without limitation, with the same liquid (30) that is aerosolized or deployed by the apparatus in the present invention. Without limitation, surfaces that contact one another are often difficult to reach or contact with an administered aerosol (200) or other deployed substance(s), and this embodiment, without further limitation, helps to reduce or eliminate an incomplete treatment or administration of the aerosol (200), or other treatment product(s), to all of the desired or needed surfaces in a targeted area (210). In addition, the holder(s) (995) may also be used with any other chemical or agent delivery systems or apparatuses that can deliver any, without limitation, chemical(s), agent(s), or compound(s) in the form including, but not limited to, any aerosol(s), gas(es), or vapor(s), for various purposes.

Figure 50:
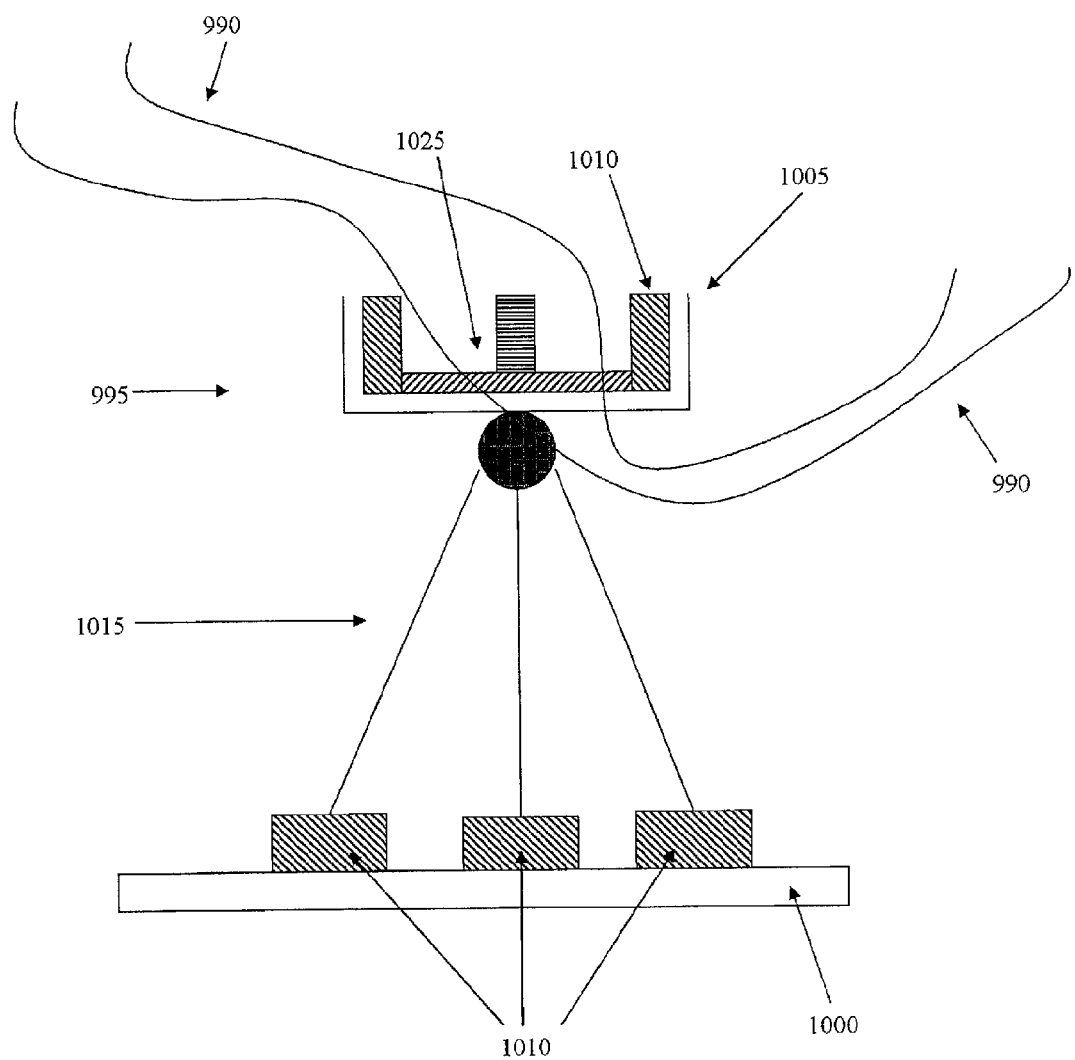
FIG. 50 is a schematic view of an embodiment of a holder that interfaces with one or a plurality of objects, and the said holder incorporates absorbent material that is positioned between the holder and any surfaces with which it interfaces including the said objects it holds and any surface on which it is placed.

Without limitation, the said holder(s) (995), as shown in FIG. 50, can consist of at least, but not limited to, the following components: (a) one or more cradle(s) or other means (herein referred to as "cradle(s)") (1005), to hold or support the cord(s) (990), (b) absorbent material(s) (1010) that is interfaced, attached, or connected to the cradle(s) (1005), (c) one or more legs or supports (1010) that extend from or are interfaced or attached to the cradle(s) (1005) or part(s) connected to the cradle(s) (1005), (d) absorbent material(s) (1010) that is interfaced, attached, applied, or connected in such a way so that it is positioned between any parts or components of the holder(s) (995) and any surfaces (1000) on which the holder(s) (995) is placed or interfaces with. Without limitation, the one or more legs or supports (1015) that extend from or are directly or indirectly interfaced or attached to the cradle(s) (1005), can be of various number and lengths, and can be designed in a manner known to those skilled in the art.

The cradle(s) (1005) or absorbent material(s) (1010) can have one or more slot(s) or a rippled shape of one or more ripple(s) (1025) so that one or more cord(s) (990) can nest or lay in or interface with the cradle(s) (1005) or absorbent material(s) (1010). The holder(s) (995) is designed and constructed in a manner known to those skilled in the art so that the cord(s) (990) cannot easily twist, fall, or move out of the cradle(s) (1005) or absorbent material(s) (1010). An absorbent material(s) (1010) is interfaced, attached, applied, or connected to the cradle(s) (1005) or holder(s) (995) in various ways known to those skilled in the art. The cradle(s) (1005) can also be constructed from any absorbent material (1010). The cradle(s) (1005) and absorbent material(s) (1010) can also be designed so that either the absorbent material(s) (1010) or even the cradle(s) (1005) can be disposable. The one or more legs or supports (1015) can also be constructed from any absorbent material (1010). The interface, attachment, application, or connection, of any absorbent material(s) (1010) to the one or more legs or supports (1015) can be accomplished in various ways known to those skilled in the art.

The absorbent material(s) (1010) that is utilized, can be made of any absorbent materials, or combinations of absorbent materials, including, but not limited to, gauze, cellulose, any sponge like material, or any material with absorbent qualities that is known to those skilled in the art. The absorbent material(s) (1010) is of a sufficient quality, thickness, density, size, shape, construction, consistency, and design, to complete its task at least once in an effective manner.

Any of the absorbent material(s) (1010) can also, without limitation, be soaked, saturated, or contacted, with any desired chemical, compound, agent, additive, or otherwise liquid (30), that would be used for various purposes. It is preferred, without limitation, that this is performed before the cord(s) (990) are interfaced or positioned in or on the cradle(s) (1005) or absorbent material(s) (1010), or the holder(s) (995) are placed on any floor or surface(s) (1000). This can, without limitation, further increase the probability that all surfaces of the cord(s) (990), holder(s) (995), or surface(s) (1000) on which the holder(s) (995) is placed, have contact with the aforementioned chemical, compound, agent, additive, or otherwise liquid (30). It is preferred, without limitation that the absorbent material(s) (1010) is saturated with the same liquid (30) that is generated into aerosol (200) in the present invention. This same absorbent material(s) (1010) can also be positioned under the wheels of the aerosol generating apparatus(s) (215). Any parts or components utilized to construct the holder(s) can be constructed from any material that is compatible, and suitable for use with the liquid (30). This embodiment may, without limitation, be used with any anti-pathogen/toxin/fungal/sporicidal agent(s) or substance(s) that may be in the form including but not limited to any liquid, gas, vapor, plasma, or aerosol, which is generated, delivered, moved, or administered, by any means.

Figure 56:
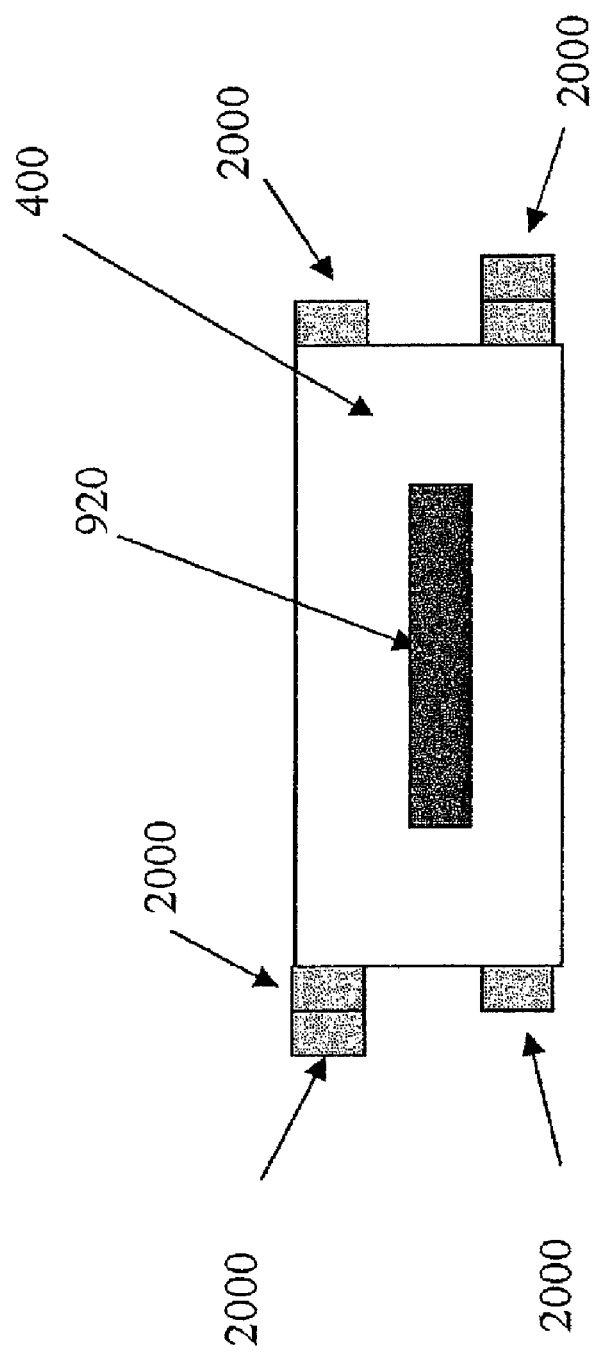
FIG. 56 is a schematic view of a buoyant object and weights that is disposed in the generator of FIG. 52.
Figure 57:
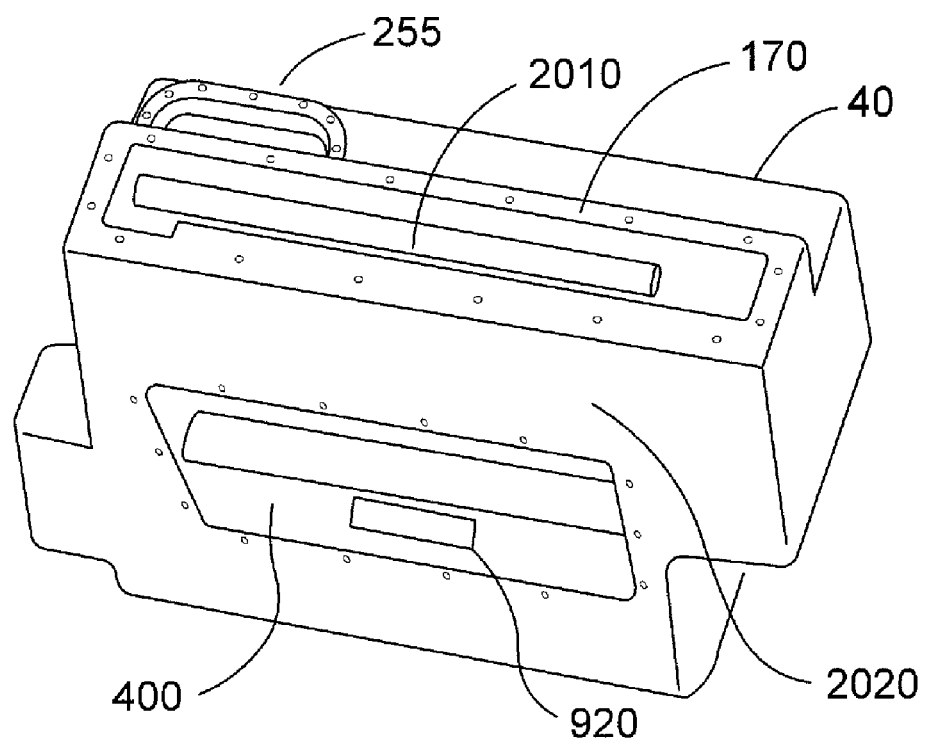
FIG. 57 is an isometric view of the tank of FIG. 56.

According to embodiments, as best shown in FIGS. 56-57, the apparatus (215) can, without limitation, be designed and constructed so weight or mass can be added or removed from any parts or components in order to maintain a specific level of liquid (30), or at least an effective amount of liquid (30), that covers all of the aerosol producing transducer(s) (10). Weight or mass (2000) can be can be added or removed from any parts that are directly or indirectly connected to any of the buoyant object(s) (400), or the transducer assembly(s) (100) themselves. It is preferred, without limitation, that the weight or mass (2000) takes the form of one or more stainless steel weights (2000) that are attached to the buoyant object(s) (400) in a manner known to those skilled in the art, and the various weight(s) (2000) are added to numerous positions or locations on the buoyant object(s) (400) in order to maintain a specific and/or effective liquid level (30) above each of the one or more aerosol producing transducer(s) (10).

Figure 64:
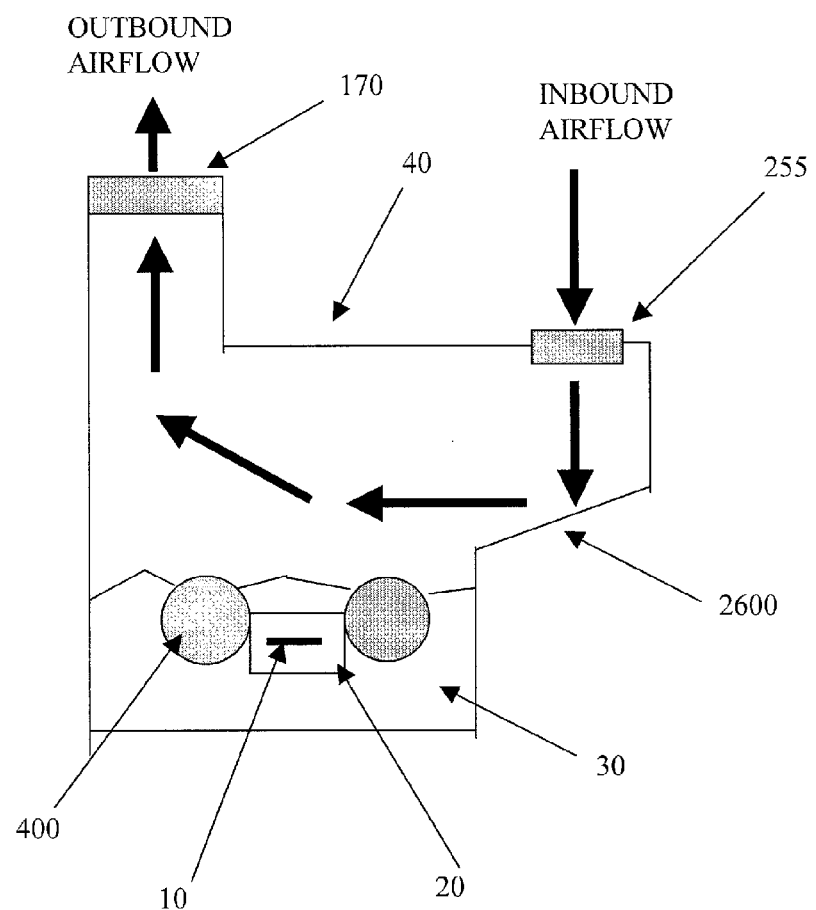
FIG. 64 is a schematic view of an embodiment of the generator of FIG. 52 including an air flow distribution shelf.

According to an embodiment shown in FIG. 64, the apparatus (215) can, without limitation, be designed and constructed so that the one or more buoyant object(s) (400), or even the transducer assembly(s) (100) themselves may freely float within the liquid (30) in the reservoir (40). It is preferred, without limitation, the one or more transducer assembly(s) (100) is attached to only one buoyant object (400) and the transducers are centered in connecting holes (920) cut in the buoyant object (400). The buoyant object (400), and one or more transducer assembly(s) (100) are connected to any wall of the reservoir (40). It is preferred, without limitation, that the one or more pieces of flexible tubing (375) that contains the wiring from the drive electronics (645) or amplifier(s) (230), emanates from a common wall of the reservoir (40), and connects to the side of each respective transducer housing (20) in order to power the one or more of the aerosol producing transducer(s) (10).

Figure 58:
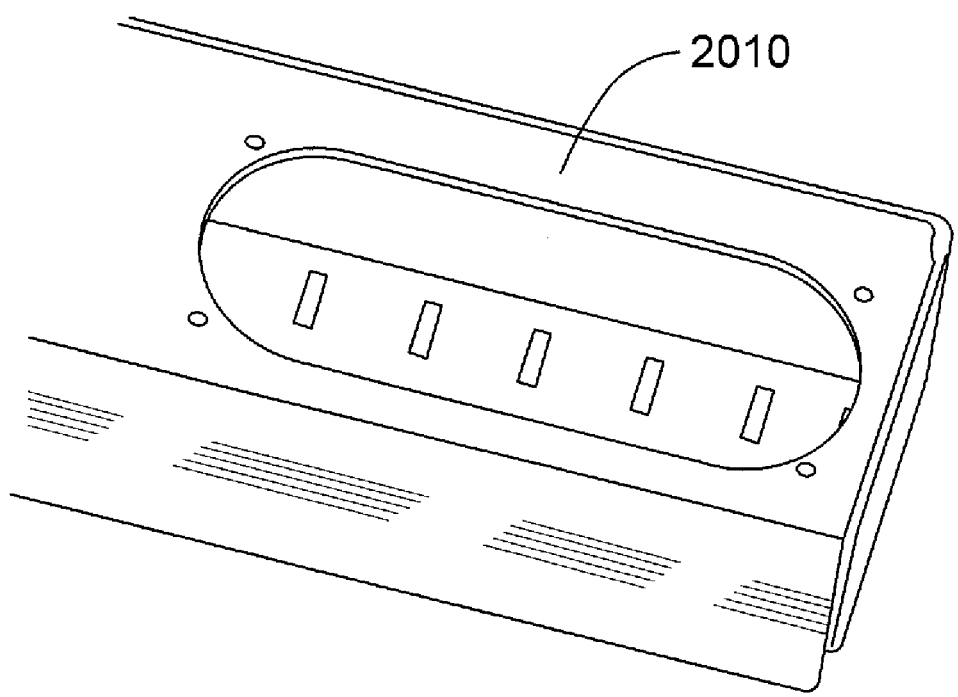
FIG. 58 is an isometric view of an airflow distribution channel for the tank of FIG. 57.
Figure 59:
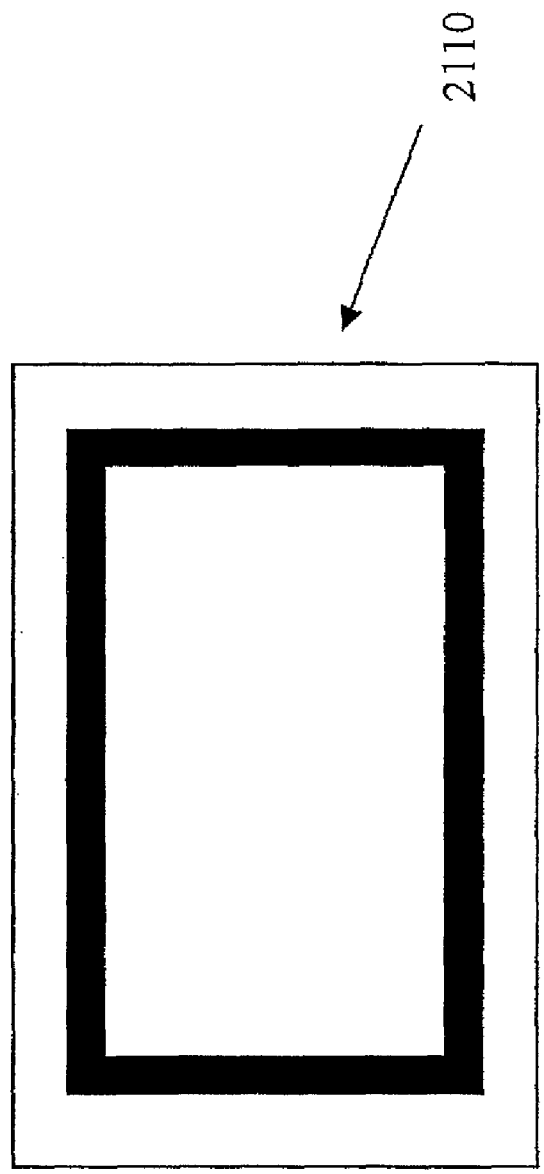
FIG. 59 is a bottom plan view of a wall vent.

According to an embodiment shown in FIGS. 57-58, the apparatus (215) can, without limitation, be designed and constructed so that air, or any combination of gas(s), enters the fog tank or reservoir (40) through one or more inlets or intake orifices (255), located opposite from the one or more air outlets, exit orifices, or openings (170) that are located on the top, roof, or ceiling of the reservoir (40). It is preferred, without limitation, that the one or more air outlets, exit orifices, or openings (170), consists of only one opening and the air outlet is formed or positioned at the end of a chimney (2020). Both the air inlets and air outlets can be any shape or size. It is also preferred, without limitation, that the inbound air or gas is directed downward at various angles, including vertically, into the fog tank or reservoir (40). According to another embodiment, the downward moving air stream may, without limitation, strike one or more surfaces that cause the inbound airflow to be redirected in various directions and angles inside of the reservoir (40). It is preferred, without limitation, that one or more redistribution surfaces are located near the bottom of the reservoir, but at least above the highest possible liquid (30) level. The fog tank or reservoir(s) (40) can be any, without limitation, size, shape, or geometry, and it can have any height of air space or volume above the liquid (30) that is located in the bottom of the reservoir (40). The liquid (30) in the bottom of the reservoir (40) can be, without limitation, any effective depth.

Figure 69:
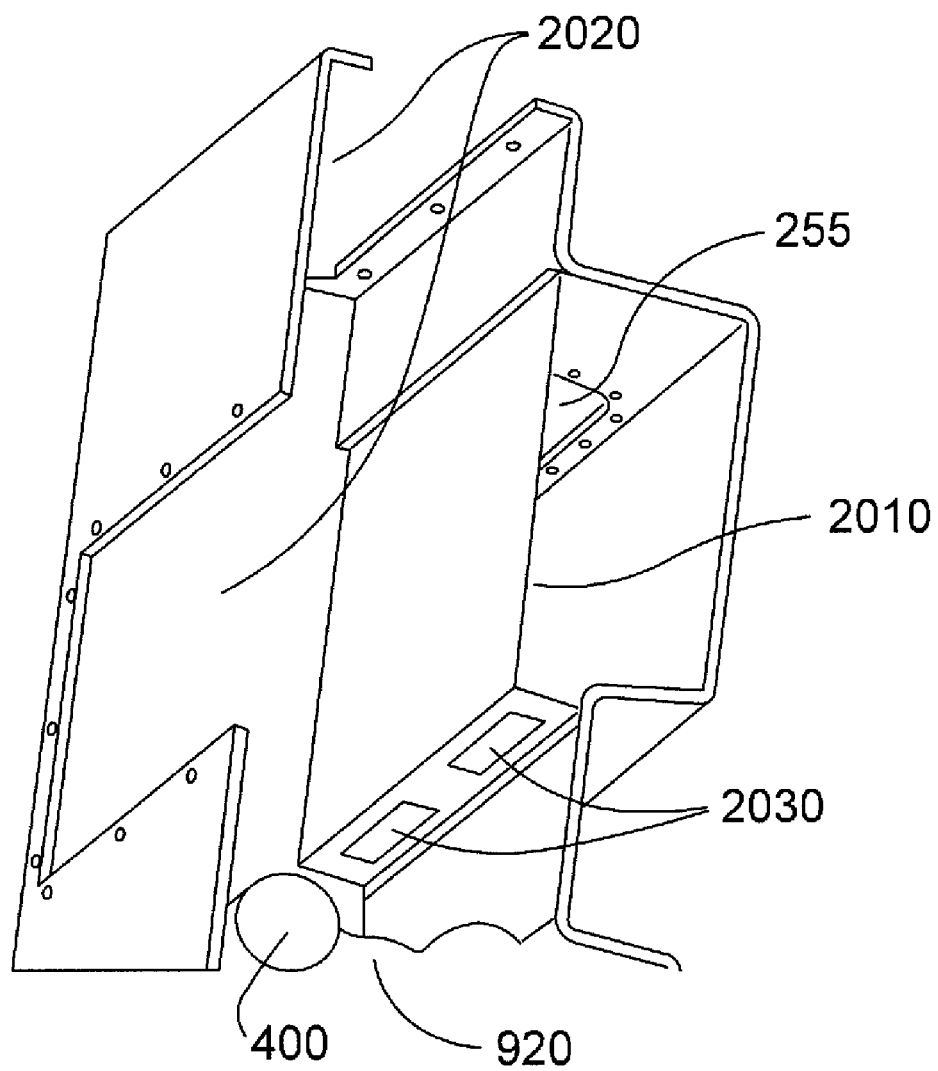
FIG. 69 is an isometric view of the tank of FIG. 56.
Figure 70:
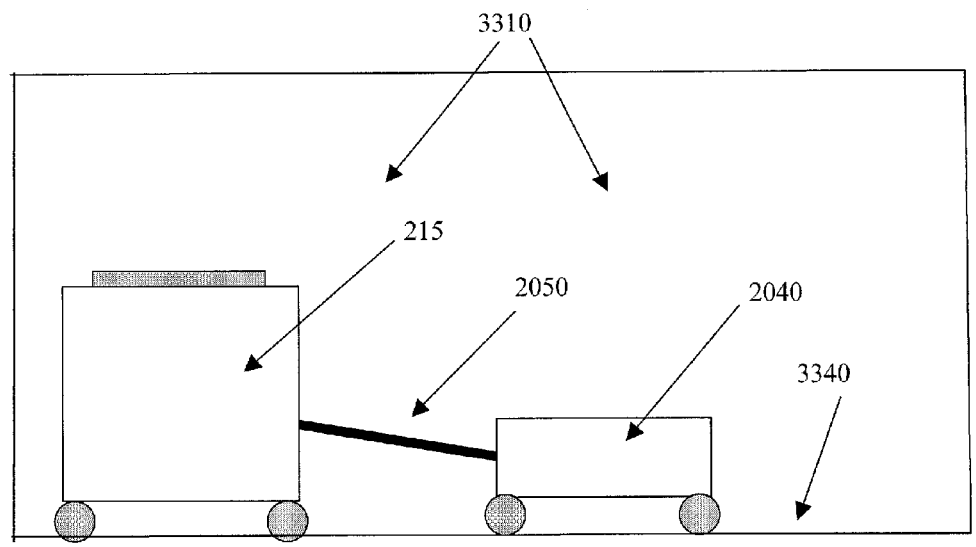
FIG. 70 is a schematic view of an embodiment of the aerosol generator including a dehumidifier of FIG. 52 in an enclosed space.
Figure 71:
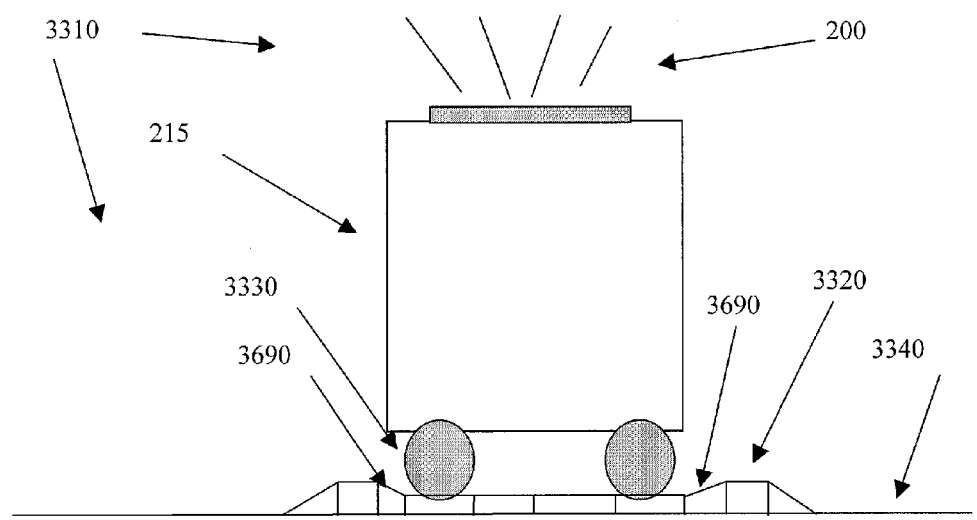
FIG. 71 is a schematic view of a first embodiment of an interface assembly used with the generator of FIG. 70.
Figure 72:
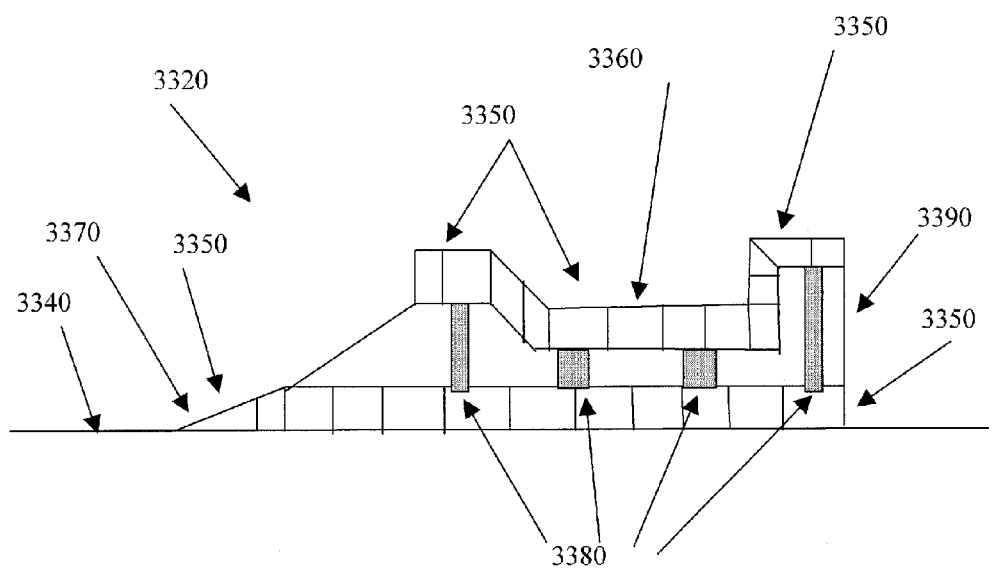
FIG. 72 is a schematic view of the interface assembly of FIG. 71.
Figure 73:
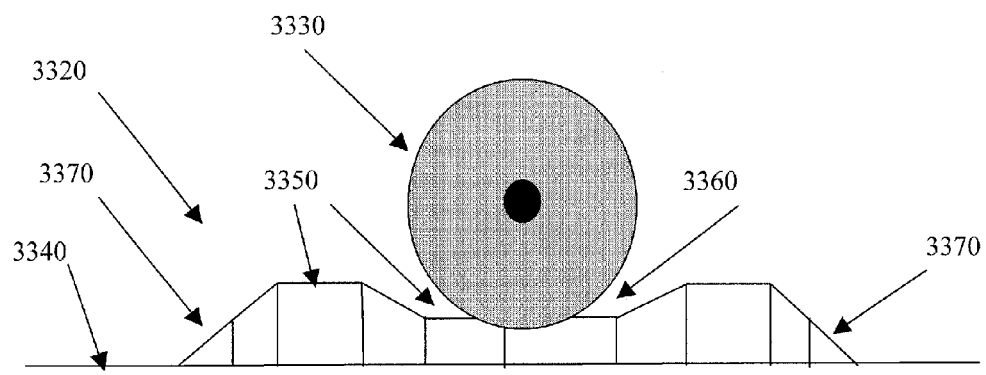
FIG. 73 is a schematic view of a wheel engaged with the interface assembly of FIG. 71.
Figure 74:
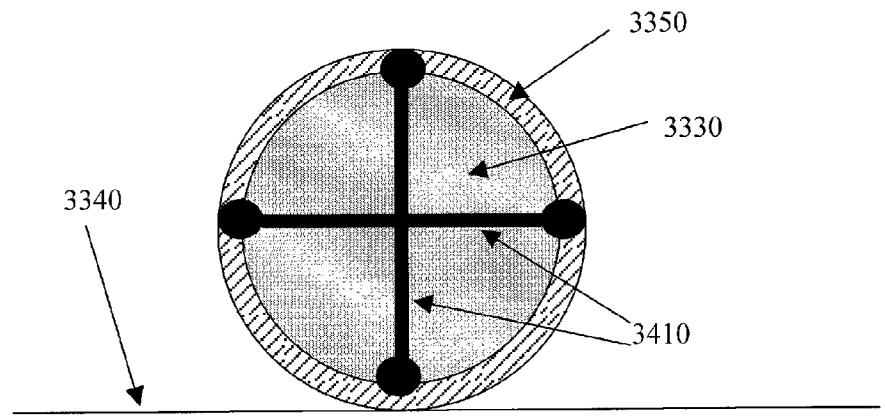
FIG. 74 is a schematic view of a second embodiment of an interface assembly used with the generator of FIG. 70.
Figure 75:
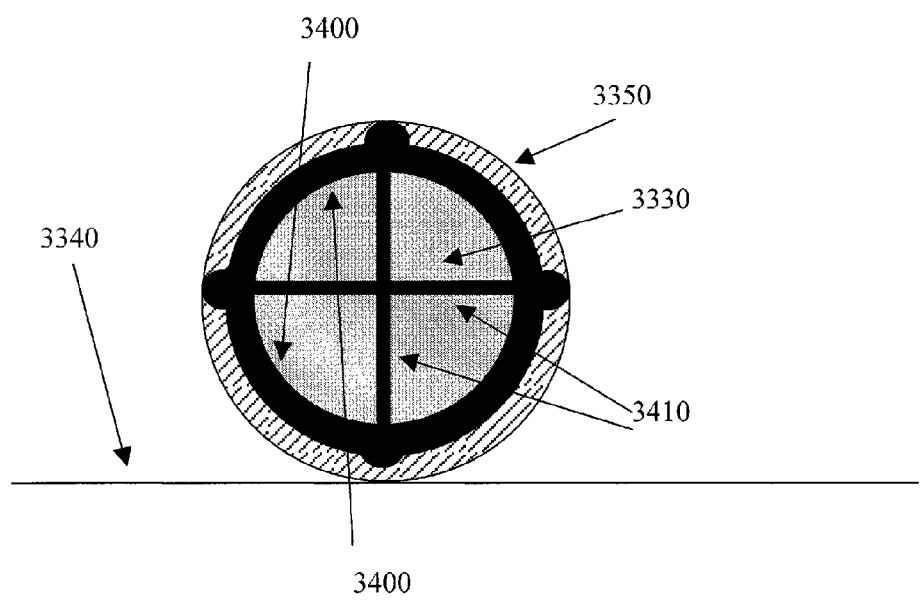
FIG. 75 is a schematic view of a third embodiment of an interface assembly used with the generator of FIG. 70.

According to an embodiment shown in FIGS. 57-58 and 69, the apparatus (215) can, without limitation, be designed and constructed so that the air entering the reservoir (40) is distributed to one or more locations inside of the reservoir (40) via means such as, but not limited to, conduit, piping, tubing, channels (2010). According to an embodiment, these means to move the air can be easily removed for cleaning. According to another embodiment, this means to move, channel, or distribute the inbound air to one or more locations throughout the fog tank or reservoir (40) can have various lengths, shapes, and geometries, and can have one or more holes or perforations (2030) of various sizes and shapes in various orientations, as best shown in FIG. 69. They can also be partially or completely enclosed. These embodiments can reduce, diminish, or eliminate, unwanted air patterns or airflow in the reservoir and/or fog tank (40) such as, but not limited to, stagnant airflow, uneven or unbalanced airflow, turbulent airflow, or vortices. It is preferred, without limitation, that the air exiting these holes or perforations (2030), is directed downward toward the liquid in the reservoir (40). It is even more preferred that the air is directed downward toward the bottom of the reservoir (40), and the bottom of the reservoir (40), or any area near the bottom of the reservoir (40), is designed so that the inbound air flow strikes a shelf (2600) (FIG. 64) or area that is not covered with liquid (30). The shelf (2600) can be canted at any angle. It is preferred, without limitation, the shelf (2600) is sloped downward at a forty-five degree angle toward the part of the reservoir (40) where the liquid (30) is held. It is very preferred that the air is directed along the wall of the tank or reservoir (40) opposite from the wall closest to the one or more orifices (170) though which the air and aerosol (20) exits the apparatus (215).

According to an embodiment, the apparatus (215) can, without limitation, be designed and constructed so that the velocity and/or volume of air exiting from the reservoir (40) or apparatus (215) can be reduced at any time during the aerosol generation and output cycle. It is preferred without limitation, this process occurs at or near the end of the aerosol generation and output cycle. It is also preferred, without limitation, that the velocity and/or volume of air or gas exiting from the reservoir (40) or apparatus (215) is reduced to at least 150 cubic feet or more per minute, and more preferred to at least 100 cubic feet or more per minute, and even more preferred that the air velocity be reduced to 10 cubic feet or more per minute. The decrease in the velocity and/or volume of air or gas and aerosol (200) exiting from the reservoir (40) or apparatus (215) can, without limitation, promote a more rapid build up of aerosol (200) in the area surrounding the apparatus.

According to an embodiment, the apparatus (215) can, without limitation, be designed and constructed so that it is connected to one or more sensor(s) (3530) or has communication with one or more sensor(s) (3530) to determine if or when an effective or sufficient amount of aerosol (200) is applied to the treated or targeted area (210). This embodiment includes configurations in which the sensor(s) (3530) may be directly or indirectly attached to the apparatus (215), or that one or more sensor(s) (3530) may be remotely located and operated in any location within the targeted area(s) (210) where the aerosol (200) may be administered. The one or more sensor(s) (3530) can be, without limitation, positioned in or at any, orientation, height, or location in the targeted area(s) (210), and communicate directly or indirectly with one or more aerosol generating apparatus(s) (215), or one or more of any remote device(s) that control one or more of any aerosol generating apparatus(s) (215), in various ways such as, but not limited to any, radio waves, sound, wire, cable, or fiber optics.

According to an embodiment in FIGS. 52-55, one or more means to dehumidify (2040) an area in which the aerosol (200) is administered can be operated, without limitation, at any time during or after one or more apparatus(s) (215) has stopped administering the aerosol (200). The dehumidification cycle time can vary for reasons including, but not limited to, the size of the targeted area being dehumidified, the amount of aerosol (200) that is deployed into the targeted area, the specific level of humidity that is desired or chosen for the dehumidification process or the targeted area.

According to an embodiment, the one or more means to dehumidify (2040) can delay starting the dehumidification process for any period of time after, without limitation, receiving a signal or command to begin the dehumidification process, receiving any humidity level information, or detecting a certain humidity level. This time delay can be impacted by inputs or factors such as, but not limited to, the size of the treated space, the number of means used to dehumidify (2040) the targeted area(s) (210), the number of aerosol generating apparatus(s) (215) in use, the temperature of the treated area, or the desired level of disinfection or efficacy of the process.

The one or more means to dehumidify (2040) can be any suitable means or apparatus(s) known to those skilled in the art. One or more means to dehumidify (2040) may also, without limitation, be included in the design and construction of one or more aerosol generating apparatus(s) (215). Without being limited, any suitable means known to those skilled in the art to remove humidity and/or any vapor(s) from the air or any environment surrounding the dehumidification apparatus (2040) may be used. The one or more means to dehumidify (2040) may also, without limitation, include or implement any catalytic technology known to those skilled in the art. The means to dehumidify can also be directly or remotely programmed or controlled, by any means known to those skilled in the art such as, but not limited to any, software, relays, timers, programmable logic circuits, or integrated circuits, and/or one or more of any remote controlling device(s) that can communicate and/or control either, or both, the dehumidification apparatus(s) and/or aerosol generator(s) (215) with any suitable wireless means, all in a manner known to those skilled in the art.

Figure 52:
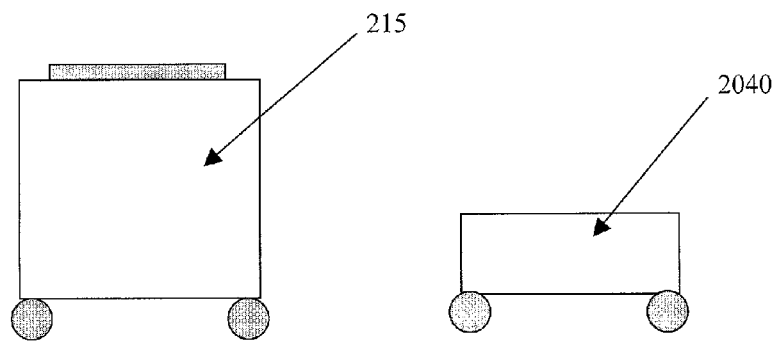
FIG. 52 is a schematic view of an aerosol generator combined with a dehumidifier.

In one embodiment shown in FIG. 52, the one or more means to dehumidify (2040) an area in which the aerosol (200) is administered is an independent apparatus that is "not" connected to the one or more aerosol generating apparatus(s) (215), and it is remotely controlled and/or programmed by one or more operator(s), all in a manner known to those skilled in the art. Without being limited, the one or more aerosol generating apparatus(s) (215) and/or the one or more means to dehumidify (2040) can be, without limitation, controlled by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device(s), via one or more of any suitable radio(s), all in a manner known to those skilled in the art.

Figure 53:
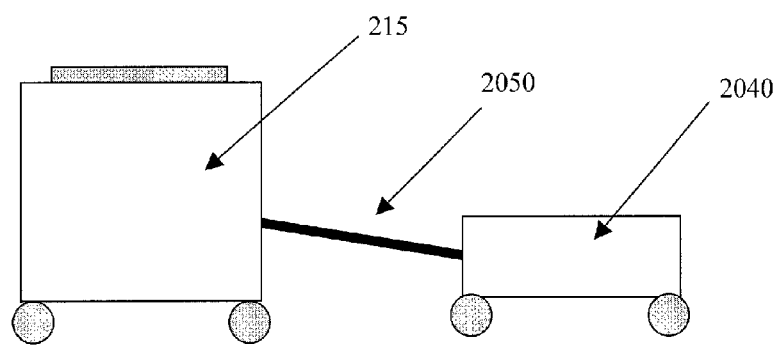
FIG. 53 is a schematic view of an aerosol generator connected to the dehumidifier.

In another embodiment shown in FIG. 53, the one or more means to dehumidify (2040) an area in which the aerosol (200) is administered, is also an independent apparatus(s), but in this particular embodiment its operation is electrically controlled by, and electrically connected to, the one or more aerosol generating apparatus(s) (215) via one or more of any suitable connection(s) (2050) known to those skilled in the art. However, the one or more means to dehumidify (2040), as well as any aerosol generating apparatus(s) (215), can still be, without limitation, controlled by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device(s), via one or more of any suitable radio(s), all in a manner known to those skilled in the art. Without being limited, the one or more means to dehumidify (2040), as well as any aerosol generating apparatus(s) (215), can also include two or more of any means for connecting any, power and/or communications, with any suitable socket and/or plug configuration, at any suitable and effective locations on the exterior of the device(s). It is preferred, without limitation, that at least one means for connecting any, power and/or communications, is positioned on either end of the means used for dehumidification (2040), and the connections have a socket configuration for electrical safety. This configuration can be used, without limitation, to facilitate the connection of more than one dehumidification apparatus(s) to the aerosol generator(s) (215).

In still another embodiment, the one or more means to dehumidify (2040) an area in which the aerosol (200) is administered, is also an independent apparatus(s), but in this particular embodiment its operation is controlled, either remotely and wireless and/or with any suitable wired connection, by one or more of any aerosol generating apparatus(s) (215), and/or one or more of any suitable, digital, electronic, or analog, controller(s) such as, but not limited to, any PLC(s), remote PLC(s) (3893), remotely located PLC(s), and/or any suitable remote controlling device, via one or more of any suitable radio(s), all in a manner known to those skilled in the art. However, it is electrically independent in this particular embodiment. In any of these embodiments, the one or more aerosol generating apparatus(s) (215) can, without limitation, communicate and interact with, and/or be controlled by, one or more of any suitable, digital, electronic, or analog, controller(s) such as, but not limited to, any PLC(s), remote PLC(s) (3893), remotely located PLC(s), and/or any suitable remote controlling device, via one or more of any suitable radio(s), all in a manner known to those skilled in the art.

Figure 54:
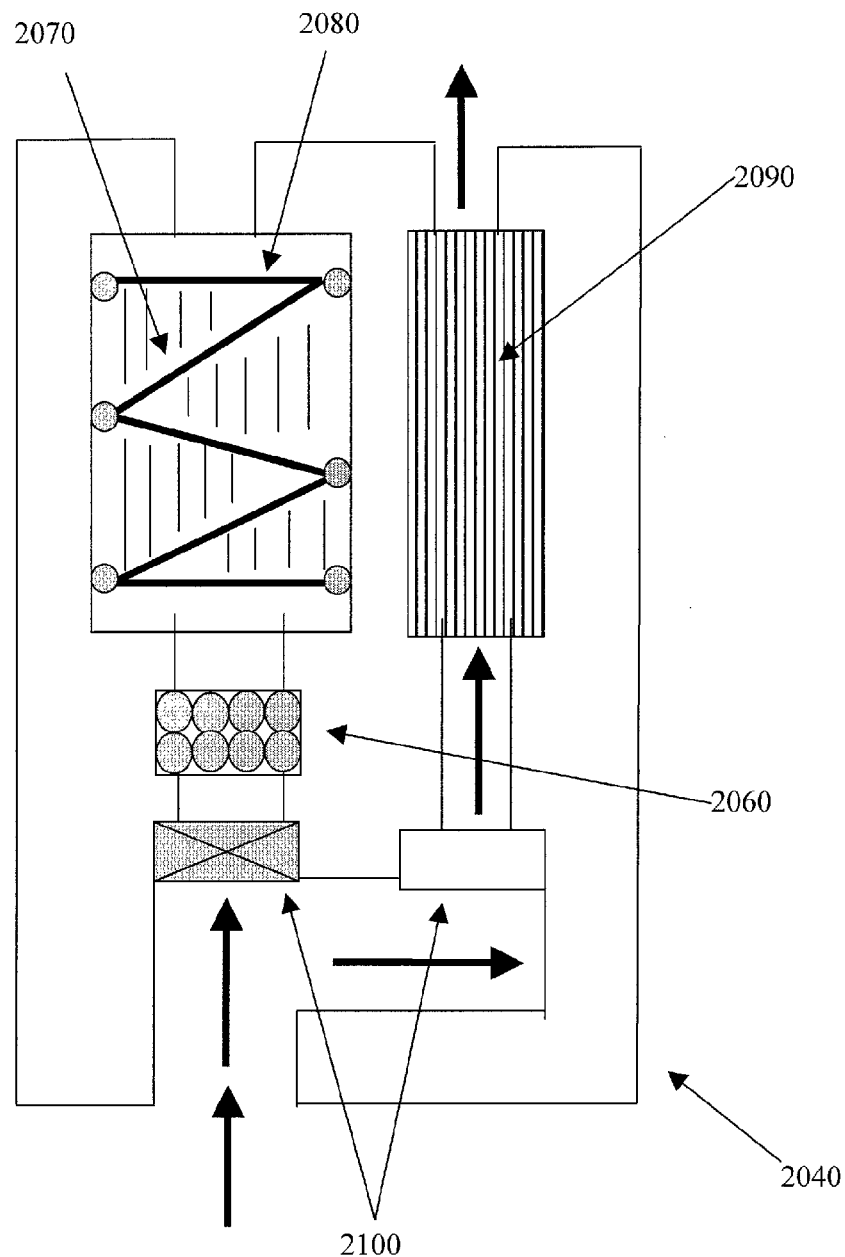
FIG. 54 is a schematic view of the dehumidifier of FIG. 52 in a first configuration.
Figure 55:
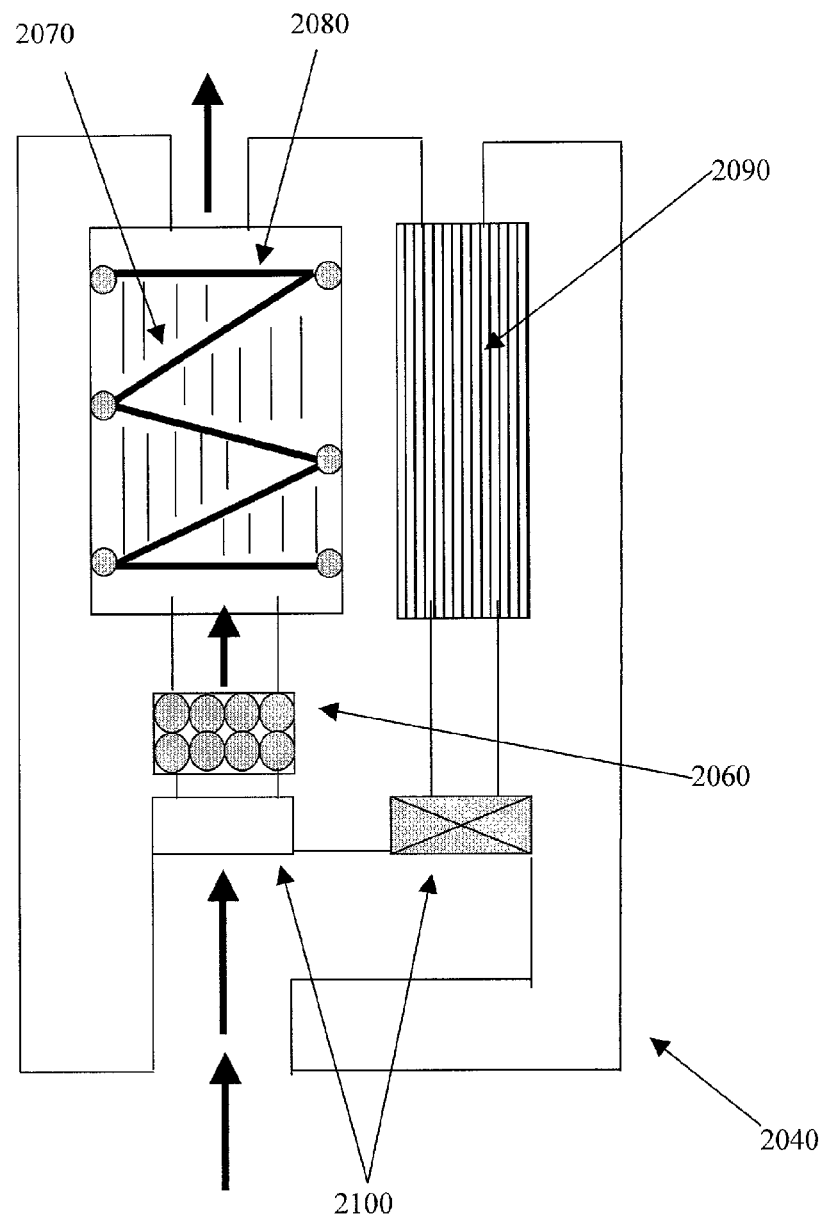
FIG. 55 is a schematic view of the dehumidifier of FIG. 52 in a second configuration.

In an embodiment shown in FIGS. 54-55, the one or more means to dehumidify (2040) an area in which the aerosol (200) is administered can contain, without limitation, one or more filter media to filter the aerosol (200) from the air during, or after it passes over the chill coils. The filter media can be any filter known in the art, but it is preferred, without limitation, that the filter media or mechanism consists of one or more separation cones (2060) that separates the aerosol (200) from the air as the air moves through the separation cone(s) (2060).

In another embodiment, the one or more means to dehumidify (2040) an area in which the aerosol (200) is administered is designed and manufactured so that one or more stainless steel filter material or metal mesh of any porosity size, number, and shape (2070) connects with, spans between, or is interwoven with the one or more chill coils (2080) of various size and shape, that are used by the means to dehumidify (2040). This construction may also, without limitation, increase the cooling efficiency of the means to dehumidify (2040) by increasing the cooled surface area.

In another embodiment, any liquid filtered from the air, or condensed by the chill coil(s) (2080) or any connecting metal filter material(s) or mesh, can without limitation, be collected in one or more collection container(s) that can also be shared with other parts of the dehumidification apparatus(s) (2040).

In another embodiment, the one or more means to dehumidify (2040) an area in which the aerosol (200) is administered can be, without limitation, designed and built so it can receive any type of suitable signal known to those skilled in the art, such as but not limited to any signal that is transmitted wireless, and/or through any wire, and this signal may cause the means to dehumidify (2040) to switch or direct the air moving through the dehumidification apparatus(s) (2040) from moving over one or more of any chill coils (2080), or any other dehumidification device(s) known to those skilled in the art, to instead flow into or through one or more of any suitable filter(s) (2090) known to those skilled in the art, that is able to effectively remove one or more of any gas(s) and/or vapor(s), and/or any chosen or selected gas(s) or vapor(s), from the air or atmosphere within the treated area(s) (210). It is preferred, without limitation, that the one more filter(s) (2090) is constructed from any suitable type of charcoal, in a manner that is known to those skilled in the art. It is more preferred, without limitation, that the one more filter(s) (2090) is constructed from one or more of any suitable type of filter media, such as, but not limited to one or more of any suitable type of charcoal or activated charcoal. It is even more preferred, without limitation, that the one more filter(s) (2090) is constructed from one or more of any suitable type of filter media, such as, but not limited to one or more of any suitable type of charcoal or activated charcoal, that can effectively remove various compounds such as, but not limited to any, hydrogen peroxide, acetic acid, and/or peroxyacetic acid (PAA), from the atmosphere within the targeted area(s) (210). Any amount of any type of filtered vapor(s) or gas(s) that are desired to be removed, can be filtered from the air or gas(s) that are moved through the filter(s). It is preferred, without limitation that at least an efficacious, effective, and/or suitable, amount of the one or more gas(s) or vapor(s) targeted for removal, are removed by the one or more filter(s) (2090).

One or more of any door(s), flap(s), covering(s), valve(s) (Hereinafter called "valve(s) (2100)), or other means known to those skilled in the art, can be, without limitation, opened and closed, at any effective and suitable time, and for any duration of time, within the design and/or construction of the dehumidification apparatus(s) (2040). The valve(s) (2100) can be opened and closed at any suitable and effective time, and consist of any, mechanical design, electro-mechanical design, pneumatic design, and/or any other suitable design(s), known to those skilled in the art. It is preferred, without limitation, that either opening and/or closing the valve(s) will cause the air or gas(s) moving through the dehumidification apparatus (2040) to move through one or more separate channel(s), tunnel(s), and/or pipe(s), that leads to one or more of any suitable filters (2090) and/or activated charcoal filter(s) (2090), and/or any other suitable means for filtering (2090) one or more of any targeted gas(s) for removal. The air and/or various gas(s) can be, without limitation, vented out of the dehumidification apparatus(s) (2040) and back into the targeted area(s) 210), after they pass through the one or more filter(s) (2090).

The atmosphere, air, and/or gas(s) from within the targeted area(s) (210) can also be, without limitation, moved through the one or more means for dehumidification (2040), and/or the one or more means for filtering (2090), at any speed, rate, and volume per minute. It is preferred, without limitation, that the atmosphere, air, and/or gas(s) within the targeted area(s) (210) are at least moved through the one or more means for dehumidification (2040), and/or the one or more means for filtering (2090), at effective and efficacious, speed, rate, and volume per minute. Without being limited, the atmosphere, air, and/or gas(s) within the targeted area(s) (210) can be moved through the one or more means for dehumidification (2040) and/or one or more means for filtering (2090) at any time. It is preferred, without limitation, that the targeted area(s) are first effectively and efficaciously dehumidified, before any atmosphere, air, and/or gas(s), from within the targeted area(s) (210), are moved through the one or more means for filtering (2090). It is more preferred, without limitation, that the targeted area(s) are effectively and efficaciously dehumidified at the same time as any atmosphere, air, and/or gas(s), within the targeted area(s) (210), are treated and/or filtered with one or more means for filtering (2090). This can be, without limitation, performed in various ways such as, but not limited to: (a) moving effective and suitable amounts of any atmosphere, air, and/or gas(s), from within the targeted area(s) (210), through both the one or means for dehumidification (2040), and the one or more means for filtering (2090), at the same time, (b) moving effective and suitable amounts of any atmosphere, air, and/or gas(s), from within the targeted area(s) (210), first through the one or means for dehumidification (2040), and then through the one or more means for filtering (2090), and/or, (c) moving effective and suitable amounts of any atmosphere, air, and/or gas(s), from within the targeted area(s) (210), first through the one or more means for filtering (2090), and then through the one or means for dehumidification (2040).

In another embodiment, the means to dehumidify (2040) an area in which the aerosol (200) is administered or deployed, can be, without limitation, designed and built so the operator(s) can program or select various options including, but not limited to, (a) any time delay between when a certain humidity level or range of humidity is detected and when the dehumidifier would commence the dehumidification process, (b) any humidity level where the means to dehumidify (2040) would stop the dehumidification process, (c) any duration of time for moving, switching, or directing the air flowing into or through any filter (2090) that is able to effectively remove any targeted gas(s) or vapor(s) from the treated area(s), (d) any duration of time that the means to dehumidify (2040) would operate and dehumidify the room.

According to an embodiment shown in FIGS. 59-63, a means to effectively or efficaciously cover various types of inbound or outbound air vents and/or any surrounding area or surfaces of the vents (2120), in the treated area can, without limitation, be used in concert with the aerosol generating apparatus (215) or any aerosol or vapor generating apparatus, and prevent or limit the movement of air, gas, aerosol (200) and vapor(s) through these vents (2120). This vent covering assembly (2300) consists of parts including, but not limited to, a means to cover the vent (2110), any material extensions (2160) that are needed to directly or indirectly attach to the cover (2110) so that it will have sufficient clearance and cover any protruding vent (2120) parts (3010), sealing material (2130) that can seal the cover (2110) to the vent (2120) or any surface(s) surrounding the vent, any one or more pole(s) (2140) which can, without limitation, be adjusted or modified for length by the operator, a means to directly or indirectly connect the pole(s) to the vent cover (2150), one or more means to directly or indirectly connect (2500) the pole(s) (2140) to the floor or any other surface (2400). This assembly of parts can be made of any mechanically, structural, and chemically suitable materials that are known to those skilled in the art for this application.

Any parts used to construct the vent covering assembly (2300) can be constructed from various materials such as, but not limited to, stainless steel, glass, polymer, polyolefin, cellulose, or even natural or manufactured fibers that are either coated or uncoated. It is preferred, without limitation, that the vent covering assembly (2300) is constructed from one or more polymers that can include, but is not limited to, PVC, polycarbonate, polypropylene, and HDPE. The materials used to construct the vent cover (2110) or extension(s) (2160) may be rigid, semi-rigid, flexible, or pliable. It is preferred, without limitation, that the vent cover (2110) and any needed extension(s) (2160) are constructed from rigid PVC. The seal material (2130) can be any material that can create an effective seal with/against any materials that it contacts. It is preferred, without limitation, that the seal material (2130) is constructed from materials such as, but not limited to, Viton, or EPDM, with a durometer of at least 10. The seal material can be, without limitation, any foam, open or closed cell material, and any shape or construction known in the art. The sealing material (2130) can also vary with variables including but not limited to its, size, shape, width, surface area, geometry, fit, thickness, density, hardness, elasticity, porosity, permeability, mechanical properties, physical properties, and other variables known to those skilled in the art. One or more strips or layers of various seal material(s) (2130) may also be utilized and can be used in various orientations, including, but not limited to, parallel to one another. It is preferred, without limitation, that the seal material consists of a single row of closed cell EPDM foam. Any of the surfaces of the vent covering assembly (2300) can, without limitation, be electrically or electrostatically charged in order to attract the "applied agent". The vent covering assembly (2300) can be designed and constructed for single or multiple uses.

According to another embodiment, the vent cover (2110) and/or its extensions (2160) can, without limitation, be constructed from, or be molded with, any material that can create an effective seal, or otherwise function as the seal, which negates the use of a separate seal material and/or seal layer (2130). This represents the vent cover (2110) in its simplest form. In this case, the vent cover (2110) and/or its extensions (2160) is designed and constructed so that it incorporates the purpose, performance, traits, attributes, and characteristics of both the seal material and/or seal layer (2130) and the vent cover (2110) and/or extensions (2160).

In another embodiment, any parts connected directly or indirectly to the means to cover the vent (2110) can be adjusted for height in order to create or maintain effective compression on any seal that is formed to effectively or efficaciously seal or cover the air or gas vents (2120). It is preferred, without limitation, that the one or more pole(s) (2140) is constructed in a manner known to those skilled in the art, so that its length can be adjusted and locked into position once sufficient or effective force is exerted onto any part of the vent covering assembly (2300) such as, but not limited to, a means to cover the vent (2110) and/or the seal material (2130).

It is preferred, without limitation, that the means to cover the vent (2110) is any shape, size, construction, or geometry that is sufficiently large enough so that the sealing means and/or seal material (2130) can effectively seal to or around any air vents (2120). It is even more preferred, without limitation, that the means to cover the vent (2110) is in the shape of a plate or bowl. This means to cover the vent (2110) can, without limitation, have one or more structural supports that are positioned in a manner known in the art to prevent any unwanted flexing of the means to cover the vent (2110) during use. The means to cover the vent (2110) can also, without limitation, have extensions (2160) directly or indirectly attached to allow the various vent cover components (2170) to effectively fit over the vent (2120) and any protruding vent parts (3010). The extensions (2160) can be made of the same materials as the means to cover the vent (2110), and have any thickness, width, length, height, geometry, or construction. The extensions (2160) can, without limitation, follow the outline of the means to cover the vent (2110).

The seal material (2130) can be attached to the vent cover (2110) or its extensions (2160) in various ways known to those skilled in the art. The seal material (2130) can be made from any compatible and suitable material. However, it is preferred, without limitation, that the seal material (2130) consists of any suitable material and design that has sufficient compression and/or compliance to form an effective seal when it is compressed or contacts between the vent cover (2110) and/or extension(s) (2160) and the vent (2120) or any surface surrounding the vent. It is even more preferred that the seal material (2130) has absorbent properties. A lip or other effective means can also be built or formed around the seal material (2130) to catch or hold any liquid if it is compressed out of the seal material (2130).

Any pole (2140) known to those skilled in the art, can be used in the present invention, but it is preferred, without limitation, that the pole (2140) has an adjustable length, and a locking means (3020) (FIG. 61) known in the art to maintain the effective or chosen pole length. Any method known to those skilled in the art can be used to incorporate a pole (2140) adjustable for length into the present invention. It is preferred, without limitation, that the pole (2140) consists of two parts, and the length of the combined poles can either gain length or loose length depending on which way the operator screws or ratchets the two pole pieces. The pole (2140) connects either directly or indirectly to the means to cover the vent (2110) and this connection can, without limitation, swivel. It is preferred, without limitation, that the pole screws into a bracket or threaded block that is directly mounted to the means to cover the vent (2110). The end of the pole that contacts the floor or other surface, can also without limitation, be adjustable for length, and have the ability to swivel. The end of the pole or support mechanism (2800) can be, without limitation, formed from, molded, coated, adhered, or covered, with any absorbent material so that the surface and/or area below the pole can be treated with any liquid. The end of the pole or support mechanism (2800) can also, without limitation, be manufactured with any material that will decrease the movement or slipping of the pole.

According to an embodiment, installation includes, but is not limited to, pressing the means to cover the vent (2110) and its accompanying seal material (2130), up against or around the vent (2110) and extending the pole until sufficient pressure is formed against or around the vent (2110), and the end of the pole (2140). Before, during, or after installation, the seals (2130) and end of the pole (2140) can be, without limitation, soaked with or saturated with any liquid consisting of any anti-pathogen, toxin, fungal, sterilization, disinfection, or sporicidal agent(s) or mixtures thereof (herein collectively "agent(s)").

Figure 63:
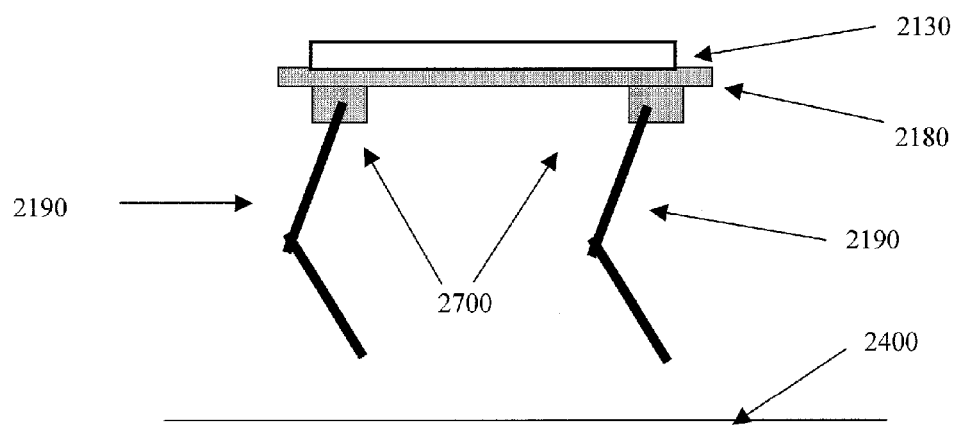
FIG. 63 is a schematic view of a fourth embodiment of a vent cover of FIG. 60.

According to an embodiment shown in FIG. 63, one or more attachment points (2700) can be added to the design of a magnetic vent cover (2180) so that a means (2190), can be attached to the vent cover to pull it from the ceiling vent without the need for a person to use a means such as, but not limited to, a ladder to reach it. This means (2190) used for pulling can include, but is not limited to, rope, cord, thread, wire, cable, twine, tube, that can be various, size, length, materials, and construction. Protruding objects (2200) of various lengths, shapes, and construction, can also, without limitation, be attached to the magnetic vent cover (2180) in various ways known in the art, for the same purposes. The protruding objects can include, but is not limited to, any dowel, pipe, or conduit, and can also be constructed from any suitable materials, and have various flexibility or rigidity. The construction of the magnetic vent cover (2180) is known to those skilled in the art, but it can, without limitation, be made by laminating a sheet of magnetic material between two or more polymer layers. The magnetic material can have any thickness, power, or strength, and the polymer coatings or laminations, can be any suitable polymer. According to another embodiment, the magnetic vent cover (2180) can, without limitation, incorporate any deformable seal material (2130), which can increase the ability of the magnetic vent cover (2180) to effectively seal the vent (2120). The seal material (2130) can without limitation, contact the vent (2120), surround the vent (2120), or contact any area near the vent (2120). The seal material (2130) can be encompassed or enclosed on one or more sides by any magnetic material (2900) of any strength. The seal material (2130) can be, without limitation, separated from the magnetic material (2900) by one or more layers of any suitable polymer of any thickness.

Figure 60:
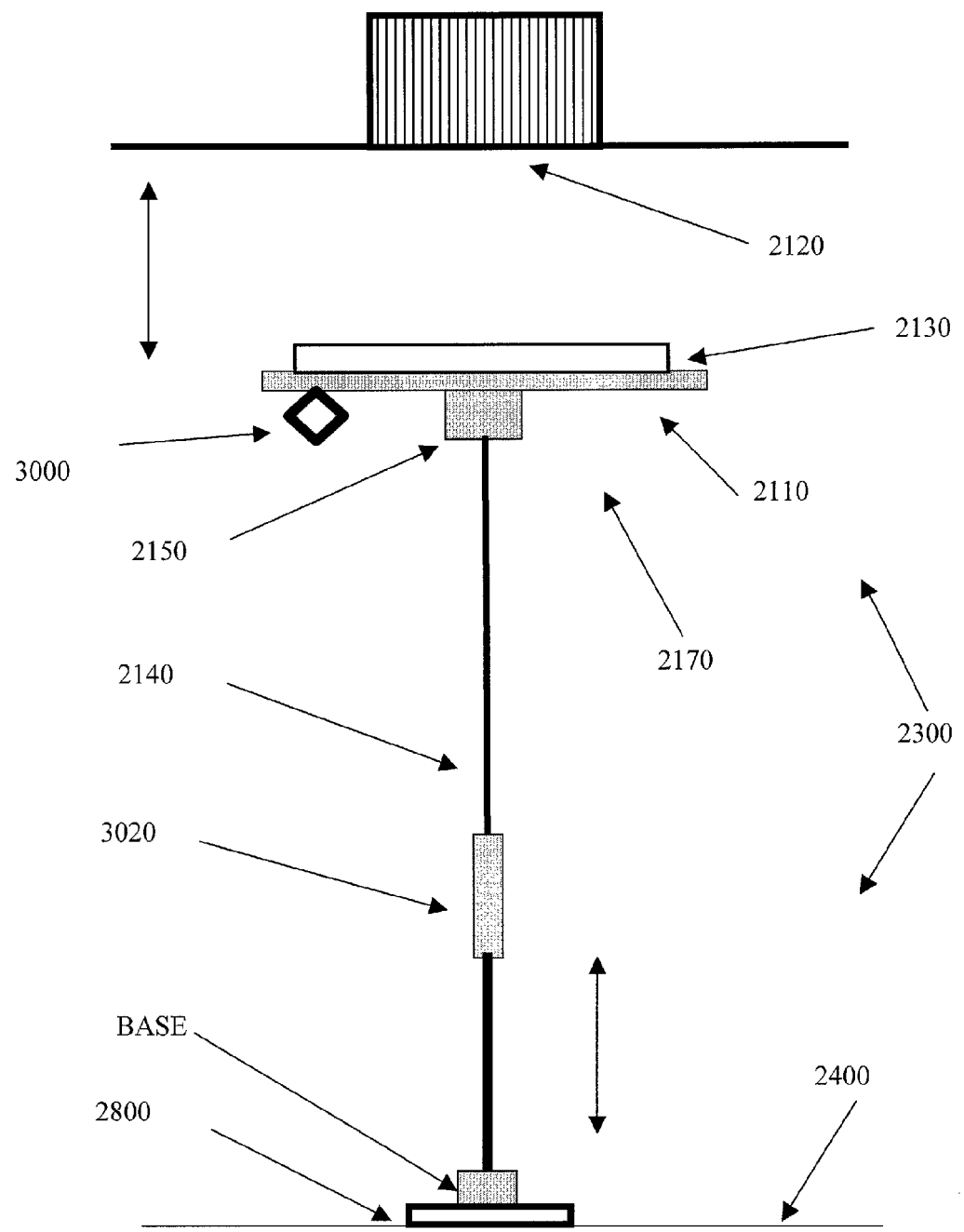
FIG. 60 is schematic view of a first embodiment of a cover engaged with the wall vent of FIG. 59.
Figure 61:
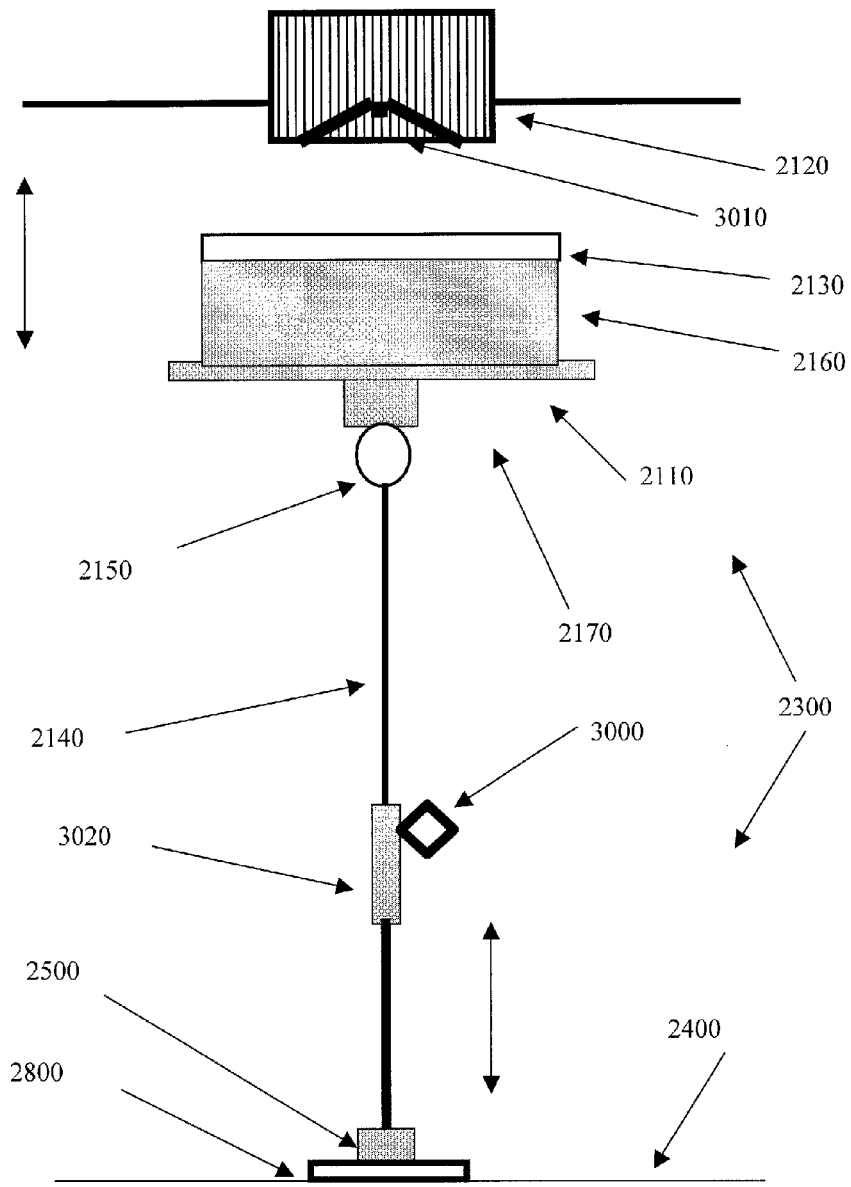
FIG. 61 is a schematic view of a second embodiment of the cover of FIG. 60.
Figure 62:
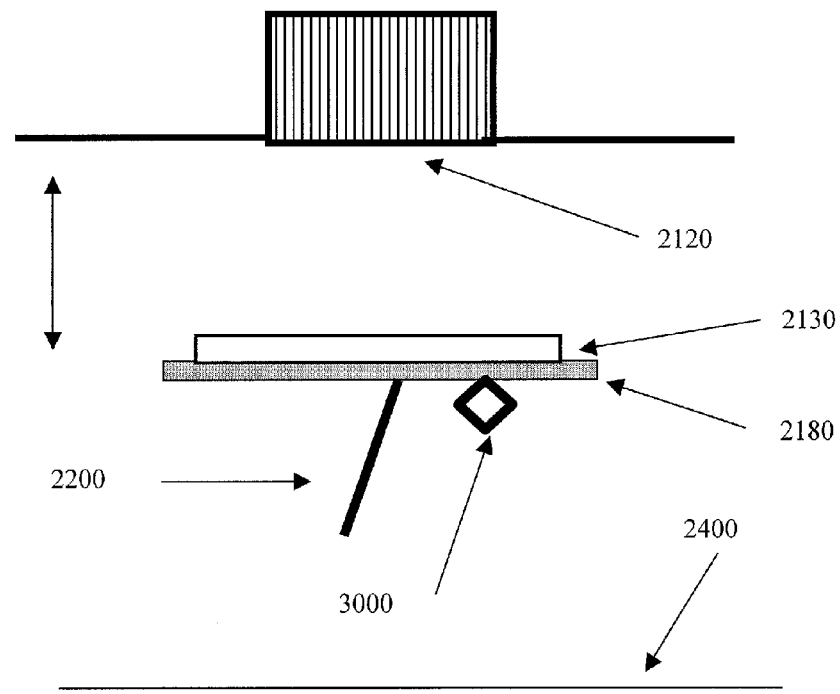
FIG. 62 is a schematic view of a third embodiment of the cover of FIG. 60.

According to an embodiment shown in FIGS. 60-61, one or more chemical contact or biological indicators (hereinafter "indicator(s)") (3000) of any size, type, or construction, may be mounted, held, hung, positioned, or placed, on any part including, but not limited to, the vent covering assembly (2300), or any part directly or indirectly connected to the vent covering assembly (2300) or magnetic vent cover (2180). It is preferred, without limitation, that the indicator (3000) is attached to a surface that faces the treated area. The vent covering assembly (2300) can be designed for the addition as well as removal of these accessories, in a manner known to those skilled in the art. The indicator (3000) provides a means for communicating or assuring that proper sanitization, detoxification, disinfection, high level disinfection, or sterilization has occurred, without limitation, on surfaces on or surrounding the vent covering assembly (2300). A detailed description of the indicator (3000) is not specifically set forth, but is known to those skilled in the art.

According to embodiment shown in FIGS. 65-68, the "application enclosure(s)" (930) can include, without limitation, one or more wall(s) (935), of any material, that form one or more enclosed, semi-enclosed, or unenclosed area(s) (940). The one or more wall(s) (935) of the application enclosure(s) (930) may also have one or more openings or holes (herein referred to as hole(s)) (955) of any size, shape, or dimension, and the interface of these hole(s) (955) with any surface(s) (945), or any object(s) (3030), forms one or more enclosed area(s) (950) which can vary with respect to variables such as, but not limited to any, size, shape, or geometry.

According to an embodiment, the application enclosure (930) can also, without limitation, be designed and constructed so that it has one or more opening(s) or orifice(s) ("hole(s)") (955), and one or more object(s) (3030) with one or more various surfaces (945) can be positioned or inserted through these hole(s) (955), and the direct or indirect contact or interface of the object(s) (3030) with these hole(s) (955) results or causes the enclosed area(s) (950) to become, without limitation, effectively sealed. The hole(s) (955) can also be formed around one or object(s) (3030). The object(s) (3030) can, without limitation, be oriented, located, or inserted, completely through the enclosed area (950) in any orientation, through the one or more hole(s) (955). The hole(s) (955) can be any size, geometry, orientation, or in any location. The holes(s) (955) and/or any parts of the application enclosure (930) can, without limitation, be of any construction, and be adjusted by various means known in the art, to accommodate any object(s)'s attributes including, but not limited to size, width, length, shape, and/or geometry. The application enclosure (930) can also, without limitation, be designed and constructed in a manner known to those skilled in the art, so that it can be temporarily or permanently mounted, strapped, or connected to any table, bench, or other surface.

Figure 65:
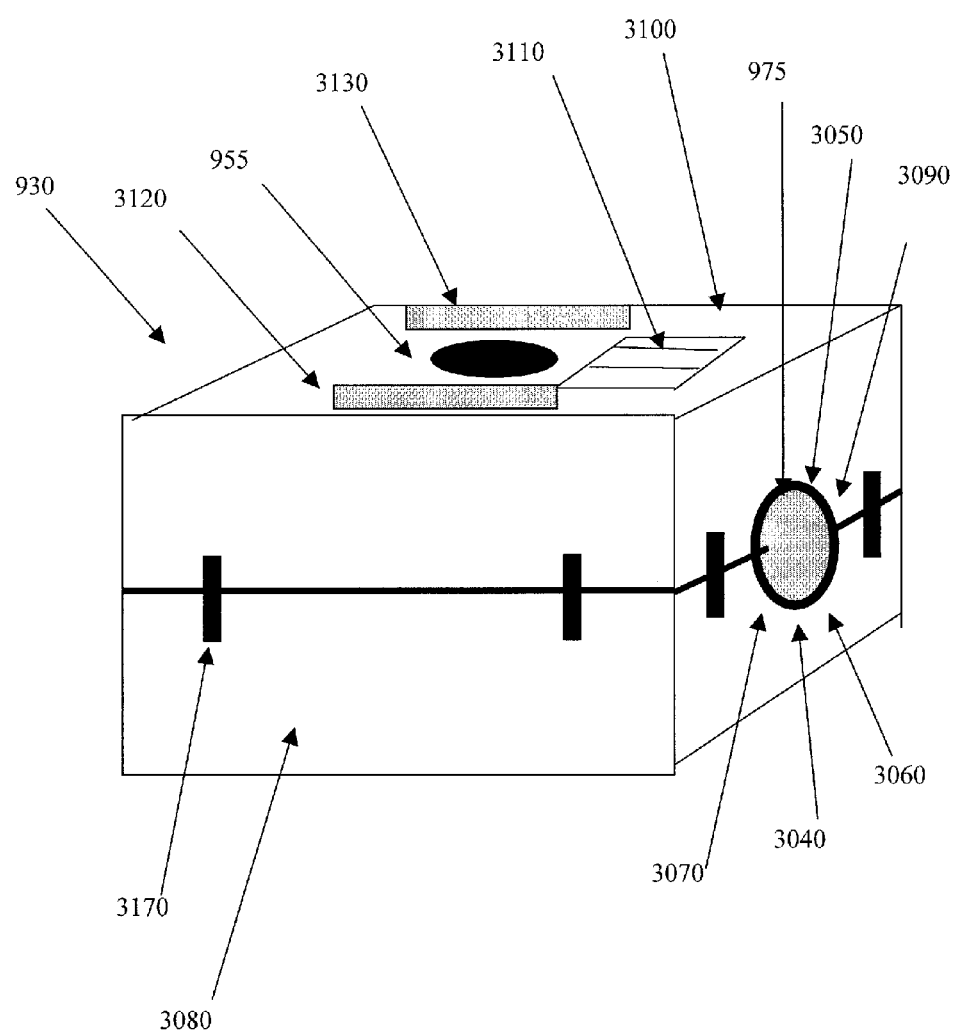
FIG. 65 is a schematic view of another alternative embodiment of the enclosure for the aerosol generator of FIG. 52.
Figure 66:
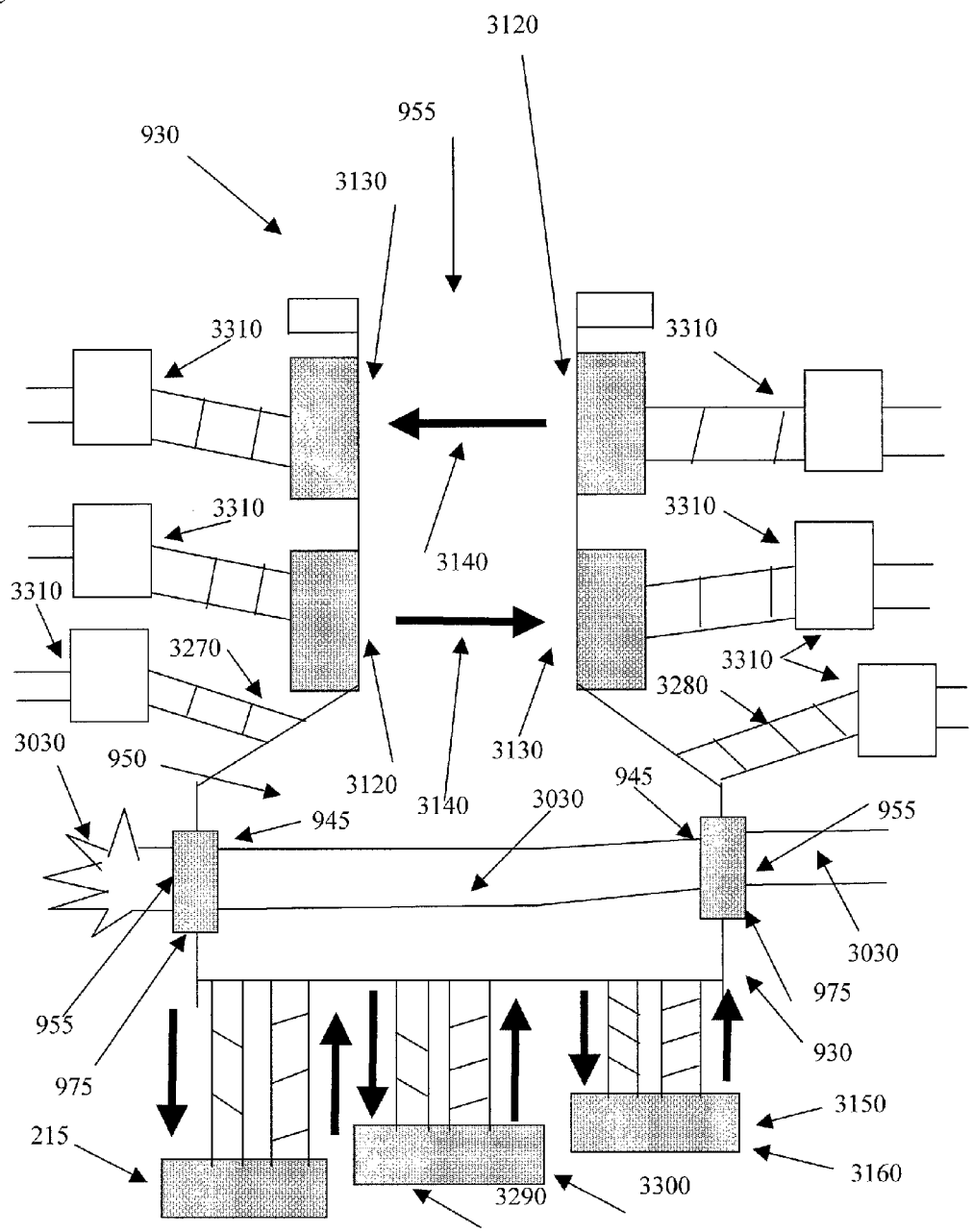
FIG. 66 is a schematic view of another alternative embodiment of the enclosure for the aerosol generator of FIG. 52.
Figure 67:
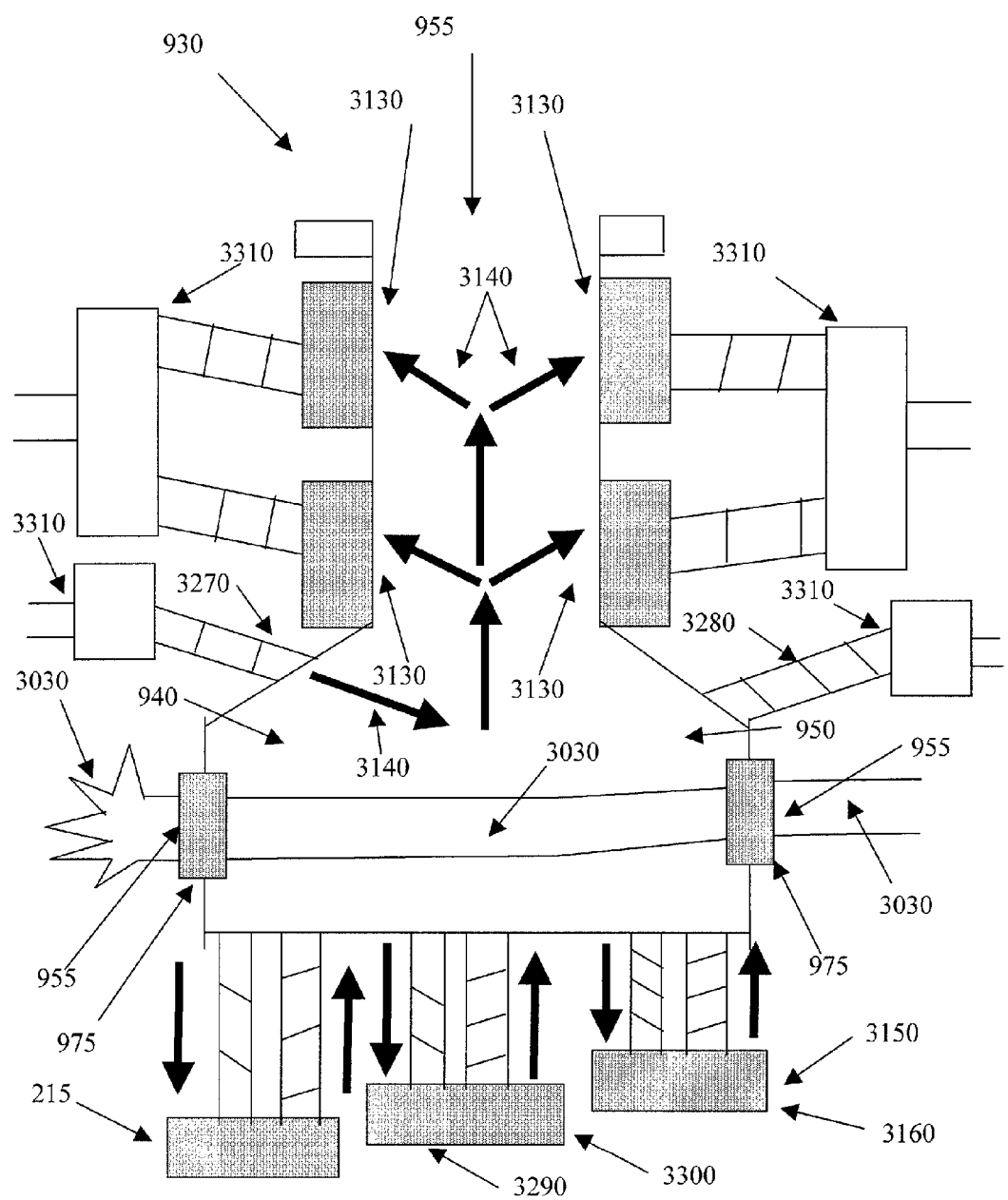
FIG. 67 is a schematic view of another alternative embodiment of the enclosure for the aerosol generator of FIG. 52.

Looking now at FIGS. 65-67, according to an embodiment, the application enclosure (930) can, without limitation, be designed and constructed so that one or more object(s) (3030) or any combination of objects (3030) can be positioned in or onto one or more section(s) (3040) of the one or more hole(s) (955) and/or their seal material (975), and the one or more opposing section(s) (3050) of each hole(s) (955) and/or their seal material (975), is then brought together by connecting the one or more component(s) (3060) that create an effectively sealed enclosed area(s) (950) when joined. It is preferred, without limitation, that this is accomplished by placing any number or combination of object(s) (3030) such as, but not limited to any legs, head, feet, hands, arms, or torso, inside or onto any part of the lower half (3070) of the section of hole(s) (955) and/or any seal material (975) directly or indirectly connected to any parts constituting the lower half (3080) of the enclosed area (950), and then enabling contact of these object(s) (3030) with any part of the upper half (3090) of the section of the hole(s) (955) and/or any seal material (975) that is directly or indirectly connected to any parts constituting the upper half (3100) of the enclosed area (950). It is preferred, without limitation, that the upper half and lower half of the enclosed area (950) are connected. It is even more preferred that upper (3100) and lower (3080) halves are able to hinge open and closed in a manner known in the art. The various application enclosure (930) parts, such as but not limited to the upper (3100) and lower (3080) halves can also, without limitation, be connected with one or more of any mechanical means (3170) known to those skilled in the art, to apply pressure to areas such as, but not limited to any seal between the upper (3100) and lower (3080) halves, and the one or more seals or interfaces between the object(s) and any part of the lower half (3070) and upper half (3090) sections, or any other sealing segments, of any hole(s) (955).

Any segments or parts of the hole(s) (955) can, without limitation, interface with the object(s) (3030) with one or more of any materials of any construction. It is preferred, without limitation, that this material is any seal forming material (975) or combination of materials (975), or any other means to form an effective seal (975), and is known to those skilled in the art. It is even more preferred, without limitation, that the seal (975) or any seal that interfaces with the object(s) (3030) can be directly or indirectly adjusted in any way, for effectiveness and fit and/or integrity, and can accommodate and effectively seal to objects (3030) of various size, shape, width, length, and geometry, and is known to those skilled in the art. The application enclosure (930) can, without limitation, seal or effectively interface with one or more of any object(s) (3030) in a manner known in the art, but it can be as simple as inserting the object(s) (3030) such as, but not limited to, any or all parts of a patient's body through any of the one or more hole(s) (955), and tightening or sealing any part connected to the object (3030) interfacing seal material (975), or interface material, that is directly or indirectly in contact with each or all of the object(s) (3030) or body part(s), to form, without limitation, an effective seal that can effectively seal the hole(s) (955). This can also be utilized, without limitation, for the hands or arms of any surgeons, nurses, technicians, or other personnel or operators, that need to access the inside of the application enclosure(s) (930) for any reason. Any pneumatic means consisting of any materials, any sealing materials (975), and construction, known to those skilled in the art, may also, without limitation, be used to effectively seal directly or indirectly around any object(s), or hand(s) or arm(s) of one or more of any personnel that interface with the application enclosure (930) in any way for any reason. One or more gloves (965) can also attach to any port(s), opening(s), or airlock(s) (960) or hole(s) (955) and be hermetically sealed to the application enclosure(s) (930). Furthermore, the gloves or gauntlets (965), and or any interface they may have with the application enclosure (930) can, without limitation, be designed in a manner known to those skilled in the art, so that they may be easily or quickly removed and replaced. It is preferred, without limitation, that the gloves or gauntlets (965) are disposable, and they can be replaced after each use of the application enclosure (930).

According to an embodiment, the application enclosure (930) can, without limitation, have one or more sources of pressurized or moving air or any gas, and these resulting flows or streams (herein referred to as "stream") of air or gas (3140) can move in various ways over, under, or across (herein referred to as "across") any door or hole (955) which personnel or robotics may use to access the inside of the application enclosure (930). The supplied air or gas stream (3140) can move, without limitation, completely or partially across any part or entirety of any door or hole (955) opening, at any angle, and at any velocity or volume. It is preferred, without limitation, that the air or gas stream is active or enabled for any door or hole (955) that is open or unsealed in any way, and the air or gas stream (3140) completely covers the door or hole (955) area and/or any area in close proximity to the door or hole (955). The one or more source(s) (3120) of the air or gas stream (3140) can be, without limitation, any size, shape, length, width, geometry, orientation, or construction, and can be positioned in any locations in various effective proximity to any door, opening, or hole (955). The air or gas can, without limitation, be directed with any form of baffles located anywhere within the application enclosure (930). It is also preferred, without limitation, that the outlet orifice for the source(s) (3120) of the air or gas stream (3140) is rectangular in shape and spans at least the width of the door or hole (955). The one or more sources (3120) of the air or gas stream (3140) can be, without limitation, located above one another, directly or indirectly opposed to one another, and separated by any distance. The one or more source(s) (3120) of the air or gas stream (3140) can also be, without limitation, perforated, and the perforations can be, without limitation, any number, size, shape, or orientation. Any air or gas that is used to form the air or gas stream (3140) can be, without limitation, filtered before being deployed or flowed, by any type of filter or filtering method (3310) including, but not limited to, a HEPA filter, all in a manner known by those skilled in the art.

It is also preferred, without limitation, that one or more door(s) or hole (955) cover(s) (Herein called "door(s)" (3110) can slide open and out of the way of the one or more human operator(s) or any robotic arms or tools, when access is needed to reach through the one or more hole(s) to work or perform any tasks anywhere inside of the enclosed area (950). The design and construction of the sliding door(s) (3110) is known to those skilled in the art. The hole(s) (955) as well as any door(s) (3110) can be any, size, width, length, depth, shape, thickness, construction, and material, and the door(s) (3110) can move via any means, and any construction, known to those skilled in the art. It is preferred without limitation that the sliding door(s) (3110) possesses sufficient attributes known in the art so that it can effectively seal the application enclosure (930) when it is closed. Any number of door(s) (3110) can be located at any location on the application enclosure (930). It is preferred, without limitation, that at least one door(s) (3110) is located on the top of the application enclosure (930). The application enclosure (930), any structures inside of the enclosed area(s) (950), and any hole(s) (955), are designed and constructed so that the hole(s) (955) are positioned or located, without limitation, at any height, distance, or location, from any objects located inside of the application enclosure (930).

According to another embodiment, an object (3030) can, without limitation, be placed completely inside the application enclosure (930), and all hole(s) (955) are either closed with door(s) (3110), or at least one hole (955) is kept open or partially open to enable personnel access into the application enclosure (930) to conduct work or tasks.

Any parts used to construct the application enclosure (930), or any door(s) (3110), can be constructed from various materials such as, but not limited to, stainless steel, glass, polymer, polyolefin, cellulose, or even natural or manufactured fibers that are either coated or uncoated. It is preferred, without limitation, that these parts or components are constructed from one or more polymers that can include, but is not limited to, PVC, polycarbonate, polypropylene, and HDPE. The application enclosure (930), or any door(s) (3110), can be, without limitation, flexible, rigid, semi-rigid, opaque, translucent, or transparent. It is preferred, without limitation, that rigid transparent materials are utilized.

According to an embodiment, one or more sources of vacuum (3130) (herein called "door vacuum") located near the door(s) (955) can be, without limitation, located anywhere in front of or opposed from the one or more outlet orifice(s) for the source(s) (3120) of the air or gas stream (3140) that can move various ways over, under, or across any door or hole (955). Any strength, velocity, volume, or amount of vacuum can, without limitation, be used. The orifice(s) for the door vacuum(s) (3130) can be, without limitation, any size, shape, length, width, geometry, orientation, or construction, and can be positioned in any locations in close proximity to any door, opening, or hole (955). It is preferred, without limitation, that the inlet orifice(s) for the door vacuum(s) (3130) can be rectangular in shape and span at least the width of the door or hole (955). The door vacuum(s) (3130) can be, without limitation, located above one another and separated by any distance, and be perforated with perforations that can be any, number, size, shape, or orientation. It is preferred, without limitation that the door vacuum(s) (3130) is active or enabled whiles the door or hole (955) is open or unsealed in any way, or one or more air or gas streams (3140) are present. Any air or gas that is pulled via vacuum can be, without limitation, filtered by any type of filter or filtering method (3310) including, but not limited to, a HEPA filter, all in a manner known by those skilled in the art.

The combination of the one or more stream(s) of air or gas (3140) moving in various ways over, under, or across any door or hole (955) and opposing door vacuum(s) (3130) can, create a synergistic effect that can, without limitation, reduce the chance of introducing contamination into the application enclosure (930) through any door or hole (955).

According to an embodiment, any positive pressure can, without limitation, be established or maintained inside of the application enclosure (930) at any time, and for any duration, or during any part of any cycle, by flowing air or any gas into the application enclosure (930). This positive pressure can, without limitation, be turned on or off at any time, and for any duration, before, during, or after any number of procedures or treatments are conducted inside of the application enclosure(s) (930). Furthermore, any or all doors (3110) can, without limitation, be opened or closed at any time and for any duration, during use of the application enclosure (930). Any positive pressure can, without limitation, be established or maintained inside of the application enclosure (930) whether any door(s) (3110) are open or closed. One or more means or outlets utilized to supply (3270) the air or gas under positive pressure can, without limitation, be located at any location within the application enclosure (930). The supplied (3270) air or gas can also, without limitation, be filtered before being deployed or flowed into the application enclosure (930), by any type of filter or filtering method (3310) including, but not limited to, a HEPA filter, all in a manner known by those skilled in the art. The air or gas can be supplied or flowed (3270) into the application enclosure (930) at any rate, speed or volume, and via means such as, but not limited to, one or more fan(s) or blower(s).

According to another embodiment, one or more of the door vacuum(s) (3130) sources can also operate while a positive pressure is established or maintained inside of the application enclosure (930). Any strength, velocity, volume, or amount of vacuum can, without limitation, be used. It is preferred, without limitation, that the door vacuum(s) (3130) are active or enabled while any door or hole (955) is open or unsealed in any way, or one or more supplied air or gas streams (3140) are present. Any supplied air or gas stream (3140) may also, without limitation, be active near any door(s) (955) at any time while a positive pressure is established or maintained inside of the application enclosure (930). The supplied air or gas (3270) and the vacuum can, without limitation, vary in order to maintain a desired level of positive pressure inside of the application enclosure (930). This is especially important when openings such as, but not limited to, one or more door or hole(s) (955) is open or unsealed.

According to an embodiment, the application enclosure (930) can also be designed and constructed so that it has, without limitation, (a) any means to filter (3150) and/or dehumidify (3160) the atmosphere within the application enclosure to any humidity level at any time and for any duration, (b) any means to either heat (3290) or cool (3300) the atmosphere inside the application enclosure at any time and for any duration, (c) any means, located anywhere inside of the application enclosure (930), to either increase or decrease the pressure (3270) inside of the application enclosure at any time and for any duration, (d) a means to create an additional vacuum (3280) located anywhere inside of the application enclosure (930) to remove materials such as, but not limited to, any unwanted fumes, vapors or aerosols. Any air or gas that is supplied into, or pulled via vacuum inside, the application enclosure (930), can be, without limitation, filtered by any type of filter or filtering method (3310) including, but not limited to, a HEPA filter, all in a manner known by those skilled in the art. In certain circumstances, the various filters may, without limitation, be shared by similar equipment or processes, in a manner known to those skilled in the art.

According to an embodiment, the application enclosure (930) as described in the present invention, can be used in various ways including, but not limited to, the following brief description of steps, activities, and/or or procedures, that can, without limitation, be undertaken: (a) locate the object (3030) or patient's body, torso, or other parts of the body, in the application enclosure (930), (b) seal the application enclosure (930), (c) if desired or necessary, condition the atmosphere for temperature within the application enclosure (930), (d) deploy, for any time period, the aerosol and/or vapor (200) into the application enclosure (930), (e) terminate the deployment of the aerosol and/or vapor (200) once a sufficient time has passed to effectively fill the application enclosure (930), (f) expose the surfaces inside the application enclosure (930) to the aerosol and/or vapor (200) for a sufficient amount of time to achieve an efficacious outcome, (g) dehumidify, to any desired humidity range, and/or remove the remaining aerosol and/or vapor (200) from inside the application enclosure (930), (h) conduct surgery on the patient, (i) if necessary or desired, redeploy, for any time period, the aerosol and/or vapor (200) into the application enclosure (930) during surgery and remove any humidity and/or aerosol as needed, (j) complete surgery, (k) if needed or desired, terminate the surgery with a final redeployment of the aerosol and/or vapor (200), for any time period, into the application enclosure (930) (l) dehumidify, to any desired humidity range, and/or remove the remaining aerosol and/or vapor (200) from inside the application enclosure (930), (m) remove the patient from the application enclosure (930). These steps or procedures are only a small and incomplete example of the numerous combinations of various steps, activities, and/or procedures, that can take place within the application enclosure (930).

According to another embodiment, the application enclosure (930) can have various equipment located inside, such as, but not limited to any, lights, robotic apparatus(s) used for any purpose, imaging equipment, means to support or hold any objects, surgical or medical equipment or accessories, and manufacturing equipment.

Figure 68:
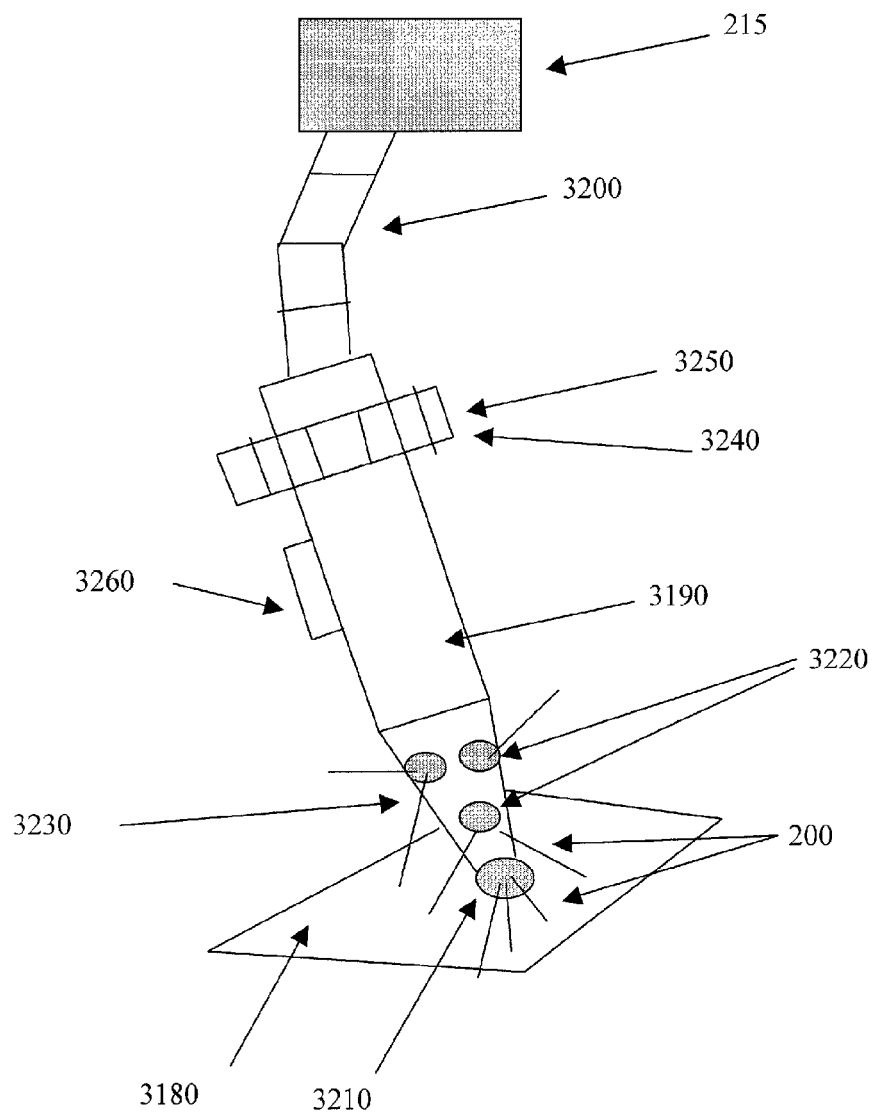
FIG. 68 is a schematic view of another alternative embodiment of the enclosure for the aerosol generator of FIG. 52.

Looking now at FIG. 68, according to an embodiment, an aerosol and/or vapor is generated by a means such as, but not limited to, the aerosol (200) generating apparatus (215) in the present invention, and the aerosol and/or vapor (200) is delivered into one or more targeted areas such as, but not limited to, any wound, any body cavity, surgical plain or surgical incision (3180). Any aerosol (200) or vapor generating means can be used in this embodiment. The aerosol and/or vapor is delivered via one or more tube, pipe, or conduit (herein called "application wand" or "wound wand") (3190) which can be any, without limitation, angle, size, length, orientation, diameter, width, or geometry. The wound wand (3190) can be connected to the aerosol (200) generating apparatus (215) in various ways knows to those skilled in the art. The wound wand (3190) can also be designed and constructed so that it can be easily connected or disconnected from any aerosol and/or vapor (200) supply line(s) (3200), and it can be effectively cleaned, sterilized, or disinfected, in a manner known to those skilled in the art. Various types of flexible pipe or tubing (3200) can, without limitation, connect to the application wand (3190) in a manner known to those skilled in the art.

It is further preferred, without limitation, that one or more perforations (3220) can be located at any location(s) on the application wand (3190). The perforations (3220) can be, without limitation, any size, pattern, shape, angle, geometry, and any orientation. The application wand (3190) can also be designed to interface with interchangeable tips (3230) that vary in attributes such as, but not limited to, length, diameter, any exit orifice (3210) attributes, number or size of perforations (3220), angle of perforations (3220). The interchangeable tips (3230) can connect to the application wand (3190) in a manner known to those skilled in the art. The exit orifice (3210) can be, without limitation, any shape, size, geometry, in order to develop an effective and efficacious device.

According to an embodiment, the application wand (3190) can, without limitation, incorporate any means anywhere on its surface which when actuated or activated (3240), controls and/or stops the flow of aerosol (200) and/or vapor that emanates from the application wand (3190) or any of its interchangeable tips (3230). These control functions can be separate or combined control interfaces. These means (3240) can, without limitation, be any mechanical/electrical means known to those skilled in the art.

According to an embodiment, any parts used to construct the application wand (3190) can be constructed from various materials such as, but not limited to, stainless steel, glass, polymer, polyolefin, cellulose, or even natural or manufactured fibers that are either coated or uncoated. It is preferred, without limitation, that the application wand (3190) is constructed from one or more polymers that can include, but is not limited to, PVC, polycarbonate, polypropylene, and HDPE. The materials used to construct the application wand (3190) may have any rigidity. Any surfaces of the application wand (3190) may have any electrical charge.

According to another embodiment, the application wand (3190) can, without limitation, incorporate any means, known to those skilled in the art, to mount or attach to, integrate, attach, or combine, either temporarily or permanently, any devices or to any devices, such as, but not limited to any, source of light, means to present or create suction, camera or any other imaging or video device, cauterization, robotic grips or hands, scalpel, means for suture application or removal, or any means for applying electrical shock or pulses.

Any, (a) liquid, (b) mixture or solids suspended in any liquid, (c) solution, (d) medication, (e) organisms, (f) anti-pathogen/toxin/fungal/sporicidal agent(s) or substance(s), (g) micro machine(s) or structure(s), (h) nano machine(s) or structure(s), may also, without limitation, be used in these embodiments.

According to an embodiment shown in FIGS. 70-73, a means (herein called "multi interface assembly") (3320) is designed and constructed to cover or at least isolate or prohibit the whole or at least a part of, one or more of any means that enable movement for the apparatus (215) or any other equipment or accessories located in the targeted or treated area (3310) such as but not limited to any wheels, tracks, rollers, or other movable means (herein collectively "wheel(s)") (3330), from having any contact with any floor or surface that they rest on (herein called "floor") (3340) in various situations such as, but not limited to, when the apparatus (215) or other equipment or accessories is moved, stopped, or held in a static or semi-static position, and the wheel(s) (3330) are in direct or indirect contact with one or more of any absorbent material(s) (3350) that can hold, contain, or absorb any liquid. The absorbent materials (3350) or any construct containing absorbent materials (3350) are either treated or pretreated in various ways known to those skilled in the art, with any liquid agent(s), so that both the wheel(s) (3330) and the floor (3340) can come in contact with the liquid agent(s). It is preferred, without limitation that the absorbent material(s) (3350) is saturated with the same liquid (30) that is generated into aerosol (200) in the present invention.

In the first part of this embodiment, the multi interface assembly (3320) can include one or more materials or parts, where the wheel(s) (3330) are moved or rolled onto or into one or more basin or indentation (herein called "basin") (3360). One or more walls or edges of any basin(s) (3360) can, without limitation, be formed of any angled material or ramps (3690), of any angle, size, construction, or length, to facilitate unhindered and easy movement of any wheel(s) (3330) into and out of the basin(s) (3360). The multi interface assembly (3320) can be made of one or more materials such as, but not limited to, stainless steel, glass, cellulose, polyolefin, paper, polymer, natural or manufactured fibers or materials, that may be coated or uncoated, or constructed with combinations of these materials, or other materials known in the art. However, any of the materials that can have any contact with the wheel(s) (3330) and any floor surface(s) (3340) shall have absorbent properties and can, without limitation, be any thickness and have any durometer. The basin(s) (3360) can, without limitation, be constructed from, or lined with, absorbent material(s) (3350) of any thickness, and it can have any dimensions, including any depth. The basin (3360) can, without limitation, have one or more directly or indirectly connecting lips or ramps (3370) of various length and angle, extending into one or more directions, to facilitate easier entry of the wheel(s) (3330) into the basin (3360), and/or onto the multi interface assembly (3320), from the floor (3340). This can, without limitation, help the operator so that they do not have to lift the apparatus to position the wheel(s) onto the absorbent material(s) (3350). The absorbent material(s) (3350) can be pretreated with one or more liquid agent(s), or the operator can moisten the absorbent material(s) (3350) with one or more liquid agent(s) in a manner known in the art, before or after the wheel(s) (3330) have had contact with the absorbent material(s) (3350). The multi interface assembly (3320) may, without limitation, also have one or more of any tube, duct, pipe, conduit, tunnel, pathway, or connection (herein called "basin tube") (3380), that connects any part of the basin (3360), or any other structure or component that directly or indirectly connects to any part of any basin (3360), with any of the absorbent material(s) (3350) that can have contact with any floor surface(s) (3340), so that any liquid or moisture may be transported, moved, or flow, at any rate or speed, from the basin (3360) to any of the absorbent material(s) (3350) contacting any floor (3340) surfaces. It is also possible, without limitation, to exclude the basin (3360), but keep one or more of any other attributes of the multi interface assembly (3320), which represents the multi interface assembly (3320) in its simplest form.

The multi interface assembly (3320) may, without limitation, also have one or more ridges (3390) of effective height that protrude vertically or on any effective angle to perform functions such as, but not limited to, prohibiting movement of the wheel(s), and maintaining the position of the wheel(s) (3330) on the absorbent material(s) (3350). The ridges (3390) may also be lined with absorbent materials (3350). The multi interface assembly (3320) may, without limitation, also have one or more handles or grip points attached or built into its design to facilitate easier handling.

According to an embodiment shown in FIGS. 74-75, the multi interface assembly (3320) may, without limitation, also include one or more removable absorbent material(s) (3350), and can be, without limitation, be directly attached to any wheel(s) (3330) and held or positioned into place with a variety of methods or combination of methods known in the art, including, but not limited to, the use of one or more pieces of elastic material (3400) around one or more edges of the absorbent material(s), and/or the use of one or more string laces or elastic bands or other material (3410) connected to the inside diameter of the absorbent material(s) assembly. This version represents the multi interface assembly (3320) in its most simple form.

According to an embodiment shown in FIG. 76, the apparatus (215) or any aerosol generator can, without limitation, be designed and constructed so that one or more filters (3420), known to those skilled in the art, can be connected to any parts of the plumbing anywhere in the design of the apparatus (215), as well as located anywhere inside of the various tanks used in the design of the apparatus (215). The filter(s) can, without limitation, be disposable and they can be designed for use in the apparatus (215), in a manner known to those skilled in the art, so that they are effective and easy to replace. In addition, all of the various devices and plumbing in the apparatus (215) such as, but not limited to any, feed tank(s) (280), reservoir(s) (40), feed tank valve(s) (300), pump(s) (130), filter(s) (3420), blower drain valve (3430) and system drain valve(s) (660), can be located and designed so that when the apparatus (215) is drained of all of the liquid agent(s) within it, it may be fully emptied of all liquid. This can, without limitation, facilitate thorough cleaning of the apparatus (215) and reduce any potential for damage resulting from any freezing liquid. Furthermore, the apparatus (215) may, without limitation, have one or more cleaning function(s) or program(s) designed into its hardware and/or system operating software so that all of the various valves in the system can simultaneously open in order to help purge or entirely drain the apparatus (215). This functionality can also, without limitation, be used to drain the various systems and plumbing of the apparatus (215) as it is being flushed and cleaned out.

Figure 76:
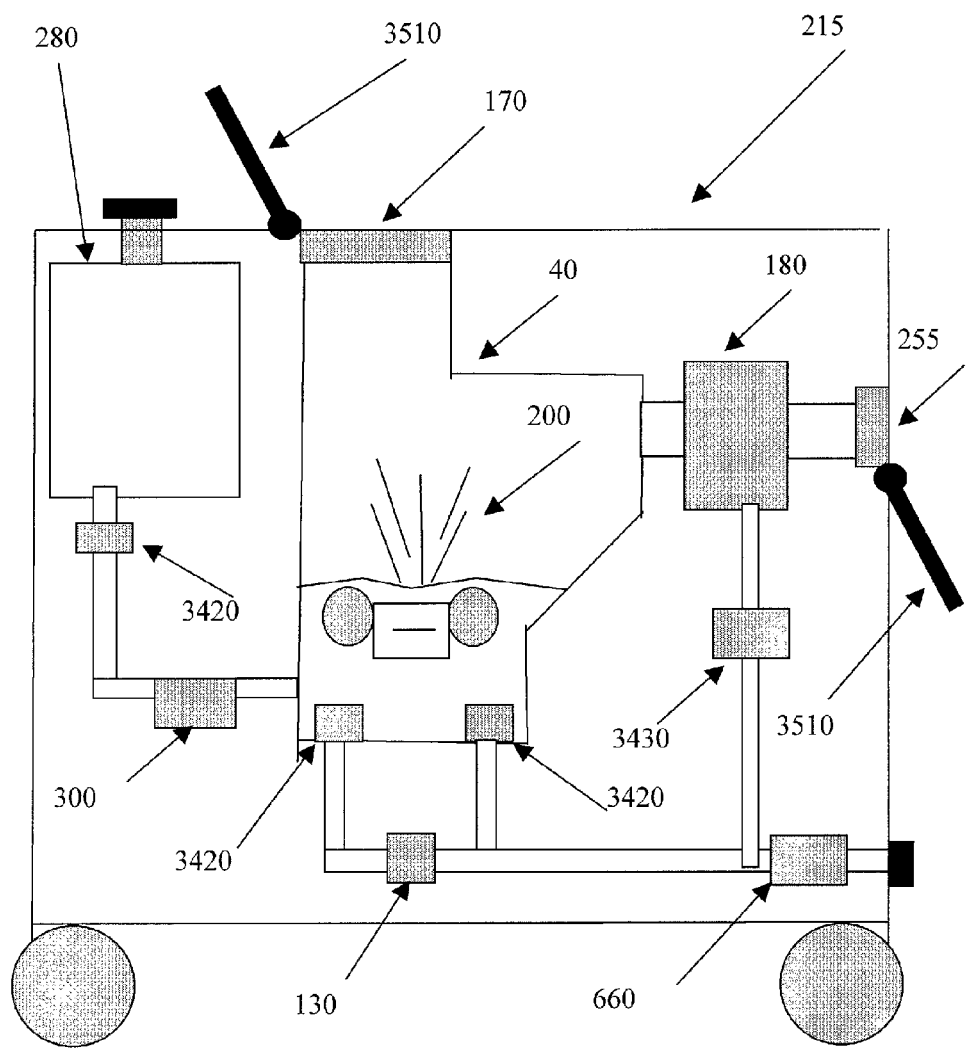
FIG. 76 is a schematic view of the generator of FIG. 70 including a number of filters.
Figure 77:
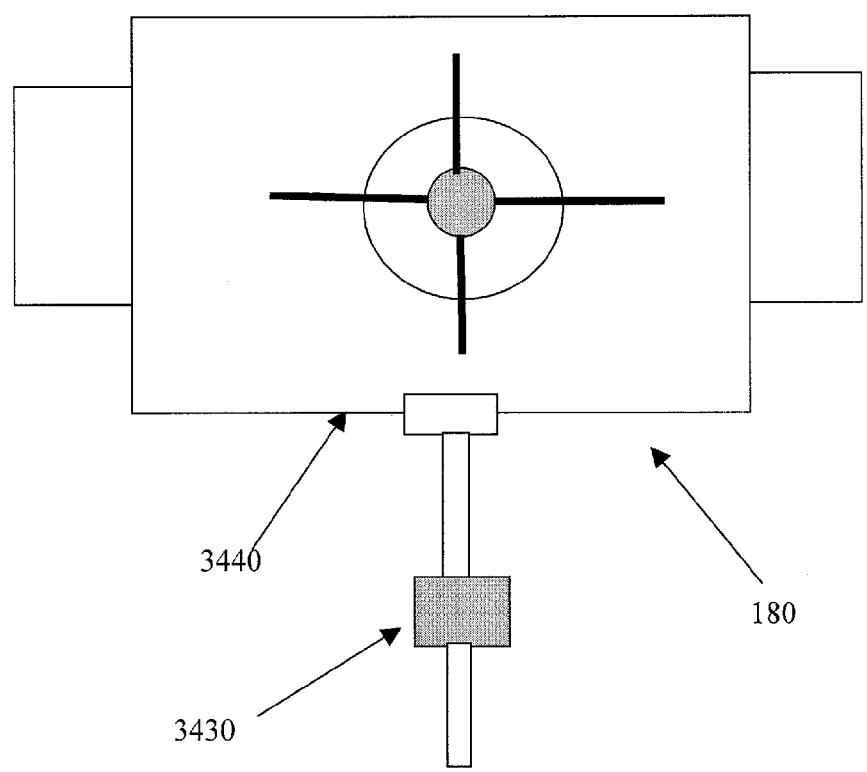
FIG. 77 is a schematic view of a blower housing for the generator of FIG. 70.

According to an embodiment shown in FIGS. 76-77, the apparatus (215) or any aerosol generator can, without limitation, be designed and constructed so that any enclosure(s), cover(s), or housing(s) (herein called "blower housing") (3440), that enclose or hold any fan, blower, or other source of pressurized air (180), including, without limitation, any attached conduit(s), pipe(s), or tubing, may be drained of any liquid that may build up in these areas during operation or cleaning of the apparatus (215). This liquid can, without limitation, be drained, in a manner known to those skilled in the art, to any tank(s), holding tank(s), drain port(s), or tank(s) and/or reservoir(s) (40) where the aerosol (200) is created. The apparatus (215) can be plumbed in various ways known to those skilled in the art, so that this liquid can be fully drained and removed from the apparatus (215) or any device. The liquid can also, without limitation, be drained back into the tank(s) or reservoir(s) (40) where the aerosol (200) is created.

Figure 78:
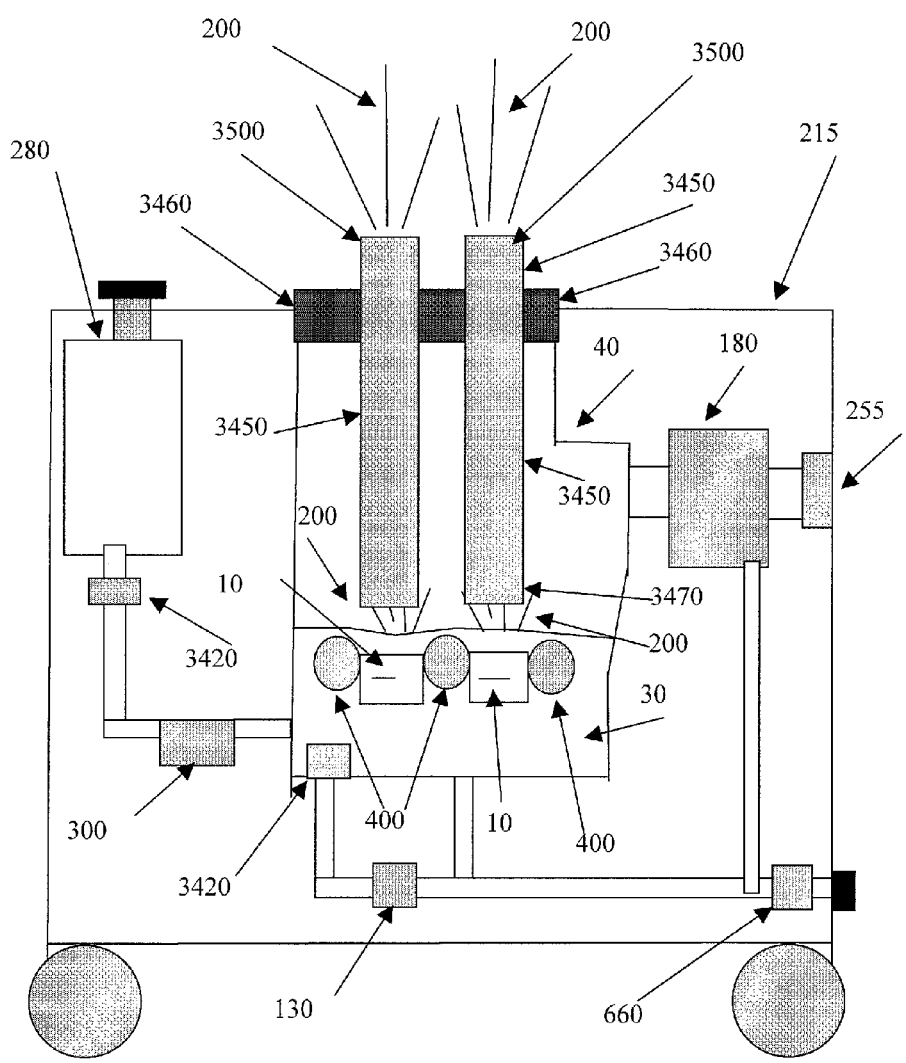
FIG. 78 is a schematic view of the generator of FIG. 70 including a first embodiment of a fog tube.
Figure 79:
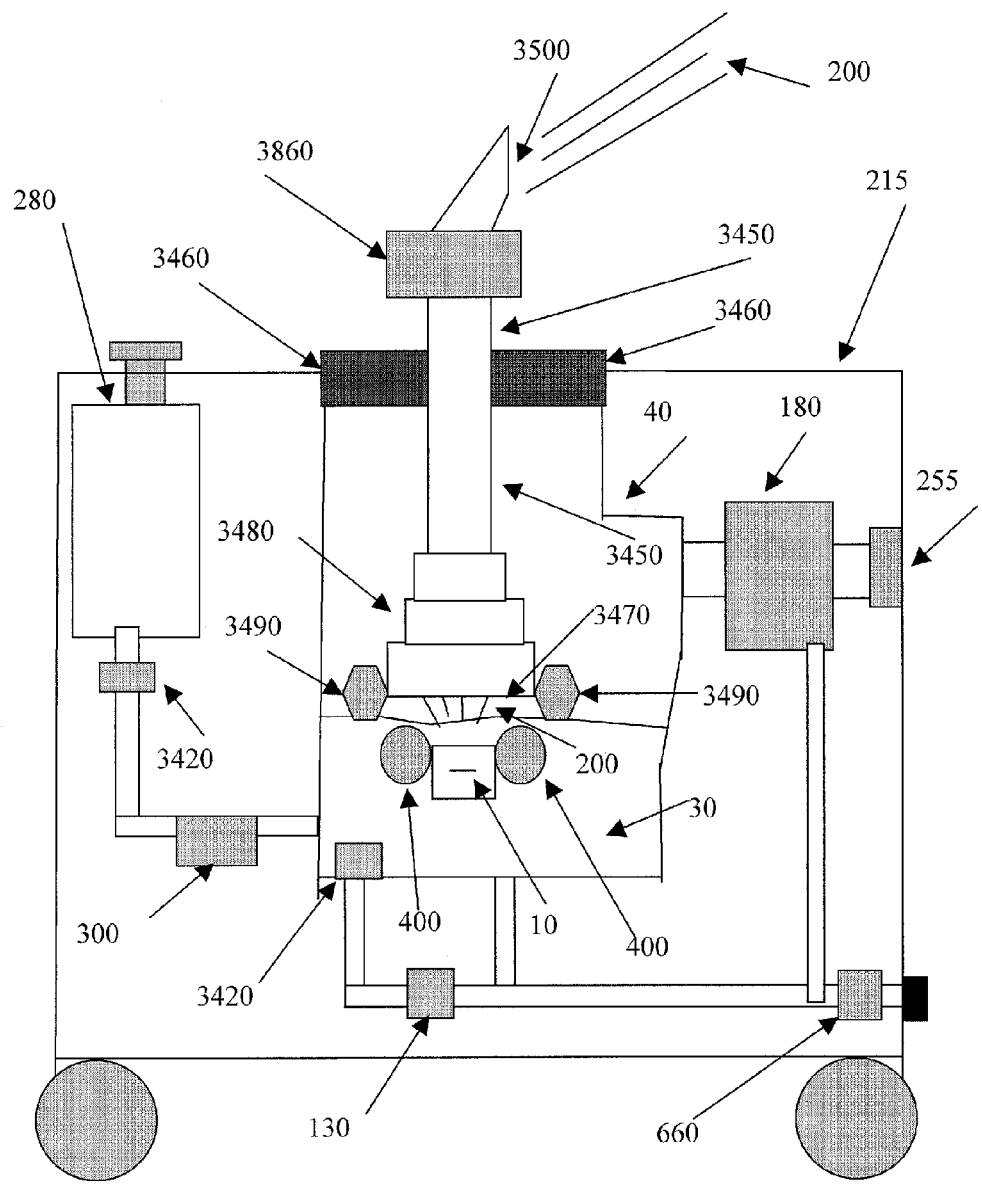
FIG. 79 is a schematic view of the generator of FIG. 70 including a second embodiment of a fog tube.

According to an embodiment shown in FIGS. 78-79, one or more of any pipe(s), tube(s), hose(s), or other enclosed or semi-enclosed means for transporting any amount of generated aerosol (herein collectively "fog tube(s)") (3450), are positioned within any tank or reservoir(s) (40) in which aerosol is created, and connect the inside of the reservoir(s) (40) with their exterior and/or the exterior of the apparatus (215). The reservoir(s) (40) are connected to one or more of any fan, blower, or other source of pressurized air (180) that can, without limitation, move any quantity of air at any rate into and through the reservoir(s). It is preferred, without limitation, that a blower (180) is used that has an output of at least 90 cubic feet/minute (cfm) or more. It is more preferred, without limitation, that a blower (180) is used that has an output of at least 150 cfm or more. It is even more preferred, without limitation, that a blower (180) is used that has an output of at least 250 cfm or more. It is very preferred, without limitation, that a blower (180) is used that has an output of at least 350 cfm or more. It is very preferred, without limitation, that a blower (180) is used that has an output of at least 450 cfm or more. In addition, the tanks or reservoir(s) (40) can be, without limitation, sealed, semi-sealed, or unsealed. It is preferred, without limitation, that the tanks or reservoir(s) (40) are sealed.

One or more of the fog tube(s) (3450) can, without limitation, connect or pass through one or more plate(s) (3460) or other structure, that can be attached to various parts of the apparatus (215) or any reservoir(s) (40). It is preferred, without limitation, that the plate(s) can be designed and constructed so that they and any attached fog tube(s) (3450) can be easily removed from the apparatus (215) or reservoir(s) (40). This can help with activities such as, but not limited to, installation, removal, and cleaning, of the plate(s) (3460) and the fog tube(s) (3450). It is preferred, without limitation, that the plate(s) (3460) and the fog tube(s) (3450) are constructed so that they form a sealed assembly when they are directly or indirectly attached to the apparatus (215) or any reservoir(s) (40).

The one or more open tube end(s) (3470) of each fog tube (3450) is positioned effectively and approximately above each transducer (10) or other source of the generated aerosol (200). However, the one or more open tube end(s) (3470) of each fog tube (3450) can also be located, without limitation, effectively and approximately to any sides, or any other angle or angled aspect, relative to each transducer (10), other source of the generated aerosol (200), or any geyser or eruption formed on the surface of any liquid (30) above any transducer (10). It is preferred, without limitation, that each open tube end(s) (3470) is horizontally angled above each geyser or eruption formed on the surface of any liquid (30) above any transducer (10), or other source of the generated aerosol (200).

In another part of this embodiment, one or more open tube end(s) (3470) can, without limitation, be positioned effectively and approximately above or near any group of one or more transducer(s) (10), or other source of the generated aerosol (200).

In another part of this embodiment, the distance that each open tube end (3470) is positioned relative to each geyser or eruption formed on the surface of any liquid (30) above any transducer (10), or other source of the generated aerosol (200), is an important part of this embodiment and the present invention. It is preferred, without limitation, that each open tube end (3470) is positioned approximately 0 to 6 inches or more from the surface of any liquid (30) above any transducer (10), or other source of the generated aerosol (200). It is more preferred, without limitation, that each open tube end (3470) is positioned approximately 0.5 to 1 inches or more from the surface of any liquid (30) above any transducer (10), or other source of the generated aerosol (200). It is even more preferred, without limitation, that each open tube end (3470) is positioned approximately 1 to 2 inches or more from the surface of any liquid (30) above any transducer (10), or other source of the generated aerosol (200). It is very preferred, without limitation, that each open tube end (3470) is positioned approximately 2 to 3 inches or more from the surface of any liquid (30) above any transducer (10), or other source of the generated aerosol (200). It is most preferred, without limitation, that each open tube end (3470) is positioned approximately 3 to 4 inches or more from the surface of any liquid (30) above any transducer (10), or other source of the generated aerosol (200). Investigation in the laboratory has found that the maximum effective distance is approximately four (4) inches from the surface of the liquid agent(s) (30) above each transducer (10), when using one or more transducer(s) (10), and after that distance the performance, effectiveness, and/or efficacious, quickly diminishes.

In another part of this embodiment, the length and/or position of the fog tube(s) (3450) can, without limitation, change inside any reservoir(s) (40) to accommodate any changing liquid (30) levels and to maintain the effective distance of any open tube end(s) (3470) to the surface of any liquid (30) above any transducer(s) (10), or other source of the generated aerosol (200). This can, without limitation, be achieved in various ways including, but not limited to, designing and constructing the fog tube(s) (3450) so they are flexible or made from one or more movable or collapsible segments (3480), and the open tube end(s) (3470) are maintained at a specific distance from the surface of any liquid (30) through the use and any direct or indirect connection of one or more of any float(s) (3490) that can float on the surface of the liquid agent(s) (30) in the reservoir(s) (40).

In another part of this embodiment, the total length of each fog tube(s) (3450) is also an important part of this embodiment and the present invention. The fog tube(s) (3450) can, without limitation, have any total length, but this length should at least be effective and efficacious. However, it is preferred, without limitation, that the fog tube(s) (3450) have a total length of approximately between six (6) and sixty (60) or more inches. It is more preferred, without limitation, that the fog tube(s) (3450) have a total length of approximately between fourteen (14) and twenty-four (24) or more inches. It is even more preferred, without limitation, that the fog tube(s) (3450) have a total length of approximately thirty-six (36) or more inches. It is very preferred, without limitation, that the fog tube(s) (3450) have a total length of approximately forty-eight (48) or more inches.

In another part of this embodiment, the fog tube(s) (3450) can also, without limitation, have any diameter, but the diameter should at least be functional, effective, and/or efficacious. It is preferred, without limitation, that the fog tube(s) (3450) have a diameter of approximately three (3) inches. The fog tube(s) (3450) can, without limitation, be positioned in any pattern and any distance from each other. It is preferred, without limitation, that the fog tube(s) (3450) are located approximately 2.5 inches edge to edge of their outside diameter (OD) from each other in a linear row. The fog tube(s) (3450) can, without limitation, extend any length and in any direction or angle as they exit the apparatus (215) or any reservoir(s) (40). It is preferred, without limitation, that the fog tube(s) (3450) extend approximately three (3) inches vertically out of one or more reservoir(s) (40) which are connected directly or indirectly with the exterior skin of the apparatus (215).

The one or more external open tube end(s) (3500) of each fog tube (3450), located external to the apparatuses (215) or any reservoir(s) (40), can terminate in any direction or angle, which can be altered in certain embodiments as a result of the construction of the tube(s) (3450). It is preferred, without limitation, that the one or more external open tube end(s) (3500) are angled at least at a 45 degree angle, and they are pointed in a direction away from the apparatus (215). It is more preferred, that the one or more external open tube end(s) (3500) are pointing vertically. It is even more preferred, that the one or more external open tube end(s) (3500) are pointed towards the middle of the targeted or treated area (3310).

In another part of this embodiment, the fog tube(s) (3450) within the reservoir(s) (40) can, without limitation, have one or more of any bends or geometries before the open tube end(s) (3470) of any fog tube(s) (3450) are located, without limitation, effectively and approximately to any sides, above, or any other angle or angled aspect, relative to each transducer (10), other source of the generated aerosol (200), or any geyser or eruption formed on the surface of any liquid (30) above any transducer(s) (10).

In another part of this embodiment, one or more open tube end(s) (3470) can, without limitation, be configured to directly or indirectly attach to any external tubing, any dispersal implement(s), or any fixture(s) or attachment(s) used to interface with any enclosures, rooms, or other targeted areas or structures.

In another part of this embodiment, any filter (3860) can be functionally located or attached along the path of any fog tube(s) (3450), or to the one or more external open tube end(s) (3500) of each fog tube (3450). The one or more of any filter(s) (3860) can filter the output or any air/gas and/or aerosol (200) before it leaves the apparatus (215). The filter(s) can remove any quantity or any size of aerosol particles. It is preferred, without limitation, that the filter(s) (3860) remove any aerosol droplets above 5 micron or more in size. It is more preferred, without limitation, that the filter(s) (3860) remove any aerosol droplets above 3 micron or more in size. It is even more preferred, without limitation, that the filter(s) (3860) remove any aerosol droplets above 1 microns or more in size. It is very preferred, without limitation, that the filter(s) (3860) remove any aerosol droplets above 0.5 microns or more in size.

According to an embodiment shown in FIG. 76, the apparatus (215) or any aerosol generator can, without limitation, be designed and constructed so that any of its inlets or intake orifices (255), or any air outlets, exit orifices, or openings (170), can have one or means (herein called "door(s)" (3510)) to effectively cover and/or seal closed one or more of these openings. It is preferred, without limitation, that these door(s) (3510) can effectively seal to keep any liquid, gases, or vapor from escaping from the apparatus (215). It is also preferred, without limitation, that the door(s) (3510) is designed and constructed in such a way so that it can effectively be opened and closed in a manner known to those skilled in the art. It is even more preferred that the door(s) (3510) are attached either directly or indirectly to the apparatus (215) via any type of hinge known to those skilled in the art. The door(s) (3510) can be removable, or permanently attached to the apparatus (215). Any sensor known to those skilled in the art can also, without limitation, be utilized so that the apparatus cannot be operated if any of the door(s) (3510) are closed, or any of the inlets or intake orifices (255), or any air outlets, exit orifices, or openings (170), are covered in any way. The door(s) (3510) can, without limitation, be automatically opened or closed and controlled by any software, electronics, PLC (315), or HMI (320).

According to an embodiment, the apparatus (215) or any aerosol generator can, without limitation, be designed and constructed so that any software, hardware, electronics, PLC (315), or HMI (320) (herein collectively called "PLC" (315)), shall monitor, log, or record when, and/or the time between when, the apparatus (215) is fully drained of any liquid (30) in its various components. This can be monitored in various ways including, but not limited to, using any liquid level sensors known to those skilled in the art to determine when all of the various reservoir(s) (40) are empty of any liquid (30), or the PLC (315) monitoring the time that the one or more of any valve(s) such as, but not limited to any feeder tank valve(s) (300), or any main drain valve(s) (660), are open to release the liquid (30) out the apparatus (215), and determining whether these various valves(s) are open long enough to fully drain the apparatus (215). The apparatus (215) can, without limitation, be programmed to take various actions after any liquid (30) in the apparatus (215) has expired, or reached a point of time either for the life of the liquid and/or for the time the liquid is in the apparatus (215) where the liquid (30) has expired, the liquid (30) has reached an unacceptable level of degradation, or the liquid (30) is at a point where it is near expiring, or the liquid (30) is otherwise at a point where it is at or near a point where it can lose its efficaciousness. These actions include, but are not limited to, the apparatus (215) ceasing to operate, the inability or refusal of the apparatus (215) to begin an operation cycle, the apparatus (215) notifying its operator, in various ways known to those skilled in the art, that the liquid (30) in the apparatus needs to be purged or drained in order for the apparatus (215) to resume operation either separately or in combination with one another. In addition, the apparatus (215) can be programmed so that the operator of the apparatus is only warned that the liquid (30) has or is near expiration, and the apparatus (215) does not take any further action than that. It is preferred, without limitation, that if the liquid (30) is at a point where it reaches a level of unacceptable degradation, the apparatus (215) shall not operate until all of the various valves (300) (660) in the apparatus (215) are open at least long enough to fully drain the apparatus if it was filled to capacity. The draining of the apparatus (215) can also, without limitation, take place in one or more interrupted or uninterrupted timed stages. This can, without limitation, be controlled with the use of any software or PLC (315), in a manner known by those skilled in the art.

Figure 80:
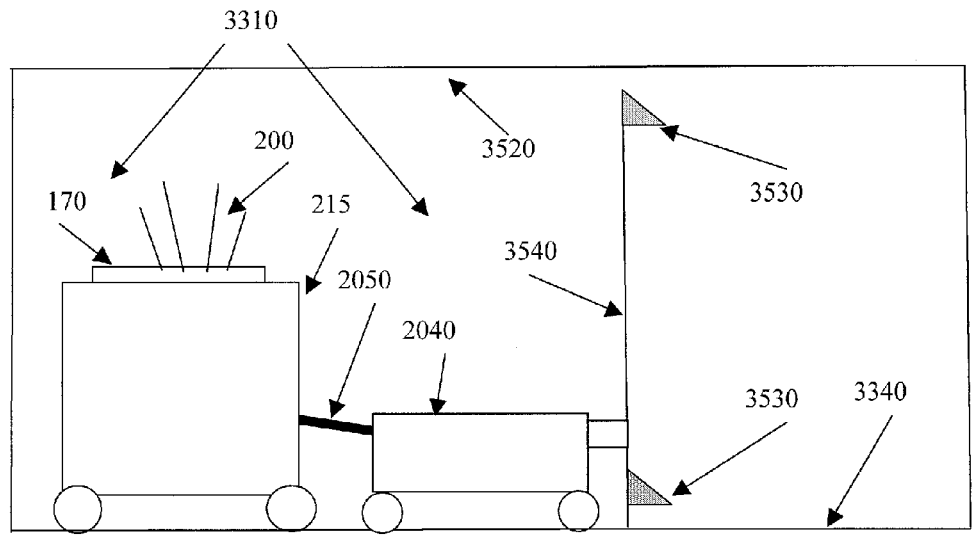
FIG. 80 is a schematic view of the generator of FIG. 70 including a first embodiment of an agent sensor.
Figure 81:
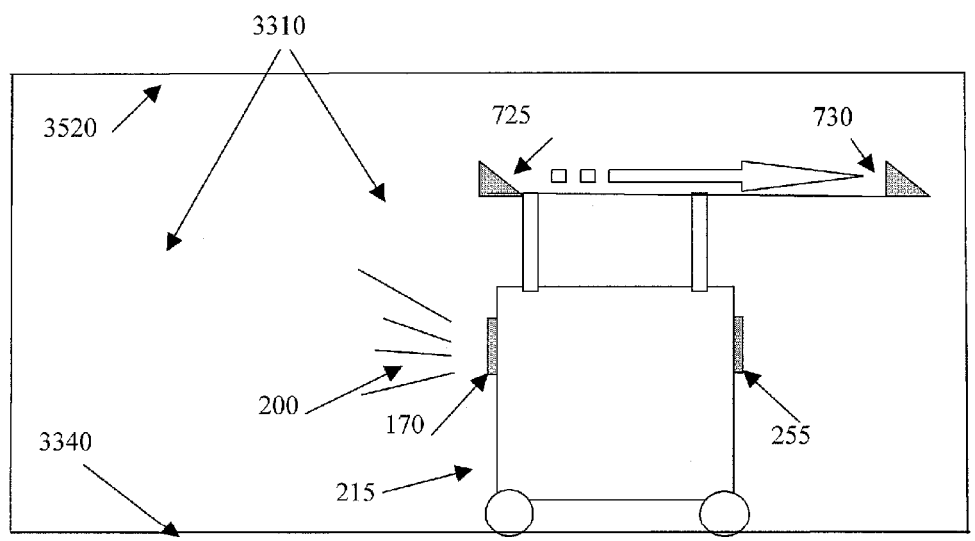
FIG. 81 is a schematic view of the generator of FIG. 70 including a second embodiment of an agent sensor.
Figure 82:
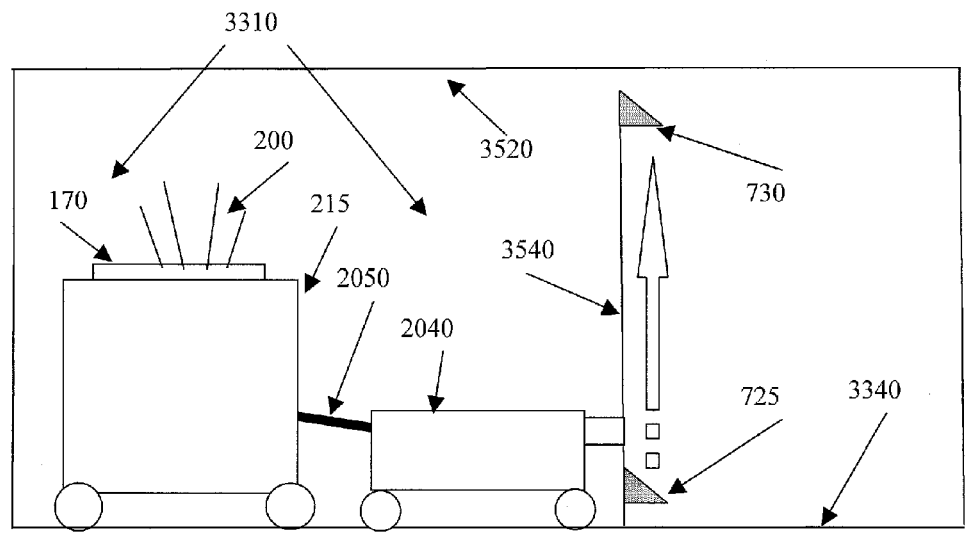
FIG. 82 is a schematic view of the generator of FIG. 70 including a third embodiment of an agent sensor.
Figure 83:
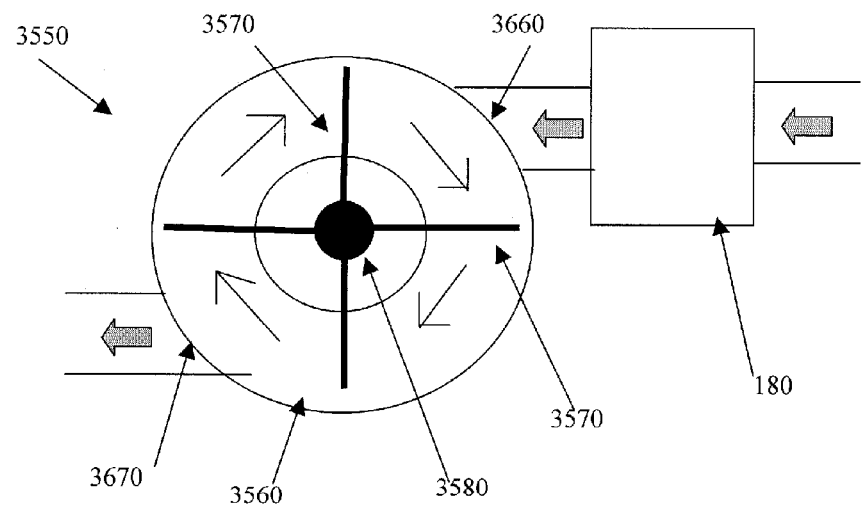
FIG. 83 is a schematic view of the generator of FIG. 70 including a first embodiment of an impaction device.
Figure 84:
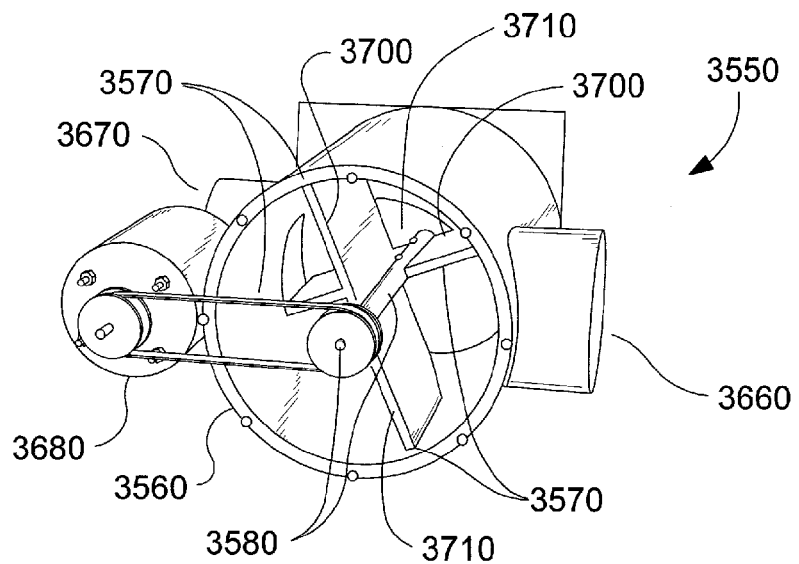
FIG. 84 is a schematic view of the generator of FIG. 70 including a second embodiment of an impaction device.
Figure 85:
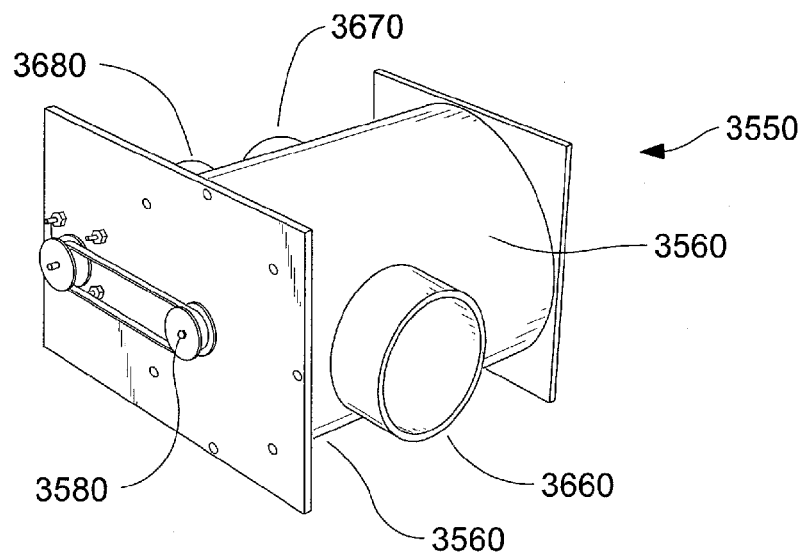
FIG. 85 is a rear view of the impaction device of FIG. 84.
Figure 86:
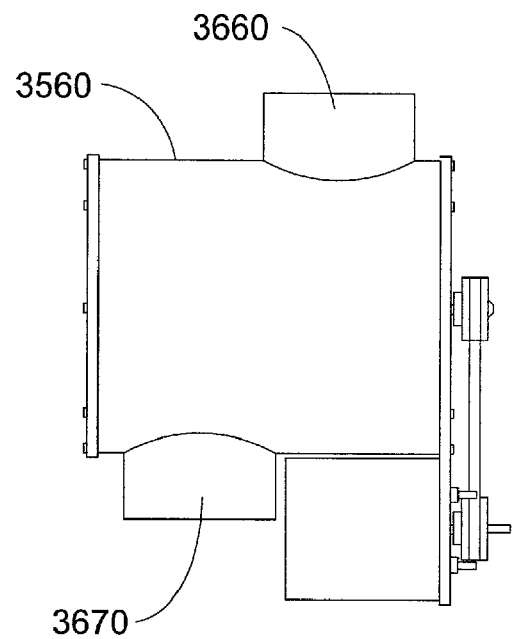
FIG. 86 is a top plan view of the impaction device of FIG. 84.
Figure 87:
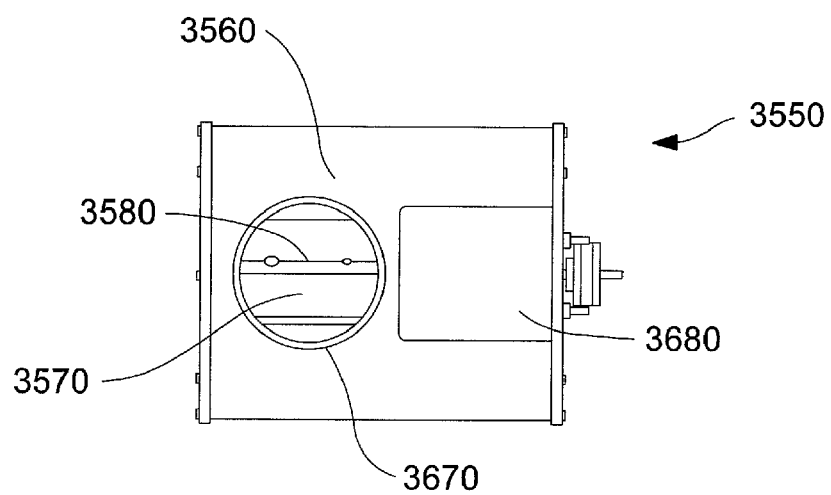
FIG. 87 is a side plan view of the impaction device of FIG. 84.
Figure 88:
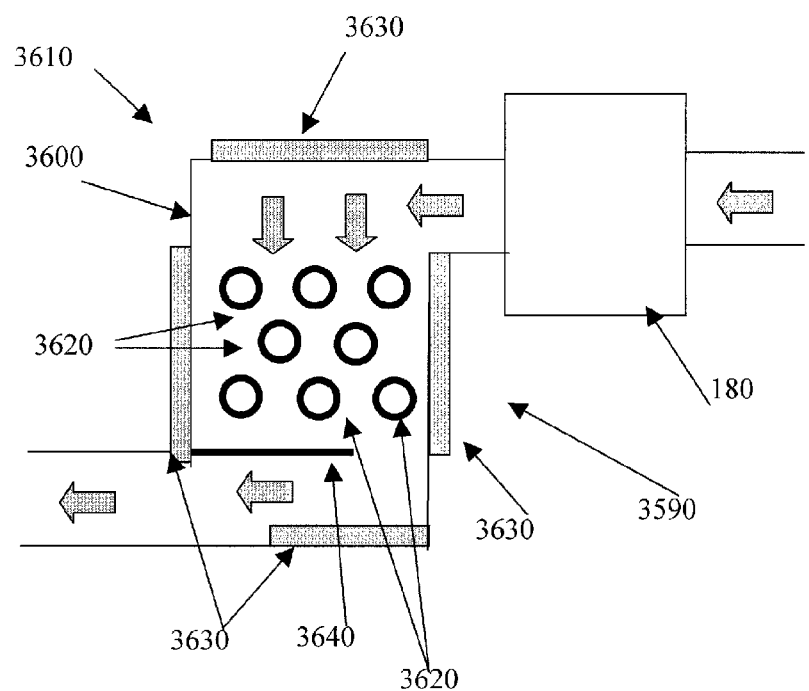
FIG. 88 is a schematic view of a first embodiment of a UV light device of the dehumidifier of FIG. 70.

According to an embodiment shown in FIGS. 80-82, the one or more of any sensor(s) (herein called "agent sensor(s)" (3530), that are utilized to determine if an effective, efficacious, or sufficient amount of any vapor or aerosol (200) has been applied to the targeted or treated area (3310) and/or surfaces can, without limitation, be located in various or any locations or areas including, but not limited to, near the ceiling(s), highest area(s), or near the highest surface(s) (herein called "ceiling" (3520), within one or more space(s) or area(s), or targeted areas (210), where the vapor or aerosol (200) is deployed. The agent sensor(s) (3530) can be any, without limitation, light source (725) and light sensor (730), humidity sensor, or moisture sensor, or combinations thereof.

The one or more agent sensor(s) (3530) can be located at any distance from the ceiling (3520). It is preferred, without limitation, that the agent sensor(s) (3530) are located approximately zero to fourteen (0-14) inches from the ceiling (3520). It is even more preferred that the sensor(s) (3530) are located three to six (3-6) inches from the ceiling (3520). In addition, the agent sensor(s) (3530) can also, without limitation, be located in various locations or areas including, but not limited to, near or approximate to any, floor(s), lowest area(s), or lowest surface(s) in the targeted or treated area (3310) (herein called "floor" (3340), within one or more space(s) or area(s) where the vapor or aerosol (200) is deployed. The agent sensor(s) (3530) can be located at any distance from the floor (3340). It is preferred, without limitation, that the agent sensor(s) (3530) are located approximately zero to fourteen (0-14) inches from the floor (3340). It is even more preferred that the sensors are located three to six (3-6) inches from the floor (3340).

One or more agent(s) sensor(s) (3530) can, without limitation, be located on or attached to any structure or support mechanism. Without being limited, the one or more agent(s) sensor(s) (3530) may also be positioned or located anywhere on any structure or support mechanism such as, but not limited to, one or more of any pole(s) (3540) of any length and design. Without being limited, the one or more pole(s) (3540) can also be constructed in a manner known in the art, so they can be easily adjustable for any effective length or height. It is preferred, without limitation, that the one or more sensor(s) (3530) are located at either end of one or more poles (3540) attached to one or more of any apparatus (215), or one or more of any dehumidifier (2040). It is more preferred, without limitation, that on each mounting structure or pole (3540) that is used, at least one light source (725) is located effectively at one end of the pole (3540) near the floor (3340), and at least one light sensor (730) is located in-line and vertically above the light source (725) effectively near the ceiling (3520), on the other end of the pole (3540). The location of the light source (725) and the light sensor (730), may also be, without limitation, reversed in this configuration. One or more agent sensor(s) (3530) can also, without limitation, directly or indirectly communicate with one or more PLC (315) or HMI (320), or with one or more aerosol generating apparatus(s) (215), or one or more of any remote device(s) that control one or more of any aerosol generating apparatus(s) (215), in various ways such as, but not limited to any, radio, radio waves, sound, wire, cable, or fiber optics.

According to an embodiment, it is intended, without limitation, that the one or more of any dehumidifier(s) (2040) in the present invention is any means that can dehumidify any air, gas, or atmosphere, in the targeted area(s) (3310) using various technologies and parts such as, but not limited to, any blower (180), chiller surface(s) or chill coil(s), cooling tub(s), cooling surface(s), compressor, refrigerant, or other parts or combination of parts, known to those skilled in the art. Any humidity level can be set as the target point for the dehumidification process to meet. However, it is preferred, without limitation, that the humidity level is reduced to 70% or lower after any treatment process(s) or operational cycle(s) have are complete. It is more preferred, without limitation, that the humidity level is reduced to 50% or lower following any treatment process(s) or operational cycle(s) are complete. It is even more preferred, without limitation, that the humidity level is reduced to 40% or lower following any treatment process(s) or operational cycle(s) are complete. It is most preferred, without limitation, that the humidity level is reduced to 30% or lower following any treatment process(s) or operational cycle(s) are complete.

According to an embodiment, the one or more of any dehumidifier(s) (2040) in the present invention can be any means that can dehumidify any air, gas, or atmosphere, in the targeted area(s) (3310) using any technologies and parts known to those skilled in the art, and can transfer the dehumidified air flow to the generator (215), such as by a conduit (2050).

According to an embodiment shown in FIGS. 83-87, an enhanced impaction device (3550) improves the present art and it can, without limitation, be utilized to remove any quantity of aerosol (200) from any air or gas that is flowed through it. This impaction device (3550) consists of one or more of any housing or area, or "blade housing(s)" (3560). The blade housing(s) (3560) can, without limitation, be any size, shape, length, width, geometry, or diameter. It is preferred, without limitation, that the blade housings are at least large enough to effectively accommodate the impacting surfaces or paddles (3570). The various blade housing(s) can be, without limitation, interconnected, and they can be positioned in series or in parallel.

It is preferred, without limitation, that the blade housing(s) (3560) includes at least one inlet(s) (3660) through which air/gas and aerosol (200) enters the blade housing(s) (3560), and at least one outlet (3670) through which air/gas and aerosol (200) exits the blade housing(s) (3560). The inlet(s) (3660) and outlet(s) (3670) can, without limitation, be any size, shape, length, width, geometry, or diameter. It is preferred, without limitation, that the inlet(s) (3660) and outlet(s) (3670) are constructed from tubing that is at least four inches in diameter. The inlet(s) (3660) and outlet(s) (3670) can, without limitation, be located on or connect anywhere to, the blade housing(s) (3560). It is also preferred, without limitation, that the inlet(s) (3660) and outlet(s) (3670) are located directly in front of at least one set, cluster, or group of paddle(s) (3570), so the centerline of the inlet strikes the centerline of the shaft (3580) to which the paddle(s) (3570) are connected.

Inside the blade housing(s) (3560), one or more of any structure(s) that can act as one or more impacting surface(s) (3570) is connected to one or more of any rotating shaft or other means or source of rotation (herein called "shaft" (3580). The impacting surface(s) (3570) can be, without limitation, one or more of any paddle, blade, or cage, that can be of any design, configuration, or structure (herein called "paddles") (3570). The impacting surfaces(s) can, without limitation, be any size, and be positioned at any angle. It is preferred, without limitation, that the paddles(s) (3570) are formed of four (4) solid shapes that are approximately four (4) inches wide, and four (4) inches long, that are attached to a common shaft (3580) at ninety (90) degrees to one another. It is also preferred, without limitation, that the blade housing(s) are circular in shape.

The paddles (3570) can also be, without limitation, located in one or more independent moving group(s) (3700) including one or more paddles (3570). These independent moving group(s) (3700) of one or more paddles (3570) can be, without limitation, located in the same blade housing (3560) or any interconnected blade housing(s) (3560). Each independent moving group(s) (3700) of one or more paddles (3570) can also be, without limitation, directly or indirectly connected to their own motor (3680) and shaft (3580), or they can directly or indirectly share the same motor (3680) or shaft (3580). It is preferred, without limitation, that the one or more independent moving group(s) (3700) are connected to the same motor (3680) and the same shaft (3580). Referring to FIGS. 83-87, it is preferred, without limitation, that the air or gas and aerosol (200) mixture is moved through the inlet(s) (3660) and into the blade housing(s) (3560) where two different independent moving groups (3700) of one or more paddle(s) (3570) are located.

The paddles(s) (3570) can, without limitation, be rotated by any motor (3680), at any revolutions per minute (RPM), however it is preferred that they are at least rotated at a speed where they are effective at removing the desired or needed amount of aerosol from the air or gas that is moved through the blade housing(s) (3560). It is preferred, without limitation, that the blade housing(s) (3560) and shaft (3580) are at least effectively sealed, but it is more preferred that they are hermetically sealed in a manner known to those skilled in the art. The blade housing(s) (3560) can be, without limitation, designed to effectively interface with various means known in the art to transport air or gas, such as, but not limited to, any pipe, hose, or ducts. The blade housing(s) (3560) can be located anywhere before or after any blower, fan, or other source of pressurized air (180). The air or gas in which the aerosol (200) is carried, can be moved into the blade housing(s) (3560) at any quantity or speed. It is preferred, without limitation, that the air or gas is moved between 50 to 900 cfm. The air or gas is moved into the blade housing(s) (3560) by any blower, fan, or other source of pressurized air (180), that is either directly or indirectly connected by any effective means known in the art, such as, but not limited to, any tube, duct, pipe, conduit, or tunnel.

According to an embodiment, the one or more paddles (3570) can all, without limitation, be moved, rotated, or spun, in the same direction that is counter to any inbound flow of air or gas that is brought into the device and, into or through the blade housing(s) (3560).

According to another embodiment, the one or more paddles (3570) can all, without limitation, be moved, rotated, or spun, in the same direction as any inbound flow of air or gas that is brought into the device and, into or through the blade housing(s) (3560).

According to another embodiment, a plurality of paddles (3570) are, without limitation, moved, rotated, or spun, in any direction or pattern that is counter or opposite to the paddle (3570) that it is next to it or in close proximity to another paddle (3570).

According to another embodiment, the paddles (3570) can be, without limitation, located in one or more independent moving group(s) (3700) including one or more paddles (3570), that can be moved, rotated, or spun, in any direction or pattern that is counter or opposite to another independent moving group (3700) including one or more paddles (3570).

According another embodiment, the paddles (3570) can be, without limitation, located in one or more independent moving group(s) (3700) including one or more paddles (3570), that can be moved, rotated, or spun, in the same direction as any inbound flow of air or gas that is brought into the device and, into or through the blade housing(s) (3560).

According to another embodiment, the paddles (3570) can be, without limitation, located in one or more independent moving group(s) (3700) including one or more paddles (3570), that can be moved, rotated, or spun, in any direction or pattern that is opposite to any inbound flow of air or gas that is brought into the device and, into or through the blade housing(s) (3560).

According to a preferred embodiment, the paddles (3570) can be, without limitation, located in one or more moving group(s) (3710) including one or more paddles (3570), that can be moved, rotated, or spun, in any direction or pattern that is opposite to any inbound flow of air or gas that is brought into the device and, into or through the blade housing(s) (3560). It is preferred, without limitation, that two moving groups (3710) are utilized and attached to a shared shaft (3580), and the one or more paddles (3570) within each moving group are arranged or located so they are offset from the other moving group (3710).

According to an embodiment, any dehumidifier (2040), the apparatus (215) or any aerosol generator, or other device can, without limitation, be designed and constructed so that any blade housing(s) (3560), including, without limitation, any attached conduit(s), pipe(s), or tubing, may be drained of any liquid that may build up in these areas during operation or cleaning of the blade housing(s) (3560). This liquid can, without limitation, be drained, in a manner known to those skilled in the art, to any tanks, holding tank(s), or drain port(s), and the liquid can be fully drained and removed from any apparatus that it is installed into.

In still another part of this embodiment, this enhanced impaction device (3550) can be utilized independently as its own device, or utilized with other devices such as, but not limited to, the apparatus (215) in the present invention or any other aerosol generator(s). It can also, without limitation, be used with any dehumidifier (2040) design. The enhanced impaction device (3550) can, without limitation, be positioned anywhere in the air/gas stream in the design of any of these devices, and operated at any time by any means in order to create a means to impact aerosol particles and move aerosol particles or any coallessed particles on the impactor against the walls of the blade housing (3560). The device (3550) can also be positioned within a tortuous pathway through the device (3550) that creates a tortuous path for the air and aerosol mixture through the dehumidifier (20-40) in order to create as much dwell time within the dehumidification device (20-40) and the blade housing (3560) to increase the chance of removing aerosol from the air. It is preferred, without limitation, that the enhanced impaction device (3550) is controlled by any software, PLC (315) or HMI (320).

According to an embodiment shown in FIGS. 88-91, an enhanced ultraviolet (UV) light device (3590) can, without limitation, be designed and constructed so one or more of any geometries, sides, walls, or ceilings (herein called "enclosure walls" (3600), of any enclosure (3610) that houses one more of any UV light source(s) (3620), is lined or constructed from one or more of any mirrored surfaces or mirror(s) (3630). It is preferred, without limitation, that all of the interior enclosure walls (3640) are mirrored or constructed from mirrors. It is also preferred, without limitation, that the mirror(s) are highly efficient in their reflectivity, and they are constructed in a manner known to those skilled in the art. The basic construction of an enclosure, and the construction and use of the various UV light source(s) (3620), is known by those skilled in the art. The mirror(s) (3630) and enclosure(s) (3610) may be constructed from any chemically resistant material. Preferably, the mirror(s) (3630) and the enclosure(s) (3610) have a high chemical resistance to the liquid (30) used.

It is even more preferred, that the mirror(s) (3630) are constructed from any acid and/or alkaline resistant glass such as, for example, quartz, or Type I (borosilicate glass or Pyrex) or Type II glass as defined by the United States Pharmacopoeia. It is very preferred, that the mirror(s) (3630) are constructed from materials that absorb as little of the UV light as possible.

According to an embodiment, the enclosure(s) (3610) and any source of pressurized air or gas such as, but not limited to, one or more of any fan(s) or blower(s) (180), can be designed and constructed, in a manner known to those skilled in the art, to provide and accommodate any amount of air or gas that is flowed through the enclosure at any speed and volume and with any amount of air or gas flow characteristics or turbulence. However, after testing in a laboratory, it was found that odor removal in an area treated with peroxyacetic acid (PAA), was able to be accomplished in a shorter amount of time when greater amounts of air or gas from the treated area, including, without limitation, varying amounts of aerosol, were flowed through the enclosure that housed the sources of UV light(s) (3620). It is preferred, without limitation, that air or gas from the treated area is moved through the enclosure(s) (3610) at a measurement of at least 50 cfm or more. It is more preferred, without limitation, that air or gas from the treated area is moved through the enclosure(s) (3610) at a measurement of at least 800 cfm or more. It is even more preferred, without limitation, that air or gas from the treated area is moved through the enclosure(s) (3610) at a measurement of at least 1000 cfm or more. It is very preferred, without limitation, that air or gas from the treated area is moved through the enclosure(s) (3610) at a measurement of at least 1500 cfm or more. It is most preferred, without limitation, that air or gas from the treated area is moved through the enclosure(s) (3610) at a measurement of at least 2000 cfm or more. The air or gas can, without limitation, contain any quantity of any vapor or aerosol (200) that contains any agent(s) (30). In addition, one or more of any UV light source(s) (3620) can be used and they can be packed into a space in any number density or any light output density for a given area. However, it is preferred, without limitation, that at least three (3) UV light source(s) (3620) are used. The UV light source(s) (3620) can be any UV light source known to those skilled in the art.

Figure 89:
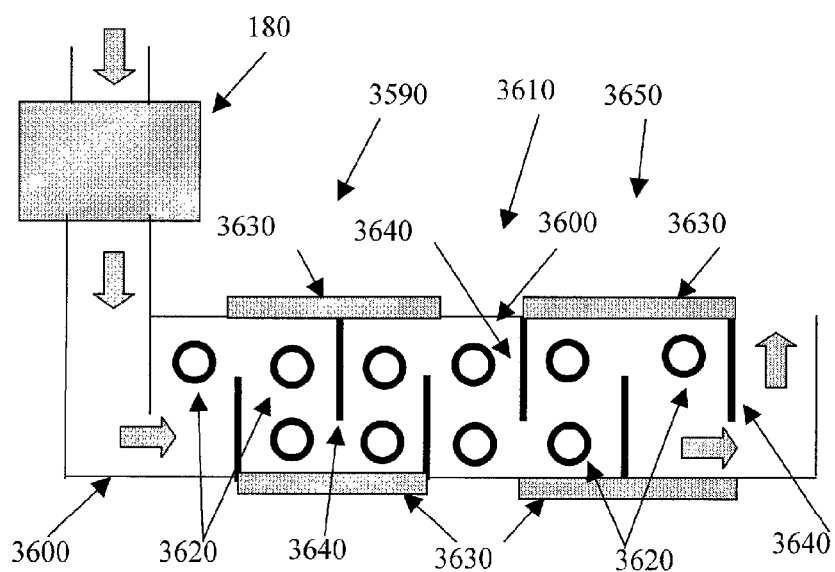
FIG. 89 is a schematic view of a second embodiment of a UV light device of the dehumidifier of FIG. 70.

According to an embodiment shown in FIG. 89, the enhanced ultraviolet (UV) light device (3620) can, without limitation, be designed and constructed so that any air or gas that is flowed into the enclosure(s) (3610), including any air or gas from any area treated with any agent(s) from any vapor or aerosol (200) generator, is moved through one or more complex maze(s), convoluted paths, complex channel(s), or tortuous path(s) (herein called "tortuous path(s)" (3650), which are mirrored on one or more walls (3600), interior walls (3640), or structures. It is preferred, without limitation, that all of the walls (3600) (3640) for this construct are made from one or more mirror(s) or mirrored surface(s). Referring to FIG. 89, this embodiment of the invention includes locating one or more UV light source(s) (3620) in various locations as well as patterns inside or in various locations within the tortuous path(s) (3650). The enclosure(s) (3610) or tortuous path(s) (3650) can be designed for any amount of air or gas at any speed, and can be any size, shape, diameter, or construct. The mirrored tortuous path(s) (3650) can, without limitation, increase the UV light exposure to the air or gas, and any aerosol (200) if it is still in the targeted area when its air or gas is processed.

Figure 90:
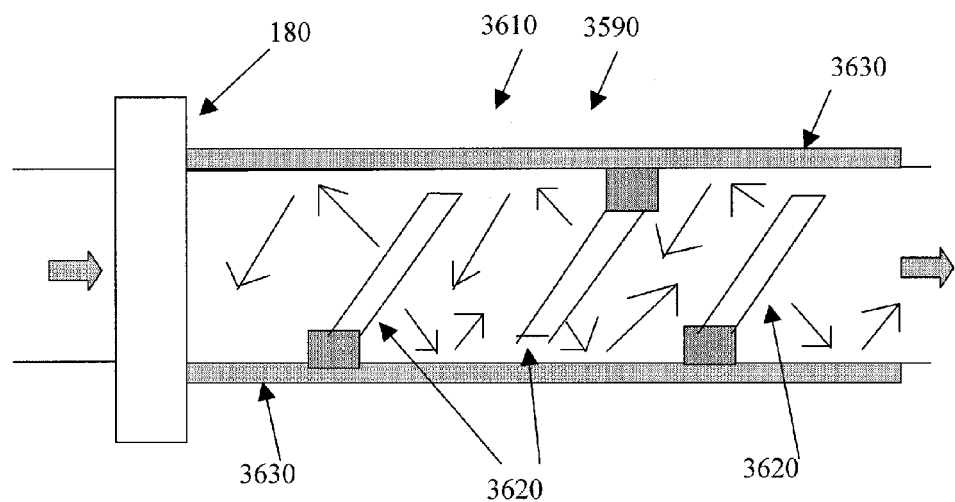
FIG. 90 is a schematic view of a third embodiment of a UV light device of the dehumidifier of FIG. 70.

According to an embodiment shown in FIG. 90, an enhanced ultraviolet (UV) light device (3590) can, without limitation, be designed and constructed so that the UV light source(s) (3620) are mounted, positioned, or located, at any angle or orientation, except 90 and 180 degrees, as well as orientated in any vertical or parallel orientation, all being respective to the direction of the air or gas flow moving through the enclosure(s) (3610). It is preferred, without limitation, that the one or more UV light source(s) (3620) are mounted, positioned, or located within the enclosure(s) (3610), at a forty-five (45) degree angle respective to the direction of the air or gas flow moving either towards or away from the UV light source(s) (3620). It is also preferred, without limitation, that this is combined with lining or constructing any enclosure walls (3600), with one or more of any mirrored surfaces or mirror(s) (3630) from which the emitted UV light can be redirected or reflected.

Figure 91:
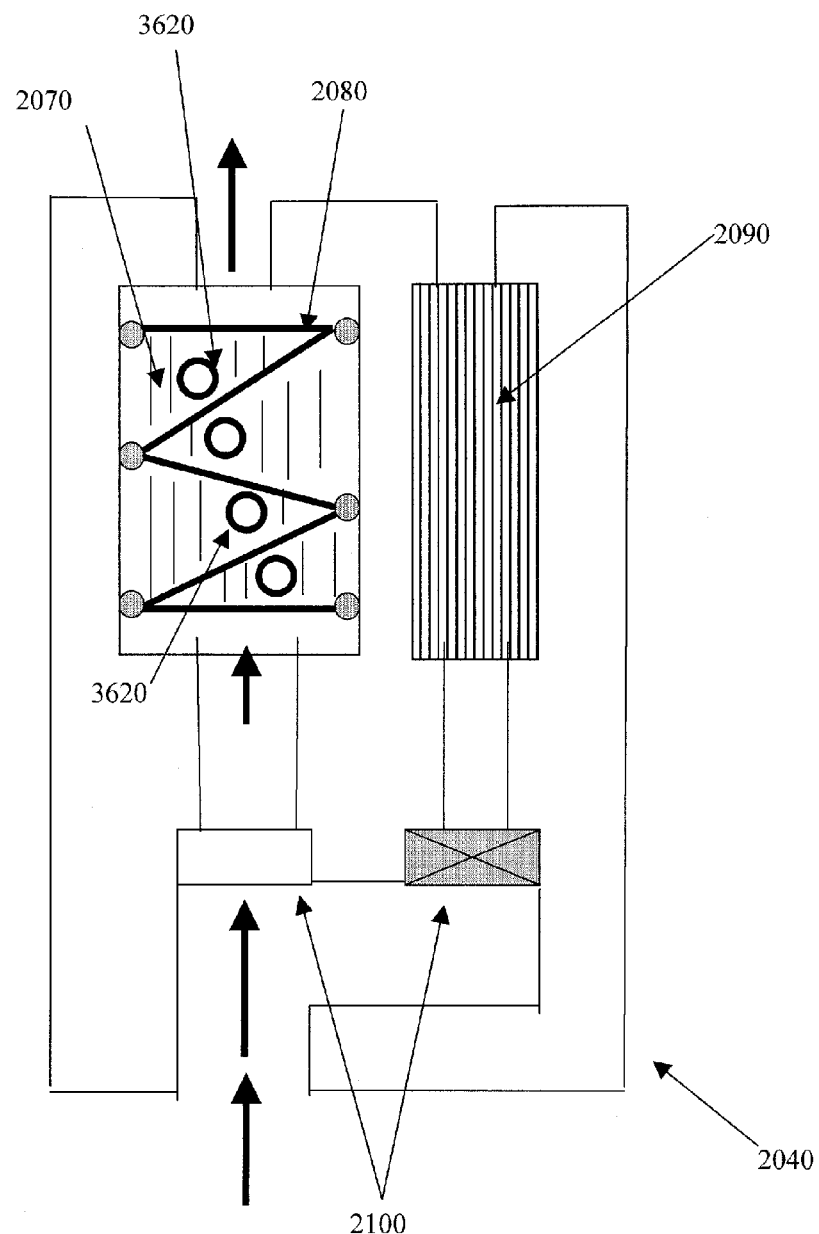
FIG. 91 is a schematic view of a fourth embodiment of a UV light device of the dehumidifier of FIG. 70.

According to an embodiment shown in FIG. 91, according to an embodiment, any ultraviolet (UV) light device such as but not limited to the present invention and those described in U.S. Patent and U.S. application Ser. Nos. 09/855,546 and 10/671,837 to Morneault et al., and U.S. Pat. No. 7,045,096 B2 to D'Ottone, and any of their references, can, without limitation, be coupled with any dehumidification technology known to those skilled in the art. It is preferred, without limitation, that the dehumidification is achieved through the use of a dehumidifier (2040) that uses one or more cooling surface(s) or chill coil(s) (herein collectively called "chill coils" (2080)) as known by those skilled in the art. The cooling surface(s) or chill coil(s) (2080) can be, without limitation, one or more of any cooled surface(s) or cooling tube(s) that can remove humidity from the surrounding air or atmosphere, or any air or atmosphere that is moved past the chill coil(s) (2080).

Referring to FIG. 91, the cooling surfaces(s) or chill coil(s) (2080) can be located effectively near, or positioned in the same area, housing, or even enclosure(s) (3610) as the UV light source(s) (3620). It is preferred without limitation, that the UV light source(s) (3620) are positioned or located in close proximity to the chill coil(s) (2080). The air or gas can, without limitation, contain any quantity or concentration of any vapor or aerosol (200) that contains any agent(s) from the treated or targeted area(s) (3310). The air or gas stream can be dehumidified at any time, and for any duration, during any point in a treatment cycle. The chill coil(s) (2080) can, without limitation, maintain the UV light source(s) (3620), or any area in which they reside, at any temperature. It is preferred, without limitation, that the UV light source(s) (3620) are maintained during their operation, by the chill coil(s) (2080), at a temperature where they will not become frosted with moisture or ice, and this can be accomplished with various sensors and software controls known to those skilled in the art. The chill coil(s) (2080) can be operated at different times or at the same time as the UV light source(s) (3620). In addition, the chill coil(s) (2080) or any other means for dehumidification or aerosol removal, can, without limitation, operate at any time, and for any duration, during any point in a treatment cycle that is performed before the UV light source(s) (3620) are utilized. It is preferred, without limitation, that the temperature of the air or gas near the UV light source(s) (3620) is maintained between 0-70 degree Centigrade. It is even more preferred, without limitation, that the temperature of the air or gas near the UV light source(s) (3620) is maintained between 0-15 degree Centigrade. The cooling surface(s) or chill coil(s) (2080) can be maintained at any temperature, but at least at a temperature that is effective. The effective operation of any cooling surface(s) or chill coil(s) (2080) in any dehumidifier (2040) is known to those skilled in the art.

According to an embodiment, the apparatus (215) or any aerosol generator can, without limitation, be designed and constructed so that it incorporates into its design or operation, one or more UV light source(s) (3620), as well as one or more dehumidifier(s) (2040) that uses one or more chill coil(s) (2080).

According to an embodiment, any ultraviolet (UV) light device such as but not limited to the present invention and those described in U.S. Patent and U.S. application Ser. Nos. 09/855,546 and 10/671,837 to Morneault et al., and U.S. Pat. No. 7,045,096 B2 to D'Ottone, and any of their references, can, without limitation, be utilized with the apparatus (215) or any vapor or aerosol generator, that is used to treat an area with one or more aqueous agent(s) consisting of any quantity of hydrogen peroxide, or peroxyacetic acid (PAA). It is even more preferred, without limitation, that these UV light devices can be used with the apparatus (215) or any vapor or aerosol (200) generator, that is used to treat an area (3310) with one or more aqueous agent(s) including any aqueous agent(s) that are acidic. It is more preferred, without limitation, that these UV light devices can be used with the apparatus (215) or any vapor or aerosol (200) generator, that is used to treat any area (3310) with one or more aqueous agent(s) including any aqueous agent(s).

According to an embodiment, any (UV) light source device or dehumidifier (2040) can, without limitation, be designed and constructed so that any part of their design, including, but not limited to, any enclosure (3610) for any (UV) light source(s) (3620), fan or blower housing(s) (3440), or any attached conduit(s), pipe(s), or tubing, or any other components, may be drained of any liquid that may build up in these areas during operation or cleaning. This liquid can, without limitation, be drained, in a manner known to those skilled in the art, to any holding tank(s), drain port(s), or tank(s). These devices can be plumbed in various ways known to those skilled in the art, so that this liquid can be fully drained and removed from them.

According to an embodiment, the apparatus (215) or other aerosol generator can, without limitation, be designed and constructed so that any software, hardware, electronics, PLC (315), or HMI (320) (herein collectively called "PLC" (315)), can adjust the time allocated, chosen, or needed, for any step in the treatment process(es) for any targeted area(s) and/or surface(s), as well as any time between each step. This can also, without limitation, be accomplished automatically, or with any algorithm designed into any software controlling the apparatus (215) or treatment process.

Any time allocated for any step or between any step, or any timing sequence, for any part of any treatment process(es) of any targeted area(s) and/or surface(s) operation, that involves any apparatus (215) or any other associated equipment, can be adjusted, changed, or accommodated, to account for any variables or combination of variables that may impact the performance or efficacy of any treatment or process step such as, but not limited to, any volume of any treated space(s), temperature of any air or gas in the treated area(s), temperature of any surface(s) in the treated area(s) (3310), any relative humidity in the treated area(s), any dew point(s) in the treated area(s) (3310), any atmospheric pressure or any pressures in the treated area(s) (3310). These variables can be measured by, and reported to any PLC (315), via any means known to those skilled in the art.

The one or more of any time period(s) or timing sequence(s) involved with a treatment process(es) can also involve or pertain to any ancillary equipment associated with the treatment of any targeted space(s) or area(s), or the operation of the apparatus (215) such as, but not limited to, any dehumidifier (2040), or any odor removing apparatus that utilizes ultraviolet light (3620).

The PLC (315) can, without limitation, monitor, log, or report, any change to any part of any treatment process(es) including, but not limited to, any process step or between any process step, or any timing sequence(s). This information can be reported to anywhere in any format in any manner know to those skilled in the art. This information can accompany any other data relating to any successful or unsuccessful treatment process(es) or operation cycle(s) attempted.

According to an embodiment, the apparatus (215) or other aerosol generator can, without limitation, be designed and constructed so that it can conduct, operate, or execute various operational steps or sequences. One or more of the following steps can also, without limitation, be bypassed either temporarily or permanently per the desires or needs of any operator or control input. Each step can vary for any length of time for any reason known to those skilled in the art. In addition the time between each step can also vary for any length of time for any reason.

The first step is aerosol generation and deployment of the aerosol (200) into the one or more targeted area(s) (3310). This step includes, without limitation, the additional step of heating the liquid (30) that will be aerosolized, to any preset temperature. The second step is giving the deployed aerosol (200) and any vapor component(s) adequate time to effectively and efficaciously move within the targeted area(s) (3310) and contact any surfaces in the targeted area(s) (3310), all in a manner known to those skilled in the art (also known as dwell time).

The third step is dehumidification. Dehumidification can be achieved in various ways known to those skilled in the art, and with any dehumidifier (2040). Any humidity level can be set as the target point for the dehumidification process to meet or achieve. Dehumidification can also, without limitation, consist of operating any rotating paddles (3570) as mentioned in the present invention, and this can, without limitation, be operated with our without any other dehumidification device(s) or methodologies. The fourth step is deodorization. This is achieved by using one or more UV light source(s) (3620) as described in the present invention. The fifth step is filtering the air with one or more of any filter(s) (2070) to remove any amount of any unwanted gases or vapor. Furthermore, the aerosol generating apparatus (215) may stop all other steps and enter into or start the dehumidification step at any time for any reason. The dehumidification step may be started for reasons including, but not limited to, the apparatus (215) or operator or other input, has detected a fault with any part or operation of the apparatus (215) or any other ancillary piece of equipment, an emergency stop has been actuated, or the operator has chosen to abort or stop the function of the apparatus (215). Finally, the operator of the apparatus (215) can, without limitation, manually operate the dehumidification step or deodorization step either any time before the aerosol (200) generating apparatus (215) has started to generate and deploy any aerosol (200), or any time after the treatment process(es) or entire operational cycle is complete.

Figure 92:
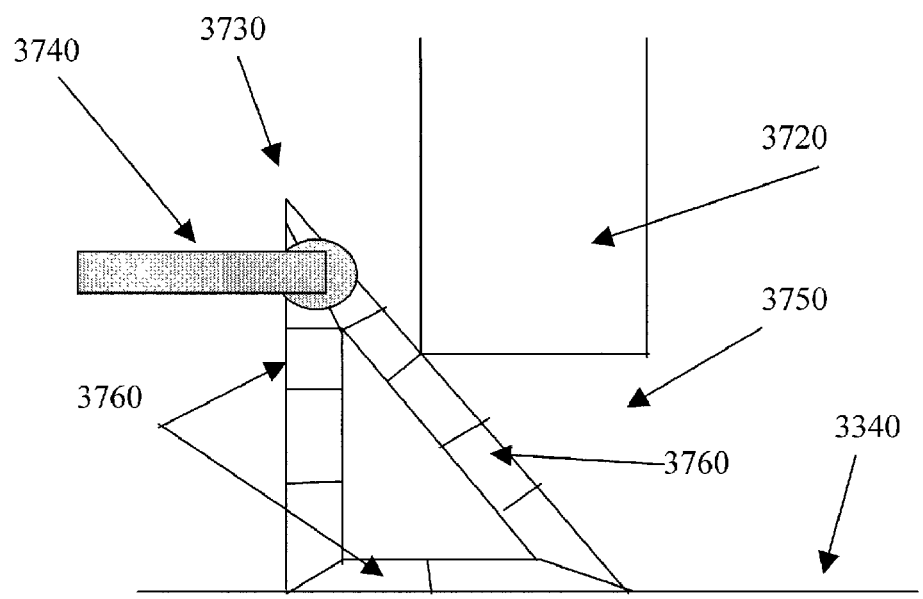
FIG. 92 is a schematic view of a first embodiment of a door seal utilized with the generator and dehumidifier of FIG. 70.
Figure 93:
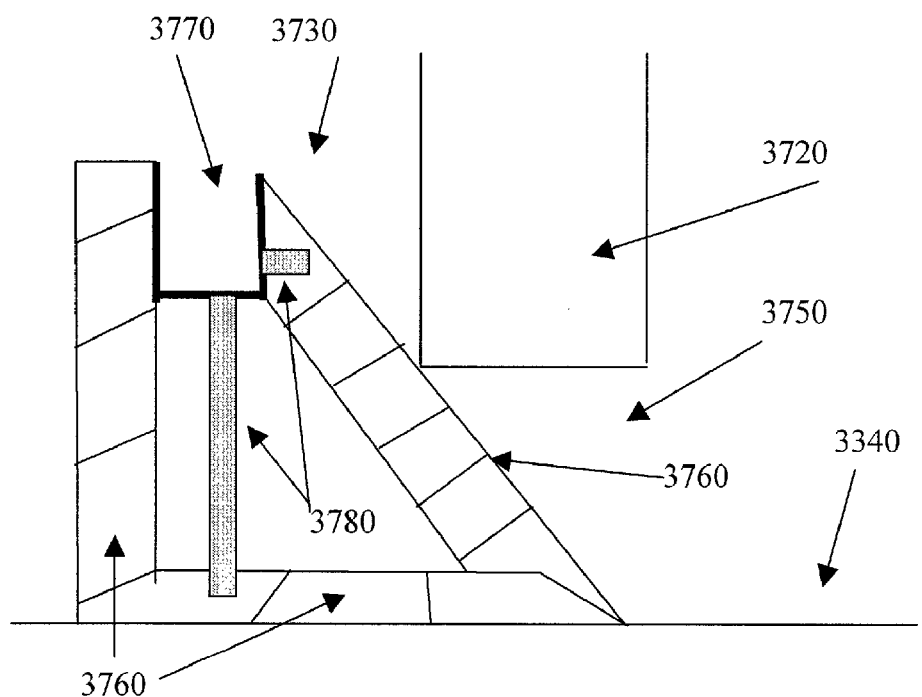
FIG. 93 is a schematic view of a second embodiment of a door seal utilized with the generator and dehumidifier of FIG. 70.

According to an embodiment shown in FIGS. 92-93, a means (herein called "door seal") (3730) is designed and constructed to cover, plug, or seal any space (herein called "door gap(s)") (3750) that can exist between any door frame or door (herein called "door") (3720) and any floor (3340) or other materials below it. The door seal (3730) can, without limitation, be friction fitted under and/or against either side of any door (3720). The door seal (3730) can, without limitation, be any length, width, height, and have any floor, doorway, or door interfacing geometries. The door seal (3730) can also be, without limitation, designed in a manner known to those skilled in the art, so that its length, width, or height, can be easily adjusted to accommodate and effectively seal with various doorway and door (3720) designs and sizes.

The door seal (3730) can, without limitation, be flexible, and have any durometer rating. It is preferred, without limitation, that the door seal (3730) has a durometer rating that allows it to be easily inserted under a door or at least effectively interfaced with one or more door gap(s) (3750). The door seal (3730) can, without limitation, be constructed from, fully covered, or at least covered on its critical interfacing surfaces, with one or more of any absorbent material(s) (3760) that can hold, contain, or absorb any liquid. Any absorbent material(s) (3760) can, without limitation, have any type, depth, length, and number, of textures or indentions, and can be any thickness or construction. The absorbent material(s) (3760) can be constructed from, without limitation, one or more materials such as, but not limited to, cellulose, paper, natural or manufactured fibers or materials, that may be coated or uncoated, or constructed with combinations of these materials, or other materials known in the art. The absorbent materials (3760) or any construct containing absorbent materials (3760) are either treated by the operator or pretreated in various ways known to those skilled in the art, with any liquid agent(s), so that the surfaces of the doorway and/or door(s) (3720) and the floor (3340) or any flooring or other materials under the door(s) (3720), can come in contact with the liquid agent(s). It is preferred, without limitation that the absorbent material(s) (3760) is saturated with the same liquid agent(s) (30) that is generated into aerosol (200) in the present invention. The door seal (3730) can also, without limitation, incorporate one or more handle(s) (3740) of various size, length, and shape, into its design to facilitate easier placement and retrieval.

According to an embodiment, the door seal (3730) can, without limitation, be designed and constructed to include one or more reservoir(s) or basin(s) (herein called "seal basin" (3770)) which can be either internally or externally located. They can be any size and shape and filled with any liquid agent(s). The seal basin(s) (3770) can also, without limitation, have one or more removable covers that can effectively directly or indirectly seal to the door seal (3730). The seal basin(s) (3770) may, without limitation, also have one or more of any tube, duct, pipe, conduit, tunnel, pathway, or connection (herein called "feed tube") (3780), that connects any part of the seal basin(s) (3770), or any other structure or component that directly or indirectly connects to any part of any seal basin(s) (3770), with any of the absorbent material(s) (3760), so that any liquid or moisture may be transported, moved, or flow, at any rate or speed, from the seal basin(s) (3770) to any of the absorbent material(s) (3760).

Figure 94:
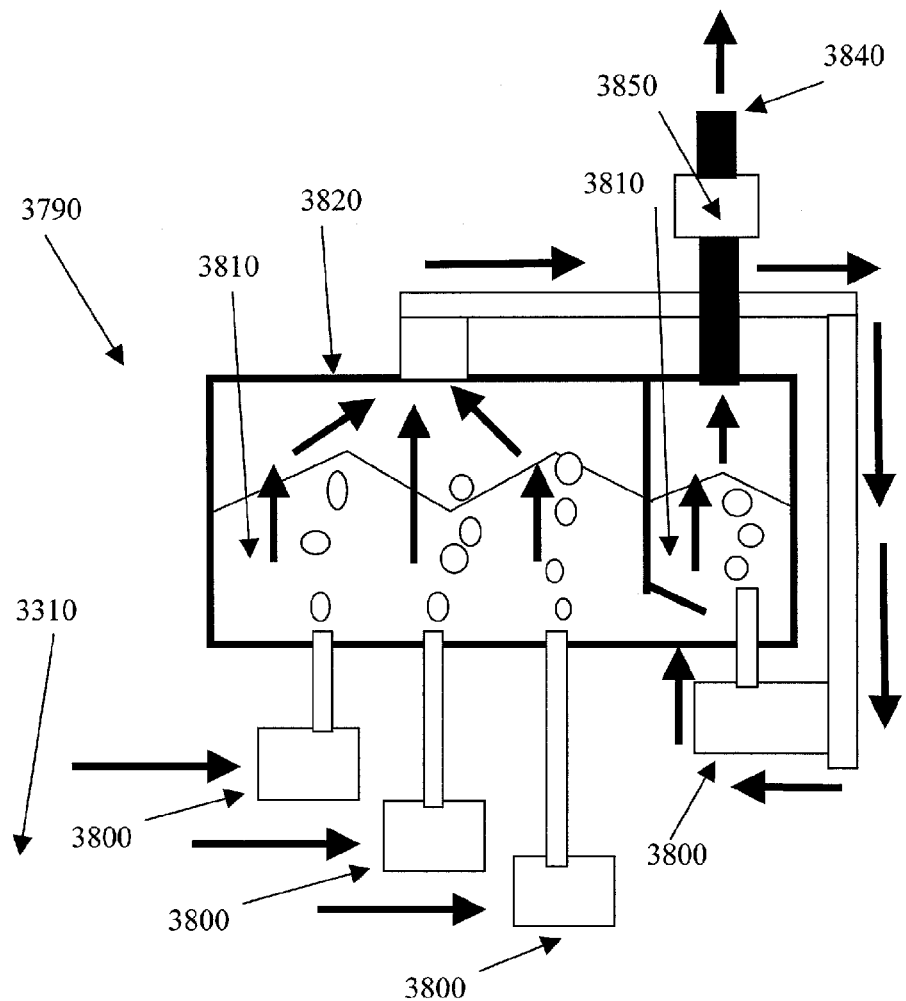
FIG. 94 is a schematic view of a deodorizing chamber utilized with the generator and dehumidifier of FIG. 70.

According to an embodiment shown in FIG. 94, a means (herein called "odor remover tank") (3790) can, without limitation, be designed and constructed so that air or gas from one or more targeted area(s) (3310) can be pumped, flowed, compressed, or moved, into and through one or more various types of liquids contained in one or more enclosed tanks or reservoirs (herein called "tank(s)") (3820). The air or gas can also, without limitation, contain any amount of any aerosol (200). The liquid(s) (herein called "neutralizer liquid(s)") (3810) held in the tank(s) (3820) can, without limitation, neutralize, degrade, or remove, any odors or vapors from the air, as well as neutralize or degrade any liquid agent(s) (30) that the aerosol (200) may contain. Any neutralizer liquid(s) (3810) can be utilized. It is preferred, without limitation, that the neutralizer liquid(s) (3810) is an aqueous solution containing any effective amount of sodium bicarbonate when the treated air or gas is from an area that is treated with an aerosol containing substances such as, but not limited to, hydrogen peroxide, or peroxyacetic acid (PAA).

It is preferred, without limitation, that one or more of any high capacity air/gas compressor(s) known to those skilled in the art, is used to move the air or gas from the treated area(s) (3310) into the neutralizer liquid(s) (3810). The air or gas can be pumped, flowed, compressed, or moved, through one or more of any adequate tube, duct, pipe, conduit, tunnel, pathway, or connection, anywhere into the neutralizer liquid(s) (3810) at any effective pressure or flow rate. The neutralizer liquid(s) (3810) can be maintained at any volume, depth, and temperature. The neutralizer liquid(s) (3810) can also, without limitation, be stirred at any time and for any duration in a manner known in the art. The air or gas may also be recirculated one or more times through the neutralizer liquid(s) (3810) before it is released from the odor remover tank (3790) out of an air outlet (3840) and back into the treated area(s) (3310) or vented into a separate area. Any air or gas can be, without limitation, processed by any effective or necessary filtering means (3850) known to those skilled in the art before it leaves any odor remover tank(s) (3790) or any connecting system of tube(s), duct(s), pipe(s), conduit(s), tunnel(s), pathway(s), or connection(s). All of the odor remover tank (3790) functions can, without limitation, be controlled directly or indirectly by any software, electronics, PLC (315), or HMI (320). The odor remover tank (3790) can be operated at anytime when it is needed or desired to remove any odors or vapor from the targeted area(s) or treated space(s) (3310). The odor remover tank (3790) device can be, without limitation, combined or operated with any aerosol (200) generating device or dehumidifier (2040).

Without being limited, and according to a preferred embodiment and with reference to FIGS. 98-102 and FIGS. 119-132, a description is given, of an enhanced use of one or more remotely located or positioned sensor(s) (3530), hereinafter called "remote aerosol sensor(s)" (5010), that can be used to determine if or when an effective or sufficient amount of aerosol (200) is applied to the one or more treated or targeted area(s) (210). Without being limited, the remote aerosol sensor(s) (5010) can also be used with any aerosol generating means, as well as any vapor and/or gas generating apparatus(s), that deploy any generated aerosol, gas, and/or vapor, into one or more targeted area(s) (210). The remote aerosol sensor(s) (5010), and/or any of its components, can also be used, without limitation, within, and/or incorporated into the design and construction of, any treatment chamber(s), or any other effectively sealed treatment area(s), of any apparatus that is used to treat the surfaces of objects with any aerosol, gas, and/or vapor.

The remote aerosol sensor(s) (5010) can incorporate or contain, and operate, without limitation, one or more of any sensing device(s) (5080), or any combination of various sensing device(s) (5080), such as, but not limited to any, light sensor(s) (730), temperature sensor(s) (5085), humidity or relative humidity sensor(s) (Hereinafter called "humidity sensor(s)" (5090)), dew point sensor(s) and/or hygrometer(s) (Hereinafter called dew point sensor(s) (3888)), that can capture data or conditions pertaining to the environment or atmosphere surrounding the remote aerosol sensor (5010) or in which the remote aerosol sensor(s) (5010) is located. In addition, the remote aerosol sensor(s) (5010) can incorporate or contain, and operate, without limitation, one or more of any components, support component(s), or accessory(s), related to, or work with, any sensing device(s) (5080) such as, but not limited to any, light source(s) (725) that can, without limitation, work with any light sensor(s) (730). The remote aerosol sensor(s) (5010) can also incorporate or contain, and operate, without limitation, one or more of any sensing device(s) (5080) such as, but not limited to any, sensor(s) that can sense the presence of any deposited aerosol (200) droplets, or at least a sufficient quantity of deposited aerosol (200), that is deposited on any monitored surface (Hereinafter aerosol deposit sensor(s) (3880). This particular sensor does not in any way include, or refer to, any relative humidity sensor(s), dew point sensor(s), and/or hygrometer(s), already known to those in the art. Without being limited, one or more of any, digital, electronic, or analog, controller(s) such as, but not limited to, any PLC(s), remote PLC(s) (3893), as well as any sensing device(s) (5080), light source(s) (725), and/or any other related component(s), or any part of these various sensor(s), component(s), or part(s), that need protection from the environment or atmosphere within the targeted area(s) (210), can be suitably and effectively packaged or hermetically sealed within the one or more one or more housing(s) (5100) of the remote aerosol sensor(s) (5010).

One or more of these various sensing device(s) (5080), as well as any components, support component(s), or accessory(s), related to, or work with, any sensing device(s) (5080) can be, without limitation, located or interfaced in or on, any effective, location, position, or orientation, related to the remote aerosol sensor(s) (5010) and any of its associated parts. One or more of these various components and/or sensing device(s) (5080) can also be, without limitation, constructed or located within, under, or as a part of, one or more of any slot(s), channel(s), indentation(s), cavern(s), of any size, shape, depth, length, or complex geometry, that may connect directly or indirectly to any environment or atmosphere that interfaces with, or surrounds, the remote aerosol sensor(s) (5010). It is preferred, without limitation, that these various sensing device(s) (5080), as well as any component(s), support component(s), or accessory(s), related to, or work with, any sensing device(s) (5080) such as, but not limited to any, light source(s) (725), are located and operated in a manner so that they can effectively collect and report any needed data pertaining to the targeted area(s) (210). Any data that is collected by the one or more of any sensing device(s) (5080), as well as any component(s), support component(s), or accessory(s), related to, or work with, any sensing device(s) (5080) can be, without limitation, directly or indirectly reported or communicated to one or more of any digital, electronic, or analog, controller(s) such as, but not limited to, any "programmable logic circuit(s)" or otherwise "PLC(s)", at any time, and can be utilized for various purposes including, but not limited to, determining if or when the targeted area(s) (210) is filled with a sufficient amount of aerosol (200) that will result in an efficacious outcome within the targeted area(s) (210) with the administered aerosol (210). The one or more PLC(s) may be used for any purpose(s), and may be located in or at any location(s), such as, but not limited to, inside or a part of the remote aerosol sensor(s) (5010), any aerosol generator(s) (215), any remote or indirectly connected device(s) that communicates with and/or controls the various aerosol generator(s) (215) and/or remote aerosol sensor(s) (5010).

The remote aerosol sensor(s) (5010) can be, without limitation, constructed and/or configured with or without one or more aerosol deposit sensor(s) (3880). It is preferred, without limitation, that the remote aerosol sensor(s) (5010) incorporates at least one or more aerosol deposit sensor(s) (3880) in its design or construction. If the remote aerosol sensor(s) (5010) device is constructed and/or configured with one or more aerosol deposit sensor(s) (3880), certain configurations are preferable more than others, but this does not in any way limit the scope in which the remote aerosol sensor(s) (5010) can be configured, constructed, and/or utilized. It is preferred, without limitation, that the remote aerosol sensor(s) (5010), incorporates at least one or more of any, aerosol deposit sensor(s) (3880). It is more preferred, without limitation, that the remote aerosol sensor(s) (5010), incorporates at least one or more of any, aerosol deposit sensor(s) (3880), and temperature sensor(s) (5085). It is even more preferred, without limitation, that the remote aerosol sensor(s) (5010), incorporates at least one or more of any, aerosol deposit sensor(s) (3880), temperature sensor(s) (5085), and relative humidity sensor(s) (5090). It is very preferred, without limitation, that the remote aerosol sensor(s) (5010), incorporates at least one or more of any, aerosol deposit sensor(s) (3880), temperature sensor(s) (5085), light source(s) (725), light sensor(s) (730). It is extremely preferred, without limitation, that the remote aerosol sensor(s) (5010), incorporates at least one or more of any, aerosol deposit sensor(s) (3880), temperature sensor(s) (5085), light source(s) (725), light sensor(s) (730), humidity sensor(s) (5090), and/or dew point sensor(s) (3888).

However, if the remote aerosol sensor(s) (5010) device is constructed and/or configured without utilizing one or more aerosol deposit sensor(s) (3880), certain configurations are preferable more than others, but this does not in any way limit the scope in which the remote aerosol sensor(s) (5010) can be configured, constructed, and/or utilized. It is preferred, without limitation, that the remote aerosol sensor(s) (5010), that are devoid of one or more aerosol deposit sensor(s) (3880), have at least one or more of any, light source(s) (725) and light sensor(s) (730). It is more preferred, without limitation, that the remote aerosol sensor(s) (5010), that are devoid of one or more aerosol deposit sensor(s) (3880), have at least one or more of any, light source(s) (725) and light sensor(s) (730), and temperature sensor(s) (5085). It is even more preferred, without limitation, that the remote aerosol sensor(s) (5010), that are devoid of one or more aerosol deposit sensor(s) (3880), have at least one or more of any, light source(s) (725), light sensor(s) (730), and relative humidity sensor(s) (5090). It is very preferred, without limitation, that the remote aerosol sensor(s) (5010), that are devoid of one or more aerosol deposit sensor(s) (3880), have at least one or more of any, light source(s) (725), light sensor(s) (730), temperature sensor(s) (5085), humidity sensor(s) (5090), and/or dew point sensor(s) (3888).

The use of two or more of any sensing device(s) (5080) together such as, but not limited to any, humidity sensor (5090), and light sensor (730), can be, without limitation, helpful in situations where at least one sensor, or even more than one sensor, for example the light sensor (730) and/or the humidity sensor (5090), may be reporting inaccurate or erroneous data. In this case, any one or more of any digital, electronic, or analog, controller(s) such as, but not limited to, any PLC(s), that controls one or more aerosol producing apparatus(s) (215), or remotely communicates with and controls one or more of any aerosol producing apparatus(s) (215), can, without limitation, be notified of this event or situation, and either ignore the one or more remote aerosol sensor(s) (5010) that have any problem(s) or error(s), or take various actions or combination of actions, such as, but not limited to, (a) stopping the administration or deployment of any aerosol (200) within the targeted area(s) (210), (b) shutting down one or more of any aerosol generating apparatus(s) (215), (c) ignoring one or more of any erroneous or problematic sensor(s) and any of their data, for any amount of time, depending on various criteria, logic, or operating conditions, that may be established or encountered. This can, without limitation, happen in various possible circumstances, such as, but not limited to, (a) the humidity sensor (5090) reports accurate data supporting the presence of an efficacious amount of aerosol (200) within the targeted area(s) (210), but the light sensor (730) incorrectly reports the absence of an efficacious amount of aerosol (200) within the targeted area(s) (210), (b) the light sensor (730) reports accurate data supporting the presence of an efficacious amount of aerosol (200) within the targeted area(s) (210), but the humidity sensor (5090) incorrectly reports the absence of an efficacious amount of aerosol (200) within the targeted area(s) (210), (c) both the light sensor (730) and the humidity sensor (5090) fail to report that there is an efficacious amount of aerosol (200) within the targeted area(s) (210). Without being limited, the use of two or more of any other sensing devices (5080) such as, but not limited to any, aerosol deposit sensor(s) (3880), light sensor(s) (730), temperature sensor(s) (5085), humidity sensor(s) (5090), and dew point sensor(s) (3888), may also be helpful in situations where one or more sensors, may be reporting inaccurate or erroneous data, and can result in similar outcomes or actions.

Any one or more of any digital, electronic, or analog, controller(s) such as, but not limited to, any PLC(s), that controls one or more of any aerosol producing apparatus(s) (215), or remotely communicates with and controls one or more of any aerosol producing apparatus(s) (215) can, without limitation, be programmed or configured to accommodate or compensate for various variables such as, but not limited to, any temperature, any humidity, any density of deployed aerosol (200), any size of deployed aerosol (200), any atmospheric pressure within the targeted area(s) (210), any amount of deposited aerosol (200) sensed by any aerosol deposit sensor(s) (3880) at any time, by either extending or shortening the total amount of time that the one or more aerosol generating apparatus(s) (215) deploy aerosol (200) into the one or more targeted area(s) (210). Any modifications that may be made to the time that the one or more aerosol generating apparatus(s) (215) deploy aerosol (200) can, without limitation, be made at any time before or during the deployment of any aerosol by any aerosol producing apparatus(s) (215).

Various operational variables such as, but not limited to, the temperature of the atmosphere within any part of the targeted area(s) can have, without limitation, an effect on the outcome of the treatment for the targeted area(s) (210). This may be, without limitation, found in harsh or extreme environments. For example, and without being limited, any elevated temperatures in one or more targeted area(s) (210) may, without limitation, increase the need for longer aerosol (200) deployment times by the one or more aerosol generating apparatus(s) (215), in order to achieve the desired or efficacious results. Any detected temperature within the targeted area (210) can also, without limitation, result in any extended time for aerosol (200) deployment from any initially chosen or calculated treatment time that was decided before the treatment cycle for the targeted area(s) (210) began. Any detected temperature within the targeted area (210) can also, without limitation, result in any shortening of the time needed for aerosol (200) deployment from any initially chosen or calculated treatment time for a given volume of the targeted area(s) (210).

The humidity sensor(s) (5090) can, without limitation, have various capabilities and attributes such as, but not limited to, the ability to sense any humidity or airborne moisture level, any sensitivity, and/or the ability to be controlled and/or communicate with one or more of any digital, electronic, or analog, controller(s) such as, but not limited to, any PLC(s). The humidity sensor(s) (5090) can, without limitation, indicate or communicate to any directly or indirectly connected, digital, electronic, or analog, controller(s) such as, but not limited to, any PLC(s), any moisture or humidity data it collects, which can be accomplished in a manner known to those skilled in the art. It is preferred, without limitation, that the one or more of any remote and/or directly connected, digital, electronic, or analog, controller(s) such as, but not limited to, any PLC(s), is indicated or receives any information about the status of any humidity level or data that is detected in the targeted area(s) (210), in various ways such as, but not limited to, receiving any, signal, electrical signal, electrical value or intensity of any electrical signal, or lack of any electrical signal(s) from the humidity sensor(s) (5090). This communication can result in various actions or combination of actions, such as, but not limited to: (a) shutting down any drive electronics (645) or amplifier(s) (230), (b) shutting down the blower(s) (180) or flow of pressurized air, (c) shutting down the apparatus(s) (215), (d) stopping the production of aerosol, (e) stopping the deployment of aerosol (200) into the targeted area(s) (210). Without being limited, any effective humidity sensor(s) (5090), known in the art, may be utilized in the present invention. The humidity sensor(s) (5090) can, without limitation, be positioned in any location, effective direction, angle, orientation, configuration, or position.

An effective or sufficient amount of administered aerosol (200) within the targeted area(s) (210) can be indicated, without limitation, by any humidity or relative humidity data, levels, or percentages (hereinafter called "humidity level(s)"). These various humidity or relative humidity levels or percentages can be, without limitation, sustained for any effective amount of time, but preferably at least an effective and/or efficacious amount of time, before various actions or combination of actions are taken, such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215). Without being limited, the effective, sufficient amount, or specified quantity, of administered aerosol (200) into the targeted area(s) (210) and any associated humidity levels or data, can also vary for any intended or unintended reasons or designs, before various actions or combination of actions are taken, such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

The humidity level within the targeted area(s) (210), can without limitation, rise from the humidity level that is detected before any aerosol (200) or vapor is deployed into the targeted area(s) (210), to any humidity level, preferably between 80-100 percent, and more preferably between a 95-100 percent or more humidity level, and even more preferably between a humidity level of 99-100 percent, when the targeted area(s) (210) is completely full of aerosol and has reached a quantity or concentration of aerosol (200) that is effective or gives a level of efficaciousness that is desired.

In addition, and without limitation, the humidity level that is detected before any aerosol (200) or vapor is deployed into the targeted area(s) (210), can effect the total amount of time that is necessary to reach a quantity or concentration of aerosol (200) within the targeted area(s) (210) that is effective or gives a level of efficaciousness that is desired. For example, and without limitation, the less humidity that is detected before any aerosol (200) or vapor is deployed into the targeted area(s) (210), the longer amount of time it may take to reach a quantity or concentration of aerosol (200) within the targeted area(s) (210) that is effective or gives a level of efficaciousness that is desired. Conversely, and without limitation, the more humidity that is detected before any aerosol (200) or vapor is deployed into the targeted area(s) (210), the shorter the amount of time it may take to reach a quantity or concentration of aerosol (200) within the targeted area(s) (210) that is effective or gives a level of efficaciousness that is desired.

For any given temperature and/or humidity level, the total amount of time that is needed to expose the various surfaces(s) within the targeted area(s) (210) to the aerosol (200) may also, without limitation, vary, and can include any amount of time between after the deployment of any aerosol (200) into the targeted area(s) (210) has stopped, and the targeted area(s) (210)s are evacuated of any aerosol (200) and/or vapor in one or more ways, or combination of ways, including, but not limited to, allowing fresh ventilation air to flow through the targeted area(s) (210), operating one or more of any effective dehumidification equipment within the targeted area(s) (210), flowing the atmosphere within the targeted area(s) (210) through one or more of any adequate filter(s) or charcoal activated filter(s).

The light source (725) and light sensor (730) can be directly or indirectly connected, or they can be placed or positioned independent from one another. The distance between the light source (725) and light sensor (730) can be any distance, but should be at least an effective distance. The light source (725) and light sensor (730) can be, without limitation, separated by a distance of one (1) foot or less. However, it is preferred, without limitation, that the light source (725) and light sensor (730) are at separated by a distance of one (1) foot or more. It is more preferred, without limitation, that the light source (725) and light sensor (730) are separated by a distance of two (2) feet or more. It is even more preferred, without limitation, that the light source (725) and light sensor (730) are separated by a distance of four (4) feet or more. Without being limited, any effective source of light or light source (725), and any effective means for sensing any presence and/or any change in light or the amount of light, or light sensor (730), known to those skilled in the art, may be utilized in the present invention. The light source(s) (725) can have, without limitation, any power, wavelength, and intensity. The light sensor(s) (730) can, without limitation, have any sensitivity, and sense light with various attributes including, but not limited to any, power, wavelength, light level, and intensity. It is preferred, without limitation that the one or more of any light source(s) (725) and light sensor(s) (730), that are utilized, have attributes that are at least suitable for their intended application. Each remote aerosol sensor(s) (5010) can, without limitation, consist of at least one or more of any effective laser, of any power or class type, for a light source (725), and at least one or more of any photoelectric sensor, of any type and sensitivity (730), for a light sensor (730). The one or more light source(s) (725) and one or more light sensor(s) (730) that are utilized can be, without limitation, configured or positioned so that the light sensor(s) (730) receives light in various ways including, but not limited to, directly from one or more light source(s) (725), indirectly from one or more light source(s) (725), from any reflected light that is generated from one or more light sources(s) (725). Any light that is reflected back to the one or more light sensor(s) after being generated by one or more of any light source(s) (725) may reflect off of one or more of any surface(s) or substance(s) including, but not limited to any, aerosol (200), or one or more reflecting surface(s) or mirrored surface(s) (hereinafter called "reflector(s)" (5030)). The aerosol (200) may be of any effective density and size. Without being limited, the light source(s) (725) and light sensor(s) (730) may be positioned in any effective direction, angle, orientation, configuration, or position. If light from one or more reflected surface(s) or reflector(s) (5030) is utilized, the one or more surface(s) or reflector(s) (5030) from which the light is reflected back to the light sensor(s) (730) can be, without limitation, positioned at any effective distance and any effective orientation or angle from the one or more light sensor(s) (730) and one or more light source(s) (725). The reflective surface(s) or reflector(s) (5030) may be, without limitation, any suitable size and shape.

The emitted light or energy, or light source (725) can have, without limitation, any traits or attributes including, but not limited to, any: (a) intensity(s), (b) brightness, (c) period(s), (d) frequency(s), type of light(s), and (e) wavelength(s). The one or more light source(s) (725) and light sensor(s) (730) can, without limitation, be controlled and/or communicate with one or more of any digital, electronic, or analog, controller(s) such as, but not limited to, any PLC(s). The means to sense the light (730) can, without limitation, vary widely in its sensitivity and ability to sense any kind of light consisting of any traits or attributes including, but not limited to, any: (a) intensity(s), (b) brightness, (c) period(s), (d) frequency(s), type of light(s), and (e) wavelength(s). Without being limited, the means to sense the light (730) can also have various capabilities known in the art, including, without limitation, the ability to have any adjustable sensitivity and trigger level(s), or the ability to communicate with one or more of any digital, electronic, or analog, controller(s) such as, but not limited to, any PLC(s) or any other suitable components, that can also have any adjustable sensitivity and trigger level(s). The light sensor(s) (730) can, without limitation, indicate to or communicate with one or more of any digital, electronic, or analog, controller(s) such as, but not limited to, any PLC(s), if or when it either receives or ceases to receive any trait or attribute pertaining to any light such as, but not limited to, any desired or set level of light stimulus or light intensity. Without being limited, the light sensor(s) (730) can also, indicate to or communicate with, one or more of any digital, electronic, or analog, controller(s) such as, but not limited to, any PLC(s), by way of sending or communicating with, one or more of any variation of any, power level(s), voltage(s), and/or amperage(s), to communicate any information pertaining to any light that is detected such as, but not limited to, the presence or absence of any light, and/or any level, intensity, or power of any light. The said communication can be accomplished in various ways known in the art. This communication can result in various actions or combination of actions, such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

Without limitation, an effective or sufficient amount of administered aerosol (200) into one or more targeted area(s) (210) in this embodiment is indicated by its causing any, disruption, diminishment, decrease, or cessation, of the light that is emitted from the light source(s) (725), before it reaches any light sensor(s) (730). The effective, sufficient amount, or specified quantity, of administered aerosol (200) into any targeted area(s) (210) can vary for any intended or unintended reasons or designs, and the trigger or sensitivity levels for the light sensor(s) (730) can, without limitation, be varied, calibrated, or adjusted, to any amount or level of light disruption, for each situation or any level of aerosol that is equated with an efficacious outcome.

One or more remote aerosol sensor(s) (5010), as well as any of its components, including, but not limited to any, temperature sensor(s) (5085), humidity sensor(s) (5090), light source(s) (725), light sensor(s) (730), dew point sensor(s) (3888), and aerosol deposit sensor(s) (3880), can be, without limitation, controlled and/or communicate directly or indirectly with one or more of any, digital, electronic, or analog, controller(s) such as, but not limited to, any PLC(s), and communicate any data, information, status(s), or condition(s). The one or more remote aerosol sensor(s) (5010) can also, without limitation, communicate directly or indirectly with one or more of any aerosol generating apparatus(s) (215), and/or one or more of any remote device(s) that controls one or more aerosol generating apparatus(s) (215), in various ways such as, but not limited to any, radio, radio waves, sound, wire, cable, or fiber optics, and communicate any data, information, status(s), and/or condition(s). Without being limited, any information or data reported by the remote aerosol sensor(s) (5010) to any device(s), such as, but not limited to one or more of any aerosol generating apparatus(s) (215), and/or one or more of any remote device(s) that controls one or more aerosol generating apparatus(s) (215), can be used by one or more of any of these devices to modify any operating attributes, variables, or activities, such as, but not limited to any, aerosol deploy time(s), dwell time(s) before dehumidification, pause in any operation(s), dehumidification time(s), air filtering time(s), deodorization time(s), in order to achieve an outcome in the targeted area(s) (210) that is efficacious and effective.

Any data, information, status, and/or condition(s), reported by one or more of any remote aerosol sensor(s) (5010) to any device(s), such as, but not limited to one or more of any aerosol generating apparatus(s) (215), and/or one or more of any remote device(s) that controls one or more aerosol generating apparatus(s) (215), can also be used, without limitation, by any of these devices to take various actions or combination of actions, such as, but not limited to, (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

Referring to FIGS. 98-102 and FIGS. 119-132, it is preferred, without limitation, that each remote aerosol sensor (5010), contains at least one or more of any, digital, electronic, or analog, controller(s) such as, but not limited to, any PLC(s) (Hereinafter called "remote PLC(s)" (3893). It is more preferred, without limitation, that at least one or more suitable remote PLC (3893) is utilized in the design of the remote aerosol sensor (5010). It is also preferred, without limitation, that each remote aerosol sensor(s) (5010) communicates directly or indirectly via one or more of any suitable radio(s), with one or more of any aerosol generating apparatus(s) (215) and/or any other device(s) and/or remote device(s) that controls and/or communicates with one or more aerosol generating apparatus(s) (215). However, the remote aerosol sensor(s) (5010) can also, without limitation, communicate with one or more of any aerosol generating apparatus(s) (215), and/or any other device(s) and/or remote device(s), that controls and/or communicates with one or more aerosol generating apparatus(s) (215), with other means known to those skilled in the art, such as, but not limited to any, sound, fiber optics, or wires, all in a manner known to those skilled in the art.

The location or position of each remote aerosol sensor(s) (5010) within the targeted area(s) (210) can, without limitation, impact the accuracy of the true progress and actual efficaciousness of the treatment within the targeted area(s). One or more of any remote aerosol sensor(s) (5010) may be, without limitation, located at any location and orientation within the one or more targeted area(s) (210). It is preferred, without limitation, that at least one or more remote aerosol sensor(s) (5010) and/or sensing device(s) (5080) is positioned as close to the highest ceiling surface(s) or at least a higher ceiling surface(s) (Hereinafter called "highest ceiling surface(s)" or "ceiling surface(s)" (5005)), as possible, and is also located as far away from the aerosol generator (215) as possible. This is especially useful in situations where, without limitation, the aerosol (200) fills the targeted area (210) from the floor(s) (5000) to the ceiling(s) (5005). In situations where the targeted area(s) (210) are alternatively filled with aerosol (200) from the ceiling(s) (5005) to the floor(s) (5000), it is preferred, without limitation, that at least one or more remote aerosol sensor(s) (5010) and/or sensing device(s) (5080) is positioned as close to the lowest floor surface(s) or at least a lower floor surface(s) (Hereinafter called "lowest floor surface(s)" or "floor surfaces(s)" (5000)), as possible, and is also located as far away from the aerosol generator (215) as possible.

The one or more of any sensing device(s) (5080), as well as one or more of any light source(s) (725), can be, without limitation, effectively positioned or located within one or more exterior facing cavity(s) or orifice(s) (hereinafter called "sensor cavity(s)" (5070). The sensor cavity(s) (5070) can be any effective, size, shape, or design, and have one or more openings of any size and shape. The sensor cavity(s) (5070) can also, without limitation, connect with or be, one or more of any suitable tunnel(s), or conduit(s). Without being limited, the sensor cavity(s) (5070) can also protrude fully through one or more of any parts(s) of the remote aerosol sensor(s) (5010) and/or its housing(s) (5100). It is preferred, without limitation, that the various attributes of the sensor cavity(s) (5070), and any other related component(s), are at least suitable and effective. It is also preferred, without limitation, that any of the one or more sensing device(s) (5080), or even the one or more light source(s) (725), located within the sensor cavity(s) (5070), are protected from any damage by covering or protecting the one or more openings of the sensor cavity(s) (5070) with one or more structure(s) or object(s) such as, but not limited to any protective and suitable, bar(s), cover(s), grate(s), grill(s), or screen(s), (hereinafter called "protective cover(s)" (5075)). The protective cover(s) (5075) can be, without limitation, any suitable and effective thickness, porosity, density, width, design, and construction, to allow the various sensing device(s) (5080) to effectively operate, as well for any light source(s) (725) to emit any effective light, and/or any light sensor(s) (730) to effectively sense any of the generated light, but still all interact with and/or sense the environment or atmosphere that surrounds the remote aerosol sensor(s) (5010), in an effective and efficacious way. It is preferred, without limitation, that the various attributes of the one or more of any sensor cavity(s) (5070), and any protective cover(s) (5075) that are utilized, are at least suitable and effective, especially with regards to the various one or more of any sensing device(s) (5080), or even the one or more light source(s) (725), that may be utilized. Any light source(s) (725) and/or light sensor(s) (730) may also, without limitation, be protected with, or located behind, one or more of any suitable and effective protective cover(s) (5075) such as, but not limited to any, window(s), that would protect these various components from any environment(s) that surrounds the remote aerosol sensor(s) (5010). It is preferred, without limitation, that the various cover(s) (5075) suitably and effectively interface with the housing(s) (5100) of the remote aerosol sensor(s) (5010).

Without being limited, the one or more of any sensing device(s) (5080) can have various capabilities and attributes including, but not limited to any, sensitivity, trigger level(s), and/or the ability to be controlled and/or communicate with one or more of any digital, electronic, or analog, controller(s) such as, but not limited to, any PLC(s). It is preferred, without limitation, that the various components of the remote aerosol sensor(s) (5010) communicate with at least one or more PLC(s) that is incorporated into the design of the remote aerosol sensor(s) (5010). It is more preferred, without limitation, that the various components of the remote aerosol sensor(s) (5010) directly or indirectly communicate with at least one or more PLC(s) that is incorporated into the design of the remote aerosol sensor(s) (5010), as well as one or more of any aerosol generating apparatus(s) (215), and/or one or more of any remote device(s) that controls any aerosol generating apparatus(s) (215). Any data that is collected and reported by any sensing devices (5080), or any other components of the remote aerosol sensor(s) (5010), to any PLC can, without limitation, result in various actions or combination of actions, for one or more aerosol generating apparatus(s) (215), such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

In addition, any data that is collected and reported by any sensing devices (5080), or any other components of the remote aerosol sensor(s) (5010), to any PLC can, without limitation, result in the delay of any amount of time before various actions or combination of actions are taken, for one or more aerosol generating apparatus(s) (215) such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215). However, it is preferred, without limitation, that any data, reported data, or any signal(s) from one or more of any remote aerosol sensor(s) (5010) that are located the furthest from the one or more aerosol generating apparatus(s) (215) in the targeted area(s) (210), is utilized to determine various operational activities such as, but not limited to, shutting down one or more of any apparatus(s) (215), stopping the application or deployment of any aerosol (200) into the targeted area(s) (210), determining if any time delay is needed before either shutting down the one or more of any apparatus(s) (215) and/or stopping the application or deployment of any aerosol (200) into the targeted area(s) (210), or calculating or determining any time delay that may be needed for an efficacious or successful outcome from the deployment of the aerosol (200), before either shutting down the one or more of any apparatus(s) (215) and/or stopping the application or deployment of any aerosol (200) into the targeted area(s) (210).

If a delay is utilized, before various actions or combination of actions are taken, for one or more aerosol generating apparatus(s) (215) such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215), it is preferred, without limitation, that the delay is five (5) minutes or less of time. It is more preferred, without limitation, that if a delay is utilized, it is ten (10) minutes or less of time. It is even more preferred, without limitation, that if a delay is utilized, it is ten (10) minutes or more of time. It is very preferred, without limitation, that if a delay is utilized, it is one (1) minute or more of time.

Instead of using a time delay as previously mentioned, any digital, electronic, or analog, controller(s) such as, but not limited to, any PLC(s), that controls one or more aerosol producing apparatus(s) (215), or remotely communicates with and controls one or more of any aerosol producing apparatus(s) (215) can, without limitation, solely refer to or utilize any data from any one or more remote aerosol sensor(s) (5010) that reports or communicates any data that has not significantly differed, and/or has had the least amount of differing data, from any of it's data that was reported before or just prior to any aerosol (200) or vapor that is deployed into the targeted area(s) (210), in order to determine if or when an efficacious or sufficient amount of aerosol (200) is present in the entire targeted area(s) (210), so that the production and/or deployment of aerosol (200) into the targeted area(s) (210) can be terminated. It is preferred, without limitation, that the data from the last remote aerosol sensor(s) (5010) that reports any data, or combinations of any data, such as, but not limited to, (a) the lowest humidity level(s), (b) highest temperature(s), (c) presence of light from any light source(s) (725), (d) sensing the strongest presence of light from any light source(s) (725), (e) the absence of any signal, current, and/or amperage from any aerosol deposit sensor(s) (3880), (f) the absence of any significant signal, current, and/or amperage from any aerosol deposit sensor(s) (3880), (g) sensing the lowest signal, current, and/or amperage from any aerosol deposit sensor(s) (3880), is utilized to determine if or when an efficacious or sufficient amount of aerosol (200) is present in all of the targeted area(s) (210) so that functions such as, but not limited to, the production and/or deployment of aerosol (200) into the targeted area(s) (210) can be terminated at the most efficacious time.

This referencing of certain remote aerosol sensor(s) (5010) by any PLC(s), that controls one or more aerosol producing apparatus(s) (215), or remotely communicates with and controls one or more of any aerosol producing apparatus(s) (215), within the targeted area(s) (210), based on certain criteria for their reported data values, or after comparing their reported data with the reported data from other remote aerosol sensor(s) (5010), and/or utilizing any time extensions to accommodate for variables such as, but not limited to, temperature or humidity, all in order to effectively manage and control the efficacious operation of the aerosol generating apparatus(s) (215) within the same targeted area(s) (210), can be, without limitation, utilized to compensate for circumstances such as, but not limited to, (a) any elevated temperature anomalies that may be detected in one or more locations within the targeted area(s) (210), or (b) where one or more remote aerosol sensor(s) (5010) within the targeted area(s) (210) may be immersed within the deployed aerosol (200) and reporting the presence of an efficacious amount of aerosol (200), or conditions to indicate an efficacious amount of aerosol (200) is present, while one or more additional remote aerosol sensor(s) (5010) report either the absence or insufficient amount of deployed aerosol (200) within the targeted area(s) (210) because they are positioned in locations of the targeted area(s) (210) that have not been filled, or not adequately filled, with the deployed aerosol (200).

It is preferred, without limitation, that all of the light sensor(s) (730) located in all of the various remote aerosol sensor(s) (5010) positioned within the targeted area(s) (210), must report to any PLC(s) that controls one or more aerosol producing apparatus(s) (215), or remotely communicates with and controls one or more of any aerosol producing apparatus(s) (215), the presence of an efficacious or sufficient amount of aerosol (200) before the production and/or deployment of aerosol (200) into the targeted area(s) (210) can be terminated. It is even more preferred, without limitation, that before the production and/or deployment of aerosol (200) into the targeted area(s) (210) is terminated, all humidity sensor(s) (5090) that are utilized within the targeted area(s) (210) must report a humidity level preferably between 90-100 percent, and any light sensor(s) (730) that are also utilized in the targeted area(s) (210) must report the presence of an efficacious or sufficient amount of aerosol (200), where the data is all reported to any PLC(s), that controls one or more aerosol producing apparatus(s) (215), or remotely communicates with and controls one or more of any aerosol producing apparatus(s) (215).

According to an embodiment, and according to FIGS. 98-102, the remote aerosol sensor(s) (5010) can incorporate and utilize one or more of any light source(s) (725) in combination with one or more of any light sensor(s) (730), all in any of its various possible configurations. In the first aspect, one or more light source(s) (725) can be, without limitation, effectively located opposite to one or more light sensor(s) (730). It is preferred, without limitation, that the one or more light source(s) (725) can be, without limitation, directly or indirectly connected to, or located within, one or more housing(s) (5100) of the remote aerosol sensor(s) (5010), and the one or more light sensor(s) (730) is externally located to the one or more light source(s) (725) at any effective distance, and effectively faces or approximately faces, the light source(s) (725). It is also preferred, without limitation, that the light sensor(s) (730) is positioned, located, or attached to, one or more mounting extension(s) (5035). The mounting extension(s) (5035) can be, without limitation, designed and constructed, and directly or indirectly attach to the remote aerosol sensor(s) (5010), all in any manner known to those skilled in the art. The mounting extension(s) (5035) can be, without limitation, permanently positioned or located. The mounting extension(s) (5035) and/or the light sensor(s) (730) can also be, without limitation, moved in any way into any suitable position or into any suitable length and/or height, to effectively position the light sensor(s) (730), all in a manner known to those skilled in the art. It is preferred, without limitation, that the mounting extension(s) (5035) can be designed and constructed in a manner known in the art, so it can be, without limitation, extended, refracted, or telescope, to any effective length. In addition, the mounting extension(s) (5035) can also, without limitation, be designed and constructed in a manner known in the art, so it can move and lock into an effective location or place when needed or desired. It is preferred, without limitation, that the light sensor(s) (730) can be repeatedly moved to the same approximate, location, orientation, and/or distance, each time that it is moved. The light source(s) (725) and light sensor(s) (730) can also, without limitation, switch places or locations, which discloses this first aspect in an alternative form.

In the second aspect, one or more of both the light source(s) (725) and light sensor(s) (730) can be, without limitation, effectively located opposite to one or more of any reflecting surface(s), mirrored surface(s), or reflector(s) (5030). It is preferred, without limitation, that the light source(s) (725), light sensor(s) (730), and reflector(s) (5030), are all positioned at effective angle(s) and/or locations so that the various components may work effectively together to determine if or when an efficacious or sufficient amount of aerosol (200) is present in the targeted area(s) (210). The various components may also, without limitation, be positioned at any effective height relative to one another. It is preferred, without limitation, that the one or more of both the light source(s) (725) and light sensor(s) (730) can be, without limitation, directly or indirectly connected to, or located anywhere effectively within, one or more housing(s) (5100) of the remote aerosol sensor(s) (5010), and one or more reflector(s) (5030) is externally located to the remote aerosol sensor(s) (5010) at any effective distance, and effectively faces or approximately faces the light source(s) (725) and light sensor(s) (730). It is preferred, without limitation, that the reflector(s) (5030) is positioned and angled sufficiently so that a sufficient amount of light from the light source(s) (725) is effectively reflected back into the light sensor(s) (730).

The distance between both the light source(s) (725) and light sensor(s) (730), and the reflector(s) (5030), can be, without limitation, any distance, but should be at least an effective distance. The distance between both the light source(s) (725) and light sensor(s) (730), and the reflector(s) (5030), can be, without limitation, separated by a distance of one (1) foot or less. However, it is preferred, without limitation, that the distance between both the light source(s) (725) and light sensor(s) (730), and the reflector(s) (5030), is at least one (1) foot or more. It is more preferred, without limitation, that the distance between both the light source(s) (725) and light sensor(s) (730), and the reflector(s) (5030), is at least two (2) feet or more. It is even more preferred, without limitation, that the distance between both the light source(s) (725) and light sensor(s) (730), and the reflector(s) (5030), is at least four (4) feet or more.

It is preferred, without limitation, that both the light source(s) (725) and light sensor(s) (730) can be, without limitation, directly or indirectly connected to, or located within, one or more housing(s) (5100) of the remote aerosol sensor(s) (5010), and the one or more reflector(s) (5030) is externally located to both the light source(s) (725) and light sensor(s) (730), at any effective distance, and faces or approximately faces, both the light source(s) (725) and light sensor(s) (730). It is also preferred, without limitation, that the reflector(s) (5030) is positioned, located, or attached to, one or more mounting extension(s) (5035). The mounting extension(s) (5035) can be, without limitation, designed and constructed, and directly or indirectly attach to the remote aerosol sensor(s) (5010), all in any manner known to those skilled in the art. The mounting extension(s) (5035) can be, without limitation, permanently positioned or located. The mounting extension(s) (5035) and/or the reflector(s) (5030) can also be, without limitation, moved in any way into any suitable position or into any suitable length and/or height, to effectively position the reflector(s) (5030), all in a manner known to those skilled in the art. It is preferred, without limitation, that the mounting extension(s) (5035) can be designed and constructed in a manner known in the art, so it can be, without limitation, extended, refracted, or telescope, to any effective length. In addition, the mounting extension(s) (5035) can also, without limitation, be designed and constructed in a manner known in the art, so it can move and lock into an effective location or place when needed or desired. It is preferred, without limitation, that the reflector(s) (5030) can be repeatedly moved to the same approximate, location, orientation, and/or distance, each time that it is moved. Both the light source(s) (725) and light sensor(s) (730), and reflector(s) (5030), can also, without limitation, switch places or locations, which discloses this first aspect in an alternative form.

In the third aspect, one or more of both the light source(s) (725) and light sensor(s) (730) can be, without limitation, effectively located in the same area and pointed in the same direction and monitor one or more of any sized part of the targeted area(s) (210). It is preferred, without limitation, that the light source(s) (725) and light sensor(s) (730), are all positioned at effective angle(s) and/or locations so that the various components may work effectively together to determine if or when an efficacious or sufficient amount of aerosol (200) is present in the targeted area(s) (210). The various components may also, without limitation, be positioned at any effective height relative to one another. It is preferred, without limitation, that the one or more of both the light source(s) (725) and light sensor(s) (730) can be, without limitation, directly or indirectly connected to, or located anywhere effectively within, one or more housing(s) (5100) of the remote aerosol sensor(s) (5010). It is preferred, without limitation, that both the light source(s) (725) and light sensor(s) (730) are configured so that a sufficient amount of light that emanates from the light source(s) (725) is reflected off of any aerosol (200) that may be present in the targeted area(s) (210) and back to the light sensor(s) (730). Any data regarding any reflected light that is collected from the light sensor(s) (730) can be used by any digital, electronic, or analog, controller(s) such as, but not limited to, any PLC(s), that controls the one or more aerosol producing apparatus(s) (215), or remotely communicates with and controls the one or more of any aerosol producing apparatus(s) (215), to determine if or when an efficacious or sufficient amount of aerosol (200) is present in the entire targeted area(s) (210), so that the production and/or deployment of aerosol (200) into the targeted area(s) (210) can be terminated. It is preferred, without limitation, that both the light source(s) (725) and light sensor(s) are positioned and angled sufficiently so that a sufficient amount of light from the light source(s) (725) is effectively reflected back into the light sensor(s) (730). The light source(s) (725) and light sensor(s) can be separated by any effective distance.

According to another embodiment, and according to FIGS. 98-102, the remote aerosol sensor(s) (5010) can also, without limitation, incorporate and utilize at least one or more, layer or window (Hereinafter called "aerosol deposit window(s)" (3890)) anywhere in front of the one or more of any light sensor(s) (730), and/or between one or more of any light source(s) (725) and one or more of any light sensor(s) (730), all in various possible configurations. The one or more aerosol deposit window(s) (3890) can be, without limitation, located or positioned at any suitable distance(s), location(s), and position(s) from the one or more of any light source(s) (725), and/or light sensor(s) (730), including, but not limited to, being located in any suitable location(s) within the atmosphere of the targeted area(s) (210). The one or more aerosol deposit window(s) (3890) can also be, without limitation, located or positioned as an independent component any distance from, and/or between, the one or more of any light source(s) (725) and light sensor(s) (730). Without being limited, the one or more aerosol deposit window(s) (3890) can be suitably connected, positioned, located, or attached, indirectly or directly on or to, one or more of any mounting extension(s) (5035) that may be used. It is preferred, without limitation, that the aerosol deposit window(s) (3890) is at least located or positioned at an effective distance(s) from the light source(s) (725) and/or light sensor(s) (730). It is also preferred, without limitation, that the one or more aerosol deposit window(s) (3890) is at least suitably located anywhere within the line of site between and/or in front of any of the light source(s) (725) and/or any light sensor(s) (730).

Without being limited, the one or more aerosol deposit window(s) (3890) can be used to determine, or at least help determine, if an effective or efficacious amount of aerosol (200) has been deposited on the various surface(s) within the targeted area(s) (210), as the aerosol (200) that is deployed into the targeted area(s) (210) can be deposited onto one or more sides of the aerosol deposit window(s) (3890), and the one or more light sensor(s) (730) can sense or detect any change in the light that passes through the aerosol deposit window(s) (3890) as a result of the deposited aerosol (200), or any film or deposition coating that conglomerates on the aerosol deposit window(s) (3890). The light sensor(s) (730) can, without limitation, indicate to or communicate with any PLC(s) if or when it either receives or ceases to receive any trait or attribute pertaining to light such as, but not limited to, any level of light, power of light, and/or light intensity. The said communication can be accomplished in various ways known in the art. This communication can result in various actions or combination of actions, such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

Without being limited, the one or more aerosol deposit window(s) (3890), as well as the one or more of any light source(s) (725) and/or light sensor(s) (730), can be located in any suitable orientation, angle, or direction. One or more sides of the one or more aerosol deposit window(s) (3890) can also be, without limitation, exposed to the environment or atmosphere within the targeted area(s) (210). It is preferred, without limitation, that at least one side of the one or more aerosol deposit window(s) (3890) is exposed to the environment or atmosphere within the targeted area(s) (210). The aerosol deposit window(s) (3890) can be, without limitation, positioned, interfaced with, or located at or on, any suitable location(s), within, within any side of, or anywhere outside of, the remote aerosol sensor(s) (5010) and/or the housing(s) (5100) of the remote aerosol sensor(s) (5010). The aerosol deposit window(s) (3890) can also be, without limitation, located in or more more separate compartments within the remote aerosol sensor(s) (5010), with one or more of any light source(s) (725) and/or light sensor(s) (730). It is preferred, without limitation, that if one or more aerosol deposit window(s) (3890) is utilized, it is located or positioned within, or interfaced with, the one or more housing(s) (5100) of the remote aerosol sensor(s) (5010). It is more preferred, without limitation, that if one or more aerosol deposit window(s) (3890) is utilized, it is located or positioned within, or interfaced with, the one or more housing(s) (5100) of the remote aerosol sensor(s) (5010), and at least one suitable light sensor(s) (730) is effectively positioned behind the aerosol deposit window(s) (3890). It is even more preferred, without limitation, that if one or more aerosol deposit window(s) (3890) is utilized, it is located or positioned within, or interfaced with, the one or more housing(s) (5100) of the remote aerosol sensor(s) (5010), and at least one suitable light sensor(s) (730) is effectively positioned behind the aerosol deposit window(s) (3890), and one or more light source(s) (725) is effectively positioned to effectively interact with the aerosol deposit window(s) (3890) and the light sensor(s) (730).

The aerosol deposit window(s) (3890) can be, without limitation, manufactured or constructed from any suitable material. The aerosol deposit window(s) (3890) can also be, without limitation, manufactured or constructed from any suitable light transmitting material and have any effective amount of light transmission. It is preferred, without limitation, that the aerosol deposit window(s) (3890) is at least suitably clear, transparent, and/or translucent. It is also preferred, without limitation, that the aerosol deposit window(s) (3890) are constructed from any suitable glass and/or plastic. It is more preferred, without limitation, that the aerosol deposit window(s) (3890) is constructed from any suitable glass and/or plastic. It is even more preferred, without limitation, that the aerosol deposit window(s) (3890) is constructed from any suitable glass or plastic that is clear or transparent. The aerosol deposit window(s) (3890) can be any suitable thickness, size, and shape.

Any surface(s) of the aerosol deposit window(s) (3890) can also have, without limitation, any suitable surface treatment(s) known to those skilled in the art. The various surface(s) of the aerosol deposit window(s) (3890) can have, without limitation, any suitable surface tension and/or wettability. It is preferred, without limitation, that at least the various surface(s) of the aerosol deposit window(s) (3890) that interact with the atmosphere or environment within the targeted area(s) (210) have a sufficient and suitable material property(s), surface tension, and/or wettability, that can allow the aerosol deposit window(s) (3890) to indicate or cause a result that is detectable by any light sensor(s) (730), that an efficacious and effective amount of aerosol (200) is deployed into the targeted area(s) (210). It is more preferred, without limitation, that the various surface(s) of the aerosol deposit window(s) (3890) that interact with the atmosphere or environment within the targeted area(s) (210) have at least a material property(s), surface tension, and/or wettability, that can cause at least a suitable and effective amount of the aerosol (200) that is deposited on the surface(s) to remain in various forms or shapes such as, but not limited to any, beaded form, partial beaded form, droplet form, partial droplet form, convex shape, and/or partially shape, but at least in a shape of form that can allow the aerosol deposit window(s) (3890) to indicate or cause a result that is detectable by any light sensor(s) (730), that an efficacious and effective amount of aerosol (200) is deployed into the targeted area(s) (210). The various material(s), surface(s), and/or surface treatment(s), of the aerosol deposit window(s) (3890) can be, without limitation, engineered and tailored, in a manner known to those skilled in the art, for any agent(s) that any deployed aerosol (200) may consist of and be deposited on the aerosol deposit window(s) (3890). The aerosol deposit window(s) may also, without limitation, be used with any agent that is deployed into the targeted area(s) (210) in a vapor form.

The aerosol deposit window(s) (3890) can also be, without limitation, heated and/or cooled to any suitable temperature, at any time, and for any duration of time, depending on the operating environment that the remote aerosol sensor(s) (5010) is operating within, and/or the result(s) or effect(s) that are desired. The aerosol deposit window(s) (3890) can be heated with one or more of any suitable heating means (Hereinafter called "deposit window heater(s)" (3884)), and/or cooled with one or more of any suitable cooling means (Hereinafter called "deposit window cooler(s)" (3891)), all known to those skilled in the art. The aerosol deposit window(s) (3890) can be heated and/or cooled at any effective and suitable time, for any effective and suitable duration, and to one or more of any effective temperature(s) or temperature range(s). It is preferred, without limitation, that if the aerosol deposit window(s) (3890) is heated or cooled, this is accomplished with one or more of any suitable device(s) known to those skilled in the art such as, but not limited to any, thermoelectric cooler (TEC), peltier device, or peltier heat pump, that can heat or cool the aerosol deposit window(s) (3890) directly and/or indirectly. The one or more means or devices used for heating and/or cooling the aerosol deposit window(s) (3890) can be, without limitation, controlled and/or communicate with one or more of any digital, electronic, or analog, controller(s) such as, but not limited to, any PLC(s). Without being limited, the aerosol deposit window(s) (3890) can be heated and/or cooled directly or indirectly with any means known to those skilled in the art, such as, but not limited to any, conduction, or heating or cooling with any cooled or heated, air, atmosphere, or gas, that contacts the aerosol deposit window(s) (3890).

According to an embodiment, the remote aerosol sensor(s) (5010) can be located in various ways in one or more of any suitable location(s) within the targeted area(s) (210). It is preferred, without limitation, that the remote aerosol sensor(s) (5010) has one or more feet or support(s) structures (5040) that can support the remote aerosol sensor(s) (5010) when it is placed on any suitable surface(s) within the targeted area(s) (210). The remote aerosol sensor(s) (5010) may also have, without limitation, one or more suspension points (5015) of any size and design, from which the remote aerosol sensor(s) (5010) can be suspending in the atmosphere in the targeted area(s) (210) with one or more of any suitable material(s) or object(s) such as, but not limited to any, rope, chain, wire, bracket, or string, (Hereinafter called "suspension material(s)" (5110)) that can be constructed from any suitable material. The remote aerosol sensor(s) (5010) may also have, without limitation, one or more permanent or temporary wall or surface mounting hardware or bracket(s) (Hereinafter called "mounting hardware") (5012). The surface mounting hardware (5012) can be any size or shape, and constructed in a manner known in the art. The remote aerosol sensor(s) (5010) may also, without limitation, be designed and constructed so that it may be removably attached either directly or indirectly to any part of the apparatus (215).

According to an embodiment, and according to FIGS. 98-102 and FIGS. 119-132, it is preferred, without limitation, that the remote aerosol sensor(s) (5010) incorporates and utilizes at least one or more of any aerosol deposit sensor(s) (3880), all in any of its various possible configurations. It is preferred, without limitation, that the aerosol deposit sensor(s) (3880) is the primary sensor(s) within the remote aerosol sensor(s) (5010) that can be used by the one or more of any digital, electronic, or analog, controller(s) such as, but not limited to, any PLC(s), to make decisions regarding certain actions or outcomes, or take various actions or combination of actions, such as, but not limited to: (a) shutting down any drive electronics (645) or amplifier(s) (230), (b) shutting down any blower(s) (180) or flow of pressurized air, (c) stopping the production of aerosol, (d) stopping the deployment of aerosol (200) into the targeted area(s) (210), or (e) shutting down one or more of any apparatus(s) (215).

The aerosol deposit sensor(s) (3880) can be, without limitation, any suitable and effective, size, shape, thickness, and geometry. Without being limited, the one or more aerosol deposit sensor(s) (3880) can be located or interfaced in or on, any effective, location, position, or orientation, in any effective manner known to those skilled in the art. It is preferred, without limitation, that the aerosol deposit sensor(s) (3880) is located in a vertical position. The aerosol deposit sensor(s) (3880), or at least the one or more aerosol (200) contact surface(s) (3898), can be directly or indirectly exposed to, or have direct or indirect contact with, the atmosphere or environment within the one or more targeted area(s) (210). Indirect exposure to, or indirect contact with, the atmosphere or environment within the one or more targeted area(s) (210), can include, without limitation, positioning the aerosol deposit sensor(s) (3880) and/or its contact surface(s) (3898) in one or more of any area(s) or space(s) such as, but not limited to any, enclosed area(s), and/or semi-enclosed area(s), where direct contact may be difficult with the aerosol (200) that may be present within the targeted area(s) (210), and moving any sampled gas(s) and/or aerosol (210) from these areas to the aerosol deposit sensor(s) (3880), or at least the one or more aerosol (200) contact surface(s) (3898), via one or more of any sources of pressurized air such as, but not limited to any, fan, blower, or pump, via one or more of any conduit(s), hose(s), pipe(s), and tunnel(s). It is preferred, without limitation, that the one or more aerosol deposit sensor(s) (3880), and/or its aerosol (200) contact surface(s) (3898), at least have direct contact with the atmosphere or environment within the targeted area(s). It is more preferred, without limitation, that the one or more remote aerosol sensor(s) (5010) and/or its aerosol (200) contact surface(s) (3898), face out towards any space within the targeted area(s) (210).

Referring to FIGS. 98-102 and FIGS. 119-132, and without being limited, the aerosol deposit sensor(s) (3880) can include, at least one or more aerosol (200) contact surface(s) (3898), consisting of at least one or more non-conductive material(s) (Hereinafter called "insulator material(s) (3882)) that is exposed to the atmosphere within the targeted area(s) (210), and this contact surface(s) (3898) is suitably connected to at least two or more conductors (3881) that are connected to at least one or more suitable sensor(s) (3897), and/or one or more of any digital, electronic, or analog, controller(s) such as, but not limited to, any PLC(s), or remote PLC(s) (3893), that can monitor and/or report various data such as, but not limited to, (a) the presence or absence of any electrical signal(s) that may be established between the at least two or more electrodes that are being utilized, (b) any amount of conductivity that may be established between the at least two or more electrodes that are being utilized, (c) any amount of electrical current that may be established between the at least two or more electrodes that are being utilized, and/or (d) any change in any electrical current, amperage, or any other electrical characteristics that would indicate the completion of a circuit, as a result of any contact of the contact surface(s) (3898) with a sufficient amount of aerosol (200).

Without being limited, and referring to FIGS. 98-102 and FIGS. 119-132, the aerosol deposit sensor(s) (3880) is constructed so that little to no conductivity may exist, and little to no amount of current will pass, between the two or more conductors (3881), until a sufficient and effective amount of aerosol (200) is deposited onto the one or more aerosol deposit sensor(s) (3880), and more specifically the one or more contact surface(s) (3898), causing a sufficient and effective deposition of aerosol (200) (Hereinafter called "deposited aerosol" or "deposited aerosol droplets" (3883)), and/or liquid film (3899) to form, on the contact surface(s) (3898) and sufficiently connecting the two or more electrodes or conductors (Hereinafter called "conductor(s)" (3881)) electrically and completing one or more electrical circuit(s). It is preferred, without limitation that the various components of the aerosol deposit sensor(s) (3880), such as, but not limited to, the contact surface(s) (3898), insulator material(s) (3882), conductors (3881), are all designed and constructed so that a sufficient and/or significantly strong enough, electrical connection is established between the two or more conductors (3881) to create an electrical circuit that can be detected, monitored, and/or communicated, by one or more of any conductivity sensor(s) (3897) and/or remote PLC(s), to indicate or significantly indicate when a sufficient and efficacious amount of aerosol (200) is deployed into the one or more targeted area(s) (210).

The aerosol deposit sensor(s) (3880) can also include, without limitation, any suitable and effective means known to those skilled in the art, to monitor, sense, and/or communicate, various inputs such as, but not limited to, (a) the presence or absence of any electrical signal(s) that may be established between the at least two or more electrodes that are being utilized, (b) any amount of conductivity that may be established between the at least two or more electrodes that are being utilized, and/or (c) any amount of electrical current that may be established between the at least two or more electrodes that are being utilized, and/or (d) any change in any electrical current, amperage, or any other electrical characteristics that would indicate the completion of a circuit, as a result of any contact of the contact surface(s) (3898) with a sufficient amount of aerosol (200). Without being limited, this means (Hereinafter called "conductivity sensor" (3897)), that is used to monitor or sense various inputs or data pertaining to the aerosol deposit sensor(s) (3880) such as, but not limited to, (a) any electrical signal(s), (b) any presence of conductivity, (c) any presence or absence of electrical current, (d) any amount of conductivity, and/or (e) any amount of electrical current, can include, but is not limited to, one or more of any suitable, digital, electronic, or analog, controller(s) such as, but not limited to, any PLC(s), or remote PLC(s) (3893). The conductivity sensor (3897) may also include, without limitation, any suitable and effective, voltage, amperage, and/or current sensor(s) known to those skilled in the art. The one or more conductivity sensor(s) (3897) and/or one or more of any suitable, digital, electronic, or analog, controller(s) such as, but not limited to, any PLC(s), or remote PLC(s) (3893), can be placed in any suitable location(s) or position(s) between each conductor (3881) that is utilized, and the one or more of any PLC(s) or remote PLC(s) that are utilized, as well as effectively near or on the various conductor (3881) that are utilized.

It is preferred, without limitation, that this conductivity sensor(s) (3897) is any suitable sensor that can monitor and communicate the presence and/or absence of any current. This type of sensor(s) (3897) can also, without limitation, report the presence or absence of current, change in current, and/or the amount of current that is being sensed. It is preferred, without limitation, that the amount of current that may flow between the at least two or more conductors (3881) is monitored and/or reported. The at least one or more conductivity sensor(s) (3897) can also be, without limitation, incorporated into the design of one or more of any digital, electronic, or analog, controller(s) such as, but not limited to, any PLC(s), or remote PLC(s) (3893).

Figure 127:
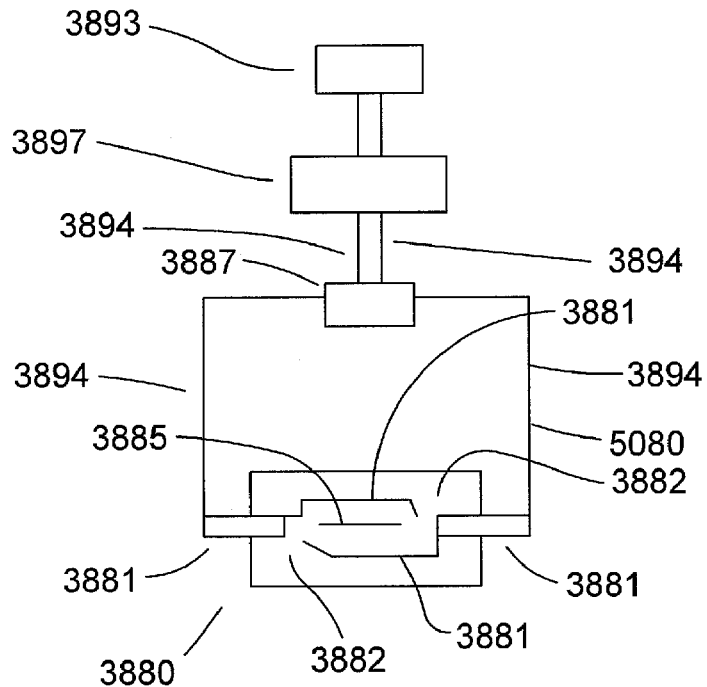

Referring to FIG. 127, and without being limited, one or more of any suitable means for electrical signal and/or power amplification or any suitable amplifier(s) (3887) known to those skilled in the art, may also be utilized to boost and/or amplify any needed electrical signal and/or electrical characteristics before any electrical related information, data, or signal, is communicated, conducted, or transmitted to various locations such as, but not limited to, the one or more conductivity sensor(s) (3897), and/or one or more of any suitable, digital, electronic, or analog, controller(s) such as, but not limited to, any PLC(s), or remote PLC(s) (3893).

The presence of the aerosol (200), or deposited aerosol (3883), on the contact surface(s) (3898) can create, without limitation, a liquid film (3899) on the various surface(s) of the contact surface(s) (3898) depending on various conditions. The aerosol (200) and the resulting liquid film (3899), and/or deposited aerosol (3883) droplets, can, without limitation, consist of any suitable liquid with any suitable polarity and/or charge. Without being limited, the aerosol (200) and the resulting liquid film (3899), and/or deposited aerosol (3883) droplets, can have any suitable ion content and/or number of ions. It is preferred, without limitation, that various characteristics and attributes of the aerosol (200) and the resulting liquid film (3899), and/or deposited aerosol (3883) droplets, such as, but not limited to any, polarity, charge, ion content, number of ions, is at least effective, efficacious, and suitable. It is also preferred, without limitation, that the deposited aerosol (200) and liquid is at least effectively and suitably, electrically conductive when used with the aerosol deposit sensor(s) (3880). It is more preferred, without limitation, that the deposited liquid is at least any suitable aqueous solution, and is effectively and suitably electrically conductive.

The aerosol (200) that is deposited on the contact surface(s) (3898), and any liquid film (3899) that may result on the contact surface(s) (3898), can also be any, without limitation, thickness, width, density, uniformity, cohesiveness, volume, and/or mass. It is preferred, without limitation, that the aerosol (200) that is deposited on the contact surface(s) (3898), and/or any liquid film (3899) is at least a sufficient, thickness, width, density, uniformity, cohesiveness, volume, and/or mass, so that one or more sufficient and effective electrical circuit(s), or electrical connection(s) between the various conductor(s) (3881), can be established, as well as detected and monitored by one or more of any conductivity sensor(s) (3897) and/or remote PLC(s) (3893), indicating or significantly indicating when a sufficient and efficacious amount of aerosol (200) is deployed into the one or more targeted area(s) (210). It is preferred, without limitation, that full efficacy of the aerosol deployment within the targeted area(s) (210), is achieved with as thin of, an aerosol (200) deposit(s), a film of deposited aerosol (3883), and/or a deposited liquid layer(s) (3899), from the deployed aerosol (200) contacting the contact surface(s) (3898), as well as any other surfaces within the targeted area(s) (210), as possible. However, one or more certain application(s) may also, without limitation, require thicker, aerosol (200) deposit(s), a film of deposited aerosol (3883), and/or deposited liquid layer(s) (3899), from the deployed aerosol (200) contacting the contact surface(s) (3898) and the various surfaces within the targeted area(s) (210).

Referring to FIGS. 98-102 and FIGS. 119-132, and without being limited, the aerosol deposit sensor(s) (3880) can have at least one or more insulator material(s) (3882) that is located or positioned between two or more electrodes or conductors (3881). Without being limited, the one or more contact surface(s) (3898), with which the aerosol (200) in the targeted area(s) (210) contacts, is constructed, or at least partially and suitably constructed, from the one or more insulator material(s) (3882). The various contact surface(s) (3898) can be, without limitation, constructed in a manner so that a sufficient amount of insulator material(s) (3882) is utilized to electrically insulate the various electrodes or conductors (3881), but still allow the aerosol (200) that is deposited to electrically connect the two or more electrodes or conductors (3881) when a sufficient amount of aerosol (200) to have an efficacious or desired effect within the targeted area(s) has interacted with the contact surface(s) (3898).

The insulator material(s) (3882) can be, without limitation, any suitable, length, width, thickness, shape, and geometry. The insulator material(s) (3882) can also be, without limitation, constructed from one or more of any suitable material(s) such as, but not limited to glass or polymer with suitable electrical insulating properties. It is preferred, without limitation, that the insulator material(s) (3882) are non-conductive. It is more preferred, without limitation, that the insulator material(s) (3882) are at least non-conductive enough so that the aerosol deposit sensor(s) (3880) may properly function. It is even more preferred, without being limited, that the insulator material(s) (3882) are at least sufficiently non-conductive so that the one or more of any suitable, digital, electronic, or analog, controller(s) such as, but not limited to, any PLC(s), conductivity sensor(s) (3897), and/or remote PLC(s) (3893), may be able to effectively and accurately determine when a sufficient amount of aerosol (200) has contacted the aerosol deposit sensor(s) (3880) and indicate when a sufficient and efficacious amount of aerosol (200) is deployed into the one or more targeted area(s) (210).

Figure 122:
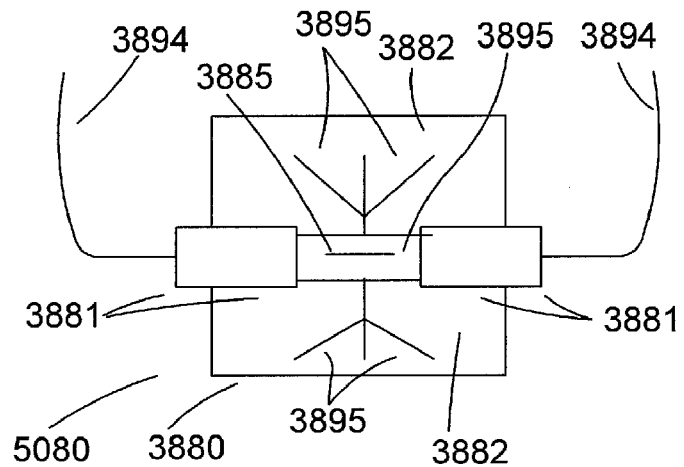
Figure 123:
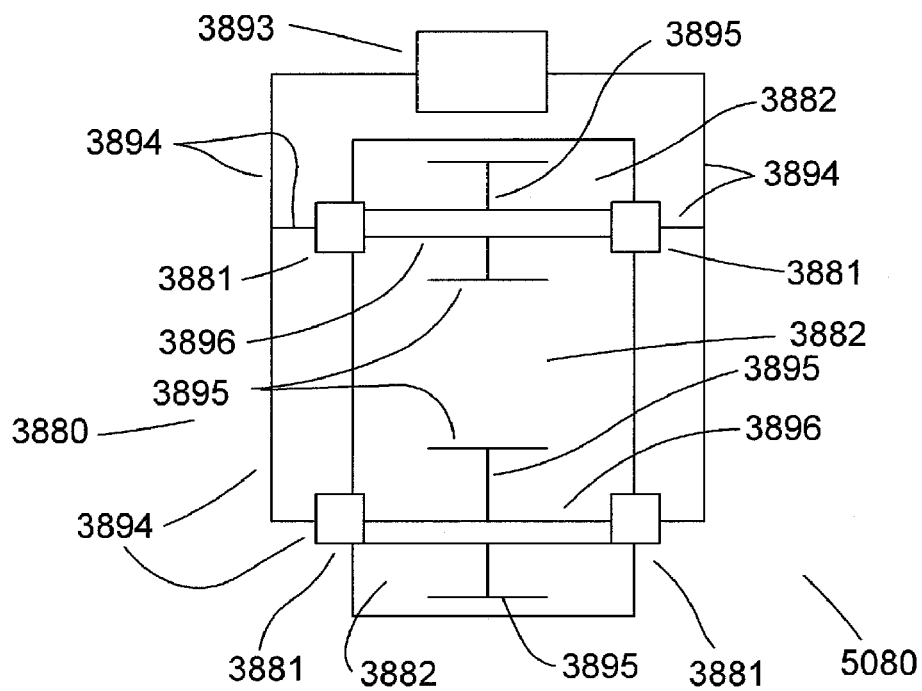

Referring to FIGS. 122-123, the various contact surface(s) (3898) and/or insulator material(s) (3882) can have, without limitation, one or more trough(s), groove(s), cut(s), and/or channels (Hereinafter called "channel(s)" (3895). These channel(s) (3895) can be any, without limitation, length, width, depth. The one or more channel(s) (3895) can also be, without limitation, located or positioned in one or more of any pattern(s) or orientation(s). The one or more channel(s) (3895) can also be, without limitation, connected, partially connected, or not connected. It is preferred, without limitation, that the various channel(s) (3895) interconnect. It is also preferred, without limitation, that if any channel(s) (3895) are utilized, at least one or more channel(s) (3895) within the insulator material(s) (3882) and/or the various contact surface(s) (3898) connect the two or more electrodes or conductors (3881) together with the channel(s) (3895). Without being limited the channel(s) (3895) can help divert any substantial amount of liquid or aerosol droplet(s) (200) that is deposited on the contact surface(s) (3898), to the various electrodes or conductors (3881). This can be, without limitation, used for various purposes including process safety and/or quality control of the process, as a greater amount of channeled liquid in the channel(s) (3895) can increase the chance for completing the electrical connection between at least two or more of the electrodes or conductors (3881) signifying that a sufficient and efficacious amount of aerosol (200) is deployed into the one or more targeted area(s) (210). The one or more insulator material(s) (3882) and/or the various contact surface(s) (3898) can also be, without limitation, canted or angled at any angle toward one or more of any channel(s) (3895). It is preferred, without limitation, that the one or more insulator material(s) (3882) and/or the various contact surface(s) (3898) are at least effectively canted or angled toward one or more of any channel(s) (3895). It is more preferred, without limitation, that the one or more insulator material(s) (3882) and/or the various contact surface(s) (3898) are at least effectively canted or angled toward at least one or more channel(s) (3895) that connects at least two or more electrodes or conductors (3881) that when electrically connected, their electrical connection can accurately and effectively signify that a sufficient and efficacious amount of aerosol (200) is deployed into the one or more targeted area(s) (210).

Figure 119:
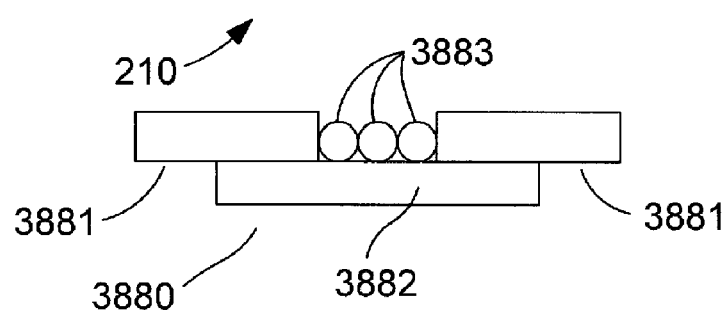
Figure 120:
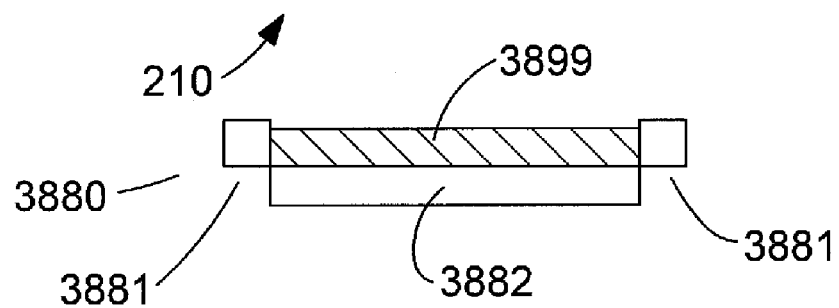
Figure 121:
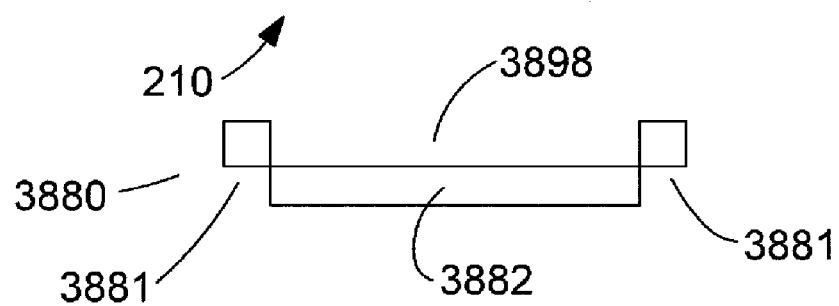

Referring to FIGS. 119-121, and without being limited, side views of the aerosol deposit sensor(s) (3880) are given. Without being limited, FIGS. 119-121, show a few of the various possible results if the aerosol (200) that is in the targeted area(s) (210), makes contact with the "contact surface(s)" (3898). The deposited aerosol (3883) and liquid, on the contact surface(s) (3898) can, without limitation, take one or more of any forms such as, but not limited to, a uniform covering of numerous deposited aerosol droplets (3883), a non-uniform covering of numerous deposited aerosol droplets (3883), a uniform film (3899) of deposited liquid, a non-uniform film (3899) of deposited liquid, and/or any combinations of these forms, all depending on one or more variables known to those skilled in the art. Any surface(s) of the aerosol deposit sensor(s) (3880), and more specifically, the contact surface(s) (3898), can also have, without limitation, any suitable and effective surface treatment(s) known to those skilled in the art. This can be used, without limitation, to modify the behavior of the deposited aerosol (200) and liquid on the one or more contact surface(s) (3898). The various surface(s) of the aerosol deposit sensor(s) (3880), and more specifically, the contact surface(s) (3898), can have, without limitation, any suitable and effective surface tension and/or wettability.

It is preferred, without limitation, that at least the various surface(s) of the aerosol deposit sensor(s) (3880), and more specifically, the contact surface(s) (3898), that interact with the atmosphere or environment within the targeted area(s) (210) have a sufficient, effective, and suitable material property, surface tension, and/or wettability, that can allow the aerosol deposit sensor(s) (3880) to interact with deposited aerosol (200) and liquid in a manner to indicate or cause a result that is detectable by any conductivity sensor(s) (3897) and/or remote PLC(s) (3893), when an efficacious and effective amount of aerosol (200) is deployed into the targeted area(s) (210). It is more preferred, without limitation, that at least the various surface(s) of the aerosol deposit sensor(s) (3880), and more specifically, the contact surface(s) (3898), that interact with the atmosphere or environment within the targeted area(s) (210) have a sufficient and suitable material property, surface tension, and/or wettability, that can allow and/or help promote at least a sufficient quantity of deposited aerosol (200) and liquid to effectively interact with the at least two or more conductors (3881) in a manner to indicate or cause a result that is detectable by any conductivity sensor(s) (3897) and/or remote PLC(s) (3893), when an efficacious and effective amount of aerosol (200) is deployed into the targeted area(s) (210).

The various material(s), surface(s), and/or surface treatment(s), of the aerosol deposit sensor(s) (3880), and more specifically, the contact surface(s) (3898), can be, without limitation, engineered and tailored, in a manner known to those skilled in the art, for any agent(s) that may be contained in any deployed aerosol (200) and deposited on the contact surface(s) (3898) of the aerosol deposit sensor(s) (3880). The aerosol deposit sensor(s) (3880), and more specifically, the contact surface(s) (3898) may also, without limitation, be used with any agent that is deployed into the targeted area(s) (210) in any vapor form.

Referring to FIGS. 119-132, and without being limited, the aerosol deposit sensor(s) (3880) can have at least two or more electrodes or conductors (3881) that are effectively and electrically separated or isolated with one or more suitable insulator material(s) (3882). The various electrodes or conductors (3881) can be, without limitation, positioned any distance from one another. It is preferred, without limitation, that the electrodes or conductors (3881) are at least located at an effective distance from one another. It is more preferred, without limitation, that the various electrodes or conductors (3881) are at least separated from each other at a distance that can effectively and accurately indicate when a sufficient and efficacious amount of aerosol (200) is not only deployed into the one or more targeted area(s) (210), but also deposited onto the contact surface(s) (3898). The electrodes or conductors (3881) can be, without limitation, constructed from one or more of any suitable and effective material(s) that are electrically conductive. It is preferred, without limitation, that the electrodes and conductors (3881) are constructed from stainless steel.

The various electrodes or conductors (3881) can be, without limitation, any suitable, length, width, height, shape, and/or geometry. Without being limited, the one or more electrodes or conductors (3881) can also consist of one or more pieces or components. These pieces or components cans also, without limitation, branch out in one or more directions, with one or more branches. The various electrodes or conductors (3881) can have or utilize, without limitation, any amount of surface area exposed to any contact surface(s) (3898) and/or insulator material(s) (3882). It is preferred, without limitation, that at least an effective amount of surface area is exposed to any contact surface(s) (3898) and/or insulator material(s) (3882), and any aerosol (200) or liquid that is deposited on these surfaces.

The two or more electrodes or conductors (3881) can also, without limitation, interface with the various contact surface(s) (3898) and/or insulator material(s) (3882), in various ways including, but not limited to any suitable, orientation, angle, geometry, and/or location. The two or more electrodes or conductors (3881) can also, without limitation, be located or positioned anywhere on or within the surface of any contact surface(s) (3898) and/or insulator material(s) (3882), in any suitable location(s). Without being limited, the two or more electrodes or conductors (3881) can also, without limitation, be located or positioned at any suitable depth within the surface of any contact surface(s) (3898) and/or insulator material(s) (3882). It is preferred, without limitation that if the two or more electrodes or conductors (3881) are positioned or located within the contact surface(s) (3898) and/or insulator material(s) (3882), at least a sufficient amount of the surface(s) of the electrodes or conductors (3881) is effectively exposed to any aerosol (200) or liquid that is deposited on these surfaces, so that any PLC(s), remote PLC(s) (3893), and/or conductivity sensor(s) (3897) may be able to effectively and accurately determine when a sufficient and efficacious amount of aerosol (200) is not only deployed into the one or more targeted area(s) (210), but also deposited onto the contact surface(s) (3898).

Figure 128:
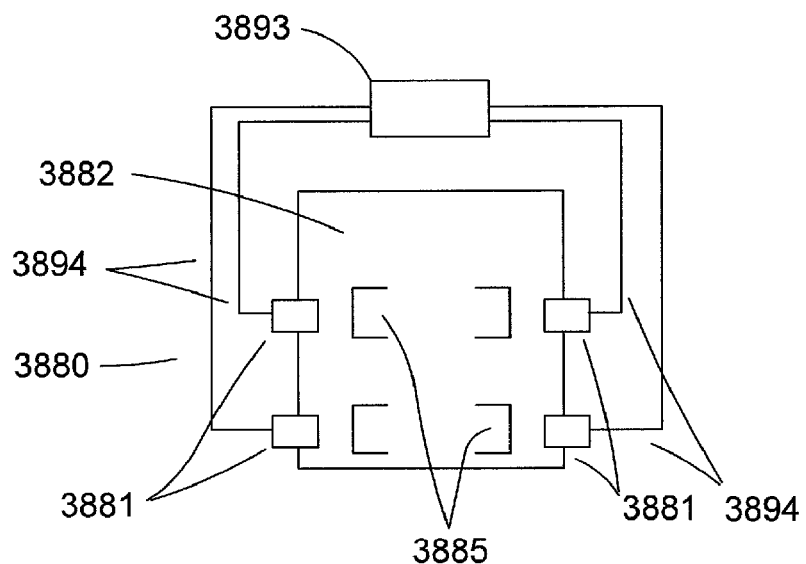
Figure 129:
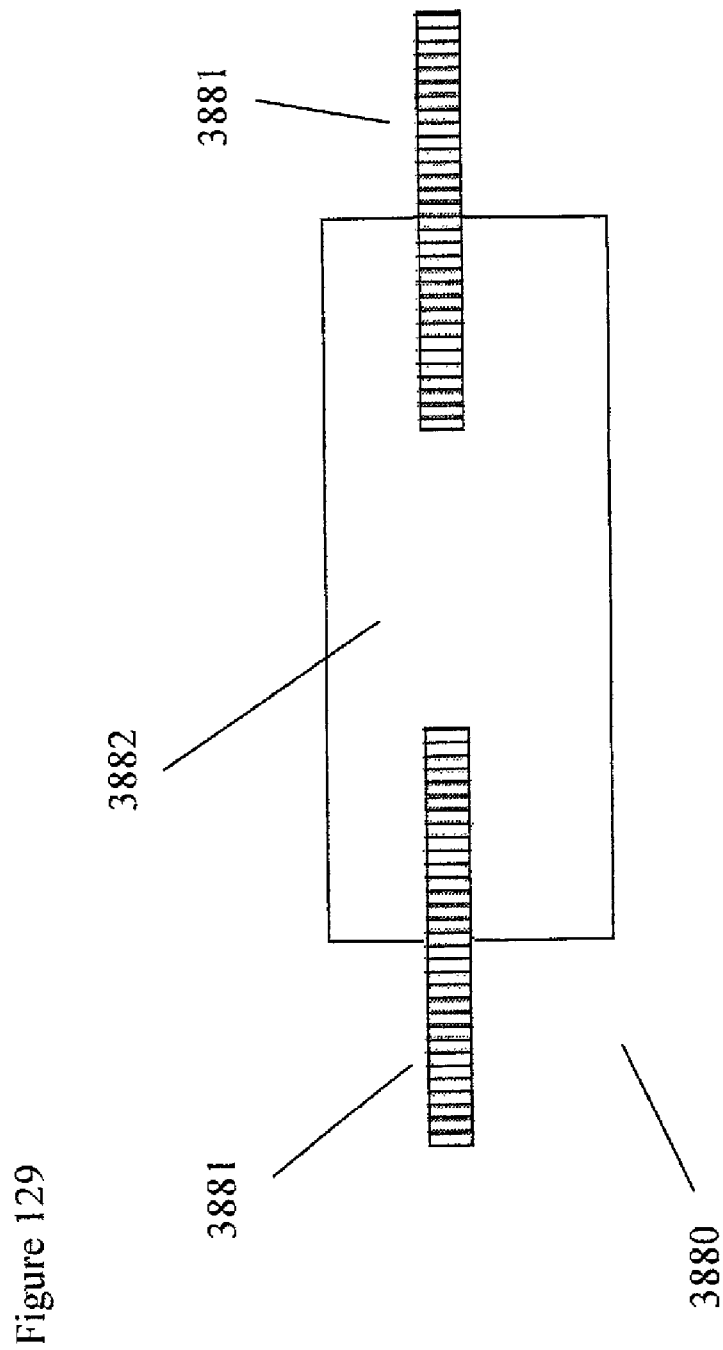

Referring to FIGS. 127-128, and without being limited, one or more electrodes or conductors (3881), and/or any other suitable conductive material(s) (Hereinafter called "conductive path(s)" (3885)), may also be located in one or more of any effective and suitable way(s) and/or location(s), or various combinations thereof, such as, but not limited to, (a) within or partially within, (b) effectively isolated, within or partially within, (c) partially on and/or within, (d) effectively isolated, and partially on and/or within, (e) on the surface of, (f) effectively isolated, and on the surface of, (g) embedded on and/or within, (h) effectively isolated, and embedded on and/or within, (i) partially embedded on and/or within, (j) effectively isolated, and partially embedded on and/or within, (k) fully and/or partially embedded on and/or within, and effectively exposed to the surface of, (l) effectively isolated, and fully and/or partially embedded on and/or within, and effectively exposed to the surface of, the one or more insulator material(s) (3882).

Alternatively, and without being limited, one or more insulator material(s) (3882) may also be located in one or more of any effective and suitable way(s) and/or location(s), or various combinations thereof, such as, but not limited to, (a) within or partially within, (b) effectively isolated, within or partially within, (c) partially on and/or within, (d) effectively isolated, and partially on and/or within, (e) on the surface of, (f) effectively isolated, and on the surface of, (g) embedded on and/or within, (h) effectively isolated, and embedded on and/or within, (i) partially embedded on and/or within, (j) effectively isolated, and partially embedded on and/or within, (k) fully and/or partially embedded on and/or within, and effectively exposed to the surface of, (l) effectively isolated, and fully and/or partially embedded on and/or within, and effectively exposed to the surface of, the one or more of any suitable conductive material(s) or effectively sized conductive path(s) (3885) that is suitably and effectively connected to at least two or more electrodes or conductors (3881).

These conductive path(s) (3885) can be, without limitation, either electrically isolated and merely serve as a partial and/or non-partial conductive path(s) across the insulator material(s) (3882), and/or they can also connect with one or more of any conductivity sensor(s) (3897) and/or remote PLC(s), and be utilized to indicate when a sufficient and efficacious amount of aerosol (200) is not only deployed into the one or more targeted area(s) (210), but also deposited onto the contact surface(s) (3898). It is preferred, without limitation, that the conductive path(s) (3885) are electrically isolated and merely serve as a partial and/or non-partial conductive path(s) across the insulator material(s) (3882) with which they are directly and/or indirectly interfaced with. Without being limited, and referring to FIG. 122, one or more conductive path(s) (3885) can also be directly or indirectly positioned or interfaced with, and/or located on or within, the one or more channel(s) (3895) that may be utilized.

The one or more materials such as, but not limited to the, conductive path(s) (3885), electrodes or conductors (3881), and/or insulator material(s) (3882) can be, without limitation, interfaced with each other in various ways known to those skilled in the art, such as, but not limited to, (a) embedding one or more of these material(s), partially or completely, into the other one or more of these material(s) (ie: one or more conductive path(s) (3885) are completely or partially embedded into the one or more insulator material(s) (3882), or vice versa), (b) printing or marking one or more of these material(s) into or onto the other one or more of these material(s) (ie: one or more conductive path(s) (3885) are printed into or onto one or more insulator material(s) (3882), or vice versa). Any amount of the conductive path(s) (3885), electrodes or conductors (3881), and insulator material(s) (3882) may be utilized. It is preferred, without limitation, that at least a suitable and effective amount of the one or more conductive path(s) (3885), electrodes or conductors (3881), and/or insulator material(s) (3882), are utilized. It is more preferred, without limitation, that at least a suitable and effective amount of the one or more conductive path(s) (3885), electrodes or conductors (3881), and/or insulator material(s) (3882), are utilized and exposed to the environment within the targeted area(s) (210).

Figure 124:
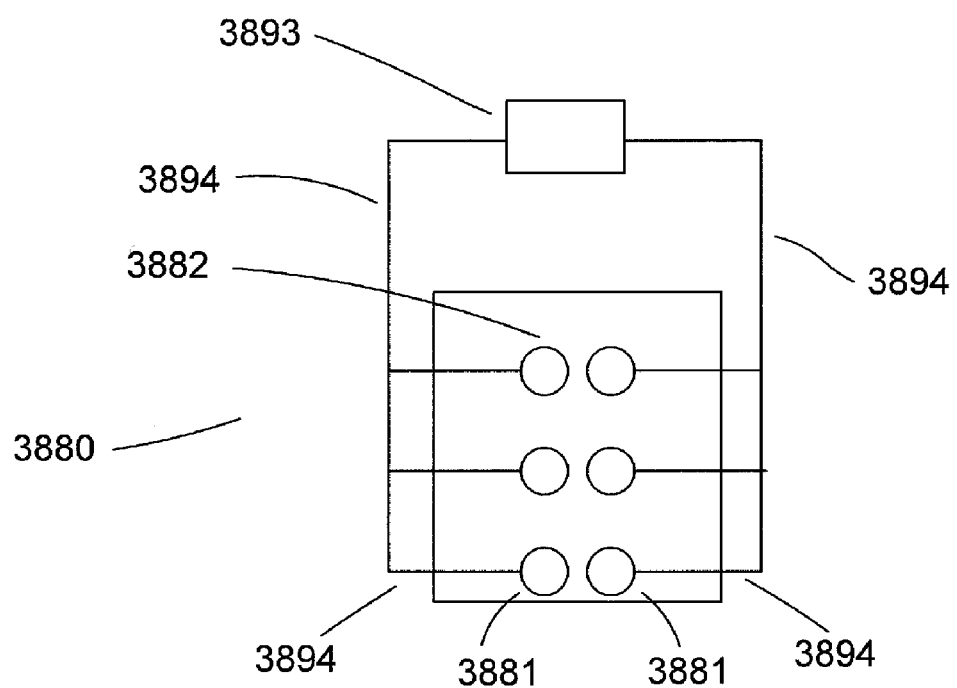
Figure 125:
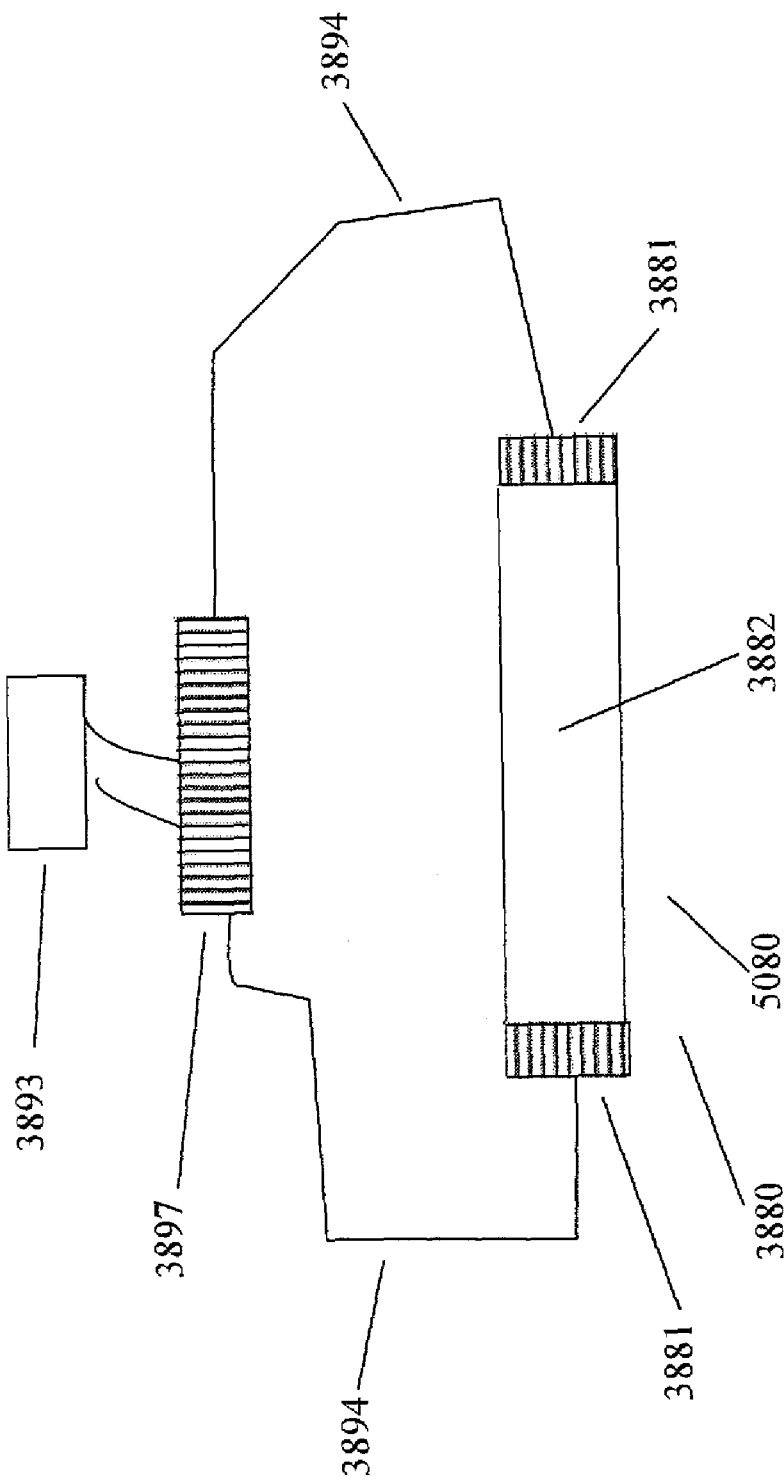
Figure 126:
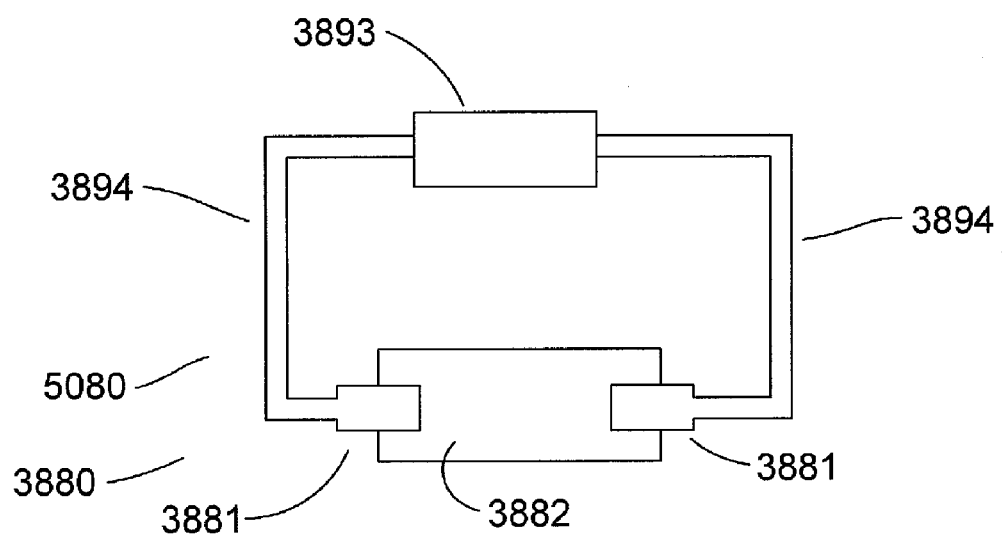

Referring to FIGS. 119-132, and without being limited, at least two or more electrodes or conductors (3881) are connected to at least one or more of any suitable, digital, electronic, or analog, controller(s) such as, but not limited to, any PLC(s), conductivity sensor(s) (3897), and/or remote PLC(s) (3893). Any number of electrodes or conductors (3881) can be, without limitation, used with each aerosol deposit sensor(s) (3880) and contact surface(s) (3898) that are used. It is preferred, without limitation, that at least two or more electrodes or conductors (3881) are used with each aerosol deposit sensor(s) (3880) and contact surface(s) (3898), and they are suitably wired or cabled, with one or more of any suitable wires or cables (Hereinafter called "wire(s)" (3894)), to one or more of any PLC(s), conductivity sensor(s) (3897), and/or remote PLC(s) (3893). Referring to FIGS. 123-124, and FIG. 128, and without being limited, more than two electrodes or conductors (3881) can share the same circuit or connection(s) to one or more of any PLC(s), conductivity sensor(s) (3897), and/or remote PLC(s) (3893), on either side of the insulator material(s) that keeps the electrical circuit(s) from being completed.

The electrodes or conductors (3881) can be, without limitation, configured and wired according to any effective electrical design(s) that allows the aerosol deposit sensor(s) (3880) to perform effectively and accurately. The electrodes or conductors (3881) can also be, without limitation, configured and wired to establish one or more of any suitable and effective electrical circuit(s) of any complexity, including, but not limited to any, circuit(s) that is configured in parallel and/or series. The electrodes or conductors (3881), insulator material(s), and contact surface(s) (3898), can be, without limitation, configured and wired so that current may flow between any of the two or more electrodes or conductors (3881) in order to complete one or more circuit(s) and indicate when a sufficient and efficacious amount of aerosol (200) is not only deployed into the one or more targeted area(s) (210), but also deposited onto the contact surface(s) (3898).

Any suitable and effective amperage, current, and voltage may flow through the electrodes or conductors (3881) and any other connected wiring and/or related systems at any time. It is preferred, without limitation, that the current that is used to flow between the various electrodes or conductors (3881), is any current that would typically be measured in units of microamp or milliamp, by those skilled in the art. It is also preferred, without limitation, that at least a safe amount of current is utilized. One or more of any guards or protective structures can also, without limitation, be used to guard, cover, and/or protect one or more of any components such as, but not limited to, the aerosol deposit sensor(s) (3880), the contact surface(s) (3898), and/or the electrodes or conductors (3881). The one or more guard(s), cover(s), and/or protective structure(s), that are utilized, can also have, without limitation, any suitable number and size of any, grates, perforations, and/or holes. It is preferred, without limitation, that if any guard(s), cover(s), and/or protective structure(s), are utilized, they are at least sufficiently and effectively designed to allow an effective and representative amount of aerosol (200) from the targeted area(s) (210) access the aerosol deposit sensor(s) (3880), and more specifically, the contact surface(s) (3898).

With reference to FIGS. 95-97, FIGS. 103-118, and FIGS. 133-138, and according to an embodiment an optimized and miniaturized aerosol generator (3800) is described, which optimizes and enhances the design of the aerosol producing apparatus (215) that was previously disclosed. Without being limited, it was discovered that the aerosol generating device (215) design possessed certain limitations that needed further improvement(s) such as, but not limited to: (a) the overall design was too large for certain applications, and needed to be more compact, (b) it took an unacceptable amount of time for the liquid (30) in any and/or all of the reservoir(s) (40) and/or feed tank(s) (280) to heat up to an effective or sufficient temperature either before and/or during the deployment of aerosol (200), and (c) the size of the air space(s) above the transducers (10) in the tank(s) or reservoir(s) (40) in which they are located, was sufficiently large enough and/or had sufficient geometries to allow for an undesired amount of turbulent air flow and/or one or more vortices to be generated, where it can be reasonable to assume that aerosol (200) conglomeration could thus transpire, which is typically not desired, causing larger aerosol (200) droplets to be generated and dispersed. The present invention addresses these issues, as well as other various additional improvements to the design of the aerosol generating device (215) and the optimized and miniaturized aerosol generator (3800). Without being limited, the result is a smaller more compact optimized and miniaturized aerosol generator (3800) and apparatus (215) that is able to produce an aerosol (200) that not only appears thicker, but the aerosol (200) also visually looks lighter and has a longer persistence time, which is a good indicator that a thicker cloud of smaller aerosol (200) droplets are being created. The optimized and miniaturized aerosol generator (3800) can be, without limitation, viewed as either a subcomponent of the aerosol generating device (215), or as a separate independent device.

In one aspect, the tank(s), pressurized enclosure(s), or otherwise reservoir(s) (40), in which the one or more transducer(s) (10) are located, as well as the means for monitoring and controlling the liquid level in the reservoir(s) (40), is redesigned to have multiple performance enhancing changes.

First, and referring to FIGS. 95-97, FIGS. 103-108, and FIGS. 133-137, one or more airflow outlet(s) (4015) can be, without limitation, positioned near or approximately above one or more transducers(s) (10). More specifically, one or more airflow outlet(s) (4015) can be located, without limitation, approximately centered and directly above each transducer (10). It is preferred, without limitation, that the one or more airflow outlet(s) (4015) and/or one or more air outlet pipe(s) (4025), are suitably and effectively centered above, below, and/or around, the one or more transducer(s) (10) and/or the direction of their emitted energy or ultrasonic output or signal. It is even more preferred, without limitation, that the one or more surfaces and/or materials of the airflow outlet(s) (4015), air outlet pipe(s) (4025), or any other parts and components located within the reservoir(s) (40), are suitably and effectively located so that they are not damaged by the energy, ultrasonic output, or signal(s), that is emitted, radiated, and/or transmitted, by the one or more transducer(s) (10). Without being limited, this can be important when utilizing transducer(s) (10) such as, but not limited to those described in the present invention, due to their power and the length of the field of energy, ultrasonic output, or signal(s), that they can emit, radiate, and/or transmit. The one or more airflow outlet(s) (4015) can also be, without limitation, positioned at any angle or orientation. However, it is preferred, without limitation, that the airflow outlet(s) (4015) are positioned so that each orifice is approximately horizontal with the surface of the liquid (30) within the reservoir (40). The one or more airflow outlet(s) (4015) can also be, without limitation, positioned effectively close to, level with, or approximately flush with, the one or more reservoir ceiling(s) (4055) within the reservoir(s) (40). The airflow outlet(s) (4015) can be positioned at any effective height above the transducer(s) (10).

However, to take advantage of the improvements in this invention, the one or more airflow outlet(s) (4015) should be, without limitation, located within a certain height range or gap (denoted in FIG. 103 by distance "A") above any liquid (30) that covers the transducer(s) as follows. It is preferred, without limitation, that at least one or more airflow outlet(s) (4015) is positioned between 0.04 inches to 12.0 inches above the surface of the liquid that is above each aerosol (200) producing transducer (10). It is more preferred, without limitation, that at least one or more airflow outlet(s) (4015) is positioned between 0.04 inches to 3.0 inches above the surface of the liquid that is above each aerosol (200) producing transducer (10). It is even more preferred, without limitation, that at least one or more airflow outlet(s) (4015) is positioned between 0.04 inches to 1.5 inches above the surface of the liquid that is above each aerosol (200) producing transducer (10). It is very preferred, without limitation, that at least one or more airflow outlet(s) (4015) is positioned between 0.05 inches to 1.0 inches above the surface of the liquid that is above each aerosol (200) producing transducer (10). It is extremely preferred, without limitation, that at least one or more airflow outlet(s) (4015) is positioned between 0.06 inches to 0.08 inches above the surface of the liquid that is above each aerosol (200) producing transducer (10). Without being limited, the use of at least one or more airflow outlet(s) (4015) located above each transducer (10), can also be utilized to increase performance. It is preferred, without limitation, that only one airflow outlet(s) (4015), having an effective diameter, is located approximately above each transducer (10).

The liquid (30) should also be maintained at least at an effective depth above the transducers (10) located within the reservoir(s) (40). It is preferred, without limitation that the depth of the liquid (30) is maintained at a depth between 0.25 inches to 8 inches above the transducer(s) (10). It is even more preferred, without limitation that the depth of the liquid (30) is maintained at a depth between 0.5 inches to 5 inches above the transducer(s) (10). It is even more preferred, without limitation that the depth of the liquid (30) is maintained at a depth between approximately 1.25 inches to 1.32 inches above the transducer(s) (10). It is very preferred, without limitation that the depth of the liquid (30) is maintained at a depth of approximately 1.28 inches above the transducer(s) (10). Without being limited, it is important that the liquid (30) depth above the transducer(s) is maintained as constant as possible, especially with the more shallow liquid (30) depths above the transducer(s) (10).

Second, the design of the optimized and miniaturized aerosol generator (3800) and aerosol generating device (215) can be, without limitation, enhanced by special placement of the airflow outlet(s) (4015) respective to the geyser (4045) of raised liquid (30) and any associated aerosol plume (4050) that the transducer generates above the surface of the liquid (30). Referring to FIGS. 103-106, including FIGS. 106-A and 106-B, FIGS. 107-108, and FIGS. 133-137, the geyser (4045) of raised liquid (30) and any associated aerosol plume (4050) that the transducer(s) (10) generates above the surface of the liquid (30) can be located anywhere below the airflow outlet(s) (4015). However, for optimum performance, it is preferred, without limitation, that at least an effective portion of the geyser(s) (4045) of raised liquid (30) and any associated aerosol plume(s) (4050) is located within and/or below the airflow outlet(s) (4015), or otherwise within and/or below the one or more air outlet pipe(s) (4025). It is preferred, without limitation, that at least 0.5 percent or more of the geyser(s) (4045) of raised liquid (30) and any associated aerosol plume(s) (4050) that the transducer generates above the surface of the liquid is located within or below the airflow outlet(s) (4015) or otherwise within the one or more air outlet pipe(s) (4025). It is more preferred, without limitation, that at least 7 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is even more preferred, without limitation, that at least 75 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is very preferred, without limitation, that at least 90 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025). It is extremely preferred, without limitation, that at least 98 percent or more of the geyser(s) (4045) of raised liquid (30) and any associated aerosol plume(s) (4050) that the transducer(s) generates above the surface of the liquid is located within or below the airflow outlet(s) (4015) or otherwise within the one or more air outlet pipe(s) (4025).

Any effective number of geyser(s) (4045) of raised liquid (30) and any associated aerosol plume(s) (4050) that the one or more transducer(s) generates above the surface of the liquid can be, without limitation, located within and/or below the one or more airflow outlet(s) (4015) and/or the one or more air outlet pipe(s) (4025). It is preferred, without limitation, that the one or more airflow outlet(s) (4015), and/or one or more air outlet pipe(s) (4025), are suitably and approximately centered above, below, and/or around, the one or more geyser(s) (4045) of raised liquid (30) and any associated aerosol plume(s) (4050), and/or the transducer(s) (10). One or more of any airflow outlet(s) (4015) and/or air outlet pipe(s) (4025), can be, without limitation, allocated to or effectively function with, one or more of any geyser(s) (4045) of raised liquid (30) and any associated aerosol plume(s) (4050), and/or one or more of any transducer(s) (10).

Without being limited, at least an effective number of geyser(s) (4045) of raised liquid (30) and any associated aerosol plume(s) (4050) can be located within and/or below the airflow outlet(s) (4015) or otherwise within the one or more air outlet pipe(s) (4025). It is preferred, without limitation, that at least one or more geyser(s) (4045) of raised liquid (30) and any associated aerosol plume(s) (4050) that the one or more transducer(s) generates above the surface of the liquid (30) can be located within and/or below the one or more airflow outlet(s) (4015) and/or within the one or more air outlet pipe(s) (4025). However, it is more preferred, without limitation, that only one geyser (4045) of raised liquid (30) and any associated aerosol plume(s) (4050), generated by only one transducer, is generated above the surface of the liquid (30), and is located within and/or below only one airflow outlet (4015) or otherwise within only one air outlet pipe (4025).

Referring to FIGS. 95-97, FIGS. 103-109, FIG. 111-112, and FIGS. 117A-117B, and without limitation, the one or more airflow outlet(s) (4015) can also be connected to one or more of any suitable conduit, hose, or pipe (Herein called air outlet pipe(s) (4025)). These pipe(s) may also, without limitation, connect with one or more of any other air outlet pipe(s) (4025) at any location. The airflow outlet(s) (4015) and air outlet pipe(s) (4025) may, without limitation, have any diameter or any change in diameter at any location. The shape and diameter of the airflow outlet(s) (4015) and air outlet pipe(s) (4025) should at least be, without limitation, any effective shape and diameter. It is preferred, without limitation, that the diameter of the airflow outlet(s) (4015) and/or air outlet pipe(s) (4025) is between 0.5 inches to 6 inches or more. It is more preferred, without limitation, that the diameter of the airflow outlet(s) (4015) and/or air outlet pipe(s) (4025) is between 1.75 inches to 4 inches. It is even more preferred, without limitation, that the diameter of the airflow outlet(s) (4015) and/or air outlet pipe(s) (4025) is between 2 inches to 3 inches.

The air outlet pipe(s) (4025) may also, without limitation, extend any distance into the reservoir(s) (40) in order to position the airflow outlet(s) (4015) into any location within the reservoir(s) (40), and more preferably position the airflow outlet(s) (4015) into any preferred distance from the surface of the liquid (30) as previously mentioned. The air outlet pipes(s) (4025) can also be, without limitation, any effective and efficacious length and terminate with one or more exhaust outlet(s) (4060) from which the generated aerosol (200) is deployed into the targeted area(s) (210). Without being limited, any, filter, screen or mesh material, and/or grate material, may be located or positioned within the design of the airflow outlet(s) (4015) and/or the air outlet pipes(s) (4025). The exhaust outlet(s) (4060) can also, without limitation, incorporate one or more of any design enhancements such as, but not limited to one or more of any, filter(s), screen or mesh material(s), or grate material(s). The exhaust outlet(s) (4060) may also, without limitation, interface with one or more of any attachment port(s), socket(s), plug(s), and/or component(s), whose design and construction is known to those skilled in the art, so that it may connect with one or more of any accessories known in the art, and/or one or more of any other delivery pipe(s), hose(s), or conduit(s). The exhaust outlet(s) (4060) can also, without limitation, be any size or shape. It is preferred, without limitation, that the air outlet pipes(s) (4025) are a total length between 0.25 inches to 30 inches or more. It is more preferred, without limitation, that the air outlet pipes(s) (4025) are a total length between 1 inches to 14 inches. It is even more preferred, without limitation, that the air outlet pipes(s) (4025) are a total length between 3 inches to 12 inches. It is very preferred, without limitation, that the air outlet pipes(s) (4025) are a total length between 12 inches to 26 inches.

Figure 105:
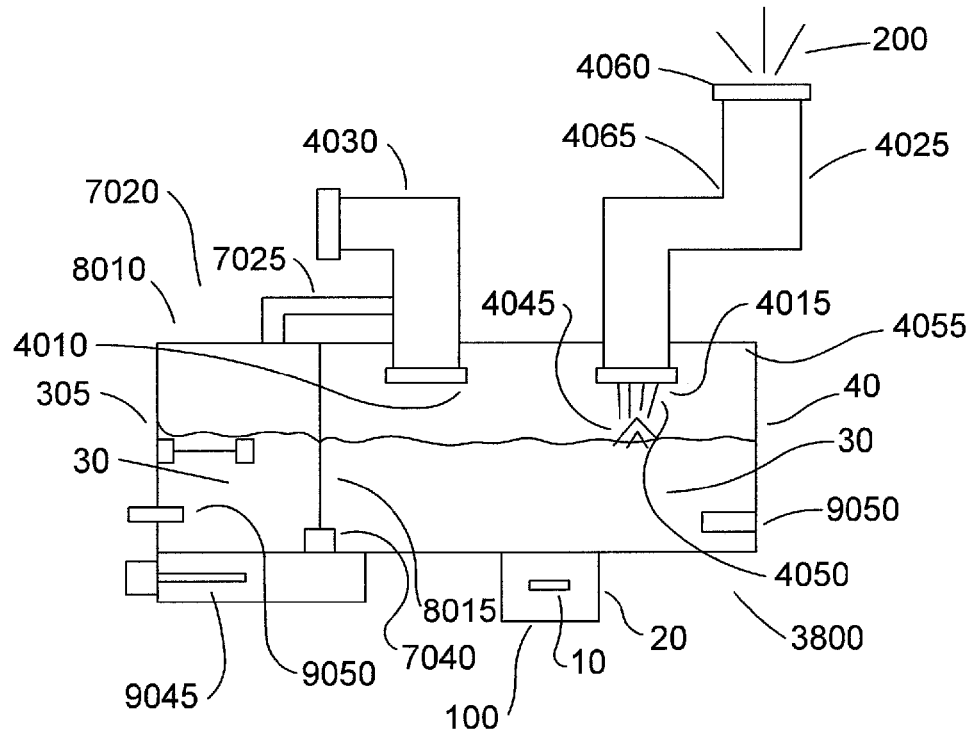
FIG. 105 is a schematic view of an optimized and miniaturized aerosol generator, showing a float chamber and an aerosol chamber according to the present invention.

Third, and referring to FIG. 103 and FIG. 105, the design of the optimized and miniaturized aerosol generator (3800) and aerosol generating device (215) can also, without limitation, be enhanced by incorporating one or more of any geometry changes or bend(s) (Hereinafter called "bend(s)" (4065)), of any suitable angle or shape, in any locations of one or more of any air outlet pipes(s) (4025), between the airflow outlet(s) (4015) and before any exhaust outlet(s) (4060). The geometry changes or bend(s) (4065) can be used for various purposes including, but not limited to, minimizing or eradicating larger droplets of liquid (30) that may be splashed or ejected from the geyser (4045) and/or aerosol plume (4050) and have entered the air outlet pipes(s) (4025). It is preferred, without limitation, one or more bends (4065) between 30 to 90 degree is utilized before the exhaust outlet(s) (4060). It is more preferred, without limitation, one or more bends (4065) between 30 to 180 degree is utilized before the exhaust outlet(s) (4060). It is even more preferred, without limitation, that one or more bends (4065) between 90 degree and 180 degree, is utilized before the exhaust outlet(s) (4060). It is very preferred, without limitation, that at least two 90 degree bends (4065) are utilized before the exhaust outlet(s) (4060). Without being limited, the air outlet pipes(s) (4025) can also, without limitation, have any length between the various bend(s) (4065) if they are utilized. It is preferred, without limitation, that the air outlet pipes(s) (4025) terminate in about a vertical orientation, however they may be positioned in and terminate at any suitable angle. The air outlet pipes(s) (4025) may also, without limitation, terminate at any suitable location within, on, or outside of, the aerosol producing apparatus (215).

Referring to FIGS. 95-97, FIGS. 103-108, and FIGS. 117-A to 117-B and without being limited, one or more air outlet pipes(s) (4025) may also terminate within or into one or more of any shared outlet(s) or common outlet(s) (hereinafter called "shared outlet(s)" (9080)). The one or more shared outlet(s) (9080) can be, without limitation, positioned in various locations such as, but not limited to, inside, outside, partially inside, the one or more housing(s) of the aerosol generating apparatus (215). It is preferred, without limitation, that the shared outlet(s) (9080) are located within the housing of the aerosol generating apparatus (215). Without being limited, the one or more shared outlet(s) (9080) can have one or more drain(s) that can be plumbed to one or more of any suitable location(s) including, but not limited to, any catch pan or catch container. The one or more shared outlet(s) (9080) may also have, without limitation, one or more opening(s) or orifice(s) (Herein after called "shared outlet opening(s)" (9086). The one or more shared outlet(s) (9080), as well as the one or more shared outlet opening(s) (9086), may be, without limitation, any, shape, geometry, length, width, height, and/or depth. It is preferred, without limitation, that the dimensions and sizes of the one or more shared outlet(s) (9080), as well as the one or more shared outlet opening(s) (9086), are at least suitable and effective. The one or more shared outlet(s) (9080), shared outlet opening(s) (9086), and/or exhaust outlet(s) (4060), can be, without limitation, located in one or more of any effective and suitable location(s).

Without being limited, the one or more shared outlet(s) (9080), shared outlet opening(s) (9086), and/or exhaust outlet(s) (4060), can incorporate one or more of any design enhancements such as, but not limited to any, filter(s), screen or mesh material(s), or grate material(s). Without being limited, one or more shared outlet(s) (9080), shared outlet opening(s) (9086), and/or one or more exhaust outlet(s) (4060), can also suitably and effectively interface, with one or more of any attachment port(s), socket(s), plug(s), and/or component(s), whose design and construction is known to those skilled in the art, so that the shared outlet(s) (9080), shared outlet opening(s) (9086), and/or one or more exhaust outlet(s) (4060), may suitably connect, and effectively function, with one or more of any accessories known in the art, and/or one or more of any other delivery pipe(s), hose(s), plug(s), and/or conduit(s).

Fourth, and referring to FIGS. 104-108, the design of the optimized and miniaturized aerosol generator (3800) and aerosol generating device (215) can be enhanced by the positioning of one or more inbound airflow inlet(s) (4010) that supply air/gas flow into or inside the one or more tank(s) or reservoir(s) (40) in which the transducer(s) (10) are located. One or more inbound airflow inlet(s) (4010) may be used to supply the moving or pressurized air or gas, to the reservoir(s) (40) in which the transducer(s) (10) are located, but it is preferred, without limitation, that one inbound airflow inlet(s) (4010) is utilized. Referring to FIGS. 95-97, and FIGS. 103-108, the one or more inbound airflow inlet(s) (4010) can be, without limitation, positioned anywhere, and at any angle and orientation, within the reservoir(s) (40). However, it is preferred, without limitation, that the inbound airflow inlet(s) (4010) are located not only at any effective location above the liquid (30) and/or effectively near the one or more transducers(s) (10) within the reservoir(s) (40), but their output is also directed downward toward the liquid (30) within the reservoir(s) (40). The one or more inbound airflow inlet(s) (4010) can also be, without limitation, positioned effectively close to, level with, or approximately flush with, the one or more reservoir ceiling(s) (4055) within the reservoir(s) (40). It is also preferred, without limitation, that the inbound airflow inlet(s) (4010) are positioned so that each orifice of the airflow inlet(s) (4010) is approximately horizontal with the surface of the liquid (30) within the reservoir (40). The one or more inbound airflow inlet(s) (4010) can also be, without limitation, positioned at any effective distance from the one or more airflow outlet(s) (4015) and/or transducer(s) (10). More specifically, it is preferred, without limitation, that the one or more inbound airflow inlet(s) (4010) are located, approximately above the liquid (30) and between or amongst the one or more airflow outlets (4015) which are located approximately above the one or more transducer(s) (10). It is more preferred, without limitation, that the one or more inbound airflow inlet(s) (4010) are located effectively next to the one or more airflow outlets (4015). It is even more preferred, without limitation, that one inbound airflow inlet (4010) is located effectively between two airflow outlets (4015). It is very preferred, without limitation, that one inbound airflow inlet (4010) is located effectively and centered between two airflow outlets (4015).

The inbound airflow inlet(s) (4010) can be, without limitation, located at any distance above the surface of the liquid (30) that covers the transducer(s) (10) or the surface of the liquid (30) within the reservoir(s) (40). It is preferred, without limitation, that the inbound airflow inlet(s) (4010) are at least located at an effective distance from the surface of the liquid (30). However, to take advantage of the improvements in this invention, the one or more inbound airflow inlet(s) (4010) should be, without limitation, located within a certain height range or gap (denoted in FIG. 103 by distance "B") above any liquid (30) that covers the transducer(s) as follows. It is preferred, without limitation, that at least one or more inbound airflow inlet(s) (4010) is positioned between 0.04 inches to 12 inches above the surface of the liquid that is above each aerosol (200) producing transducer (10). It is more preferred, without limitation, that at least one or more inbound airflow inlet(s) (4010) is positioned between 0.04 inches to 3.0 inches above the surface of the liquid that is above each aerosol (200) producing transducer (10). It is even more preferred, without limitation, that at least one or more inbound airflow inlet(s) (4010) is positioned between 0.04 inches to 1.5 inches above the surface of the liquid that is above each aerosol (200) producing transducer (10). It is very preferred, without limitation, that at least one or more inbound airflow inlet(s) (4010) is positioned between 0.05 inches to 1.0 inches above the surface of the liquid that is above each aerosol (200) producing transducer (10). It is extremely preferred, without limitation, that at least one or more inbound airflow inlet(s) (4010) is positioned between 0.06 inches to 0.08 inches above the surface of the liquid that is above each aerosol (200) producing transducer (10). Without being limited, the use of at least one or more inbound airflow inlet(s) (4010) located approximately between two airflow outlets (4015), each having an effective diameter, can also be utilized to increase performance. It is preferred, without limitation, that only one inbound airflow inlet (4010), having an effective diameter, is located approximately between two airflow outlets (4015).

More than one inbound airflow inlet(s) (4010) can also, without limitation, be positioned within the reservoir(s) (40) in a manner so that the delivered air or gas is more evenly distributed or supplied to the airflow outlet(s) (4015). This can, without limitation, help to increase the efficiency and performance of the apparatus (215). The inbound airflow inlet(s) (4010) can be positioned in any effective angle or orientation. However, it is preferred, without limitation that at least two inbound airflow inlet(s) (4010) are located opposite to one another within the reservoir(s) (40). It is even more preferred, without limitation, that at least two pairs of inbound airflow inlet(s) (4010) are located opposite to one another within the reservoir(s) (40). It is very preferred, without limitation, that at least one pair of inbound airflow inlet(s) (4010) are located opposite to one another respective to each airflow outlet(s) (4015). It is extremely preferred, without limitation, that at least two pairs of inbound airflow inlet(s) (4010) are located opposite to one another respective to each airflow outlet(s) (4015). The use of one or more baffles or other structures may also, without limitation, be used within the reservoir (40) to increase the efficiency of the air flow, as well as reduce any turbulence or vortices, as the air or gas flows from the inbound airflow inlet(s) (4010) to the airflow outlet(s) (4015).

Without being limited, the gap or amount of space (distance "A"), at the preferred distances previously mentioned, between the surface of the liquid (30) and the one or more airflow outlet(s) (4015), can establish increased air velocities not only near the airflow outlet(s) (4015), but also near the geyser(s) (4045) and aerosol plume(s) (4050), that can be similar to a venturi-like effect, that helps to more effectively capture and move the generated aerosol (200) out of the tank or reservoir (40), and into the targeted area(s) (210) while minimizing the chance for aerosol (200) coalescence in the process. It is preferred, without limitation, that the air/gas within the reservoir(s) (40) flows uniformly through the airflow outlet(s) (4015) and into the air outlet pipe(s) (4025). It is also preferred, without limitation, that this air/gas flow, and/or venturi-like effect, is uniformly experienced all the way around the geyser(s) (4045) and aerosol plume(s) (4050) for greater performance and efficiency. It is desired, without limitation, that the airflow outlet(s) (4015) are as close to the liquid (30) surface as effectively and efficaciously as possible, for increased performance and desired effect on the process. However, care needs to be taken, because if the airflow outlet(s) (4015) are too low to the surface of the liquid (30) undesired effects can result such as, but not limited to, the liquid (30) can be pushed and/or pulled up through the airflow outlet(s) (4015), or the air/gas within the reservoir(s) (40) will be unable to escape. Without being limited, the net effect of these improvements is an aerosol (200) output that not only appears visually thicker and of increased quantity, but also appears lighter and more wispy, which is typically indicative of an aerosol (200) consisting of smaller droplets. These improvements have not been seen with previous designs known in the art.

Referring to FIGS. 95-97, FIGS. 103-109, and FIGS. 117A-117B, and without limitation, the one or more inbound airflow inlet(s) (4010) can also be connected to one or more of any suitable conduit, hose, or pipe (Herein called air inlet pipe(s) (4030)). These pipe(s) may also, without limitation, connect with one or more of any other air inlet pipe(s) (4030) at one or more of any suitable location(s). The inbound airflow inlet(s) (4010) and air inlet pipe(s) (4030) may, without limitation, have any diameter or any change in diameter at any location(s). The shape and diameter of the inbound airflow inlet(s) (4010) and air inlet pipe(s) (4030) should at least be, without limitation, any effective shape and diameter. It is preferred, without limitation, the diameter of the inbound airflow inlet(s) (4010) and/or air inlet pipe(s) (4030) is between 0.5 inches to 6 inches or more. It is more preferred, without limitation, that the diameter of the inbound airflow inlet(s) (4010) and/or air inlet pipe(s) (4030) is between 0.75 inches to 4 inches. It is even more preferred, without limitation, that the diameter of the inbound airflow inlet(s) (4010) and/or air inlet pipe(s) (4030) is between 1.5 inches to 3 inches. The air inlet pipe(s) (4030) may also, without limitation, extend any distance into the reservoir(s) (40) in order to position the inbound airflow inlet(s) (4010) into any location within the reservoir(s) (40), and more preferably position the inbound airflow inlet(s) (4010) into any preferred distance from the surface of the liquid (30) as previously mentioned. The air inlet pipe(s) (4030) can also be, without limitation, any effective and efficacious length.

Figure 106A:
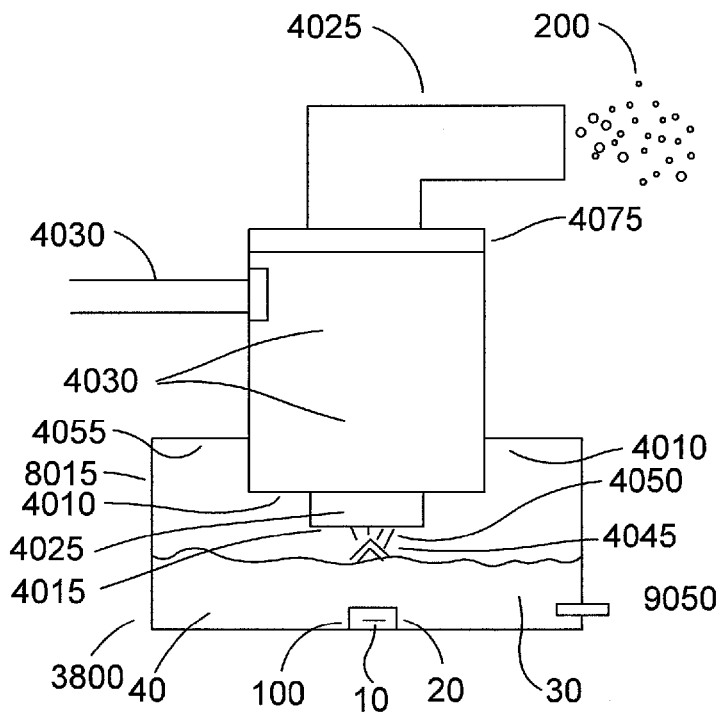
FIG. 106-A is a schematic view of an optimized and miniaturized aerosol generator, showing an air outlet pipes located within an air inlet pipe, according to the present invention.
Figure 106B:
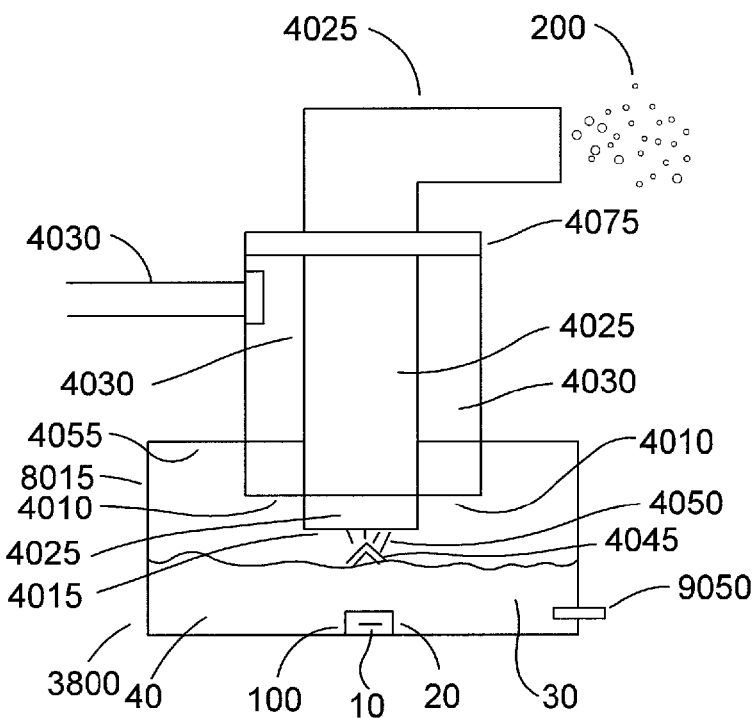
Figure 109:
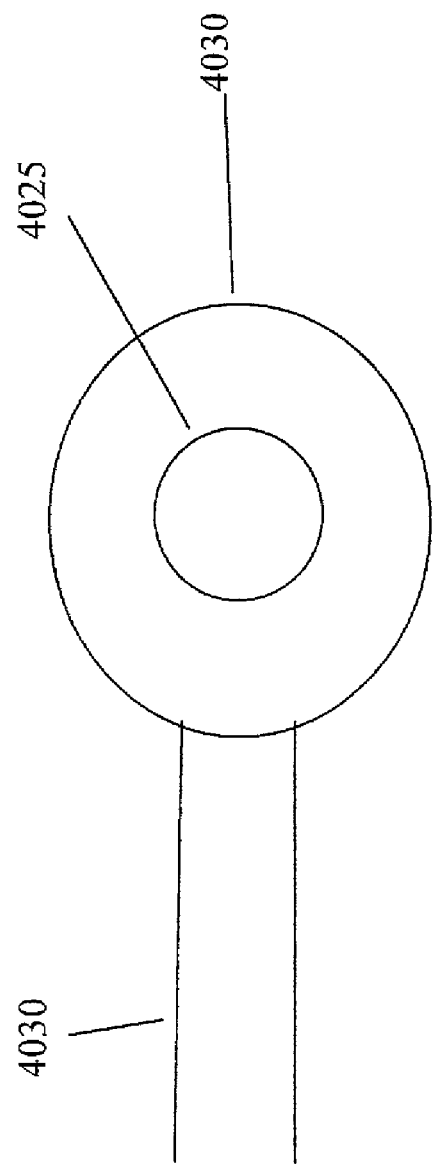
FIG. 109 is an interior schematic top view of an air outlet pipes located within an air inlet pipe of an optimized and miniaturized aerosol generator according to the present invention.

Referring to FIGS. 106-109, including FIGS. 106-A and 106-B, and FIG. 134, and without being limited, where FIGS. 106-109 is an interior view that shows the presence of one or more air outlet pipes(s) (4025) positioned within the one or more air inlet pipe(s) (4030), and FIG. 109 being a top view shows the presence of the one or more air outlet pipes(s) (4025) positioned within the one or more air inlet pipe(s) (4030). It is preferred, without limitation, that only one air outlet pipe (4025) is located within one air inlet pipe (4030) in this configuration. Any suitable sealing device, design, or material (Herein called "air inlet top seal" (4075)), can be, without limitation, used to effectively, or at least suitably, seal, cover, or interface with, the air inlet pipe(s) (4030), so that the air/gas that is flowed through the air inlet pipe(s) (4030) cannot escape. It is preferred, without limitation, that the air inlet top seal also effectively, or at least suitably, seals, covers, or interfaces with, the air outlet pipes(s) (4025), so that the air/gas that is flowed through the air inlet pipe(s) (4030) cannot escape.

Referring to FIGS. 105-109, and without being limited, the air inlet pipe(s) (4030) and inbound airflow inlet(s) (4010) can extend any distance past the air outlet pipes(s) (4025) and/or the airflow outlet(s) (4015). Without being limited, the air inlet pipe(s) (4030) and inbound airflow inlet(s) (4010) can extend any effective and efficacious distance past the air outlet pipes(s) (4025) and/or the airflow outlet(s) (4015). It is preferred, without limitation, that the inbound airflow inlet(s) (4010) extend between 0 to 12 or more inches past the airflow outlet(s) (4015). It is more preferred, without limitation, that the inbound airflow inlet(s) (4010) extend between 0 to 12 inches past the airflow outlet(s) (4015). It is even more preferred, without limitation, that the inbound airflow inlet(s) (4010) extend at least between 0 to 2 inches past the airflow outlet(s) (4015). It is very preferred, without limitation, that the inbound airflow inlet(s) (4010) extend between 0 to 1 inches past the airflow outlet(s) (4015). It is extremely preferred, without limitation, that the inbound airflow inlet(s) (4010) extend between 0 to 0.5 inches past the airflow outlet(s) (4015).

Alternatively, and without limitation, the air outlet pipes(s) (4025) and the airflow outlet(s) (4015) can extend any distance past the air inlet pipe(s) (4030) and/or inbound airflow inlet(s) (4010). Without being limited, the air outlet pipes(s) (4025) and the airflow outlet(s) (4015) can extend any effective and efficacious distance past the air inlet pipe(s) (4030) and/or inbound airflow inlet(s) (4010). It is preferred, without limitation, that the airflow outlet(s) (4015) extend between 0 to 12 or more inches past the inbound airflow inlet(s) (4010). It is more preferred, without limitation, that the airflow outlet(s) (4015) extend between 0 to 12 inches past the inbound airflow inlet(s) (4010). It is even more preferred, without limitation, that the airflow outlet(s) (4015) extend at least between 0 to 2 inches past the inbound airflow inlet(s) (4010). It is very preferred, without limitation, that the airflow outlet(s) (4015) extend between 0 to 1 inches past the inbound airflow inlet(s) (4010). It is extremely preferred, without limitation, that the airflow outlet(s) (4015) extend between 0 to 0.5 inches past the inbound airflow inlet(s) (4010).

Referring to FIGS. 103-106B, and FIG. 108, and without being limited, it is important to note that a suitable and effective air gap, space, or distance, should be present between the top surface of the liquid (30) within the reservoir(s) (40), and a bottom of the air inlet pipe(s) (4030), inbound airflow inlet(s) (4010), air outlet pipe(s) (4025), and/or airflow outlet(s) (4015), to allow at least an effective quantity of air/gas to pass through the reservoir(s) (40) with at least an effective velocity, in order for the optimized and miniaturized aerosol generator(s) (3800) to either function and/or function with at least an effective level of performance.

Figure 107:
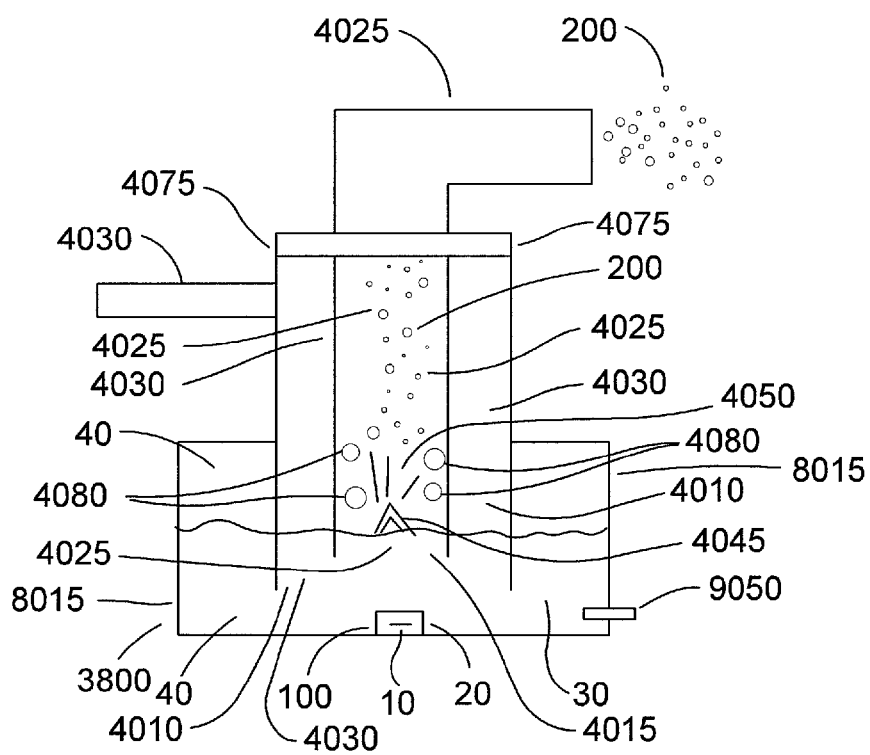
FIG. 107 is a schematic view of an optimized and miniaturized aerosol generator, showing an air outlet pipes located within an air inlet pipe and where the air inlet pipe the air outlet pipe are located effectively within the liquid in the reservoir according to the present invention.
Figure 108:
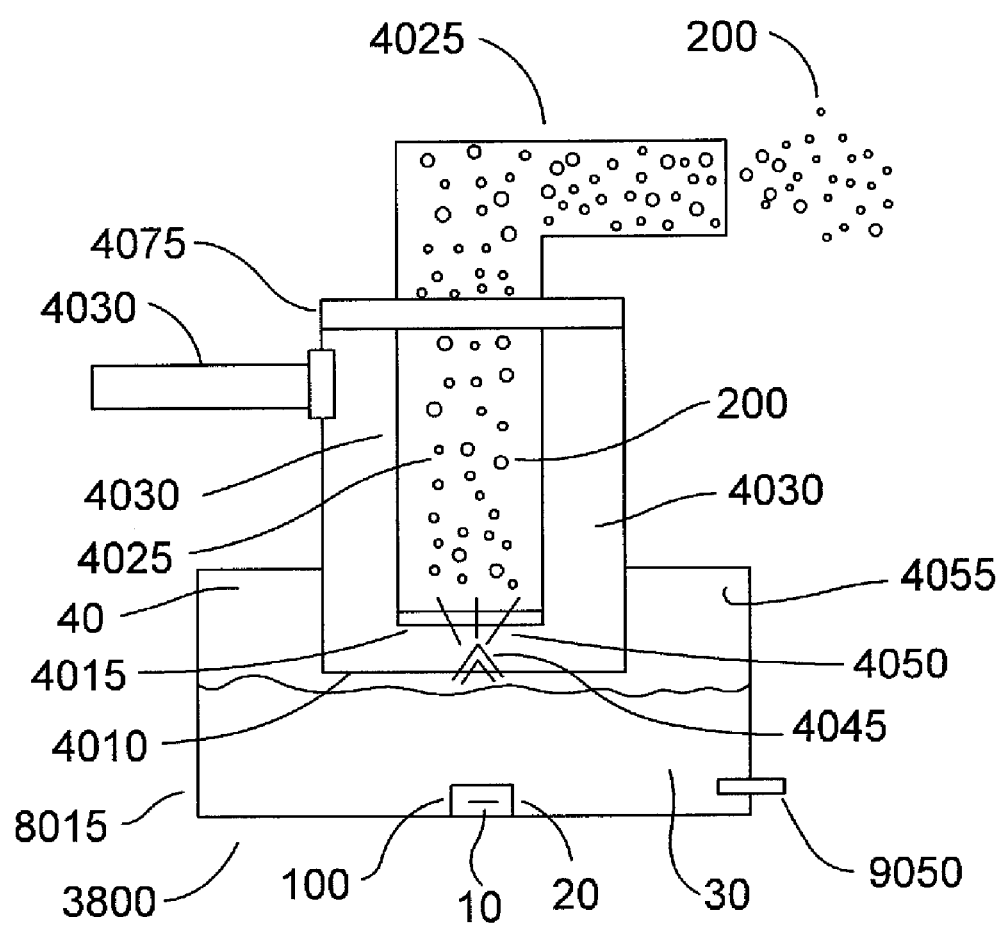
FIG. 108 is a schematic view of an optimized and miniaturized aerosol generator, showing the air outlet pipes(s) located within the air inlet pipe(s), and the airflow outlet located higher than the inbound airflow inlet according to the present invention.

Referring to FIG. 107, the one or more air inlet pipe(s) (4030), inbound airflow inlet(s) (4010), air outlet pipe(s) (4025), and/or airflow outlet(s) (4015), can, without limitation, extend any distance into the liquid (30) within the reservoir(s) (40). It is preferred, without limitation that this distance is at least an effective distance. Various combinations of these various components effectively extending into the liquid (30) can be utilized such as, but not limited to, (a) the one or more air inlet pipe(s) (4030) and/or inbound airflow inlet(s) (4010) are effectively located within or immersed in the liquid (30), while the one or more air outlet pipe(s) (4025) and/or airflow outlet(s) (4015) are effectively positioned outside of or above the liquid (30), (b) the one or more air outlet pipe(s) (4025) and/or airflow outlet(s) (4015) are effectively located within or immersed in the liquid (30), while the one or more air inlet pipe(s) (4030) and/or inbound airflow inlet(s) (4010) are effectively positioned outside of or above the liquid (30), (c) the one or more air outlet pipe(s) (4025), airflow outlet(s) (4015), air inlet pipe(s) (4030), and/or inbound airflow inlet(s) (4010), are effectively located within or immersed in the liquid (30). It is preferred, without limitation, that the one or more air inlet pipe(s) (4030) and/or inbound airflow inlet(s) (4010) are effectively located within or immersed in the liquid (30), while the one or more air outlet pipe(s) (4025) and/or airflow outlet(s) (4015) are effectively positioned outside of or above the liquid (30).

The air outlet pipes(s) (4025) can be, without limitation, perforated in one or more of any suitable and effective location(s), with one or more air flow holes (4080) of any effective shape(s) and size(s), at any effective distance(s), especially above the liquid (30). These air flow hole(s) (4080) can help facilitate an effective flow of air or gas from the air inlet pipe(s) (4030) to the air outlet pipes(s) (4025) in order to remove the generated aerosol (200) out of the reservoir(s) (40) and/or the air outlet pipes(s) (4025). The air flow holes are formed through a side wall of outlet pipe (4025).

It is also preferred, without limitation, that the one or more air inlet pipe(s) (4030), inbound airflow inlet(s) (4010), air outlet pipe(s) (4025), and/or airflow outlet(s) (4015), are effectively, suitably, and approximately centered above, below, and/or around, the one or more geyser(s) (4045) of raised liquid (30) and any associated aerosol plume(s) (4050), and/or the transducer(s) (10). It is also even more preferred, without limitation, that the one or more surfaces and/or materials of parts and components such as, but not limited to, the air inlet pipe(s) (4030), inbound airflow inlet(s) (4010), air outlet pipe(s) (4025), and/or airflow outlet(s) (4015), are suitably and effectively located so that they are not damaged by the energy, ultrasonic output, or signal, that is emitted, radiated, and/or transmitted, by the one or more transducer(s) (10). Without being limited, and as previously mentioned, this can be important when utilizing transducer(s) (10) described in the present invention due to their power and the length of the field of energy, ultrasonic output, or signal, that they can emit, radiate, and/or transmit. One or more of any air inlet pipe(s) (4030), inbound airflow inlet(s) (4010), air outlet pipe(s) (4025), and/or airflow outlet(s) (4015), can be, without limitation, allocated to or effectively function with, one or more of any geyser(s) (4045) of raised liquid (30) and any associated aerosol plume(s) (4050), and/or one or more of any transducer(s) (10).

Referring to FIG. 103-108, and without being limited, the air inlet pipe(s) (4030) and inbound airflow inlet(s) (4010), as well as the air outlet pipes(s) (4025) and the airflow outlet(s) (4015), can have, without limitation, one or more opening(s), of any, size(s), shape(s), and geometry(s), at one or more of any location(s). It is preferred, without limitation, that the number of opening(s) for these location(s) and/or structures, as well as their size(s), shape(s), geometry(s), position(s), and location(s), are at least effective and efficacious. It is also preferred, without limitation, that the one or more, air inlet pipe(s) (4030), inbound airflow inlet(s) (4010), air outlet pipes(s) (4025), and airflow outlet(s) (4015), are suitably and effectively positioned. Without being limited, at least one air outlet pipes(s) (4025), and airflow outlet(s) (4015), can be centered above and/or around at least one, transducer (10), transducer housing (20), and/or transducer assembly (100). The at least one, air inlet pipe(s) (4030), inbound airflow inlet(s) (4010), air outlet pipes(s) (4025), and airflow outlet(s) (4015), can also be, without limitation, centered above and/or around at least one, transducer (10), transducer housing (20), and/or transducer assembly (100) in various effective configurations and distances. It is preferred, without limitation, that the one or more, air inlet pipe(s) (4030), inbound airflow inlet(s) (4010), air outlet pipes(s) (4025), and airflow outlet(s) (4015), are not only suitably and effectively positioned and spaced from each other and the transducer(s) (10), but they do not adversely interfere with, or adversely effect the performance of, the one or more transducer(s) (10) that are utilized.

Figure 117A:
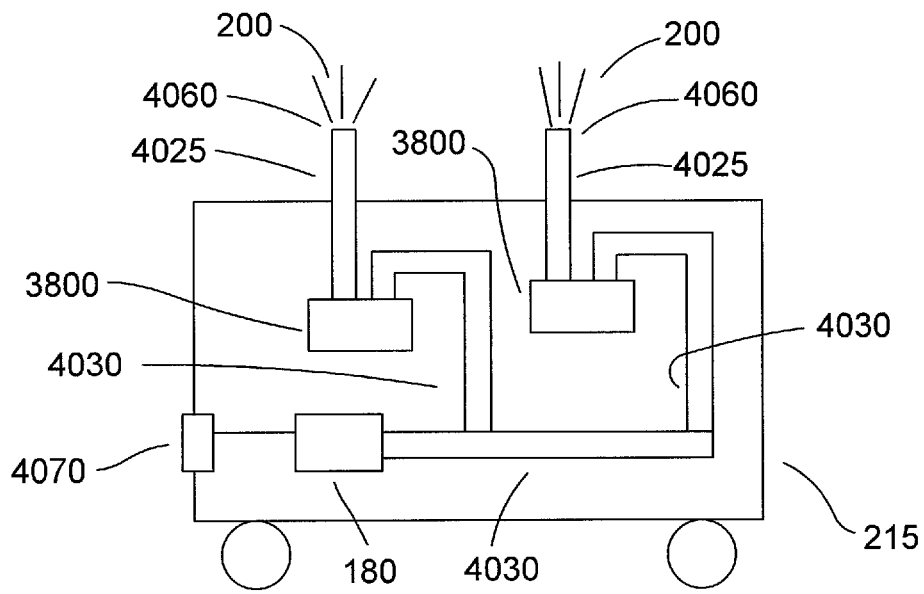
FIG. 117-A is a schematic view of an optimized and miniaturized aerosol generating connected to a shared fan according to the present invention.
Figure 117B:
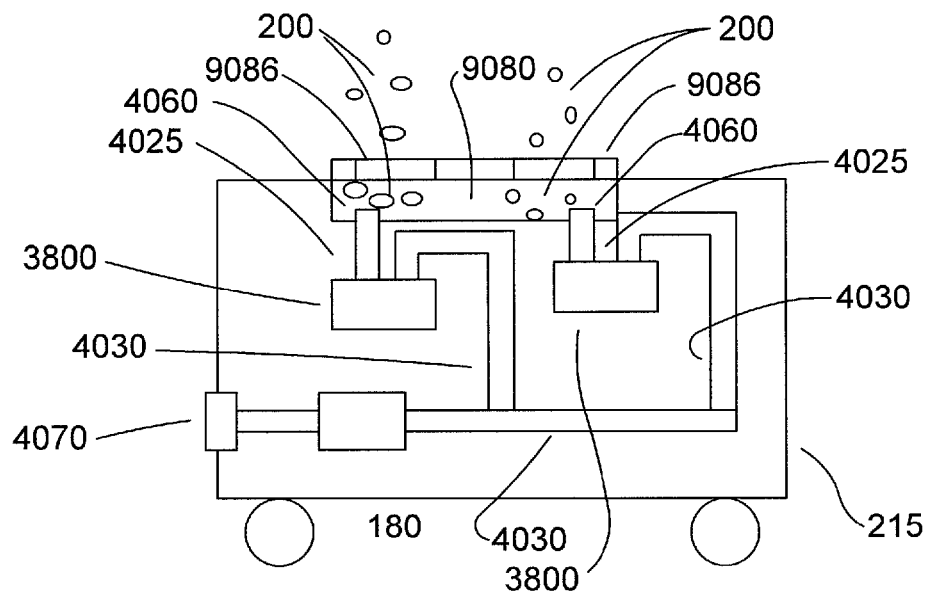

Referring to FIGS. 117A-117B, the one or more air inlet pipe(s) (4030) can, without limitation, be suitably connected to, one or more of any, blower(s), fan(s), or any other effective or suitable source(s) of any pressurized air or gas(s) (180). Each optimized and miniaturized aerosol generator(s) (3800) can be, without limitation, solely connected to, or even share, one or more blower(s), fan(s), or any other effective or suitable source(s) of any pressurized air or gas(s) (180). It is preferred, without limitation, that the various optimized and miniaturized aerosol generator(s) (3800) are connected to at least one of any suitable fan(s) or blower(s) (180). It is more preferred, without limitation, that the various optimized and miniaturized aerosol generator(s) (3800) used in the aerosol generating apparatus (215) are all connected to, and share the airflow from, one or more of any, blower(s), fan(s), or any other effective or suitable source(s) of any pressurized air or gas(s) (180). It is even more preferred, without limitation, that the various optimized and miniaturized aerosol generator(s) (3800) used in the aerosol generating apparatus (215) are all connected to, and share the airflow from, exactly one of any suitable, blower or fan (180). Without being limited, the one or more of any, blower(s), fan(s), or any other effective and suitable source(s) of any pressurized air or gas(s) (180), can connect in any suitable and effective way know in the art, to one or more of any air/gas entry point(s) (4070) located at one or more of any suitable and effective location(s) such as, but not limited to, inside, outside, on the exterior surface of, and/or or within, the apparatus(s) (215).

Any quantity and velocity of air or any gas may be supplied to the reservoir(s) (40) for any length of time by the source(s) of pressurized air or gas(s) that is utilized. However, it is preferred, without limitation, that a blower (180) of effective size and output is utilized. It is preferred, without limitation that the source of pressurized air or gas or blower (180) is able to provide air or gas to the reservoir at measurement of between approximately 3-2000 or more cubic feet per minute (cfm). It is more preferred, without limitation that the source of pressurized air or gas or blower (180), is able to provide air or gas to the reservoir at measurement of between approximately 3-500 cubic feet per minute (cfm). It is more preferred, without limitation that the source of pressurized air or gas or blower (180), is able to provide air or gas to the reservoir at measurement of between approximately 10-100 cubic feet per minute (cfm). It is more preferred, without limitation that the source of pressurized air or gas or blower (180), is able to provide air or gas to the reservoir at measurement of between approximately 20-40 cubic feet per minute (cfm).

Also, referring to FIGS. 117A-117B, the one or more entry points or inlet(s) (Herein called "air entry point(s)" (4070)) where the air or gas enters the air inlet pipe(s) (4030) may also, without limitation, be located at any suitable and effective location anywhere on or inside the aerosol (200) producing apparatus (215). The one or more air entry point(s) (4070) can, without limitation, incorporate one or more of any design enhancements such as, but not limited to any, filter, screen or mesh material, and/or grate material. The air entry point(s) (4070) may also, without limitation, interface with one or more of any attachment port(s) or attachment component(s) whose design and construction is known to those skilled in the art, so that it may connect with one or more of any accessories and/or any other delivery pipe(s), hose(s), or conduit(s). The air entry point(s) (4070) can also, without limitation, be any size or shape.

Fifth, and referring to FIGS. 95-97, and FIGS. 103-108, the design of the optimized and miniaturized aerosol generator (3800) and aerosol generating device (215) can be enhanced, without limitation, by reducing the amount of space between the one or more reservoir ceiling(s) (4055) and the liquid (30) within the reservoir(s) (40). In addition, this enhancement can also, without limitation, be aided by reducing the total amount of air/gas volume, above the liquid (30) and inside of the reservoir(s) (40). Desired attributes such as, but not limited to, a faster air/gas flow, or increased volume of air/gas, supplied to the air outlet pipes(s) (4025) and/or the airflow outlet(s) (4015), can be, without limitation, established by creating a small gap between the surface of the liquid (30) and/or limiting the amount of space within the reservoir(s) (40). This can also, without limitation, help to establish a stronger venturi-like effect that reduces aerosol dwell time, decreases the chance for unwanted vortices, and increases aerosol (200) output from the apparatus. The airflow outlet(s) (4015) and inbound airflow inlet(s) (4010) can be, without limitation, positioned at any effective distance from the one or more reservoir ceiling(s) (4055) inside of the reservoir(s) (40), however it is preferred, without limitation, that the airflow outlet(s) (4015) and inbound airflow inlet(s) (4010) are positioned so that they are flush with the reservoir ceiling(s) (4055).

Without being limited, the one or more reservoir ceiling(s) (4055) can consist of one or more components. It is preferred, without limitation, that the one or more reservoir ceiling(s) (4055) consists of one component and it is made from one piece of suitable material. The one or more reservoir ceiling(s) (4055) can be positioned, without limitation, at one or more of any angle(s), geometry(s), orientation(s), and/or distance(s) above the liquid (30) within the reservoir(s) (40). It is preferred, without limitation, that the one or more reservoir ceiling(s) (4055) is positioned at an effective, angle(s), geometry(s), orientation(s), and/or distance(s) above the liquid (30) within the reservoir(s) (40), as well as the transducer(s) (10). It is also preferred, without limitation, that the reservoir ceiling(s) (4055) is positioned so that it is approximately horizontal with the surface of the liquid (30) within the reservoir (40). The one or more reservoir ceiling(s) (4055) can also be, without limitation, positioned effectively close to, level with, or approximately flush with, one or more of any parts or components within the reservoir(s) (40) such as, but not limited to any, airflow outlet(s) (4015), and/or inbound airflow inlet(s) (4010).

However, to take advantage of the improvements in this invention, the one or more reservoir ceiling(s) (4055) should be, without limitation, located within a certain height range or gap (denoted in FIG. 103 by distance "C") above any liquid (30) that covers the transducer(s) as follows. It is preferred, without limitation, that the reservoir ceiling(s) (4055) is positioned between 0.04 inches to 12.0 inches above the surface of the liquid that is above each aerosol (200) producing transducer (10). It is more preferred, without limitation, that the reservoir ceiling(s) (4055) is positioned between 0.04 inches to 3.0 inches above the surface of the liquid that is above each aerosol (200) producing transducer (10). It is even more preferred, without limitation, that the reservoir ceiling(s) (4055) is positioned between 0.04 inches to 1.5 inches above the surface of the liquid that is above each aerosol (200) producing transducer (10). It is very preferred, without limitation, that the reservoir ceiling(s) (4055) is positioned between 0.05 inches to 1.0 inches above the surface of the liquid that is above each aerosol (200) producing transducer (10). It is extremely preferred, without limitation, that the reservoir ceiling(s) (4055) is positioned between 0.06 inches to 0.08 inches above the surface of the liquid that is above each aerosol (200) producing transducer (10).

Sixth, and referring to FIGS. 95-97, FIGS. 103-108 to FIGS. 114-116, and FIGS. 117A-117B, the design of the optimized and miniaturized aerosol generator (3800) and aerosol generating device (215) can be enhanced, without limitation, by improving the way that the liquid (30) is heated before it is converted into an aerosol (200) by the transducer(s) (10). The prior art has described heating the liquid before it is aerosolized. For example, this is described in (col. 4, line 4-8) of U.S. Pat. No. 4,366,125 (Kodera et al., 1980), which is incorporated herein by reference in its entirety, including any references cited therein, where heating the liquid is described in the following quote: "The germacidal liquid (19) is held in an upper basin (25), the bottom of which is immersed in the warm water (18) in the lower basin (21). The upper basin (25) is supplied with the germacidal liquid from a tank and through a heating element (both not shown) and an inlet pipe (24).". Another example is described in (col. 8, line 9-12) of U.S. Pat. No. 5,878,355 (Berg et al. 1996), and (col. 8, line 15-18) of U.S. Pat. No. 6,102,992 (Berg et al. 1998), which is incorporated herein by reference in its entirety, including any references cited therein, where heating the liquid is described in the following quote: "Referring back to FIG. 2, it is preferred that the overflow reservoir include a heating element (72) for heating the capture liquid before generating an aerosol."

However, the current art as currently described has proven to be ineffective and not enabling for maintaining the needed effective and efficacious liquid (30) temperatures, in the reservoir in which multiple transducer(s) (10) are located, for aerosol generation between 80 to 150 degree Fahrenheit or more, and more so for liquid (30) temperatures between 85 to 150 degree Fahrenheit, and even more so for liquid (30) temperatures between 90 to 150 degree Fahrenheit, and very much so for liquid (30) temperatures between 95 to 128 degree Fahrenheit. This is, without limitation, due to various interacting variables such as, but not limited to, (a) the amount of liquid (30) in the reservoir (40) in which the transducer(s) (10) are located, (b) the temperature to which the liquid (30) is initially heated for the aerosol (200) production to begin, (c) the heat loss due to the amount of air flowing over the surface of the liquid (30) above the transducer(s) (10), (d) the heat lost due to any air temperature variation that may be encountered between the inside of the reservoir(s) (40) and the environment outside of the apparatus (215), (e) the number of transducers (10) that are required for effective operation of the apparatus (215) and the resulting amperage required, (f) the minimum effective temperature of the liquid

(30) above the transducer(s) (10), (g) the total amperage available to the entire apparatus (215), and (h) the amount of liquid (30) removed from the reservoir(s) (40) in the form of any aerosol (200).

Without being limited, these variables must be considered, or the aerosol (200) generating apparatus (215) may not be a successful product in the market place, especially if at least two to four, but preferably at least six or more transducers, are needed for acceptable performance. The prior art failed to mention these various issues and their effect on sufficiently heating the liquid (30) and the resulting amperage availability problems. However, and without being limited, an improved apparatus (215) utilizing the various enhancements, including, but not limited to, operating at least one, but preferably two, and even more preferably three, of the new optimized and miniaturized aerosol generators (3800), can successfully operate for extended periods of time with at least a 20 amp 115 VAC rated single commercial power source. It is important to remember, without limitation, that in order to meet electrical safety standards in the United States, especially for a mobile apparatus (215), an apparatus can only utilize power from one electrical source, which further complicates the amperage availability dilemma for heating and maximizing the number of transducer(s) that can be effectively and efficaciously operated.

First, one problem with depending on a large volume reservoir (40), or even combining a large reservoir with a secondary reservoir as described in Berg et al. 1996 & 1998), to supply the liquid (30) used for covering the transducer(s) (10), is that the more liquid that is used to fill these places, the longer it takes to initially warm that liquid (30) to at least the minimum operating temperature, and the more amperage it then takes to sustain the established or necessary operating liquid (30) temperature(s) once the transducer(s) (10) are operating and air is flowing over the transducers to remove the aerosol (200).

Heat can be lost from the liquid (30) above the transducer(s) (10), in various ways including, but not limited to, (a) heat lost to the air flowing over the liquid covering the transducer(s) (10), (b) heat conducted to any materials surrounding the liquid (30), (c) heat lost as large ejected droplets that cooled in the air and/or on surfaces, fall back into the liquid surrounding the transducer(s) (10), or (d) heat lost as the heated liquid (30) is removed from the reservoir(s) (40), in aerosol (200) form.

Without being limited, it was observed in the laboratory that once the transducer(s) are producing aerosol (200), amperage availability for heating the liquid (30) becomes scarce due to the large amounts of amperage that is necessary to produce the aerosol (200). The more aerosol (200) that is needed or desired to be produced, means more transducers (10) are needed to be operated, and this increases the total amount of amperage that is needed by the apparatus (215). The result is that this severely reduces or even eliminates the amount of amperage available to heat the liquid (30) while the transducer(s) are operated. This is, without limitation, especially a problem when operating at least two to four, but preferably at least six or more transducers, in the apparatus (215), since operating the transducers requires a large majority of the available amperage. These issues are especially relevant, without limitation, for operating scenarios where the liquid (30) must be kept at high operating temperatures for the entire time the transducer(s) (10) are producing aerosol (200) and multiple transducers are operated.

Over heating the liquid (30) and using the heated liquid (30) as a way to store and use the heat over time may, without limitation, work in certain applications. However this also has inherent problems in situations including, but not limited to, (a) the liquid is thermally sensitive and over heating the liquid to a sufficient temperature to store a sufficient amount of heat will degrade the chemical(s) in the liquid (30), and/or (b) the amount of stored heat in the liquid (30) is insufficient to provide an adequate operating liquid temperature for the duration of a full aerosol (200) generation and deploy cycle. Both of these situations have been witnessed in the laboratory.

Another problem related to (Kodera et al., 1980) is that they were silent with respect to maintaining the germicidal liquid in the reservoir with the transducer at an effective temperature or within an effective temperature range during the full operating cycle. When considering the various variables that can cool a liquid in a reservoir, it is reasonable to determine that only the "warm water" (Kodera et al., 1980) circulated under the reservoir in which the transducer is located would not be sufficient alone, even when combined with the heated liquid that would replenish the tank, to keep the germicidal liquid at a constant temperature. This is especially relevant given the notoriously small amounts of liquid, and thus small amounts of additional inputted heat, that are utilized to replenish the liquid covering the ultrasonic transducers over a given amount of time. In addition, (Kodera et al., 1980) was silent with respect to utilizing a thermocouple to control the liquid temperature, which meant that their apparatus was most likely designed for a steady state environment, and not one where operating variables could change necessitating more heat being applied to maintain a constant liquid temperature in the aerosolized liquid. The lower bath was only described as being "warm" and in cases where the heat may be removed faster from the whole system than heat is being added, the germicidal liquid above the transducers can not be expected to remain close to the same temperature and the reproducibility of the system would be lost.

Referring to FIGS. 95-97, FIGS. 103-108, and FIGS. 114-117B, and without limitation, maintaining the liquid (30) temperature surrounding the transducer(s) (10) at the desired or needed temperature(s) or temperature range(s), is also impacted by various variables such as, but not limited to, (a) the number of transducers being operated in each optimized and miniaturized aerosol generator (3800), (b) the number of optimized and miniaturized aerosol generator(s) (3800) being operated in each apparatus (215), (c) the total volume of the liquid (30) in the reservoir(s) (40) in which the transducer(s) (10) are located, and any other liquid (30) directly connected to this liquid (30) in areas such as, but not limited to any liquid sensor compartment(s) (8010), (d) the minimum temperature and/or the temperature range(s) that the liquid (30) must be held while generating the aerosol (200), (e) the amount of wattage allocated to each heater element that heats the liquid (30) in each reservoir(s) (40) in which the transducer(s) (10) are located, (f) allocation or method of allocation of amperage between all heater element(s) to maintain the temperature of the liquid (30), and (g) the amount of aerosol (200) that is generated and deployed per unit of time.

Any number of transducer(s) (10) may be located within the reservoir(s) (40) of the optimized and miniaturized aerosol generator (3800) and/or aerosol generating device (215). It is preferred, without limitation, that the number of transducer(s) (10) is at least effective and sufficient. However, and without being limited, the more transducer(s) (10) that are located within the reservoir(s) (40), the harder it is to keep the liquid at the desired or needed temperature(s), for reasons including, but not limited to, (a) more liquid (30) is needed to effectively and sufficiently cover the transducer(s) (10), and (b) the more transducer(s) that are located within the reservoir(s) (40), typically the more air that is needed to circulate through the reservoir(s) to effectively remove the aerosol (200) that is generated to avoid conglomeration of the generated aerosol within the reservoir(s) (40). It is preferred, without limitation, that at least one transducer(s) (10) is located in the reservoir(s) (40). It is more preferred, without limitation, that two or more transducer(s) (10) are located in the reservoir(s) (40). It is even more preferred, without limitation, that two transducers (10) are located in the reservoir(s) (40). It is very preferred, without limitation, that between one to two transducer(s) (10) are located in the reservoir(s) (40). This can, without limitation, help to increase the performance of the optimized and miniaturized aerosol generator(s) (3800) and/or apparatus (215).

Any number of optimized and miniaturized aerosol generator(s) (3800) may be located within the aerosol generating device (215). It is preferred, without limitation, that the number of optimized and miniaturized aerosol generator(s) (3800) is at least effective and sufficient. However, and without being limited, this number is typically dictated by considerations such as, but not limited to, the intended market and/or purpose of the apparatus (215), as well as the total amount of amperage available to the apparatus (215). It is not uncommon to have each apparatus (215) limited to 20 amps of available power due to various safety regulations and standards encountered in the market place. It is preferred, without limitation, that each aerosol (200) generating apparatus (215) includes at least one optimized and miniaturized aerosol generator(s) (3800). It is more preferred, without limitation, that each aerosol (200) generating apparatus (215) includes two or more optimized and miniaturized aerosol generator(s) (3800). It is even more preferred, without limitation, that each aerosol (200) generating apparatus (215) includes three optimized and miniaturized aerosol generator(s) (3800). It is very preferred, without limitation, that each aerosol (200) generating apparatus (215) includes three or more optimized and miniaturized aerosol generator(s) (3800).

Any volume of liquid (30) may be utilized in the reservoir(s) (40) in which the transducer(s) (10) are located, as well as any other connecting areas such as, but not limited to any liquid sensor compartment(s) (8010). It is preferred, without limitation, that the volume of liquid (30) is at least effective and a sufficient volume. However, and without being limited, in order to obtain maximum performance, it is preferred, without limitation, that the liquid (30) capacity of the reservoir(s) (40) in which the transducer(s) (10) are located, is as small as possible while still enabling an effective and sufficient amount of liquid (30) to cover the transducer(s) (10) while they are operating. In addition, and without being limited, as more liquid (30) surrounds the transducer(s) (10) various costs are associated such as, but not limited to, (a) it will take longer to heat the liquid (30) in the reservoir(s) (40) to at least the minimum accepted temperature(s) or within the accepted temperature range(s) when starting the apparatus (215), (b) more amperage will be required by the one or more heating elements to not only preheat the liquid (30) to at least the minimum accepted temperature(s) or within the accepted temperature range(s), but also maintain the liquid (30) at those temperature(s).

Without being limited, the total volume of the liquid (30) in the reservoir(s) (40) in which the transducer(s) (10) are located, and any other liquid (30) directly connected to this liquid (30) in areas such as, but not limited to any, liquid sensor compartment(s) (8010), can range from about 0.05 liter to about 15 liters or more, preferably between about 0.1 liters to at least 2 liters or more, more preferably between about 0.1 liter to about 1 liter, even more preferably about 0.1 liters to about 0.8 liter, and very preferably about 0.1 to about 0.6 liter.

Referring to FIGS. 95-97, and FIGS. 103 and 113, and without being limited, the liquid sensor compartment(s) (8010) can be located in any effective and suitable location(s). It is preferred, without limitation, that the liquid sensor compartment(s) (8010) are located along the length of the reservoir(s) (40) in which the transducer(s) (10) are located. It is also preferred, without limitation, that the length of the liquid sensor compartment(s) (8010) is controlled or influenced by the length of the reservoir(s) (40) in which the transducer(s) (10) are located. The liquid sensor compartment(s) (8010) can have any effective and suitable length(s), width(s), and/or diameter(s). Without being limited, the width of the liquid sensor compartment(s) (8010) can range from about 0.25 inches to about 4 inches or more, preferably between about 0.25 inches to at least about 2.0 inches, more preferably between about 0.5 inches to about 1.75 inches, even more preferably about 1.0 inches to about 1.5 inches, and very preferably about 1.25 inches. Without being limited, the volume of the liquid (30) within the liquid sensor compartment(s) (8010) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.18 liter.

Referring to FIGS. 103-108, and FIGS. 133-138, and without being limited, the reservoir(s) (40) in which the transducer(s) (10) are located can also have any effective and suitable length(s), width(s), and/or diameter(s). Without being limited, the width of these one or more reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, very preferably about 2.5 inches.

Referring to FIGS. 133-138, and without being limited, the reservoir(s) (40), or the various areas or parts of the reservoir(s) (40), in which the transducer(s) (10) are located, can also be separated into, or designated as, one or more area(s), segment(s), or zone(s) (Hereinafter called reservoir building segment(s) (9091)) which are designated for one or more of any function(s) or activity(s), or one or more of any combination(s) of any function(s) or activity(s), such as, but not limited to, one or more area(s) where the airflow inlet(s) (4010) are located (Hereinafter called air inlet zone(s) (9093)), one or more area(s) where the airflow outlet(s) (4015) are located (Hereinafter called air outlet zone(s) (9094)), and/or one or more area(s) where the transducer(s) and/or their corresponding geyser(s) (4045) of raised liquid (30) are located (Hereinafter called aerosol production zone(s) (9092)).

The reservoir building segment(s) (9091) can have any width and length. It is preferred, without limitation, that the width and length of the reservoir building segment(s) (9091) is at least suitable and effective. Without being limited, the length, width, and/or diameter of each of the one or more reservoir building segment(s) (9091) can range from about 0.5 inches to about 4.5 inches or more, preferably between about 1 inch to at least about 4 inches, more preferably between about 1 inch to about 3 inches, even more preferably about 1.5 inches to about 2.75 inches, very preferably about 2.5 inches. Also without being limited, the volume of each of the one or more reservoir building segment(s) (9091) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.1 liter.

The volume of liquid (30) in one or more of any reservoir building segment(s) (9091) can also, without being limited, range from about 0.0 liters to about 0.5 liters or less. Without being limited, the one or more reservoir building segment(s) (9091) can contain or hold limited amounts of liquid (30), or little to no liquid (30), in situations such as, but not limited to, the one or more reservoir building segment(s) (9091) are only designed and constructed to accommodate or interface with one or more of various parts and components such as, but not limited to, the air inlet pipe(s) (4030), inbound airflow inlet(s) (4010), air outlet pipes(s) (4025), and/or the airflow outlet(s) (4015), and contain or hold small amounts of liquid (30), contain or hold little to no liquid (30), and/or not contain or hold any liquid (30).

Referring to FIG. 138, and without being limited, the one or more reservoir building segment(s) (9091) can be designed and constructed to have one or more shelve(s), structure(s), or island(s), of material (Hereinafter called "reservoir shelve(s)" (9096)) that can rise out of the liquid (30) in the reservoir(s) (40), or be located within the liquid (30) within the reservoir(s) (40). The one or more reservoir shelve(s) (9096) can be, without limitation, located in any effective and suitable location(s) within the reservoir(s) (40). The reservoir shelves (9096) may be, without limitation, located in one or more of any locations such as, but not limited to, under each inlet pipe(s) (4030) and/or inbound airflow inlet(s) (4010).

Without being limited, the reservoir shelve(s) (9096) can be any height, length, and/or width, and can be constructed from one or more of any suitable and effective material(s). It is preferred, without limitation, that the various dimensions of the reservoir shelves(s) (9096) are at least effective and suitable. It is more preferred, without limitation, that the reservoir shelve(s) (9096) are at least high enough to so that they rise out of the highest point of the liquid (30) within the reservoir(s) (40) and/or their top surface(s) (9097) are not submerged under the liquid (30) in the reservoir(s) (40).

Without being limited, the reservoir shelves(s) (9096) can serve various functions such as, but not limited to, reduce the amount of liquid (30) located within the reservoir(s) (40) and/or the one or more reservoir building segment(s) (9091), (b) limit the amount of liquid (30) that may be directly exposed to the air/gas that flows out of the airflow inlet(s) (4010), (c) deflect or redirect the air/gas that flows into the reservoir, into one or more of any other parts or areas within the reservoir(s) (40). It is preferred, without limitation, that if the reservoir shelve(s) (9096) are used, they are positioned under the each inlet pipe(s) (4030) and/or inbound airflow inlet(s) (4010), and their length and width approximately matches the inside area of the inlet pipe(s) (4030) and/or inbound airflow inlet(s) (4010) that are centered above them.

Without being limited, one or more feature(s) or structure(s) such as, but not limited to any, channel(s), tunnel(s), conduit(s), and/or groove(s) (Hereinafter called "reservoir connection(s)" (9095)) can be also utilized with the reservoir shelve(s) (9096), and enable the liquid (30) within the reservoir(s) (40) to flow or connect between the one or more of any reservoir building segment(s) (9091) or other parts of the reservoir(s) (40). The one or more reservoir connection(s) (9095) can be, without limitation, used to connect all of the liquid within the reservoir(s) (40) and also help to effectively drain all of the liquid in the reservoir(s) when needed.

One or more reservoir connection(s) (9095) can be, without limitation, located in one or more of any effective and suitable location(s) within, between, or through, the reservoir shelves(s) (9096). It is preferred, without limitation, that if a reservoir connection(s) (9095) is needed, it is utilized in the form of any effective and suitably sized groove(s) or channel(s). The reservoir connection(s) (9095) can be, without limitation, any effective and suitable length, width and height. It is preferred, without limitation, that the reservoir connection(s) (9095) are at least constructed so that an effective and suitable amount of liquid (30) is able to flow or move within the reservoir(s) (40) as needed, as well as cover the trans ducer(s) (10) with a sufficient and effective amount of liquid (30). It is also preferred, without limitation, that the bottom surface(s) of the reservoir connection(s) (9095) are at least flush with, or at least approximately even with, the various bottom surfaces or floor(s) of the reservoir(s) (40).

Referring to FIGS. 133-138, any effective and suitable number of these various reservoir building segment(s) (9091) can be, without limitation, assembled together in any suitable and effective, order, design, pattern, and/or format, in order to form one or more of any effective operating reservoir(s) (40) and/or component(s) of the optimized and miniaturized aerosol generator(s) (3800). Any effective and suitable height(s), depth(s), length(s), width(s), and/or diameter(s), may be used for these reservoir building segment(s) (9091). Without being limited, one or more of any reservoir building segment(s) may also have one or more different dimension(s), than one or more of any other reservoir building segment(s) (9091) that are utilized. It is preferred, without limitation, that all of the utilized reservoir building segment(s) (9091) have similar dimensions.

Referring to FIGS. 133-134, and without being limited, the reservoir(s) (40) in which the transducer(s) (10) are located, can be formed and organized, as well as condensed, combined, or concentrated, so that all of the various parts, components, function(s), and/or activity(s), that are related to, or interface with or within, the reservoir(s) (40), such as, but not limited to, the area(s) where the airflow inlet(s) (4010) are located, the area(s) where the airflow outlet(s) (4015) are located, and/or the area(s) where the transducer(s) and/or their corresponding geyser(s) (4045) of raised liquid (30) are located, can all be located within or interface with the same, or around the same, area(s) of the reservoir(s) (40). More specifically, and without being limited, the various zones such as, but not limited to, the air inlet zone(s) (9093), air outlet zone(s) (9094), and aerosol production zone(s) (9092), can all be located within, or interfaced to, the same reservoir building segment (9091).

Without being limited, in this simple and compact form, the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, in this simple and compact form, the length of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, in this simple and compact form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.1 liter.

Referring to FIGS. 133 and 134, and without limitation, the one or more airflow outlet(s) (4015), and/or the one or more air outlet pipe(s) (4025), are suitably and effectively centered above, below, and/or around, the one or more transducer(s) (10) and/or the direction of their emitted energy or ultrasonic output or signal, within the reservoir(s) (40) in which the transducer(s) (10) are located. Also referring to FIG. 133, and without limitation, the one or more airflow inlet(s) (4010) and/or air inlet pipe(s) (4030) can be positioned within, or interfaced with, the reservoir(s) (40), in one or more of any suitable and effective locations. Also, referring to FIG. 134, and without limitation, the one or more airflow outlet(s) (4015) and/or one or more air outlet pipe(s) (4025), can be effectively and suitably positioned within the one or more airflow inlet(s) (4010) and/or air inlet pipe(s) (4030), and suitably and effectively centered above, below, and/or around, the one or more transducer(s) (10) and/or the direction of their emitted energy or ultrasonic output or signal, within the reservoir(s) (40) in which the transducer(s) (10) are located.

Referring to FIG. 136, and without being limited, the reservoir(s) (40) in which the transducer(s) (10) are located can be formed and organized so that one area of the reservoir(s) (40) is dedicated to the air inlet zone(s) (9093), and the other area is dedicated to both the aerosol production zone(s) (9092) and the air outlet zone(s) (9094). More specifically, and without being limited, the one or more airflow outlet(s) (4015) and/or one or more air outlet pipe(s) (4025), can be suitably and effectively centered above, below, and/or around, the one or more transducer(s) (10) and/or the direction of their emitted energy or ultrasonic output or signal, within the reservoir(s) (40), and the one or more airflow inlet(s) (4010) and/or air inlet pipe(s) (4030) can be effectively and suitably positioned in one or more different area(s) or location(s) within, or interfaced with, the same reservoir(s) (40).

Without being limited, in this form or organization of the reservoir (40), where two reservoir building segment(s) (9091) are utilized, the width of these reservoir(s) (40) the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also, without being limited, the length of these reservoir(s) (40) can range from about 1 inch to about 9 inches or more, preferably between about 2 inches to at least about 8 inches, more preferably between about 2 inches to about 6 inches, even more preferably about 3 inches to about 5.5 inches, and very preferably about 5 inches. Also, without being limited, in this reservoir form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.2 liter.

Referring to FIG. 137, and without being limited, the reservoir(s) (40) in which the transducer(s) (10) are located can be formed and organized so that one area of the reservoir(s) (40) is dedicated to the air inlet zone(s) (9093), and two different or distinct areas are dedicated to both the aerosol production zone(s) (9092) and the air outlet zone(s) (9094). More specifically, and without being limited, one or more airflow outlet(s) (4015) and/or one or more air outlet pipe(s) (4025), can be suitably and effectively centered above, below, and/or around, each of the one or more transducer(s) (10) and/or the direction of their emitted energy or ultrasonic output or signal, within the reservoir(s) (40), and the one or more airflow inlet(s) (4010) and/or air inlet pipe(s) (4030) can be effectively and suitably positioned in one or more different area(s) or location(s) within, or interfaced with, the same reservoir(s) (40). It is preferred, without limitation, that the one or more airflow inlet(s) (4010) and/or air inlet pipe(s) (4030) are located between each of the transducer(s) (10) and their respective airflow outlet(s) (4015) and/or one or more air outlet pipe(s) (4025). It is even more preferred, without limitation, that two separate transducers (10) are utilized within a reservoir (40), and each transducer (10) has its own dedicated airflow outlet (4015) and air outlet pipe (4025).

Without being limited, in this form or organization of the reservoir (40), where three reservoir building segment(s) (9091) are utilized, the width of these reservoir(s) (40) can range from about 0.5 inches to about 4.5 inches or more, preferably between about 1 inch to at least about 4 inches, more preferably between about 1 inch to about 3 inches, even more preferably about 1.5 inches to about 2.75 inches, and very preferably about 2.5 inches. Also without being limited, the length of these reservoir(s) (40) can range from about 1.5 inches to about 13.5 inches or more, preferably between about 3 inches to at least about 12 inches, more preferably between about 3 inches to about 9 inches, even more preferably about 4.5 inches to about 8.25 inches, and very preferably about 7.75 inches. Also, without being limited, in this simple and compact form, the volume of the liquid (30) in these reservoir(s) (40) can range from about 0.01 liter to about 15 liters or more, preferably between about 0.01 liter to at least 2 liters or more, more preferably between about 0.04 liter to about 1 liter, even more preferably about 0.05 liters to about 0.5 liter, very preferably about 0.1 to about 0.5 liter, and extremely preferred about 0.3 liter.

Without being limited, suitable and effective length and/or width dimensions can also be used for the reservoir(s) (40) in which the transducer(s) (10) are located, and at least suitable and effective reservoir (40) dimensions should be utilized to accommodate the various size(s) and number(s) of the various parts and components that are utilized such as, but not limited to, the transducer(s) (10), air inlet pipe(s) (4030), inbound airflow inlet(s) (4010), air outlet pipes(s) (4025), and/or the airflow outlet(s) (4015).

It is important that a sufficient and effective amount, depth, and/or height, of liquid (30) is maintained above the face or energy radiating side of the one or more transducer(s) (10) that is in contact with the liquid (30) within the reservoir(s) (40) of the optimized and miniaturized aerosol generator(s) (3800), at least while they are operating and receiving power. This can, without limitation, prevent damage to the transducer(s) (10). Any sufficient and effective amount, depth, and/or height, of liquid (30) may be utilized and maintained above the face or energy radiating side of the one or more transducer(s) (10) that is in contact with the liquid (30) within the reservoir(s) (40) of the optimized and miniaturized aerosol generator(s) (3800). It is preferred, without limitation, that the depth, and/or height, of the liquid (30) that is utilized or maintained above the transducer(s) (10) is between about 0.25 inches to about 8.0 inches. It is more preferred, without limitation, that the depth, and/or height, of the liquid (30) that is utilized or maintained above the transducer(s) (10) is between about 0.25 inches to about 5.0 inches. It is even more preferred, without limitation, that the depth, and/or height, of the liquid (30) that is utilized or maintained above the transducer(s) (10) is between about 0.25 inches to about 2.0 inches. It is very preferred, without limitation, that the depth, and/or height, of the liquid (30) that is utilized or maintained above the transducer(s) (10) is between about 0.5 inches to about 2.0 inches. It is extremely preferred, without limitation, that the depth, and/or height, of the liquid (30) that is utilized or maintained above the transducer(s) (10) is between about 1.0 inches to about 1.5 inches. It may also be, without limitation, possible to operate the optimized and miniaturized aerosol generator(s) (3800) by utilizing or maintaining a liquid (30) depth, and/or height, above the transducer(s) (10), that is below 0.25 inches if lower power(s) and/or frequency(s) are utilized to operate the transducer(s) (10).

Without being limited, the transducer(s) (10) within the optimized and miniaturized aerosol generator(s) (3800) can be operated at any suitable and/or effective frequency. It is preferred, without limitation, that the transducer(s) (10) are operated at any frequency between about 0.025 MHz to about 10 MHz or higher. It is more preferred, without limitation, that the transducer(s) (10) are operated at any frequency between about 0.5 MHz to about 4 MHz. It is even more preferred, without limitation, that the transducer(s) (10) are operated at any frequency between about 0.5 MHz to about 3.0 MHz. It is very preferred, without limitation, that the transducer(s) (10) are operated at any frequency between about 1.0 MHz to about 3.0 MHz. It is extremely preferred, without limitation, that the transducer(s) (10) are operated at any frequency between about 1.2 MHz to about 2.5 MHz.

Without being limited, the transducer(s) (10) within the optimized and miniaturized aerosol generator(s) (3800) may also be operated at any suitable and/or effective power. It is preferred, without limitation, that the transducer(s) (10) are operated at any suitable and effective power or peak to peak voltage, between about 20 (Vp-p) to about 300 volts peak to peak (Vp-p). It is more preferred, without limitation, that the transducer(s) (10) are operated at any suitable and effective power or peak to peak voltage, between about 50 (Vp-p) to about 300 volts peak to peak (Vp-p). It is even more preferred, without limitation, that the transducer(s) (10) are operated at any suitable and effective power or peak to peak voltage, between about 75 (Vp-p) to about 300 volts peak to peak (Vp-p). It is very preferred, without limitation, that the transducer(s) (10) are operated at any suitable and effective power or peak to peak voltage, between about 100 (Vp-p) to about 260 volts peak to peak (Vp-p). It is extremely preferred, without limitation, that the transducer(s) (10) are operated at any suitable and effective power or peak to peak voltage, between about 190 (Vp-p) to about 230 volts peak to peak (Vp-p).

Any effective and suitable aerosol (200) producing transducer(s) known to those skilled in the art may be, without limitation, utilized or included in the design of the optimized and miniaturized aerosol generator(s) (3800). However, it is preferred, without limitation that the transducer(s) (10) that are utilized, are constructed in a manner described in this document and are at least protected with a suitable and effective protective barrier. Without being limited, the transducer(s) (10) may be operated with one or more of any suitable and/or effective combination(s) of power and frequency. It is preferred, without being limited, the transducer(s) (10) are be operated at a frequency between about 1.0 MHz to about 3.0 MHz, and at a suitable and effective power or peak to peak voltage, between about 100 (Vp-p) to about 260 volts peak to peak (Vp-p). The transducer(s) (10) may also have a diameter or width of various lengths. It is preferred, without limitation, that the transducer(s) (10) at least have a diameter or width that is suitable and effective. Without being limited, the diameter or width of the transducer(s) (10) can range from about 0.25 inches to about 3 inches or more, preferably between about 0.5 inches to at least about 2.5 inches, more preferably between about 0.75 inches to about 2 inches, and even more preferably about 1 inch.

Any liquid (30) temperature or range of temperatures may be utilized in the reservoir(s) (40) in which the transducer(s) (10) are located, as well as any other connecting areas such as, but not limited to any liquid sensor compartment(s) (8010). Without being limited, the effective operating temperature of the liquid (30) may also vary depending upon parameters and attributes such as, but not limited to, the desired aerosol (200) output volume, the type of liquid (30) used, and the surface tension of the liquid (30). It is preferred, without limitation, that the temperature, or range of temperatures, of the liquid (30) that at least surrounds and/or covers the transducer(s), is at least effective, efficacious, and sufficient, and this temperature(s) is at least maintained while the one or more transducer(s) is producing aerosol (200). It is also preferred, without limitation, that at least the liquid (30) that surrounds and/or covers the transducer(s) (10), is preheated to any effective or desired temperature or range of temperatures, before the transducer(s) start to produce aerosol (200). The temperature of the liquid (30) above the transducer(s) (10) may also, without limitation, start to drop to any temperature, and more preferably to any effective temperature, after aerosol (200) generation has started and/or finished. It is preferred, without limitation, that if the temperature of the liquid (30) above the transducer(s) (10) drops during an aerosol (200) generation cycle, it at least drops within an effective, efficacious, and/or desired temperature range. It is preferred, without limitation, that at least the liquid (30) that surrounds and/or covers the transducer(s) (10), is kept at a temperature of at least 80 degree Fahrenheit or more. It is more preferred, without limitation, that at least the liquid (30) that surrounds and/or covers the transducer(s) (10), is kept at a temperature between 80 to 150 degree Fahrenheit or more. It is even more preferred, without limitation, that at least the liquid (30) that surrounds and/or covers the transducer(s) (10), is kept at a temperature between 90 to 150 degree Fahrenheit. It is very preferred, without limitation, that at least the liquid (30) that surrounds and/or covers the transducer(s) (10), is kept at a temperature between 90 to 130 degree Fahrenheit.

Referring to FIGS. 95-97, FIGS. 103-108, the temperature of the liquid (30) that surrounds and/or covers the transducer(s) (10), or any other liquid used within the apparatus (215), can be, without limitation, monitored by one or more of any liquid temperature sensing device(s) (Hereinafter called temperature sensor(s) (9050)) such as, but not limited to, any, thermocouple(s), or RTD(s). The temperature sensor(s) (9050) can communicate with one or more of any digital, electronic, or analog, controller(s), such as, but not limited to, any PLC(s). Without being limited, the one or more of any digital, electronic, or analog, controller(s), such as, but not limited to, any PLC(s), can control, one or more of any liquid heating source(s) (9045) used in any suitable or desirable locations. It is preferred, without limitation, that one or more of any suitable heat source(s) are at least located in, or at least directly or indirectly interfaced with the liquid (30) that surrounds and/or covers the transducer(s) (10), or the reservoir(s) (40) in which the transducer(s) (10) are located. It is more preferred, without limitation, that at least one or more heating source(s) (9045) is interfaced with the bottom of the reservoir (40) in which the transducer(s) (10) are located. It is even more preferred, without limitation, that only one suitable heating source (9045) is utilized to increase the performance of the apparatus (215). The one or more heating source(s) (9045) can be, without any limitation, any suitable heat source, or combination of any suitable heat sources, known in the art, that is or has any, watt density, design, and power. Without being limited, the one or more heating source(s) (9045) can directly and/or indirectly heat any liquid(s) used to make or mix the liquid (30) that is utilized, any of the mixed liquid (30) before it enters the reservoir(s) (40), the liquid (30) in the reservoir(s) (40) in which the transducer(s) are located (10), and/or any other liquid (30) in one or more of any, tank(s), reservoir(s), compartment(s), and/or container(s), using any suitable and effective means known to those skilled in the art.

Without being limited, the one or more heating source(s) (9045) can be located at or in one or more of any suitable location(s) such as, but not limited to, within any reservoir(s) (40) in which the one or more transducer(s) (10) are located, within one or more of any walls or floor(s) of any reservoir(s) (40), attached to the exterior of one or more of any walls or floors of the reservoir(s) (40). It is preferred, without limitation, that the heating source (9045) that is utilized is any suitable heating element or cartridge type heater (Hereinafter called "heating element" (9045)). It is also preferred, without limitation, that the heating element (9045) is inserted into, and sufficiently interfaces with, a suitable hole that is centered and located within the bottom of each reservoir (40) material, and heats the liquid (30) in the reservoir(s) in which the transducer(s) (10) are located. The heat source(s) (9045) can be any suitable size or length, but it is preferred, without limitation, that the heat source(s) (9045) or heating element (3856) is at least large and/or long enough to also heat the liquid (30) in the one or more liquid sensor compartment(s) (8010). The reservoir(s) (40), or any other tank(s), reservoir(s), or compartment(s), can be constructed from any suitable material. It is preferred, without limitation, that at least the bottom of the reservoir(s) (40) is constructed from stainless steel. It is more preferred, without limitation, that the bottom of both the reservoir(s) (40) and the liquid sensor compartment(s) (8010) are constructed from stainless steel. It is even more preferred, without limitation, that the bottom of both the reservoir(s) (40) that the transducer(s) (10) are located in, and the liquid sensor compartment(s) (8010), are constructed from the same piece of material.

The one or more heating source(s) (9045) in the one or more aerosol (200) generating apparatus (215) can be, without limitation, operated at any time, for any duration, and in one or more of any operational combination(s). It is preferred, without limitation, that the heating source(s) (9045) are at least operated for any effective time, duration, and/or operational combination(s). The one or more heating source(s) (9045) can also have, or be rated for, any power or wattage. It is preferred, without limitation, that the heating source(s) (9045) have a power or wattage rating between 25 watts to 2000 watts or more. It is more preferred, without limitation, that the heating source(s) (9045) have a power or wattage rating between 25 watts to at least 1600 watts. It is even more preferred, without limitation, that the heating source(s) (9045) have a power or wattage rating between 250 watts to 1500 watts. It is very preferred, without limitation, that each heating source (9045) has a power or wattage rating between 300 watts to 700 watts.

It has been found that depending on the number of transducers (10) that are operated in the aerosol generating apparatus (215), the availability of sufficient power or amperage to the aerosol generator(s) (3800) and/or aerosol (200) generating apparatus (215) can, without limitation, at least impact the ability of the heating source(s) (9045) to effectively or suitably maintain the temperature of the liquid (30) that surrounds or covers the transducer(s) (10), at the needed or desired temperature(s) or within the needed or desired temperature range(s). This can be, without limitation, especially problematic when it is desired to operate as many transducer(s) (10) as possible, and produce as much aerosol (200) as possible, for any desired period of time, while still preserving enough power or amperage to maintain the temperature of the liquid (30) that surrounds and covers the transducer(s) (10), at the needed or desired temperature(s) or within the needed or desired temperature range(s).

Without being limited, one way to maximize the number of transducers (10) that are operating in the aerosol (200) generating apparatus (215) and also simultaneously maintain the liquid (30) above and/or surrounding the transducer(s) (10) at or within the desired or needed temperature(s) or temperature range(s), is to reallocate, and/or consolidate and allocate, the available power or amperage for any heating, to one or more heating source(s) (9045), and then cycling this power from one or more dedicated heating source(s) (9045) to another one or more dedicated heating source(s) (9045) as needed. Without being limited, this can be accomplished by controlling the power that is supplied to the more than one or plurality of heating source(s) (9045) via one or more of any digital, electronic, or analog, controller(s) such as, but not limited to, any PLC(s), as well as any other electrical components known to those skilled in the art, and cycling a sufficient amount of power between the various heating source(s) (9045) when it is needed.

Any amount of power or amperage can be, without limitation, cycled between or amongst the various heating source(s) (9045) at any time and for any duration of time. It is preferred, without limitation, that the available power or amperage for the heating source(s) (9045) is at least cycled between or amongst the one or more heating source(s) (9045) that are responsible for heating the liquid (30) in each reservoir(s) (40) in which the transducer(s) (10) are located. It is also preferred, without limitation, that at least an effective amount of power or amperage is cycled between or amongst the various heating source(s) (9045). Any available power or amperage that can be allocated to the various heating source(s) (9045) can be, without limitation, cycled amongst one or more of any of the heating source(s) (9045) at any time associated with the apparatus (215). It is preferred, without limitation, that any available power or amperage is dedicated to only one heating source (9045) at a time, and more preferably at least one heating source(s) (9045) that is located in, or interfaced with, each optimized and miniaturized aerosol generator (3800). This power or amperage can also be, without limitation, allocated to more than one heating source(s) (9045) at the same time, if sufficient power or amperage is available. Sufficient power or amperage may not always, without limitation, need to be cycled, allocated, and/or consolidated, between or amongst the various heating source(s) (9045) for reasons including, but not limited to, the optimized and miniaturized aerosol generator(s) (3800) is not generating aerosol (200), but the apparatus (215) is operational, and the power or amperage that would typically be used to generate aerosol (200) is all, or at least sufficiently, allocated by the one or more of any digital, electronic, or analog, controller(s) such as, but not limited to, any PLC(s), to at least all of the various heating source(s) (9045) responsible for heating the liquid (30) in all of the different reservoir(s) (40) in which the transducer(s) (10) are located.

Without being limited, at least a sufficient amount of power is cycled between or amongst the various heating source(s) (9045) for any effective and efficacious amount of time. It is preferred, without limitation, that at least a sufficient amount of power or amperage is allocated to at least one or more heating source(s) (9045) between 1 second or less to 5 minutes or more, before being allocated to one or more different heating source(s) (9045). It is more preferred, without limitation, that at least a sufficient amount of power or amperage is allocated to at least one or more heating source(s) (9045) between 0.1 seconds to 4 minutes, before being allocated to one or more different heating source(s) (9045). It is even more preferred, without limitation, that at least a sufficient amount of power or amperage is allocated to at least one or more heating source(s) (9045) for at least 10 seconds to 60 seconds, before being allocated to one or more different heating source(s) (9045). It is very preferred, without limitation, that at least a sufficient amount of power or amperage is allocated to at least one or more heating source(s) (9045) for at least 15 seconds to 40 seconds, before being allocated to one or more different heating source(s) (9045).

The power or amperage provided to the various heating source(s) (9045) can be, without limitation, cycled between or amongst the various heating source(s) (9045) any number of times per any time period. It is preferred, without limitation, that the power or amperage provided to the various heating source(s) (9045) is cycled between or amongst the various heating source(s) (9045) for any effective and efficacious number of times per any effective and efficacious time period. It is more preferred, without limitation, that the temperature of the liquid (30), above and/or surrounding the transducer(s) (10), and/or within the reservoir(s) (40) in which the transducer(s) are located, determines exactly where or to which heating source(s) (9045), the power or amperage is allocated or cycled between or amongst the various heating source(s) (9045). Any liquid (30) temperature can, without limitation, determine which heating source(s) (9045) are allocated sufficient power or amperage. However, it is preferred, without limitation, that the coldest liquid (30), and more preferably the coldest one or more reservoir(s) (40) in which the transducer(s) (10) are located, determines exactly where or to which one or more heating source(s) (9045), the power or amperage is allocated or cycled between or amongst the various heating source(s) (9045).

For example, and without limitation, one or more of any PLC(s) can sense and determine which liquid (30) within three different reservoirs (40) in which the transducer(s) (10) are located, of three different optimized and miniaturized aerosol generator(s) (3800) located within an aerosol generating apparatus (215), has the coldest temperature, and then allocate the available power or amperage to the heating source (9045) that is responsible for heating that coldest liquid (30) until it reaches the needed or desired temperature(s), or is within the needed or desired temperature range(s). Once this liquid (30) is sufficiently heated, the one or more PLC(s) can then repeat the process and sense and determine again which liquid (30) within those three different reservoirs (40), in which the transducer(s) are located, has the newest coldest temperature, and then reallocate the available power or amperage to the heating source (9045) that is responsible for heating that coldest liquid (30) until it too reaches the needed or desired temperature(s), or is within the needed or desired temperature range(s). Without being limited, this process can be, without limitation, repeated as needed for any number of times or cycles, or it can be utilized until various situations take place such as, but not limited to, (a) the apparatus (215) and/or optimized and miniaturized aerosol generator (s) (3800) is shut down, (b) the optimized and miniaturized aerosol generator(s) (3800) are not generating aerosol (200), but the apparatus (215) is still operational, and the power or amperage that would typically be used to generate aerosol (200) is all, or at least sufficiently, allocated by the one or more of any digital, electronic, or analog, controller(s) such as, but not limited to, any PLC(s), to all of the various heating source(s) (9045) responsible for heating the liquid (30) in all of the different reservoir(s) (40) in which the transducer(s) (10) are located, (c) the one or more of any digital, electronic, or analog, controller(s) such as, but not limited to, any PLC(s), has shut down all of the one or more optimized and miniaturized aerosol generator(s) (3800) so they are not generating aerosol (200), but the apparatus (215) is still operational, and the power or amperage that would typically be used to generate aerosol (200) is all, or at least sufficiently, allocated to one or more of any dehumidifier(s) (2040) and/or suitable deodorization filter(s) (2090).

Figure 95:
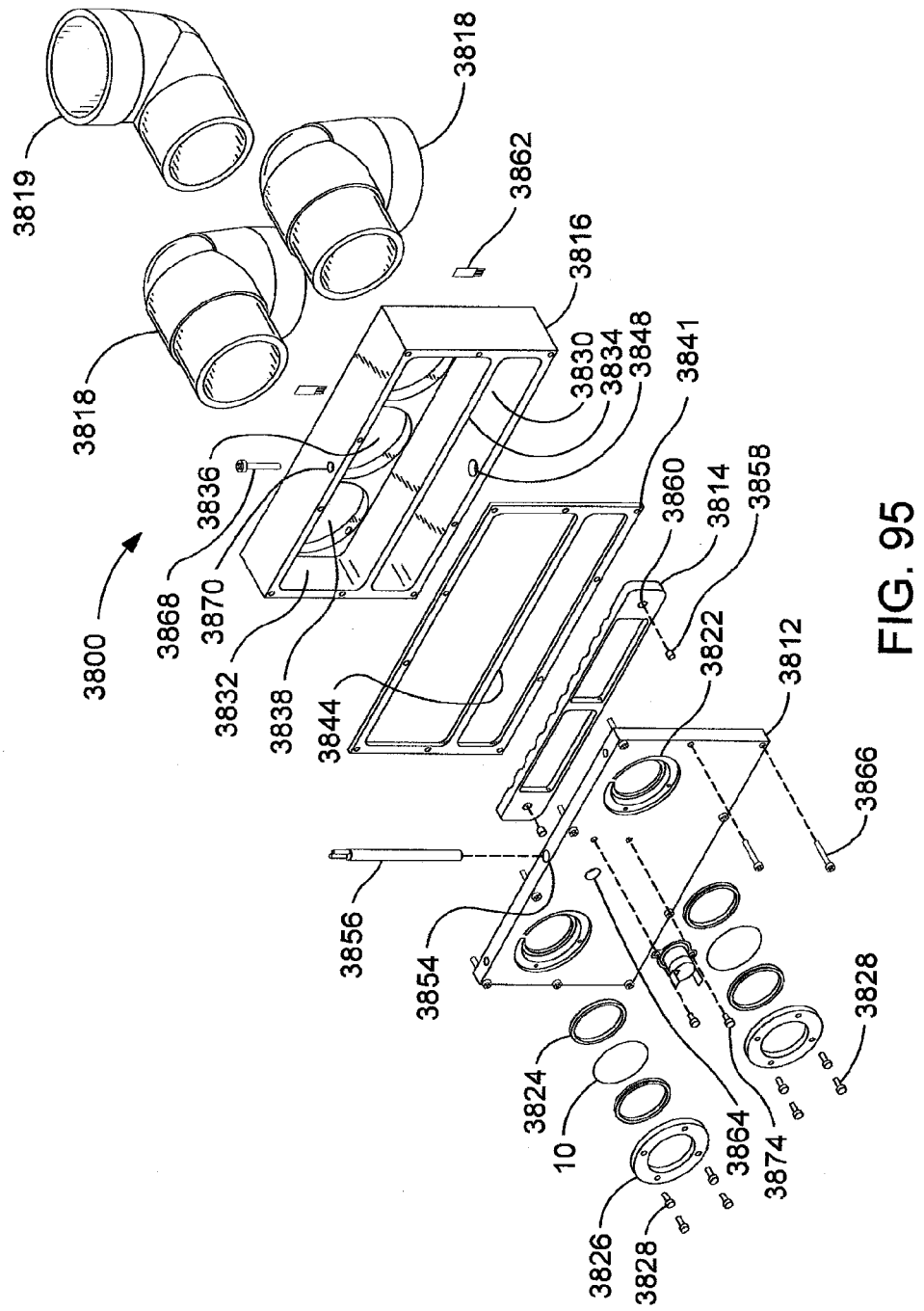
FIG. 95 is an exploded perspective view of a optimized and miniaturized aerosol generator.
Figure 96:
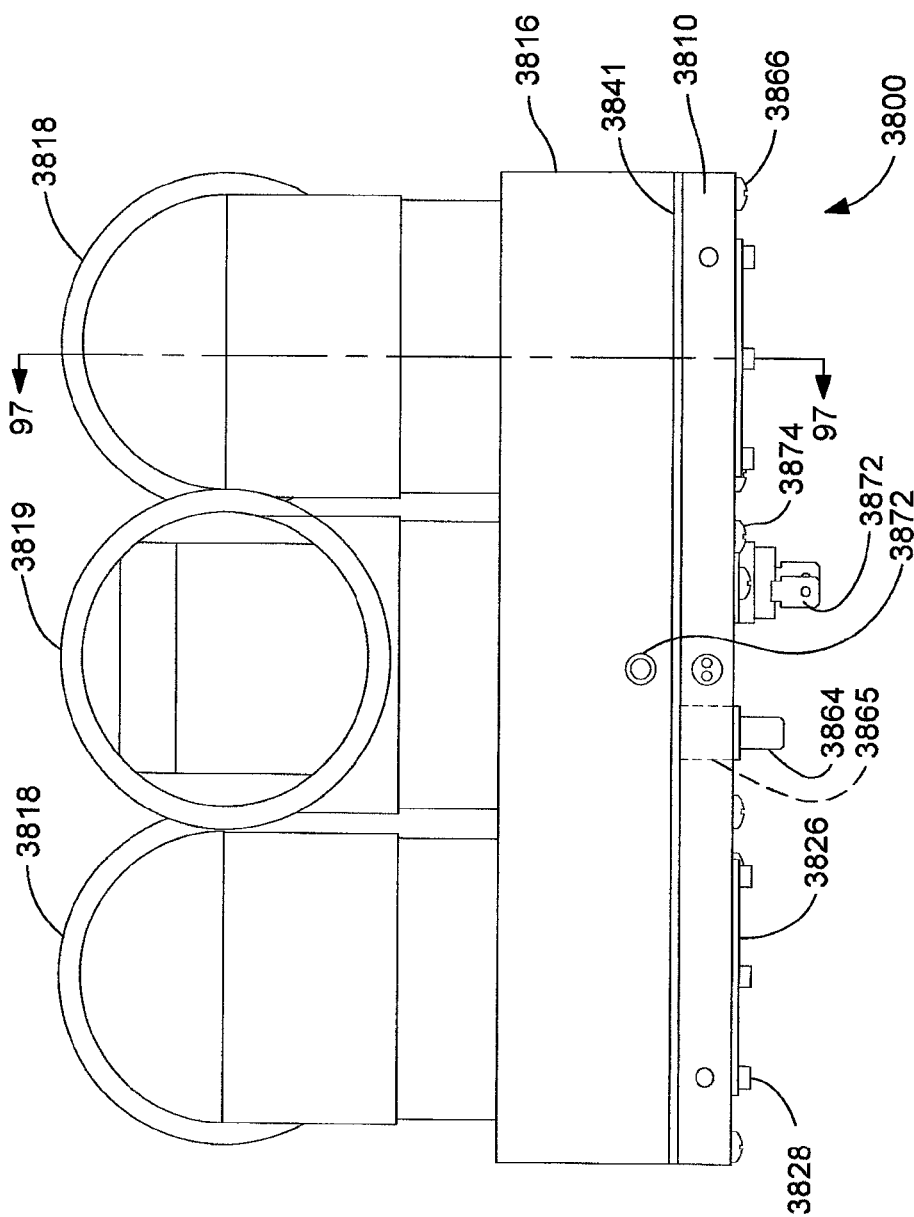
FIG. 96 is a side view of a optimized and miniaturized aerosol generator.
Figure 97:
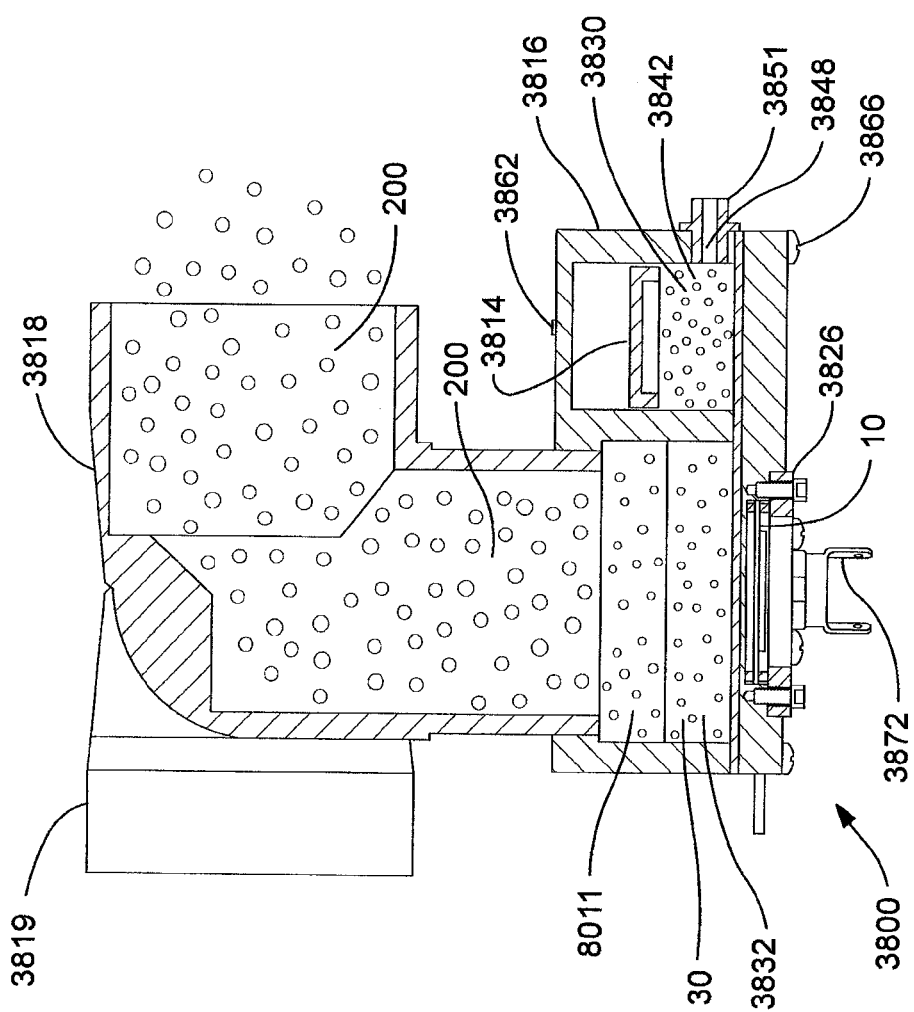
FIG. 97 is a cross sectional view of a optimized and miniaturized aerosol generator cut through FIG. 96.
Figure 98:
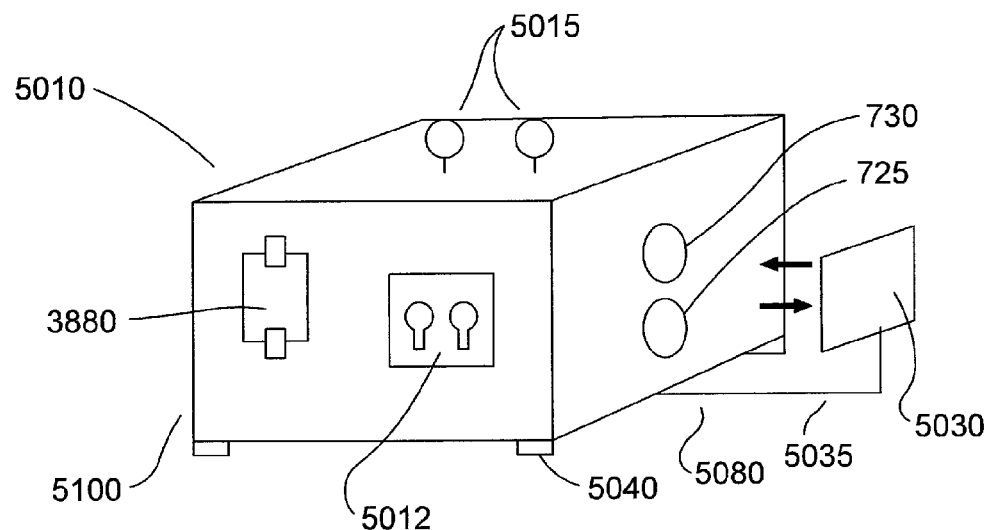
FIG. 98 is a perspective view of a remote aerosol sensor to remotely sense the environment within an area targeted for aerosol deployment according to the present invention.
Figure 99:
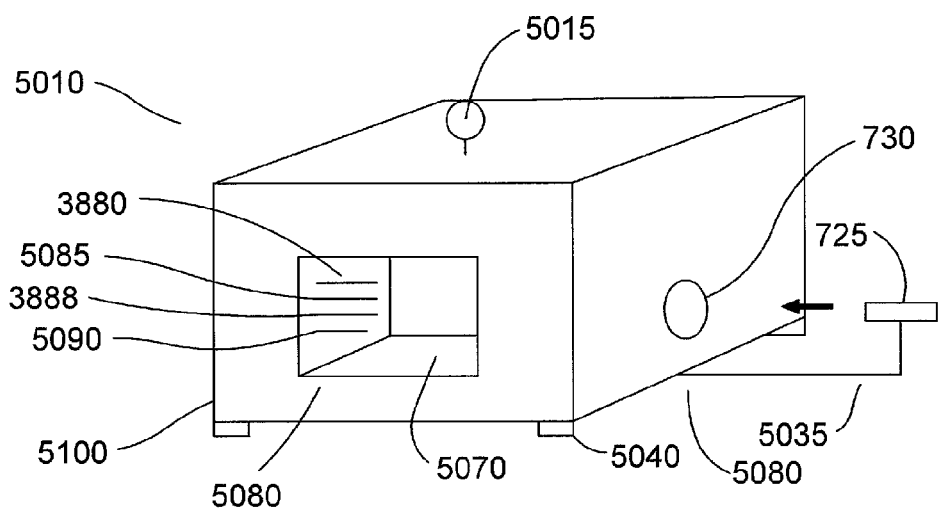
FIG. 99 is a perspective view of a remote aerosol sensor with a sensor cavity to remotely sense the environment within an area targeted for aerosol deployment, according to the present invention.
Figure 100:
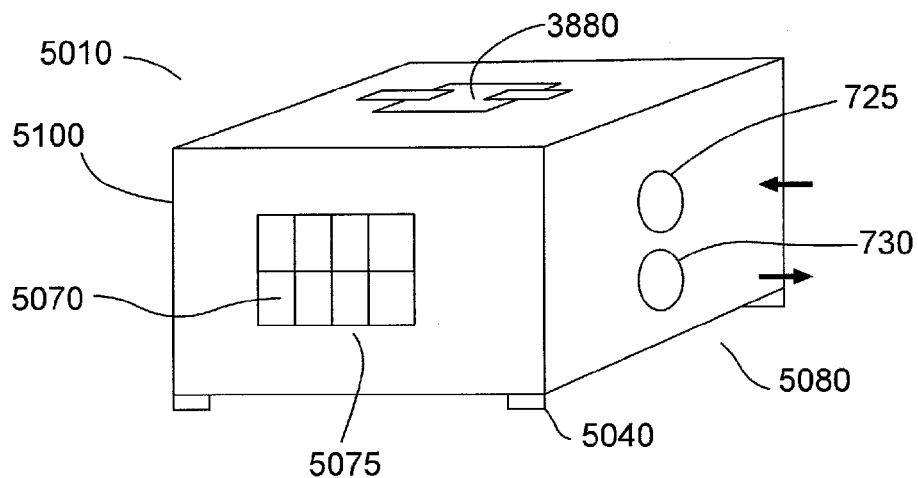
FIG. 100 is a perspective view of a remote aerosol sensor with a aerosol deposit sensor to remotely sense the environment within an area targeted for aerosol deployment according to the present invention.
Figure 101:
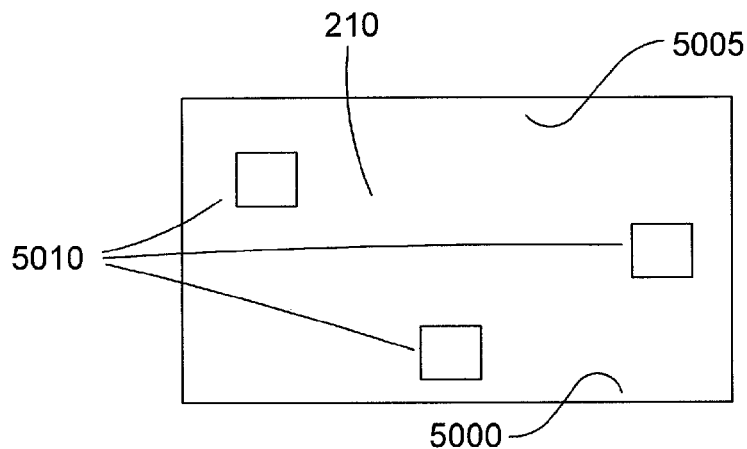
FIG. 101 is a schematic view of one or more targeted area(s) in which one or more remote aerosol sensor(s) are located in various locations in an enclosed area, according to the present invention.
Figure 102:
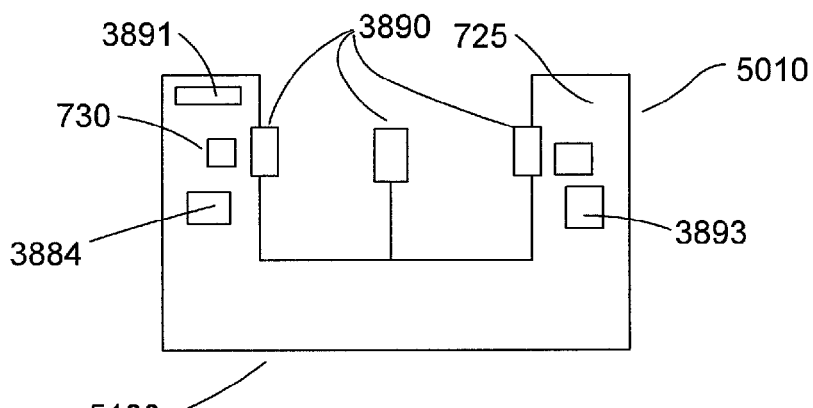
FIG. 102 is a schematic view of an embodiment of various parts and components of a means to remotely sense the environment within an area targeted for aerosol deployment according to the present invention.
Figure 118:
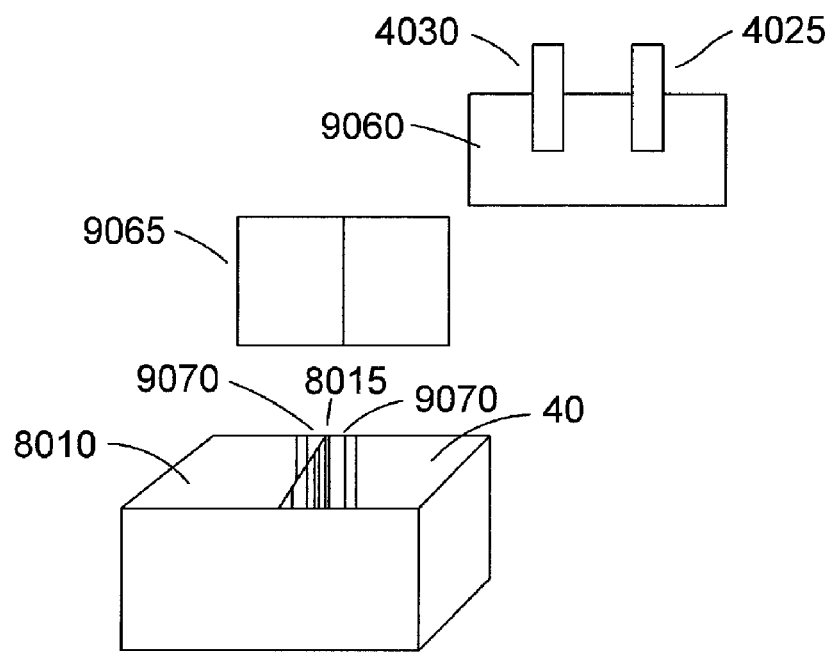

Referring to FIGS. 95-97, FIGS. 103-108, FIGS. 111-112, and FIG. 118, the reservoir(s) (40) in which the transducer(s) (10) are located, including, but not limited to any, liquid sensor compartment(s) (8010), can be constructed from one or more of any suitable components or materials. It is preferred, without limitation, that the reservoir(s) (40) and the liquid sensor compartment(s) (8010) at least share a common floor or base (Hereinafter called "transducer plate" (3812)). It is preferred, without limitation, that the transducer plate (3812) is at least constructed from any suitable grade of stainless steel. The transducer plate (3812) can also be any suitable thickness. It is preferred, without limitation, that the transducer plate (3812) is at least a suitable thickness to work effectively with any suitable heating source(s) (9045) that may be interfaced with it, as well as accommodate any interfaced transducer(s) (10). Referring to FIGS. 95-97, various components are, without limitation, utilized to construct and seal the walls and floor, of the reservoir(s) (40) in which the transducer(s) (10) are located, and the liquid sensor compartment(s) (8010). Referring to FIG. 118, and without being limited, in a more simple aspect, any or all of the outer wall(s) and/or floor(s) of the reservoir(s) (40) in which the transducer(s) (10) are located, and the liquid sensor compartment(s) (8010), can be, without limitation, constructed from the same material or manufactured to function as one component. This can be accomplished in any suitable manner known to those skilled in the art such as, but not limited to any, injection molding, thermo-molding, or even plastic welding the various wall and floor components together. Without being limited, one or more separate roof(s) or ceiling(s) component(s) (Hereinafter "removable cover" (9060)) can then be, without limitation, interfaced with one or more of any components such as, but not limited to any, air inlet pipe(s) (4030), airflow inlet(s) (4010), air outlet pipe(s) (4025), airflow outlet(s) (4015), or any other component(s), and then be connected or interfaced with one or more of any suitable seal(s) or gasket(s) (9065), to the various walls of the reservoir(s) (40) and/or liquid sensor compartment(s) (8010). In this more simple aspect, the one or more wall(s), structure(s), or barrier(s) (Hereinafter called "separation wall(s)" (8015)), that forms or establishes at least one or more suitable, barrier(s), complete barrier(s), and/or partial barrier(s), between the liquid sensor compartment(s) (8010) and the reservoir(s) (40) can also be, without limitation, constructed from any number of independent part(s) and can slide in and out for repair, replacement, or cleaning, via one or more of any suitable grooves, tracks, or indentations (Hereinafter called "tracks" (9070). It is preferred, without limitation, that only one wall or separation wall(s) (8015) would separate the liquid sensor compartment(s) (8010) from the reservoir(s) (40) in which the transducer(s) (10) are located, and they would slide in and out via one or more tracks or indentations (9070) that would be present between the liquid sensor compartment(s) (8010) and reservoir(s) (40) at any suitable location where the wall(s) or barrier(s) would be positioned.

Seventh, and referring to FIGS. 95-97, FIGS. 103 and 105, and FIGS. 111-112, the design of the optimized and miniaturized aerosol generator (3800) and aerosol generating device (215) can be enhanced, without limitation, by improving how the liquid (30) depth above the transducer(s) (10) is maintained within the reservoir(s) (40). The use of one or more of any suitable liquid level sensor(s) (305) located anywhere within the reservoir(s) (40) in which the transducer(s) is located, is known in the art. However, it has been found that the environment within the reservoir(s) (40) in which the transducer(s) (10) are located, can be turbulent due to influences such as, but not limited to any, liquid (30) wave action inherent to this environment. The wave action can be, without limitation, especially disruptive to gathering effectively accurate liquid (30) level or liquid (30) depth readings, especially in smaller and more compact reservoir(s) (40) in which the transducer(s) (10) are located. This is especially true with respect to the various improvements just described in the current invention. Accurate liquid level and/or depth readings are important for reasons including, but not limited to, maintaining an effective and/or sufficient amount of liquid (30) above the transducer(s) (10) within the reservoir(s) (40). This liquid (30) wave action, and more specifically, any wave action on the surface of the liquid (30), can be created from sources such as, but not limited to, any liquid (30) turbulence created as a result of operating the transducer(s) (10), any ejected droplets of liquid (30) returning back to the liquid (30) in the reservoir(s) (40), or any air flow within the reservoir(s) (40).

Referring to FIGS. 95-97, FIGS. 103 and 105, and FIGS. 111-112, it has been found that the turbulence within the reservoir(s) (40) can be avoided by positioning one or more of any suitable liquid level sensor(s) (305) known in the art within, without limitation, one or more protected areas or compartments (hereinafter called "liquid sensor compartment(s)" (8010)), thereby effectively isolating or protecting them from any adverse wave effects experienced within the reservoir(s) (40) in which the transducer(s) (10) are located. It is preferred, without limitation, that one or more, and more preferably only one, liquid sensor compartment(s) (8010) is suitably and effectively interfaced with the reservoir(s) (40) in which the transducer(s) (10) are located. One or more suitable liquid level sensor(s) (305) known in the art may also, without limitation, be utilized within the reservoir(s) (40) in which the transducer(s) (10) are located as well. It is preferred, without limitation, that the liquid level sensor compartment(s) (8010) are effectively connected to the reservoir(s) (40) in which the transducer(s) (10) are located, so that the liquid level experienced in the reservoir(s) (40) is also effectively and sufficiently reflected or experienced within the liquid level sensor compartment(s) (8010). The liquid level sensor compartment(s) (8010) can be, without limitation, directly or indirectly connected in any various effective ways to the reservoir(s) (40) in which the transducer(s) (10) are located. The liquid level sensor compartment(s) (8010) can be located, without limitation, within the reservoir(s) (40), or located anywhere outside of the reservoir(s) (40). It is preferred, without limitation, that the one or more liquid level sensor compartment(s) (8010) are at least, suitably and effectively, separated, completely separated, and/or partially separated, from the one or more reservoir(s) (40) by one or more of any suitable wall(s), barrier(s), structure(s), or otherwise separation wall(s) (8015) of any effective thickness and height. It is more preferred, without limitation, that the one or more liquid level sensor compartment(s) (8010) are suitably and effectively separated from the one or more reservoir(s) (40) by one or more of any suitable wall(s), barrier(s), structure(s), or otherwise separation wall(s) (8015) of any effective thickness and height, and the only connection with the reservoir(s) (40) is through one or more of any reservoir connection orifice(s) (7040). It is further preferred, without limitation, that the liquid level sensor compartment(s) (8010) is effectively sealed to prevent the escape of various things such as, but not limited to any, water vapor, aerosol, or any gases(s) or vapor(s) from the agent or liquid (30).

The reservoir(s) (40) and liquid level sensor compartment(s) (8010) can be, without limitation, sufficiently and effectively connected at any effective distance beneath the surface of the liquid (30) in the reservoir(s) (40) and/or the liquid level sensor compartment(s) (8010), so that any adverse effects such as, but not limited to, any undesired amount of, liquid (30) turbulence, air turbulence, or liquid (30) wave action, is either not experienced within the liquid level sensor compartment(s) (8010) or at least not experienced enough to significantly impact or have a detrimental effect on the accuracy of any means used to measure the depth or volume of the liquid (30) in these areas. More specifically, the reservoir(s) (40) in which the transducer(s) (10) are located and the liquid level sensor compartment(s) (8010) can be, without limitation, suitably connected with one or more of any, opening, tunnel, conduit, pipe, shaft, or orifice (hereinafter called "reservoir connection orifice" (7040)). The reservoir connection orifice(s) (7040) can be, without limitation, any effective shape, size, geometry, or length. It is preferred, without limitation, that the reservoir connection orifice(s) (7040) is between 0.10 inch to 2.0 inches or more in diameter. It is more preferred, without limitation, that the reservoir connection orifice(s) (7040) is between 0.10 inch to 1.5 inch in diameter. It is even more preferred, without limitation, that the reservoir connection orifice(s) (7040) is between 0.10 inch to 1.25 inch in diameter. It is very preferred, without limitation, that the reservoir connection orifice(s) (7040) is between 0.120 inch to 1.0 inch in diameter. The reservoir connection orifice(s) (7040) can also be, without limitation, located at one or more locations within the liquid level sensor compartment(s) (8010) and/or the reservoir(s) (40).

The liquid level sensor compartment(s) (8010) can be, without limitation, any sized tank, compartment, or reservoir, and can hold any effective or desired amount of liquid. It is preferred, without limitation, that the liquid level sensor compartment(s) (8010) holds approximately 0.1 liter to 15 liters or more of liquid (30). It is more preferred, without limitation, that the liquid level sensor compartment(s) (8010) holds approximately 0.1 liter to at least 2 liters of liquid (30). It is even more preferred, without limitation, that the liquid level sensor compartment(s) (8010) holds approximately 0.1 liter to 1 liter of liquid (30). It is very preferred, without limitation, that the liquid level sensor compartment(s) (8010) holds approximately 0.1 liter to 0.5 liter of liquid (30). One or more of any liquid level sensor(s) (305) known to those skilled to in the art, can be, without limitation, utilized within the liquid level sensor compartment(s) (8010) to communicate and/or help maintain any suitable or desired liquid (30) volume, liquid (30) level, or depth of liquid (30).

It is preferred, without limitation, that the liquid level sensor compartment(s) (8010) is separated from the reservoir(s) (40) in which the transducer(s) (10) are located, by at least one or more separation wall(s) (8015) and connected with at least one or more reservoir connection orifice(s) (7040). It is also preferred, without limitation, that at least part of the reservoir connection orifice(s) (7040) interfaces with the bottom surface or floor of the reservoir(s) (40) and liquid level sensor compartment(s) (8010). It is also preferred, without limitation, that both the reservoir(s) (40) and the liquid level sensor compartment(s) (8010) share a common base plate, floor, or bottom. However, the various reservoir(s) (40) and liquid level sensor compartment(s) (8010) may also, without limitation, be completely independent. Referring to FIG. 118, the reservoir(s) (40) and the liquid level sensor compartment(s) (8010) may also be, without limitation, constructed out of the same piece of material, or at least the various side-walls and floor components are sufficiently welded or bonded together, which could eliminate the need for any bottom sealing gasket(s) (3841) as shown in FIGS. 95-96. Referring to FIGS. 95-96, it is preferred, without limitation, that the reservoir(s) (40) in which the transducer(s) (10) are located and the liquid level sensor compartment(s) (8010) are constructed from at least two different components, the transducer plate (3812) and the fluid container (3816), separated by one or more gasket(s) or sealing gasket (3841).

With reference to FIG. 96, one or more drains (3865) may also, without limitation, be located in one or more of any suitable location(s) such as, but not limited to, the reservoir(s) (40) in which the transducer(s) (10) are located, and the liquid level sensor compartment(s) (8010). One or more drainage grooves or troughs of any suitable depth, shape, length, and width, may also, without limitation, be positioned anywhere on the bottom or floor(s) of the various reservoir(s) (40) and/or liquid level sensor compartment(s) (8010) and connect with the one or more drain(s) (655), and help with draining the liquid (30). However, it is preferred, without limitation, that at least one or more drain(s) (655) is located in the reservoir(s) (40) and the one or more drainage grooves or troughs connect not only with one another, but also connect the various areas within both the reservoir(s) (40) and liquid level sensor compartment(s) (8010) to the at least one or more drain(s) (655).

Referring to FIGS. 95-97, FIG. 103, FIG. 105, FIG. 110, FIG. 113, and FIG. 118, an improved liquid level sensor (7020) is described that may be, without limitation, utilized to determine any, liquid level, liquid volume, or liquid depth, of any kind of liquid, in one or more of any tank(s), reservoir(s), or container(s), including, but not limited to, the reservoir(s) (40) in which the transducer(s) (10) are located and/or the liquid level sensor compartment(s) (8010). Without being limited, this improved sensor improves the art by offering an alternative for remotely sensing any liquid depth, liquid volume, or liquid level, especially in areas experiencing high electrical noise or electrical interference. It is preferred, without limitation, that at least one or more improved liquid level sensor(s) (7020) is utilized to determine the liquid level, liquid volume, or liquid depth, of any liquid (30) that may be present in at least the liquid level sensor compartment(s) (8010). However, one or more of any other suitable means known in the art may also, without limitation, be utilized to determine the volume or depth of the liquid that is either in the reservoir(s) (40) in which the transducer(s) (10) are located, and/or in the liquid level sensor compartment(s) (8010).

Figure 103:
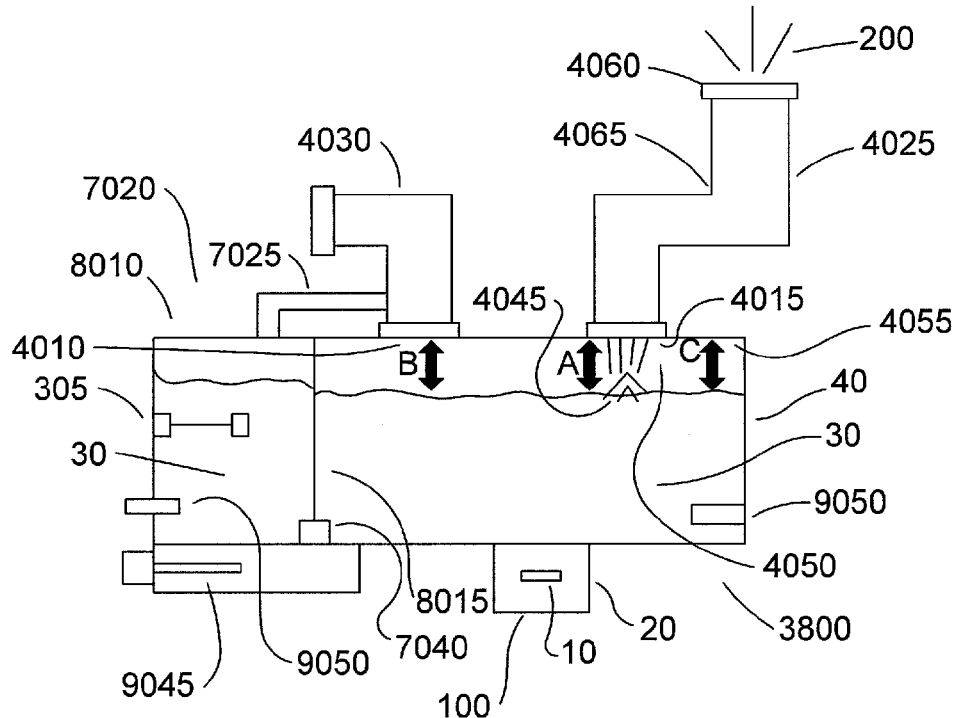
FIG. 103 is a schematic view of an optimized and miniaturized aerosol generator according to the present invention.
Figure 104:
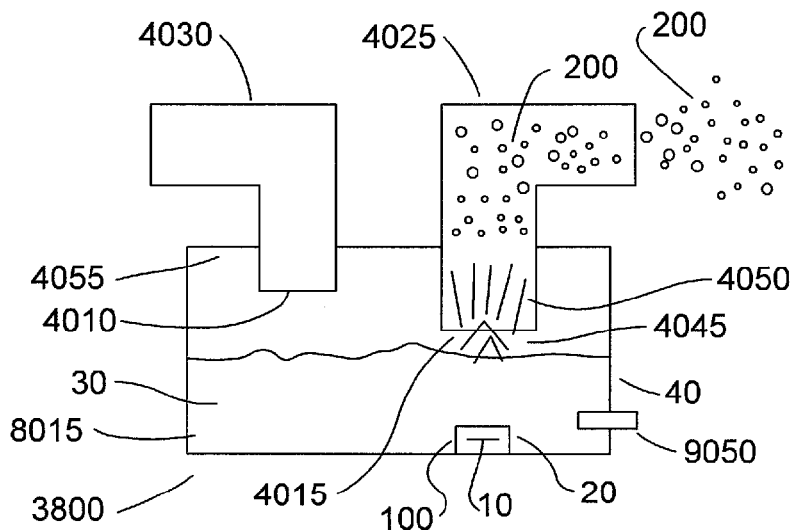
FIG. 104 is a schematic view of an optimized and miniaturized aerosol generator, showing an air outlet pipes position directly over a transducer according to the present invention.

Referring to FIGS. 95-97, FIG. 103, FIG. 105, FIG. 110, FIG. 113, and FIG. 118, and without being limited, the improved liquid level sensor (7020) includes various components. First, it includes one or more float(s) (3814) that can have, without limitation, any effective size, shape, thickness, or material construction. It is preferred, without limitation, that one or more float(s) (3814), and more preferably only one float (3814), is positioned in each liquid sensor compartment (8010). The one or more float(s) (3814) may be, without limitation, located in any suitable reservoir(s), tank(s), or container(s), and float on, or be suitably suspended within, any liquid contained within these spaces. It is preferred, without limitation, that the one or more float(s) (3814) are located inside of the liquid level sensor compartment(s) (8010). It is also preferred, without limitation, that the float(s) (3814) are made from a polymer material that effectively floats in water, or any other liquid that the float(s) (3814) may be located in. With reference to FIG. 103, the air space above the liquid (30) within the liquid level sensor compartment(s) (8010), or any suitable reservoir(s), tank(s), or container(s), can also be, without limitation, plumbed or effectively connected with one or more of any suitable, tube(s), conduit, pipe(s), or duct(s) (Hereinafter called "vent pipe(s)" (7025), to one or more of any suitable and effective location(s). The vent pipe(s) (7025) can be used for purposes such as, but not limited to, enabling a sufficient flow of air/gas in or out of the liquid level sensor compartment(s) (8010), or any other tank(s), reservoir(s), or container(s), as the liquid (30) depth fluctuates, in order to prevent the float(s) (3814) from locking into one or more various position(s). It is preferred, without limitation, that any suitably sized vent pipe(s) (7025) are connected to either the air inlet pipe(s) (4030) or the air outlet pipe(s) (4025).

Figure 110:
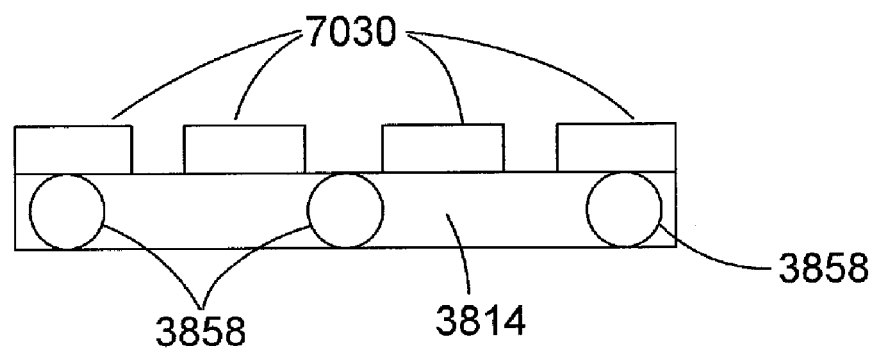
FIG. 110 is a schematic view of a level float of an optimized and miniaturized aerosol generator according to the present invention.
Figure 113:
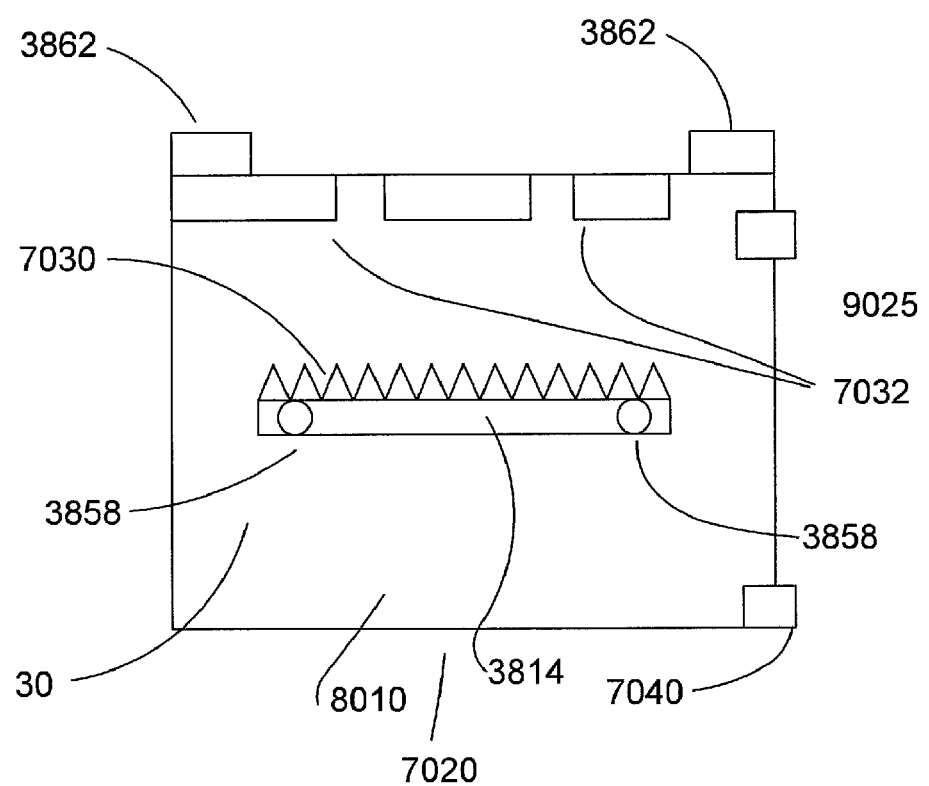
FIG. 113 is a schematic view of a liquid level sensor compartment of an optimized and miniaturized aerosol generator, according to the present invention.

Referring to FIGS. 95 and 113, and without being limited, the float(s) (3814) can have one or more pockets or indentions (Hereinafter called "air pocket(s)" (3815) of any suitable depth, height, geometry, size, and shape, located under, on top of, and/or within, the float(s) (3814), to offer various functions such as, but not limited to, decrease the mass of the float(s) (3814), and create one or more air pockets, that can all aid in float (3814) buoyancy. Referring to FIG. 110 and FIG. 113, the float(s) (3814) can have, without limitation, one or more of any connecting or non-connecting, protrusions, grooves, pockets, indentations, or sufficient texture (Hereinafter called "texture" (7030)), located at the top surface(s) of the float(s) (3814) that can prevent vacuum or suction from occurring that may otherwise result in the float(s) (3814) sticking to the top of the liquid level sensor compartment(s) (8010), or any other tank(s), reservoir(s), or container(s), if the liquid level fluctuates to a sufficient maximum depth for this to occur. The roof or interior surface of the liquid level sensor compartment(s) (8010), or any other tank(s), reservoir(s), or container(s), may also have one or more of any connecting or non-connecting, protrusions, grooves, pockets, indentations, or sufficient texture (Hereinafter called "roof texture" (7032)), to fulfill the same purpose as the texture (7030) on the float(s) (3814). It is preferred, without limitation, that if any protrusions, grooves, pockets, indentations, or sufficient texture (7030), are utilized, they are configured or constructed in a manner so that the float(s) (3814) can remain level on or within, any liquid contained in any of the tank(s), reservoir(s), or container(s), including, but not limited to, the reservoir(s) (40) in which the transducer(s) (10) are located, and the float(s) (3814) don't stick or get affixed to their roof(s).

The one or more float(s) (3814) can also directly or indirectly interface with or include, without limitation, one or more magnet(s) (3858) of any effective strength. The one or more magnet(s) (3858) can be, without limitation, located or directly or indirectly interfaced anywhere, on, within, or around, the one or more float(s) (3814). It is preferred, without limitation, that the magnet(s) (3858) are located within the float (3814), or at least sealed within the float (3814) or the float material, and are protected from the liquid (30) in various ways known to those skilled in the art. The magnet(s) (3858) can also, without limitation, be effectively encapsulated with any suitable protective material, of any suitable thickness.

The magnet(s) (3858) can be, without limitation, interfaced or located in, on, or within, any effective, location, position, or orientation, of the float(s) (3814). It is preferred, without limitation, that at least two or more magnet(s) (3858) are utilized with each float (3814), and each magnet (3858) is at least located in a machined hole located at either end of each float (3814), and effectively sealed into the float (3814). It is also preferred, without limitation, that each magnet(s) (3858) is paired with at least one or more hall effect sensor(s)" (3862).

One or more hall effect sensor(s) (3862) may be, without limitation, placed in any suitable location, and in any suitable proximity, to the magnet(s) (3858). The one or more hall effect sensor(s) (3862) may also be, without limitation, located at any depth or height within, or more preferably outside of, the various tanks(s), reservoir(s), or container(s). It is preferred, without limitation, that any wall or ceiling material(s) used to construct the various tank(s), reservoir(s), or container(s), and/or any structure(s), component(s), or means used to cover the various tank(s), reservoir(s), or container(s), are at least effectively compatible with the hall effect sensor(s) (3862) and magnet(s) (3858) that are utilized.

The one or more hall effect sensor(s) (3862) may also, without limitation, interact or function with one or more magnet(s) (3858). The one or more float(s) (3814) and magnet(s) (3858) can, without limitation, move any distance to or from the hall effect sensor(s) (3862) at any time, and be within any proximity to the one or more hall effect sensor(s) (3862). It is preferred, without limitation, that the one or more float(s) (3814) and magnet(s) (3858) at least move within an effective distance of, or range within, the one or more hall effect sensor(s) (3862). Without being limited one or more of any, float(s) (3814), magnet(s) (3858), and/or hall effect sensor(s) (3862), can be positioned at any distance, or move any distance, at any time, respective to one another. Any type of hall effect sensor(s) (3862) may be, without limitation, utilized and may have any sensitivity and accuracy. It is preferred, without limitation, that the sensitivity and accuracy of the hall effect sensor(s) (3862) is at least effective. It is also preferred, without limitation, that the one or more hall effect sensor(s) (3862) are effectively located outside of the one or more of any reservoir(s), tank(s), or container(s). It is more preferred, without limitation, that the hall effect sensor(s) (3862) are effectively located outside of the liquid level sensor compartment(s) (8010). It is even more preferred, without limitation, that the hall effect sensor(s) (3862) are suitably positioned and effectively located on top of the one or more of any, reservoir(s), tank(s), container(s), or area(s), including, but not limited to, the liquid level sensor compartment(s) (8010).

Without being limited, the voltage output from these sensor(s) (3862) is proportional to the distance of the various magnet(s) (3858), and this in turn can be interpreted by one or more of any digital, electronic, or analog, controller(s) such as, but not limited to, any PLC(s), as the liquid (30) depth. Any voltage, and/or voltage change, reported by the hall effect sensor(s) (3862) can be interpreted as any liquid depth and/or liquid level. It is preferred, without limitation, that the voltage output from the hall effect sensor(s) (3862) is proportional to the magnetic flux density that is sensed by the hall effect sensor(s) (3862), and the closer the magnet(s) is to the sensor(s) (3862), the more voltage output is generated by the sensor(s) (3862) and communicated to one or more of any digital, electronic, or analog, controller(s) such as, but not limited to, any PLC(s). Using more than one pairs of magnet(s) (3858) and hall effect sensor(s) (3862) can offer, without limitation, greater redundancy. It is preferred, without limitation, that the lowest voltage signal reported is equated with, or is assigned, the priority for any decision or logic choice made to fill the various reservoir(s) (40), tank(s), reservoir(s), or container(s).

When used with the new optimized and miniaturized aerosol generator (3800), it is preferred, without limitation, that the various parts such as, but not limited to, the float(s) (3814), magnet(s) (3858), hall effect sensor(s) (3862), and digital, electronic, or analog, controller(s) such as, but not limited to, any PLC(s), are constructed and configured so that if the liquid (30) level in the reservoir(s) (40) in which the transducer(s) (10) are located, and/or the liquid level sensor compartment(s) (8010), drops below, or even rises above, one or more of any set point(s), liquid depth(s), or range of liquid depth(s), that is established, one or more of any digital, electronic, or analog, controller(s) such as, but not limited to, any PLC(s), can cause the apparatus (215), and/or optimized and miniaturized aerosol generator (3800), and/or one more of any of its components, to shut down and/or enter a fault or error mode.

It is also preferred, without limitation, that the various parts such as, but not limited to, the float(s) (3814), magnet(s) (3858), hall effect sensor(s) (3862), and digital, electronic, or analog, controller(s) such as, but not limited to, any PLC(s), are constructed and configured so that if the liquid (30) level in the reservoir(s) (40) in which the transducer(s) (10) are located, and/or the liquid level sensor compartment(s) (8010), drops below, or rises above, one or more of any set point(s), liquid depth(s), or range of liquid depth(s), that is established, one or more of any digital, electronic, or analog, controller(s) such as, but not limited to, any PLC(s), can cause or make the logic choice to either fill the various reservoir(s) (40), tank(s), reservoir(s), or container(s), or stop any filling activity.

Any suitable hall effect sensor(s) (3862) can, without limitation, be utilized. However, it is preferred, without limitation, that hall effect sensor(s) (3862) with higher resolution are utilized in order to obtain more exact liquid (30) level data, and liquid (30) level control over the transducer(s) (10). This manner of suppling liquid (30) to the reservoir(s) (40) in which the transducer(s) (10) are located, or any other chamber(s), compartments, or tank(s) connected to the reservoir(s) (40), can be, without limitation, utilized in the design and construction of the new optimized and miniaturized aerosol generator (3800).

Figure 111:
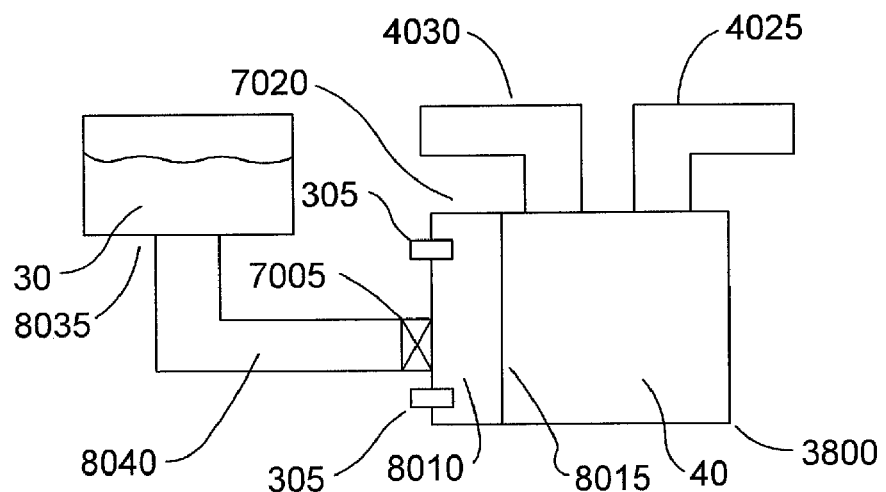
FIG. 111 is a schematic view of a feed tank with pre-mixed liquid connected to an optimized and miniaturized aerosol generator via according to the present invention.
Figure 112:
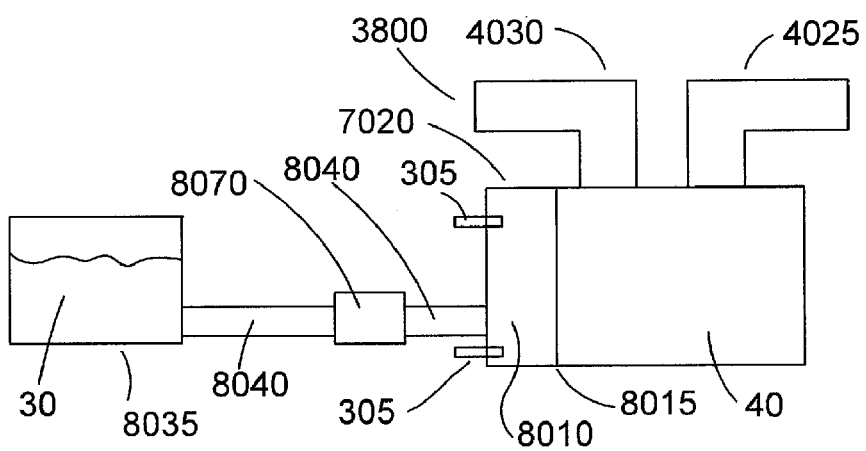
FIG. 112 is a schematic view of a feed tank and pump connected to an optimized and miniaturized aerosol generator according to the present invention.

Another improvement to the design of the optimized and miniaturized aerosol generator (3800) and aerosol generating device (215), includes, without limitation, changing how the agent, in liquid concentrate form or concentrated liquid (Hereinafter called "concentrated agent liquid", "liquid agent in concentrated form", "concentrated agent", "liquid concentrate", or the like, (9005)), is mixed with one or more of any other suitable liquid(s) such as, but not limited to, any kind or type of water (Hereinafter called "dilution liquid(s)" (9010)), before it is supplied to any reservoir(s) (40), or any other chamber(s) or tank(s) connected to the reservoir(s) (40). Referring to FIG. 111 and FIG. 112, traditionally, the liquid (30) is typically diluted or premixed from a concentrated liquid (9005) outside of the apparatus (215), and it is then deposited into one or more feed tank(s) (8035) of various sizes, that supply agent liquid (30) via one or more of any suitable, pipe(s), hose(s), tube(s), or conduit (Hereinafter called "supply tube(s) (8040)), to the reservoir(s) (40) in which the transducer(s) (10) are located, as it is needed. The mixed liquid (30) can be, without limitation, supplied to the reservoir(s) (40) in which the transducer(s) (10) are located, or any other connecting reservoir(s), in various ways such as, but not limited to, via any gravity feed system(s), or the liquid (30) can be pumped directly into the reservoir(s) (40) with any suitable pump (8070), all of which is known to those skilled in the art. The supply of this liquid (30) is typically, without limitation, controlled by one or more of any sufficient reservoir valve(s) (7005), and/or one or more of any sufficient pump(s) (8070), which is in turn controlled by one or more digital, electronic, or analog, controller(s) such as, but not limited to, any PLC(s). This manner of suppling liquid (30) to the reservoir(s) (40) in which the transducer(s) (10) are located, or any other chamber(s), compartment(s), or tank(s) connected to the reservoir(s) (40), can be, without limitation, utilized with one or more of the new optimized and miniaturized aerosol generator(s) (3800) or any of the new enhancements that are disclosed. However, this means for supplying liquid (30) to the various reservoir(s) (40) can be, without limitation, problematic for reasons including, but not limited to, the amount of time that is needed to preheat the one or more feed tank(s) (8035) may be too excessive for certain customers, and certain mixed liquids (30) may have a finite shelf life once they are mixed and may not be completely used before they have expired or experienced an unacceptable level of degradation.

Referring to FIGS. 114-115, it is preferred, without limitation, that a new and improved means is utilized for mixing a liquid agent in concentrate form(s) (9005) with one or more liquid(s) such as, but not limited to, any kind or type of water, before it is supplied to any reservoir(s) (40), or one or more of any other connecting tank(s), reservoir(s), or compartment(s), as the mixed liquid (30) end product. This new and improved means can offer, without limitation, various advantages including, but not limited to, (a) enabling small amounts of mixed liquid (30) to be presented to the reservoir(s) (40) in which the transducer(s) (10) are located on demand, or when needed, (b) providing small amounts of liquid (30) that is mixed with suitable or acceptable accuracy and repeatability, (c) providing a more efficient supply and use of liquid concentrate and mixed liquid (30) for at least one or more aerosol (200) deployment cycle(s), (d) providing a design that is more compact and space saving.

This new means consists of various attributes. Referring to FIGS. 114-115, the first attribute, is the source of the liquid (30). It is preferred, without limitation, that the agent liquid (30) that fills the reservoir(s) (40), is sourced from one or more of any suitable agent liquid(s) that is in any suitable concentrated form(s) (9005), and is then mixed with one or more of any suitable liquid(s), or dilution liquid(s) (9010), such as, but not limited to, any water. The one or more source(s) of the concentrated agent liquid(s) (9005), (Hereinafter called "liquid concentrate source(s)" (8050)), can be, without limitation, one or more of any suitable, container(s), reservoir(s), tank(s), carboy(s), bottle(s), suitable package(s), or cartridge(s), of any suitable design, size, and construction, that directly or indirectly interfaces with the apparatus(s) (215) or any hardware or components connected to the apparatus(s) (215) and/or the optimized and miniaturized aerosol generator(s) (3800), and contains and supplies the concentrated agent, or agent liquid, in any concentrated, or suitably concentrated, form (9005). Without being limited, one or more of any concentrated agent liquid(s) (9005) can be utilized. These concentrated agent liquid(s) (9005) can then be, without limitation, mixed or diluted to any suitable and efficacious percentage(s) or parts per million in solution, as shown later. Without being limited, the concentrated agent liquid(s) (9005) can also be one or more of any liquid, chemical, solution, compound, and/or any other suitable liquid, that is desired or needed to be diluted to any amount(s) or any percentage(s), by the one or more of any dilution liquid(s) (9010). It is preferred, without limitation, that the concentrated agent liquid(s) (9005) is at least diluted with the dilution liquid(s) (9010), to one or more of any effective and/or suitable amount(s) or percentage(s). It is also preferred, without limitation, that the concentrated agent liquid(s) (9005) consists of at least peroxyacetic acid (PAA) in any suitable concentrate form. It is more preferred, without limitation, that the concentrated agent liquid(s) (9005) includes a peroxyacetic acid concentrate having the following ingredients: (a) 4.5% of Peroxyacetic acid (PAA), (b) 22% of hydrogen peroxide, 9% of Acetic acid, (c) 64.5% of Distilled water, and (d) 73.5% of Inert ingredients.

The liquid concentrate source(s) (8050) can be, without limitation, fixed component(s), and/or releasably secured, and attach or interface anywhere to any suitable part of the apparatus(s) (215), and/or the optimized and miniaturized aerosol generator(s) (3800), all in a manner known in the art. In addition, any one or more parts of the liquid concentrate source(s) (8050) can, without limitation, interface with one or more of any suitable sleeves or receptacle(s) connected to or are a part of the apparatus(s) (215), in a manner known in the art. It is preferred, without limitation, that the liquid concentrate source(s) (8050) are at least one single or multi use container(s), or bottle(s), that interface with at least one or more receptacle(s) connected to or are a part of the apparatus(s) (215), and/or the optimized and miniaturized aerosol generator(s) (3800). This type of container(s) or bottle(s) can be, without limitation, designed and constructed in a manner known to those skilled in the art. However, a fixed liquid concentrate source(s) (8050), in the form of one or more of any suitably sized reservoir(s), tank(s), container(s), that are directly or indirectly connected or plumbed to any reservoir(s) (40), may also, without limitation, be utilized, and have one or more of any resealable closure(s) that is of any suitable size and construction. It is preferred, without limitation, that this type of liquid concentrate source(s) (8050) is easily refillable by the operator of the aerosol generating apparatus (215).

The one or more liquid concentrate source(s) (8050) and/or one or more dilution liquid source(s) (8055), can also be, without limitation, marked or tagged in any suitable location with one or more of any, identifier, marking, code, RFID chip or tag, barcode, symbol code, symbol, or image (Hereinafter called "identification code(s)" (8090)). The identification code(s) (8090) can be, without limitation, unique or non-unique. The identification code(s) (8090) utilized can be, without limitation, any optical or radio frequency machine-readable representation of data. It is preferred, without limitation, that the identification code(s) (8090) utilized, are in the form of any barcode, and each barcode is unique for each bottle, package, container, or liquid concentrate source (8050). It is also preferred, without limitation, that the identification code(s) (8090) are at least located approximately on or effectively near the area of the spout, drain, outlet, or neck, of the package(s) or container(s), where the liquid concentrate would leave the liquid concentrate source(s) (8050).

The identification code(s) (8090) can contain, communicate, or relate to, without limitation, one or more of any relevant information or data known to those skilled in the art including, but not limited to, date of product manufacture, date of product expiration, lot number, and part number. It is preferred, without limitation, that the identification code(s) (8090) at least contain information related to the specific lot number or production batch number that the liquid concentrate source (8050) belongs to. It is more preferred, without limitation, that the identification code(s) (8090) at least contain information related to the specific lot number or production batch number that the liquid concentrate source (8050)

belongs to, and a unique part number. It is even more preferred, without limitation, that the identification code(s) (8090) at least contain information related to the specific lot number or production batch number that the liquid concentrate source (8050) belongs to, a unique part number, and the date of manufacture. It is very preferred, without limitation, that the identification code(s) (8090) at least contain information related to the specific lot number or production batch number that the liquid concentrate source (8050) belongs to, a unique part number, the date of manufacture, and the product expiration date.

The identification code(s) (8090) can be, without limitation, detected and deciphered by one or more of any suitable identification code reading device (8095) known to those skilled in the art. The identification code reading device (8095) can, report, communicate, or signal, with one or more of any digital, electronic, or analog, controller(s) such as, but not limited to, any PLC(s) (315). Without being limited, the one or more of any digital, electronic, or analog, controller(s) such as, but not limited to, any PLC(s) (315), can utilize any of the reported information from the identification code reading device(s) (8095), and be programmed to execute various outcomes or actions such as, but not limited to: (a) limit the number of times the apparatus(s) (215) and/or the optimized and miniaturized aerosol generator(s) (3800), can be operated with one or more of, a specific identification code(s) (8090), a certain lot number(s) or production batch number(s), or a certain part or product number(s) or product identification data, and (b) prevent the apparatus(s) (215) and/or the optimized and miniaturized aerosol generator(s) (3800) from being operated with a liquid concentrate source (8050) whose liquid contents (9005) have expired.

Figure 114:
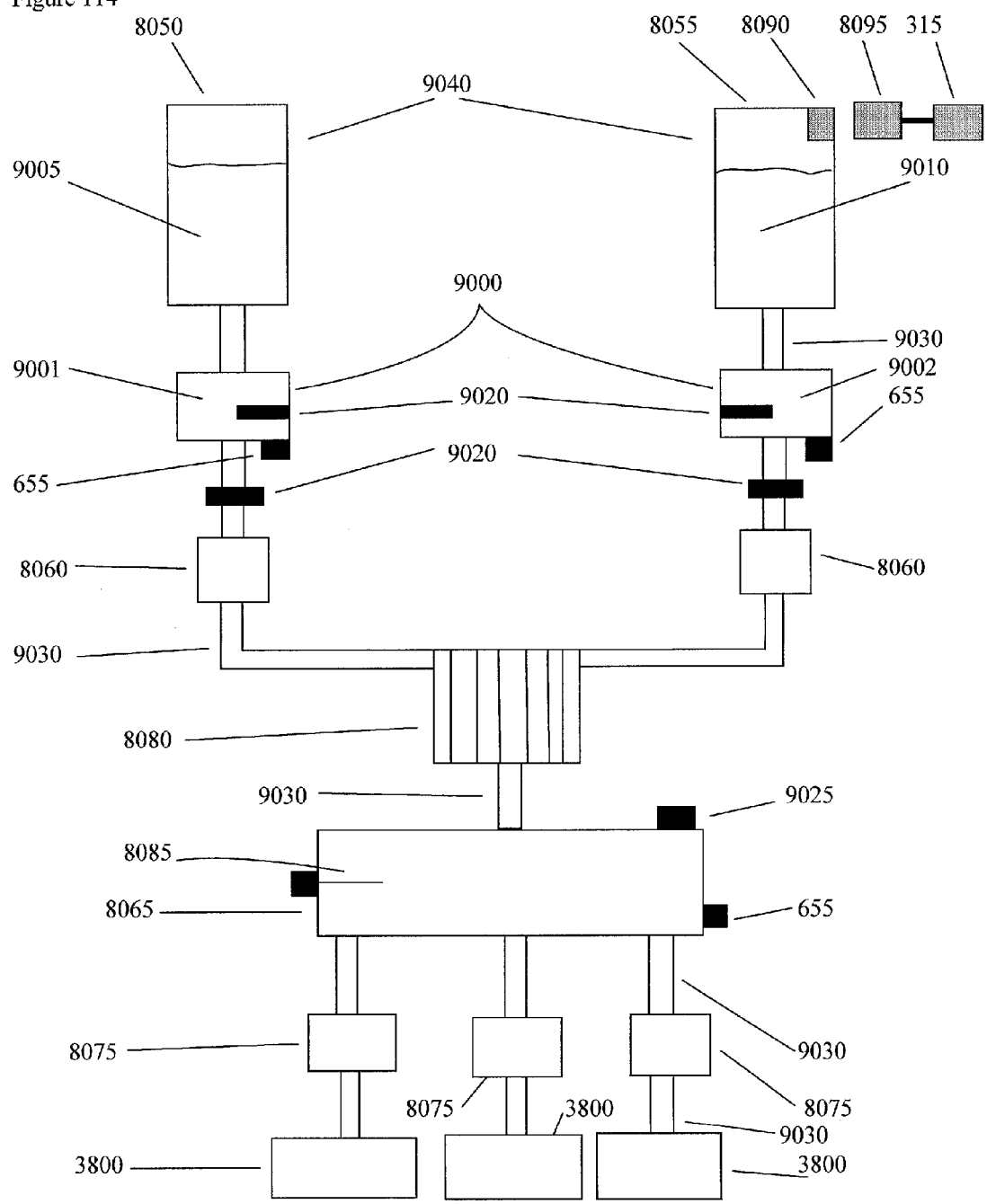
FIG. 114 is a schematic view of two pre-mix reservoirs feeding a mixing apparatus for supplying liquid to a plurality of optimized and miniaturized aerosol generators all according to the present invention.
Figure 115:
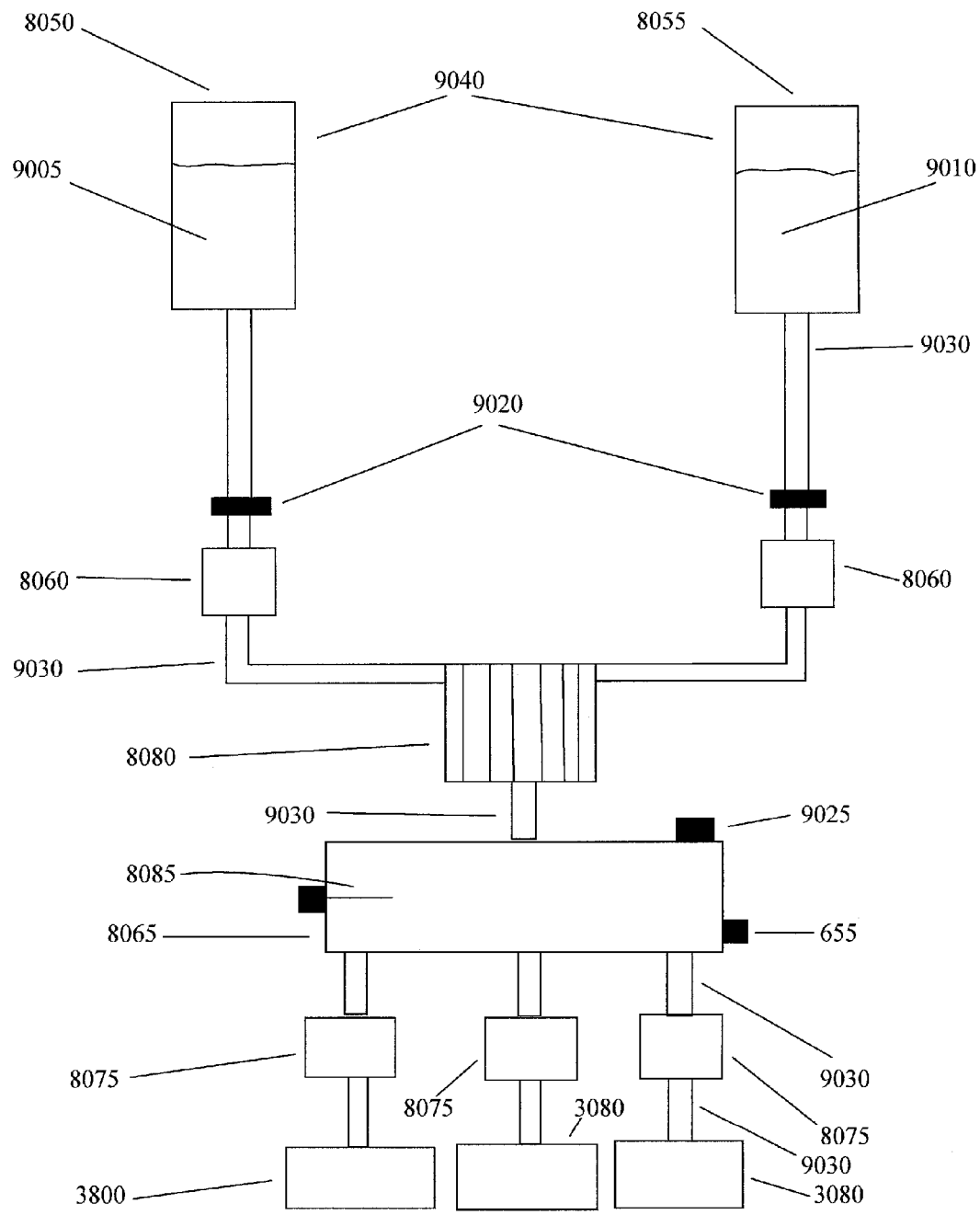
FIG. 115 is a schematic view of a mixing apparatus for supplying liquid to a plurality of optimized and miniaturized aerosol generators according to the present invention.

Referring to FIGS. 114-115, the second attribute for this new means, is the one or more source(s), of the one or more of any suitable dilution liquid(s) (9010) (hereinafter called "dilution liquid source(s)" (8055)), that is mixed with the liquid concentrate (9005). It is preferred, without limitation, that the dilution liquid(s) (9010) is any effective kind or type of water. The dilution liquid source(s) (8055) can be, without limitation, one or more of any suitable, container(s), reservoir(s), tank(s), carboy(s), bottle(s), suitable package(s), or cartridge(s), of any design, size, and construction, that directly or indirectly interfaces with the apparatus(s) (215) or any hardware or components connected to the apparatus(s) (215) and/or the optimized and miniaturized aerosol generator(s) (3800), and contains and supplies one or more of any suitable dilution liquid(s) (9010). The dilution liquid source(s) (8055) can be, without limitation, fixed component(s), and/or releasably secured, and attach or interface anywhere to any suitable part of the apparatus(s) (215), and/or the optimized and miniaturized aerosol generator(s) (3800), all in a manner known in the art. In addition, any one or more parts of the dilution liquid source(s) (8055) can, without limitation, interface with one or more of any suitable sleeves or receptacle(s) connected to or are a part of the apparatus(s) (215), in a manner known in the art.

It is preferred, without limitation, that the dilution liquid source(s) (8055) are fixed container(s), tanks(s), or reservoir(s) that connect to or are a part of the apparatus(s) (215), and/or the optimized and miniaturized aerosol generator(s) (3800). However, the dilution liquid source(s) (8055) may also, without limitation, be any single or multi use container(s), or bottle(s), that interface with at least one or more receptacle(s) connected to or are a part of the apparatus(s) (215), and/or the optimized and miniaturized aerosol generator(s) (3800). This type of container(s) or bottle(s) can be, without limitation, designed and constructed in a manner known to those skilled in the art. The dilution liquid source(s) (8055) can also be, without limitation, marked or tagged in any suitable and effective location with one or more of any, identifier, marking, code, RFID chip or tag, barcode, symbol code, symbol, image, or identification code(s) (8090).

Referring to FIGS. 114-115, and without being limited, in order for this new means to work effectively and efficaciously, at least a sufficient and/or desired amounts of both the concentrated agent liquid (9005) and dilution liquid (9010) must be available and supplied when needed. If either, or both, of the concentrated agent liquid (9005) and/or dilution liquid (9010) are unavailable for mixing, the final liquid (30) that is presented, if any, to the reservoir(s) (40) may be, without being limited, not mixed to the required or desired concentration, or even not presented at all to the reservoir(s) (40).

Various means known to those skilled in the art may, without limitation, be utilized to monitor and report any availability, quantity, absence, presence, and/or supply, of these various liquids, especially before being mixed. For example, one or more of any sensors known to those skilled in the art, that are used to directly or indirectly sense the presence, absence, volume, flow rate, and/or liquid level, of any, liquid, flow of any liquid, or liquid level (Hereinafter called "liquid detector(s)" (9020)), may be, without limitation, utilized or located anywhere inside and/or outside of one more of any of the following locations including, but not limited to, (a) the liquid concentrate source(s) (8050), (b) the dilution liquid source(s) (8055), (c) any pre-mix reservoir(s) (9000) that may be used such as, but not limited to any, concentrate pre-mix reservoir(s) (9001) and/or dilution liquid premix reservoir(s) (9002), (d) mixed liquid buffer tank(s) (8065), (e) any reservoir(s) (40), compartment(s), and/or container(s) located within or associated with the optimized and miniaturized aerosol generator(s) (3800), (f) one or more of any other additional tank(s), reservoir(s), or container(s) of any size, that may be used for any purpose, (g) any location(s) along any suitable tube(s), conduit(s), pipe(s), or hose(s) (Hereinafter called supply pipe(s) (9030)) that may be used to connect the various components together such as, but not limited to, the liquid concentrate source(s) (8050) and dilution liquid source(s) (8055), to the one or more mixing apparatus(s) (8080), and eventually to the optimized and miniaturized aerosol generator(s) (3800), and/or (h) one or more of any additional tank(s), reservoir(s), or container(s) of any size and used for any purpose, that may be connected anywhere between the liquid concentrate source(s) (8050) and/or the dilution liquid source(s) (8055), and the one or more mixing apparatus(s) (8080) and/or the optimized and miniaturized aerosol generator(s) (3800).

The liquid detector(s) (9020) can include, without limitation, one or more of any devices such as, but not limited to any, transducer(s), and/or photo interrupter(s), and any other related parts or components. The liquid detector(s) (9020) can, without limitation, communicate any data with, and/or be controlled by, one or more of any digital, electronic, or analog, controller(s) such as, but not limited to, any PLC(s). It is preferred, without limitation, that if any of these liquid detector(s) (9020) sense and report one or more of the various liquid conditions including, but not limited to, the absence of any liquid, the absence of any liquid flow, insufficient liquid presence or depth, and/or insufficient liquid flow, when these conditions are undesirable or will lead to an outcome that is not efficacious, the liquid detector(s) (9020), may communicate these conditions or information to one or more of any digital, electronic, or analog, controller(s) such as, but not limited to, any PLC(s), that will then cause the apparatus (215), and/or optimized and miniaturized aerosol generator (3800), and/or one more of any of its components, to shut down and/or enter a fault or error mode. The liquid detector(s) (9020) can have, without limitation, any suitable and effective sensitivity and/or any trigger levels.

Without being limited, one or more of any tank(s), reservoir(s), or container(s) (Hereinafter called pre-mix reservoir(s) (9000)), consisting of any suitable size, shape, and construction, can also be located or suitably connected or plumbed between the one or more mixing apparatus(s) (8080) and the one or more of any liquid concentrate source(s) (8050) (Hereinafter called "concentrate pre-mix reservoir(s)" (9001)), and/or between the one or more mixing apparatus(s) (8080) and the one or more dilution liquid source(s) (8055) (Hereinafter called "dilution liquid premix reservoir(s)" (9002)). Any amount of liquid from the liquid concentrate source(s) (8050) and/or dilution liquid source(s) (8055) may, without limitation, flow at any rate, flow with and/or without any restrictions, or even be pumped into these pre-mix reservoir(s) (9000) at any time. Without being limited, if the pre-mix reservoir(s) (9000) are utilized, at least an effective and suitable amount of liquid is moved or flowed, with or without the assistance of one or more of any suitable pump(s), into the various pre-mix reservoir(s) (9000). In place of any reliance on one or more of any pump(s), any suitable gravity feed system or configuration can also be, without limitation, established and utilized, as known to those skilled in the art, to flow any liquids as needed in this invention. Without being limited, the flow of any liquids into the various pre-mix reservoir(s) (9000), or any other locations, can be controlled by one or more of any digital, electronic, or analog, controller(s) such as, but not limited to, any PLC(s), that can control any pumps and/or valves that may be used.

One or more of any suitable pump(s) and/or valve(s) may also be, without limitation, positioned or located between the one or more liquid concentrate source(s) (8050) and the one or more concentrate pre-mix reservoir(s) (9001), and/or the one or more dilution liquid source(s) (8055) and the one or more dilution liquid premix reservoir(s) (9002). Without being limited, if any of these pump(s) and/or valve(s) are utilized, they can be actuated, started, stopped, opened, and/or closed, at any time and for any duration of time, and can be controlled, without limitation, by one or more of any digital, electronic, or analog, controller(s) such as, but not limited to, any PLC(s). It is preferred, without limitation, that each liquid type is designated one or more of its own pre-mix reservoir(s) (9000). For example, and without being limited, the concentrated agent liquid (9005) can flow, with or without being pumped with any suitable pump(s), from the liquid concentrate source(s) (8050) to the concentrate pre-mix reservoir(s) (9001), and/or the dilution liquid (9010) can flow, with or without being pumped with any suitable pump(s), from the dilution liquid source(s) (8055) to the one or more dilution liquid premix reservoir(s) (9002).

However, it is preferred, without limitation, that if the pre-mix reservoir(s) (9000) are utilized, the various liquids can freely flow without being pumped, and freely fill at least the various concentrate pre-mix reservoir(s) (9001) from the liquid concentrate source(s), and/or freely fill the dilution liquid premix reservoir(s) (9002) from the dilution liquid source(s) (8055). It is more preferred, without limitation, that that if the pre-mix reservoir(s) (9000) are utilized, at least one pre-mix reservoir(s) (9000) of suitable size, is suitably connected or plumbed to the liquid concentrate source(s) (8050), and when one or more concentrate source(s) (8050) that at least holds a sufficient or effective amount of liquid, is interfaced with the apparatus (215), and/or directly or indirectly connected to the pre-mix reservoir(s) (9000), all of the liquid contents, or at least a suitable or an effective amount of the liquid in the liquid concentrate source(s) (8050), freely flows into at least one pre-mix reservoir(s) (9000), and more specifically into at least one concentrate pre-mix reservoir(s) (9001).

The one or more of any pre-mix reservoir(s) (9000) can also, without limitation, interface with or possess one or more of any suitable liquid level sensor(s) (305) such as, but not limited to, any float switch(s), infrared liquid level sensor(s), and/or the improved liquid level sensor(s) described later that includes parts such as, but not limited to, suitable float(s) (3814), magnet(s) (3858), and hall effect sensor(s) (3862). These one or more of any suitable liquid level sensor(s) (305), can also, without limitation, be used to detect and communicate the depth, liquid level, and/or volume of the liquid (30) within any pre-mix reservoir(s) (9000). Any other suitable liquid level sensor(s) (305) known in the art, may also be used. This data can be, without limitation, communicated to any one or more of any digital, electronic, or analog, controller(s) such as, but not limited to, any PLC(s), and result in various actions such as, but not limited to, (a) cause concentrated agent liquid (9005) to either move, or stop movement, from the liquid concentrate source(s) (8050) through any valve(s) and/or pump(s), if any are utilized, to the concentrate pre-mix reservoir(s) (9001) when its liquid level(s) reaches any certain depths and/or liquid levels, (b) cause dilution liquid (9010) to either move, or stop movement, from the dilution liquid source(s) (8055) through any valve(s) and/or pump(s), if any are utilized, to the dilution liquid premix reservoir(s) (9002) when its liquid level(s) reaches any certain depth(s) and/or liquid level(s), (c) stop the flow of any liquid, if possible and/or desired, into the pre-mix reservoir(s) (9000), (d) cause the apparatus (215), and/or optimized and miniaturized aerosol generator (3800), and/or one more of any of its components, to shut down and/or enter a fault or error mode, when the depth or level of liquid in the one or more pre-mix reservoir(s) (9000) reaches one or more of any minimum and/or maximum depth(s) or liquid level(s). The one or more of any pre-mix reservoir(s) (9000) can also have, without limitation, one or more suitable drain(s) in any suitable location, that can be manually controlled and/or automated. The drain(s) can be, without being limited, plumbed to one or more of any suitable location(s) including, but not limited to, any catch pan or catch container.

The one or more of any digital, electronic, or analog, controller(s) such as, but not limited to, any PLC(s), can also, without limitation, use any data reported pertaining to the amount of liquid, or volume of liquid, that is available in one or more of any liquid source(s) such as, but not limited to, the liquid concentrate source(s) (8050), dilution liquid source(s) (8055), concentrate pre-mix reservoir(s) (9001), dilution liquid premix reservoir(s) (9002), and/or feed tank(s) (8035) filled with any pre-mixed liquid, and communicate to the operator various information such as, but not limited to, (a) the total amount of aerosol (200) deployment time that is available or remaining, (b) the amount or volume of liquid concentrate (9005) available, (c) the amount or volume of dilution liquid (9010) available, and/or (d) the total amount of cubic feet or cubic meters that is available, or remaining, for treatment by the aerosol generating apparatus(s) (215). Without being limited, the machine operator may also be warned if they choose to deploy aerosol (200) for a specific or even range of aerosol deployment time, and the one or more of any digital, electronic, or analog, controller(s) such as, but not limited to, any PLC(s), determines that an insufficient amount of any needed liquid(s) is available.

The one or more of any digital, electronic, or analog, controller(s) such as, but not limited to, any PLC(s), can also, without limitation, monitor, determine, and/or calculate, the amount of liquid concentrate (9005) and/or dilution liquid (9010) that is pumped from one or more of any liquid source(s) such as, but not limited to, the liquid concentrate source(s) (8050), dilution liquid source(s) (8055), concentrate pre-mix reservoir(s) (9001), and/or dilution liquid pre-mix reservoir(s) (9002), to the one or more mixing apparatus(s) (8080) by the one or more of any pumps, and preferably by the one or more stepper motor driven peristaltic pump(s) (8060) and/or any other similar performing pump(s) known to those skilled in the art. Without being limited, by keeping track of when one or more new liquid concentrate source(s) (8050) and/or dilution liquid source(s) (8055), of a known quantity or volume, or approximate quantity or volume, and more preferably any information gathered by reading any number of identification code(s) (8090) that may be present on any liquid concentrate source(s) (8050) and/or dilution liquid source(s) (8055) that are interfaced with the apparatus (215), in addition to any data or information such as, but not limited to, the number of pumping cycles, number of pump revolutions, any operation time or operation cycle(s) time, and/or the quantity or volume of liquid that is pumped, by one or more of any pump(s) (8060), the one or more of any digital, electronic, or analog, controller(s) such as, but not limited to, any PLC(s), can calculate and/or determine various data, information, or outcomes. This data, information, or outcomes can then be communicated in any manner known to those skilled in the art, to the one or more operator(s) of the apparatus(s) (215) such as, but not limited to, (a) the total amount of aerosol (200) deployment time that is available or remaining, (b) the amount or volume of liquid concentrate (9005) available, (c) the amount or volume of dilution liquid (9010) available, and/or (d) the total amount of cubic feet or cubic meters of treatable space that is available or remaining. Without being limited, the operator may also be warned if they choose to deploy aerosol (200) for a specific or even range of aerosol deployment time, and the one or more of any digital, electronic, or analog, controller(s) such as, but not limited to, any PLC(s), determines that an insufficient amount of one or more of any necessary liquid(s) is available.

It is also preferred, without limitation, that at least one or more liquid detector(s) (9020) is located anywhere along the paths of either, and/or both, the concentrated agent liquid (9005) and dilution liquid (9010) before they are mixed together. It is further preferred, without limitation, that the liquid detector(s) (9020) is any suitable "photo interrupter" known to those skilled in the art. The photo interrupter(s) may be, without limitation, positioned either on or suitably and effectively close to the supply pipe(s) (9030) that are utilized. It is also preferred, without limitation, that the supply pipe(s) (9030) are at least constructed from an effectively clear or transparent polymer. Without being limited, the "photo interrupter" typically consists of at least one or more infrared light emitter(s) that is positioned on one side of the supply pipe (9030), and at least one or more infrared light detector(s) that is positioned across from the emitter(s) on the other side of the supply pipe (9030), all in a manner known to those skilled in the art. Without being limited, if the liquid detector(s) (9020) detects the absence, and/or lack of sufficient flow, of the concentrated agent liquid(s) (9005) and/or dilution liquid(s) (9010) when the various liquid(s) is needed and should be present, at least in sufficient quantity(s), this condition, data, and/or information, can be communicated to one or more of any digital, electronic, or analog, controller(s) such as, but not limited to, any PLC(s), that can then cause the apparatus (215), and/or optimized and miniaturized aerosol generator (3800), and/or one more of any of its components, to take any one or more action(s), such as, but not limited to, shut down and/or enter a fault or error mode.

The various liquid conditions described including, but not limited to, the absence of any liquid, the absence of any liquid flow, insufficient liquid presence or depth, and/or insufficient liquid flow, may also have, without limitation, various unexpected causes including, but not limited to, any one or more obstruction(s) caused by any foreign object debris caught in any components such as, but not limited to any, tube(s), hose(s), conduit(s), tank(s), reservoir(s) and/or container(s). One or more of any suitable filter(s) may be, without limitation, positioned anywhere inside and/or between one or more location(s) such as, but not limited to, the liquid concentrate source(s) (8050) and/or dilution liquid source(s) (8055), and reservoir(s) (40), to aid in preventing any blockage(s) that could occur in one or more of any component(s) and/or location(s), that connect the liquid concentrate source(s) (8050) and dilution liquid source(s) (8055) to the reservoir(s) (40) in which the transducer(s) (10) are located. One or more of any suitable filter(s) may also be, without limitation, positioned at any suitable location(s) inside of the various liquid concentrate source(s) (8050) and/or dilution liquid source(s) (8055).

Figure 116:
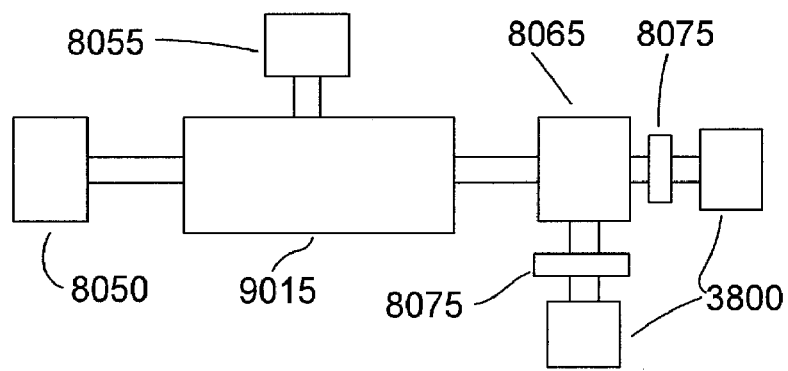
FIG. 116 is a schematic view of a system for mixing concentrated liquid agent for an optimized and miniaturized aerosol generator according to the present invention.

The third attribute for the new and improved means for mixing the liquid (30) from its concentrated form, is the manner in which the liquid concentrate (9005), and the liquid or dilution liquid(s) (9010) used to dilute the concentrate, is actually mixed. Referring to FIG. 116, and without being limited, the concentrated agent liquid (9005) and the dilution liquid (9010) can be mixed with any traditional means known to those skilled in the art, such as, but not limited to, any venturi or venturi-like mixing system (9015). These types of systems typically include, without limitation, pumping and moving the dilution liquid (9010), such as, but not limited to any water, under pressure, and one or more venturi-like mechanism(s) in the mixing device (9015) pulls the concentrated agent liquid (9005) out of its container(s) and mixes it with the flow of the moving dilution liquid (9010) or water. The mix ratio can be modified, without limitation, in various ways known to those skilled in the art, including but not limited to, changing the venturi size or the various venturi or venturi-like dynamics.

However, and without being limited, the traditional means of mixing the various liquids was found to be undesirable for use with the optimized and miniaturized aerosol generator(s) (3800), and the new and improved means for creating the mixed liquid (30) from a more concentrated liquid form, since these traditional mixing means were found to have various undesired attributes such as, but not limited to, (a) a flow output rate and quantity that was too large, (b) a design that did not offer the finite control that is needed when pumping and mixing the small amounts of the concentrated agent liquid (9005) and dilution liquid (9010) that is needed, especially when considering the reduced rate of liquid (30) that is supplied to and required by the optimized and miniaturized aerosol generator(s) (3800). This may be, without limitation, overcome in various ways including, but not limited to, using one or more larger mixed liquid buffer tank(s) (8065) from which the various reservoir(s) (40) can be fed from, but this then defeats the space savings gained, and increases the amount of mixed liquid (30) that may need to be thrown out from time to time by the operator after it has expired.

Referring to FIGS. 114-115, a preferred means is shown for mixing the liquid (30) from the liquid concentrate source(s) (8050) and dilution liquid source(s) (8055). It is preferred, without limitation, that the concentrated agent liquid (9005) is pumped from one or more liquid concentrate source(s) (8050) into one or more mixing apparatus(s) (8080), and the dilution liquid (9010) is pumped from one or more dilution liquid source(s) (8055) into the same one or more mixing apparatus(s) (8080) that the concentrated agent liquid (9005) also enters. It is also preferred, without limitation, that the liquid from each liquid concentrate source(s) (8050), and dilution liquid source(s) (8055), is pumped or moved with at least one or more pump(s) (8060) that is dedicated to each tank, reservoir, or container, and/or at least one or more tank(s), reservoir(s), or container(s) that hold the same liquid(s). Any suitable and effective pump(s) and associated pumping components known to those skilled in the art can be, without limitation, utilized. It is preferred, without limitation, that one or more pump(s) (8060) which are able to supply at least a suitable and effective quantity of any liquid(s), at the needed flow rate(s), are utilized. Without being limited, any suitable pump(s) (8060) can also be combined, and/or function with, one or more of any suitable part(s) and/or component(s), in any suitable and effective location(s), that can restrict, reduce, diminish, and/or control, the flow of the pumped liquid to the desired or needed flow rate(s), all in a manner known to those skilled in the art. However, it is preferred, without limitation, that each pump is a suitable peristaltic pump. It is even more preferred, without limitation, that the liquid moved from the liquid concentrate source(s) (8050) and dilution liquid source(s) (8055) is pumped with its own stepper motor driven peristaltic pump (8060). The stepper motor driven peristaltic pumps (8060) can be expensive, but they offer advantages such as, but not limited to, the ability to precisely control the pump rates and/or flow rate of the liquid that is moved out of each liquid concentrate source (8050) and/or dilution liquid source(s) (8055).

The use of more than one stepper motor driven peristaltic pumps (8060) that is designated to each liquid type, also offers, without limitation, additional advantages such as, but not limited to, the ability to control the ratio in which the liquids are pumped from the liquid concentrate source(s) (8050) and dilution liquid source(s) (8055). This can be accomplished, without limitation, by changing the number of pumping operations that are conducted per unit of time for each tank or reservoir such as, but not limited to, the liquid concentrate source(s) (8050) and dilution liquid source(s) (8055). Any ratio of pumping from the various tanks or reservoirs such as, but not limited to the liquid concentrate source(s) (8050) and dilution liquid source(s) (8055) may be utilized. It is preferred, without limitation, that the stepper motor driven peristaltic pumps (8060) are configured, programmed, and/or timed, so that the liquid that is pumped from one liquid concentrate source (8050) is pumped only one (1) time for every twenty-five (25) times that liquid is pumped from one dilution liquid source (8055), assuming that the output of the stepper motor driven peristaltic pumps (8060) that are utilized, is approximately identical, or at least effectively similar. It is more preferred, without limitation, that the stepper motor driven peristaltic pumps (8060) are configured, programmed, and/or timed, so that one (1) unit of any measure of liquid is pumped or flowed from one liquid concentrate source (8050) for every twenty-five (25) units of any measure of liquid that is pumped or flowed from one dilution liquid source (8055).

The stepper motor driven peristaltic pumps (8060) can also be, without limitation, configured, programmed, and/or controlled, at any time by one or more of any digital, electronic, or analog, controller(s) such as, but not limited to, any PLC(s), so that the ratio(s) of any liquid mixing can change, even during the deployment of any aerosol (200) by the optimized and miniaturized aerosol generator(s) (3800). It is preferred, without limitation, that this is achieved by either slowing down or speeding up the stepper motor of each stepper motor driven peristaltic pumps (8060) that are used, which either decreases or increases the pumping rate or liquid flow rate of each pump (8060). The stepper motor can be controlled by one or more of any digital, electronic, or analog, controller(s) such as, but not limited to, any PLC(s). Without being limited, the stepper motor driven peristaltic pumps (8060), or any other pumps that may be used, may be controlled and/or communicate with one or more of any digital, electronic, or analog, controller(s) such as, but not limited to, any PLC(s), all in a manner known to those skilled in the art.

Without being limited, any combination of any number of different types of feed reservoir(s) (9040) containing any suitable types of liquids, may be utilized together, with any pumping ratio or flow rate from any of the feed reservoir(s) (9040), and feed into one or more of any mixing apparatus(s) (8080), at any time. It is preferred, without limitation, that each liquid concentrate source (8050) is paired with only one dilution liquid source (8055) and they both feed into at least one or more mixing apparatus(s) (8080) where the pumped liquids are suitably mixed. It is preferred, without limitation, that at least effective pumping ratio(s) or flow rate(s) from any of the feed reservoir(s) (9040) are utilized.

The one or more mixing apparatus(s) (8080), can be any suitable means, known to those skilled in the art, to effectively mix two or more liquids together. The mixing apparatus(s) (8080) can accept, without limitation, one or more of any fluid source inputs, and have one or more fluid outputs, after the various inputed liquids are suitably and effectively mixed. It is preferred, without limitation, that the mixing apparatus(s) (8080) utilized is any "in-line mixer". It is more preferred, without limitation, that the "in-line mixer" is a "static in-line mixer", whereby the various fluids are mixed as they are joined in at least one or more common space(s) and are mixed by traveling through one or more of any suitable and effective turbulent path(s). Without being limited, one or more of any suitable and effective "in-line mixer(s)" and/or "static in-line mixer(s)" known to those skilled in the art, may be utilized. Any suitable "in-line mixer" can, without limitation, be used that can achieve an effective mixture of the concentrated agent liquid (9005) and dilution liquid (9010). It is preferred, without limitation, that one or more mixing apparatus(s) (8080), is suitably and effectively connected to one or more liquid concentrate source(s) (8050) and one or more dilution liquid source(s) (8055). It is more preferred, without limitation, that one or more mixing apparatus(s) (8080), in the form of any "static in-line mixer", is suitably and effectively connected to one or more liquid concentrate source(s) (8050) and one or more dilution liquid source(s) (8055). It is even more preferred, without limitation, that only one mixing apparatus(s) (8080), in the form of any "static in-line mixer", is connected to both a liquid concentrate source (8050) and a dilution liquid source (8055). It is very preferred, without limitation, that one or more mixing apparatus(s) (8080), at least in the form of any "static in-line mixer", is not only connected to at least one or more stepper motor driven peristaltic pump(s) (8060) that is suitably connected to at least one or more liquid concentrate source(s) (8050), but is also suitably connected to at least one or more stepper motor driven peristaltic pump(s) (8060) that is suitably connected to at least one or more dilution liquid source(s) (8055).

The fourth attribute for the new and improved means for mixing the liquid (30) from its concentrated form, or deriving the aerosolized liquid (30), is the manner and/or locations in which the mixed liquid is allocated after it has been mixed. Traditionally, the mixed liquid (30) can be, without limitation, premixed and it is supplied to the reservoir(s) (40) in which the transducer(s) (10) are located via one or more feed tank(s) (280). Alternatively, after the liquid from the liquid concentrate source(s) (8050) and dilution liquid source(s) (8055) is mixed, it can be, without limitation, moved, flowed, and/or pumped, directly into the reservoir(s) (40) in which the transducer(s) (10) are located. Without being limited, this was found to be undesirable when operating and supplying mixed liquid (30) to more than one optimized and miniaturized aerosol generator(s) (3800), for reasons including, but not limited to, one or more of the optimized and miniaturized aerosol generator(s) (3800) can have a different, significantly different, and/or effectively different liquid (30) consumption rate. This can be, without limitation, especially critical for the optimized and miniaturized aerosol generator(s) (3800) because of the limited or small amount of liquid that can be intentionally designed to be utilized within the, optimized and miniaturized aerosol generator(s) (3800), and/or apparatus (215). Depending on variables such as, but not limited to, the number of transducer(s) (10) that are used, and the amount of aerosol (200) output per transducer(s) (10), this can, without limitation, cause one or more reservoir(s) (40) of various optimized and miniaturized aerosol generators (3800), to experience one or more of various conditions such as, but not limited to being, over filled, and/or under filled.

Referring to FIGS. 114-115, and without limitation, a preferred means is shown for supplying mixed liquid (30) to the one or more reservoir(s) (40) in which the transducer(s) (10) are located, and more preferably to the liquid sensor compartment(s) (8010). It is preferred, without limitation, that before the mixed liquid (30) is moved, flowed, and/or pumped, into the liquid sensor compartment(s) (8010), and/or the one or more reservoir(s) (40) in which the transducer(s) (10) are located, it is first deposited into one or more holding tank(s), reservoir(s), or container(s) (Hereinafter called mixed liquid buffer tank(s) (8065)). It is also preferred, without limitation, that at least one or more mixed liquid buffer tank(s) (8065) is assigned to, connected to, or utilized for, each optimized and miniaturized aerosol generator(s) (3800). It is more preferred, without limitation, that only one mixed liquid buffer tank (8065) is allocated to supply the one or more optimized and miniaturized aerosol generator(s) (3800) that are utilized in each aerosol generating apparatus (215).

The mixed liquid buffer tank(s) (8065) can be any suitable size, shape, and construction. It is preferred, without limitation, that the mixed liquid buffer tank(s) (8065) have a capacity between at least 0-2 liters or more. It is more preferred, without limitation, that the mixed liquid buffer tank(s) (8065) have a capacity between 0-1 liters or more. It is even more preferred, without limitation, that the mixed liquid buffer tank(s) (8065) have a capacity between 0.25-0.5 liters. It is very preferred, without limitation, that the mixed liquid buffer tank(s) (8065) have a capacity between at least 0.1-0.25 liters.

Without being limited, the mixed liquid buffer tank(s) (8065), and/or one or more of any other reservoir(s), tank(s), compartment(s), and container(s) used in the present invention, can be sufficiently and effectively vented when needed, with one or more of any suitable vent(s) (9025) located in any suitable and effective location(s), all in a manner known to those skilled in the art. The one or more of any, feed reservoir(s) (9040) and/or pre-mix reservoir(s) (9000), may also be, without being limited, suitably and effectively vented in a manner known to those skilled in the art. One or more of any hose(s), tube(s), or pipe(s), may be, without limitation, used to connect to one or more of any vent(s) (9025) and vent the mixed liquid buffer tank(s) (8065), or any other tank(s), container(s), compartment(s), and/or reservoir(s), to one or more of any suitable and effective location(s). It is preferred, without limitation, that at least one or more of any suitable hose(s), tube(s), pipe(s), or conduit(s) is utilized. It is also preferred, without limitation, that the mixed liquid buffer tank(s) (8065) is suitably and effectively vented and it is suitably connected to one or more of any air inlet pipe(s) (4030) or air outlet pipe(s) (4025), or any other suitable location(s) located within the apparatus(s) (215) and/or on the exterior of the apparatus(s) (215). Without being limited, the one or more of any hose(s), tube(s), or pipe(s), or conduit(s), utilized for venting the mixed liquid buffer tank(s) (8065) can be used for purposes such as, but not limited to, provide a suitable means for any gas(s) or vapor(s) to escape, enabling a sufficient flow of air/gas in or out of the mixed liquid buffer tank(s) (8065), or any other tank(s), reservoir(s), or container(s), especially during any pumping activities. Without being limited, the mixed liquid buffer tank(s) (8065), or any other tank(s), reservoir(s), or container(s), that are utilized, can also have, without limitation, one or more of any suitable drain(s) (655) in any suitable location, that can be manually controlled and/or automated. The drain(s) (655) can be, without being limited, plumbed to any suitable location(s) including, but not limited to, one or more of any catch pan(s) or catch container(s).

One or more of any suitable liquid level sensor(s) (305) such as, but not limited to, any float switch(s), infrared liquid level sensor(s), and/or the improved liquid level sensor(s) previously described that consists of suitable float(s) (3814), magnet(s) (3858), and hall effect sensor(s) (3862), can also, without limitation, be used to detect and communicate the depth, liquid level, or volume of the liquid (30) within the mixed liquid buffer tank(s) (8065). Any other suitable liquid level, depth, or volume, sensors known in the art, may also be used. This data can be, without limitation, communicated to one or more of any digital, electronic, or analog, controller(s) such as, but not limited to, any PLC(s), and result in various actions such as, but not limited to, (a) cause more mixed liquid (30) to be generated and fill the mixed liquid buffer tank(s) (8065) when its liquid (30) level reaches a certain depth and/or liquid level, (b) cause the flow of the generated mixed liquid (30) to stop filling the mixed liquid buffer tank(s) (8065) when its liquid (30) level reaches a certain depth and/or liquid level, (c) cause the apparatus (215), and/or optimized and miniaturized aerosol generator (3800), and/or one more of any of its components, to shut down and/or enter a fault or error mode, when the depth or level of liquid (30) in the mixed liquid buffer tank(s) (8065) reaches one or more of any minimum or maximum depth(s) or liquid level(s).

Once the mixed liquid (30) is in the mixed liquid buffer tank(s) (8065), any amount of this liquid (30) can be, without limitation, moved or flowed with any valve control, and/or pumped, into the liquid sensor compartment(s) (8010), or the one or more reservoir(s) (40) in which the transducer(s) (10) are located, at any time when needed, at any suitable flow rate, and for any suitable duration of time. Referring to FIG. 114-115, and FIG. 116, it is preferred, without limitation, that any suitable amount of the mixed liquid (30) that is in the mixed liquid buffer tank(s) (8065) can be pumped into the liquid sensor compartment(s) (8010) and/or any reservoir(s) (40) in which the transducer(s) (10) are located, or any other reservoir(s) connected to these reservoir(s) (40), with at least one or more of any suitable pump(s) (Hereinafter called "feed pump(s)" (8075)). It more preferred, without limitation, that each optimized and miniaturized aerosol generator(s) (3800)

is connected to only one feed pump (8075), and the various feed pump(s) (8075) that are connected to each optimized and miniaturized aerosol generator(s) (3800) all source their mixed liquid (30) from at least one or more common or shared mixed liquid buffer tank(s) (8065). It is also preferred, without limitation, that each feed pump (8075) that is utilized, is controlled, and/or communicates with, one or more of any digital, electronic, or analog, controller(s) such as, but not limited to, any PLC(s), all in a manner known to those skilled in the art.

Any number of any suitable feed pump(s) (8075) can be, without limitation, utilized. However, it is preferred, without limitation, that each feed pump (8075) utilized is any suitable peristaltic pump. It is even more preferred, without limitation, that these feed pump(s) (8075) are gear motor driven, and they cycle on and off when needed, at a fixed speed that adequately fulfills and replenishes the liquid (30) needs of the optimized and miniaturized aerosol generator(s) (3800) as it generates aerosol (200).

Any suitable tube(s), conduit(s), pipe(s), conduit(s), or hose(s), or otherwise supply pipe(s) (9030), may be, without limitation, utilized to connect the various feed reservoir(s) (9040) such as, but not limited to, the liquid concentrate source(s) (8050) and dilution liquid source(s) (8055) to the various components, and ultimately to the reservoir(s) (40) located within the optimized and miniaturized aerosol generator(s) (3800). It is preferred, without limitation, that the various tube(s), conduit(s), pipe(s), conduit(s), or hose(s), or otherwise supply pipe(s) (9030), are any suitably clear and flexible tubing.

One or more of any suitable pH sensors (8085) known in the art, may also be, without limitation, positioned or effectively interfaced anywhere within and/or between the liquid concentrate source(s) (8050) and/or dilution liquid source(s) (8055), and the reservoir(s) (40) in which the transducer(s) (10) are located. It is preferred, without limitation, that at least one or more pH sensor(s) is suitably located within each mixed liquid buffer tank(s) (8065) that are utilized. The pH sensor(s) can, without limitation, sense any pH range. However, it is preferred, without limitation, that the pH sensor(s) at least accurately sense a pH in the range between 2-8. It is more preferred, without limitation, that the pH sensor(s) at least accurately sense a pH in the range between 1-10.

The pH sensors (8085) can communicate with one or more of any digital, electronic, or analog, controller(s) such as, but not limited to, any PLC(s). Without being limited, if the pH is not within a specified or expected range at any time, the one or more of any digital, electronic, or analog, controller(s) such as, but not limited to, any PLC(s), can cause various outcomes to happen such as, but not limited to (a) change the mix ratios that are used with the various liquids that are mixed, or (b) cause the apparatus (215), and/or optimized and miniaturized aerosol generator(s) (3800), and/or one or more of any of its components, to shut down and/or enter a fault or error mode.

Referring to FIGS. 95-97, and FIGS. 103-118, and without being limited, any components directly or indirectly connected to, or interfaced with, the optimized and miniaturized aerosol generator (3800) can be positioned in any suitable location or orientation. In addition, one or more of any optimized and miniaturized aerosol generator(s) (3800) may be, without limitation, utilized within the design and construction of any aerosol (200) generating apparatus(s) (215). The one or more optimized and miniaturized aerosol generator(s) (3800) may be incorporated in any suitable or effective way into the design and construction of the aerosol generating apparatus(s) (215). It is preferred, without limitation, that at least one or more optimized and miniaturized aerosol generator(s) (3800) is incorporated into the design of the aerosol generating apparatus (215). It is more preferred, without limitation, that at least two to three optimized and miniaturized aerosol generator(s) (3800) are incorporated into the design of the aerosol generating apparatus (215). It is even more preferred, without limitation, that at least three or more optimized and miniaturized aerosol generator(s) (3800) are incorporated into the design of the aerosol generating apparatus (215).

Without being limited, and according to a preferred embodiment and with reference to FIGS. 95-97, an even more specific description of the optimized and miniaturized aerosol generator (3800) is given. The optimized and miniaturized aerosol generator (3800) preferably includes the transducer plate (3812), the at least one transducer (10), the level float (3814), the fluid container (3816), at least one aerosol output member (3818) and an air input member (3819). At least one transducer counterbore (3822) is formed through a bottom of the transducer plate (3810). Without being limited, each side of the transducer (10), and more preferably, the protective barrier (not shown) that is interfaced with the transducer (10), is sandwiched between at least two polymer rings (3824).

Without being limited, at least one of these polymer sealing rings (3824) may be used in this particular assembly, but this can diminish safety and quality, and therefore at least two polymer rings (3824) are suggested to be utilized. It is preferred, without limitation, that the polymer rings (3824) are constructed from one or more of any suitable and effective polymer consisting of any suitable and effective hardness. It is more preferred, without limitation, that the polymer rings (3824) are constructed from one or more of any suitable and effective material(s), or any combination of material(s), such as, but not limited to any, Butyl, Teflon, PTFE, Nitrile, Neoprene, and/or Viton. Without being limited, the aerosolized liquid (30) can include one or more of various chemical agents that can necessitate that different polymer rings (3824), of various construction, may need to be utilized for chemical compatibility, as known to those skilled in the art. Any suitable and effective construction techniques and polymer ring (3824) design(s), can also be, without limitation, utilized.

Each transducer (10), and/or any transducer assembly, is retained in the counterbore (3822) with at least one retaining ring (3826). The retaining ring (3826) is secured in the counterbore (3822) with at least two ring fasteners (3828). The fluid container (3816) includes a float chamber (3830) and an aerosol chamber (3832). A middle rib (3834) separates the float chamber (3830) and the aerosol chamber (3832). An input hole (3836) is formed through a top of the fluid container (3816) to receive the air input member (3819). At least one output hole (3838) is formed through a top of the fluid container (3816) to receive the at least one aerosol output member (3818). The two output holes (3838) are preferably formed adjacent the air input hole (3836). The sum of the surface areas of the air input hole (3836) and the two aerosol output holes (3838) take-up at least 50% of a surface area of a top of the aerosol chamber (3832).

A sealing gasket (3841) is preferably placed between a top of the transducer plate (3812) and a bottom of the fluid container (3816) to prevent leakage of aerosol solution (30) in the float chamber (3830) and the aerosol chamber (3832). At least one solution passage (3844) is preferably cut through a middle rib (3846) of the sealing gasket (3841). The level float (3814) is contained in the float chamber (3830). The aerosol solution (30) is pumped into the float chamber (3830) through a solution input port (3848). A pipe nipple (3851) or the like of a supply pipe or hose is threaded into the solution input port (3848). The aerosol solution (30) flows through the at least one solution passage (3844) into the aerosol chamber (3832). Air is pumped into the aerosol chamber (3832) through the air input member (3819) from an air blower, such as the blower (180) shown FIG. 6 or FIG. 117-A and FIG. 117-B. However, any suitable air-blowing device may be used. One or more transducer driver(s) (not shown), or any suitable electronics and components known to those skilled in the art, and as previously disclosed, that are needed for effectively operating the one or more transducer(s) such as, but not limited to one or more of any suitable, variable frequency oscillator(s) or signal generator(s), and power amplifier(s), is used to operate the at least one transducer(s) (10). The at least one transducer(s) (10) vibrates and produces an aerosol (200) from the aerosol solution (30), which exits the at least one aerosol output member (3818). The transducer plate (3812) is preferably fabricated from a metal, such as 316 stainless steel for heat conducting purposes. At least one heater bore (3854) is formed through the transducer plate (3812) to receive at least one heater element (3856). The heater element (3856) heats the transducer plate (3812), which heats the aerosol solution (30) in the float and aerosol chambers.

A magnet (3858) is secured in a magnet hole (3860) formed through each end of the level float (3814). A pair of hall effect sensors (3862) or the like are attached to a top of the fluid container (3816). The pair of hall effect sensors (3862) detect a height of the level float (3814) in the float chamber (3830). The pair of hall effect sensors (3862) can be, without limitation, connected to any suitable A/C converter and/or an electronic controller, such as the electronic controller (315) shown in FIG. 10 and FIG. 114, which determines an average voltage signal of the two hall effect sensors (3862). If the height of the level float (3814) is too low, the electronic controller sends a signal to a supply pump, such as the supply pump (8075) shown in FIG. 114. The supply pump shown in FIG. 114 pumps the aerosol solution (30) through the solution input port (3848) from one or more of any reservoir(s), tank(s), and/or mixed liquid buffer tank(s) (8065). A drain valve (3864) can be, without limitation, opened by the electronic controller to drain the float and aerosol chambers of the aerosol solution (30), when the optimized and miniaturized aerosol generator (3800) is turned off. The drain valve (3864) is connected to the reservoir. The drain valve (3864) is threaded into a drain hole (3865) formed through the transducer plate (3810) and located below a middle of the aerosol chamber (3832). A plurality of container fasteners (3866) are used to secure the transducer plate (3810) and the sealing gasket (3841) to a bottom of the fluid container (3816). A heat sensor (3868) is threaded into a sensor hole (3870) in a side wall of the aerosol chamber (3832). The heat sensor (3868) monitors a temperature of the aerosol liquid (30) in the aerosol chamber (3832). The heat sensor (3668) is connected to the electronic controller. If a temperature of the aerosol liquid (30) becomes too hot, the electronic controller will activate a power cutoff switch (3872), which cuts power to every electrical component in the optimized and miniaturized aerosol generator (3800). The cutoff switch (3872) may also be operated by a manual control. The cutoff switch (3872) is preferably attached to a bottom of the transducer plate (3810) with at least two fasteners (3874).

Without being limited, by operating the optimized and miniaturized aerosol generator(s) (3800) with the various attributes and configurations such as, but not limited to, those related to the temperature of the liquid (30) that is aerosolized, the frequency that the transducer(s) (10) are operated at, the power or volts peak to peak that the transducer(s) are operated at, and the various design and construction characteristics of the optimized and miniaturized aerosol generator(s) (3800) the result can be, the production and deployment of an aerosol (200) where the average particle size may range from less than one micron to about 10 microns, preferably less than about 5 microns, more preferably less than one micron, and even more preferably about 0.68 microns. In addition, and without limitation, the output of the optimized and miniaturized aerosol generator(s) (3800), or the amount of aerosolized liquid (30) that is generated and then deployed into the targeted area(s) (210), can range from 10 to 2,500 milliliters (mL) or more, preferably between 500 to at least 2,500 milliliters (mL), more preferably between 800 to 2,500 milliliters (mL) or more, and even more preferably between 1,100 to 2,500 milliliters (mL) or more. Without being limited, the optimized and miniaturized aerosol generator(s) (3800) improves the art by enabling a very dense cloud of extremely small aerosol particles to be continuously generated within a steady range of efficacious temperature, all within at least one small aerosol generation reservoir and aerosol generating apparatus.

Various alternatives are contemplated as being within the scope of the following claims particularly pointing out and distinctly claiming the subject matter regarded as the invention.

We claim:

1. An optimized and miniaturized aerosol generator comprising:
    a fluid container includes an aerosol chamber, a float chamber, at least one aerosol output and an air input, said at least one aerosol output and said air input are disposed over said aerosol chamber;
    a transducer plate includes at least one transducer, said transducer plate is attached to said fluid container, said at least one transducer communicates with aerosol solution retained in said aerosol chamber, a passage is formed between said aerosol chamber and said float chamber to allow the passage of the aerosol solution therebetween, wherein providing electrical power to said at least one transducer generates an aerosol; and
    a float member is movably retained in said float chamber to monitor a level of the aerosol solution in said float chamber; and
    a heater element is retained in said transducer plate to increase a temperature of the aerosol solution in said float and aerosol chambers.

2. The optimized and miniaturized aerosol generator of claim 1, further comprising:
    at least one magnet is retained in said float member, a magnet sensor is disposed adjacent each one of said at least one magnet to determine a height of said float member.

3. The optimized and miniaturized aerosol generator of claim 1, further comprising:
    a heat sensor monitors a temperature in said aerosol chamber.

4. The optimized and miniaturized aerosol generator of claim 1, further comprising:
    an aerosol inlet is formed through a side wall of said float chamber for the introduction of the aerosol solution.

5. The optimized and miniaturized aerosol generator of claim 1, further comprising:
    a sealing gasket is disposed between said transducer plate and said fluid container.

6. An optimized and miniaturized aerosol generator comprising:

a fluid container includes an aerosol chamber, a float chamber, at least one aerosol output opening and an air input opening, said at least one aerosol output opening and said air input opening are disposed over said aerosol chamber;

a transducer plate includes at least one transducer, said transducer plate is attached to said fluid container, said at least one transducer communicates with aerosol solution retained in said aerosol chamber, a passage is formed between said aerosol chamber and said float chamber to allow the passage of the aerosol solution there between;

a float member is movably retained in said float chamber to monitor a level of the aerosol solution in said float chamber; and a drain valve is retained in said transducer plate below said aerosol chamber to drain the aerosol solution therein.

7. An optimized and miniaturized aerosol generator comprising:

a fluid container includes an aerosol chamber and a float chamber, said aerosol chamber includes a peripheral side wall and a top wall, at least one air input opening for retaining at least one air input member and at least one output opening for retaining at least one aerosol output member both occupy substantially all of a surface area of said top wall;

a transducer plate includes at least one transducer, said transducer plate is attached to said fluid container, said at least one transducer communicates with aerosol solution retained in said aerosol chamber, a passage is formed between said aerosol chamber and said float chamber to allow the passage of the aerosol solution therebetween; and a float member is movably retained in said float chamber to monitor a level of the aerosol solution in said float chamber.

8. The optimized and miniaturized aerosol generator of claim 7, further comprising:

a heat sensor monitors a temperature in said aerosol chamber.

9. The optimized and miniaturized aerosol generator of claim 7, further comprising:

an aerosol inlet is formed through a side wall of said float chamber for the introduction of the aerosol solution.

10. The optimized and miniaturized aerosol generator of claim 7, further comprising:

a sealing gasket is disposed between said transducer plate and said fluid container.

11. The optimized and miniaturized aerosol generator of claim 6, further comprising:

at least one magnet is retained in said float member, a magnet sensor is disposed adjacent each one of said at least one magnet to determine a height of said float member.

12. The optimized and miniaturized aerosol generator of claim 6, further comprising:

a heat sensor monitors a temperature in said aerosol chamber.

13. The optimized and miniaturized aerosol generator of claim 6, further comprising:

an aerosol inlet is formed through a side wall of said float chamber for the introduction of the aerosol solution.

14. The optimized and miniaturized aerosol generator of claim 6, further comprising:

a sealing gasket is disposed between said transducer plate and said fluid container.

* * * * *